(12) United States Patent
Burger et al.

(10) Patent No.: US 8,822,497 B2
(45) Date of Patent: *Sep. 2, 2014

(54) PIM KINASE INHIBITORS AND METHODS OF THEIR USE

(75) Inventors: Matthew Burger, Albany, CA (US);
Mika Lindvall, Oakland, CA (US);
Wooseok Han, San Ramon, CA (US);
Jiong Lan, Moraga, CA (US); Gisele Nishiguchi, Albany, CA (US); Cynthia Shafer, Moraga, CA (US); Cornelia Bellamacina, Castro Valley, CA (US);
Kay Huh, San Mateo, CA (US);
Gordana Atallah, Fremont, CA (US);
Christopher McBride, San Diego, CA (US); William Antonios-McCrea, Jr., Moraga, CA (US); Tatiana Zavorotinskaya, Moraga, CA (US);
Annette Walter, Mill Valley, CA (US);
Pablo Garcia, Oakland, CA (US)

(73) Assignee: Novartis AG, Basel (CH)

( * ) Notice: Subject to any disclaimer, the term of this patent is extended or adjusted under 35 U.S.C. 154(b) by 1005 days.

This patent is subject to a terminal disclaimer.

(21) Appl. No.: 12/449,701

(22) PCT Filed: Mar. 3, 2008

(86) PCT No.: PCT/US2008/055724
§ 371 (c)(1),
(2), (4) Date: Dec. 22, 2009

(87) PCT Pub. No.: WO2008/106692
PCT Pub. Date: Sep. 4, 2008

(65) Prior Publication Data
US 2012/0208815 A1    Aug. 16, 2012

(51) Int. Cl.
*A61K 31/4545* (2006.01)
*C07D 401/14* (2006.01)

(52) U.S. Cl.
USPC ...... 514/318; 514/255.05; 514/275; 544/129; 544/405; 546/193

(58) Field of Classification Search
USPC ............... 514/318, 255.05, 275; 546/193; 544/129, 405
See application file for complete search history.

(56) References Cited

U.S. PATENT DOCUMENTS

| 2002/0010185 | A1 | 1/2002 | Cai et al. | |
|---|---|---|---|---|
| 2006/0004197 | A1 | 1/2006 | Thrash | |
| 2012/0225062 | A1* | 9/2012 | Burger et al. | 424/133.1 |
| 2012/0226062 | A1* | 9/2012 | Bostick et al. | 554/230 |

FOREIGN PATENT DOCUMENTS

| EP | 684241 | 8/1997 |
|---|---|---|
| WO | WO 01/55115 | 8/2001 |
| WO | WO 2002/76986 | 10/2002 |
| WO | WO 03/092686 | 11/2003 |
| WO | WO 2004/069803 | 8/2004 |
| WO | WO 2005/033097 | 4/2005 |
| WO | WO 2005/042488 | 5/2005 |
| WO | WO 2005/056547 | 6/2005 |
| WO | WO 2006/053227 | 5/2006 |
| WO | WO 2006/105081 | 10/2006 |
| WO | WO 2007/019344 | 2/2007 |
| WO | WO 2007/042806 | 4/2007 |
| WO | WO 2007/072999 | 6/2007 |

OTHER PUBLICATIONS

Burger "Preparation of . . . " CA149:332352 (2008).*
Dorwald :side reactions . . . p. ix, 1-12, 40-41 (2005).*
Vandromme, Lucie, "Beneficial Effect of Mukaiyama Reagent on Macrobislactamization Reactions" Synlett 20:3423-3426, 2006.
Derwent Publications 2005-346843 (Takeda Pharmaceutical).
Graham Atwell et al., "Potential Antitumor Agents, 55. 6-Phenylphenanthridine-4-carboxamides: A New Class of DNA-Intercalating Antitumor Agents" *J. Med. Chem.* 31:774-779, 1988.

* cited by examiner

*Primary Examiner* — Celia Chang
(74) *Attorney, Agent, or Firm* — Stephen Johnson; Michael Smith

(57) ABSTRACT

New compounds, compositions and methods of inhibition of kinase activity associated with tumorigenesis in a human or animal subject are provided. In certain embodiments, the compounds and compositions are effective to inhibit the activity of at least one serine/threonine kinase or receptor tyrosine kinase. The new compounds and compositions may be used either alone or in combination with at least one additional agent for the treatment of a serine/threonine kinase- or receptor tyrosine kinase-mediated disorder, such as cancer.

9 Claims, No Drawings

SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: Pim phosphorylation site on Bad
<220> FEATURE:
<221> NAME/KEY: misc_feature
<223> OTHER INFORMATION: BAD peptide

<400> SEQUENCE: 1

Arg Ser Arg His Ser Ser Tyr Pro Ala Gly Thr
1               5                  10

<210> SEQ ID NO 2
<211> LENGTH: 15
<212> TYPE: PRT
<213> ORGANISM: Artificial Sequence
<220> FEATURE:
<223> OTHER INFORMATION: Pim phosphorylation site on Shc
<220> FEATURE:
<221> NAME/KEY: MISC_FEATURE
<222> LOCATION: (15)..(15)
<223> OTHER INFORMATION: biotinylated

<400> SEQUENCE: 2

Leu Asn Gln Val Asn Val Tyr Ser Pro Asp Asp Phe Leu Gly Gly
1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Pim phosphorylation site on VEGF
<220> FEATURE:
<221> NAME/KEY: MISC_FEATURE
<222> LOCATION: (15)..(15)
<223> OTHER INFORMATION: Biotinylated

<400> SEQUENCE: 3

Ile Pro Leu Val Ile Tyr Asp Lys Gly Asp Gln Gly Gly Gly Gly
1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: substrate for PKC assay

<400> SEQUENCE: 4

Glu Arg Met Arg Pro Arg Lys Arg Gln Gly Ser Val Arg Arg Arg Val
1               5                  10                  15

PIM KINASE INHIBITORS AND METHODS OF THEIR USE

FIELD OF THE INVENTION

The present invention relates to new compounds and their tautomers and stereoisomers, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND

Infection with the Maloney retrovirus and genome integration in the host cell genome results in development of lymphomas in mice. Provirus Integration of Maloney Kinase (PIM-Kinase) was identified as one of the frequent proto-oncogenes capable of being transcriptionally activated by this retrovirus integration event (Cuypers H T et al., "Murine leukemia virus-induced T-cell lymphomagenesis: integration of proviruses in a distinct chromosomal region," *Cell* 37(1): 141-50 (1984); Selten G, et al., "Proviral activation of the putative oncogene Pim-1 in MuLV induced T-cell lymphomas" *EMBO J.* 4(7):1793-8 (1985)), thus establishing a correlation between over-expression of this kinase and its oncogenic potential. Sequence homology analysis demonstrated that there are 3 highly homologous Pim-Kinases (Pim 1, 2 & 3), Pim1 being the proto-oncogene originally identified by retrovirus integration. Furthermore, transgenic mice over-expressing Pim1 or Pim2 show increased incidence of T-cell lymphomas (Breuer M et al., "Very high frequency of lymphoma induction by a chemical carcinogen in pim-1 transgenic mice" *Nature* 340(6228):61-3 (1989)), while over-expression in conjunction with c-myc is associated with incidence of B-cell lymphomas (Verbeek S et al., "Mice bearing the E mu-myc and E mu-pim-1 transgenes develop pre-B-cell leukemia prenatally" *Mol Cell Biol* 11(2):1176-9 (1991)). Thus, these animal models establish a strong correlation between Pim over-expression and oncogenesis in hematopoietic malignancies. In addition to these animal models, Pim over-expression has been reported in many other human malignancies. Pim1, 2 & 3 over-expression is frequently observed in many hematopoietic malignancies (Amson R et al., "The human protooncogene product p33pim is expressed during fetal hematopoiesis and in diverse leukemias," *PNAS USA* 86(22):8857-61 (1989); Cohen A M et al., "Increased expression of the hPim-2 gene in human chronic lymphocytic leukemia and non-Hodgkin lymphoma," *Leuk Lymph* 45(5):951-5 (2004), Huttmann A et al., "Gene expression signatures separate B-cell chronic lymphocytic leukaemia prognostic subgroups defined by ZAP-70 and CD38 expression status," *Leukemia* 20:1774-1782 (2006)) and in prostate cancer (Dhanasekaran S M, et al., "Delineation of prognostic biomarkers in prostate cancer," *Nature* 412(6849): 822-6 (2001); Cibull T L, et al., "Overexpression of Pim-1 during progression of prostatic adenocarcinoma," *J Clin Pathol* 59(3):285-8 (2006)), while over-expression of Pim3 is frequently observed in hepatocellular carcinoma (Fujii C, et al., "Aberrant expression of serine/threonine kinase Pim-3 in hepatocellular carcinoma development and its role in the proliferation of human hepatoma cell lines," *Int J Cancer* 114:209-218 (2005)) and pancreatic cancer (Li Y Y et al., "Pim-3, a proto-oncogene with serine/threonine kinase activity, is aberrantly expressed in human pancreatic cancer and phosphorylates bad to block bad-mediated apoptosis in human pancreatic cancer cell lines," *Cancer Res* 66(13):6741-7 (2006)).

Pim1, 2 & 3 are Serine/Threonine kinases normally function in survival and proliferation of hematopoietic cells in response to growth factors and cytokines. Cytokines signaling through the Jak/Stat pathway leads to activation of transcription of the Pim genes and synthesis of the proteins. No further post-translational modifications are required for the Kinase Pim activity. Thus, signaling down stream is primarily controlled at the transcriptional/translational and protein turnover level. Substrates for Pim kinases include regulators of apoptosis such as the Bcl-2 family member BAD (Aho T et al., "Pim-1 kinase promotes inactivation of the pro-apoptotic Bad protein by phosphorylating it on the Ser112 gatekeeper site: *FEBS Letters* 571: 43-49 (2004)), cell cycle regulators such as $p21^{WFA1/CIP1}$ (Wang Z, et al., "Phosphorylation of the cell cycle inhibitor p21Cip1/WAF1 by Pim-1 kinase," *Biochim Biophys Acta* 1593:45-55 (2002)), CDC25A (1999), C-TAK (Bachmann M et al., "The Oncogenic Serine/Threonine Kinase Pim-1 Phosphorylates and Inhibits the Activity of Cdc25C-associated Kinase 1 (C-TAK1). A novel role for Pim-1 at the G2/M cell cycle checkpoint," *J Biol Chem* 179: 48319-48328 (2004)) and NuMA (Bhattacharya N, et al., "Pim-1 associates with protein complexes necessary for mitosis," *Chromosoma* 111(2):80-95 (2002)) and the protein synthesis regulator 4EBP1 (Hammerman P S et al., "Pim and Akt oncogenes are independent regulators of hematopoietic cell growth and survival," *Blood* 105(11):4477-83 (2005)). The effects of Pim(s) in these regulators are consistent with a role in protection from apoptosis and promotion of cell proliferation and growth. Thus, over-expression of Pim(s) in cancer is thought to play a role in promoting survival and proliferation of cancer cells and, therefore, their inhibitions should be an effective way of treating cancers on which they are over-expressed. In fact several reports indicate that knocking down expression of Pim(s) with siRNA results in inhibition of proliferation and cell death (Dai J M, et al., "Antisense oligodeoxynucleotides targeting the serine/threonine kinase Pim-2 inhibited proliferation of DU-145 cells," *Acta Pharmacol Sin* 26(3):364-8 (2005); Fujii et al. 2005; Li et al. 2006). Furthermore, mutational activation of several well know oncogenes in hematopoietic malignancies are thought exert its effects at least in part through Pim(s). For example, targeted down regulation of pim expression impairs survival of hematopoietic cells transformed by Flt3 and BCR/ABL (Adam et al. 2006). Thus, inhibitors to Pim1, 2 & 3 would be useful in the treatment of these malignancies. In addition to a potential role in cancer treatment and myeloproliferative diseases, such inhibitor could be useful to control expansion of immune cells in other pathologic condition such as autoimmune diseases, allergic reactions and in organ transplantation rejection syndromes. This notion is supported by the findings that differentiation of Th1 Helper T-cells by IL-12 and IFN-α results in induction of expression of both Pim1&2 (Aho T et al., "Expression of human Pim family genes is selectively up-regulated by cytokines promoting T helper type 1, but not T helper type 2, cell differentiation," *Immunology* 116: 82-88 (2005)). Moreover, Pim(s) expression is inhibited in both cell types by the immunosuppressive TGF-β (Aho et al. 2005). These results suggest that Pim kinases are involved in the early differentiation process of Helper T-cells, which coordinate the immunological responses in autoimmune diseases, allergic reaction and tissue transplant rejection.

In addition to PIM-Kinase, several other kinases have been shown to be directly involved in cancer, such as Flt3, KDR and PKCε. For example, several types of activating mutations in Flt3 are found in 20-30% of patients with Acute Myeloid Leukemia (AML). These activating mutations are thought to be the most relevant transformation event on these patients and currently several Flt3 inhibitors are being tested for the treatment on these patients in clinical trials (for a recent review see Tichenbrock L et al., "Emerging Flt3 kinase inhibitors in the treatment of leukaemia," *Expert Opin Emerg Drugs* 11:153-165 (2006)). KDR is one of the receptors for VEGF that plays a critical role in tumor angiogenesis and it's the target for the clinically validated bevacizumab drug (for a recent review see Ranieri G et al., "Vascular endothelial growth factor (VEGF) as a target of bevacizumab in cancer: from the biology to the clinic," *Curr Med Chem* 13: 1845-1857 (2006)). Finally, over-expression in NIH3T3 cells of PKCε has been shown to transform cell in vitro and promote tumor formation in vivo (Perletti et al. *Oncogene* 12: 847 (1996); Mischak et al., J Biol Chem 268: 6090 (1993)). In addition, over-expression of PKCε in the LNCaP cell line results in its transformation to an androgen-independent tumor growth in nude nice (Wu et al., *Cancer Research* 62: 2423 (2002)). Furthermore, over-expression of PKCε in transgenic mouse epithelium accelerates the development of highly malignant and rapidly metastasizing squamous cell carcinomas (Jansen et al., *Cancer Research* 61: 808 (2001)). Finally, clinically if has been observed that high PKCε expression in human tumors is associated with poor disease-free and poor overall survival (Pan et al., *Cancer Research* 65: 8366 (2005)). Thus, the compounds described here could be useful in treating cancer by inhibiting these well validated targets of cancer drugs.

A continuing need exists for compounds that inhibit the proliferation of capillaries, inhibit the growth of tumors, treat cancer, modulate cell cycle arrest, and/or inhibit molecules such as Pim1, Pim2, Pim3, Flt3, KDR and PKCε, and pharmaceutical formulations and medicaments that contain such compounds. A need also exists for methods of administering such compounds, pharmaceutical formulations, and medicaments to patients or subjects in need thereof.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

New compounds, their tautomers and stereoisomers, and pharmaceutically acceptable salts thereof or esters having a solubility enhancing moieties or prodrugs thereof are provided of the formula (I):

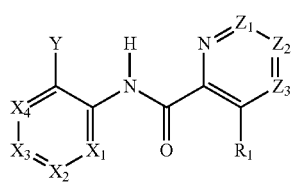

wherein, $X_1$, $X_2$, $X_3$ and $X_4$ are independently selected from $CR_2$ and N; provided that not more than two of $X_1$, $X_2$, $X_3$ and $X_4$ can be N;

Y is substituted or unsubstituted amino, alkoxy, cycloalkyl, heterocycloalkyl, aryl or heteroaryl;

$Z_1$, $Z_2$ and $Z_3$ are independently selected from $CR_2$ and N; provided that not more than one of $Z_1$, $Z_2$ and $Z_3$ can be N;

$R_1$ is selected from the group consisting of hydrogen, halo, allyl, cycloalkyl, —CN, —$NO_2$, and —$NHR_3$;

each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;

$R_3$ is selected from the group consisting of hydrogen, —CO—$R_4$ and substituted or unsubstituted alkyl, cycloalkyl, heterocyclyl, aryl and heteroaryl; and $R_4$ is selected from the group consisting of alkyl, substituted alkyl, alkoxy, substituted alkoxy, amino, substituted amino, and alkylamino.

In other embodiments, new compounds are provided of the formula (II):

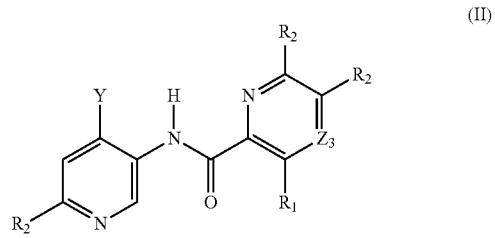

wherein,

Y is substituted or unsubstituted amino, cycloalkyl, heterocycloalkyl, aryl or heteroaryl;

$Z_3$ is selected from $CR_2$ and N;

$R_1$ is selected from the group consisting of hydrogen, halo, alkyl, cycloalkyl, —CN, —$NO_2$, and —$NHR_3$;

each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;

$R_3$ is selected from the group consisting of hydrogen, —CO—$R_4$ and substituted or unsubstituted alkyl, cycloalkyl, heterocyclyl, aryl and heteroaryl; and $R_4$ is selected from the group consisting of alkyl, substituted alkyl, alkoxy, substituted alkoxy, amino, substituted amino, and alkylamino.

In other embodiments, new compounds are provided of the formula (III):

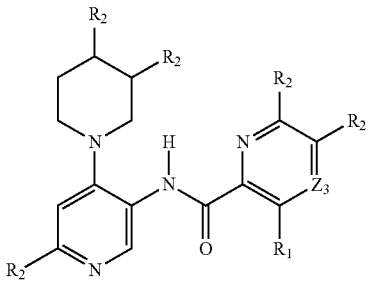

wherein, $Z_3$ is selected from $CR_2$ and N;

$R_1$ is selected from the group consisting of hydrogen, halo, alkyl, cycloalkyl, —CN, —$NO_2$, and —$NHR_3$;

each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;

$R_3$ is selected from the group consisting of hydrogen, —CO—$R_4$ and substituted or unsubstituted alkyl, cycloalkyl, heterocyclyl, aryl and heteroaryl; and $R_4$ is selected from the group consisting of alkyl, substituted alkyl, alkoxy, substituted alkoxy, amino, substituted amino, and alkylamino.

Also disclosed are compounds of the following formula (IV):

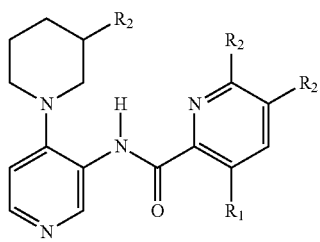

wherein, $R_1$ is selected from the group consisting of hydrogen, halo, alkyl, cycloalkyl, —CN, —$NO_2$, and —$NHR_3$;

each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;

$R_3$ is selected from the group consisting of hydrogen, —CO—$R_4$ and substituted or unsubstituted alkyl, cycloalkyl, heterocyclyl, aryl and heteroaryl; and $R_4$ is selected from the group consisting of alkyl, substituted alkyl, alkoxy, substituted alkoxy, amino, substituted amino, and alkylamino.

In other embodiments, new compounds are provided of formulas (I)-(IV), wherein Y is substituted or unsubstituted piperidinyl or piperazinyl. In other embodiments, new compounds are provided of formulas (I)-(IV), wherein $R_1$ is hydrogen. In other embodiments, new compounds are provided of formulas (I)-(IV), wherein $R_2$ is independently selected from the group consisting of hydrogen, halo, hydroxyl, amino, nitro, cyano, $SO_3H$ and substituted or unsubstituted alkyl, aminoalkyl and phenyl.

In other aspects, the present invention provides methods for treating PIM related disorders in a human or animal subject in need of such treatment comprising administering to said subject an amount of a compound of formula (I), (II), (III) or (IV) effective to PIM activity in the subject.

In other aspects, the present invention provides methods for treating PIM related disorders in a human or animal subject in need of such treatment comprising administering to said subject an amount of a compound of formula (I), (II), (III) or (IV) effective to reduce or prevent tumor growth in the subject.

In yet other aspects, the present invention provides methods for treating PIM related disorders in a human or animal subject in need of such treatment comprising administering to said subject an amount of a compound of formula (I), (II), (III) or (IV) effective to reduce or prevent tumor growth in the subject in combination with at least one additional agent for the treatment of cancer.

In yet other aspects, the present invention provides therapeutic compositions comprising at least one compound of formula (I), (II), (III) or (IV) in combination with one or more additional agents for the treatment of cancer, as are commonly employed in cancer therapy.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

In another aspect, the present invention relates to methods of inhibiting at least one serine/threonine kinase in the Jak/Stat signaling pathway in a subject, or treating a biological condition mediated by a serine/threonine kinase in the Jak/Stat signaling pathway in a subject, comprising administering a therapeutic composition comprising at least one compound of formula (I), (II), (III) or (IV) effective to inhibit the Jak/Stat signaling pathway in the subject. The therapeutic compositions are useful for treating patients with a need for such inhibitors (e.g., those suffering from cancer mediated by abnormal Jak/Stat signaling).

In another aspect, the present invention relates to methods of inhibiting at least one serine/threonine kinase receptor selected from the group consisting of Pim1, Pim2 Pim3, Flt3, KDR and PKCε in a subject, or treating a biological condition mediated by at least one of Pim1, Pim2 Pim3, Flt3, KDR and PKCε comprising administering a therapeutic composition comprising at least one compound of formula (I), (II), (III) or (IV) effective to inhibit the kinase receptor in the subject. The therapeutic compounds are useful for treating patients with a need for such inhibitors (e.g., those suffering from cancer mediated by abnormal serine/threonine kinase receptor signaling).

The invention further provides compositions, methods of use, and methods of manufacture as described in the detailed description of the invention.

DETAILED DESCRIPTION

In accordance with one aspect of the present invention, compounds, their tautomers and stereoisomers, and pharmaceutically acceptable salts thereof or esters having a solubility enhancing moieties or prodrugs thereof are provided of the formula (I):

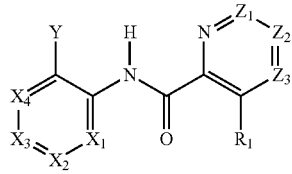

(I)

wherein,
$X_1$, $X_2$, $X_3$ and $X_4$ are independently selected from $CR_2$ and N; provided that not more than two of $X_1$, $X_2$, $X_3$ and $X_4$ can be N;
Y is substituted or unsubstituted amino, alkoxy, cycloalkyl, heterocycloalkyl, aryl or heteroaryl;
$Z_1$, $Z_2$ and $Z_3$ are independently selected from $CR_2$ and N; provided that not more than one of $Z_1$, $Z_2$ and $Z_3$ can be N;
$R_1$ is selected from the group consisting of hydrogen, halo, alkyl, cycloalkyl, —CN, —$NO_2$, and —$NHR_3$;
each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;
$R_3$ is selected from the group consisting of hydrogen, —CO—$R_4$ and substituted or unsubstituted alkyl, cycloalkyl, heterocyclyl, aryl and heteroaryl; and
$R_4$ is selected from the group consisting of alkyl, substituted alkyl, alkoxy, substituted alkoxy, amino, substituted amino, and alkylamino.

In other embodiments, new compounds are provided of the formula (II):

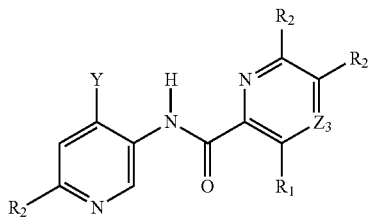

(II)

wherein,
Y is substituted or unsubstituted amino, cycloalkyl, heterocycloalkyl, aryl or heteroaryl;

$Z_3$ is selected from $CR_2$ and N;
$R_1$ is selected from the group consisting of hydrogen, halo, alkyl, cycloalkyl, —CN, —$NO_2$, and —$NHR_3$;
each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;
$R_3$ is selected from the group consisting of hydrogen, —CO—$R_4$ and substituted or unsubstituted alkyl, cycloalkyl, heterocyclyl, aryl and heteroaryl; and
$R_4$ is selected from the group consisting of alkyl, substituted alkyl, alkoxy, substituted alkoxy, amino, substituted amino, and alkylamino.

In other embodiments, new compounds are provided of the formula (III):

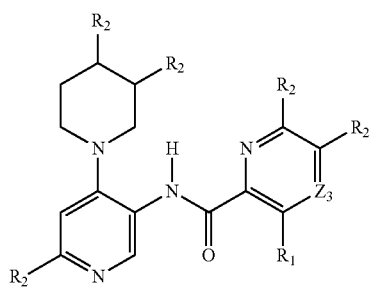

(III)

wherein,
$Z_3$ is selected from $CR_2$ and N;
$R_1$ is selected from the group consisting of hydrogen, halo, alkyl, cycloalkyl, —CN, —$NO_2$, and —$NHR_3$;
each $R_2$ is independently selected from the group consisting of hydrogen, halo, hydroxyl, nitro, cyano, $SO_3H$ and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;
$R_3$ is selected from the group consisting of hydrogen, —CO—$R_4$ and substituted or unsubstituted alkyl, cycloalkyl, heterocyclyl, aryl and heteroaryl; and
$R_4$ is selected from the group consisting of alkyl, substituted alkyl, alkoxy, substituted alkoxy, amino, substituted amino, and alkylamino.

Also disclosed are compounds of the following formula (IV):

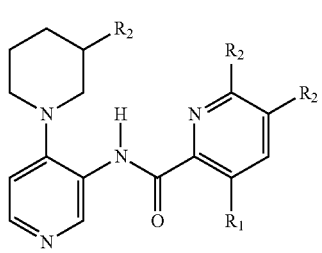

wherein,

R₁ is selected from the group consisting of hydrogen, halo, alkyl, cycloalkyl, —CN, —NO₂, and —NHR₃;

each R₂ is independently selected from the group consisting of hydrogen, halo, hydroxyl, nitro, cyano, SO₃H and substituted or unsubstituted alkyl, alkenyl, alkynyl, alkoxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy;

R₃ is selected from the group consisting of hydrogen, —CO—R₄ and substituted or unsubstituted alkyl, cycloalkyl, heterocyclyl, aryl and heteroaryl; and R₄ is selected from the group consisting of alkyl, substituted alkyl, alkoxy, substituted alkoxy, amino, substituted amino, and alkylamino.

In other embodiments, new compounds are provided of formulas (I)-(IV), wherein Y is substituted or unsubstituted piperidinyl or piperazinyl. In some embodiments, new compounds are provided of formulas (I)-(IV), wherein X₁, X₃, and X₄ are —CH₂— and X₂ is —NH—. In some embodiments, new compounds are provided of formulas (I)-(IV), wherein X₅ is —CH₂—. In some embodiments, new compounds are provided of formulas (I)-(IV), wherein X₆ is —CH(NH₂)—. In other embodiments, new compounds are provided of formulas (I)-(IV), wherein R₁ is hydrogen. In other embodiments, new compounds are provided of formulas (I)-(IV), wherein R₂ is independently selected from the group consisting of hydrogen, halo, hydroxyl, amino, nitro, cyano, SO₃H and substituted or unsubstituted alkyl, aminoalkyl and phenyl.

In other aspects, the present invention provides methods for treating PIM related disorders in a human or animal subject in need of such treatment comprising administering to said subject an amount of a compound of formula (I), (II), (III) or (IV) effective to PIM activity in the subject.

In other aspects, the present invention provides methods for treating PIM related disorders in a human or animal subject in need of such treatment comprising administering to said subject an amount of a compound of formula (I), (II), (III) or (IV) effective to reduce or prevent tumor growth in the subject.

In yet other aspects, the present invention provides methods for treating PIM related disorders in a human or animal subject in need of such treatment comprising administering to said subject an amount of a compound of formula (I), (II), (III) or (IV) effective to reduce or prevent tumor growth in the subject in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-α, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formula (I), (II), (III) or (IV) are known to those skilled in the art.

In preferred embodiments, anticancer agents to be used in combination with compounds of the present invention comprise agents that induce or stimulate apoptosis. Agents that induce apoptosis include, but are not limited to, radiation (e.g., W); kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol]; cellular signaling molecules; ceramides and cytokines; and staurosprine, and the like.

In yet other aspects, the present invention provides therapeutic compositions comprising at least one compound of formula (I), (II), (III) or (IV) in combination with a pharmaceutically acceptable carrier, and optionally with one or more additional agents for the treatment of cancer, as are commonly employed in cancer therapy.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

In another aspect, the present invention relates to methods of inhibiting at least one serine/threonine kinase in the Jak/Stat signaling pathway in a subject, or treating a biological condition mediated by a serine/threonine kinase in the Jak/Stat signaling pathway in a subject, comprising administering a therapeutic composition comprising at least one compound of formula (I), (II), (III) or (IV) effective to inhibit the Jak/Stat signaling pathway in the subject. The therapeutic compositions are useful for treating patients with a need for such inhibitors (e.g., those suffering from cancer mediated by abnormal Jak/Stat signaling).

In another aspect, the present invention relates to methods of inhibiting at least one serine/threonine kinase receptor selected from the group consisting of Pim1, Pim2 Pim3, Flt3, KDR and PKCε in a subject, or treating a biological condition mediated by at least one of Pim1, Pim2 Pim3, Flt3, KDR and PKCε comprising administering a therapeutic composition comprising at least one compound of formula (I), (II), (III) or (IV) effective to inhibit the kinase receptor in the subject. The therapeutic compounds are useful for treating patients with a need for such inhibitors (e.g., those suffering from cancer mediated by abnormal serine/threonine kinase receptor signaling).

In another aspect, the present invention relates to methods of inhibiting the activity of at least one kinase selected from the group consisting of Pim1, Pim2 Pim3, Flt3, KDR and PKCε in a subject, or treating a biological condition mediated by at least one of Pim1, Pim2 Pim3, Flt3, KDR and PKCε, in a human or animal subject in need of such treatment, comprising administering to the subject at least one compound of formula (I), (II), (III) or (IV) in an amount effective to inhibit the kinase in the subject. The therapeutic compounds are useful for treating patients with a need for such inhibitors (e.g., those suffering from cancer mediated by abnormal serine/threonine kinase receptor signaling).

In other aspects, the present invention provides methods of manufacture of compounds of formula (I), (II), (III) or (N) as described herein.

The invention further provides compositions, methods of use, and methods of manufacture as described in the detailed description of the invention.

"PIM inhibitor" is used herein to refer to a compound that exhibits an $IC_{50}$ with respect to PIM Kinase activity of no more than about 100 μM and more typically not more than about 50 μM, as measured in the PIM depletion assays described hereinbelow.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH₃)₂, —CH(CH₃)(CH₂CH₃), —CH(CH₂CH₃)₂, —C(CH₃)₃, —(CH₂CH₃)₃, —CH₂CH(CH₃)₂, —CH₂CH(CH₂CH₃)₂, —CH₂CH(CH₃)(CH₂CH₃), —CH₂C(CH₂CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂—CH(CH₃)₂, —CH(CH₃)CH(CH₃)CH(CH₃)₂, —CH(CH₂CH₃)CH(CH₃) CH(CH₃)(CH₂CH₃), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

As used herein "loweralkyl" includes both substituted or unsubstituted straight or branched chain alkyl groups having from 1 to 6 carbon atoms. Representative loweralkyl groups include, for example, methyl, ethyl, propyl, isopropyl, n-butyl, tert-butyl, neopentyl, trifluoromethyl, pentafluoroethyl and the like. Loweralkyl groups may be substituted, such as with halo, hydroxy, amino, nitro and/or cyano groups, and the like. Representative of halo-substituted and hydroxy-substituted loweralkyl include chloromethyl, trichloromethyl, chloroethyl, hydroxyethyl, and the like. Other suitable substituted loweralkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

"Loweralkoxy" as used herein refers to RO— wherein R is loweralkyl. Representative examples of loweralkoxy groups include methoxy, ethoxy, t-butoxy, trifluoromethoxy and the like.

As used herein, the term "halogen" or "halo" refers to chloro, bromo, fluoro and iodo groups. "Haloalkyl" refers to an alkyl radical substituted with one or more halogen atoms. The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Amino" refers herein to the group —NH₂. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term "alkoxyalkyl" refers to the group -alk₁-O-alk₂ where alk₁ is alkyl or alkenyl, and alk₂ is alkyl or alkenyl. The term "loweralkoxyalkyl" refers to an alkoxyalkyl where alk₁ is loweralkyl or loweralkenyl, and alk₂ is loweralkyl or loweralkenyl. The term "aryloxyalkyl" refers to the group -alkyl-O-aryl. The term "aralkoxyalkyl" refers to the group -alkylenyl-O-aralkyl, where aralkyl is a loweraralkyl.

The term "aminocarbonyl" refers herein to the group —C(O)—NH₂. "Substituted aminocarbonyl" refers herein to the group —C(O)—NRR' where R is loweralkyl and R' is hydrogen or a loweralkyl. In some embodiments, R and R', together with the N atom attached to them may be taken together to form a "heterocycloalkylcarbonyl" group. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)₂—NH₂. "Substituted aminosulfonyl" refers herein to the group —S(O)₂—NRR' where R is loweralkyl and R' is hydrogen or a loweralkyl. The term "aralkylaminosulfonlyaryl" refers herein to the group -aryl-S(O)₂—NH-aralkyl, where the aralkyl is loweraralkyl.

"Carbonyl" refers to the divalent group —C(O)—. "Carboxy" refers to —C(=O)—OH. "Alkoxycarbonyl" refers to ester —C(=O)—OR wherein R is alkyl. "Loweralkoxycarbonyl" refers to ester —C(=O)—OR wherein R is loweralkyl. "Cycloalkyloxycarbonyl" refers to —C(=O)—OR wherein R is cycloalkyl. "Aryloxycarbonyl" refers to —C(=O)—OR wherein R is aryl. "Heterocyclyloxycarbonyl" refers to —C(=O)—OR wherein R is heterocyclyl.

The term "aralkoxycarbonyl" refers herein to the group —C(O)—O-aralkyl, where the aralkyl is loweraralkyl.

The term "sulfonyl" refers herein to the group —SO₂—. The term "sulfanyl" refers herein to the group —S—. "Loweralkylsulfonyl" refers to a substituted sulfonyl of the structure —SO₂R— in which R is loweralkyl. "Loweralkylsulfanyl" refers to a substituted sulfanyl of the structure —SR— in which R is loweralkyl. Alkylsulfonyl and alkylsulfanyl groups employed in compounds of the present invention are typically loweralkylsulfonyl or loweralkylsulfanyl groups having from 1 to 6 carbon atoms in its backbone structure. Thus, typical alkylsulfonyl and loweralkylsulfanyl groups employed in compounds of the present invention include, for example, methylsulfonyl and methylsulfanyl (i.e., where R is methyl), ethylsulfonyl and ethylsulfanyl (i.e., where R is ethyl), propylsulfonyl and propylsulfanyl (i.e., where R is propyl), and the like. The term "arylsulfonyl" refers herein to the group —SO₂-aryl. The term "aralkylsulfonyl" refers herein to the group —SO₂-aralkyl, in which the aralkyl is loweraralkyl. The term "sulfonamido" refers herein to —SO₂NH₂.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—R, where R is a straight or branched chain loweralkyl, cycloalkyl, or aryl or loweraralkyl.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperidinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclic moieties can be unsubstituted or monosubstituted or disubstituted with various substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl.

The heterocyclic groups may be attached at various positions as will be apparent to those having skill in the organic and medicinal chemistry arts in conjunction with the disclosure herein.

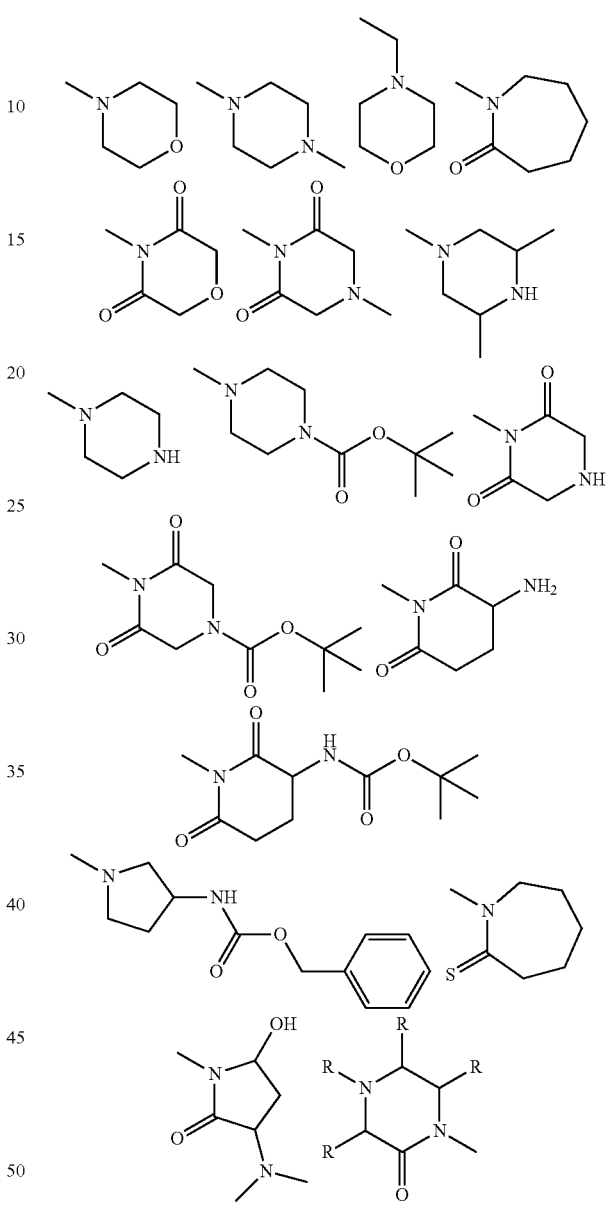

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

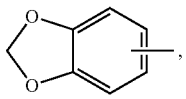

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

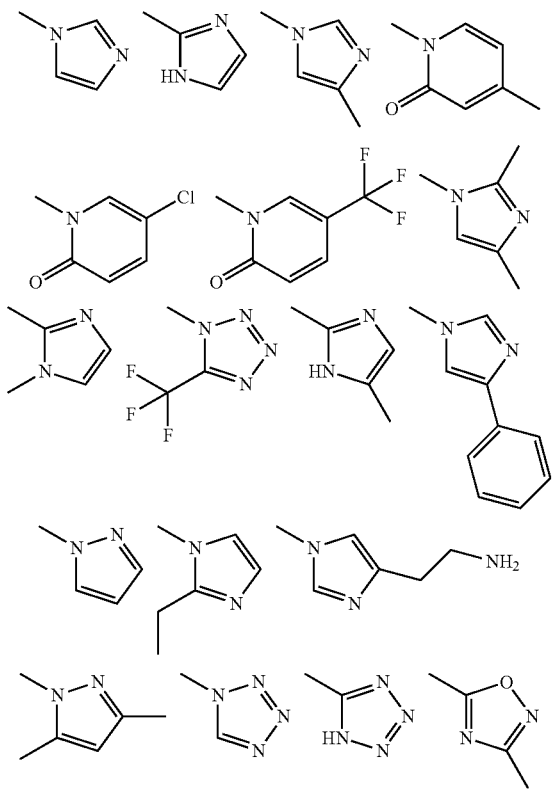

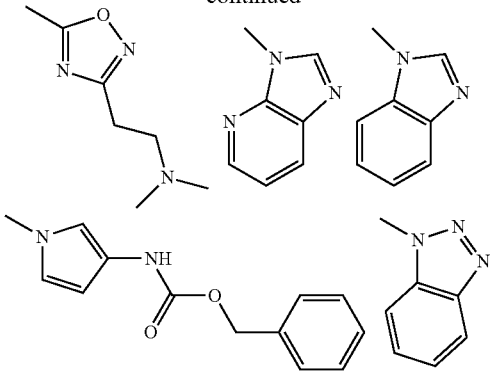

Representative heteroaryls include, for example, imidazolyl, pyridyl, piperazinyl, azetidinyl, thiazolyl, triazolyl benzimidazolyl, benzothiazolyl, and benzoxazolyl.

"Optionally substituted" or "substituted" refers to the replacement of one or more hydrogen atoms with a monovalent or divalent radical. Suitable substitution groups include, for example, hydroxy, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkylamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxy, loweralkyl, loweralkoxy, aminocarbonyl, —SR, thioamido, —SO₃H, —SO₂R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, including the compounds of compounds of formulas (I), (II), (III) or (IV) or their stereoisomers, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

The compounds of the invention, including the compounds of formulas (I), (II), (III) or (IV) or their tautomers, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or alkaline earth metal salts of the compounds of Formulas (I), (II), (III) or (IV). These salts can be prepared in situ during the final isolation and purification of the compounds of Formulas (I), (II), (III) or (IV), or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the invention, including the compounds of formulas (I), (II), (III) or (IV) or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of formulas (I), (II), (III) or (IV) or their tautomers, prodrugs and stereoisomers, as well as the pharmaceutically acceptable salts, esters and prodrugs of any of them, are included within the invention.

The term "cancer" refers to cancer diseases that can be beneficially treated by the inhibition of Pim kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma and erythroleukemia), adenomas (e.g., villous colon adenoma) and sarcomas (e.g., osteosarcoma).

In other aspects, the present invention relates to the processes for preparing the compounds of Formulas (I), (II) f(III) or IV, and to the synthetic intermediates useful in such processes, as described in detail below.

Synthetic Methods

The compounds of the invention can be obtained through procedures known to the skilled in the art. For example, as shown in Scheme 1,4-chloro, 3-nitro pyridine can be reacted with a nucleophile yielding after nitro reduction a 4-substituted 3-amino pyridine I. Alternatively, 3-bromo 4-nitro pyridine N-oxide can be reacted with a nucleophile, yielding after nitro and N-oxide reduction a 3-substituted 4-amino pyridine II. The substituted amino pyridines I and II can be acylated with carboxylic acids with the aid of coupling agents, or with acid halides or acid anhydrides yielding 3,4 disubstituted pyridines III and IV. Compounds of the invention containing 3,4 disubstituted phenyls can be obtained using chemistry analogous to that in Scheme 1 when 3 halo 4 nitro benzenes are the starting materials.

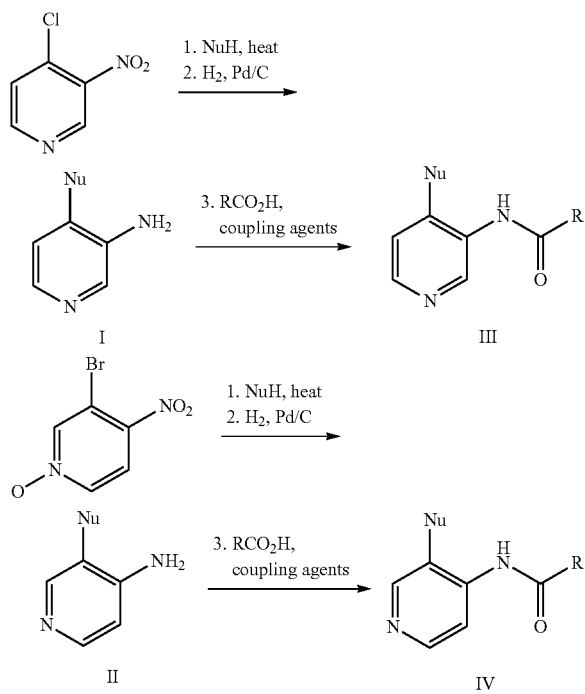

Alternatively 3,4 disubstituted pyridines, as depicted in Scheme 2, can be obtained by reacting halo nitro pyridines with boronic acids under Suzuki conditions, followed by nitro or nitro and N-oxide reduction yielding amino substituted pyridines V and VII. Subsequent amine acylation yields 3,4-disubstituted pyridines VI and VIII. Compounds of the invention containing 3,4-disubstituted phenyls can be obtained using chemistry analogous to that in Scheme 2 when 3-halo, 4-nitro benzenes are the starting materials.

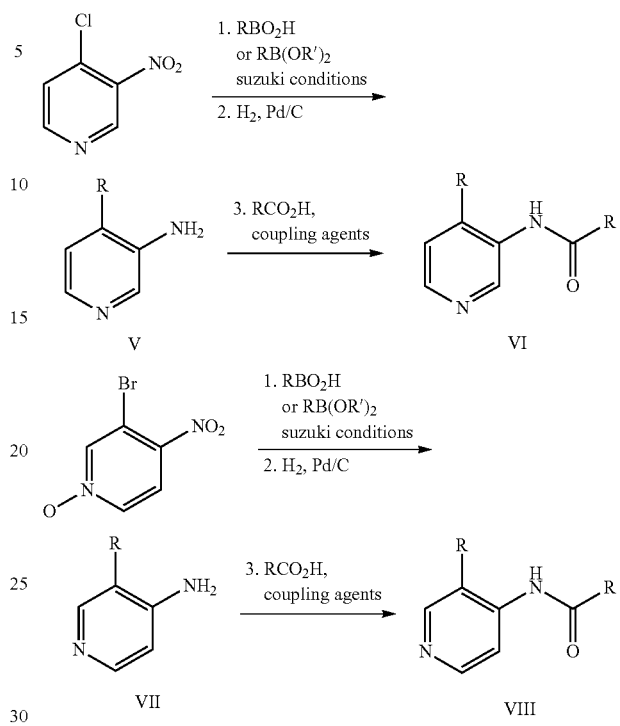

In an alternative manner, 3,4-disubstituted pyridines can be obtained as depicted in Scheme 3. Formation of the bis-anion of N-Boc-3-aminopyridine or N-pivaloyl-3-aminopyridine and reaction with an electrophile yields 4-substituted, 3-N-protected amino pyridine IX. Acidic removal of the Boc or Piv protecting group and subsequent acylation yields the 3,4-substituted pyridine X. Compounds of the invention containing 3,4-disubstituted phenyls can be obtained using chemistry analogous to that in Scheme 3 when suitably protected anilines are the starting materials.

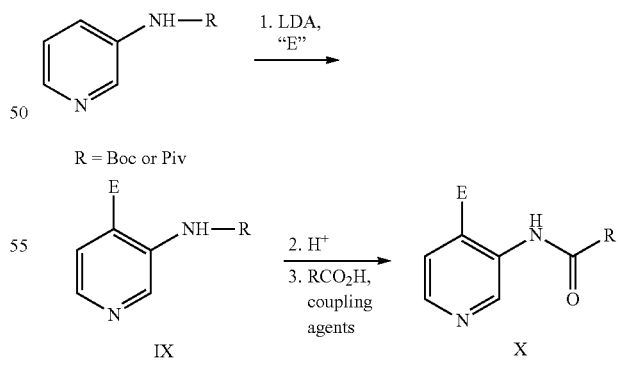

Compounds of the invention containing 5-substituted, 4-aminoacyl pyrimidones such as XII and XIII can be obtained as depicted in Scheme 4. Nucleophilic substitution or Suzuki type coupling of 5-bromocytosine followed by N-acylation yields the 5-substituted, 4-aminoacyl pyrimidones.

Scheme 4.

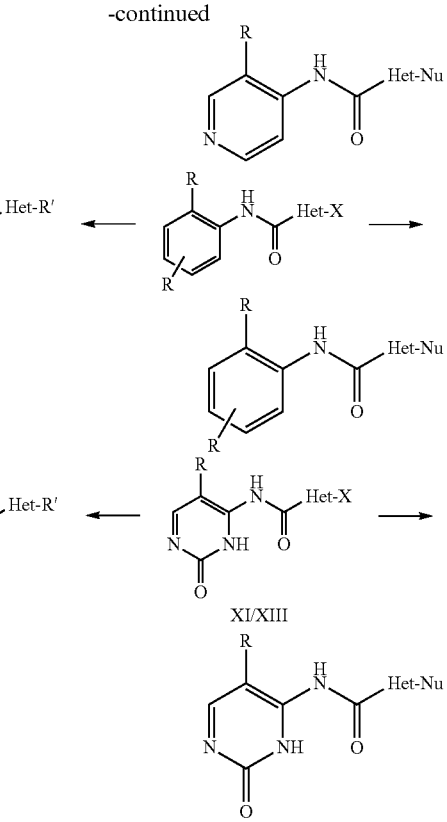

When the amide portion of substituted pyridines, benzenes or pyrimidones contains a haloheteroaryl group, the substituted pyridines, benzenes or pyrimidones can be modified as depicted in Scheme 5. Direct carbon linked groups (R') can be attached to the heteroaryl group using Suzuki, Neghishi, Grignard or other organometallic methodologies. Alternatively nitrogen, oxygen, sulfur and carbon nucleophiles can be attached to the heteroaryl group utilizing standard methodologies including SnAr or Buchwald/Hartwig conditions.

Scheme 5.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Pim activity by any of the assays described herein, by other Pim kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.Y., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Estrogen receptor modulators are compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydra-zone, and SH646.

Androgen receptor modulators are compounds which interfere with or inhibit the binding of androgens to an androgen receptor. Representative examples of androgen receptor modulators include finasteride and other 5α-reductase inhibitors, nilutamide, flutamide, bicalutamide, liarozole, and abiraterone acetate. Retinoid receptor modulators are compounds which interfere or inhibit the binding of retinoids to a retinoid receptor. Examples of retinoid receptor modulators include bexarotene, tretinoin, 13-cis-retinoic acid, 9-cis-retinoic acid, α-difluoromethylornithine, LX23-7553, trans-N-(4'-hydroxyphenyl) retinamide, and N4-carboxyphenyl retinamide.

Cytotoxic and/or cytostatic agents are compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarmino-mycin, annamycin, galarubicin, elinafide, MEN10755, and 4-demethoxy-3-deamino-3-aziridinyl-4-methylsulphonyl-daunorubicin (see WO 00/50032). A representative example of a hypoxia activatable compound is tirapazamine. Proteasome inhibitors include, but are not limited to, lactacystin and bortezomib. Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydro-vinblastine, N,N-dimethyl-L-valyl-L-valyl-N-methyl-L-valyl-L-prolyl-L-proline-t-butyl-amide, TDX258, the epothilones (see for example U.S. Pat. Nos. 6,284,781 and 6,288,237) and BMS188797. Representative examples of topoisomerase inhibitors include topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b)]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)-ethyl]-N-methylamino]ethyl]-5-[4-hydroOxy-3,5-dimethoxyphenyl]-5,5a,6,8,8a,9-hexa-hydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo-[g]isoquinoline-5,10-dione, 5-(3-aminopropylamino)-7,10-dihydroxy-2-(2-hydroxyethyl-aminomethyl)-6H-pyrazolo[4,5,1'-de]acridin-6-one, N-[1-[2 (diethylamino)ethylamino]-7-methoxy-9-oxo-9H-thioxanthen-4-ylmethyl]formamide, N-(2-(dimethylamino) ethyl)-acridine-4-carboxamide, 6-[[2-(dimethylamino)ethyl] amino]-3-hydroxy-7H-indeno[2,1-c]quinolin-7-one, and dimesna. Examples of inhibitors of mitotic kinesins, such as the human mitotic kinesin KSP, are described in PCT Publications WO 01/30768 and WO 01/98278, WO 03/050,064 (Jun. 19, 2003), WO 03/050,122 (Jun. 19, 2003), WO 03/049, 527 (Jun. 19, 2003), WO 03/049,679 (Jun. 19, 2003), WO 03/049,678 (Jun. 19, 2003) and WO 03/39460 (May 15, 2003) and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Inhibitors of kinases involved in mitotic progression include, but are not limited to, inhibitors of aurora kinase, inhibitors of Polo-like kinases (PLK) (e.g., inhibitors of PLK-1), inhibitors of bub-1 and inhibitors of bub-R1. Antiproliferative agents include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzo-furyl)sulfonyl]-N'-(3,4-dichlorophenyl)urea, N6-[4-deoxy-4-[N2-[2(E),4(E)-tetradeca-dienoyl]glycylamino]-glycero-B-L-manno-heptopyranosyl] adenine, aplidine, ectein-ascidin, troxacitabine, 4-[2-amino-4-oxo-4,6,7,8-tetrahydro-3H-pyrimidino[5,4-b]-[1,4] thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diaza-tetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone. Examples of monoclonal antibody targeted therapeutic agents include those therapeutic agents which have cytotoxic agents or radioisotopes attached to a cancer cell specific or target cell specific monoclonal antibody. Examples include, for example, Bexxar. HMG-CoA reductase inhibitors are inhibitors of 3-hydroxy-3-methylglutaryl-CoA reductase. Compounds which have inhibitory activity for HMG-CoA reductase can be readily identified by using assays well-known in the art such as those described or cited in U.S. Pat. No. 4,231,938 and WO 84/02131. Examples of HMG-CoA reductase inhibitors that may be used include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. In an embodiment, the HMG-CoA reductase inhibitor is selected from lovastatin and simvastatin.

Prenyl-protein transferase inhibitors are compounds which inhibit any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-

5-imidazolylmethyl-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-butyl-1-(2-methylphenyl)-4-[1(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl-4-(3-chlorobenzyl)-piperidine-1-ylmethyl]-2-methylimidazol-1-yl-methyl}benzonitrile, 4-{3-[4-(2-oxo-2H-pyridin-1-yl)benzyl]-3H-imidazol-4-ylmethyl}-benzonitrile, 4-{3-[4-(5-chloro-2-oxo-2H-[1,2']bipyridin-5'-ylmethyl]-3H-imidazol-4-yl-methyl}benzonitrile, 4-{3-[4-(2-oxo-2H-[1,2']bipyridin-5'-ylmethyl]-3H-imidazol4-yl-methyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k]-[1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14] oxatriazacycloeicosine-9-carbonitrile, and (.+−.)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* 35(9):1394-1401 (1999).

Angiogenesis inhibitors refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSA/Ds) like aspirin and ibuprofen as well as selective cyclooxygenase-2 inhibitors like celecoxib and rofecoxib (*PNAS* 89:7384 (1992); *JNCI* 69:475 (1982); *Arch. Ophthalmol.* 108:573 (1990); *Anat. Rec.*, (238):68 (1994); *FEBS Letters* 372:83 (1995); *Clin. Orthop.* 313:76 (1995); *J. Mol. Endocrinol.* 16:107 (1996); *Jpn. J. Pharmacol.* 75:105 (1997); *Cancer Res.* 57:1625 (1997); *Cell* 93:705 (1998); *Intl. J. Mol. Med.* 2:715 (1998); *J. Biol. Chem.* 274:9116 (1999)), steroidal anti-inflammatories (such as corticosteroids, mineralocorticoids, dexamethasone, prednisone, prednisolone, methylpred, beta-methasone), carboxyamidotriazole, combretastatin A4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, 17:963-968 (October 1999); Kim et al., *Nature*, 362:841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002). The invention also encompasses combinations of the compounds of the invention with NSAIDs which are selective COX-2 inhibitors (generally defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays). Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Representative inhibitors of COX-2 that are useful in the methods of the present invention include 3-phenyl-4-(4-(methylsulfonyl)phenyl)-2-(5H)-furanone; and 5-chloro-3-(4-methylsulfonyl)phenyl-2-(2-methyl-5-pyridinyl)pyridine. Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, U.S. Pat. No. 5,932,598, issued Aug. 3, 1999, U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998. Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-di-chloro-4-(4-chlorobenzoyl)phenyl]methyl]-1H-1,2,3-triazole-4-carboxamide, CM101, squalamine, combretastatin, RPI4610, NX31838, sulfated mannopentanose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Agents that interfere with cell cycle checkpoints are compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Inhibitors of cell proliferation and survival signaling pathway are pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents include activators of TNF receptor family members (including the TRAIL receptors).

In certain presently preferred embodiments of the invention, representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al., *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formulas (I), (II), (III) and (IV) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Gleevec, a small molecule tyrosine kinase inhibitor, as a result of inhibition of Ab1 kinase activity. However, many patients with advanced stage disease respond to Gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the compounds of formulas (I), (II), (III) and (N) are used in combination with at least one additional agent, such as Gleevec, in the treatment of hematological cancers, such as chronic myelogenous leukemia (CML), to reverse or prevent resistance to the at least one additional agent.

In another aspect, the present invention relates to methods of inhibiting at least one serine/threonine kinase in the Jak/Stat signaling pathway in a subject, or treating a biological condition mediated by a serine/threonine kinase in the Jak/Stat signaling pathway in a subject, comprising administering a therapeutic composition comprising at least one compound of formula (I), (II), (III) or (IV) effective to inhibit the activity of the at least one serine/threonine kinase in the Jak/Stat signaling pathway in the subject.

The therapeutic compositions in accordance with this aspect of the invention are useful for treating patients with a need for such inhibitors (e.g., those suffering from cancer mediated by abnormal Jak/Stat signaling). Cancer types mediated by abnormal Jak/Stat signaling include, for example, melanoma, papillary cancer, thyroid cancer, ovarian cancer, colon cancer, pancreatic cancer, non-small cell lung cancer (NSCLC), acute lymphoblastic leukemia (ALL), and acute myeloid leukemia.

In one embodiment, the invention provides a method of inhibiting Pim1, Pim2 Pim3, Flt3, KDR or PKCε in a human or animal subject. The method includes administering an effective amount of a compound, or a pharmaceutically acceptable salt thereof, of any of the embodiments of compounds of formula (I), (II), (III) or (IV) to a subject in need thereof.

The present invention will be understood more readily by reference to the following examples, which are provided by way of illustration and are not intended to be limiting of the present invention.

Representative side chains for use in the compounds of the following examples may generally be prepared in accordance with the following procedures:

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18 –5μ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of three LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.), another Waters System (ACQUITY HPLC system and a ZQ 2000 system; Column: ACQUITY HPLC HSS-C18, 1.8 um, 2.1×50 mm; gradient: 5-95% (or 35-95%, or 65-95% or 95-95%) acetonitrile in water with 0.05% TFA over a 1.3 min period; flow rate 1.2 mL/min; molecular weight range 150-850; cone Voltage 20 V; column temperature 50° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

GCMS analysis was performed on a Hewlett Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the compounds is assessed by elemental analysis (Desert Analytics, Tucson, Ariz.).

Melting points are determined on a Laboratory Devices MeI-Temp apparatus (Holliston, Mass.).

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

ABBREVIATIONS

| ABBREVIATIONS | |
|---|---|
| DAST | (diethylamino)sulfurtrifluoride |
| DCM | dichloromethane |
| DIEA | diisopropylethylamine |
| DMA | dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | Ethyl dimethylaminopropylazodicarboxylate hydrochloride |
| EtOAc | ethyl acetate |
| EtOH | Ethanol |
| HOAT | Hydroxyazabenzotriazole |
| MeCN | acetonitrile |
| MeOH | methanol |
| $Na_2CO_3$ | sodium carbonate |
| $NaHCO_3$ | sodium bicarbonate |
| NBS | N-bromosuccinimide |
| NMP | N-methyl-2-pyrrolidone |
| RT or rt | room temperature |
| TDMSCl | tert-butyldimethylsilylchloride |
| TEA | triethylamine |
| THF | tetrahydrofuran |

Example 1

Synthesis of 3-nitro-4-(piperidin-1-yl)pyridine

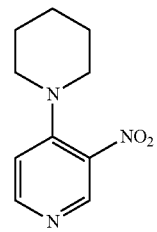

A solution of 4-chloro-3-nitropyridine (1.0 equiv.) and piperidine (2.0 equiv.) in ethanol, at a concentration of 0.5 M, was stirred at rt for 48 hours at which time the ethanol was removed in vacuo. The residue was partitioned between EtOAc (300 mL) and $Na_2CO_{3(sat)}$ (75 mL), was washed further with $H_2O$ (50 mL), $NaCl_{(sat.)}$ (50 mL), was dried over $MgSO_4$, was filtered and the volatiles were removed in vacuo yielding 3-nitro-4-(piperidin-1-yl)pyridine (95%). LCMS (m/z): 207.7 (MH$^+$); LC R$_t$=1.60 min. $^1$H NMR (CDCl$_3$): δ 8.80 (s, 1H), 8.31 (d, J=5.7, 1H), 6.84 (d, J=6.3, 1H), 3.18-3.21 (m, 4H), 1.64-1.78 (m, 6H).

Example 2

Synthesis of tert-butyl 1-(3-nitropyridin-4-yl)piperidin-3-ylcarbamate

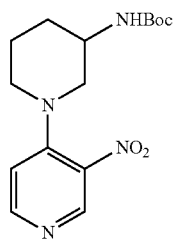 [SMILES: CC(C)(C)OC(=O)NC1CCCN(c2ccncc2[N+](=O)[O-])C1]

The method of Example 1 was followed using 1 eq each of 4-chloro-3-nitropyridine, 3-N-Boc-amino piperidine and diisopropylethylamine yielding tert-butyl 1-(3-nitropyridin-4-yl)piperidin-3-ylcarbamate, (89%). LCMS (m/z): 323.1 (MH$^+$); LC R$_t$=2.13 min.

Example 3

Synthesis of (R)-tert-butyl 1-(3-nitropyridin-4-yl)piperidin-3-ylcarbamate

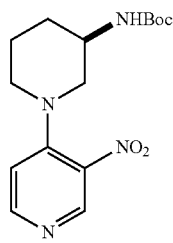 [SMILES: CC(C)(C)OC(=O)N[C@@H]1CCCN(c2ccncc2[N+](=O)[O-])C1]

The method of Example 1 was followed using 1 eq each of 4-chloro-3-nitropyridine, (R)-3-N-Boc-amino piperidine and diisopropylethylamine yielding (R)-tert-butyl 1-(3-nitropyridin-4-yl)piperidin-3-ylcarbamate, (99%). LCMS (m/z): 323.1 (MH$^+$); LC R$_t$=2.13 min.

Example 4

Synthesis of (S)-tert-butyl 1-(3-nitropyridin-4-yl)piperidin-3-ylcarbamate

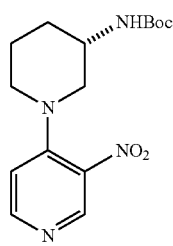 [SMILES: CC(C)(C)OC(=O)N[C@H]1CCCN(c2ccncc2[N+](=O)[O-])C1]

The method of Example 1 was followed using 1 eq each of 4-chloro-3-nitropyridine, (S)-3-N-Boc-amino piperidine and diisopropylethylamine yielding (S)-tert-butyl 1-(3-nitropyridin-4-yl)piperidin-3-ylcarbamate, (99%). LCMS (m/z): 323.1 (MH$^+$); LC R$_t$=2.13 min.

Example 5

Synthesis of tert-butyl (1-(3-nitropyridin-4-yl)piperidin-3-yl)methylcarbamate

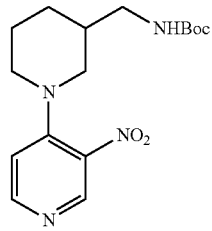 [SMILES: CC(C)(C)OC(=O)NCC1CCCN(c2ccncc2[N+](=O)[O-])C1]

The method of Example 1 was followed using 1 eq each of 4-chloro-3-nitropyridine, tert-butyl piperidin-3-ylmethylcarbamate and diisopropylethylamine yielding tert-butyl (1-(3-nitropyridin-4-yl)piperidin-3-yl)methylcarbamate (99%). LCMS (m/z): 336.9 (MH$^+$); LC R$_t$=2.27 min. $^1$H NMR (CDCl$_3$): δ 8.80 (s, 1H), 8.33 (d, J=6.0 Hz, 1H), 6.85 (d, J=6.3 Hz, 1H), 4.63 (bs, 1H), 3.28-3.46 (m, 2H), 2.89-3.15 (m, 3H), 2.69-2.86 (m, 1H), 1.55-1.99 (m, 5H), 1.45 (s, 9H).

Example 6

Synthesis of 1-(3-nitropyridin-4-yl)piperazine

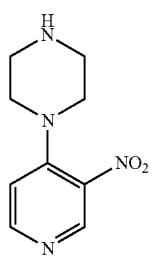

The method of Example 1 was followed using 1 eq of 4-chloro-3-nitropyridine and 10 eq of piperazine yielding tert-butyl 1-(3-nitropyridin-4-yl)piperazine (99%). LCMS (m/z): 208.6 (MH$^+$); LC R$_t$=0.42 min. $^1$H NMR (CDCl$_3$): δ 8.83 (s, 1H), 8.37 (d, J=6.0, 1H), 6.85 (d, J=6.0, 1H), 3.20-3.23 (m, 4H), 3.00-3.03 (m, 4H).

Example 7

Synthesis of tert-butyl 1-(2-nitrophenyl)piperidin-3-ylcarbamate

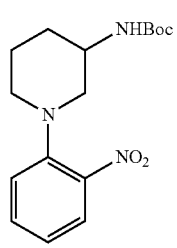

The method of Example 1 was followed using 1-fluoro-2-nitrobenzene (1.0 eq), 3-N-Boc-aminopiperidine (1.0 eq), and DIEA (2.0 eq) in EtOH at 50° C. for 48 hours yielding tert-butyl 1-(2-nitrophenyl)piperidin-3-ylcarbamate (85%). LCMS (m/z): 322.2 (MH$^+$); LC R$_t$=3.23 min.

Example 8

Synthesis of tert-butyl 1-(2-nitrophenyl)piperidin-4-ylcarbamate

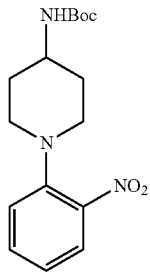 [SMILES: CC(C)(C)OC(=O)NC1CCN(c2ccccc2[N+](=O)[O-])CC1]

The method of Example 1 was followed using 1-fluoro-2-nitrobenzene (1.0 eq), 4-N-Boc-aminopiperidine (1.2 eq), and TEA (2.0 eq) in EtOH at 55° C. for 48 hours yielding tert-butyl 1-(2-nitro phenyl)piperidin-4-ylcarbamate (100%). LCMS (m/z): 322.2 (MH$^+$); LC R$_t$=3.15 min.

Example 9

Synthesis of tert-butyl 4-(2-nitrophenyl)piperazine-1-carboxylate

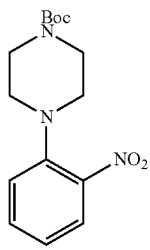 [SMILES: CC(C)(C)OC(=O)N1CCN(c2ccccc2[N+](=O)[O-])CC1]

The method of Example 1 was followed using 1-fluoro-2-nitrobenzene (1.0 eq), 1-Boc-piperazine (1.2 eq), and TEA (2.0 eq) in EtOH at 55° C. for 72 hours yielding tert-butyl 4-(2-nitro phenyl)piperazine-1-carboxylate (100%). LCMS (m/z): 308.1 (MH$^+$); LC R$_t$=3.25 min.

Example 10

Synthesis of tert-butyl 1-(3-nitropyridin-2-yl)piperidin-3-ylcarbamate

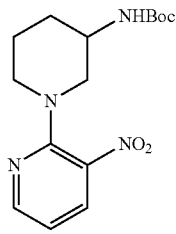

The method of Example 1 was followed using 2-chloro-3-nitropyridine (1.0 eq), 3-N-Boc-aminopiperidine (1.2 eq), and DIEA (2.0 eq) yielding tert-butyl 1-(3-nitropyridin-2-yl)piperidin-3-yl carbamate (95%). LCMS (m/z): 323.2 (MH$^+$); LC R$_t$=3.00 min.

Example 11

Synthesis of N,N-dimethyl-1-(3-nitropyridin-4-yl)piperidin-4-amine

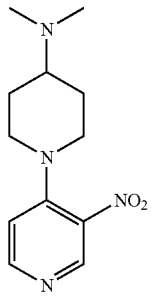

The method of Example 1 was followed using 4-dimethylamino-piperidine yielding N,N-dimethyl-1-(3-nitropyridin-4-yl)piperidin-4-amine. LCMS (m/z): 251.2 (MH$^+$).

Example 12

Synthesis of 8-(3-nitropyridin-4-yl)-1,4-dioxa-8-azaspiro[4.5]decane

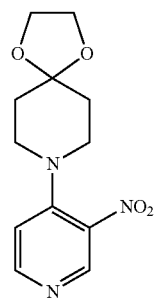

The method of Example 1 was followed using 1,4 dioxa-8-azaspiro[4.5]decane yielding 8-(3-nitropyridin-4-yl)-1,4-dioxa-8-azaspiro[4.5]decane. LCMS (m/z): 266.2 (MH$^+$).

Example 13

Synthesis of tert-butyl 4-(3-nitropyridin-4-yl)-1,4-diazepane-1-carboxylate

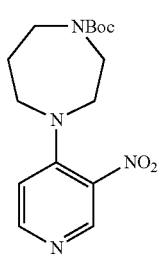 [SMILES: CC(C)(C)OC(=O)N1CCCN(c2ccncc2[N+](=O)[O-])CC1]

The method of Example 1 was followed using 1-Boc-homopiperazine yielding tert-butyl 4-(3-nitropyridin-4-yl)-1,4-diazepane-1-carboxylate. LCMS (m/z): 293.3 (MH$^+$);

Example 14

Synthesis of N¹,N¹,N²-trimethyl-N²-(3-nitropyridin-4-yl)ethane-1,2-diamine

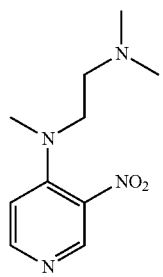

The method of Example 1 was followed using 4-chloro-3-nitropyridine (1.0 eq), N¹,N¹,N²-trimethyl ethane-1,2-diamine (2.0 eq), and DIEA (2.0 eq) in EtOH yielding N¹,N¹,N²-trimethyl-N²-(3-nitropyridin-4-yl)ethane-1,2-diamine which was concentrated and taken on as is. LCMS (m/z): 225.1 (MH⁺); LC $R_t$=0.574 min.

Example 15

Synthesis of tert-butyl 1-(3-nitropyridin-4-yl)pyrolidin-3-ylcarbamate

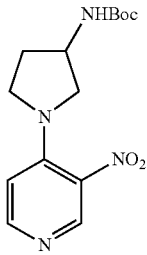 [SMILES: CC(C)(C)OC(=O)NC1CCN(c2ccncc2[N+](=O)[O-])C1]

The method of Example 1 was followed using 4-chloro-3-nitropyridine (1.0 eq), tert-butyl pyrrolidin-3-ylcarbamate (2.0 eq), and DIEA (2.0 eq) in EtOH yielding tert-butyl 1-(3-nitropyridin-4-yl)pyrrolidin-3-ylcarbamate (95%) LCMS (m/z): 309.1 (MH⁺); LC $R_t$=1.922 min.

Example 16

Synthesis of (R)-tert-butyl[1-(3-nitropyridin-4-yl)pyrrolidin-2-yl]methylcarbamate

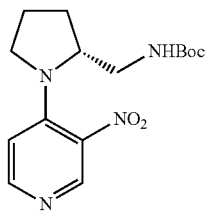 [SMILES: CC(C)(C)OC(=O)NC[C@H]1CCCN1c1ccncc1[N+](=O)[O-]]

The method of Example 1 was followed using 4-chloro-3-nitropyridine (1.0 eq), (R)-pyrrolidin-2-ylmethanamine (2.0 eq), and DIEA (2.0 eq) in EtOH yielding (R)-tert-butyl[1-(3-nitropyridin-4-yl)pyrrolidin-2-yl]methylcarbamate (95%) LCMS (m/z): 323.1 (MH⁺); LC $R_t$=1.855 min.

Example 17

Synthesis of 2-chloro-5-nitro-4-(piperidin-1-yl)pyrimidine

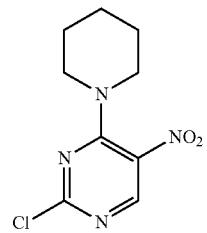 [SMILES: O=[N+]([O-])c1cnc(Cl)nc1N1CCCCC1]

Method 1 was followed using 2,4-dichloro-5-nitropyrimidine (1.0 eq), and piperidine (2.0 eq) in EtOH at 0° C. to rt, yielding after washing with 1M citric acid and 1M HCl (to remove the bis addition product), 2-chloro-5-nitro-4-(piperidin-1-yl)pyrimidine (67%) LCMS (m/z): 242.9 (MH⁺); LC $R_t$=4.09 min.

Example 18

Synthesis of tert-butyl 1-(3-fluoro-2-nitrophenyl)piperidin-4-ylcarbamate

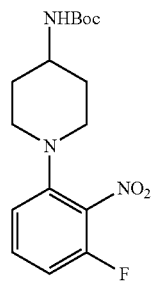

Method 1 was followed using 1 eq each of 2,6-difluoronitrobenzene, 4-(N-Boc-amino) piperidine, and TEA in EtOH yielding tert-butyl 1-(3-fluoro-2-nitrophenyl)piperidin-4-ylcarbamate (93%). LCMS (m/z): 340.1 (MH⁺); LC $R_t$=3.30 min.

Example 19

Synthesis of tert-butyl 1-(5-fluoro-2-nitrophenyl)piperidin-4-ylcarbamate

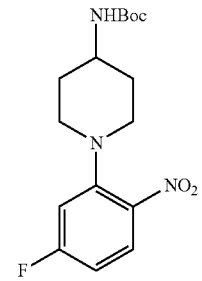 [SMILES: CC(C)(C)OC(=O)NC1CCN(c2cc(F)ccc2[N+](=O)[O-])CC1]

Method 1 was followed using 1 eq each of 1,3-difluoro-4-nitrobenzene, 4-(N-Boc-amino) piperidine, and TEA yielding tert-butyl 1-(5-fluoro-2-nitrophenyl)-piperidin-4-ylcarbamate (93%). LCMS (m/z): 340.1 (MH$^+$); LC R$_t$=3.24 min.

Example 20

Synthesis of tert-butyl
1-(4-fluoro-2-nitrophenyl)piperidin-4-ylcarbamate

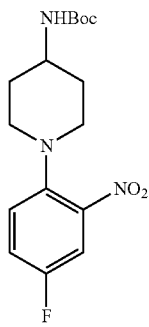 [SMILES: CC(C)(C)OC(=O)NC1CCN(c2ccc(F)cc2[N+](=O)[O-])CC1]

Method 1 was followed using 2,5-difluoronitrobenzene (1.0 eq), 4-(N-Boc-amino) piperidine (1.4 eq), and TEA (2.0 eq) at 55° C. overnight yielding tert-butyl 1-(4-fluoro-2-nitrophenyl)piperidin-4-ylcarbamate (97%). LCMS (m/z): 340.1 (MH$^+$); LC R$_t$=3.28 min.

Example 21

Synthesis of tert-butyl
1-(4-benzoyl-2-nitrophenyl)piperidin-3-ylcarbamate

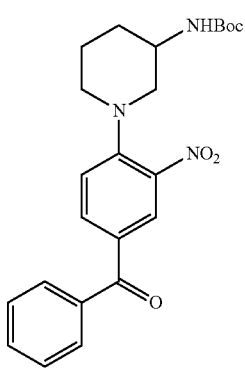 [SMILES: CC(C)(C)OC(=O)NC1CCCN(c2ccc(C(=O)c3ccccc3)cc2[N+](=O)[O-])C1]

Method 1 was followed using 4-chloro-3-nitrobenzophenone (1.0 eq), 3-(N-Boc-amino) piperidine (1.1 eq), and TEA (2.0 eq) in NMP yielding tert-butyl 1-(4-benzoyl-2-nitro phenyl)piperidin-3-ylcarbamate (90%). LCMS (m/z): 426.2 (MH$^+$); LC R$_t$=3.49 min.

Example 22

Synthesis of tert-butyl
1-(4-benzoyl-2-nitrophenyl)piperidin-4-ylcarbamate

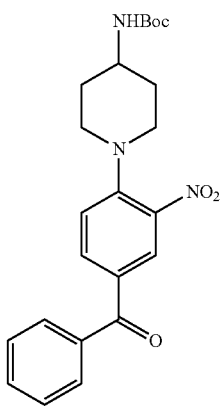 [SMILES: CC(C)(C)OC(=O)NC1CCN(c2ccc(C(=O)c3ccccc3)cc2[N+](=O)[O-])CC1]

Method 1 was followed using 4-chloro-3-nitrobenzophenone (1.0 eq), 4-(N-Boc-amino) piperidine (1.1 eq), and TEA (2.0 eq) in NMP yielding tert-butyl 1-(4-benzoyl-2-nitro phenyl)piperidin-4-ylcarbamate (95%). LCMS (m/z): 426.2 (MH$^+$); LC R$_t$=3.46 min.

Example 23

Synthesis of tert-butyl 4-(4-benzoyl-2-nitrophenyl)piperazine-1-carboxylate

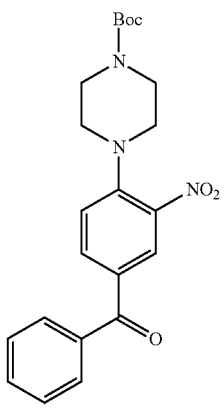

Method 1 was followed using 4-chloro-3-nitrobenzophenone (1.0 eq), 1-Boc-piperazine (1.1 eq), and TEA (2.0 eq) in NMP yielding tert-butyl 4-(4-benzoyl-2-nitrophenyl)piperazine-1-carboxylate (93%). LCMS (m/z): 412.2 (MH$^+$); LC R$_t$=3.59 min.

Example 24

Synthesis of tert-butyl 4-(4-acetyl-2-nitrophenyl)piperazine-1-carboxylate

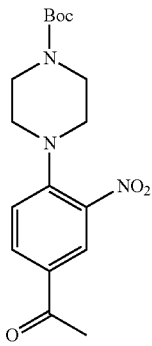

Method 1 was followed using 4-chloro-3-nitroacetophenone (1.0 eq), t-Boc-piperazine (1.2 eq), and TEA (2.0 eq) at 55° C. overnight yielding tert-butyl 4-(4-acetyl-2-nitro phenyl)piperazine-1-carboxylate (99%). LCMS (m/z): 350.1 (MH$^+$); LC R$_t$=3.06 min.

Example 25

Synthesis of tert-butyl 1-(4-acetyl-2-nitrophenyl)piperidin-4-ylcarbamate

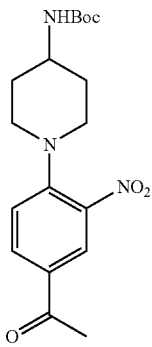 [SMILES: CC(=O)c1ccc(N2CCC(NC(=O)OC(C)(C)C)CC2)c([N+](=O)[O-])c1]

Method 1 was followed using 4-chloro-3-nitroacetophenone (1.0 eq), 4-(N-Boc-amino) piperidine (1.2 eq), and TEA (2.0 eq) at 55° C. overnight yielding tert-butyl 1-(4-acetyl-2-nitrophenyl)piperidin-4-ylcarbamate (95%). LCMS (m/z): 364.1 (MH$^+$); LC R$_t$=2.99 min.

Example 26

Synthesis of tert-butyl 1-(4-acetyl-2-nitrophenyl)piperidin-3-ylcarbamate

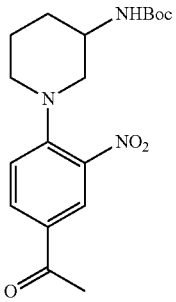

Method 1 was followed using 4-chloro-3-nitroacetophenone (1.0 eq), 3-(N-Boc-amino) piperidine (1.2 eq), and TEA (2.0 eq) at 55° C. overnight tert-butyl 1-(4-acetyl-2-nitro phenyl)piperidin-3-ylcarbamate (99%). LCMS (m/z): 364.1 (MH$^+$); LC R$_t$=3.03 min.

Example 27

Synthesis of tert-butyl 1-(4-acetyl-2-nitrophenyl)piperidin-3-ylcarbamate

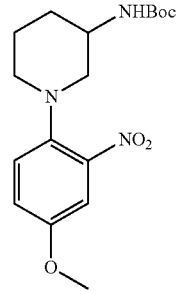 [SMILES: COc1ccc(N2CCCC(NC(=O)OC(C)(C)C)C2)c([N+](=O)[O-])c1]

Method 1 was followed using 4-chloro-3-nitroanisole (1.0 eq), 3-(N-Boc-amino) piperidine (1.2 eq), and TEA (2.0 eq) at 60° C. for 72 hours yielding tert-butyl 1-(4-methoxy-2-nitrophenyl)piperidin-3-ylcarbamate (50%). LCMS (m/z): 352.1 (MH$^+$); LC R$_t$=3.27 min.

Example 28

Synthesis of tert-butyl 1-(4-methoxy-2-nitrophenyl)piperidin-4-ylcarbamate

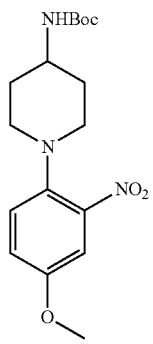

Method 1 was followed using 4-chloro-3-nitroanisole (1.0 eq), 4-(N-Boc-amino) piperidine (1.2 eq), and TEA (2.0 eq) at 60° C. for 72 hours yielding tert-butyl 1-(4-methoxy-2-nitrophenyl)piperidin-4-ylcarbamate (75%). LCMS (m/z): 352.1 (MH$^+$); LC R$_t$=3.22 min.

Example 29

Synthesis of tert-butyl 4-(4-methoxy-2-nitrophenyl)piperazine-1-carboxylate

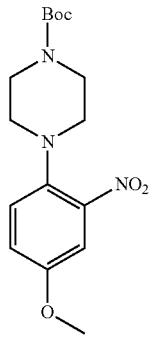

Method 1 was followed using 4-chloro-3-nitroanisole (1.0 eq), 1-Boc-piperazine (1.2 eq), and TEA (2.0 eq) in NMP at 100° C. for 16 hours yielding tert-butyl 4-(4-methoxy-2-nitro phenyl)piperazine-1-carboxylate (50%). LCMS (m/z): 338.2 (MH$^+$); LC R$_t$=3.37 min.

Example 30

Synthesis of tert-butyl 4-(4-chloro-2-nitrophenyl)piperazine-1-carboxylate

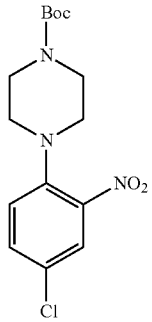 [SMILES: CC(C)(C)OC(=O)N1CCN(c2ccc(Cl)cc2[N+](=O)[O-])CC1]

Method 1 was followed using 1 eq each of 4-chloro-1-fluoro-2-nitrobenzene, 1-Boc-piperazine, and TEA yielding tert-butyl 4-(4-chloro-2-nitrophenyl)piperazine-1-carboxylate (95%). LCMS (m/z): 342.0 (MH$^+$); LC R$_t$=3.50 min.

Example 31

Synthesis of tert-butyl 1-(4-chloro-2-nitrophenyl)piperidin-4-ylcarbamate

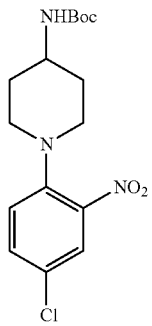 [SMILES: CC(C)(C)OC(=O)NC1CCN(c2ccc(Cl)cc2[N+](=O)[O-])CC1]

Method 1 was followed using 1 eq each of 4-chloro-1-fluoro-2-nitrobenzene, 4-N-Boc-aminopiperidine, and TEA yielding tert-butyl 1-(4-chloro-2-nitrophenyl)piperidin-4-ylcarbamate (95%). LCMS (m/z): 356.1 (MH$^+$); LC R$_t$=3.43 min.

Example 32

Synthesis of tert-butyl 1-(4-chloro-2-nitrophenyl)piperidin-3-ylcarbamate

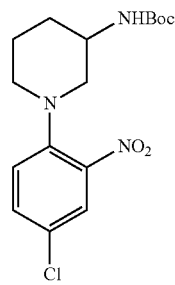 [SMILES: CC(C)(C)OC(=O)NC1CCCN(c2ccc(Cl)cc2[N+](=O)[O-])C1]

Method 1 was followed using 1 eq each of 4-chloro-1-fluoro-2-nitrobenzene, 3-(N-Boc-amino) piperidine, and TEA yielding tert-butyl 1-(4-chloro-2-nitrophenyl)piperidin-4-ylcarbamate (97%). LCMS (m/z): 356.1 (MH$^+$); LC R$_t$=3.47 min.

Example 33

Synthesis of tert-butyl 4-(4-methyl-2-nitrophenyl)piperazine-1-carboxylate

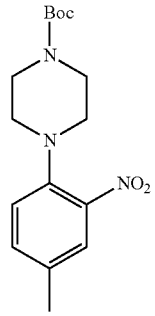

Method 1 was followed using 4-fluoro-3-nitrotoluene (1.0 eq), 1-Boc-piperazine (1.2 eq), and TEA (1.5 eq) at 55° C. for 48 hours yielding tert-butyl 4-(4-methyl-2-nitrophenyl)piperazine-1-carboxylate (90%). LCMS (m/z): 322.1 (MH$^+$); LC R$_t$=3.46 min.

Example 34

Synthesis of tert-butyl 1-(4-methyl-2-nitrophenyl)piperidin-4-ylcarbamate

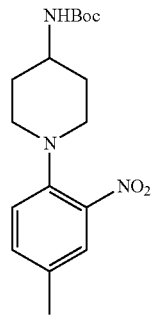

Method 1 was followed using 4-fluoro-3-nitrotoluene (1.0 eq), 4-(N-Boc-amino) piperidine (1.2 eq), and TEA (1.5 eq) at 55° C. for 48 hours yielding tert-butyl 1-(4-methyl-2-nitrophenyl)piperidin-4-ylcarbamate (87%). LCMS (m/z): 336.1 (MH$^+$); LC R$_t$=3.32 min.

Example 35

Synthesis of tert-butyl 1-(4-methyl-2-nitrophenyl)piperidin-3-ylcarbamate

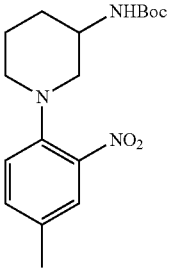 [SMILES: Cc1ccc(N2CCCC(NC(=O)OC(C)(C)C)C2)c([N+](=O)[O-])c1]

Method 1 was followed using 4-fluoro-3-nitrotoluene (1.0 eq), 3-(N-Boc-amino) piperidine (1.2 eq), and TEA (1.5 eq) at 55° C. for 48 hours yielding tert-butyl 1-(4-methyl-2-nitrophenyl)piperidin-3-ylcarbamate (87%). LCMS (m/z): 336.1 (MH$^+$); LC R$_t$=3.41 min.

Example 36

Synthesis of tert-butyl 1-(2-nitro-4-(trifluoromethyl)phenyl)piperidin-3-ylcarbamate

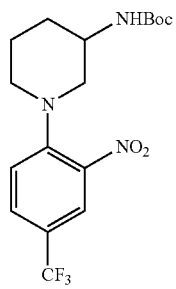 [SMILES: CC(C)(C)OC(=O)NC1CCCN(c2ccc(C(F)(F)F)cc2[N+](=O)[O-])C1]

Method 1 was followed using 1-fluoro-2-nitro-4-(trifluoromethyl)benzene (1.0 eq), 3-(N-Boc-amino) piperidine (1.2 eq), and TEA (1.5 eq) at 55° C. for 1 hour yielding tert-butyl 1-(2-nitro-4-(trifluoromethyl)phenyl)piperidin-3-ylcarbamate (99%). LCMS (m/z): 390.1 (MH$^+$); LC R$_t$=3.58 min.

Example 37

Synthesis of tert-butyl 1-(2-nitro-4-(trifluoromethyl)phenyl)piperidin-4-ylcarbamate

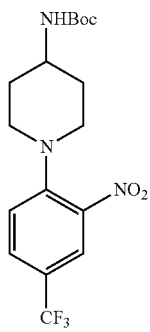 [SMILES: CC(C)(C)OC(=O)NC1CCN(c2ccc(C(F)(F)F)cc2[N+](=O)[O-])CC1]

Method 1 was followed using 1-fluoro-2-nitro-4-(trifluoromethyl)benzene (1.0 eq), 4-(N-Boc-amino) piperidine (1.2 eq), and TEA (2.0 eq) at 55° C. for 1 hour yielding tert-butyl 1-(2-nitro-4-(trifluoromethyl)phenyl)piperidin-4-ylcarbamate (99%). LCMS (m/z): 390.1 (MH$^+$); LC R$_t$=3.51 min.

Example 38

Synthesis of tert-butyl 4-(2-nitro-4-(trifluoromethyl)phenyl)piperazine-1-carboxylate

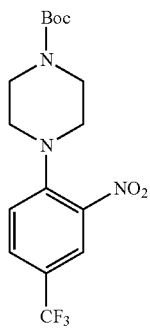 [SMILES: CC(C)(C)OC(=O)N1CCN(c2ccc(C(F)(F)F)cc2[N+](=O)[O-])CC1]

Method 1 was followed using 1-fluoro-2-nitro-4-(trifluoromethyl)benzene (1.0 eq), 1-Boc-piperazine (1.2 eq), and TEA (2.0 eq) at 55° C. for 1 hour yielding tert-butyl 4-(2-nitro-4-(trifluoromethyl)phenyl)piperazine-1-carboxylate (99%). LCMS (m/z): 376.1 (MH$^+$); LC R$_t$=3.58 min.

Example 39

Synthesis of tert-butyl 4-(5-methyl-2-nitrophenyl)piperazine-1-carboxylate

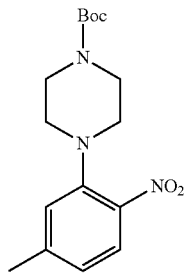 [SMILES: Cc1ccc([N+](=O)[O-])c(N2CCN(C(=O)OC(C)(C)C)CC2)c1]

Method 1 was followed using 3-fluoro-4-nitrotoluene (1.0 eq), 1-Boc-piperazine (1.2 eq), and TEA (2.0 eq) at 55° C. for 48 hours yielding tert-butyl 4-(5-methyl-2-nitrophenyl)piperazine-1-carboxylate (97%). LCMS (m/z): 322.1 (MH$^+$); LC R$_t$=3.43 min.

Example 40

Synthesis of tert-butyl 1-(5-methyl-2-nitrophenyl)piperidin-4-ylcarbamate

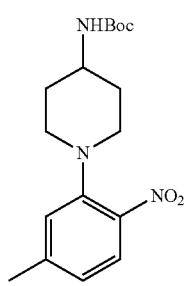 [SMILES: Cc1ccc([N+](=O)[O-])c(N2CCC(NC(=O)OC(C)(C)C)CC2)c1]

Method 1 was followed using 3-fluoro-4-nitrotoluene (1.0 eq), 4-(N-Boc-amino) piperidine (1.2 eq), and TEA (2.0 eq) at 55° C. for 48 hours yielding tert-butyl 1-(5-methyl-2-nitrophenyl)piperidin-4-ylcarbamate (97%). LCMS (m/z): 336.1 (MH$^+$); LC R$_t$=3.32 min

Example 41

Synthesis of tert-butyl 1-(4-methyl-2-nitrophenyl)piperidin-3-ylcarbamate

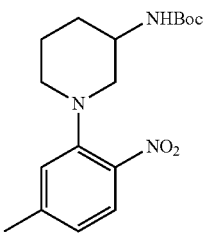

Method 1 was followed using 3-fluoro-4-nitrotoluene (1.0 eq), 3-(N-Boc-amino) piperidine (1.2 eq), and TEA (2.0 eq) at 55° C. for 48 hours yielding tert-butyl 1-(4-methyl-2-nitrophenyl)piperidin-3-ylcarbamate (98%). LCMS (m/z): 336.1 (MH$^+$); LC R$_t$=3.40 min.

Example 42

Synthesis of tert-butyl 1-(4-cyano-2-nitrophenyl)piperidin-3-ylcarbamate

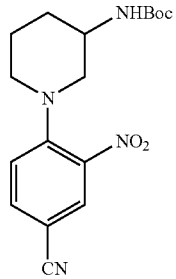 [SMILES: CC(C)(C)OC(=O)NC1CCCN(c2ccc(C#N)cc2[N+](=O)[O-])C1]

Method 1 was followed using 4-chloro-3-nitrobenzonitrile (1.0 eq), 3-(N-Boc-amino) piperidine (1.0 eq), and DIEA (2.4 eq) at 55° C. for 24 hours yielding tert-butyl 1-(4-cyano-2-nitrophenyl)piperidin-3-ylcarbamate (95%). LCMS (m/z): 347.2 (MH$^+$); LC R$_t$=3.06 min.

Example 43

Synthesis of tert-butyl 1-(2-nitro-4-(1H-pyrazol-5-yl)phenyl)piperidin-4-ylcarbamate

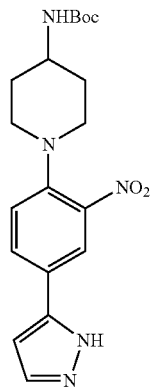 [SMILES: CC(C)(C)OC(=O)NC1CCN(c2ccc(-c3ccn[nH]3)cc2[N+](=O)[O-])CC1]

Method 1 was followed using 5-(4-chloro-3-nitrophenyl)-1H-pyrazole (1.0 eq), 4-(N-Boc-amino) piperidine (1.1 eq), and TEA (2.0 eq) at 55° C. for 24 hours yielding tert-butyl 1-(2-nitro-4-(1H-pyrazol-5-yl)phenyl)piperidin-4-ylcarbamate. LCMS (m/z): 388.1 (MH$^+$); LC R$_t$=2.84 min.

Example 44

Synthesis of tert-butyl 1-(4-(methylsulfonyl)-2-nitrophenyl)piperidin-4-ylcarbamate

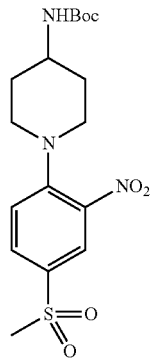 [SMILES: CC(C)(C)OC(=O)NC1CCN(c2ccc(S(C)(=O)=O)cc2[N+](=O)[O-])CC1]

Method 1 was followed using 1-fluoro-4-(methylsulfonyl)-2-nitrobenzene (1.0 eq), 4-(N-Boc-amino) piperidine (1.1 eq), and TEA (2.0 eq) at 55° C. for 24 hours yielding tert-butyl 1-(4-(methylsulfonyl)-2-nitrophenyl)piperidin-4-ylcarbamate. LCMS (m/z): 400.1 (MH$^+$); LC R$_t$=2.83 min.

Example 45

Synthesis of tert-butyl 4-(4-(cyclopropanecarbonyl)-2-nitrophenyl)piperazine-1-carboxylate

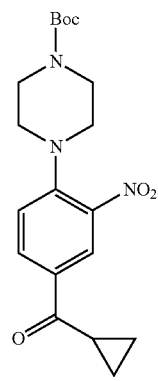 [SMILES: CC(C)(C)OC(=O)N1CCN(c2ccc(C(=O)C3CC3)cc2[N+](=O)[O-])CC1]

Method 1 was followed using 4-chloro-3-nitrophenyl cyclopropyl ketone (1.0 eq), 1-Boc-piperazine (1.2 eq), and TEA (1.5 eq) at 55° C. for 48 hours yielding tert-butyl 4-(4-(cyclopropanecarbonyl)-2-nitrophenyl)piperazine-1-carboxylate (98%). LCMS (m/z): 376.1 (MH$^+$); LC R$_t$=3.33 min.

Example 46

Synthesis of tert-butyl 1-(4-(cyclopropanecarbonyl)-2-nitrothenyl)piperidin-4-ylcarbamate

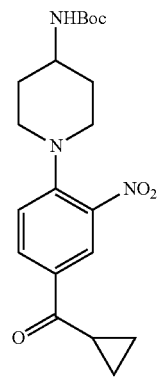

Method 1 was followed using 4-chloro-3-nitrophenyl cyclopropyl ketone (1.0 eq), 4-(N-Boc-amino)piperidine (1.2 eq), and TEA (1.5 eq) at 55° C. for 48 hours yielding tert-butyl 1-(4-(cyclopropanecarbonyl)-2-nitrophenyl)piperidin-4-ylcarbamate (95%). LCMS (m/z): 390.1 (MH$^+$); LC R$_t$=3.25 min.

Example 47

Synthesis of tert-butyl 1-(4-(cyclopropanecarbonyl)-2-nitrophenyl)piperidin-3-ylcarbamate

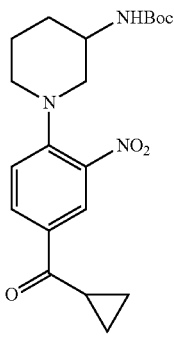 [SMILES: CC(C)(C)OC(=O)NC1CCCN(c2ccc(C(=O)C3CC3)cc2[N+](=O)[O-])C1]

Method 1 was followed using 4-chloro-3-nitrophenyl cyclopropyl ketone (1.0 eq), 3-(N-Boc-amino)piperidine (1.2 eq), and TEA (1.5 eq) at 55° C. for 48 hours yielding tert-butyl 1-(4-(cyclopropanecarbonyl)-2-nitrophenyl)piperidin-3-ylcarbamate (96%). LCMS (m/z): 390.1 (MH$^+$); LC R$_t$=3.28 min.

Example 48

Synthesis of tert-butyl 2-(3-nitropyridin-4-yloxy)ethylcarbamate

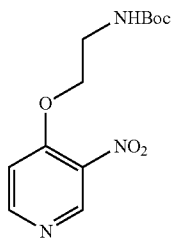 [SMILES: CC(C)(C)OC(=O)NCCOc1ccncc1[N+](=O)[O-]]

To a cooled solution (0° C.) of tert-butyl 2-hydroxyethylcarbamate (1.1 eq) in THF, NaH (1.3 eq) was added, stirred for 1 hr, and then 4-chloro-3-nitropyridine (1.0 eq) was added. The reaction mixture was stirred at RT overnight, poured into cold water, and extracted with EtOAc. Organic layer was dried over Na$_2$CO$_3$, filtered, and concentrated to yield tert-butyl 2-(3-nitropyridin-4-yloxy)ethylcarbamate. LCMS (m/z): 284.1 (MH$^+$); LC R$_t$=2.09 min.

Method 2

Example 49

Synthesis of 4-(piperidin-1-yl)pyridin-3-amine

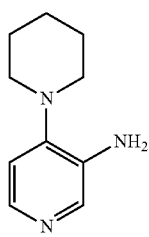

To a solution of 3-nitro-4-(piperidin-1-yl)pyridine (1.0 equiv.) in ethanol, at a concentration of 0.1 M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding 4-(piperidin-1-yl)pyridin-3-amine (93%) as an oil. LCMS (m/z): 178.0 (MH$^+$); LC R$_t$=1.68 min. NMR (CDCl$_3$): δ 8.01 (s, 1H), 7.96 (d, J=5.4, 1H), 6.78 (d, J=5.1, 1H), 3.64-3.74 (m, 2H), 2.86-2.94 (m, 4H), 1.66-1.78 (m, 4H), 1.58-1.64 (m, 2H).

Example 50

Synthesis of tert-butyl 1-(3-aminopyridin-4-yl)piperidin-3-ylcarbamate

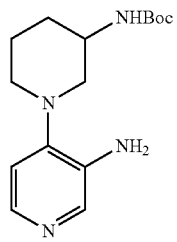 [SMILES: CC(C)(C)OC(=O)NC1CCCN(c2ccncc2N)C1]

Following the method of Example 49 (Method 2), tert-butyl 1-(3-nitropyridin-4-yl)piperidin-3-ylcarbamate was reduced yielding tert-butyl 1-(3-aminopyridin-4-yl)piperidin-3-ylcarbamate, (65%). LCMS (m/z): 293.1 (MH$^+$); LC R$_t$=2.10 min.

Example 51

Synthesis of (R)-tert-butyl 1-(3-aminopyridin-4-yl)piperidin-3-ylcarbamate

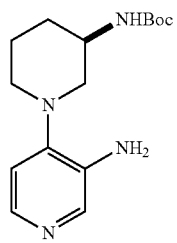

Following the method of Example 49 (Method 2), (R)-tert-butyl 1-(3-nitropyridin-4-yl)piperidin-3-ylcarbamate was reduced yielding (R)-tert-butyl 1-(3-aminopyridin-4-yl)piperidin-3-ylcarbamate, (89%). LCMS (m/z): 293.1 (MH$^+$); LC R$_t$=2.08 min.

Example 52

Synthesis of (S)-tert-butyl 1-(3-aminopyridin-4-yl)piperidin-3-ylcarbamate

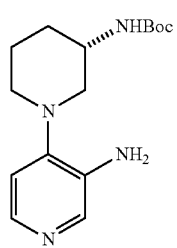

Following the method of Example 49 (Method 2), (S)-tert-butyl 1-(3-nitropyridin-4-yl)piperidin-3-ylcarbamate was reduced yielding (S)-tert-butyl 1-(3-aminopyridin-4-yl)piperidin-3-ylcarbamate, (78%). LCMS (m/z): 293.1 (MH$^+$); LC R$_t$=2.08 min.

Example 53

Synthesis of tert-butyl (1-(3-aminopyridin-4-yl)piperidin-3-yl)methylcarbamate

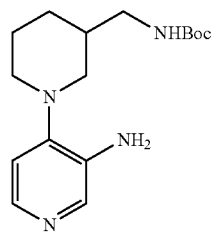 [SMILES: CC(C)(C)OC(=O)NCC1CCCN(c2ccncc2N)C1]

Following the method of Example 49 (Method 2), tert-butyl (1-(3-nitropyridin-4-yl)piperidin-3-yl)methylcarbamate was reduced yielding tert-butyl (1-(3-aminopyridin-4-yl)piperidin-3-yl)methylcarbamate (72%). LCMS (m/z): 307.2 (MH$^+$); LC $R_t$=2.28 min. $^1$H NMR (CDCl$_3$): δ 8.01 (s, 1H), 7.96 (d, J=5.4 Hz, 1H), 6.78 (d, J=5.4 Hz, 1H), 4.60 (bs, 1H), 3.68 (bs, 2H), 3.04-3.28 (m, 4H), 2.53-2.65 (m, 1H), 2.35-2.47 (m, 1H), 1.77-1.93 (m, 3H), 1.55-1.75 (m, 2H), 1.44 (s, 9H).

Example 54

Synthesis of tert-butyl 1-(2-aminophenyl)piperidin-3-ylcarbamate

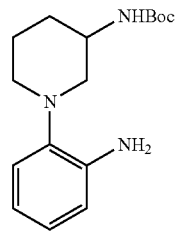 [SMILES: CC(C)(C)OC(=O)NC1CCCN(c2ccccc2N)C1]

Following the method of Example 49 (Method 2), tert-butyl 1-(2-nitrophenyl)piperidin-3-ylcarbamate was reduced yielding tert-butyl 1-(2-aminophenyl)piperidin-3-ylcarbamate, (90%). LCMS (m/z): 292.2 (MH$^+$). LC $R_t$=2.17 min.

Example 55

Synthesis of tert-butyl 1-(2-aminophenyl)piperidin-4-ylcarbamate

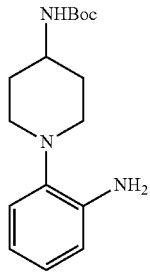 [SMILES: CC(C)(C)OC(=O)NC1CCN(c2ccccc2N)CC1]

Following the method of Example 49 (Method 2), tert-butyl 1-(2-nitrophenyl)piperidin-4-ylcarbamate was reduced yielding tert-butyl 1-(2-aminophenyl)piperidin-4-ylcarbamate, (90%). LCMS (m/z): 292.1 (MH$^+$); LC $R_t$=2.13 min.

Example 56

Synthesis of tert-butyl 4-(2-aminophenyl)piperazine-1-carboxylate

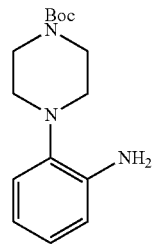

Following the method of Example 49 (Method 2), tert-butyl 4-(2-nitrophenyl)piperazine-1-carboxylate was reduced for 2 hours yielding tert-butyl 4-(2-aminophenyl)piperazine-1-carboxylate, (99%). LCMS (m/z): 278.2 (MH$^+$); LC $R_t$=2.22 min.

Example 57

Synthesis of tert-butyl 1-(3-aminopyridin-2-yl)piperidin-3-ylcarbamate

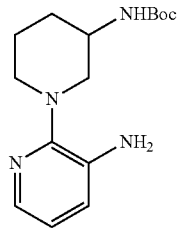 [SMILES: CC(C)(C)OC(=O)NC1CCCN(c2ncccc2N)C1]

Following the method of Example 49 (Method 2), tert-butyl 1-(3-nitropyridin-2-yl)piperidin-3-ylcarbamate was reduced yielding tert-butyl 1-(3-aminopyridin-2-yl)piperidin-3-ylcarbamate, (95%). LCMS (m/z): 293.2 (MH$^+$); LC $R_t$=1.87 min.

Example 58

Synthesis of 4-(4-(dimethylamino)piperidin-1-yl)pyridin-3-amine

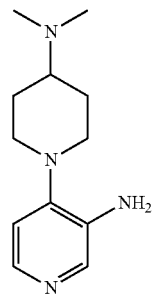

Following the method of Example 49 (Method 2), N,N-dimethyl-1-(3-nitropyridin-4-yl)piperidin-4-amine was reduced yielding 4-(4-(dimethylamino)piperidin-1-yl)pyridin-3-amine. LCMS (m/z): 221.2 (MH$^+$);

Example 59

Synthesis of 4-(1,4-dioxa-8-azaspiro[4.5]decan-8-yl)pyridin-3-amine

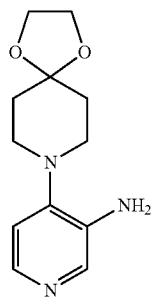 [SMILES: Nc1cnccc1N1CCC2(CC1)OCCO2]

Following the method of Example 49 (Method 2), 8-(3-nitropyridin-4-yl)-1,4-dioxa-8-azaspiro[4.5]decane was reduced yielding 4-(1,4-dioxa-8-azaspiro[4.5]decan-8-yl)pyridin-3-amine. LCMS (m/z): 236.2 (MH$^+$).

Example 60

Synthesis of tert-butyl 4-(3-aminopyridin-4-yl)-1,4-diazepane-1-carboxylate

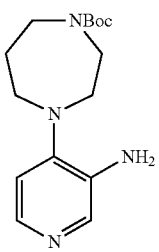 [SMILES: CC(C)(C)OC(=O)N1CCCN(c2ccncc2N)CC1]

Following the method of Example 49 (Method 2), tert-butyl 4-(3-nitropyridin-4-yl)-1,4-diazepane-1-carboxylate was reduced yielding tert-butyl 4-(3-aminopyridin-4-yl)-1,4-diazepane-1-carboxylate. LCMS (m/z): 293.3 (MH$^+$).

Example 61

Synthesis of N$^4$-[2-(dimethylamino)ethyl]-N$^4$-methylpyridine-3,4-diamine

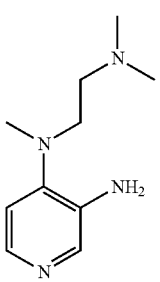

Following the method of Example 49 (Method 2), N$^1$,N$^1$,N$^2$-trimethyl-N$^2$-(3-nitropyridin-4-yl)ethane-1,2-diamine was reduced yielding N$^4$-[2-(dimethylamino)ethyl]-M-methylpyridine-3,4-diamine. Concentrated and took on as is. LCMS (m/z): 195.2 (MH$^+$); LC R$_f$=0.31 min.

Example 62

Synthesis of tert-butyl 1-(3-aminopyridin-4-yl)pyrrolidin-3-ylcarbamate

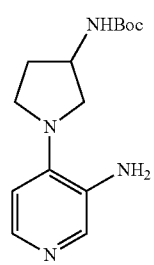

Following the method of Example 49 (Method 2), tert-butyl 1-(3-nitropyridin-4-yl)pyrrolidin-3-ylcarbamate was reduced yielding tert-butyl 1-(3-aminopyridin-4-yl)pyrrolidin-3-ylcarbamate. Concentrated and took on as is. LCMS (m/z): 279.1 (MH$^+$); LC R$_f$=1.75 min.

Example 63

Synthesis of (R)-tert-butyl[1-(3-aminopyridin-4-yl)pyrrolidin-2-yl]methylcarbamate

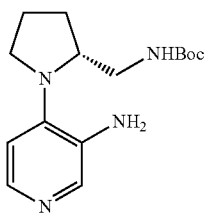

Following the method of Example 49 (Method 2), (R)-tert-butyl[1-(3-nitropyridin-4-yl)pyrrolidin-2-yl]methyl carbamate was reduced yielding (R)-tert-butyl[1-(3-aminopyridin-4-yl)pyrrolidin-2-yl]methylcarbamate. Concentrated and took on as is. LCMS (m/z): 293.1 (MH$^+$); LC R$_f$=1.79 min.

Example 64

Synthesis of 4-(piperidin-1-yl)pyrimidin-5-amine

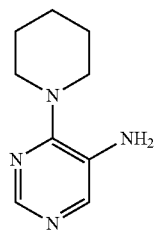 [SMILES: Nc1cncnc1N1CCCCC1]

Following the method of Example 49 (Method 2), 2-chloro-5-nitro-4-(piperidin-1-yl)pyrimidine was reduced yielding 4-(piperidin-1-yl)pyrimidin-5-amine as the HCl salt (100%). LCMS (m/z): 179.0 (MH$^+$); LC R$_f$=1.51 min

Example 65

Synthesis of tert-butyl 1-(2-amino-3-fluorophenyl)piperidin-4-ylcarbamate

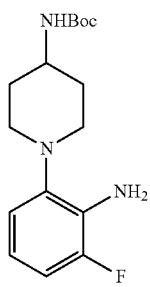 [SMILES: CC(C)(C)OC(=O)NC1CCN(c2cccc(F)c2N)CC1]

Following the method of Example 49 (Method 2), tert-butyl 1-(3-fluoro-2-nitrophenyl)piperidin-4-ylcarbamate was reduced in 75 min yielding tert-butyl 1-(2-amino-3-fluorophenyl)piperidin-4-yl-carbamate (95%). LCMS (m/z): 310.2 (MH$^+$); LC R$_t$=2.64 min.

Example 66

Synthesis of tert-butyl 1-(2-amino-5-fluorophenyl)piperidin-4-ylcarbamate

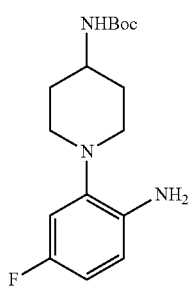 [SMILES: CC(C)(C)OC(=O)NC1CCN(c2cc(F)ccc2N)CC1]

Following the method of Example 49 (Method 2), tert-butyl 1-(5-fluoro-2-nitrophenyl)piperidin-4-ylcarbamate was reduced in 75 min yielding tert-butyl 1-(2-amino-5-fluorophenyl)piperidin-4-ylcarbamate (97%). LCMS (m/z): 310.1 (MH$^+$); LC R$_t$=2.25 min.

Example 67

Synthesis of tert-butyl 1-(2-amino-4-fluorophenyl)piperidin-4-ylcarbamate

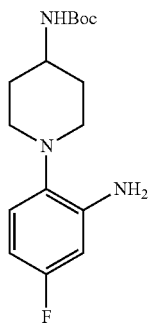 [SMILES: CC(C)(C)OC(=O)NC1CCN(c2ccc(F)cc2N)CC1]

Following the method of Example 49 (Method 2), tert-butyl 1-(4-fluoro-2-nitrophenyl)piperidin-4-ylcarbamate was reduced yielding tert-butyl 1-(2-amino-4-fluorophenyl)piperidin-4-ylcarbamate (90%). LCMS (m/z): 310.1 (MH$^+$); LC R$_t$=2.36 min.

Example 68

Synthesis of tert-butyl 1-(2-amino-4-methoxyphenyl)piperidin-3-ylcarbamate

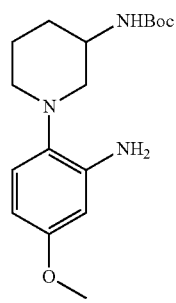

Following the method of Example 49 (Method 2), tert-butyl 1-(4-methoxy-2-nitrophenyl)piperidin-3-ylcarbamate was reduced for 24 hours yielding tert-butyl 1-(2-amino-4-methoxyphenyl)piperidin-3-yl-carbamate (25%). LCMS (m/z): 322.2 (MH$^+$); LC R$_t$=2.27 min.

Example 69

Synthesis of tert-butyl 1-(2-amino-4-methoxyphenyl)piperidin-4-ylcarbamate

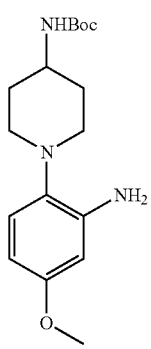

Following the method of Example 49 (Method 2), tert-butyl 1-(4-methoxy-2-nitrophenyl)piperidin-4-ylcarbamate was reduced for 24 hours yielding tert-butyl 1-(2-amino-4-methoxyphenyl)piperidin-4-ylcarbamate (50%). LCMS (m/z): 322.2 (MH$^+$); LC R$_t$=2.16 min.

Example 70

Synthesis of tert-butyl 4-(2-amino-4-methoxyphenyl)piperazine-1-carboxylate

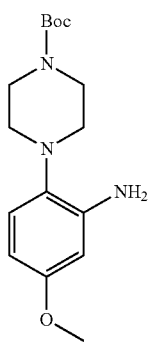

Following the method of Example 49 (Method 2), tert-butyl 4-(4-methoxy-2-nitrophenyl)piperazine-1-carboxylate was reduced for 24 hours yielding tert-butyl 4-(2-amino-4-methoxyphenyl)piperazine-1-carboxylate (20%). LCMS (m/z): 308.2 (MH$^+$); LC R$_t$=2.35 min.

Example 71

Synthesis of tert-butyl 4-(2-amino-4-methylphenyl)piperazine-1-carboxylate

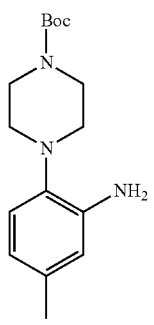

Following the method of Example 49 (Method 2), tert-butyl 4-(4-methyl-2-nitrophenyl)piperazine-1-carboxylate was reduced for 2 hours yielding tert-butyl 4-(2-amino-4-methylphenyl)piperazine-1-carboxylate (93%). LCMS (m/z): 292.1 (MH$^+$); LC R$_t$=2.33 min.

Example 72

Synthesis of tert-butyl 1-(2-amino-4-methylphenyl)piperidin-4-ylcarbamate

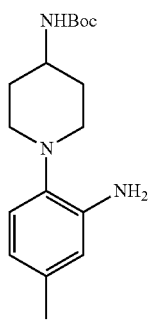

Following the method of Example 49 (Method 2), tert-butyl 1-(4-methyl-2-nitrophenyl)piperidin-4-ylcarbamate was reduced for 2 hours yielding tert-butyl 1-(2-amino-4-methylphenyl)piperidin-4-ylcarbamate (95%). LCMS (m/z): 306.2 (MH$^+$); LC R$_t$=2.22 min.

Example 73

Synthesis of tert-butyl 1-(2-amino-4-methylphenyl)piperidin-3-ylcarbamate

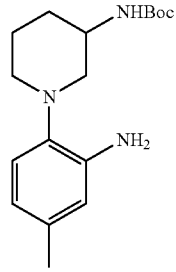

Following the method of Example 49 (Method 2), tert-butyl 1-(4-methyl-2-nitrophenyl)piperidin-3-ylcarbamate was reduced for 2 hours yielding tert-butyl 1-(2-amino-4-methylphenyl)piperidin-3-ylcarbamate (95%). LCMS (m/z): 306.2 (MH$^+$); LC R$_t$=2.30 min.

Example 74

Synthesis of tert-butyl 4-(2-amino-5-methylphenyl)piperazine-1-carboxylate

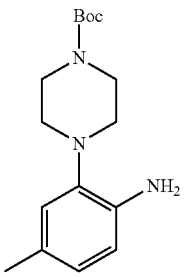

Following the method of Example 49 (Method 2), tert-butyl 4-(5-methyl-2-nitrophenyl)piperazine-1-carboxylate was reduced yielding tert-butyl 4-(2-amino-5-methylphenyl)piperazine-1-carboxylate (90%). LCMS (m/z): 292.1 (MH$^+$); LC R$_t$=2.29 min.

Example 75

Synthesis of tert-butyl 1-(2-amino-5-methylphenyl)piperidin-4-ylcarbamate

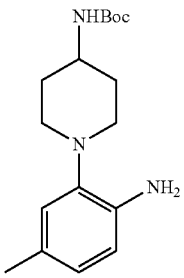

Following the method of Example 49 (Method 2), tert-butyl 1-(5-methyl-2-nitrophenyl)piperidin-4-ylcarbamate was reduced for 1 hour yielding tert-butyl 1-(2-amino-5-methylphenyl)piperidin-4-yl-carbamate (93%). LCMS (m/z): 306.2 (MH$^+$); LC R$_t$=2.25 min.

Example 76

Synthesis of tert-butyl 1-(2-amino-5-methylphenyl)piperidin-3-ylcarbamate

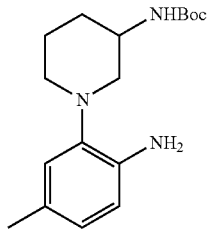 [SMILES: Cc1ccc(N)c(N2CCCC(NC(=O)OC(C)(C)C)C2)c1]

Following the method of Example 49 (Method 2), tert-butyl 1-(5-methyl-2-nitrophenyl)piperidin-3-ylcarbamate was reduced for 1 hour yielding tert-butyl 1-(2-amino-5-methylphenyl)piperidin-3-yl-carbamate (95%). LCMS (m/z): 306.2 (MH$^+$); LC R$_t$=2.29 min.

Example 77

Synthesis of tert-butyl 1-(2-amino-4-(trifluoromethyl)phenyl)piperidin-3-ylcarbamate

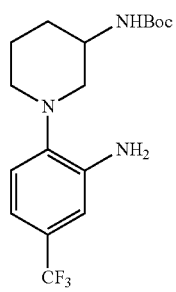 [SMILES: CC(C)(C)OC(=O)NC1CCCN(c2ccc(C(F)(F)F)cc2N)C1]

Following the method of Example 49 (Method 2), tert-butyl 1-(2-nitro-4-(trifluoromethyl)phenyl)piperidin-3-yl carbamate in MeOH was reduced yielding tert-butyl 1-(2-amino-4-(trifluoromethyl)phenyl)piperidin-3-ylcarbamate (95%). LCMS (m/z): 360.1 (MH$^+$); LC R$_t$=3.30 min

Example 78

Synthesis of tert-butyl 1-(2-amino-4-(trifluoromethyl)phenyl)piperidin-4-ylcarbamate

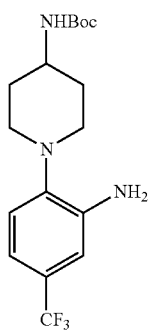

Following the method of Example 49 (Method 2), tert-butyl 1-(2-nitro-4-(trifluoromethyl)phenyl)piperidin-4-yl-carbamate in MeOH was reduced yielding tert-butyl 1-(2-amino-4-(trifluoromethyl)phenyl)piperidin-4-ylcarbamate (97%). LCMS (m/z): 360.1 (MH$^+$); LC R$_t$=3.20 min.

Example 79

Synthesis of tert-butyl 4-(2-amino-4-(trifluoromethyl)phenyl)piperazine-1-carboxylate

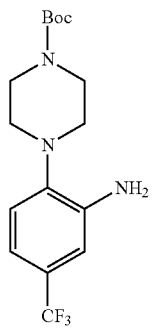

Following the method of Example 49 (Method 2), tert-butyl 4-(2-nitro-4-(trifluoro-methyl)phenyl)piperazine-1-carboxylate in MeOH was reduced yielding tert-butyl 4-(2-amino-4-(trifluoromethyl)phenyl)piperazine-1-carboxylate (99%). LCMS (m/z): 346.1 (MH$^+$); LC R$_t$=3.38 min.

Example 80

Synthesis of tert-butyl 1-(2-amino-4-cyanophenyl)piperidin-3-ylcarbamate

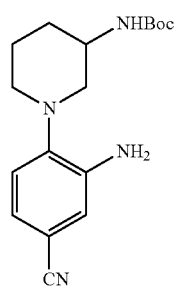

Following the method of Example 49 (Method 2), tert-butyl 1-(4-cyano-2-nitrophenyl)piperidin-3-ylcarbamate was reduced yielding tert-butyl 1-(2-amino-4-cyanophenyl)piperidin-3-ylcarbamate (95%). LCMS (m/z): 317.2 (MH$^+$); LC R$_t$=2.92 min.

Example 81

Synthesis of tert-butyl 1-(2-amino-4-(1H-pyrazol-5-yl)phenyl)piperidin-4-ylcarbamate

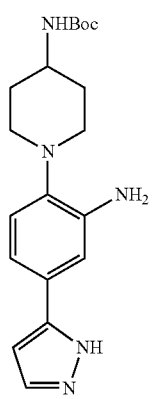

Following the method of Example 49 (Method 2), tert-butyl 1-(2-nitro-4-(1H-pyrazol-5-yl)phenyl)piperidin-4-yl-carbamate was reduced yielding tert-butyl 1-(2-amino-4-

(1H-pyrazol-5-yl)phenyl)piperidin-4-ylcarbamate (87%). LCMS (m/z): 258.1 (MH+); LC $R_t$=2.15 min.

Example 82

Synthesis of tert-butyl 1-(2-amino-4-(methylsulfonyl)phenyl)piperidin-4-ylcarbamate

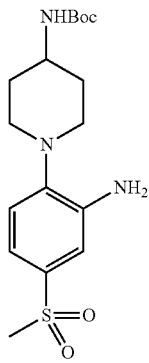 [SMILES: CC(C)(C)OC(=O)NC1CCN(c2ccc(S(C)(=O)=O)cc2N)CC1]

Following the method of Example 49 (Method 2), tert-butyl 1-(4-(methylsulfonyl)-2-nitrophenyl)piperidin-4-ylcarbamate was reduced yielding tert-butyl 1-(2-amino-4-(methylsulfonyl)phenyl)piperidin-4-ylcarbamate (76%). LCMS (m/z): 370.1 (MH+); LC $R_t$=2.52 min.

Example 83

Synthesis of tert-butyl 2-(3-aminopyridin-4-yloxy)ethylcarbamate

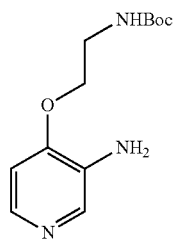 [SMILES: CC(C)(C)OC(=O)NCCOc1ccncc1N]

Following the method of Example 49 (Method 2), tert-butyl 2-(3-nitropyridin-4-yloxy)ethylcarbamate was reduced to yield tert-butyl 2-(3-aminopyridin-4-yloxy)ethylcarbamate. LCMS (m/z): 254.1 (MH+); LC $R_t$=1.76 min.

Method 3

Example 84

Synthesis of tert-butyl 3-(4-(3-nitropyridin-4-yl)piperazin-1-yl)-3-oxopropylcarbamate

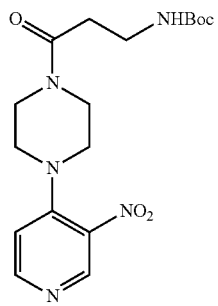

A solution containing 1.0 eq each of 1-(3-nitropyridin-4-yl)piperazine, N-Boc-beta-alanine, HOAT and EDC in DCM, at a concentration of 0.1 M, was stirred for 16 hours. The solution was diluted with EtOAc and was washed with H$_2$O, Na$_2$CO$_{3(sat)}$, NaCl$_{(sat.)}$, was dried over MgSO$_4$, was filtered and the volatiles were removed in vacuo yielding tert-butyl 3-(4-(3-nitropyridin-4-yl)piperazin-1-yl)-3-oxopropylcarbamate (93%). LCMS (m/z): 379.9 (MH+); LC $R_t$=1.92 min.

Example 85

Synthesis of tert-butyl 3-(4-(3-aminopyridin-4-yl)piperazin-1-yl)-3-oxopropylcarbamate

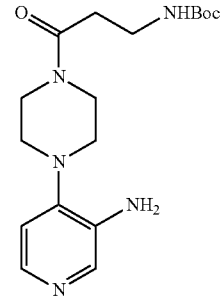 [SMILES: CC(C)(C)OC(=O)NCCC(=O)N1CCN(c2ccncc2[N+](=O)[O-])CC1]

Following the method of Example 49 (Method 2), tert-butyl 3-(4-(3-nitropyridin-4-yl)piperazin-1-yl)-3-oxopropylcarbamate was reduced yielding tert-butyl (tert-butyl 3-(4-(3-aminopyridin-4-yl)piperazin-1-yl)-3-oxopropylcarbamate (99% yield). LCMS (m/z): 349.9 (MH+); LC $R_t$=1.84 min.

Example 86

Synthesis of tert-butyl 2-(4-(3-nitropyridin-4-yl)piperazin-1-yl)-2-oxoethylcarbamate

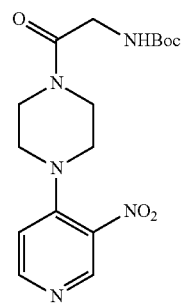 [SMILES: CC(C)(C)OC(=O)NCC(=O)N1CCN(c2ccncc2[N+](=O)[O-])CC1]

Following the method of Example 84 (Method 3), 1-(3-nitropyridin-4-yl)piperazine was coupled to N-Boc-glycine yielding tert-butyl 2-(4-(3-nitropyridin-4-yl)piperazin-1-yl)-2-oxoethylcarbamate (99% yield). LCMS (m/z): 365.8 (MH+); LC $R_t$=1.81 min.

Example 87

Synthesis of tert-butyl 2-(4-(3-aminopyridin-4-yl)piperazin-1-yl)-2-oxoethylcarbamate

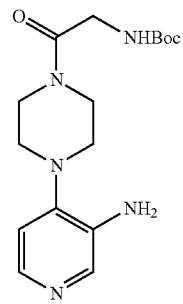

Following the method of Example 49 (Method 2), tert-butyl 2-(4-(3-nitropyridin-4-yl)piperazin-1-yl)-2-oxoethylcarbamate was reduced yielding tert-butyl (tert-butyl 2-(4-(3-

Method 4

Example 88

Synthesis of 4-nitro-3-(piperidin-1-yl)pyridine 1-oxide

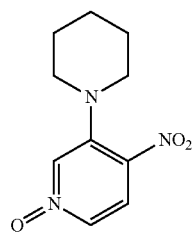 [SMILES: O=[N+]([O-])c1cc[n+]([O-])cc1N1CCCCC1]

3-bromo-4-nitropyridine-N-oxide (1.0 equiv.) and piperidine (2.0 equiv.) in ethanol, at a concentration of 0.2 M, was heated at reflux for 16 hours. Upon cooling the ethanol was removed in vacuo. The residue was partitioned between EtOAc and $Na_2CO_{3(sat)}$, and washed further with $H_2O$, $NaCl_{(sat.)}$, was dried over $MgSO_4$, was filtered and the volatiles were removed in vacuo yielding 4-nitro-3-(piperidin-1-yl)pyridine 1-oxide (92%). LCMS (m/z): 224.0 ($MH^+$); LC $R_t$=2.48 min.

Example 89

Synthesis of tert-butyl 1-(4-nitropyridin-3-yl)piperidin-3-ylcarbamate

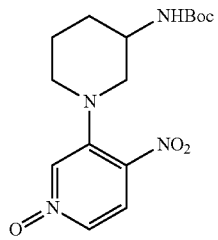 [SMILES: CC(C)(C)OC(=O)NC1CCCN(c2c[n+]([O-])ccc2[N+](=O)[O-])C1]

The method of Example 88 (Method 4) was followed using 1 eq each of 3-bromo-4-nitropyridine-N-oxide, 3-N-Boc-amino piperidine and diisopropylethylamine yielding tert-butyl 1-(4-nitropyridin-3-yl)piperidin-3-ylcarbamate (65%). LCMS (m/z): 339.1 ($MH^+$); LC $R_t$=2.88 min.

Method 5

Example 90

Synthesis of 3-(piperidin-1-yl)pyridin-4-amine

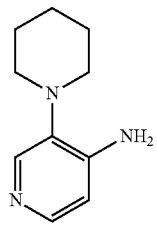

To a solution of 4-nitro-3-(piperidin-1-yl)pyridine 1-oxide (1.0 equiv.) in ethanol, at a concentration of 0.1 M, was added 10% palladium on carbon (0.1 eq.). The resultant heterogeneous solution was put under an atmosphere of hydrogen and was stirred for 15 hours. At this time LC/MS analysis indicated that the nitro was reduced to the amine, but the N-oxide was remaining. More 10% palladium on carbon (0.2 eq.) was added and the mixture was resubmitted to a balloon atmosphere of hydrogen. After stirring for 24 hours, more 10% palladium on carbon (0.2 eq.) was added and the mixture was resubmitted to a balloon atmosphere of hydrogen. After stirring for an additional 3 days the mixture was filtered through a pad of celite eluting with methanol. The volatiles were removed in vacuo yielding 3-(piperidin-1-yl)pyridin-4-amine (73%). LCMS (m/z): 178.0 ($MH^+$); LC $R_t$=1.66 min.

Example 91

Synthesis of tert-butyl 1-(4-aminopyridin-3-yl)piperidin-3-ylcarbamate

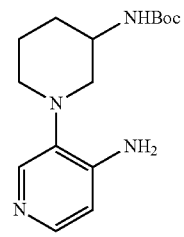

The method of Example 90 (Method 5) was followed using 1 eq of tert-butyl 1-(4-nitropyridin-3-yl)piperidin-3-ylcarbamate in 1:1 ethanol/ethyl acetate at 30 psi for 72 hours, yielding tert-butyl 1-(4-aminopyridin-3-yl)piperidin-3-ylcarbamate (79%). LCMS (m/z): 293.1 ($MH^+$); LC $R_t$=2.14 min.

Method 6

Example 92

Synthesis of 4-cyclohexenyl-3-nitropyridine

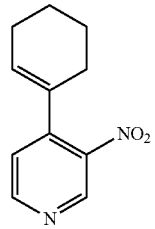 [SMILES: O=[N+]([O-])c1cnccc1C1=CCCCC1]

A solution of 4-chloro-3-nitro pyridine (1 eq.), cyclohexenyl boronic acid (1.7 eq.), and $Pd(dppf)Cl_2$—$CH_2Cl_2$ (0.05 eq) in 3:1 DME/2M $Na_2CO_3$, at a concentration of 0.1 M was heated at 95° C. for 16 hours. Upon cooling the reaction was partitioned between EtOAc and $H_2O$, was washed with $NaCl_{(sat.)}$, dried over $MgSO_4$, was filtered and the volatiles were removed in vacuo. The material was purified by $SiO_2$ chromatography (20% EtOAc/hexanes eluant) to yield 4-cyclohexenyl-3-nitropyridine (82%). LCMS (m/z): 205.0 ($MH^+$); LC $R_t$=3.84 min.

Example 93

Synthesis of 3-nitro-4-o-tolylpyridine

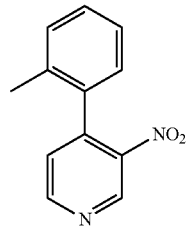 [SMILES: Cc1ccccc1-c1ccncc1[N+](=O)[O-]]

The method of Example 92 (Method 6) was followed using ortho-tolyl boronic acid for 3 hours, yielding 3-nitro-4-o-tolylpyridine (88%). LCMS (m/z): 215.1 (MH$^+$); LC R$_t$=3.58 min.

Method 7

Example 94

Synthesis of 4-cyclohexenylpyridin-3-amine

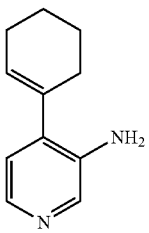 [SMILES: Nc1cnccc1C1=CCCCC1]

A heterogeneous solution of 4-cyclohexenyl-3-nitropyridine (1.0 eq.) and iron (6.0 eq) in acetic acid, at a concentration of 0.4 M, was stirred vigorously for 2 hours. The mixture was then passed through a celite pad, eluting with MeOH. Upon removal of the volatiles in vacuo, the residue was dissolved in EtOAc, washed with Na$_2$CO$_{3(sat.)}$, NaCl$_{(sat.)}$, was dried over MgSO$_4$, was filtered and the volatiles were removed in vacuo yielding 4-cyclohexenylpyridin-3-amine (99%) as an oil. LCMS (m/z): 175.0 (MH$^+$); LC R$_t$=1.86 min.

Example 95

Synthesis of 4-o-tolylpyridine-3-amine

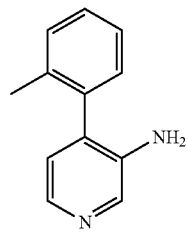

The method of Example 94 (Method 7) was followed using 3-nitro-4-O— tolylpyridine yielding 4-o-tolylpyridine-3-amine (97%). LCMS (m/z): 185.1 (MH$^+$); LC R$_t$=1.78 min.

Example 96

Synthesis of tert-butyl 1-(2-amino-4-benzoylphenyl)piperidin-3-ylcarbamate

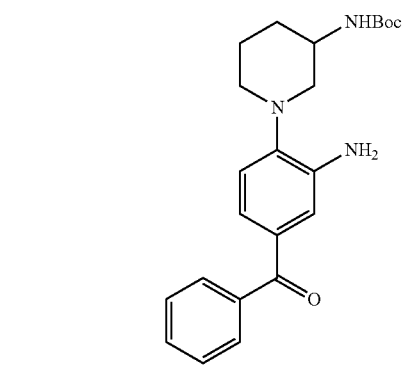

Following method 7, tert-butyl 1-(4-benzoyl-2-nitrophenyl)piperidin-3-ylcarbamate was reduced for 16 hours, filtered, and concentrated. Water was added to the residue. The resulting solids were collected by filtration and dried in vacuo yielding tert-butyl 1-(2-amino-4-benzoylphenyl)piperidin-3-ylcarbamate (90%). LCMS (m/z): 396.2 (MH$^+$); LC R$_t$=3.07 min.

Example 97

Synthesis of tert-butyl 1-(2-amino-4-benzoylphenyl)piperidin-4-ylcarbamate

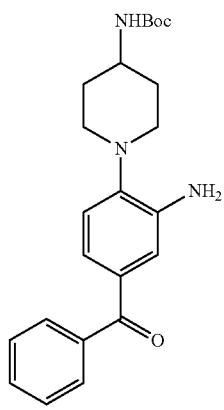 [SMILES: CC(C)(C)OC(=O)NC1CCN(c2ccc(C(=O)c3ccccc3)cc2N)CC1]

Following method 7, tert-butyl 1-(4-benzoyl-2-nitrophenyl)piperidin-4-ylcarbamate was reduced for 16 hours, filtered, and concentrated. Water was added to the residue. The resulting solids were collected by filtration and dried in vacuo yielding tert-butyl 1-(2-amino-4-benzoylphenyl)piperidin-4-ylcarbamate (83%). LCMS (m/z): 396.2 (MH$^+$); LC R$_t$=2.81 min.

Example 98

Synthesis of tert-butyl 4-(2-amino-4-benzoylphenyl)piperazine-1-carboxylate

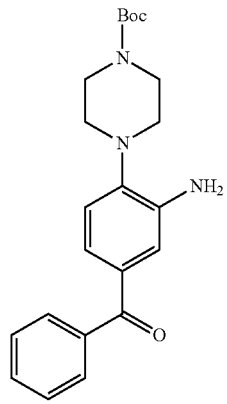

Following method 7, tert-butyl 1-(4-benzoyl-2-nitrophenyl)piperidin-4-ylcarbamate was reduced for 16 hours, filtered, and concentrated. Water was added to the residue. The resulting solids were collected by filtration and dried in vacuo yielding tert-butyl 4-(2-amino-4-benzoylphenyl)piperazine-1-carboxylate (61%). LCMS (m/z): 382.2 (MH$^+$); LC R$_t$=3.01 min.

Example 99

Synthesis of tert-butyl 4-(4-acetyl-2-amino phenyl)piperazine-1-carboxylate

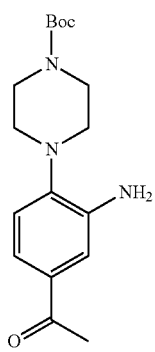

Following method 7, tert-butyl 4-(4-acetyl-2-nitrophenyl)piperazine-1-carboxylate was reduced, filtered, and concentrated. Water was added to the residue. The resulting solids were collected by filtration and dried in vacuo yielding tert-butyl 4-(4-acetyl-2-amino phenyl)piperazine-1-carboxylate (87%). LCMS (m/z): 320.2 (MH$^+$); LC R$_t$=2.58 min.

Example 100

Synthesis of tert-butyl 1-(4-acetyl-2-aminophenyl)piperidin-4-ylcarbamate

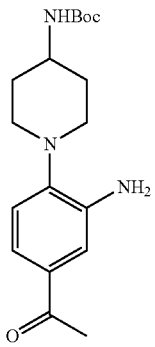

Following method 7, tert-butyl 1-(4-acetyl-2-nitrophenyl)piperidin-4-ylcarbamate was reduced, filtered, and concentrated. Water was added to the residue. The resulting solids were collected by filtration and dried in vacuo yielding tert-butyl 1-(4-acetyl-2-amino phenyl)piperidin-4-ylcarbamate (90%). LCMS (m/z): 334.2 (MH$^+$); LC R$_t$=2.42 min.

Example 101

Synthesis of tert-butyl 1-(4-acetyl-2-aminophenyl)piperidin-3-ylcarbamate

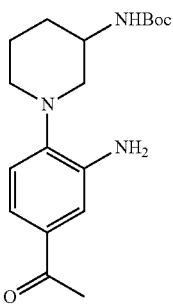 [SMILES: CC(=O)c1ccc(N2CCCC(NC(=O)OC(C)(C)C)C2)c(N)c1]

Following method 7, tert-butyl 1-(4-acetyl-2-nitro phenyl)piperidin-3-ylcarbamate was reduced, filtered, and concentrated. Water was added to the residue. The resulting solids were collected by filtration and dried in vacuo yielding tert-butyl 1-(4-acetyl-2-amino phenyl)piperidin-3-ylcarbamate (88%). LCMS (m/z): 334.2 (MH$^+$); LC R$_t$=2.49 min.

Example 102

Synthesis of tert-butyl 4-(2-amino-4-chlorophenyl)piperazine-1-carboxylate

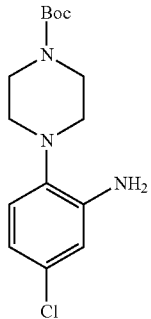

Following method 7, tert-butyl 4-(4-chloro-2-nitrophenyl)piperazine-1-carboxylate was reduced, filtered, and concentrated. Water was added to the residue. The resulting solids were collected by filtration and dried in vacuo yielding tert-butyl 4-(2-amino-4-chloro phenyl)piperazine-1-carboxylate (80%). LCMS (m/z): 312.1 (MH+); LC R$_t$=2.85 min.

Example 103

Synthesis of tert-butyl 1-(2-amino-4-chlorophenyl)piperidin-4-ylcarbamate

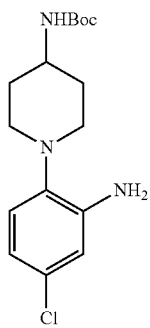 [SMILES: CC(C)(C)OC(=O)NC1CCN(c2ccc(Cl)cc2N)CC1]

Following method 7, tert-butyl 1-(4-chloro-2-nitrophenyl) piperidin-4-ylcarbamate was reduced, filtered, and concentrated. Water was added to the residue. The resulting solids were collected by filtration and dried, in vacuo yielding tert-butyl 1-(2-amino-4-chloro phenyl)piperidin-4-ylcarbamate (68%). LCMS (m/z): 326.1 (MH+); LC R$_t$=2.67 min.

Example 104

Synthesis of tert-butyl 1-(2-amino-4-chlorophenyl)piperidin-3-ylcarbamate

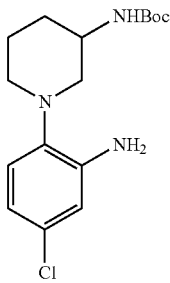 [SMILES: CC(C)(C)OC(=O)NC1CCCN(c2ccc(Cl)cc2N)C1]

Following method 7, tert-butyl 1-(4-chloro-2-nitrophenyl) piperidin-3-ylcarbamate was reduced, filtered, and concentrated. Water was added to the residue. The resulting solids were collected by filtration and dried in vacuo yielding tert-butyl 1-(2-amino-4-chloro phenyl)piperidin-3-ylcarbamate (85%). LCMS (m/z): 326.1 (MH+); LC R$_t$=2.76 min.

Example 105

Synthesis of tert-butyl 4-(4-(cyclopropanecarbonyl)-2-nitrophenyl)piperazine-1-carboxylate

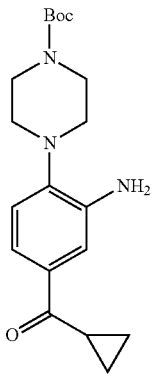

Following method 7, tert-butyl 4-(4-(cyclopropanecarbonyl)-2-nitrophenyl)piperazine-1-carboxylate was reduced, filtered, and concentrated. Water was added to the residue. The resulting solids were collected by filtration and dried in vacuo yielding tert-butyl 1-(2-amino-4-chloro phenyl)piperidin-4-ylcarbamate (90%). LCMS (m/z): 346.2 (MH+); LC R$_t$=2.83 min.

Example 106

Synthesis of tert-butyl 1-(2-amino-4-(cyclopropanecarbonyl)phenyl)piperidin-4-ylcarbamate

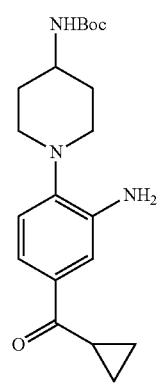

Following method 7, tert-butyl 1-(4-(cyclopropanecarbonyl)-2-nitrophenyl)piperidin-4-ylcarbamate was reduced, filtered, and concentrated. Water was added to the residue. The resulting solids were collected by filtration and dried in vacuo yielding tert-butyl 1-(2-amino-4-(cyclopropanecarbonyl) phenyl)piperidin-4-ylcarbamate (93%). LCMS (m/z): 360.1 (MH+); LC R$_t$=2.65 min.

Example 107

Synthesis of tert-butyl 1-(2-amino-4-(cyclopropanecarbonyl)phenyl)piperidin-3-ylcarbamate

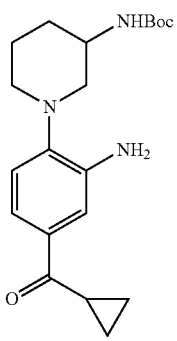

Following method 7, tert-butyl 1-(4-(cyclopropanecarbonyl)-2-nitrophenyl)piperidin-3-ylcarbamate was reduced, filtered, and concentrated. Water was added to the residue. The resulting solids were collected by filtration and dried in vacuo yielding tert-butyl 1-(2-amino-4-(cyclopropanecarbonyl) phenyl)piperidin-3-ylcarbamate (90%). LCMS (m/z): 360.1 (MH+); LC R$_t$=2.74 min.

Method 8

Example 108

Synthesis of 6-amino-5-(4-(trifluoromethyl)piperidin-1-yl)pyrimidin-2(1H)-one

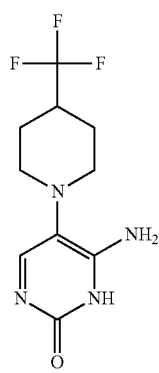

A solution of 5-bromocytosine (1.0 equiv.), 4-(trifluoromethyl)piperidine (1.25 equiv.) and diisopropylethylamine (1.25 equiv.) in N-methylpyrrolidinone (NMP), at a concentration of 0.525 M, was degassed by bubbling argon through for 10 minutes in a 125 mL high-pressure glass vessel. The glass bomb was then sealed and heated at 120° C. for 3 days. The reaction mixture was purified directly by reverse-phase HPLC and lyophilized yielding a TFA salt of the product as a crunchy orange solid (50%). LCMS (m/z): 263.0 (MH$^+$); LC R$_t$=1.81 min.

Example 109

Synthesis of 6-amino-5-(4,4-difluoropiperidin-1-yl)pyrimidin-2(1H)-one

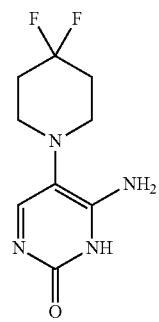 [SMILES: Nc1[nH]c(=O)ncc1N1CCC(F)(F)CC1]

Method 8 was followed using 1 eq. of 5-bromocytosine, 1.25 eq. of 3-fluoropiperidine and 2.5 eq. of diisopropylethylamine at 120° C. for 2 days yielding 6-amino-5-(4,4-difluoropiperidin-1-yl)pyrimidin-2(1H)-one as an orange crunchy solid (34%). LCMS (m/z): 231.0 (MH$^+$); LC R$_t$=1.28 min.

Example 110

Synthesis of 6-amino-5-(3-fluoropiperidin-1-yl)pyrimidin-2(1H)-one

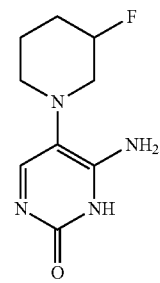 [SMILES: Nc1[nH]c(=O)ncc1N1CCCC(F)C1]

Method 8 was followed using 1 eq. of 5-bromocytosine, 1.25 eq. of 3-fluoropiperidine and 2.5 eq. of diisopropylethylamine at 120° C. for 2 days yielding 6-amino-5-(3-fluoropiperidin-1-yl)pyrimidin-2(1H)-one as an orange crunchy solid (24%). LCMS (m/z): 213.0 (MH$^+$); LC R$_t$=1.07 min.

Example 111

Synthesis of tert-butyl(1-(6-amino-2-oxo-1,2-dihydropyrimidin-5-yl)piperidin-3-yl)methylcarbamate

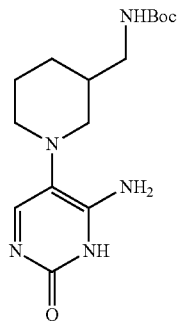 [SMILES: CC(C)(C)OC(=O)NCC1CCCN(c2cnc(=O)[nH]c2N)C1]

Method 8 was followed using 1 eq. of 5-bromocytosine, 1.05 eq. of tert-butyl piperidin-3-ylmethylcarbamate and 1.05 eq. of diisopropylethylamine yielding tert-butyl(1-(6-amino-2-oxo-1,2-dihydropyrimidin-5-yl)piperidin-3-yl)methylcarbamate as an orange crunchy solid (18%). LCMS (m/z): 324.1 (MH$^+$); LC R$_t$=1.90 min.

Example 112

Synthesis of tert-butyl(1-(6-amino-2-oxo-1,2-dihydro pyrimidin-5-yl)piperidin-3-yl)carbamate

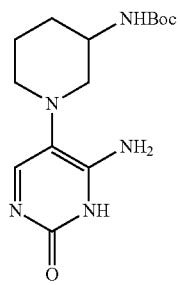 [SMILES: CC(C)(C)OC(=O)NC1CCCN(c2cnc(=O)[nH]c2N)C1]

Method 8 was followed using 1 eq. of 5-bromocytosine, 1.05 eq. of tert-butyl piperidin-3-ylmethylcarbamate and 1.05 eq. of diisopropylethylamine yielding tert-butyl(1-(6-amino-2-oxo-1,2-dihydropyrimidin-5-yl)piperidin-3-yl)carbamate as an orange crunchy solid (26%). LCMS (m/z): 310.1 (MH$^+$); LC R$_t$=1.78 min.

Example 113

Synthesis of tert-butyl 3-(4-(6-amino-2-oxo-1,2-dihydropyrimidin-5-yl)piperazin-1-yl)-3-oxopropylcarbamate

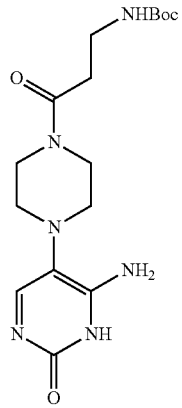 [SMILES: CC(C)(C)OC(=O)NCCC(=O)N1CCN(c2cnc(=O)[nH]c2N)CC1]

Method 8 was followed using 1 eq. of 5-bromocytosine, 1.5 eq. of tert-butyl 3-oxo-3-(piperazin-1-yl)propylcarbamate and 1.2 eq. of diisopropylethylamine yielding tert-butyl 3-(4-(6-amino-2-oxo-1,2-dihydropyrimidin-5-yl)piperazin-1-yl)-3-oxopropyl carbamate as an orange crunchy solid (65%). LCMS (m/z): 367.2 (MH$^+$); LC R$_t$=1.68 min.

Example 114

Synthesis of 6-amino-5-(piperidin-1-yl)pyrimidin-2(1H)-one

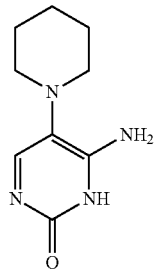 [SMILES: Nc1[nH]c(=O)ncc1N1CCCCC1]

Method 8 was followed using 1 eq. of 5-bromocytosine and 15 eq. of piperidine (as solvent). The reaction was cooled and added to CH$_2$Cl$_2$ and H$_2$O. The solid was filtered, rinsed with H$_2$O, and dried yielding 6-amino-5-(piperidin-1-yl)pyrimidin-2(1H)-one as a solid (89%). LCMS (m/z): 195.0 (MH$^+$); LC R$_t$=1.28 min.

Method 9

Example 115

Synthesis of 3-amino-N-(4-piperidin-1-yl)pyridin-3-yl)pyrazine-2-carboxamide

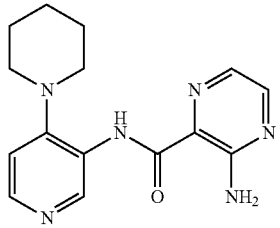 [SMILES: Nc1nccnc1C(=O)Nc1cnccc1N1CCCCC1]

A solution of 1 eq of 4-(piperidin-1-yl)pyridin-3-amine and 2 eq each of 3-aminopyrazine-2-carboxylic acid, HOAT and EDC in NMP, at a concentration of 0.2 M, was stirred for 48 hours at which time the mixture was directly purified by HPLC. Upon lyophilization, the TFA salt of 3-amino-N-(4-(piperidin-1-yl)pyridin-3-yl)pyrazine-2-carboxamide was obtained (61%). Alternatively, the HPLC fractions could be added to EtOAc and solid Na$_2$CO$_3$, separated and washed with NaCl$_{(sat.)}$. Upon drying over MgSO$_4$, filtering and removing the volatiles in vacuo the free base was obtained. Upon dissolving in MeCN/H$_2$O, adding 1 eq. of 1 N HCl and lyophilizing, the HCl salt of 3-amino-N-(4-(piperidin-1-yl)pyridin-3-yl)pyrazine-2-carboxamide was obtained (40%). LCMS (m/z): 298.8 (MH$^+$); LC R$_t$=1.88 min. $^1$H NMR of HCl salt (DMSO$_{d-6}$): δ 10.45 (s, 1H), 8.55 (d, J=0.9, 1H), 8.32 (d, J=2.1, 1H), 8.27 (dd, J=5.7, 1H), 7.93 (d, J=1.8, 1H), 7.57 (s, 1H), 7.32 (d, J=6.9, 1H), 3.76 (s, 4H), 1.59 (s, 6H).

Example 116

Synthesis of 3-amino-6-bromo-N-(4-(piperidin-1-yl)pyridin-3-yl)picolinamide

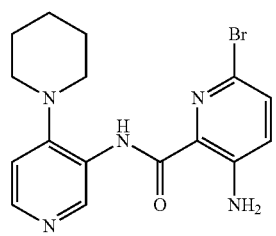 [SMILES: Nc1ccc(Br)nc1C(=O)Nc1cnccc1N1CCCCC1]

The method of Example 115 (Method 9) was followed using 4-(piperidin-1-yl)pyridin-3-amine yielding 3-amino-6-bromo-N-(4-(piperidin-1-yl)pyridin-3-yl)picolinamide (32%). LCMS (m/z): 376.1 (MH$^+$); LC R$_t$=2.77 min.

Example 117

Synthesis of 3-amino-6-bromo-N-(4-o-tolylpyridin-3-yl)picolinamide

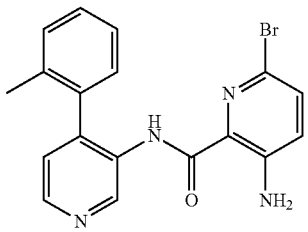 [SMILES: Cc1ccccc1-c1ccncc1NC(=O)c1nc(Br)ccc1N]

The method of Example 115 (Method 9) was followed using 4-o-tolylpyridin-3-amine yielding 3-amino-6-bromo-N-(4-o-tolylpyridin-3-yl)picolinamide (74%). LCMS (m/z): 383.0 (MH$^+$); LC R$_t$=2.99 min.

The following compounds were prepared using Method 9.

| Example | Structure | Name | MH+ | LC |
|---|---|---|---|---|
| 118 | 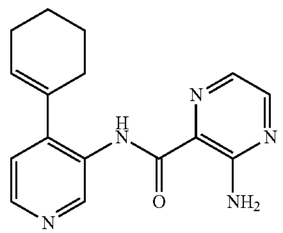 [SMILES: Nc1nccnc1C(=O)Nc1cnccc1C1=CCCCC1] | 3-amino-N-(4-cyclohex-1-en-1-ylpyridin-3-yl)pyrazine-2-carboxamide | 296.1 | 2.32 |
| 119 | 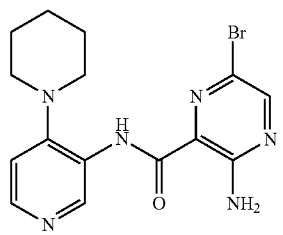 [SMILES: Nc1ncc(Br)nc1C(=O)Nc1cnccc1N1CCCCC1] | 3-amino-6-bromo-N-(4-piperidin-1-ylpyridin-3-yl)pyrazine-2-carboxamide | 377 | 2.46 |
| 120 | 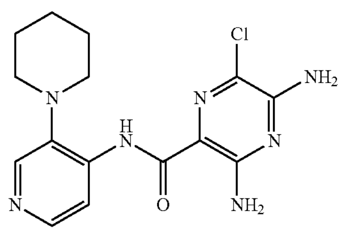 [SMILES: Nc1nc(N)c(C(=O)Nc2ccncc2N2CCCCC2)nc1Cl] | 3,5-diamino-6-chloro-N-(3-piperidin-1-ylpyridin-4-yl)-pyrazine-2-carboxamide | 348.1 | 2.43 |
| 121 | 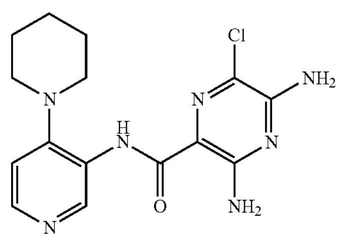 [SMILES: Nc1nc(N)c(C(=O)Nc2cnccc2N2CCCCC2)nc1Cl] | 3,5-diamino-6-chloro-N-(4-piperidin-1-ylpyridin-3-yl)-pyrazine-2-carboxamide | 347.8 | 2.17 |
| 122 | 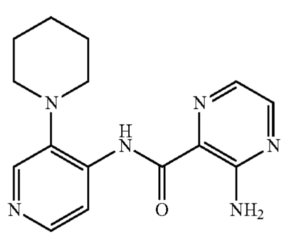 [SMILES: Nc1nccnc1C(=O)Nc1ccncc1N1CCCCC1] | 3-amino-N-(3-piperidin-1-yl-pyridin-4-yl)pyrazine-2-carboxamide | 298.8 | 2.26 |
| 123 | 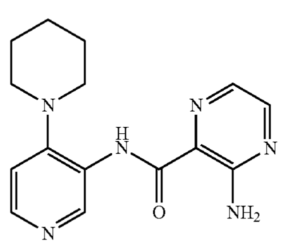 [SMILES: Nc1nccnc1C(=O)Nc1cnccc1N1CCCCC1] | 3-amino-N-(4-piperidin-1-yl-pyridin-3-yl)pyrazine-2-carboxamide | 298.8 | 1.88 |

-continued

| Example | Structure | Name | MH+ | LC |
|---|---|---|---|---|
| 124 | 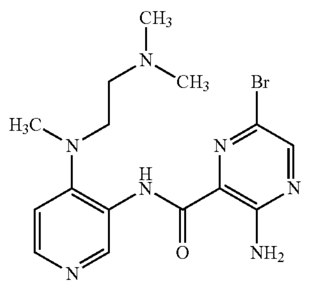 [SMILES: CN(C)CCN(C)c1ccncc1NC(=O)c1nc(Br)cnc1N] | 3-amino-6-bromo-N-(4-{[2-(dimethylamino)ethyl]-(methyl)amino}pyridin-3-yl)pyrazine-2-carboxamide | 396.0 | |
| 125 | 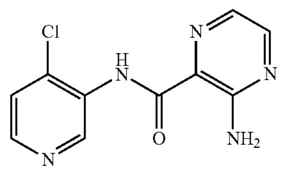 [SMILES: Nc1nccnc1C(=O)Nc1cnccc1Cl] | 3-amino-N-(4-chloropyridin-3-yl)pyrazine-2-carboxamide | 250 | 1.34 |
| 126 | 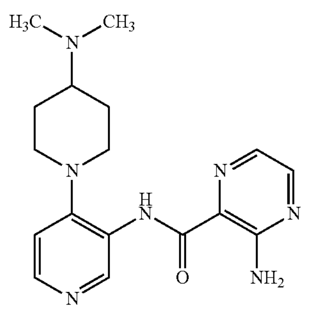 [SMILES: CN(C)C1CCN(c2ccncc2NC(=O)c2nccnc2N)CC1] | 3-amino-N-{4-[4-(dimethyl-amino)piperidin-1-yl]pyridin-3-yl}pyrazine-2-carboxamide | 342.2 | 0.92 |
| 127 | 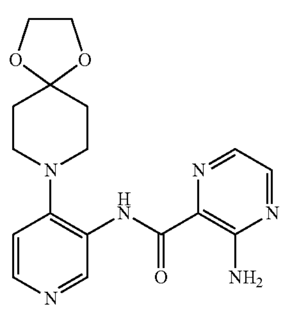 [SMILES: Nc1nccnc1C(=O)Nc1cnccc1N1CCC2(CC1)OCCO2] | 3-amino-N-[4-(1,4-dioxa-8-azaspiro[4.5]dec-8-yl)pyridin-3-yl]pyrazine-2-carboxamide | 357.1 | 1.66 |
| 128 | 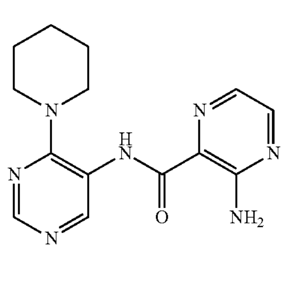 [SMILES: Nc1nccnc1C(=O)Nc1cncnc1N1CCCCC1] | 3-amino-N-(4-piperidin-1-yl-pyrimidin-5-yl)pyrazine-2-carboxamide | 299.7 | 1.72 |

-continued

| Example | Structure | Name | MH+ | LC |
|---|---|---|---|---|
| 129 | 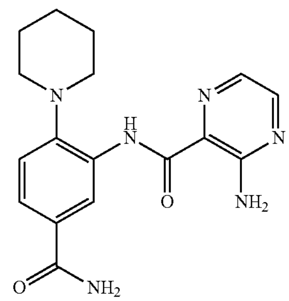 [SMILES: NC(=O)c1ccc(N2CCCCC2)c(NC(=O)c2nccnc2N)c1] | 3-amino-N-(5-carbamoyl-2-piperidin-1-ylphenyl)pyrazine-2-carboxamide | 340.8 | 3.11 |
| 130 | 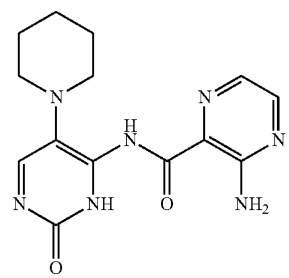 [SMILES: Nc1nccnc1C(=O)Nc1[nH]c(=O)ncc1N1CCCCC1] | 3-amino-N-(2-oxo-5-piperidin-1-yl-2,3-dihydropyrimidin-4-yl)-pyrazine-2-carboxamide | 315.7 | 2.21 |
| 131 | 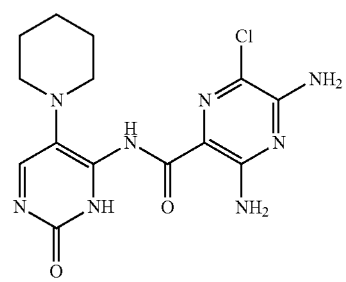 [SMILES: Nc1nc(N)c(C(=O)Nc2[nH]c(=O)ncc2N2CCCCC2)nc1Cl] | 3,5-diamino-6-chloro-N-(2-oxo-5-piperidin-1-yl-2,3-dihydro-pyrimidin-4-yl)pyrazine-2-carboxamide | 365.1 | 2.2 |
| 132 | 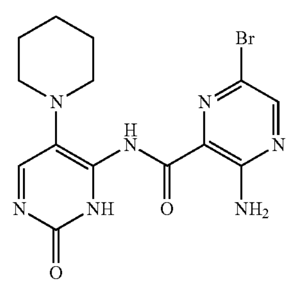 [SMILES: Nc1ncc(Br)nc1C(=O)Nc1[nH]c(=O)ncc1N1CCCCC1] | 3-amino-6-bromo-N-(2-oxo-5-piperidin-1-yl-2,3-dihydro-pyrimidin-4-yl)pyrazine-2-carboxamide | 394 | 2.81 |
| 133 | 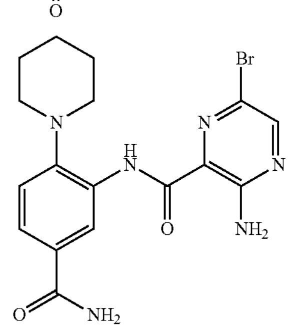 | 3-amino-6-bromo-N-(5-carbamoyl-2-piperidin-1-yl-phenyl)pyrazine-2-carboxamide | 419 | 3.98 |

| Example | Structure | Name | MH+ | LC |
|---|---|---|---|---|
| 134 | 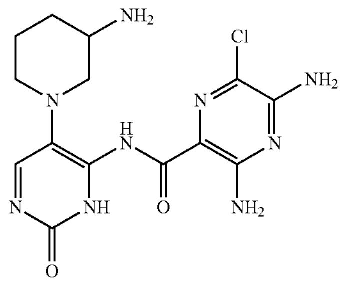 [SMILES: Nc1nc(N)c(C(=O)Nc2[nH]c(=O)ncc2N2CCCC(N)C2)nc1Cl] | 3,5-diamino-N-[5-(3-amino-piperidin-1-yl)-2-oxo-2,3-dihydropyrimidin-4-yl]-6-chloropyrazine-2-carboxamide | 380.1 | 1.29 |
| 135 | 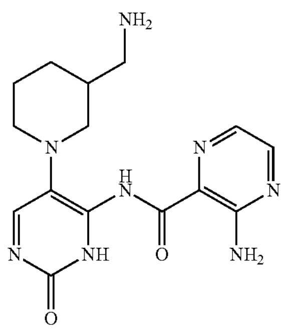 [SMILES: NCC1CCCN(c2cnc(=O)[nH]c2NC(=O)c2nccnc2N)C1] | 3-amino-N-{5-[3-(amino-methyl)piperidin-1-yl]-2-oxo-2,3-dihydropyrimidin-4-yl}-pyrazine-2-carboxamide | 345.1 | 1.39 |
| 136 | 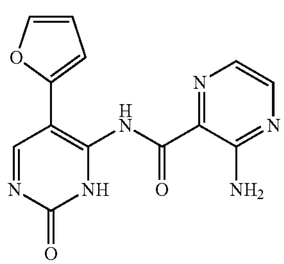 [SMILES: Nc1nccnc1C(=O)Nc1[nH]c(=O)ncc1-c1ccco1] | 3-amino-N-[5-(2-furyl)-2-oxo-2,3-dihydropyrimidin-4-yl]-pyrazine-2-carboxamide | 299 | 1.93 |
| 137 | 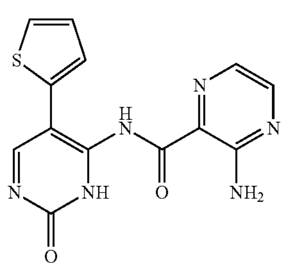 [SMILES: Nc1nccnc1C(=O)Nc1[nH]c(=O)ncc1-c1cccs1] | 3-amino-N-[2-oxo-5-(2-thienyl)-2,3-dihydropyrimidin-4-yl]-pyrazine-2-carboxamide | 315 | 2.02 |
| 138 | 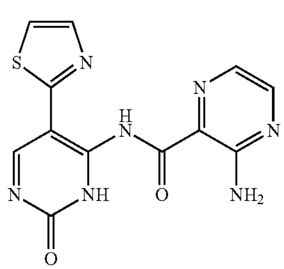 [SMILES: Nc1nccnc1C(=O)Nc1[nH]c(=O)ncc1-c1nccs1] | 3-amino-N-[2-oxo-5-(1,3-thiazol-2-yl)-2,3-dihydro-pyrimidin-4-yl]pyrazine-2-carboxamide | 316 | 1.92 |

-continued

| Example | Name | MH+ | LC |
|---|---|---|---|
| 139 | 3-amino-N-[5-(1-methyl-1H-pyrrol-2-yl)-2-oxo-2,3-dihydro-pyrimidin-4-yl]pyrazine-2-carboxamide | 312.1 | 2.02 |
| 140 | 3-amino-N-(2-oxo-5-pyridin-2-yl-2,3-dihydropyrimidin-4-yl)-pyrazine-2-carboxamide | 310 | 1.82 |
| 141 | 3-amino-6-bromo-N-[5-(2-furyl)-2-oxo-2,3-dihydro-pyrimidin-4-yl]pyrazine-2-carboxamide | 376.9 | 3.98 |
| 142 | 3-amino-6-bromo-N-[2-oxo-5-(2-thienyl)-2,3-dihydro-pyrimidin-4-yl]pyrazine-2-carboxamide | 392.9 | 2.66 |
| 143 | 3-amino-6-bromo-N-[2-oxo-5-(1,3-thiazol-2-yl)-2,3-dihydro-pyrimidin-4-yl]pyrazine-2-carboxamide | 393.9 | 2.53 |
| 144 | 3-amino-6-bromo-N-[5-(1-methyl-1H-pyrrol-2-yl)-2-oxo-2,3-dihydropyrimidin-4-yl]-pyrazine-2-carboxamide | 390 | 2.57 |

-continued

| Example | Name | MH+ | LC |
|---|---|---|---|
| 145 | 3-amino-6-bromo-N-(2-oxo-5-pyridin-2-yl-2,3-dihydro-pyrimidin-4-yl)pyrazine-2-carboxamide | 387.9 | 2.36 |
| 146 | 3-amino-N-{2-oxo-5-[3-(trifluoromethyl)piperidin-1-yl]-2,3-dihydropyrimidin-4-yl}-pyrazine-2-carboxamide | 384.1 | 2.59 |
| 147 | 3-amino-6-bromo-N-{2-oxo-5-[3-(trifluoromethyl)piperidin-1-yl]-2,3-dihydropyrimidin-4-yl}-pyrazine-2-carboxamide | 462 | 3.12 |
| 148 | 3,5-diamino-6-chloro-N-{2-oxo-5-[3-(trifluoromethyl)piperidin-1-yl]-2,3-dihydropyrimidin-4-yl}pyrazine-2-carboxamide | 433.1 | 2.51 |
| 149 | 3-amino-N-[5-(4-fluoro-piperidin-1-yl)-2-oxo-2,3-dihydropyrimidin-4-yl]pyrazine-2-carboxamide | 334.1 | 2 |

| Example | Name | MH+ | LC |
|---|---|---|---|
| 150 | 3-amino-6-bromo-N-[5-(4-fluoropiperidin-1-yl)-2-oxo-2,3-dihydropyrimidin-4-yl]pyrazine-2-carboxamide | 412 | 2.58 |
| 151 | 3,5-diamino-6-chloro-N-[5-(4-fluoropiperidin-1-yl)-2-oxo-2,3-dihydropyrimidin-4-yl]pyrazine-2-carboxamide | 383.1 | 2.02 |
| 152 | 3-amino-N-{2-oxo-5-[4-(trifluoromethyl)piperidin-1-yl]-2,3-dihydropyrimidin-4-yl}-pyrazine-2-carboxamide | 384.1 | 2.62 |
| 153 | 3-amino-6-bromo-N-{2-oxo-5-[4-(trifluoromethyl)piperidin-1-yl]-2,3-dihydropyrimidin-4-yl}-pyrazine-2-carboxamide | 462 | 3.08 |

| Example | Name | MH+ | LC |
|---------|------|-----|-----|
| 154 | 3-amino-N-[5-(3-fluoro-piperidin-1-yl)-2-oxo-2,3-dihydropyrimidin-4-yl]pyrazine-2-carboxamide | 334.1 | 1.99 |
| 155 | 3-amino-6-bromo-N-[5-(3-fluoropiperidin-1-yl)-2-oxo-2,3-dihydropyrimidin-4-yl]pyrazine-2-carboxamide | 412 | 2.58 |
| 156 | 3-amino-N-[5-(4,4-difluoro-piperidin-1-yl)-2-oxo-2,3-dihydropyrimidin-4-yl]pyrazine-2-carboxamide | 352.1 | 2.21 |
| 157 | 3-amino-6-bromo-N-[5-(4,4-difluoropiperidin-1-yl)-2-oxo-2,3-dihydropyrimidin-4-yl]-pyrazine-2-carboxamide | 430 | 2.78 |
| 158 | 3-amino-N-(2-oxo-5-piperidin-1-yl-2,3-dihydropyrimidin-4-yl)-pyridine-2-carboxamide | 315.1 | 1.97 |

-continued

| Example | Structure | Name | MH+ | LC |
|---|---|---|---|---|
| 159 | 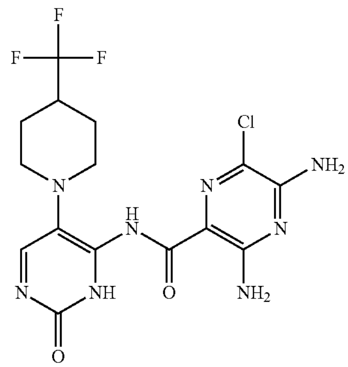 [SMILES: Nc1nc(N)c(C(=O)Nc2[nH]c(=O)ncc2N2CCC(C(F)(F)F)CC2)nc1Cl] | 3,5-diamino-6-chloro-N-{2-oxo-5-[4-(trifluoromethyl)piperidin-1-yl]-2,3-dihydropyrimidin-4-yl}pyrazine-2-carboxamide | 433.1 | 2.5 |
| 160 | 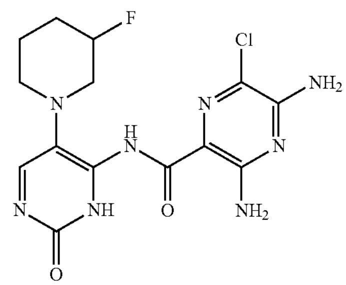 [SMILES: Nc1nc(N)c(C(=O)Nc2[nH]c(=O)ncc2N2CCCC(F)C2)nc1Cl] | 3,5-diamino-6-chloro-N-[5-(3-fluoropiperidin-1-yl)-2-oxo-2,3-dihydropyrimidin-4-yl]pyrazine-2-carboxamide | 383.1 | 1.99 |
| 161 | 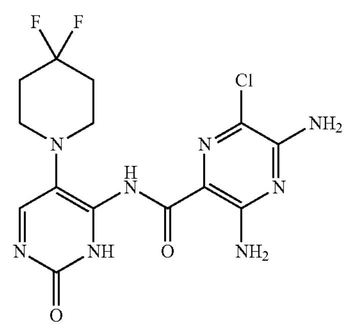 [SMILES: Nc1nc(N)c(C(=O)Nc2[nH]c(=O)ncc2N2CCC(F)(F)CC2)nc1Cl] | 3,5-diamino-6-chloro-N-[5-(4,4-difluoropiperidin-1-yl)-2-oxo-2,3-dihydropyrimidin-4-yl]-pyrazine-2-carboxamide | 401.1 | 2.23 |
| 162 | 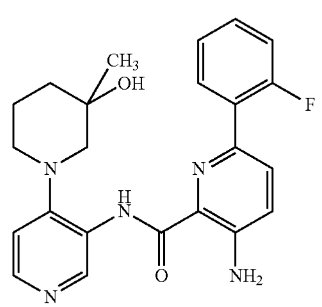 [SMILES: CC1(O)CCCN(c2ccncc2NC(=O)c2nc(-c3ccccc3F)ccc2N)C1] | 3-Amino-6-(2-fluoro-phenyl)-pyridine-2-carboxylic acid (3-hydroxy-3-methyl-3,4,5,6-tetrahydro-2H-[1,4']bipyridinyl-3'-yl)-amide | 422.2 | 2.77 |

| Example | Structure | Name | MH+ | LC |
|---|---|---|---|---|
| 163 | 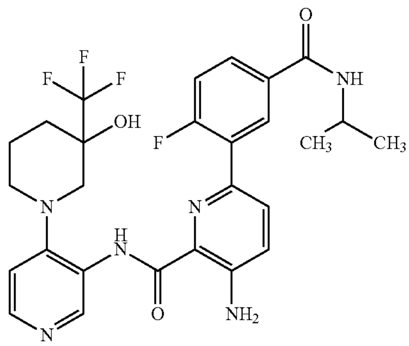 [SMILES: CC(C)NC(=O)c1ccc(F)c(-c2ccc(N)c(C(=O)Nc3cnccc3N3CCCC(O)(C(F)(F)F)C3)n2)c1] | 3-Amino-6-(2-fluoro-5-isopropylcarbamoyl-phenyl)-pyridine-2-carboxylic acid (3-hydroxy-3-trifluoromethyl-3,4,5,6-tetrahydro-2H-[1,4']bipyridinyl-3'-yl)-amide | 561.2 | 3.06 |
| 164 | 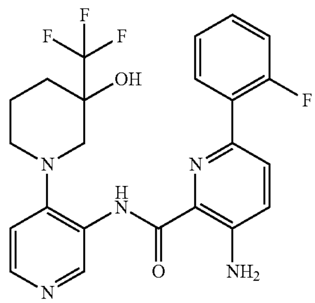 [SMILES: Nc1ccc(-c2ccccc2F)nc1C(=O)Nc1cnccc1N1CCCC(O)(C(F)(F)F)C1] | 3-Amino-6-(2-fluoro-phenyl)-pyridine-2-carboxylic acid (3-hydroxy-3-trifluoromethyl-3,4,5,6-tetrahydro-2H-[1,4']bipyridinyl-3'-yl)-amide | 476.1 | 3.14 |
| 165 | 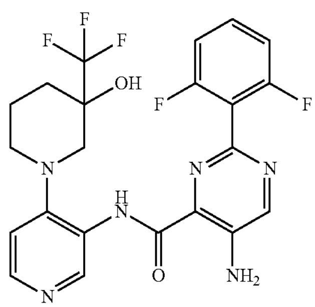 [SMILES: Nc1cnc(-c2c(F)cccc2F)nc1C(=O)Nc1cnccc1N1CCCC(O)(C(F)(F)F)C1] | 5-Amino-2-(2,6-difluoro-phenyl)-pyrimidine-4-carboxylic acid (3-hydroxy-3-trifluoromethyl-3,4,5,6-tetrahydro-2H-[1,4']bipyridinyl-3'-yl)-amide | 495.1 | 2.64 |
| 166 | 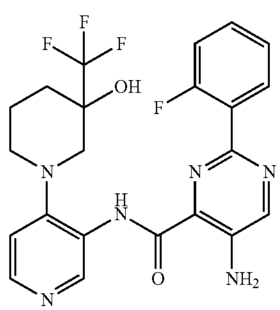 [SMILES: Nc1cnc(-c2ccccc2F)nc1C(=O)Nc1cnccc1N1CCCC(O)(C(F)(F)F)C1] | 5-Amino-2-(2-fluoro-phenyl)-pyrimidine-4-carboxylic acid (3-hydroxy-3-trifluoromethyl-3,4,5,6-tetrahydro-2H-[1,4']bipyridinyl-3'-yl)-amide | 477.1 | 2.72 |
| 167 | 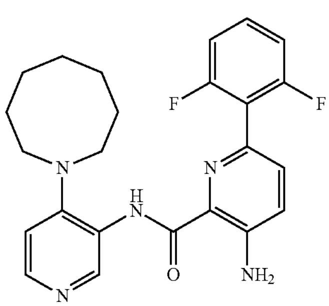 [SMILES: Nc1ccc(-c2c(F)cccc2F)nc1C(=O)Nc1cnccc1N1CCCCCCC1] | 3-Amino-6-(2,6-difluoro-phenyl)-pyridine-2-carboxylic acid (4-azocan-1-yl-pyridin-3-yl)-amide | 438.1 | 3.22 |

| Example | Structure | Name | MH+ | LC |
|---|---|---|---|---|
| 168 | 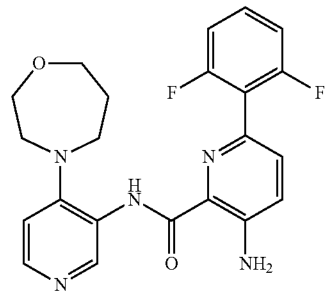 [SMILES: Nc1ccc(-c2c(F)cccc2F)nc1C(=O)Nc1cnccc1N1CCCOCC1] | 3-Amino-6-(2,6-difluoro-phenyl)-pyridine-2-carboxylic acid (4-[1,4]oxazepan-4-yl-pyridin-3-yl)-amide | 425.9 | 2.65 |
| 169 | 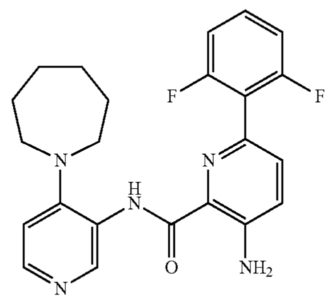 [SMILES: Nc1ccc(-c2c(F)cccc2F)nc1C(=O)Nc1cnccc1N1CCCCCC1] | 3-Amino-6-(2,6-difluoro-phenyl)-pyridine-2-carboxylic acid (4-azepan-1-yl-pyridin-3-yl)-amide | 424.1 | 3.14 |

Example 170

3-amino-N-(5-carbamoyl-2-(piperidin-1-yl)phenyl)pyrazine-2-carboxamide

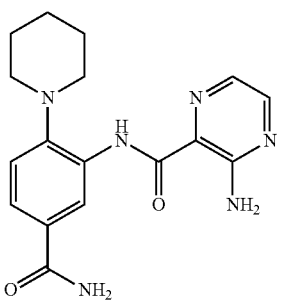 [SMILES: NC(=O)c1ccc(N2CCCCC2)c(NC(=O)c2nccnc2N)c1]

A solution of 3-amino-4-(piperidin-1-yl)benzamide (1.0 equiv.), HOAT (1.3 equiv.) and EDC (1.3 equiv.) in NMP at a concentration of 0.182 M, was stirred for 15 hours, then purified directly by reverse-phase HPLC and lyophilized yielding a TFA salt of 3-amino-N-(5-carbamoyl-2-(piperidin-1-yl)phenyl)pyrazine-2-carboxamide as a tan powder (82%). LCMS (m/z): 341.1 (MH$^+$); LC R$_f$=3.10 min.

Example 171

Synthesis of 3-amino-N-(5-cyano-2-(piperidin-1-yl)phenyl)pyrazine-2-carboxamide

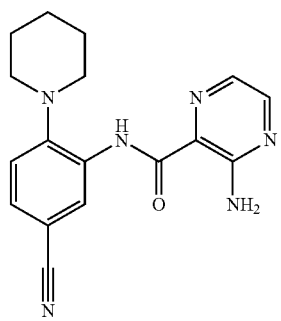 [SMILES: N#Cc1ccc(N2CCCCC2)c(NC(=O)c2nccnc2N)c1]

A milky yellow suspension of 3-amino-N-(5-carbamoyl-2-(piperidin-1-yl)phenyl)pyrazine-2-carboxamide (1 equiv.) in dichloromethane (0.0247 M) was cooled in ice bath. A solution of triflic anhydride (4.4 equiv.) in dichloromethane (0.0405 M was added dropwise, keeping the internal temperature of the solution<2.5° C. After 5 minutes the reaction was quenched with 6 mL water and the solution allowed to warm up to room temperature, then extracted with dichloromethane. The organics were washed with Na$_2$CO$_3$ (sat.), then brine, dried over Na$_2$SO$_4$, filtered and concentrated in vacuo. The crude residue was purified by reverse-phase HPLC and lyophilized yielding a TFA salt of 3-amino-N-(5- cyano-2-(piperidin-1-yl)phenyl)pyrazine-2-carboxamide as a yellow fluffy solid (24%). LCMS (m/z): 323.1 (MH+); LC $R_t$=4.62 min.

Method 10

Example 172

Synthesis of 3-amino-N-(4-(3-aminopiperidin-1-yl)pyridin-3-yl)pyrazine-2-carboxamide

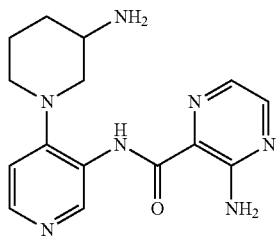 [SMILES: Nc1nccnc1C(=O)Nc1cnccc1N1CCCC(N)C1]

Following method 9,3-aminopyrazine-2-carboxylic acid was coupled to tert-butyl 1-(3-aminopyridin-4-yl)piperidin-3-ylcarbamate yielding tert-butyl 1-(3-(3-aminopyrazine-2-carboxamido)pyridin-4-yl)piperidin-3-ylcarbamate as the TFA salt after lyophilization of the HPLC product fraction. Alternatively, the free base could be obtained as described in method 8, (83% yield). LCMS (m/z): 414.2 (MH+); LC $R_t$=2.18 min.

A homogeneous solution of tert-butyl 1-(3-(3-aminopyrazine-2-carboxamido)pyridin-4-yl)piperidin-3-ylcarbamate, either TFA salt or free base, in 25% TFA/DCM was allowed to sit for 2 hours. Upon removal of volatiles in vacuo, the residue was purified by HPLC. Direct lyophilization led to the isolation of 3-amino-N-(4-(3-aminopiperidin-1-yl)pyridin-3-yl)pyrazine-2-carboxamide as the TFA salt. Alternatively, the free base and HCl salt could be obtained as described in Method 8. LCMS (m/z): 314.1 (MH+); LC $R_t$=1.02 min.

An alternative manner of removing the Boc protecting group and isolating the HCl salt was as follows: a heterogeneous solution of tert-butyl 1-(3-(3-aminopyrazine-2-carboxamido)pyridin-4-yl)piperidin-3-ylcarbamate in 4 M HCl/dioxane, at a concentration of 0.01 M, was stirred for 24 hours at which time the volatiles were removed in vacuo. After triturating and rinsing with diethyl ether the resultant solid was dissolved in MeCN/H₂O and lyophilized yielding 3-amino-N-(4-(3-aminopiperidin-1-yl)pyridin-3-yl)pyrazine-2-carboxamide as the HCl salt.

The following compounds were prepared using Method 10.

| Example | Structure | Name | MH+ | LC |
|---|---|---|---|---|
| 173 | 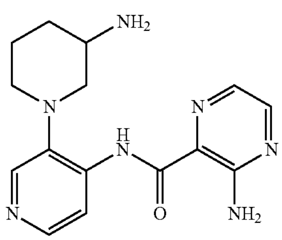 [SMILES: Nc1nccnc1C(=O)Nc1ccncc1N1CCCC(N)C1] | 3-amino-N-[3-(3-aminopiperidin-1-yl)pyridin-4-yl]pyrazine-2-carboxamide | 314.1 | 1.03 |
| 174 | 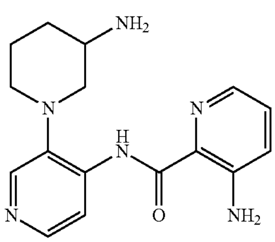 [SMILES: Nc1cccnc1C(=O)Nc1ccncc1N1CCCC(N)C1] | 3-amino-N-[3-(3-aminopiperidin-1-yl)pyridin-4-yl]pyridine-2-carboxamide | 313.2 | 1.23 |
| 175 | Chiral | 3-amino-N-{4-[(3S)-3-aminopiperidin-1-yl]pyridin-3-yl}-pyridine-2-carboxamide | 313.1 | 1.25 |

-continued

| Example | Structure | Name | MH+ | LC |
|---|---|---|---|---|
| 176 | Chiral | N-{4-[(3S)-3-aminopiperidin-1-yl]pyridin-3-yl}pyrazine-2-carboxamide | 314.1 | 1.05 |
| 177 | Chiral | 3-amino-N-{4-[(3R)-3-amino-piperidin-1-yl]pyridin-3-yl}pyrazine-2-carboxamide | 314.1 | 1.06 |
| 178 | 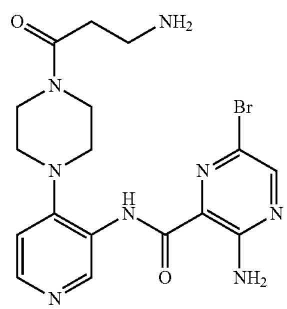 [SMILES: NCCC(=O)N1CCN(c2ccncc2NC(=O)c2nc(Br)cnc2N)CC1] | 3-amino-N-{4-[4-(3-amino-propanoyl)piperazin-1-yl]-pyridin-3-yl}-6-bromopyrazine-2-carboxamide | 449.1 | 1.31 |
| 179 | 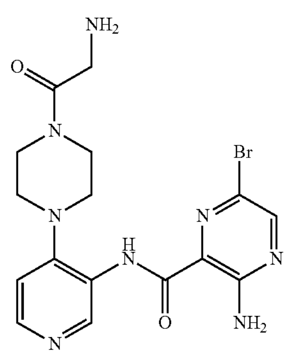 [SMILES: NCC(=O)N1CCN(c2ccncc2NC(=O)c2nc(Br)cnc2N)CC1] | 3-amino-N-{4-[4-(aminoacetyl)-piperazin-1-yl]pyridin-3-yl}-6-bromopyrazine-2-carboxamide | 435.1 | 1.23 |
| 180 | 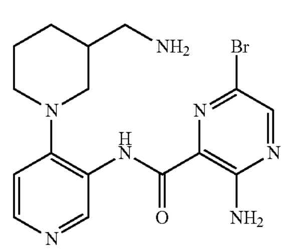 [SMILES: NCC1CCCN(c2ccncc2NC(=O)c2nc(Br)cnc2N)C1] | 3-amino-N-{4-[3-(amino-methyl)piperidin-1-yl]pyridin-3-yl}-6-bromopyrazine-2-carboxamide | 406 | 1.48 |

| Example | Structure | Name | MH+ | LC |
|---|---|---|---|---|
| 181 | 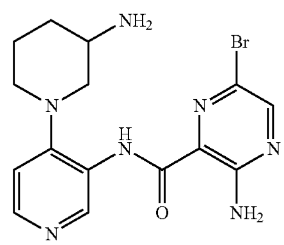 [SMILES: Nc1ncc(Br)nc1C(=O)Nc1cnccc1N1CCCC(N)C1] | 3-amino-N-[4-(3-aminopiperidin-1-yl)pyridin-3-yl]-6-bromopyrazine-2-carboxamide | 392 | 1.39 |
| 182 | 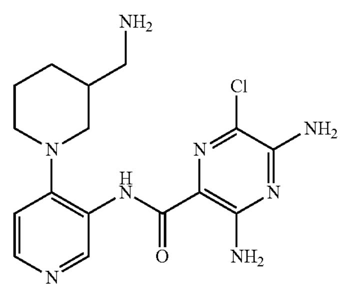 [SMILES: NCC1CCCN(c2ccncc2NC(=O)c2nc(Cl)c(N)nc2N)C1] | 3,5-diamino-N-{4-[3-(aminomethyl)piperidin-1-yl]pyridin-3-yl}-6-chloropyrazine-2-carboxamide | 377.1 | 1.21 |
| 183 | 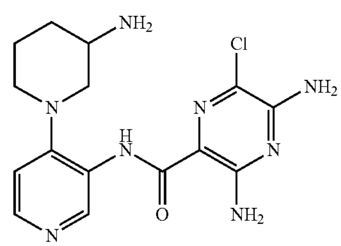 [SMILES: Nc1nc(N)c(C(=O)Nc2cnccc2N2CCCC(N)C2)nc1Cl] | 3,5-diamino-N-[4-(3-aminopiperidin-1-yl)pyridin-3-yl]-6-chloropyrazine-2-carboxamide | 363.1 | 1.13 |
| 184 | 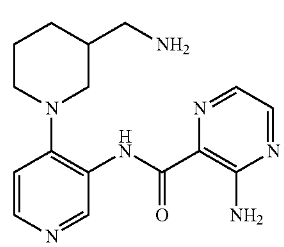 [SMILES: NCC1CCCN(c2ccncc2NC(=O)c2nccnc2N)C1] | 3-amino-N-{4-[3-(aminomethyl)piperidin-1-yl]pyridin-3-yl}pyrazine-2-carboxamide | 328.1 | 1.13 |
| 185 | 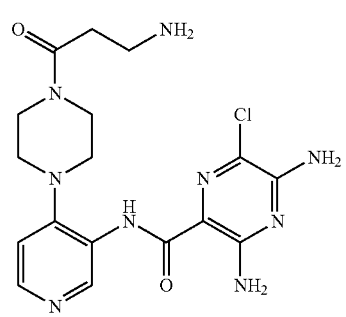 [SMILES: NCCC(=O)N1CCN(c2ccncc2NC(=O)c2nc(Cl)c(N)nc2N)CC1] | 3,5-Diamino-6-chloro-pyrazine-2-carboxylic acid {4-[4-(3-amino-propionyl)-piperazin-1-yl]-pyridin-3-yl}-amide | 420.1 | 1.2 |

-continued

| Example | Structure | Name | MH+ | LC |
|---|---|---|---|---|
| 186 | 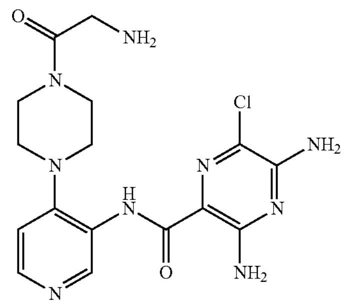 [SMILES: NCC(=O)N1CCN(c2ccncc2NC(=O)c2nc(Cl)c(N)nc2N)CC1] | 3,5-diamino-N-{4-[4-(amino-acetyl)piperazin-1-yl]pyridin-3-yl}-6-chloropyrazine-2-carboxamide | 406.1 | 1.15 |
| 187 | 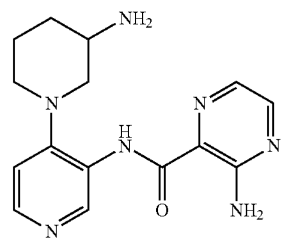 [SMILES: Nc1nccnc1C(=O)Nc1cnccc1N1CCCC(N)C1] | 3-amino-N-[4-(3-aminopiperidin-1-yl)pyridin-3-yl]pyrazine-2-carboxamide | 313.8 | 1.04 |
| 188 | 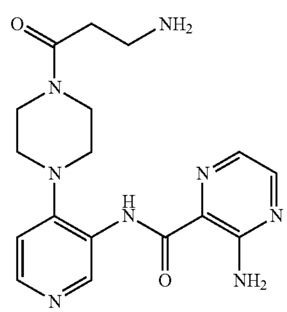 [SMILES: NCCC(=O)N1CCN(c2ccncc2NC(=O)c2nccnc2N)CC1] | 3-amino-N-{4-[4-(3-aminopropanoyl)piperazin-1-yl]pyridin-3-yl}pyrazine-2-carboxamide | 371.1 | 0.88 |
| 189 | 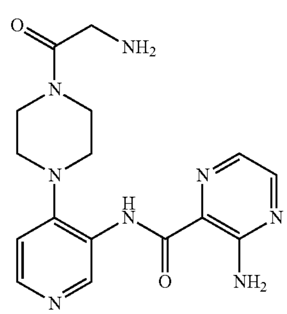 [SMILES: NCC(=O)N1CCN(c2ccncc2NC(=O)c2nccnc2N)CC1] | 3-amino-N-{4-[4-(amino-acetyl)piperazin-1-yl]pyridin-3-yl}pyrazine-2-carboxamide | 356.8 | 0.83 |
| 190 | 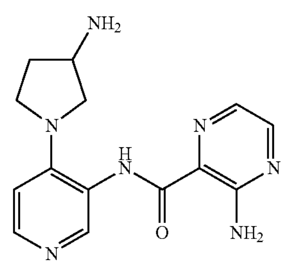 [SMILES: Nc1nccnc1C(=O)Nc1cnccc1N1CCC(N)C1] | 3-amino-N-[4-(3-amino-pyrrolidin-1-yl)pyridin-3-yl]-pyrazine-2-carboxamide | 300.1 | |

-continued

| Example | Structure | Name | MH+ | LC |
|---|---|---|---|---|
| 191 | 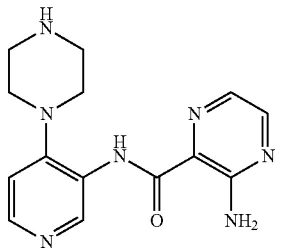 [SMILES: Nc1nccnc1C(=O)Nc1cnccc1N1CCNCC1] | 3-amino-N-(4-piperazin-1-yl-pyridin-3-yl)pyrazine-2-carboxamide | 300.1 | |
| 192 | Chiral | 3-amino-N-{4-[(2R)-2-(amino-methyl)pyrrolidin-1-yl]pyridin-3-yl}pyrazine-2-carboxamide | 314.1 | |
| 193 | 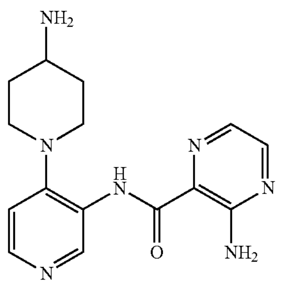 [SMILES: Nc1nccnc1C(=O)Nc1cnccc1N1CCC(N)CC1] | 3-amino-N-[4-(4-aminopiperidin-1-yl)pyridin-3-yl]pyrazine-2-carboxamide | 314.1 | |
| 194 | 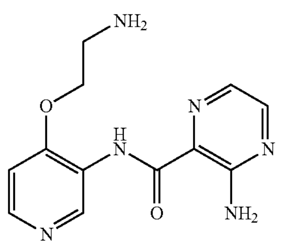 [SMILES: NCCOc1ccncc1NC(=O)c1nccnc1N] | 3-amino-N-[4-(2-amino-ethoxy)pyridin-3-yl]pyrazine-2-carboxamide | 275.1 | |
| 195 | 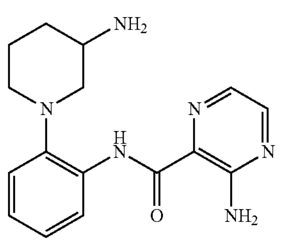 [SMILES: Nc1nccnc1C(=O)Nc1ccccc1N1CCCC(N)C1] | 3-amino-N-[2-(3-aminopiperidin-1-yl)phenyl]pyrazine-2-carboxamide | 313.2 | 2.03 |
| 196 | 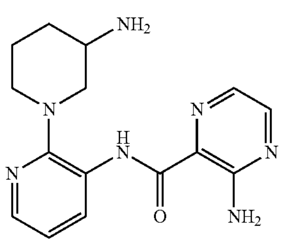 [SMILES: Nc1nccnc1C(=O)Nc1cccnc1N1CCCC(N)C1] | 3-amino-N-[2-(3-aminopiperidin-1-yl)pyridin-3-yl]pyrazine-2-carboxamide | 314.2 | 1.66 |

-continued

| Example | Structure | Name | MH+ | LC |
|---|---|---|---|---|
| 197 | 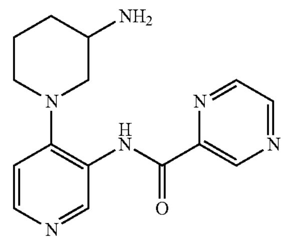 [SMILES: NC1CCCN(c2ccncc2NC(=O)c2cnccn2)C1] | N-[4-(3-aminopiperidin-1-yl)-pyridin-3-yl]pyrazine-2-carboxamide | 299.2 | 0.86 |
| 198 | 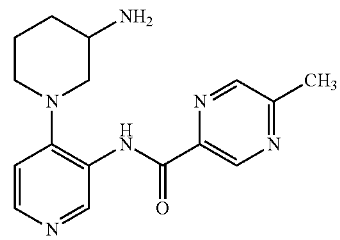 [SMILES: Cc1cnc(C(=O)Nc2cnccc2N2CCCC(N)C2)cn1] | N-[4-(3-aminopiperidin-1-yl)pyridin-3-yl]-5-methyl-pyrazine-2-carboxamide | 313.2 | 1.05 |
| 199 | 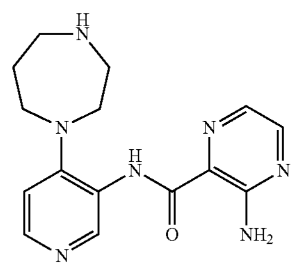 [SMILES: Nc1nccnc1C(=O)Nc1cnccc1N1CCCNCC1] | 3-amino-N-[4-(1,4-diazepan-1-yl)pyridin-3-yl]pyrazine-2-carboxamide | 314.1 | 0.55 |
| 200 | 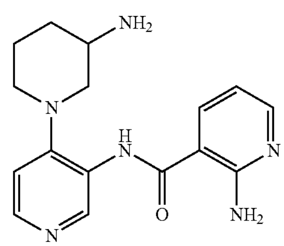 [SMILES: Nc1ncccc1C(=O)Nc1cnccc1N1CCCC(N)C1] | 2-amino-N-[4-(3-aminopiperidin-1-yl)pyridin-3-yl]nicotinamide | 313.2 | |
| 201 | 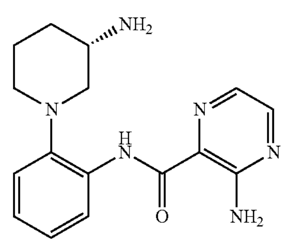 [SMILES: Nc1nccnc1C(=O)Nc1ccccc1N1CCC[C@H](N)C1] | 3-amino-N-{2-[(3S)-3-amino-piperidin-1-yl]phenyl}pyrazine-2-carboxamide | 313.12 | 2.39 |
| 202 | 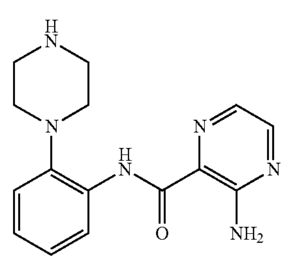 [SMILES: Nc1nccnc1C(=O)Nc1ccccc1N1CCNCC1] | 3-amino-N-(2-piperazin-1-ylphenyl)pyrazine-2-carboxamide | 299.1 | |

| Example | Name | MH+ | LC |
|---|---|---|---|
| 203 | 3-amino-N-[2-(4-aminopiperidin-1-yl)phenyl]pyrazine-2-carboxamide | 313.2 | |
| 204 | 3-amino-N-[2-(3-aminopiperidin-1-yl)phenyl]-6-bromopyrazine-2-carboxamide | 391 | 2.25 |
| 205 | 3-amino-N-[2-(4-aminopiperidin-1-yl)phenyl]-6-bromopyrazine-2-carboxamide | 391 | 2.2 |
| 206 | 3-amino-6-bromo-N-(2-piperazin-1-ylphenyl)pyrazine-2-carboxamide | 377 | 2.12 |
| 207 | 3-amino-N-[2-(4-aminopiperidin-1-yl)-5-(1H-pyrazol-5-yl)phenyl]pyrazine-2-carboxamide | 379.1 | 2.01 |

-continued

| Example | Structure | Name | MH+ | LC |
|---|---|---|---|---|
| 208 | 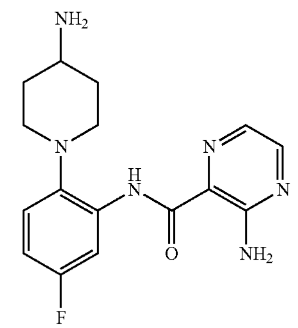 [SMILES: Nc1nccnc1C(=O)Nc1cc(F)ccc1N1CCC(N)CC1] | 3-amino-N-[2-(4-aminopiperidin-1-yl)-5-fluorophenyl]pyrazine-2-carboxamide | 331.1 | 2.47 |
| 209 | 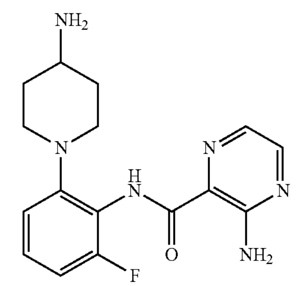 [SMILES: Nc1nccnc1C(=O)Nc1c(F)cccc1N1CCC(N)CC1] | 3-amino-N-[2-(4-aminopiperidin-1-yl)-6-fluorophenyl]pyrazine-2-carboxamide | 331.2 | 1.99 |
| 210 | 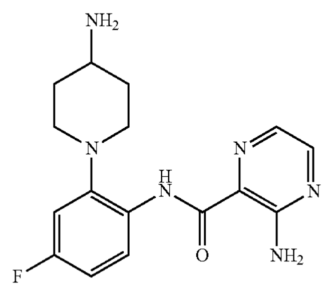 [SMILES: Nc1nccnc1C(=O)Nc1ccc(F)cc1N1CCC(N)CC1] | 3-amino-N-[2-(4-aminopiperidin-1-yl)-4-fluorophenyl]pyrazine-2-carboxamide | 331.1 | 2.38 |
| 211 | 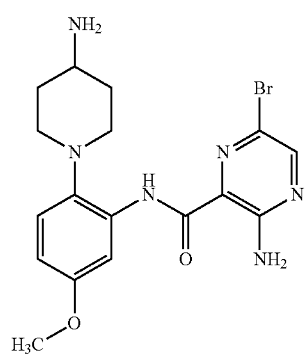 [SMILES: COc1ccc(N2CCC(N)CC2)c(NC(=O)c2nc(Br)cnc2N)c1] | 3-amino-N-[2-(4-aminopiperidin-1-yl)-5-methoxyphenyl]-6-bromopyrazine-2-carboxamide | 421.1 | 2.74 |
| 212 | 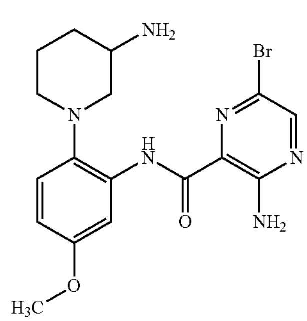 [SMILES: COc1ccc(N2CCCC(N)C2)c(NC(=O)c2nc(Br)cnc2N)c1] | 3-amino-N-[2-(3-aminopiperidin-1-yl)-5-methoxyphenyl]-6-bromopyrazine-2-carboxamide | 421.1 | 2.6 |

| Example | Structure | Name | MH+ | LC |
|---|---|---|---|---|
| 213 | 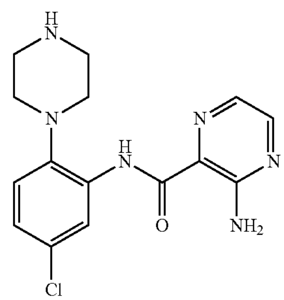 [SMILES: Nc1nccnc1C(=O)Nc1cc(Cl)ccc1N1CCNCC1] | 3-amino-N-(5-chloro-2-piperazin-1-ylphenyl)pyrazine-2-carboxamide | 333.1 | 2.48 |
| 214 | 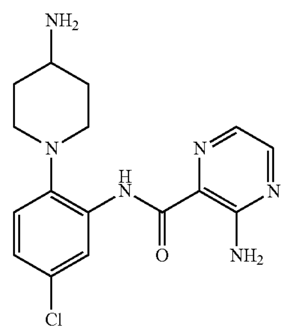 [SMILES: Nc1nccnc1C(=O)Nc1cc(Cl)ccc1N1CCC(N)CC1] | 3-amino-N-[2-(4-aminopiperidin-1-yl)-5-chlorophenyl]pyrazine-2-carboxamide | 347.1 | 2.69 |
| 215 | 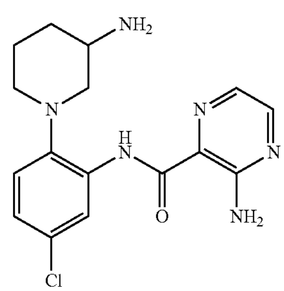 [SMILES: Nc1nccnc1C(=O)Nc1cc(Cl)ccc1N1CCCC(N)C1] | 3-amino-N-[2-(3-aminopiperidin-1-yl)-5-chlorophenyl]pyrazine-2-carboxamide | 347.1 | 2.66 |
| 216 | 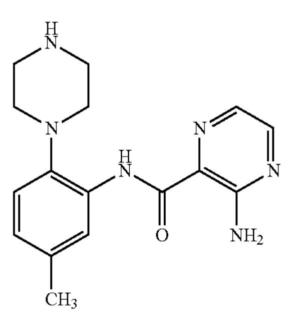 [SMILES: Cc1ccc(N2CCNCC2)c(NC(=O)c2nccnc2N)c1] | 3-amino-N-(5-methyl-2-piperazin-1-ylphenyl)pyrazine-2-carboxamide | 313.2 | 2.36 |
| 217 | 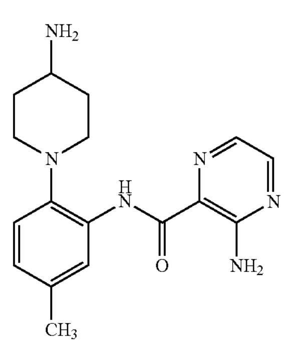 [SMILES: Cc1ccc(N2CCC(N)CC2)c(NC(=O)c2nccnc2N)c1] | 3-amino-N-[2-(4-aminopiperidin-1-yl)-5-methylphenyl]pyrazine-2-carboxamide | 327.1 | 2.48 |

-continued

| Example | Name | MH+ | LC |
|---|---|---|---|
| 218 | 3-amino-N-[2-(3-aminopiperidin-1-yl)-5-methylphenyl]pyrazine-2-carboxamide | 327.1 | 2.55 |
| 219 | N-(5-acetyl-2-piperazin-1-yl-phenyl)-3-aminopyrazine-2-carboxamide | 341.1 | 1.99 |
| 220 | N-[5-acetyl-2-(4-aminopiperidin-1-yl)phenyl]-3-aminopyrazine-2-carboxamide | 355.2 | 2.11 |
| 221 | N-[5-acetyl-2-(3-aminopiperidin-1-yl)phenyl]-3-aminopyrazine-2-carboxamide | 355.2 | 2.2 |

-continued

| Example | Structure | Name | MH+ | LC |
|---|---|---|---|---|
| 222 | 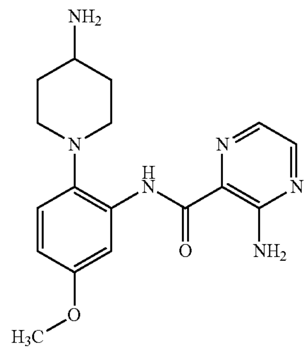 [SMILES: COc1ccc(N2CCC(N)CC2)c(NC(=O)c2nccnc2N)c1] | 3-amino-N-[2-(4-aminopiperidin-1-yl)-5-methoxyphenyl]pyrazine-2-carboxamide | 343.1 | 2.33 |
| 223 | 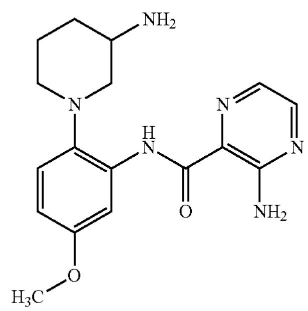 [SMILES: COc1ccc(N2CCCC(N)C2)c(NC(=O)c2nccnc2N)c1] | 3-amino-N-[2-(3-aminopiperidin-1-yl)-5-methoxyphenyl]pyrazine-2-carboxamide | 343.1 | 2.39 |
| 224 | 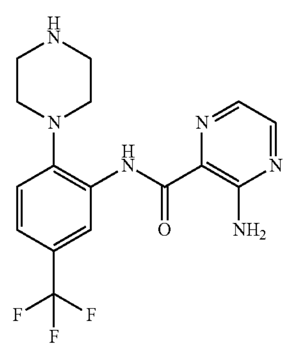 [SMILES: Nc1nccnc1C(=O)Nc1cc(C(F)(F)F)ccc1N1CCNCC1] | 3-amino-N-[2-piperazin-1-yl-5-(trifluoromethyl)phenyl]pyrazine-2-carboxamide | 367.1 | 2.72 |
| 225 | 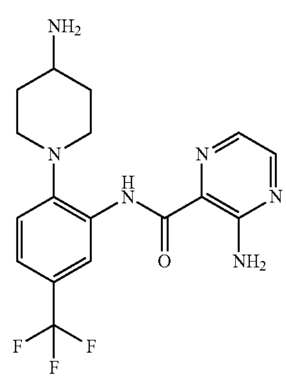 [SMILES: Nc1nccnc1C(=O)Nc1cc(C(F)(F)F)ccc1N1CCC(N)CC1] | 3-amino-N-[2-(4-aminopiperidin-1-yl)-5-(trifluoromethyl)phenyl]-pyrazine-2-carboxamide | 381.1 | 2.87 |

-continued

| Example | Name | MH+ | LC |
|---|---|---|---|
| 226 | 3-amino-N-[2-(3-aminopiperidin-1-yl)-5-(trifluoromethyl)phenyl]-pyrazine-2-carboxamide | 381.1 | 2.88 |
| 227 | 3-amino-N-(4-methyl-2-piperazin-1-ylphenyl)pyrazine-2-carboxamide | 313.2 | 2.32 |
| 228 | 3-amino-N-[2-(4-aminopiperidin-1-yl)-4-methylphenyl]pyrazine-2-carboxamide | 327.2 | 2.46 |
| 229 | 3-amino-N-[2-(3-aminopiperidin-1-yl)-4-methylphenyl]pyrazine-2-carboxamide | 327.2 | 2.53 |
| 230 | 3-amino-N-[2-(3-aminopiperidin-1-yl)-5-cyanophenyl]pyrazine-2-carboxamide | 338.2 | 2.33 |

-continued

| Example | Structure | Name | MH+ | LC |
|---|---|---|---|---|
| 231 | 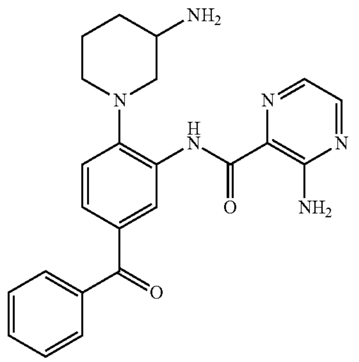 [SMILES: Nc1nccnc1C(=O)Nc1cc(C(=O)c2ccccc2)ccc1N1CCCC(N)C1] | 3-amino-pyrazine-2-carboxylic acid [2-(3-amino-piperidin-1-yl)-5-benzoyl-phenyl]-amide | 417.1 | 2.79 |
| 232 | 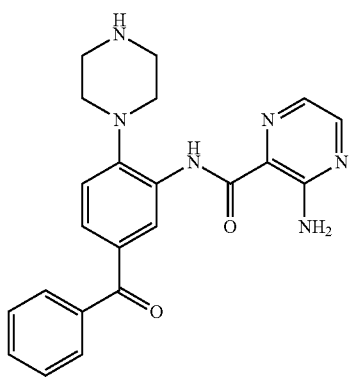 [SMILES: Nc1nccnc1C(=O)Nc1cc(C(=O)c2ccccc2)ccc1N1CCNCC1] | 3-amino-pyrazine-2-carboxylic acid (5-benzoyl-2-piperazin-1-yl-phenyl)-amide | 403.2 | 2.7 |
| 233 | 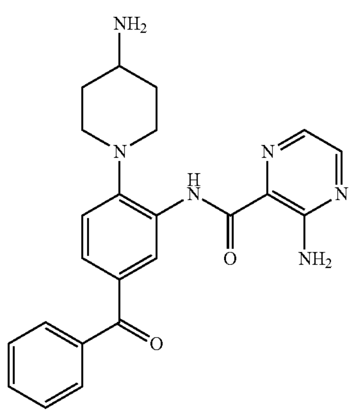 [SMILES: Nc1nccnc1C(=O)Nc1cc(C(=O)c2ccccc2)ccc1N1CCC(N)CC1] | 3-amino-pyrazine-2-carboxylic acid [2-(4-amino-piperidin-1-yl)-5-benzoyl-phenyl]-amide | 417.2 | 2.83 |
| 234 | 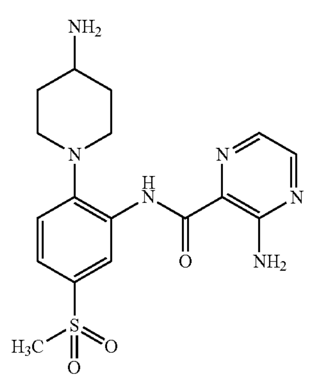 [SMILES: CS(=O)(=O)c1ccc(N2CCC(N)CC2)c(NC(=O)c2nccnc2N)c1] | 3-amino-N-[2-(4-aminopiperidin-1-yl)-5-(methylsulfonyl)phenyl]-pyrazine-2-carboxamide | 391.1 | 1.89 |

-continued

| Example | Structure | Name | MH+ | LC |
|---|---|---|---|---|
| 235 | 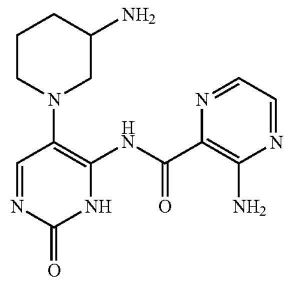 [SMILES: Nc1nccnc1C(=O)Nc1[nH]c(=O)ncc1N1CCCC(N)C1] | 3-amino-N-[5-(3-aminopiperidin-1-yl)-2-oxo-2,3-dihydro-pyrimidin-4-yl]pyrazine-2-carboxamide | 331.1 | 1.18 |
| 236 | 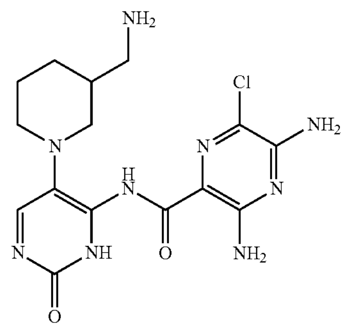 [SMILES: NCC1CCCN(c2cnc(=O)[nH]c2NC(=O)c2nc(Cl)c(N)nc2N)C1] | 3,5-diamino-N-{5-[3-(amino-methyl)piperidin-1-yl]-2-oxo-2,3-dihydropyrimidin-4-yl}-6-chloropyrazine-2-carboxamide | 394.1 | 1.47 |
| 237 | 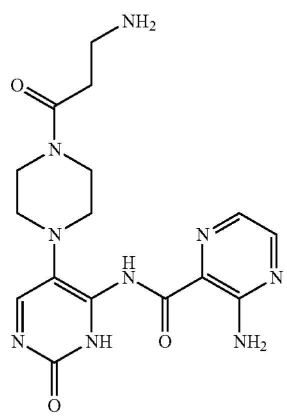 [SMILES: NCCC(=O)N1CCN(c2cnc(=O)[nH]c2NC(=O)c2nccnc2N)CC1] | 3-amino-N-{5-[4-(3-amino-propanoyl)piperazin-1-yl]-2-oxo-2,3-dihydropyrimidin-4-yl}-pyrazine-2-carboxamide | 388.1 | 1.18 |
| 238 | 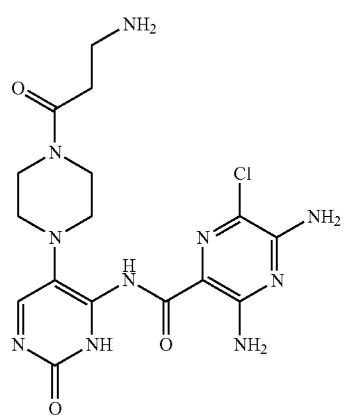 [SMILES: NCCC(=O)N1CCN(c2cnc(=O)[nH]c2NC(=O)c2nc(Cl)c(N)nc2N)CC1] | 3,5-diamino-6-chloro-pyrazine-2-carboxylic acid {5-[4-(3-amino-propionyl)-piperazin-1-yl]-2-oxo-2,3-dihydro-pyrimidin-4-yl}-amide | 437.1 | 1.27 |

-continued

| Example | Name | MH+ | LC |
|---|---|---|---|
| 239 | 3-amino-N-[5-(3-aminopiperidin-1-yl)-2-oxo-2,3-dihydro-pyrimidin-4-yl]-6-bromo-pyrazine-2-carboxamide | 409 | 1.58 |
| 240 | 3-amino-N-{5-[3-(aminomethyl)-piperidin-1-yl]-2-oxo-2,3-dihydropyrimidin-4-yl}-6-bromopyrazine-2-carboxamide | 423 | 1.72 |
| 241 | 3-amino-N-{5-[4-(3-amino-propanoyl)piperazin-1-yl]-2-oxo-2,3-dihydropyrimidin-4-yl}-6-bromopyrazine-2-carboxamide | 466.1 | 1.49 |
| 242 | 3-amino-N-[5-(3-aminopiperidin-1-yl)-2-oxo-2,3-dihydro-pyrimidin-4-yl]pyridine-2-carboxamide | 330.1 | 1.28 |
| 243 | 3-amino-pyrazine-2-carboxylic acid [2-(3-amino-piperidin-1-yl)-5-cyclopropanecarbonyl-phenyl]-amide | 381.1 | 2.49 |

-continued

| Example | Structure | Name | MH+ | LC |
|---|---|---|---|---|
| 244 | 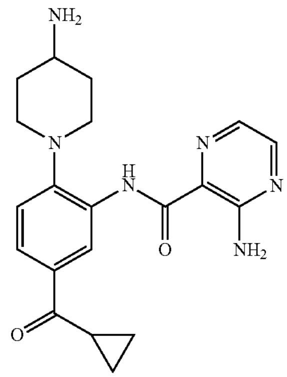 [SMILES: Nc1nccnc1C(=O)Nc1cc(C(=O)C2CC2)ccc1N1CCC(N)CC1] | 3-amino-pyrazine-2-carboxylic acid [2-(4-amino-piperidin-1-yl)-5-cyclopropanecarbonyl-phenyl]-amide | 381.1 | 2.45 |
| 245 | 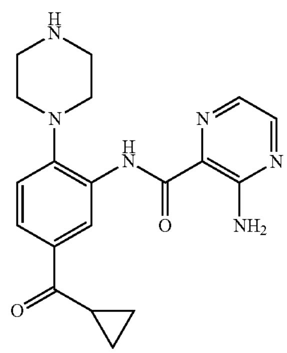 [SMILES: Nc1nccnc1C(=O)Nc1cc(C(=O)C2CC2)ccc1N1CCNCC1] | 3-amino-N-[5-(cyclopropyl-carbonyl)-2-piperazin-1-yl-phenyl]pyrazine-2-carboxamide | 367.1 | 2.32 |
| 246 | Chiral | 5-Amino-2-(2,6-difluoro-phenyl)-pyrimidine-4-carboxylic acid (3,5-diamino-3,4,5,6-tetra-hydro-2H-[1,4']bipyridinyl-3'-yl)-amide | 441.2 | 1.30 |
| 247 | Chiral | 5-Amino-2-(2-fluoro-phenyl)-pyrimidine-4-carboxylic acid (3,5-diamino-3,4,5,6-tetrahydro-2H-[1,4']bipyridinyl-3'-yl)-amide | 423.2 | 1.39 |

| Example | Structure | Name | MH+ | LC |
|---|---|---|---|---|
| 248 | Chiral | 3-Amino-6-(2-fluoro-phenyl)-pyridine-2-carboxylic acid (3,5-diamino-3,4,5,6-tetrahydro-2H-[1,4']bipyridinyl-3'-yl)-amide | 422.2 | 1.64 |
| 249 | Chiral | N-{4-[(3S)-3-aminopiperidin-1-yl]pyridin-3-yl}-2-(2,6-difluorophenyl)pyrimidine-4-carboxamide N-{4-[(3S)-3-aminopiperidin-1-yl]pyridin-3-yl}-2-(2,6-difluorophenyl)-pyrimidine-4-carboxamide | 411.1 | 1.67 |
| 250 | Chiral | N-{4-[(3S)-3-aminopiperidin-1-yl]pyridin-3-yl}-2-(2-fluoro-phenyl)pyrimidine-4-carbox-amide | 393.2 | 1.71 |
| 251 | 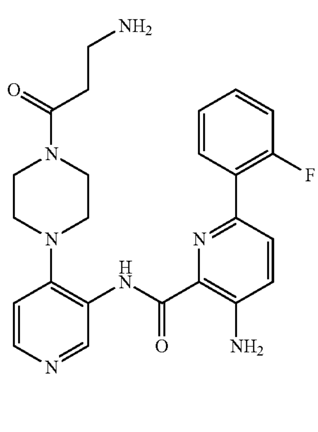 [SMILES: NCCC(=O)N1CCN(c2ccncc2NC(=O)c2nc(-c3ccccc3F)ccc2N)CC1] | 3-Amino-6-(2-fluoro-phenyl)-pyridine-2-carboxylic acid {4-[4-(3-amino-propionyl)-piperazin-1-yl]-pyridin-3-yl)-amide | 464.2 | 1.98 |

| Example | Name | MH+ | LC |
|---|---|---|---|
| 252 | 3-Amino-6-(2-fluoro-phenyl)-pyridine-2-carboxylic acid {4-[4-(2-amino-acetyl)-piperazin-1-yl]-pyridin-3-yl}-amide | 450.2 | 1.94 |
| 253 | 3-Amino-6-(2-fluoro-5-isopropylcarbamoyl-phenyl)-pyridine-2-carboxylic acid (3-amino-4-fluoro-3,4,5,6-tetra-hydro-2H-[1,4']bipyridinyl-3'-yl)-amide | 510.3 | 2.09 |
| 254 | 3-Amino-6-(2-fluoro-phenyl)-pyridine-2-carboxylic acid (3-amino-4,4-difluoro-3,4,5,6-tetra-hydro-2H-[1,4']bipyridinyl-3'-yl)-amide | 443.2 | 2.14 |
| 255 | 3-Amino-6-(2-fluoro-5-isopropylcarbamoyl-phenyl)-pyridine-2-carboxylic acid (3-amino-4,4-difluoro-3,4,5,6-tetra-hydro-2H-[1,4']bipyridinyl-3'-yl)-amide | 528.3 | 2.14 |

-continued

| Example | Structure | Name | MH+ | LC |
|---|---|---|---|---|
| 256 | 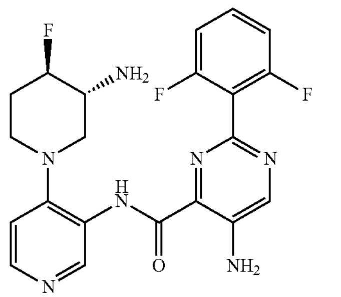 [SMILES: Nc1cnc(-c2c(F)cccc2F)nc1C(=O)Nc1cnccc1N1CC[C@@H](F)[C@H](N)C1] | 5-Amino-2-(2,6-difluoro-phenyl)-pyrimidine-4-carboxylic acid (3-amino-4-fluoro-3,4,5,6-tetrahydro-2H-[1,4']bipyridinyl-3'-yl)-amide | 444.1 | 1.71 |
| 257 | 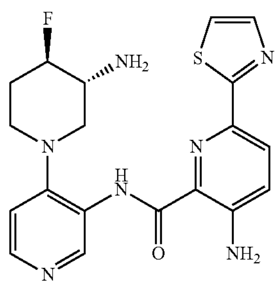 [SMILES: Nc1ccc(-c2nccs2)nc1C(=O)Nc1cnccc1N1CC[C@@H](F)[C@H](N)C1] | 3-amino-N-{4-[(3R,4R)-3-amino-4-fluoropiperidin-1-yl]pyridin-3-yl}-6-(1,3-thiazol-2-yl)pyridine-2-carboxamide | 414.1 | 1.58 |
| 258 | 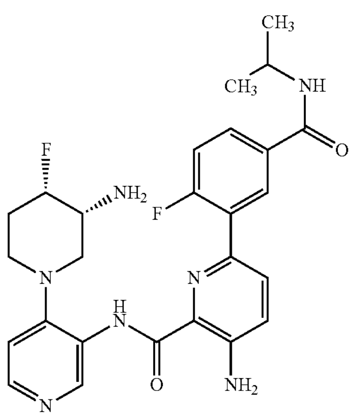 [SMILES: CC(C)NC(=O)c1ccc(F)c(-c2ccc(N)c(C(=O)Nc3cnccc3N3CC[C@H](F)[C@H](N)C3)n2)c1] | 3-Amino-6-(2-fluoro-5-isopropylcarbamoyl-phenyl)-pyridine-2-carboxylic acid (3-amino-4-fluoro-3,4,5,6-tetrahydro-2H-[1,4']bipyridinyl-3'-yl)-amide | 510.3 | 1.62 |
| 259 | 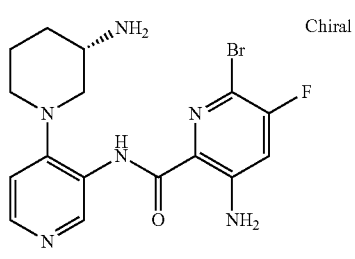 [SMILES: Nc1cc(F)c(Br)nc1C(=O)Nc1cnccc1N1CCC[C@H](N)C1] | 3-amino-N-{4-[(3S)-3-amino-piperidin-1-yl]pyridin-3-yl}-6-bromo-5-fluoropyridine-2-carboxamide | 409.1 | 1.72 |
| 260 | 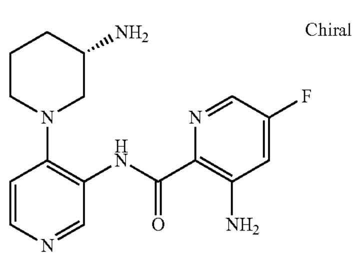 [SMILES: Nc1cc(F)cnc1C(=O)Nc1cnccc1N1CCC[C@H](N)C1] | 3-amino-N-{4-[(3S)-3-amino-piperidin-1-yl]pyridin-3-yl}-5-fluoropyridine-2-carboxamide | 331.1 | 1.42 |

-continued

| Example | Name | MH+ | LC |
|---|---|---|---|
| 261 | 5-Amino-2-phenyl-pyrimidine-4-carboxylic acid (3-amino-3-methyl-3,4,5,6-tetrahydro-2H-[1,4']bipyridinyl-3'-yl)-amide | 404.2 | 1.90 |
| 262 | 5-Amino-2-phenyl-pyrimidine-4-carboxylic acid (3-hydroxy-3-trifluoromethyl-3,4,5,6-tetrahydro-2H-[1,4']bipyridinyl-3'-yl)-amide | 459.1 | 2.89 |
| 263 | 5-Amino-2-(2-fluoro-phenyl)-pyrimidine-4-carboxylic acid (3-amino-3,4,5,6-tetrahydro-2H-[1,4']bipyridinyl-3'-yl)-amide | 408.2 | 1.78 |
| 264 | 3-Amino-5-phenyl-pyridine-2-carboxylic acid (3-amino-3,4,5,6-tetrahydro-2H-[1,4']bipyridinyl-3'-yl)-amide | 389.3 | 2.12 |
| 265 | 5-Amino-2-phenyl-pyrimidine-4-carboxylic acid (3-amino-3,4,5,6-tetrahydro-2H-[1,4']bipyridinyl-3'-yl)-amide | 390.1 | 1.86 |

-continued

| Example | Structure | Name | MH+ | LC |
|---|---|---|---|---|
| 266 | 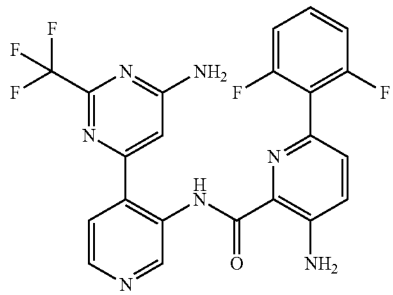 [SMILES: Nc1cc(-c2ccncc2NC(=O)c2nc(-c3c(F)cccc3F)ccc2N)nc(C(F)(F)F)n1] | 3-Amino-6-(2,6-difluoro-phenyl)-pyridine-2-carboxylic acid [4-(6-amino-2-trifluoromethyl-pyrimidin-4-yl)-pyridin-3-yl]-amide | 488.1 | 2.97 |
| 267 | 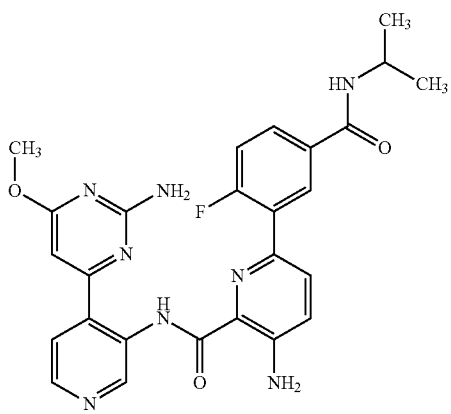 [SMILES: COc1cc(-c2ccncc2NC(=O)c2nc(-c3cc(C(=O)NC(C)C)ccc3F)ccc2N)nc(N)n1] | 3-Amino-6-(2-fluoro-5-isopropylcarbamoyl-phenyl)-pyridine-2-carboxylic acid [4-(2-amino-6-methoxy-pyrimidin-4-yl)-pyridin-3-yl]-amide | 517.2 | 2.69 |
| 268 | 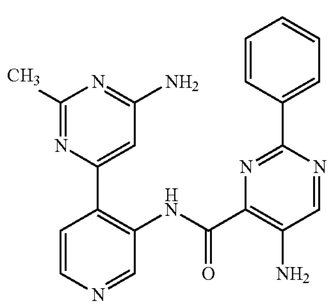 [SMILES: Cc1cc(-c2ccncc2NC(=O)c2nc(-c3ccccc3)ncc2N)cc(N)n1] | 5-Amino-2-phenyl-pyrimidine-4-carboxylic acid [4-(6-amino-2-methyl-pyrimidin-4-yl)-pyridin-3-yl]-amide | 399.2 | 2.13 |
| 269 | 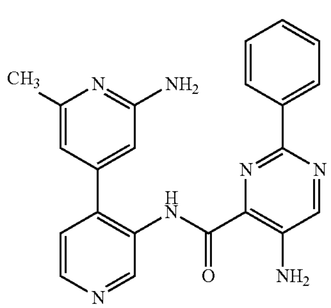 | 5-Amino-2-phenyl-pyrimidine-4-carboxylic acid (6'-amino-2'-methyl-[4,4']bipyridinyl-3-yl)-amide | 398.2 | 2.02 |

-continued

| Example | Structure | Name | MH+ | LC |
|---|---|---|---|---|
| 270 | Chiral | 5-Amino-2-(2,6-difluoro-phenyl)-pyrimidine-4-carboxylic acid (3-amino-3,4,5,6-tetrahydro-2H-[1,4']bipyridinyl-3'-yl)-amide | 426.2 | 1.72 |
| 271 | 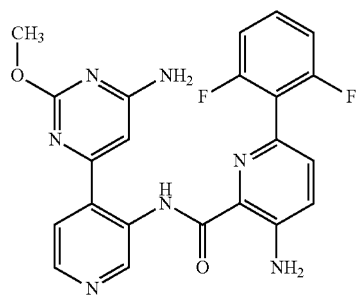 | 3-Amino-6-(2,6-difluoro-phenyl)-pyridine-2-carboxylic acid [4-(6-amino-2-methoxy-pyrimidin-4-yl)-pyridin-3-yl]-amide | 450.2 | 2.70 |
| 272 | 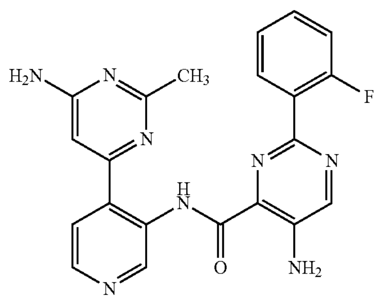 [SMILES: Cc1nc(N)cc(-c2ccncc2NC(=O)c2nc(-c3ccccc3F)ncc2N)n1] | 5-Amino-2-(2-fluoro-phenyl)-pyrimidine-4-carboxylic acid [4-(6-amino-2-methyl-pyrimidin-4-yl)-pyridin-3-yl]-amide | 2.0 | 417.00 |
| 273 | 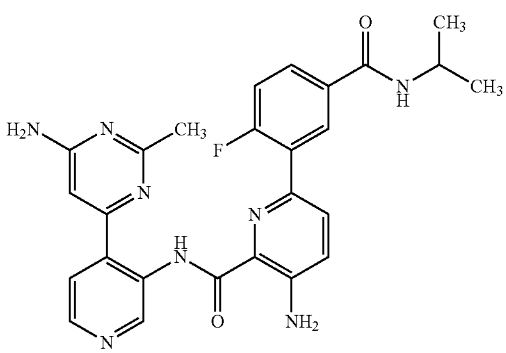 [SMILES: Cc1nc(N)cc(-c2ccncc2NC(=O)c2nc(-c3cc(C(=O)NC(C)C)ccc3F)ccc2N)n1] | 3-Amino-6-(2-fluoro-5-isopropylcarbamoyl-phenyl)-pyridine-2-carboxylic acid [4-(6-amino-2-methyl-pyrimidin-4-yl)-pyridin-3-yl]-amide | 501.2 | 2.29 |
| 274 | 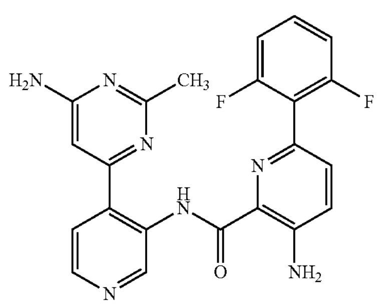 [SMILES: Cc1nc(N)cc(-c2ccncc2NC(=O)c2nc(-c3c(F)cccc3F)ccc2N)n1] | 3-Amino-6-(2,6-difluoro-phenyl)-pyridine-2-carboxylic acid [4-(6-amino-2-methyl-pyrimidin-4-yl)-pyridin-3-yl]-amide | 434.1 | 2.30 |

| Example | Structure | Name | MH+ | LC |
|---|---|---|---|---|
| 275 | 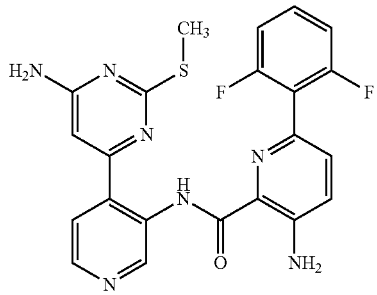 [SMILES: CSc1nc(N)cc(-c2ccncc2NC(=O)c2nc(-c3c(F)cccc3F)ccc2N)n1] | 3-Amino-6-(2,6-difluoro-phenyl)-pyridine-2-carboxylic acid [4-(6-amino-2-methylsulfanyl-pyrimidin-4-yl)-pyridin-3-yl]-amide | 466.1 | 2.89 |
| 276 | Chiral | 3-Amino-6-(2,6-difluoro-phenyl)-pyridine-2-carboxylic acid (3-amino-4-fluoro-3,4,5,6-tetrahydro-2H-[1,4']bipyridinyl-3'-yl)-amide | 443.2 | 2.05 |
| 277 | Chiral | 3-Amino-6-(2,6-difluoro-phenyl)-pyridine-2-carboxylic acid (3-amino-4-fluoro-3,4,5,6-tetrahydro-2H-[1,4']bipyridinyl-3'-yl)-amide | 443.2 | 2.05 |
| 278 | 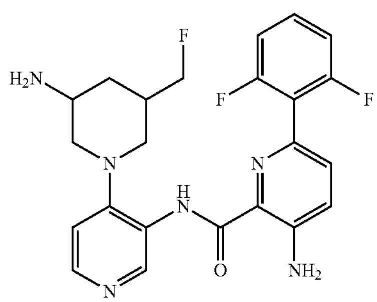 [SMILES: Nc1ccc(-c2c(F)cccc2F)nc1C(=O)Nc1cnccc1N1CC(N)CC(CF)C1] | 3-Amino-6-(2,6-difluoro-phenyl)-pyridine-2-carboxylic acid (5-amino-3-fluoromethyl-3,4,5,6-tetrahydro-2H-[1,4']bi-pyridinyl-3'-yl)-amide | 457.1 | 2.17 |
| 279 | 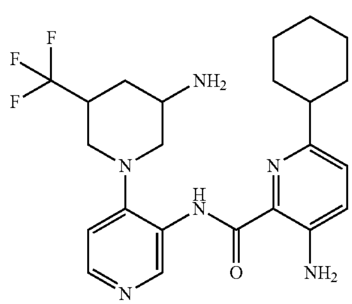 [SMILES: Nc1ccc(C2CCCCC2)nc1C(=O)Nc1cnccc1N1CC(N)CC(C(F)(F)F)C1] | 3-Amino-6-cyclohexyl-pyridine-2-carboxylic acid (3-amino-5-trifluoromethyl-3,4,5,6-tetra-hydro-2H-[1,4']bipyridinyl-3'-yl)-amide | 463.1 | 2.30 |

| Example | Structure | Name | MH+ | LC |
|---|---|---|---|---|
| 280 | 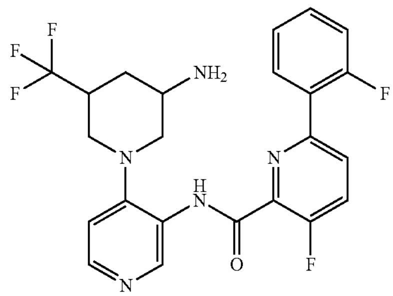 [SMILES: NC1CC(C(F)(F)F)CN(c2ccncc2NC(=O)c2nc(-c3ccccc3F)ccc2F)C1] | 3-Fluoro-6-(2-fluoro-phenyl)-pyridine-2-carboxylic acid (3-amino-5-trifluoromethyl-3,4,5,6-tetrahydro-2H-[1,4']bipyridinyl-3'-yl)-amide | 478.0 | 2.32 |
| 281 | 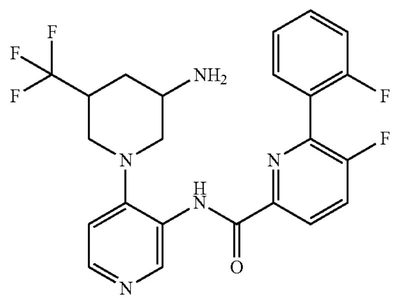 [SMILES: NC1CC(C(F)(F)F)CN(c2ccncc2NC(=O)c2ccc(F)c(-c3ccccc3F)n2)C1] | 5-Fluoro-6-(2-fluoro-phenyl)-pyridine-2-carboxylic acid (3-amino-5-trifluoromethyl-3,4,5,6-tetrahydro-2H-[1,4']bipyridinyl-3'-yl)-amide | 478.1 | 2.42 |
| 282 | 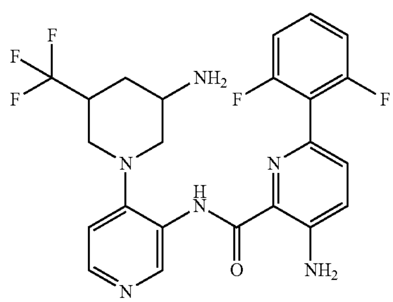 [SMILES: Nc1ccc(-c2c(F)cccc2F)nc1C(=O)Nc1cnccc1N1CC(N)CC(C(F)(F)F)C1] | 3-Amino-6-(2,6-difluoro-phenyl)-pyridine-2-carboxylic acid (3-amino-5-trifluoromethyl-3,4,5,6-tetrahydro-2H-[1,4']bipyridinyl-3'-yl)-amide | 493.1 | 2.36 |
| 283 | 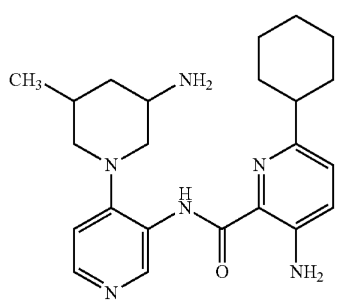 [SMILES: CC1CC(N)CN(c2ccncc2NC(=O)c2nc(C3CCCCC3)ccc2N)C1] | 3-Amino-6-cyclohexyl-pyridine-2-carboxylic acid (3-amino-5-methyl-3,4,5,6-tetrahydro-2H-[1,4']bipyridinyl-3'-yl)-amide | 409.2 | 2.44 |
| 284 | Chiral | 3-Amino-6-cyclohexyl-pyridine-2-carboxylic acid (3-amino-5-fluoro-3,4,5,6-tetrahydro-2H-[1,4']bipyridinyl-3'-yl)-amide | 413.1 | 2.27 |

-continued

| Example | Structure | Name | MH+ | LC |
|---|---|---|---|---|
| 285 | Chiral | 3-Amino-6-cyclohexyl-pyridine-2-carboxylic acid (3-amino-5-methoxy-3,4,5,6-tetrahydro-2H-[1,4']bipyridinyl-3'-yl)-amide | 425.2 | 2.31 |
| 286 | 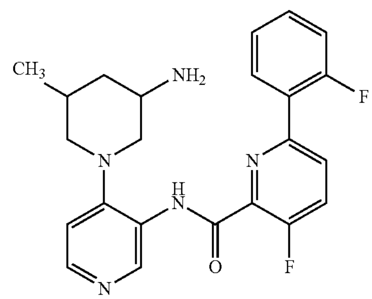 [SMILES: CC1CC(N)CN(c2ccncc2NC(=O)c2nc(-c3ccccc3F)ccc2F)C1] | 3-Fluoro-6-(2-fluoro-phenyl)-pyridine-2-carboxylic acid (5-amino-3-methyl-3,4,5,6-tetrahydro-2H-[1,4']bipyridinyl-3'-yl)-amide | 424.1 | 2.20 |
| 287 | 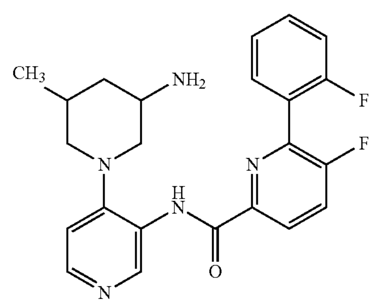 [SMILES: CC1CC(N)CN(c2ccncc2NC(=O)c2ccc(F)c(-c3ccccc3F)n2)C1] | 5-Fluoro-6-(2-fluoro-phenyl)-pyridine-2-carboxylic acid (3-amino-5-methyl-3,4,5,6-tetrahydro-2H-[1,4']bipyridinyl-3'-yl)-amide | 424.1 | 2.31 |
| 288 | 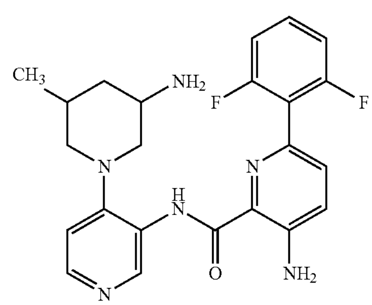 [SMILES: CC1CC(N)CN(c2ccncc2NC(=O)c2nc(-c3c(F)cccc3F)ccc2N)C1] | 3-Amino-6-(2,6-difluoro-phenyl)-pyridine-2-carboxylic acid (3-amino-5-methyl-3,4,5,6-tetrahydro-2H-[1,4']bipyridinyl-3'-yl)-amide | 439.1 | 2.27 |
| 289 | 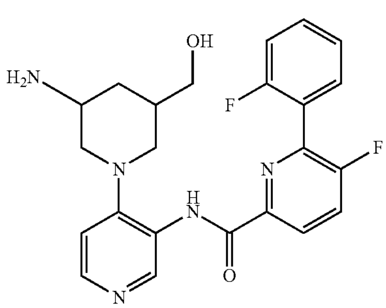 [SMILES: NC1CC(CO)CN(c2ccncc2NC(=O)c2ccc(F)c(-c3ccccc3F)n2)C1] | 5-Fluoro-6-(2-fluoro-phenyl)-pyridine-2-carboxylic acid (5-amino-3-hydroxymethyl-3,4,5,6-tetrahydro-2H-[1,4']bipyridinyl-3'-yl)-amide | 440.1 | 1.94 |

-continued

| Example | Structure | Name | MH+ | LC |
|---|---|---|---|---|
| 290 | 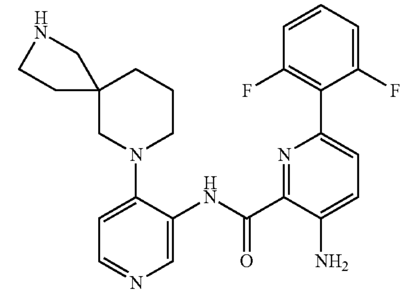 [SMILES: Nc1ccc(-c2c(F)cccc2F)nc1C(=O)Nc1cnccc1N1CCCC2(CCNC2)C1] | 3-Amino-6-(2,6-difluoro-phenyl)-pyridine-2-carboxylic acid [4-(2,7-diaza-spiro[4.5]dec-7-yl)-pyridin-3-yl]-amide | 465.1 | 2.12 |
| 291 | 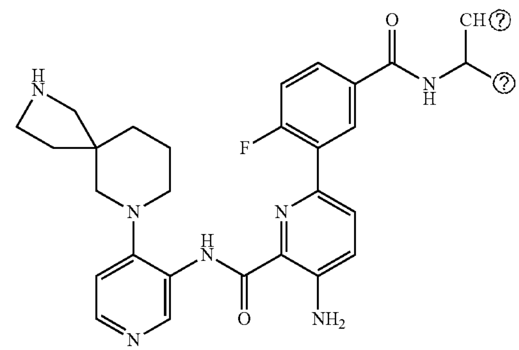 [SMILES: CC(C)NC(=O)c1ccc(F)c(-c2ccc(N)c(C(=O)Nc3cnccc3N3CCCC4(CCNC4)C3)n2)c1] | 3-Amino-6-(2-fluoro-5-isopropylcarbamoyl-phenyl)-pyridine-2-carboxylic acid [4-(2,7-diaza-spiro[4.5]dec-7-yl)-pyridin-3-yl]-amide | 532.1 | 2.02 |
| 292 | 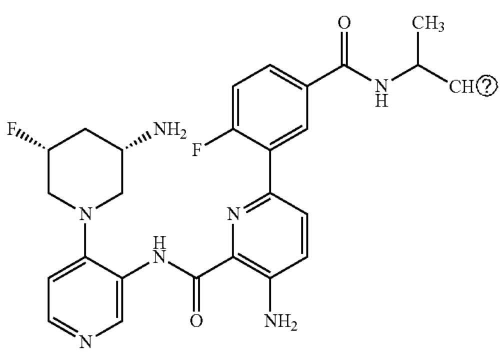 [SMILES: CC(C)NC(=O)c1ccc(F)c(-c2ccc(N)c(C(=O)Nc3cnccc3N3C[C@@H](N)C[C@@H](F)C3)n2)c1] | 3-Amino-6-(2-fluoro-5-isopropylcarbamoyl-phenyl)-pyridine-2-carboxylic acid (3-amino-5-fluoro-3,4,5,6-tetrahydro-2H-[1,4']bipyridinyl-3'-yl)-amide | 510.0 | 2.12 |
| 293 | Chiral | 3-Amino-6-(2,6-difluoro-phenyl)-pyridine-2-carboxylic acid (3-amino-5-fluoro-3,4,5,6-tetrahydro-2H-[1,4']bipyridinyl-3'-yl)-amide | 443.0 | 2.07 |

-continued

| Example | Structure | Name | MH+ | LC |
|---|---|---|---|---|
| 294 | 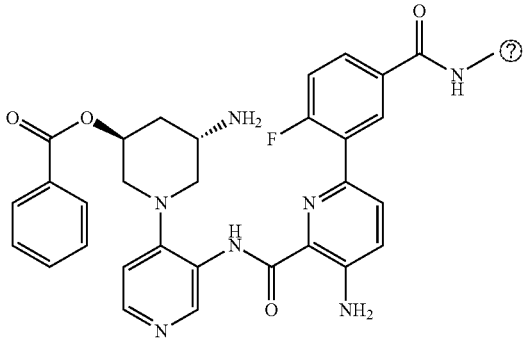 [SMILES: CNC(=O)c1ccc(F)c(-c2ccc(N)c(C(=O)Nc3cnccc3N3C[C@@H](N)C[C@H](OC(=O)c4ccccc4)C3)n2)c1] | Benzoic acid 5-amino-3'-{[3-amino-6-(2-fluoro-5-isopropylcarbamoyl-phenyl)-pyridine-2-carbonyl]-amino}-3,4,5,6-tetrahydro-2H-[1,4']bipyridinyl-3-yl ester | 612.1 | 2.49 |
| 295 | 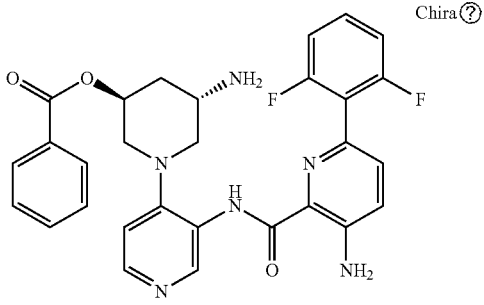 [SMILES: Nc1ccc(-c2c(F)cccc2F)nc1C(=O)Nc1cnccc1N1C[C@@H](N)C[C@H](OC(=O)c2ccccc2)C1] | Benzoic acid 5-amino-3'-{[3-amino-6-(2,6-difluoro-phenyl)-pyridine-2-carbonyl]-amino}-3,4,5,6-tetrahydro-2H-[1,4']bipyridinyl-3-yl ester | 545.0 | 2.51 |
| 296 | 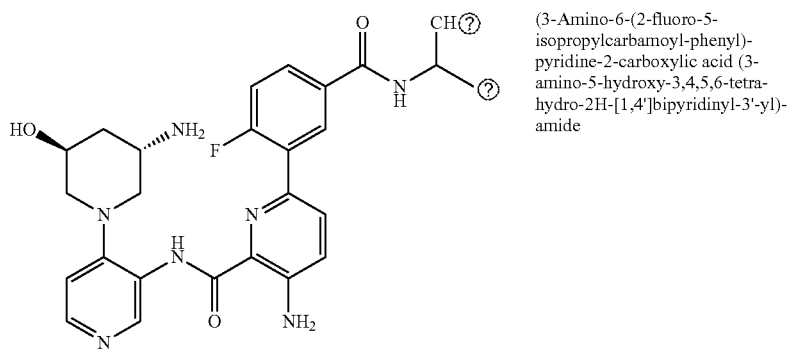 | (3-Amino-6-(2-fluoro-5-isopropylcarbamoyl-phenyl)-pyridine-2-carboxylic acid (3-amino-5-hydroxy-3,4,5,6-tetrahydro-2H-[1,4']bipyridinyl-3'-yl)-amide | 508.2 | 2.00 |
| 297 | 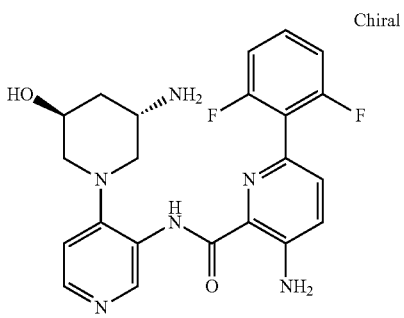 [SMILES: Nc1ccc(-c2c(F)cccc2F)nc1C(=O)Nc1cnccc1N1C[C@@H](N)C[C@H](O)C1] | 3-Amino-6-(2,6-difluoro-phenyl)-pyridine-2-carboxylic acid (3-amino-5-hydroxy-3,4,5,6-tetrahydro-2H-[1,4']bipyridinyl-3'-yl)-amide | 441.1 | 1.80 |

-continued

| Example | Structure | Name | MH+ | LC |
|---|---|---|---|---|
| 298 | 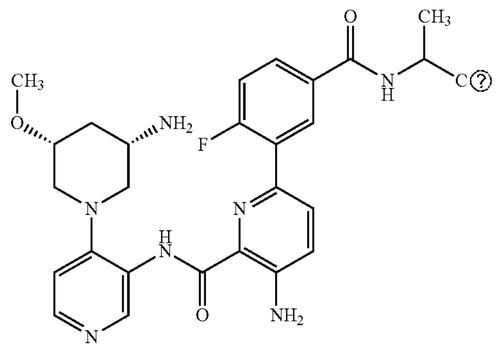 [SMILES: CO[C@@H]1C[C@H](N)CN(c2ccncc2NC(=O)c2nc(-c3cc(C(=O)NC(C)C)ccc3F)ccc2N)C1] | 3-Amino-6-(2-fluoro-5-isopropylcarbamoyl-phenyl)-pyridine-2-carboxylic acid (3-amino-5-methoxy-3,4,5,6-tetrahydro-2H-[1,4']bipyridinyl-3'-yl)-amide | 522.2 | 2.01 |
| 299 | 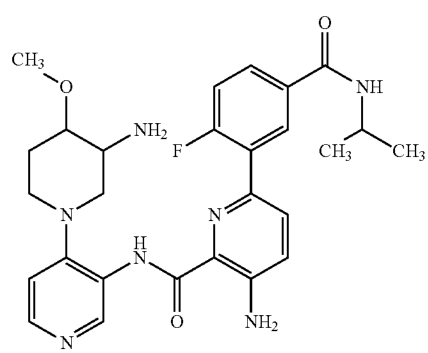 [SMILES: COC1CCN(c2ccncc2NC(=O)c2nc(-c3cc(C(=O)NC(C)C)ccc3F)ccc2N)CC1N] | 3-Amino-6-(2-fluoro-5-isopropylcarbamoyl-phenyl)-pyridine-2-carboxylic acid (3-amino-4-methoxy-3,4,5,6-tetrahydro-2H-[1,4']bipyridinyl-3'-yl)-amide | 522.0 | 2.09 |
| 300 | Chiral | 3-Amino-6-(2,6-difluoro-phenyl)-pyridine-2-carboxylic acid (3-amino-5-methoxy-3,4,5,6-tetrahydro-2H-[1,4']bipyridinyl-3'-yl)-amide | 455.2 | 1.98 |
| 301 | 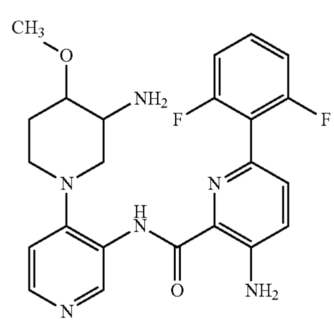 [SMILES: COC1CCN(c2ccncc2NC(=O)c2nc(-c3c(F)cccc3F)ccc2N)CC1N] | 3-Amino-6-(2,6-difluoro-phenyl)-pyridine-2-carboxylic acid (3-amino-4-methoxy-3,4,5,6-tetrahydro-2H-[1,4']bipyridinyl-3'-yl)-amide | 455.0 | 1.96 |

| Example | Structure | Name | MH+ | LC |
|---|---|---|---|---|
| 302 | Chiral | 3-Amino-6-(2,6-difluoro-phenyl)-pyridine-2-carboxylic acid [4-(2-oxo-hexahydro-oxazolo[4,5-c]pyridin-5-yl)-pyridin-3-yl] | 467.0 | 2.40 |
| 303 | Chiral | 3-Amino-6-(2,6-difluoro-phenyl)-pyridine-2-carboxylic acid [4-(2-oxo-hexahydro-oxazolo[4,5-c]pyridin-5-yl)-pyridin-3-yl]-amide | 467.0 | 2.40 |

Example 304

Synthesis of N-(4-(3-acetamidopiperidin-1-yl)pyridin-3-yl)-3-amino-6-bromopyrazine-2-carboxamide

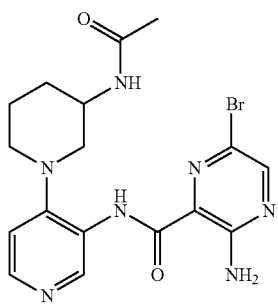 [SMILES: CC(=O)NC1CCCN(c2ccncc2NC(=O)c2nc(Br)cnc2N)C1]

To solution of 3-amino-N-(4-(3-aminopiperidin-1-yl)pyridin-3-yl)-6-bromopyrazine-2-carboxamide in $CH_2Cl_2$ at a concentration of 0.5 M at room temperature was added triethylamine (3 eq) followed by acetic anhydride (1.2 eq). The reaction was stirred at room temperature for 30 minutes, concentrated, purified by reverse phase HPLC and lyophilized to provide N-(4-(3-acetamidopiperidin-1-yl)pyridin-3-yl)-3-amino-6-bromopyrazine-2-carboxamide, as the TFA salt. LCMS (m/z): 434.1 (MH+).

Method 11

Example 305

Synthesis of tert-butyl 1-(3-(3-amino-6-bromopyrazine-2-carboxamido)pyridin-4-yl)piperidin-3-ylcarbamate

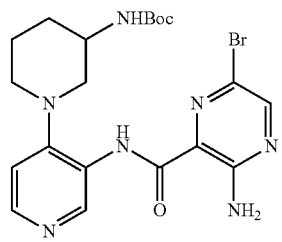 [SMILES: CC(C)(C)OC(=O)NC1CCCN(c2ccncc2NC(=O)c2nc(Br)cnc2N)C1]

A solution containing 1 eq each of tert-butyl 1-(3-aminopyridin-4-yl)piperidin-3-ylcarbamate, 3-amino-6-bromopyrazine-2-carboxylic acid, HOAT and EDC in DMF, at a concentration of 0.5 M, was stirred for 60 hours. The solution was diluted with EtOAc and was washed with $H_2O$ (4x), Na $Cl_{(sat.)}$, was dried over $MgSO_4$, was filtered and the volatiles were removed in vacuo. After purification by silica gel chromatography (EtOAc eluant), tert-butyl 1-(3-(3-amino-6-bromopyrazine-2-carboxamido)pyridin-4-yl)piperidin-3-ylcarbamate was obtained (78%). LCMS (m/z): 492.2 (MH+); LC $R_t$=2.68 min.

Example 306

Synthesis of tert-butyl 1-(2-(3-amino-6-bromopyrazine-2-carboxamido)-4-benzoylphenyl)piperidin-4-ylcarbamate

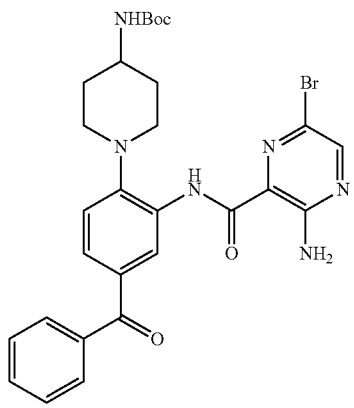 [SMILES: CC(C)(C)OC(=O)NC1CCN(c2ccc(C(=O)c3ccccc3)cc2NC(=O)c2nc(Br)cnc2N)CC1]

Following method 11, tert-butyl 1-(2-amino-4-benzoylphenyl)piperidin-4-ylcarbamate was coupled to 3-amino-6-bromopyrazine-2-carboxylic acid with TEA (1.5 eq) in ACN at 55° C. for 48 hours. Concentrated, triturated in cold ACN, filtered, and dried in vacuo yielding tert-butyl 1-(2-(3-amino-6-bromopyrazine-2-carboxamido)-4-benzoylphenyl)piperidin-4-ylcarbamate (46%). LCMS (m/z): 595.2 (MH$^+$); LC R$_t$=3.94 min.

Example 307

Synthesis of tert-butyl 1-(2-(3-amino-6-bromopyrazine-2-carboxamido)-4-benzoylphenyl)piperidin-3-ylcarbamate

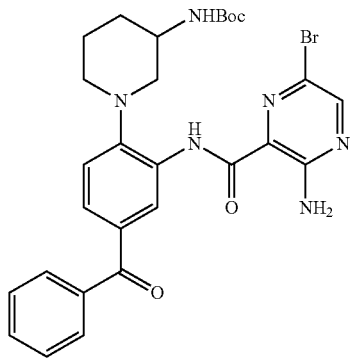 [SMILES: CC(C)(C)OC(=O)NC1CCCN(c2ccc(C(=O)c3ccccc3)cc2NC(=O)c2nc(Br)cnc2N)C1]

Following method 11, tert-butyl 1-(2-amino-4-benzoylphenyl)piperidin-3-ylcarbamate was coupled to 3-amino-6-bromopyrazine-2-carboxylic acid with TEA (1.5 eq) in ACN at 55° C. for 48 hours. Concentrated, triturated in cold ACN, filtered, and dried in vacuo yielding tert-butyl 1-(2-(3-amino-6-bromopyrazine-2-carboxamido)-4-benzoylphenyl)piperidin-3-ylcarbamate (30%). LCMS (m/z): 595.1 (MH$^+$); LC R$_t$=3.87 min.

Example 308

Synthesis of tert-butyl 4-(2-(3-amino-6-bromopyrazine-2-carboxamido)-4-benzoylphenyl)piperazine-1-carboxylate

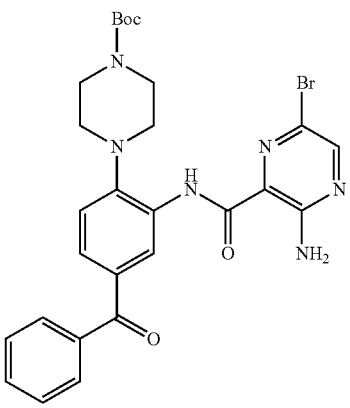 [SMILES: CC(C)(C)OC(=O)N1CCN(c2ccc(C(=O)c3ccccc3)cc2NC(=O)c2nc(Br)cnc2N)CC1]

Following method 11, tert-butyl 4-(2-amino-4-benzoylphenyl)piperazine-1-carboxylate was coupled to 3-amino-6-bromopyrazine-2-carboxylic acid with TEA (1.5 eq) in ACN at 55° C. for 48 hours. Concentrated, triturated in cold ACN, filtered, and dried in vacuo yielding tert-butyl 4-(2-(3-amino-6-bromopyrazine-2-carboxamido)-4-benzoylphenyl)piperazine-1-carboxylate (50%). LCMS (m/z): 581.1 (MH$^+$); LC R$_t$=4.00 min.

Example 309

Synthesis of tert-butyl 1-(2-(3-amino-6-bromopyrazine-2-carboxamido)-4-methoxyphenyl)piperidin-4-ylcarbamate

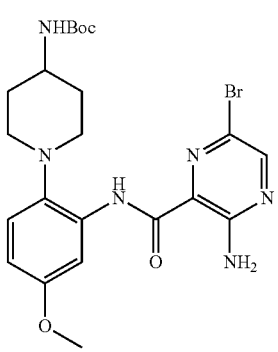 [SMILES: COc1ccc(N2CCC(NC(=O)OC(C)(C)C)CC2)c(NC(=O)c2nc(Br)cnc2N)c1]

Following method 11, tert-butyl 1-(2-amino-4-methoxyphenyl)piperidin-4-ylcarbamate was coupled to 3-amino-6-bromopyrazine-2-carboxylic acid with TEA (3 eq) in ACN at 55° C. for 48 hours. Concentrated, triturated in cold ACN, filtered, and dried in vacuo yielding tert-butyl 1-(2-(3-amino-6-bromopyrazine-2-carboxamido)-4-methoxyphenyl)piperidin-4-ylcarbamate (7%). LCMS (m/z): 521.1 (MH$^+$); LC R$_t$=3.63 min.

Example 310

Synthesis of
3,5-diamino-6-chloropyrazine-2-carboxylic acid

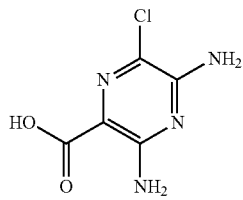 [SMILES: Nc1nc(N)c(C(=O)O)nc1Cl]

To a solution of methyl 3,5-diamino-6-chloropyrazine-2-carbamate (5 g, 0.025 mols) in 2:1 THF/MeOH (90 mL) was added 1M LiOH (62 mL, 0.062 mols). After the reaction was stirred at r.t. 72 hrs, 1N HCl (62 mL, 0.062 mols) was added. The reaction was filtered and washed with water (3×10 mL) to give 3,5-diamino-6-chloropyrazine-2-carboxylic acid as white solid 4.3 g (93% yield). LCMS (m/z): 189.1 (MH$^+$); LC R$_t$=1.05 min.

Example 311

Synthesis of 3,5-diamino-6-chloro-N-(4-(piperidin-1-yl)pyridin-3-yl)pyrazine-2-carboxamide

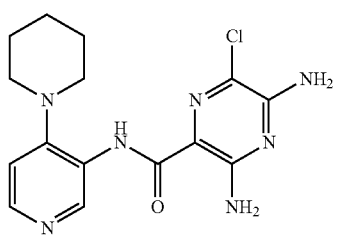 [SMILES: Nc1nc(N)c(C(=O)Nc2cnccc2N2CCCCC2)nc1Cl]

Following method 11, 4-(piperidin-1-yl)pyridin-3-amine was coupled to 3,5-diamino-6-chloropyrazine-2-carboxylic acid yielding 3,5-diamino-6-chloro-N-(4-(piperidin-1-yl)pyridin-3-yl)pyrazine-2-carboxamide (76%). LCMS (m/z): 347.8 (MH$^+$); LC R$_t$=2.17 min.

Example 312

Synthesis of 3,5-diamino-N-(4-(piperidin-1-yl)pyridin-3-yl)pyrazine-2-carboxamide

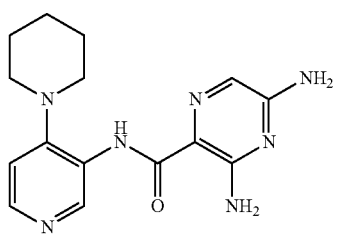 [SMILES: Nc1cnc(C(=O)Nc2cnccc2N2CCCCC2)c(N)n1]

Following method 2 where diethylamine (4.0 eq) was also included and the reaction was recharged with Pd/C and H$_2$ after 2 and 4 days, 3,5-diamino-6-chloro-N-(4-(piperidin-1-yl)pyridin-3-yl)pyrazine-2-carboxamide was reduced in 7 days yielding 3,5-diamino-N-(4-(piperidin-1-yl)pyridin-3-yl)pyrazine-2-carboxamide as the TFA salt. LCMS (m/z): 314.1 (MH$^+$); LC R$_t$=1.67 min.

Example 313

Synthesis of tert-butyl 1-(3-(3,5-diamino-6-chloropyrazine-2-carboxamido)pyridin-4-yl)piperidin-3-ylcarbamate

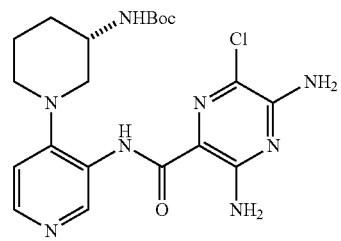 [SMILES: CC(C)(C)OC(=O)N[C@H]1CCCN(c2ccncc2NC(=O)c2nc(Cl)c(N)nc2N)C1]

Following method 11, tert-butyl 1-(3-aminopyridin-4-yl)piperidin-3-ylcarbamate was coupled to 3,5-diamino-6-chloropyrazine-2-carboxylic acid yielding (S)-tert-butyl 1-(3-(3,5-diamino-6-chloropyrazine-2-carboxamido)pyridin-4-yl)piperidin-3-ylcarbamate (57%). LCMS (m/z): 463.1 (MH$^+$); LC R$_t$=2.36 min.

Example 314

Synthesis of 3-amino-6-bromopicolinic acid

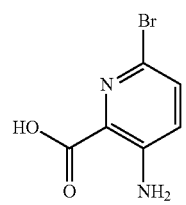 [SMILES: Nc1ccc(Br)nc1C(=O)O]

To a solution of methyl 3-amino-6-bromopicolinate (2.31 g, 10 mmoles) in 2:1 THF/MeOH (51 mL) was added 1.0 M LiOH (17 mL, 17 mmoles). After stirring for 16 hours, 1 N HCl (17 mL, 17 mmoles) was added and the THF/MeOH was removed in vacuo. The resulting solid was filtered, rinsed with cold H$_2$O (4×20 mL) and pumped on yielding 3-amino-6-bromopicolinic acid (97%). LCMS (m/z): 216.9 (MH$^+$); LC R$_t$=1.93 min.

Example 315

Synthesis of (S)-tert-butyl 1-(3-(3-amino-6-bromopicolinamido)pyridin-4-yl)piperidin-3-ylcarbamate

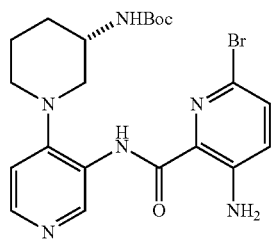 [SMILES: CC(C)(C)OC(=O)N[C@H]1CCCN(c2ccncc2NC(=O)c2nc(Br)ccc2N)C1]

Following method 11, (S)-tert-butyl 1-(3-aminopyridin-4-yl)piperidin-3-ylcarbamate was coupled to 3-amino-6-bromopicolinic acid and purified by SiO2 chromatography (EtOAc eluant) yielding (S)-tert-butyl 1-(3-(3-amino-6-bromopicolinamido)pyridin-4-yl)piperidin-3-ylcarbamate (45%). LCMS (m/z): 491.1 (MH$^+$); LC R$_t$=2.89 min.

Method 12

Example 316

Synthesis of 3-amino-N-(4-(3-aminopiperidin-1-yl)pyridin-3-yl)-6-(2-chlorophenyl)pyrazine-2-carboxamide

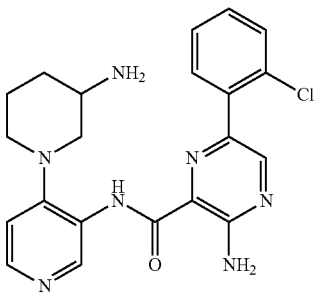 [SMILES: Nc1ncc(-c2ccccc2Cl)nc1C(=O)Nc1cnccc1N1CCCC(N)C1]

A solution of tert-butyl 1-(3-(3-amino-6-bromopyrazine-2-carboxamido)pyridin-4-yl)piperidin-3-ylcarbamate (1.0 eq), ortho-chlorophenyl boronic acid (3.0 eq.), Pd(dppf)Cl$_2$—CH$_2$Cl$_2$ and triethylamine (9.0 eq.) in dimethylacetamide (concentration=0.1 M) was heated at 130° C. with microwave irradiation for 900 seconds. Upon cooling the N-Boc Suzuki product was directly purified by reverse phase HPLC.

The product fraction was lyophilized and the resulting solid was treated with 25% TFA/DCM (at a resulting concentration of 0.05 M). After sitting for 2 hours, the volatiles were removed in vacuo and the residue was purified by reverse phase HPLC. After lyophilization, 3-amino-N-(4-(3-aminopiperidin-1-yl)pyridin-3-yl)-6-(2-chlorophenyl)pyrazine-2-carboxamide was obtained (56%) as the TFA salt. LCMS (m/z): 424.1 (MH$^+$); LC R$_t$=1.94 min.

Alternatively, the free base and HCl salt could be obtained as described in Method 9.

The following compounds were prepared using Method 12. In some instances NMP or DMF was used in place of dimethylacetamide.

| Example | Structure | Name | MH+ | LC |
|---|---|---|---|---|
| 317 | Chiral | 3-amino-6-(2-fluoro-5-isopropylcarbamoyl-phenyl)-pyridine-2-carboxylic acid ((S)-3-amino-3,4,5,6-tetrahydro-2H-[1,4']bipyridinyl-3'-yl)-amide | 492.2 | 2.04 |
| 318 | Chiral | 3-amino-6-[2-methyl-5-(piperidine-1-sulfonyl)-phenyl]-pyridine-2-carboxylic acid ((S)-3-amino-3,4,5,6-tetrahydro-2H-[1,4']bipyridinyl-3'-yl)-amide | 550.3 | 2.44 |

-continued

| Example | Structure | Name | MH+ | LC |
|---|---|---|---|---|
| 319 | Chiral | 3-amino-6-(4-methane-sulfonyl-phenyl)-pyridine-2-carboxylic acid ((S)-3-amino-3,4,5,6-tetrahydro-2H-[1,4']bipyridinyl-3'-yl)-amide | 467.2 | 1.77 |
| 320 | Chiral | 3-amino-6-(3-methane-sulfonyl-phenyl)-pyridine-2-carboxylic acid ((S)-3-amino-3,4,5,6-tetrahydro-2H-[1,4']bipyridinyl-3'-yl)-amide | 467.2 | 1.77 |
| 321 | Chiral | 3-amino-6-[2-methyl-5-(pyrrolidine-1-sulfonyl)-phenyl]-pyridine-2-carboxylic acid ((S)-3-amino-3,4,5,6-tetrahydro-2H-[1,4']bipyridinyl-3'-yl)-amide | 536.2 | 2.27 |
| 322 | Chiral | 3-amino-6-(2-chloro-5-ethoxy-phenyl)-pyridine-2-carboxylic acid ((S)-3-amino-3,4,5,6-tetrahydro-2H-[1,4']bipyridinyl-3'-yl)-amide | 467.2 | 2.43 |

| Example | Structure | Name | MH+ | LC |
|---|---|---|---|---|
| 323 | Chiral | 3-amino-6-(2-fluoro-5-phenylcarbamoyl-phenyl)-pyridine-2-carboxylic acid ((S)-3-amino-3,4,5,6-tetrahydro-2H-[1,4']bipyridinyl-3'-yl)-amide | 526.2 | 2.35 |
| 324 | Chiral | 3-amino-6-(5-cyclohexylcarbamoyl-2-fluoro-phenyl)-pyridine-2-carboxylic acid ((S)-3-amino-3,4,5,6-tetrahydro-2H-[1,4']bipyridinyl-3'-yl)-amide | 532.3 | 2.44 |
| 325 | Chiral | 4-[5-amino-6-((S)-3-amino-3,4,5,6-tetrahydro-2H-[1,4']bipyridinyl-3'-ylcarbamoyl)-pyridin-2-yl]-3-fluoro-benzoic acid methyl ester | 465.2 | 2.24 |
| 326 | Chiral | 3-amino-6-(2-fluoro-5-propylcarbamoyl-phenyl)-pyridine-2-carboxylic acid ((S)-3-amino-3,4,5,6-tetrahydro-2H-[1,4']bipyridinyl-3'-yl)-amide | 492.2 | 2.11 |

-continued

| Example | Structure | Name | MH+ | LC |
|---|---|---|---|---|
| 327 | 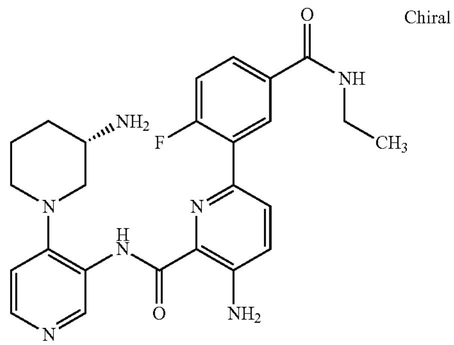 [SMILES: CCNC(=O)c1ccc(F)c(-c2ccc(N)c(C(=O)Nc3cnccc3N3CCC[C@H](N)C3)n2)c1] | Chiral 3-amino-6-(5-ethylcarbamoyl-2-fluoro-phenyl)-pyridine-2-carboxylic acid ((S)-3-amino-3,4,5,6-tetrahydro-2H-[1,4']bipyridinyl-3'-yl)-amide | 478.2 | 1.97 |
| 328 | 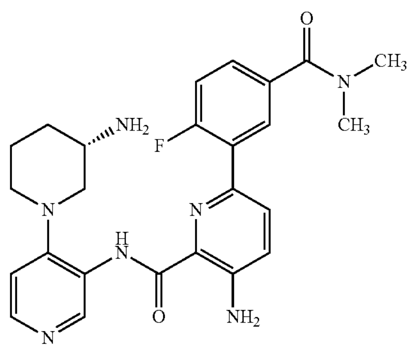 | Chiral 3-amino-6-(5-dimethylcarbamoyl-2-fluoro-phenyl)-pyridine-2-carboxylic acid ((S)-3-amino-3,4,5,6-tetrahydro-2H-[1,4']bipyridinyl-3'-yl)-amide | 478.2 | 1.98 |
| 329 | 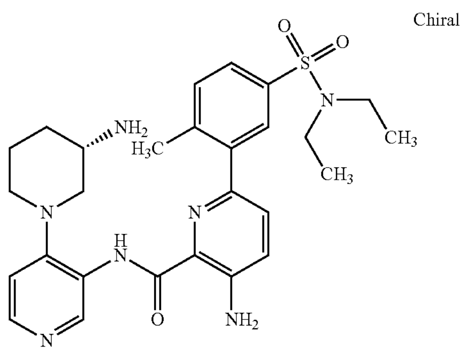 [SMILES: CCN(CC)S(=O)(=O)c1ccc(C)c(-c2ccc(N)c(C(=O)Nc3cnccc3N3CCC[C@H](N)C3)n2)c1] | Chiral 3-amino-6-(5-diethylsulfamoyl-2-methyl-phenyl)-pyridine-2-carboxylic acid ((S)-3-amino-3,4,5,6-tetrahydro-2H-[1,4']bipyridinyl-3'-yl)-amide | 538.3 | 2.41 |
| 330 | 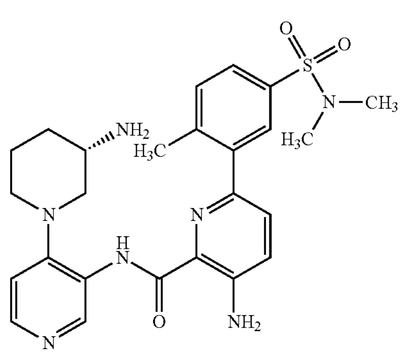 | Chiral 3-amino-6-(5-dimethylsulfamoyl-2-methyl-phenyl)-pyridine-2-carboxylic acid ((S)-3-amino-3,4,5,6-tetrahydro-2H-[1,4']bipyridinyl-3'-yl)-amide | 510.2 | 2.12 |

| Example | Structure | Name | MH+ | LC |
|---|---|---|---|---|
| 331 | Chiral | 5-amino-2'-chloro-[2,3']bi-pyridinyl-6-carboxylic acid ((S)-3-amino-3,4,5,6-tetra-hydro-2H-[1,4']bipyridinyl-3'-yl)-amide | 424.1 | 1.78 |
| 332 | Chiral | 3-amino-6-(2-cyano-phenyl)-pyridine-2-carboxylic acid ((S)-3-amino-3,4,5,6-tetra-hydro-2H-[1,4']bipyridinyl-3'-yl)-amide | 414.2 | 1.87 |
| 333 | Chiral | 3-amino-6-(2-fluoro-5-methyl-phenyl)-pyridine-2-carboxylic acid ((S)-3-amino-3,4,5,6-tetrahydro-2H-[1,4']bi-pyridinyl-3'-yl)-amide | 421.2 | 2.29 |
| 334 | Chiral | 3-amino-6-(2-fluoro-5-methylcarbamoyl-phenyl)-pyridine-2-carboxylic acid ((S)-3-amino-3,4,5,6-tetra-hydro-2H-[1,4']bipyridinyl-3'-yl)-amide | 464.2 | 1.86 |

| Example | Structure | Name | MH+ | LC |
|---|---|---|---|---|
| 335 | Chiral | 3-amino-6-(5-tert-butyl-sulfamoyl-2-methyl-phenyl)-pyridine-2-carboxylic acid ((S)-3-amino-3,4,5,6-tetrahydro-2H-[1,4']bipyridinyl-3'-yl)-amide | 538.3 | 2.36 |
| 336 | Chiral | 3-amino-6-(5-tert-butyl-sulfamoyl-2-methyl-phenyl)-pyridine-2-carboxylic acid ((S)-3-amino-3,4,5,6-tetrahydro-2H-[1,4']bipyridinyl-3'-yl)-amide | 457.2 | 2.28 |
| 337 | Chiral | 3-amino-6-(2-methoxy-phenyl)-pyridine-2-carboxylic acid ((S)-3-amino-3,4,5,6-tetrahydro-2H-[1,4']bipyridinyl-3'-yl)-amide | 419.2 | 2.11 |
| 338 | Chiral | 3-amino-6-o-tolyl-pyridine-2-carboxylic acid ((S)-3-amino-3,4,5,6-tetrahydro-2H-[1,4']bipyridinyl-3'-yl)-amide | 403.2 | 2.17 |
| 339 | Chiral | 5-amino-3'-fluoro-[2,4']bipyridinyl-6-carboxylic acid ((S)-3-amino-3,4,5,6-tetrahydro-2H-[1,4']bipyridinyl-3'-yl)-amide | 408.2 | 1.48 |

| Example | Structure | Name | MH+ | LC |
|---|---|---|---|---|
| 340 | 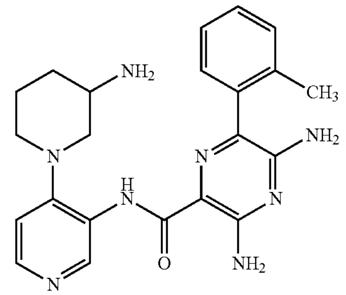 [SMILES: Cc1ccccc1-c1nc(C(=O)Nc2cnccc2N2CCCC(N)C2)c(N)nc1N] | 3,5-diamino-6-o-tolyl-pyrazine-2-carboxylic acid (3-amino-3,4,5,6-tetrahydro-2H-[1,4']bipyridinyl-3'-yl)-amide | 419.2 | 1.67 |
| 341 | 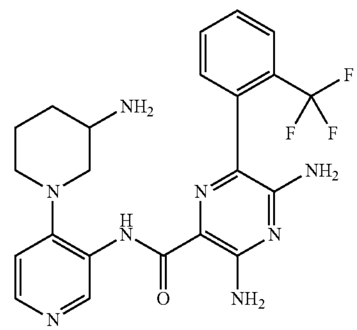 [SMILES: Nc1nc(N)c(-c2ccccc2C(F)(F)F)nc1C(=O)Nc1cnccc1N1CCCC(N)C1] | 3,5-diamino-6-(2-trifluoro-methyl-phenyl)-pyrazine-2-carboxylic acid (3-amino-3,4,5,6-tetrahydro-2H-[1,4']bipyridinyl-3'-yl)-amide | 473.2 | 1.76 |
| 342 | 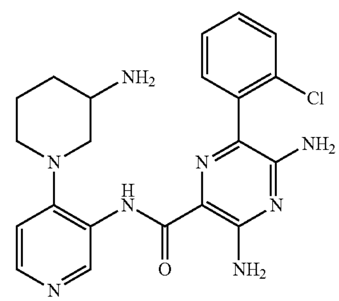 [SMILES: Nc1nc(N)c(-c2ccccc2Cl)nc1C(=O)Nc1cnccc1N1CCCC(N)C1] | 3,5-diamino-6-(2-chloro-phenyl)-pyrazine-2-carboxylic acid (3-amino-3,4,5,6-tetrahydro-2H-[1,4']bipyridinyl-3'-yl)-amide | 439.1 | 1.68 |
| 343 | 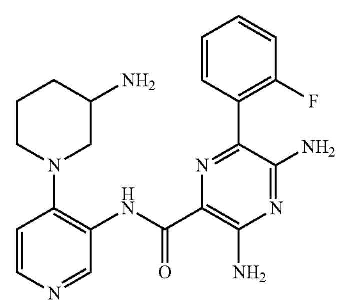 [SMILES: Nc1nc(N)c(-c2ccccc2F)nc1C(=O)Nc1cnccc1N1CCCC(N)C1] | 3,5-diamino-6-(2-fluoro-phenyl)-pyrazine-2-carboxylic acid (3-amino-3,4,5,6-tetrahydro-2H-[1,4']bipyridinyl-3'-yl)-amide | 423.1 | 1.59 |
| 344 | 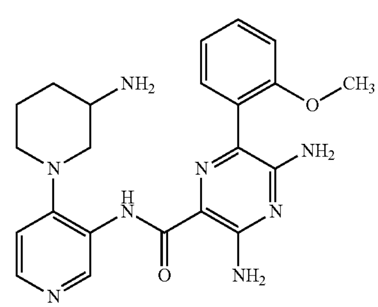 [SMILES: COc1ccccc1-c1nc(C(=O)Nc2cnccc2N2CCCC(N)C2)c(N)nc1N] | 3,5-diamino-6-(2-methoxy-phenyl)-pyrazine-2-carboxylic acid (3-amino-3,4,5,6-tetrahydro-2H-[1,4']bipyridinyl-3'-yl)-amide | 435.2 | 1.58 |

| Example | Structure | Name | MH+ | LC |
|---|---|---|---|---|
| 345 | 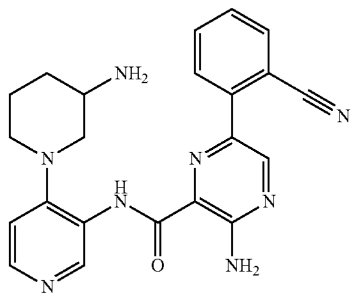 [SMILES: N#Cc1ccccc1-c1cnc(N)c(C(=O)Nc2cnccc2N2CCCC(N)C2)n1] | 3-amino-6-(2-cyano-phenyl)-pyrazine-2-carboxylic acid (3-amino-3,4,5,6-tetrahydro-2H-[1,4']bipyridinyl-3'-yl)-amide | 415.2 | 1.67 |
| 346 | 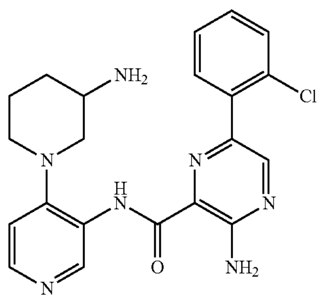 [SMILES: Nc1ncc(-c2ccccc2Cl)nc1C(=O)Nc1cnccc1N1CCCC(N)C1] | 3-amino-6-(2-chloro-phenyl)-pyrazine-2-carboxylic acid (3-amino-3,4,5,6-tetrahydro-2H-[1,4']bipyridinyl-3'-yl)-amide | 424.1 | 1.94 |
| 347 | 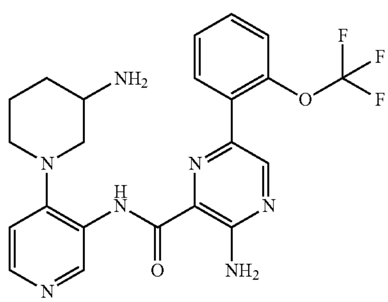 [SMILES: Nc1ncc(-c2ccccc2OC(F)(F)F)nc1C(=O)Nc1cnccc1N1CCCC(N)C1] | 3-amino-6-(2-trifluoro-methoxy-phenyl)-pyrazine-2-carboxylic acid (3-amino-3,4,5,6-tetrahydro-2H-[1,4']bipyridinyl-3'-yl)-amide | 474.2 | 2.16 |
| 348 | 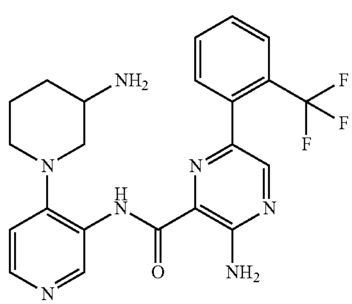 [SMILES: Nc1ncc(-c2ccccc2C(F)(F)F)nc1C(=O)Nc1cnccc1N1CCCC(N)C1] | 3-amino-6-(2-trifluoromethyl-phenyl)-pyrazine-2-carboxylic acid (3-amino-3,4,5,6-tetrahydro-2H-[1,4']bipyridinyl-3'-yl)-amide | 458.2 | 2.03 |
| 349 | 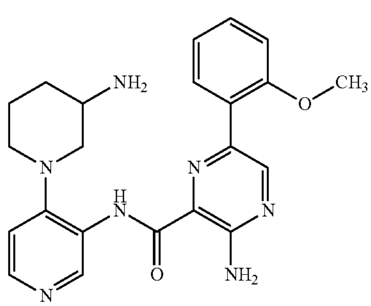 [SMILES: COc1ccccc1-c1cnc(N)c(C(=O)Nc2cnccc2N2CCCC(N)C2)n1] | 3-amino-6-(2-methoxy-phenyl)-pyrazine-2-carboxylic acid (3-amino-3,4,5,6-tetrahydro-2H-[1,4']bipyridinyl-3'-yl)-amide | 420.2 | 1.86 |

| Example | Name | MH+ | LC |
|---|---|---|---|
| 350 | 3-amino-6-(2-fluoro-phenyl)-pyrazine-2-carboxylic acid (3-amino-3,4,5,6-tetrahydro-2H-[1,4']bipyridinyl-3'-yl)-amide | 408.1 | 1.84 |
| 351 | 3-amino-6-o-tolyl-pyrazine-2-carboxylic acid (3-amino-3,4,5,6-tetrahydro-2H-[1,4']bipyridinyl-3'-yl)-amide | 404.2 | 1.9 |
| 352 | 3-amino-6-(3-chloro-phenyl)-pyrazine-2-carboxylic acid (3-amino-3,4,5,6-tetrahydro-2H-[1,4']bipyridinyl-3'-yl)-amide | 424.1 | |
| 353 | 3-amino-6-(4-chloro-phenyl)-pyrazine-2-carboxylic acid (3-amino-3,4,5,6-tetrahydro-2H-[1,4']bipyridinyl-3'-yl)-amide | 424.1 | |
| 354 | 3-amino-6-pyridin-4-yl-pyrazine-2-carboxylic acid (3-amino-3,4,5,6-tetrahydro-2H-[1,4']bipyridinyl-3'-yl)-amide | 391.2 | |

| Example | Structure | Name | MH+ | LC |
|---|---|---|---|---|
| 355 | 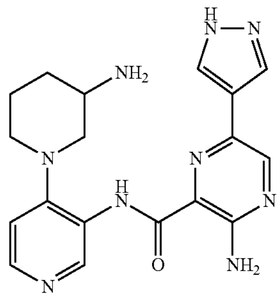 [SMILES: Nc1ncc(-c2cn[nH]c2)nc1C(=O)Nc1cnccc1N1CCCC(N)C1] | 3-amino-6-(1H-pyrazol-4-yl)-pyrazine-2-carboxylic acid (3-amino-3,4,5,6-tetrahydro-2H-[1,4']bipyridinyl-3'-yl)-amide | 380.1 | |
| 356 | 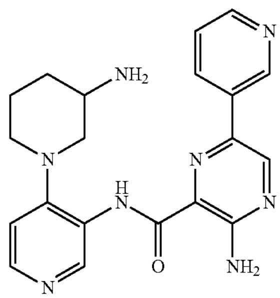 [SMILES: Nc1ncc(-c2cccnc2)nc1C(=O)Nc1cnccc1N1CCCC(N)C1] | 3-amino-6-pyridin-3-yl-pyrazine-2-carboxylic acid (3-amino-3,4,5,6-tetrahydro-2H-[1,4']bipyridinyl-3'-yl)-amide | 391.2 | |
| 357 | 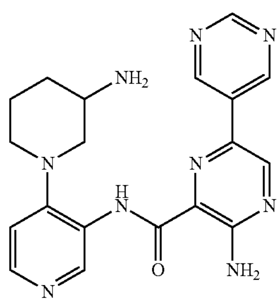 [SMILES: Nc1ncc(-c2cncnc2)nc1C(=O)Nc1cnccc1N1CCCC(N)C1] | 3-amino-6-pyrimidin-5-yl-pyrazine-2-carboxylic acid (3-amino-3,4,5,6-tetrahydro-2H-[1,4']bipyridinyl-3'-yl)-amide | 392.2 | |
| 358 | 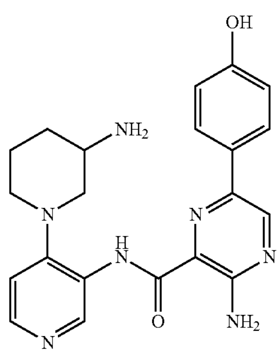 [SMILES: Nc1ncc(-c2ccc(O)cc2)nc1C(=O)Nc1cnccc1N1CCCC(N)C1] | 3-amino-6-(4-hydroxy-phenyl)-pyrazine-2-carboxylic acid (3-amino-3,4,5,6-tetrahydro-2H-[1,4']bipyridinyl-3'-yl)-amide | 406.2 | 1.58 |
| 359 | 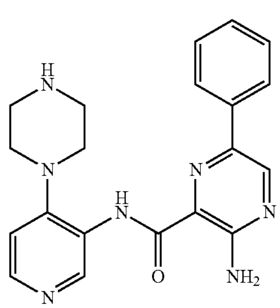 [SMILES: Nc1ncc(-c2ccccc2)nc1C(=O)Nc1cnccc1N1CCNCC1] | 3-amino-6-phenyl-pyrazine-2-carboxylic acid (4-piperazin-1-yl-pyridin-3-yl)-amide | 376.2 | 1.68 |

| Example | Structure | Name | MH+ | LC |
|---|---|---|---|---|
| 360 | 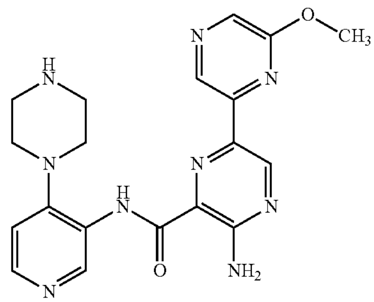 [SMILES: COc1cncc(-c2cnc(N)c(C(=O)Nc3cnccc3N3CCNCC3)n2)n1] | 5-amino-6'-methoxy-[2,2']bipyrazinyl-6-carboxylic acid (4-piperazin-1-yl-pyridin-3-yl)-amide | 408.2 | 1.6 |
| 361 | 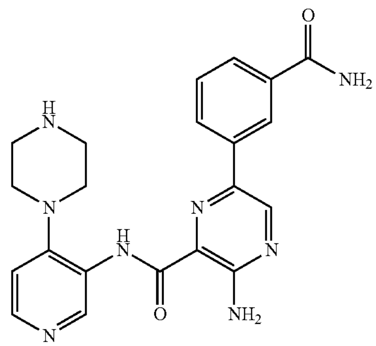 [SMILES: NC(=O)c1cccc(-c2cnc(N)c(C(=O)Nc3cnccc3N3CCNCC3)n2)c1] | 3-amino-6-(3-carbamoyl-phenyl)-pyrazine-2-carboxylic acid (4-piperazin-1-yl-pyridin-3-yl)-amide | 419.2 | 1.36 |
| 362 | 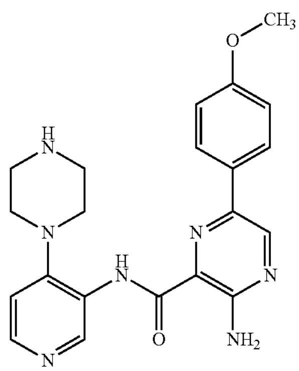 [SMILES: COc1ccc(-c2cnc(N)c(C(=O)Nc3cnccc3N3CCNCC3)n2)cc1] | 3-amino-6-(4-methoxy-phenyl)-pyrazine-2-carboxylic acid (4-piperazin-1-yl-pyridin-3-yl)-amide | 406.2 | 1.76 |
| 363 | 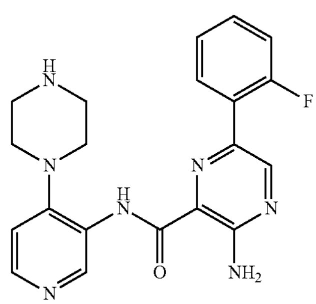 [SMILES: Nc1ncc(-c2ccccc2F)nc1C(=O)Nc1cnccc1N1CCNCC1] | 3-amino-6-(2-fluoro-phenyl)-pyrazine-2-carboxylic acid (4-piperazin-1-yl-pyridin-3-yl)-amide | 394.2 | 1.74 |
| 364 | 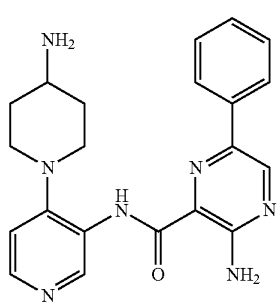 [SMILES: Nc1ncc(-c2ccccc2)nc1C(=O)Nc1cnccc1N1CCC(N)CC1] | 3-amino-6-phenyl-pyrazine-2-carboxylic acid (4-amino-3,4,5,6-tetrahydro-2H-[1,4']bipyridinyl-3'-yl)-amide | 390.2 | 1.73 |

-continued

| Example | Structure | Name | MH+ | LC |
|---------|-----------|------|------|------|
| 365 | 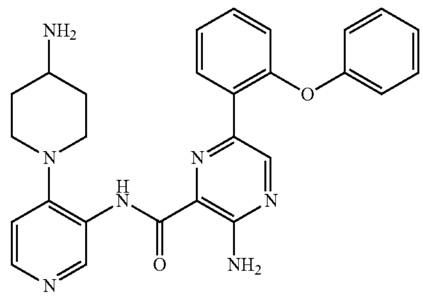 [SMILES: Nc1ncc(-c2ccccc2Oc2ccccc2)nc1C(=O)Nc1cnccc1N1CCC(N)CC1] | 3-amino-6-(2-phenoxy-phenyl)-pyrazine-2-carboxylic acid (4-amino-3,4,5,6-tetrahydro-2H-[1,4']bipyridinyl-3'-yl)-amide | 482.2 | 2.33 |
| 366 | 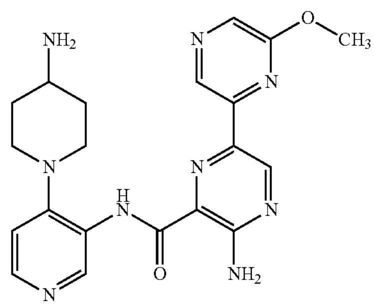 [SMILES: COc1cncc(-c2cnc(N)c(C(=O)Nc3cnccc3N3CCC(N)CC3)n2)n1] | 5-amino-6'-methoxy-[2,2']bipyrazinyl-6-carboxylic acid (4-amino-3,4,5,6-tetrahydro-2H-[1,4']bipyridinyl-3'-yl)-amide | 422.2 | 1.64 |
| 367 | 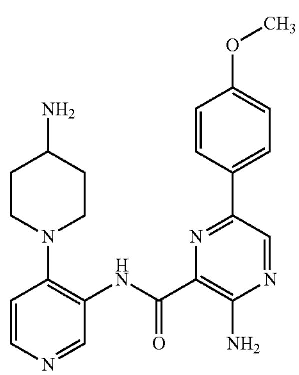 [SMILES: COc1ccc(-c2cnc(N)c(C(=O)Nc3cnccc3N3CCC(N)CC3)n2)cc1] | 3-amino-6-(4-methoxy-phenyl)-pyrazine-2-carboxylic acid (4-amino-3,4,5,6-tetrahydro-2H-[1,4']bipyridinyl-3'-yl)-amide | 420.2 | 1.8 |
| 368 | 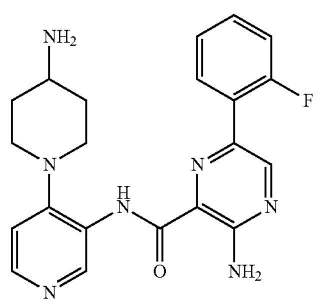 [SMILES: Nc1ncc(-c2ccccc2F)nc1C(=O)Nc1cnccc1N1CCC(N)CC1] | 3-amino-6-(2-fluoro-phenyl)-pyrazine-2-carboxylic acid (4-amino-3,4,5,6-tetrahydro-2H-[1,4']bipyridinyl-3'-yl)-amide | 408.2 | 1.79 |

| Example | Structure | Name | MH+ | LC |
|---|---|---|---|---|
| 369 | 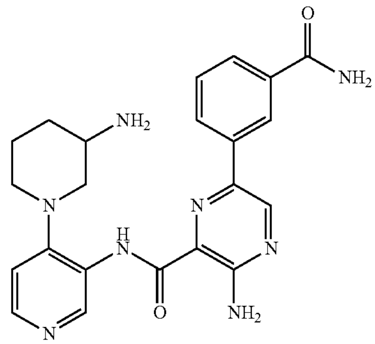 [SMILES: NC(=O)c1cccc(-c2cnc(N)c(C(=O)Nc3cnccc3N3CCCC(N)C3)n2)c1] | 3-amino-6-(3-carbamoyl-phenyl)-pyrazine-2-carboxylic acid (3-amino-3,4,5,6-tetrahydro-2H-[1,4']bipyridinyl-3'-yl)-amide | 433.2 | 1.51 |
| 370 | 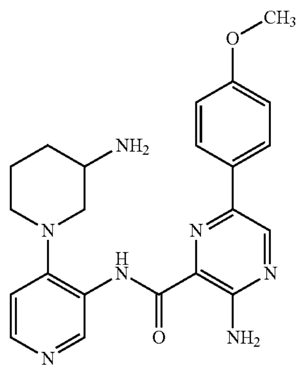 [SMILES: COc1ccc(-c2cnc(N)c(C(=O)Nc3cnccc3N3CCCC(N)C3)n2)cc1] | 3-amino-6-(4-methoxy-phenyl)-pyrazine-2-carboxylic acid (3-amino-3,4,5,6-tetrahydro-2H-[1,4']bipyridinyl-3'-yl)-amide | 420.2 | 1.8 |
| 371 | 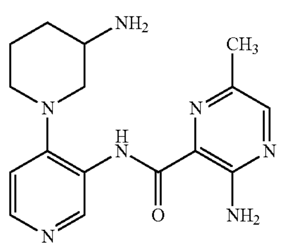 [SMILES: Cc1cnc(N)c(C(=O)Nc2cnccc2N2CCCC(N)C2)n1] | 3-amino-6-methyl-pyrazine-2-carboxylic acid (3-amino-3,4,5,6-tetrahydro-2H-[1,4']bipyridinyl-3'-yl)-amide | 328.2 | 1.23 |
| 372 | 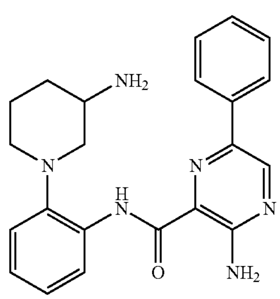 [SMILES: Nc1ncc(-c2ccccc2)nc1C(=O)Nc1ccccc1N1CCCC(N)C1] | 3-amino-6-phenyl-pyrazine-2-carboxylic acid [2-(3-amino-piperidin-1-yl)-phenyl]-amide | 389.2 | 2.99 |
| 373 | 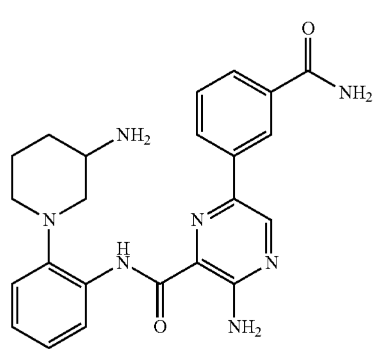 [SMILES: NC(=O)c1cccc(-c2cnc(N)c(C(=O)Nc3ccccc3N3CCCC(N)C3)n2)c1] | 3-amino-6-(3-carbamoyl-phenyl)-pyrazine-2-carboxylic acid [2-(3-amino-piperidin-1-yl)-phenyl]-amide | 432.1 | 2.54 |

-continued

| Example | Structure | Name | MH+ | LC |
|---|---|---|---|---|
| 374 | 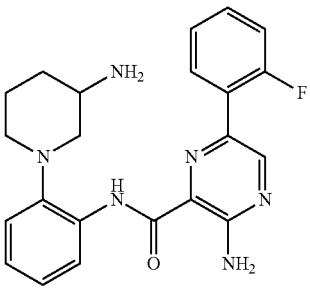 [SMILES: Nc1ncc(-c2ccccc2F)nc1C(=O)Nc1ccccc1N1CCCC(N)C1] | 3-amino-6-(2-fluoro-phenyl)-pyrazine-2-carboxylic acid [2-(3-amino-piperidin-1-yl)-phenyl]-amide | 407.2 | 3.03 |
| 375 | 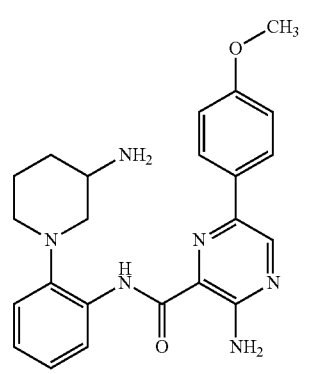 [SMILES: COc1ccc(-c2cnc(N)c(C(=O)Nc3ccccc3N3CCCC(N)C3)n2)cc1] | 3-amino-6-(4-methoxy-phenyl)-pyrazine-2-carboxylic acid [2-(3-amino-piperidin-1-yl)-phenyl]-amide | 419.2 | 3.06 |
| 376 | 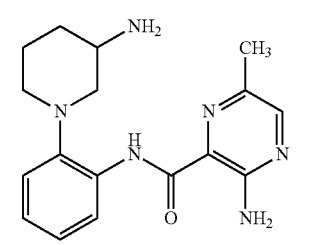 [SMILES: Cc1cnc(N)c(C(=O)Nc2ccccc2N2CCCC(N)C2)n1] | 3-amino-6-methyl-pyrazine-2-carboxylic acid [2-(3-amino-piperidin-1-yl)-phenyl]-amide | 327.2 | 2.44 |
| 377 | 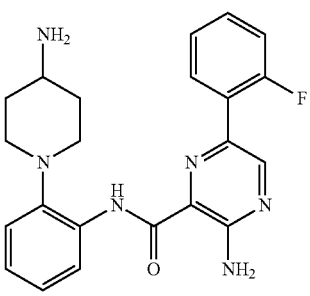 [SMILES: Nc1ncc(-c2ccccc2F)nc1C(=O)Nc1ccccc1N1CCC(N)CC1] | 3-amino-6-(2-fluoro-phenyl)-pyrazine-2-carboxylic acid [2-(4-amino-piperidin-1-yl)-phenyl]-amide | 407.2 | 2.94 |
| 378 | 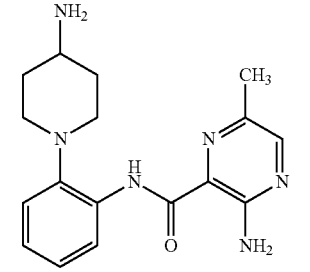 [SMILES: Cc1cnc(N)c(C(=O)Nc2ccccc2N2CCC(N)CC2)n1] | 3-amino-N-[2-(4-amino-piperidin-1-yl)phenyl]-6-methylpyrazine-2-carboxamide | 327.2 | 2.36 |

-continued

| Example | Structure | Name | MH+ | LC |
|---|---|---|---|---|
| 379 | 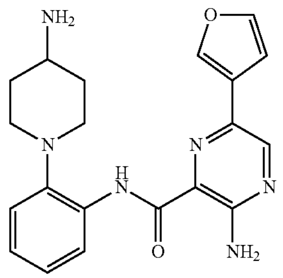 [SMILES: Nc1ncc(-c2ccoc2)nc1C(=O)Nc1ccccc1N1CCC(N)CC1] | 3-amino-6-furan-3-yl-pyrazine-2-carboxylic acid [2-(4-amino-piperidin-1-yl)-phenyl]-amide | 379.2 | 2.64 |
| 380 | 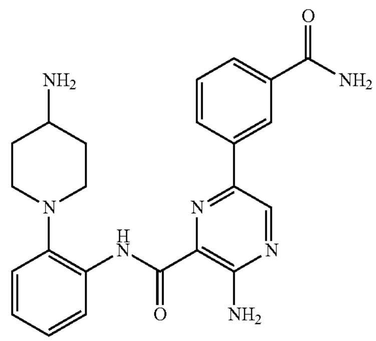 [SMILES: NC(=O)c1cccc(-c2cnc(N)c(C(=O)Nc3ccccc3N3CCC(N)CC3)n2)c1] | 3-amino-6-(3-carbamoyl-phenyl)-pyrazine-2-carboxylic acid [2-(4-amino-piperidin-1-yl)-phenyl]-amide | 432.2 | 2.56 |
| 381 | 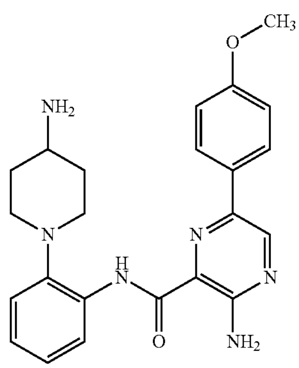 [SMILES: COc1ccc(-c2cnc(N)c(C(=O)Nc3ccccc3N3CCC(N)CC3)n2)cc1] | 3-amino-6-(4-methoxy-phenyl)-pyrazine-2-carboxylic acid [2-(4-amino-piperidin-1-yl)-phenyl]-amide | 419.1 | 2.96 |
| 382 | 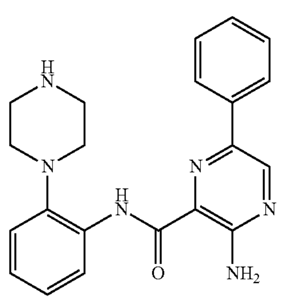 [SMILES: Nc1ncc(-c2ccccc2)nc1C(=O)Nc1ccccc1N1CCNCC1] | 3-amino-6-phenyl-pyrazine-2-carboxylic acid (2-piperazin-1-yl-phenyl)-amide | 375.1 | 2.76 |
| 383 | 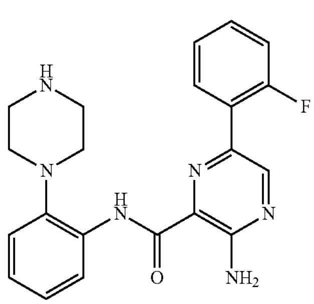 [SMILES: Nc1ncc(-c2ccccc2F)nc1C(=O)Nc1ccccc1N1CCNCC1] | 3-amino-6-(2-fluoro-phenyl)-pyrazine-2-carboxylic acid (2-piperazin-1-yl-phenyl)-amide | 393.1 | 2.8 |

| Example | Structure | Name | MH+ | LC |
|---|---|---|---|---|
| 384 | 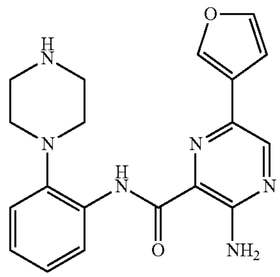 [SMILES: Nc1ncc(-c2ccoc2)nc1C(=O)Nc1ccccc1N1CCNCC1] | 3-amino-6-furan-3-yl-pyrazine-2-carboxylic acid (2-piperazin-1-yl-phenyl)-amide | 365.1 | 2.71 |
| 385 | 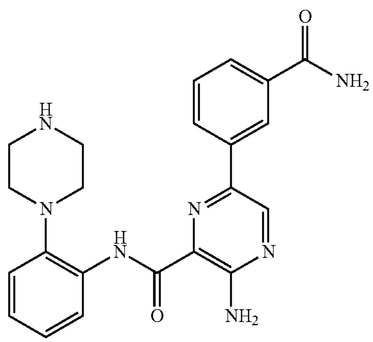 [SMILES: NC(=O)c1cccc(-c2cnc(N)c(C(=O)Nc3ccccc3N3CCNCC3)n2)c1] | 3-amino-6-(3-carbamoyl-phenyl)-pyrazine-2-carboxylic acid (2-piperazin-1-yl-phenyl)-amide | 418.2 | 2.36 |
| 386 | 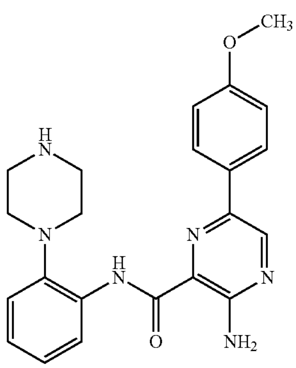 [SMILES: COc1ccc(-c2cnc(N)c(C(=O)Nc3ccccc3N3CCNCC3)n2)cc1] | 3-amino-6-(4-methoxy-phenyl)-pyrazine-2-carboxylic acid (2-piperazin-1-yl-phenyl)-amide | 405.1 | 3 |
| 387 | 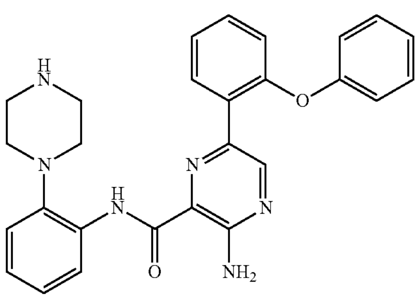 [SMILES: Nc1ncc(-c2ccccc2Oc2ccccc2)nc1C(=O)Nc1ccccc1N1CCNCC1] | 3-amino-6-(2-phenoxy-phenyl)-pyrazine-2-carboxylic acid (2-piperazin-1-yl-phenyl)-amide | 467.2 | 3.28 |
| 388 | 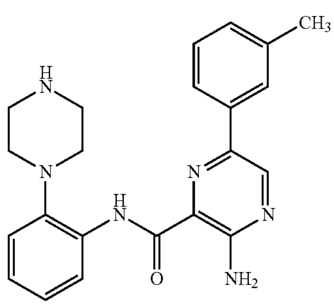 [SMILES: Cc1cccc(-c2cnc(N)c(C(=O)Nc3ccccc3N3CCNCC3)n2)c1] | 3-amino-6-m-tolyl-pyrazine-2-carboxylic acid (2-piperazin-1-yl-phenyl)-amide | 389.2 | 2.95 |

| Example | Structure | Name | MH+ | LC |
|---|---|---|---|---|
| 389 | 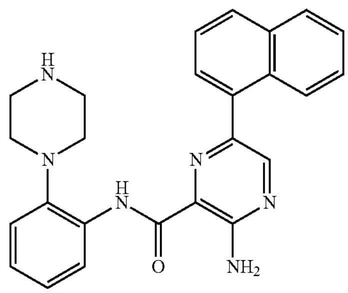 [SMILES: Nc1ncc(-c2cccc3ccccc23)nc1C(=O)Nc1ccccc1N1CCNCC1] | 3-amino-6-naphthalen-1-yl-pyrazine-2-carboxylic acid (2-piperazin-1-yl-phenyl)-amide | 425.2 | 3.06 |
| 390 | 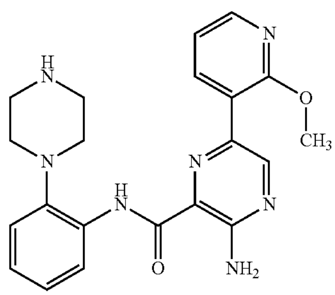 [SMILES: COc1ncccc1-c1cnc(N)c(C(=O)Nc2ccccc2N2CCNCC2)n1] | 3-amino-6-(2-methoxy-pyridin-3-yl)-pyrazine-2-carboxylic acid (2-piperazin-1-yl-phenyl)-amide | 406.2 | 2.8 |
| 391 | 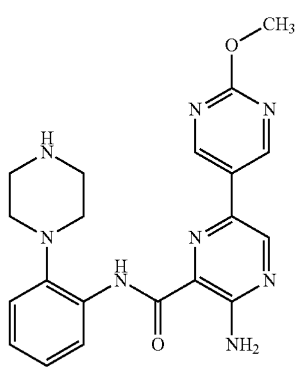 [SMILES: COc1ncc(-c2cnc(N)c(C(=O)Nc3ccccc3N3CCNCC3)n2)cn1] | 3-amino-6-(2-methoxy-pyrimidin-5-yl)-pyrazine-2-carboxylic acid (2-piperazin-1-yl-phenyl)-amide | 407.2 | 2.55 |
| 392 | 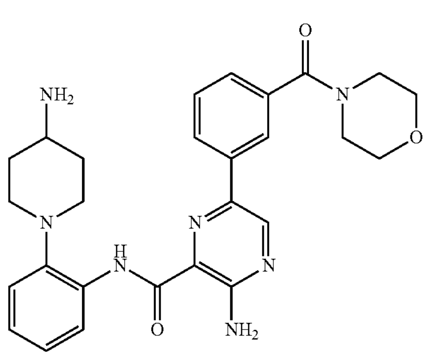 [SMILES: Nc1ncc(-c2cccc(C(=O)N3CCOCC3)c2)nc1C(=O)Nc1ccccc1N1CCC(N)CC1] | 3-amino-6-[3-(morpholine-4-carbonyl)-phenyl]-pyrazine-2-carboxylic acid [2-(4-amino-piperidin-1-yl)-phenyl]-amide | 502.1 | 2.71 |

| Example | Structure | Name | MH+ | LC |
|---|---|---|---|---|
| 393 | 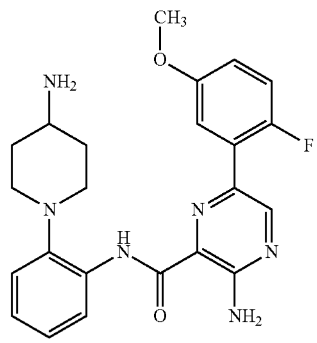 [SMILES: COc1ccc(F)c(-c2cnc(N)c(C(=O)Nc3ccccc3N3CCC(N)CC3)n2)c1] | 3-amino-6-(2-fluoro-5-methoxy-phenyl)-pyrazine-2-carboxylic acid [2-(4-amino-piperidin-1-yl)-phenyl]-amide | 437.1 | 3.05 |
| 394 | 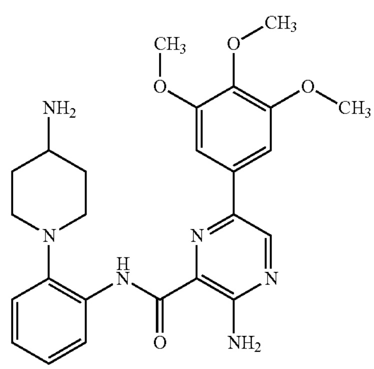 [SMILES: COc1cc(-c2cnc(N)c(C(=O)Nc3ccccc3N3CCC(N)CC3)n2)cc(OC)c1OC] | 3-amino-6-(3,4,5-trimethoxy-phenyl)-pyrazine-2-carboxylic acid [2-(4-amino-piperidin-1-yl)-phenyl]-amide | 479.2 | 2.89 |
| 395 | 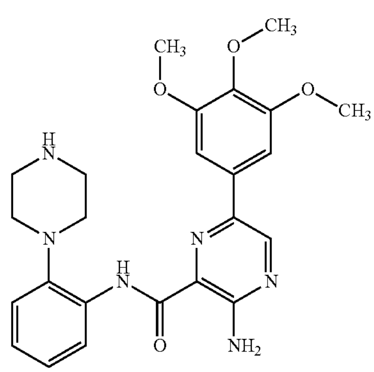 [SMILES: COc1cc(-c2cnc(N)c(C(=O)Nc3ccccc3N3CCNCC3)n2)cc(OC)c1OC] | 3-amino-6-(3,4,5-trimethoxy-phenyl)-pyrazine-2-carboxylic acid (2-piperazin-1-yl-phenyl)-amide | 465.2 | 2.74 |
| 396 | 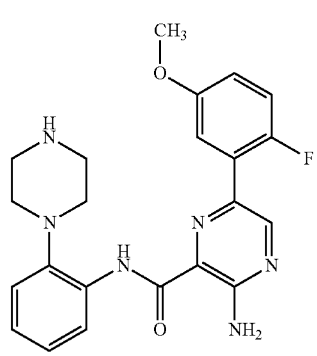 [SMILES: COc1ccc(F)c(-c2cnc(N)c(C(=O)Nc3ccccc3N3CCNCC3)n2)c1] | 3-amino-6-(2-fluoro-5-methoxy-phenyl)-pyrazine-2-carboxylic acid (2-piperazin-1-yl-phenyl)-amide | 423.2 | 2.96 |

| Example | Structure | Name | MH+ | LC |
|---|---|---|---|---|
| 397 | 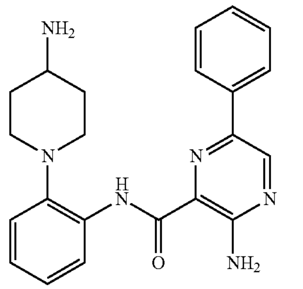 [SMILES: Nc1ncc(-c2ccccc2)nc1C(=O)Nc1ccccc1N1CCC(N)CC1] | 3-amino-6-phenyl-pyrazine-2-carboxylic acid [2-(4-amino-piperidin-1-yl)-phenyl]-amide | 389.2 | 2.37 |
| 398 | 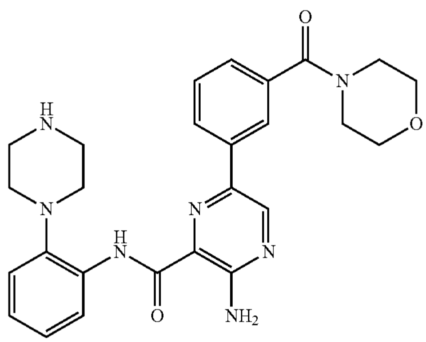 [SMILES: Nc1ncc(-c2cccc(C(=O)N3CCOCC3)c2)nc1C(=O)Nc1ccccc1N1CCNCC1] | 3-amino-6-[3-(morpholine-4-carbonyl)-phenyl]-pyrazine-2-carboxylic acid (2-piperazin-1-yl-phenyl)-amide | 488.2 | 2.5 |
| 399 | 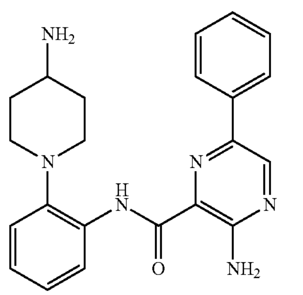 [SMILES: Nc1ncc(-c2ccccc2)nc1C(=O)Nc1ccccc1N1CCC(N)CC1] | 3-amino-6-phenyl-pyrazine-2-carboxylic acid [2-(4-amino-piperidin-1-yl)-phenyl]-amide | 389.2 | 2.37 |
| 400 | 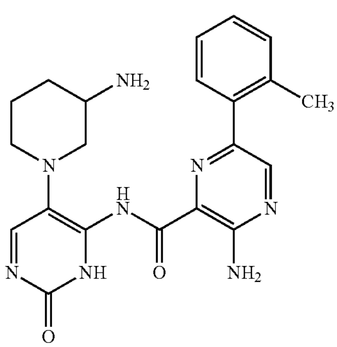 [SMILES: Cc1ccccc1-c1cnc(N)c(C(=O)Nc2[nH]c(=O)ncc2N2CCCC(N)C2)n1] | 3-amino-6-o-tolyl-pyrazine-2-carboxylic acid [5-(3-amino-piperidin-1-yl)-2-oxo-2,3-dihydro-pyrimidin-4-yl]-amide | 421.1 | 1.96 |
| 401 | 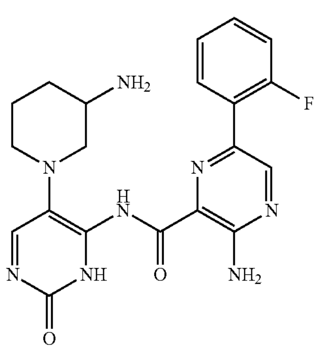 [SMILES: Nc1ncc(-c2ccccc2F)nc1C(=O)Nc1[nH]c(=O)ncc1N1CCCC(N)C1] | 3-amino-6-(2-fluoro-phenyl)-pyrazine-2-carboxylic acid [5-(3-amino-piperidin-1-yl)-2-oxo-2,3-dihydro-pyrimidin-4-yl]-amide | 425.1 | 1.92 |

| Example | Name | MH+ | LC |
|---|---|---|---|
| 402 | 3-amino-6-(2-chloro-phenyl)-pyrazine-2-carboxylic acid [5-(3-amino-piperidin-1-yl)-2-oxo-2,3-dihydro-pyrimidin-4-yl]-amide | 441.1 | 2 |
| 403 | 3-amino-6-(2-cyano-phenyl)-pyrazine-2-carboxylic acid [5-(3-amino-piperidin-1-yl)-2-oxo-2,3-dihydro-pyrimidin-4-yl]-amide | 432.1 | 1.7 |
| 404 | 3-amino-6-(2-trifluoromethyl-phenyl)-pyrazine-2-carboxylic acid [5-(3-amino-piperidin-1-yl)-2-oxo-2,3-dihydro-pyrimidin-4-yl]-amide | 475.1 | 2.09 |
| 405 | 3-amino-6-(2-trifluoro-methoxy-phenyl)-pyrazine-2-carboxylic acid [5-(3-amino-piperidin-1-yl)-2-oxo-2,3-dihydro-pyrimidin-4-yl]-amide | 491.1 | 2.19 |

Method 13

Example 406

Synthesis of (S)-3-amino-N-(4-(3-aminopiperidin-1-yl) pyridin-3-yl)-6-(2-fluoro-4-methylphenyl)picolinamide

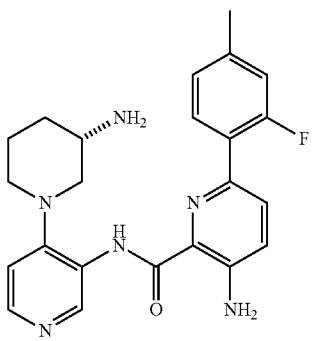 [SMILES: Cc1ccc(-c2ccc(N)c(C(=O)Nc3cnccc3N3CCC[C@H](N)C3)n2)c(F)c1]

A solution of (S)-tert-butyl 1-(3-(3-amino-6-bromopicolinamido)pyridin-4-yl)piperidin-3-ylcarbamate (1.0 eq), 2-fluoro-4-methyl phenyl boronic acid (3.0 eq.), Pd(dppf)Cl$_2$—CH$_2$Cl$_2$ (0.15 eq.) in 3:1 DME/2M Na$_2$CO$_3$ (concentration=0.1 M) was heated at 120° C. with microwave irradiation for 1200 seconds. Upon cooling the organic layer was separated, concentrated and the N-Boc Suzuki product was directly purified by reverse phase HPLC. The product fraction was lyophilized and the resulting solid was treated with 25% TFA/DCM (at a resulting concentration of 0.05 M). After sitting for 2 hours, the volatiles were removed in vacuo and the residue was purified by reverse phase HPLC. After lyophilization, (S)-3-amino-N-(4-(3-aminopiperidin-1-yl)pyridin-3-yl)-6-(2-fluoro-4-methylphenyl) picolinamide was obtained (44%) as the TFA salt. LCMS (m/z): 2.23 (MH$^+$); LC R$_t$=421.2 min.

Alternatively, the free base and HCl salt of (S)-3-amino-N-(4-(3-aminopiperidin-1-yl)pyridin-3-yl)-6-(2-fluoro-4-methylphenyl)picolinamide could be obtained as described in Method 9.

The following compounds were prepared using Method 13.

| Example | Structure | Name | MH+ | LC |
|---|---|---|---|---|
| 407 | Chiral | 3-amino-6-pyrimidin-5-yl-pyridine-2-carboxylic acid ((S)-3-amino-3,4,5,6-tetrahydro-2H-[1,4']bipyridinyl-3'-yl)-amide | 391.2 | 1.4 |
| 408 | Chiral | 5,2'-diamino-6'-fluoro-[2,3']bipyridinyl-6-carboxylic acid ((S)-3-amino-3,4,5,6-tetrahydro-2H-[1,4']bipyridinyl-3'-yl)-amide | 423.2 | 1.79 |
| 409 | Chiral | 3-amino-6-(2-amino-4-methyl-pyrimidin-5-yl)-pyridine-2-carboxylic acid ((S)-3-amino-3,4,5,6-tetrahydro-2H-[1,4']bipyridinyl-3'-yl)-amide | 420.2 | 1.21 |

| Example | Structure | Name | MH+ | LC |
|---|---|---|---|---|
| 410 | Chiral | 5,6'-diamino-4'-chloro-[2,3']bi-pyridinyl-6-carboxylic acid ((S)-3-amino-3,4,5,6-tetrahydro-2H-[1,4']bipyridinyl-3'-yl)-amide | 439.2 | 1.41 |
| 411 | Chiral | 3-amino-6-(2-amino-pyrimidin-5-yl)-pyridine-2-carboxylic acid ((S)-3-amino-3,4,5,6-tetrahydro-2H-[1,4']bipyridinyl-3'-yl)-amide | 406.2 | 1.25 |
| 412 | Chiral | 5,2'-diamino-[2,4']bipyridinyl-6-carboxylic acid ((S)-3-amino-3,4,5,6-tetrahydro-2H-[1,4']bi-pyridinyl-3'-yl)-amide | 405.2 | 1.26 |
| 413 | Chiral | 5-amino-6'-methoxy-[2,2']bi-pyridinyl-6-carboxylic acid ((S)-3-amino-3,4,5,6-tetrahydro-2H-[1,4']bipyridinyl-3'-yl)-amide | 420.2 | 1.87 |

-continued

| Example | Structure | Name | MH+ | LC |
|---|---|---|---|---|
| 414 | 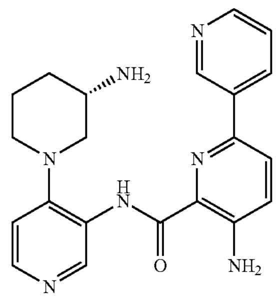 | 5-amino-[2,3']bipyridinyl-6-carboxylic acid ((S)-3-amino-3,4,5,6-tetrahydro-2H-[1,4']bipyridinyl-3'-yl)-amide | 390.2 | 1.11 |
| 415 | 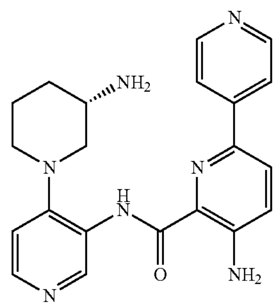 | 5-amino-[2,4']bipyridinyl-6-carboxylic acid ((S)-3-amino-3,4,5,6-tetrahydro-2H-[1,4']bipyridinyl-3'-yl)-amide | 390.2 | 1.11 |
| 416 | 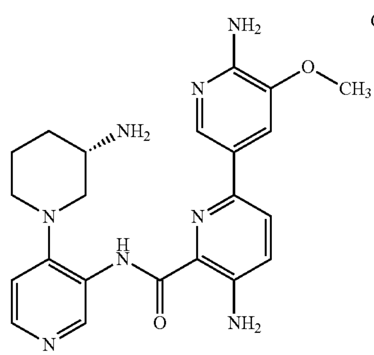 | 5,6'-diamino-5'-methoxy-[2,3']bipyridinyl-6-carboxylic acid ((S)-3-amino-3,4,5,6-tetrahydro-2H-[1,4']bipyridinyl-3'-yl)-amide | 435.2 | 1.34 |
| 417 | 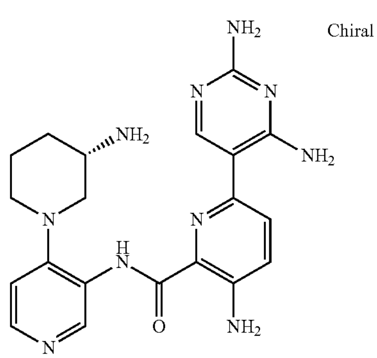 [SMILES: Nc1ncc(-c2ccc(N)c(C(=O)Nc3cnccc3N3CCC[C@H](N)C3)n2)c(N)n1] | 3-amino-6-(2,4-diamino-pyrimidin-5-yl)-pyridine-2-carboxylic acid ((S)-3-amino-3,4,5,6-tetrahydro-2H-[1,4']bipyridinyl-3'-yl)-amide | 421.2 | 1.07 |

| Example | Structure | Name | MH+ | LC |
|---|---|---|---|---|
| 418 | 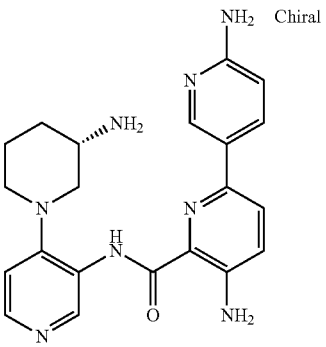 [SMILES: Nc1ccc(-c2ccc(N)c(C(=O)Nc3cnccc3N3CCC[C@H](N)C3)n2)cn1] | 5,6'-diamino-[2,3']bipyridinyl-6-carboxylic acid ((S)-3-amino-3,4,5,6-tetrahydro-2H-[1,4']bipyridinyl-3'-yl)-amide | 405.2 | 1.26 |
| 419 | 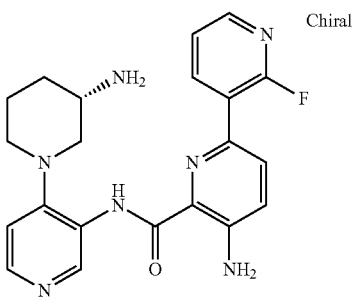 [SMILES: Nc1ccc(-c2cccnc2F)nc1C(=O)Nc1cnccc1N1CCC[C@H](N)C1] | 5-amino-2'-fluoro-[2,3']bipyridinyl-6-carboxylic acid ((S)-3-amino-3,4,5,6-tetrahydro-2H-[1,4']bipyridinyl-3'-yl)-amide | 408.2 | 1.7 |
| 420 | 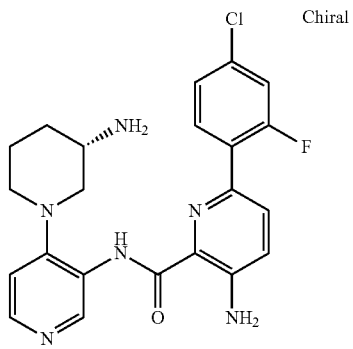 [SMILES: Nc1ccc(-c2ccc(Cl)cc2F)nc1C(=O)Nc1cnccc1N1CCC[C@H](N)C1] | 3-amino-6-(4-chloro-2-fluoro-phenyl)-pyridine-2-carboxylic acid ((S)-3-amino-3,4,5,6-tetrahydro-2H-[1,4']bipyridinyl-3'-yl)-amide | 441.2 | 2.29 |
| 421 | 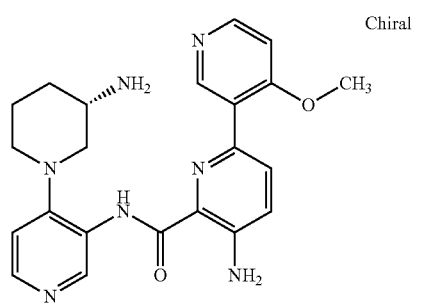 [SMILES: COc1ccncc1-c1ccc(N)c(C(=O)Nc2cnccc2N2CCC[C@H](N)C2)n1] | 5-amino-4'-methoxy-[2,3']bipyridinyl-6-carboxylic acid ((S)-3-amino-3,4,5,6-tetrahydro-2H-[1,4']bipyridinyl-3'-yl)-amide | 420.2 | 1.7 |

-continued

| Example | Structure | Name | MH+ | LC |
|---|---|---|---|---|
| 422 | 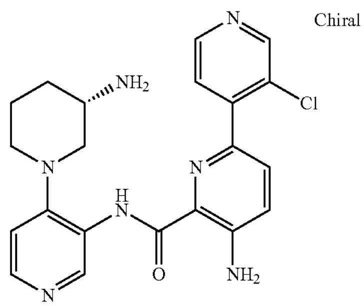 [SMILES: Nc1ccc(-c2ccncc2Cl)nc1C(=O)Nc1cnccc1N1CCC[C@H](N)C1] | 5-amino-3'-chloro-[2,4']bi-pyridinyl-6-carboxylic acid ((S)-3-amino-3,4,5,6-tetrahydro-2H-[1,4']bipyridinyl-3'-yl)-amide | 424.1 | 1.61 |
| 423 | 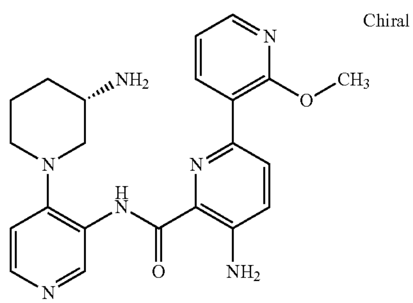 [SMILES: COc1ncccc1-c1ccc(N)c(C(=O)Nc2cnccc2N2CCC[C@H](N)C2)n1] | 5-amino-2'-methoxy-[2,3']bi-pyridinyl-6-carboxylic acid ((S)-3-amino-3,4,5,6-tetrahydro-2H-[1,4']bipyridinyl-3'-yl)-amide | 420.2 | 1.81 |
| 424 | 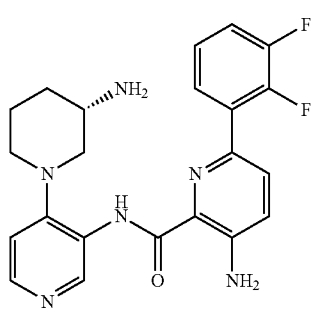 | 3-amino-6-(2,3-difluoro-phenyl)-pyridine-2-carboxylic acid ((S)-3-amino-3,4,5,6-tetrahydro-2H-[1,4']bipyridinyl-3'-yl)-amide | 425.2 | 2.15 |
| 425 | 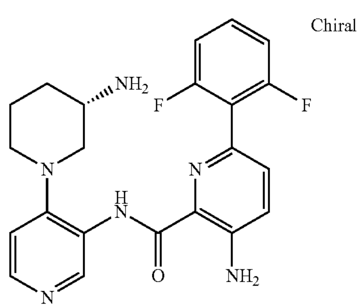 [SMILES: Nc1ccc(-c2c(F)cccc2F)nc1C(=O)Nc1cnccc1N1CCC[C@H](N)C1] | 3-amino-6-(2,6-difluoro-phenyl)-pyridine-2-carboxylic acid ((S)-3-amino-3,4,5,6-tetrahydro-2H-[1,4']bipyridinyl-3'-yl)-amide | 425.2 | 2.03 |
| 426 | 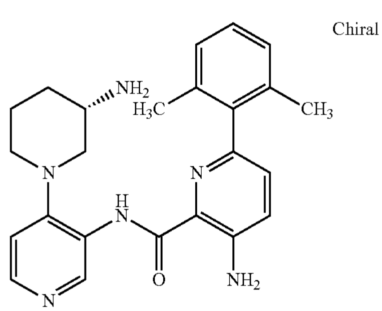 [SMILES: Cc1cccc(C)c1-c1ccc(N)c(C(=O)Nc2cnccc2N2CCC[C@H](N)C2)n1] | 3-amino-6-(2,6-dimethyl-phenyl)-pyridine-2-carboxylic acid ((S)-3-amino-3,4,5,6-tetrahydro-2H-[1,4']bipyridinyl-3'-yl)-amideQ | 417.2 | 2.2 |

-continued

| Example | Structure | Name | MH+ | LC |
|---|---|---|---|---|
| 427 | Chiral | 3-amino-6-(5-fluoro-2-methoxy-phenyl)-pyridine-2-carboxylic acid ((S)-3-amino-3,4,5,6-tetra-hydro-2H-[1,4']bipyridinyl-3'-yl)-amide | 437.2 | 2.11 |
| 428 | Chiral | 3-amino-6-(4-fluoro-2-methoxy-phenyl)-pyridine-2-carboxylic acid ((S)-3-amino-3,4,5,6-tetra-hydro-2H-[1,4']bipyridinyl-3'-yl)-amide | 437.2 | 2.15 |
| 429 | Chiral | 3-amino-6-(4-chloro-2-methyl-phenyl)-pyridine-2-carboxylic acid ((S)-3-amino-3,4,5,6-tetra-hydro-2H-[1,4']bipyridinyl-3'-yl)-amide | 437.2 | 2.39 |
| 430 | Chiral | 3-amino-6-(4-fluoro-2-methyl-phenyl)-pyridine-2-carboxylic acid ((S)-3-amino-3,4,5,6-tetra-hydro-2H-[1,4']bipyridinyl-3'-yl)-amide | 421.2 | 2.23 |

-continued

| Example | Structure | Name | MH+ | LC |
|---------|-----------|------|-----|-----|
| 431 | Chiral | 3-amino-6-(2,4-difluoro-phenyl)-pyridine-2-carboxylic acid ((S)-3-amino-3,4,5,6-tetrahydro-2H-[1,4']bipyridinyl-3'-yl)-amide | 425.2 | 2.15 |
| 432 | Chiral | 3-amino-6-(2-fluoro-4-methyl-phenyl)-pyridine-2-carboxylic acid ((S)-3-amino-3,4,5,6-tetrahydro-2H-[1,4']bipyridinyl-3'-yl)-amide | 421.2 | 2.27 |
| 433 | Chiral | 3-amino-6-(2-chloro-phenyl)-pyridine-2-carboxylic acid ((S)-3-amino-3,4,5,6-tetrahydro-2H-[1,4']bipyridinyl-3'-yl)-amide | 423.2 | 2.15 |
| 434 | Chiral | 3-amino-6-(2-fluoro-phenyl)-pyridine-2-carboxylic acid ((S)-3-amino-3,4,5,6-tetrahydro-2H-[1,4']bipyridinyl-3'-yl)-amide | 407.2 | 2.07 |

| Example | Structure | Name | MH+ | LC |
|---|---|---|---|---|
| 435 | 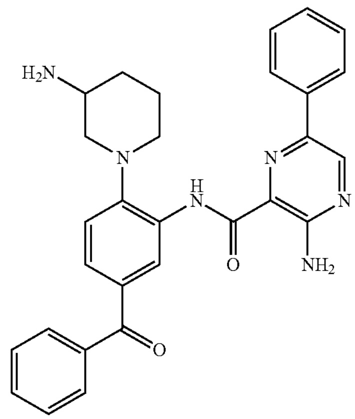 [SMILES: Nc1ncc(-c2ccccc2)nc1C(=O)Nc1cc(C(=O)c2ccccc2)ccc1N1CCCC(N)C1] | 3-amino-6-phenyl-pyrazine-2-carboxylic acid [2-(3-amino-piperidin-1-yl)-5-benzoyl-phenyl]-amide | 493.2 | 3.35 |
| 436 | 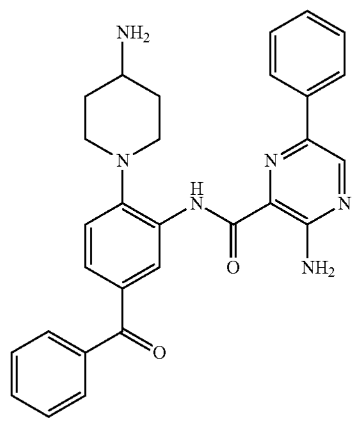 [SMILES: Nc1ncc(-c2ccccc2)nc1C(=O)Nc1cc(C(=O)c2ccccc2)ccc1N1CCC(N)CC1] | 3-amino-6-phenyl-pyrazine-2-carboxylic acid [2-(4-amino-piperidin-1-yl)-5-benzoyl-phenyl]-amide | 493.2 | 3.3 |
| 437 | 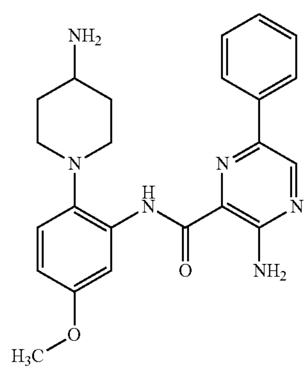 [SMILES: COc1ccc(N2CCC(N)CC2)c(NC(=O)c2nc(-c3ccccc3)cnc2N)c1] | 3-amino-6-phenyl-pyrazine-2-carboxylic acid [2-(4-amino-piperidin-1-yl)-5-methoxy-phenyl]-amide | 419.1 | 3.07 |
| 438 | 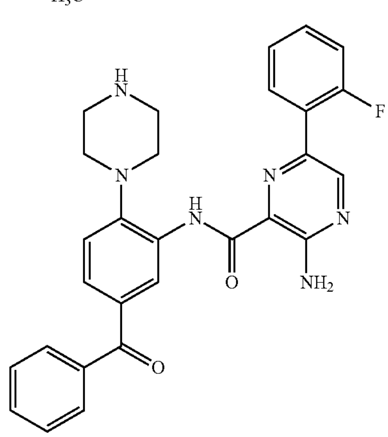 | 3-amino-6-(2-fluoro-phenyl)-pyrazine-2-carboxylic acid (5-benzoyl-2-piperazin-1-yl-phenyl)-amide | 497.2 | 3.25 |

-continued

| Example | Structure | Name | MH+ | LC |
|---|---|---|---|---|
| 439 | 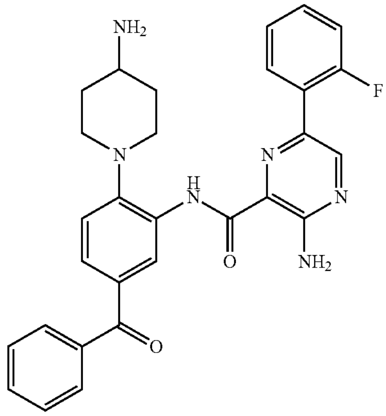 [SMILES: Nc1ncc(-c2ccccc2F)nc1C(=O)Nc1cc(C(=O)c2ccccc2)ccc1N1CCC(N)CC1] | 3-amino-6-(2-fluoro-phenyl)-pyrazine-2-carboxylic acid [2-(4-amino-piperidin-1-yl)-5-benzoyl-phenyl]-amide | 511.1 | 3.29 |
| 440 | 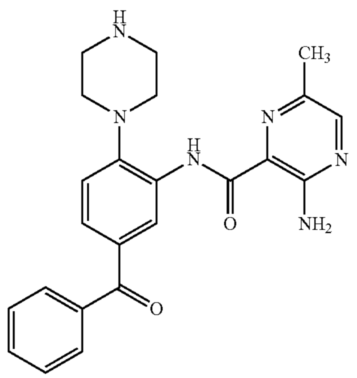 [SMILES: Cc1cnc(N)c(C(=O)Nc2cc(C(=O)c3ccccc3)ccc2N2CCNCC2)n1] | 3-amino-6-methyl-pyrazine-2-carboxylic acid (5-benzoyl-2-piperazin-1-yl-phenyl)-amide | 417.2 | 2.75 |
| 441 | 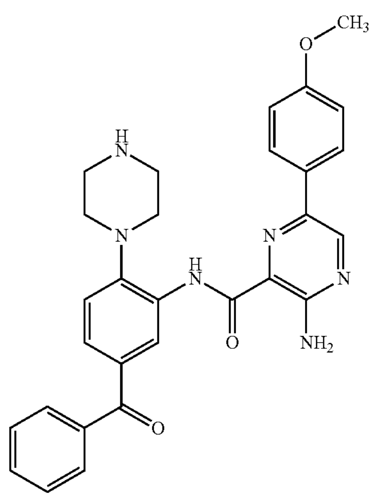 [SMILES: COc1ccc(-c2cnc(N)c(C(=O)Nc3cc(C(=O)c4ccccc4)ccc3N3CCNCC3)n2)cc1] | 3-amino-6-(4-methoxy-phenyl)-pyrazine-2-carboxylic acid (5-benzoyl-2-piperazin-1-yl-phenyl)-amide | 509.3 | 3.28 |
| 442 | Chiral | 5-Fluoro-6-phenyl-pyridine-2-carboxylic acid (3-amino-3,4,5,6-tetrahydro-2H-[1,4']bipyridinyl-3'-yl)-amide | 392.2 | 2.12 |

-continued

| Example | Structure | Name | MH+ | LC |
|---|---|---|---|---|
| 443 | 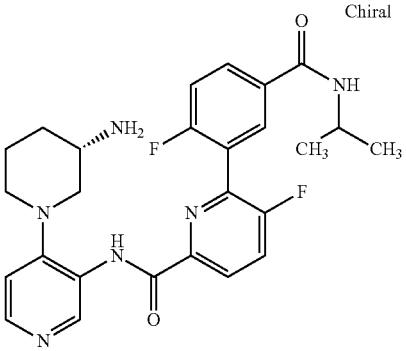 [SMILES: CC(C)NC(=O)c1ccc(F)c(-c2nc(C(=O)Nc3cnccc3N3CCC[C@H](N)C3)ccc2F)c1] Chiral | 5-Fluoro-6-(2-fluoro-5-isopropylcarbamoyl-phenyl)-pyridine-2-carboxylic acid (3-amino-3,4,5,6-tetrahydro-2H-[1,4']bipyridinyl-3'-yl)-amide | 495.2 | 2.13 |
| 444 | 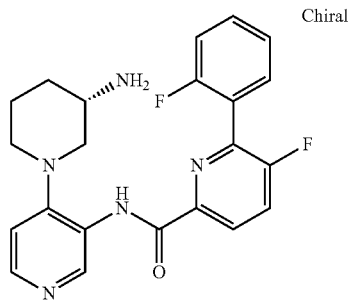 [SMILES: N[C@H]1CCCN(c2ccncc2NC(=O)c2ccc(F)c(-c3ccccc3F)n2)C1] Chiral | 5-Fluoro-6-(2-fluoro-phenyl)-pyridine-2-carboxylic acid (3-amino-3,4,5,6-tetrahydro-2H-[1,4']bipyridinyl-3'-yl)-amide | 410.1 | 2.15 |
| 445 | 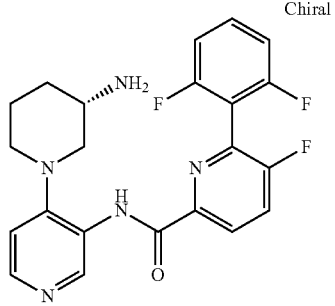 [SMILES: N[C@H]1CCCN(c2ccncc2NC(=O)c2ccc(F)c(-c3c(F)cccc3F)n2)C1] Chiral | 6-(2,6-Difluoro-phenyl)-5-fluoro-pyridine-2-carboxylic acid (3-amino-3,4,5,6-tetrahydro-2H-[1,4']bipyridinyl-3'-yl)-amide | 428.1 | 2.14 |
| 446 | 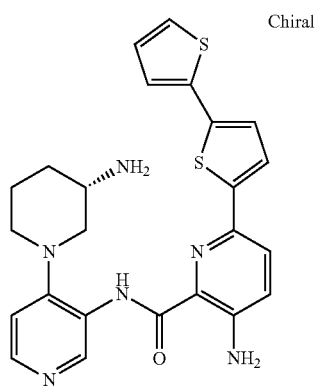 [SMILES: Nc1ccc(-c2ccc(-c3cccs3)s2)nc1C(=O)Nc1cnccc1N1CCC[C@H](N)C1] Chiral | 3-Amino-6-[2,2']bithiophenyl-5-yl-pyridine-2-carboxylic acid (3-amino-3,4,5,6-tetrahydro-2H-[1,4']bipyridinyl-3'-yl)-amide | 477.1 | 2.54 |

-continued

| Example | Structure | Name | MH+ | LC |
|---|---|---|---|---|
| 447 | 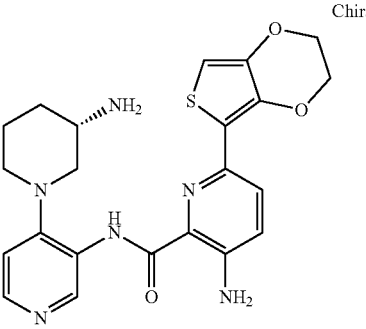 Chiral | 3-Amino-6-(2,3-dihydro-thieno[3,4-b][1,4]dioxin-5-yl)-pyridine-2-carboxylic acid (3-amino-3,4,5,6-tetrahydro-2H-[1,4']bipyridinyl-3'-yl)-amide | 453.1 | 2.02 |
| 448 | 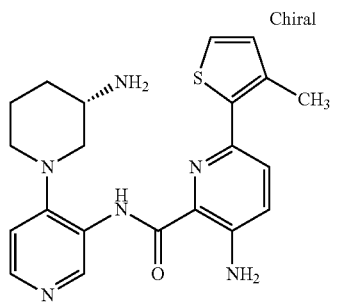 [SMILES: Cc1ccsc1-c1ccc(N)c(C(=O)Nc2cnccc2N2CCC[C@H](N)C2)n1] Chiral | 3-Amino-6-(3-methyl-thiophen-2-yl)-pyridine-2-carboxylic acid (3-amino-3,4,5,6-tetrahydro-2H-[1,4']bipyridinyl-3'-yl)-amide | 409.2 | 2.10 |
| 449 | 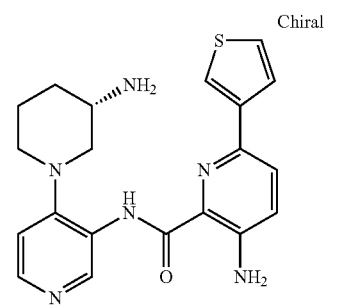 [SMILES: Nc1ccc(-c2ccsc2)nc1C(=O)Nc1cnccc1N1CCC[C@H](N)C1] Chiral | 3-Amino-6-thiophen-3-yl-pyridine-2-carboxylic acid (3-amino-3,4,5,6-tetrahydro-2H-[1,4']bipyridinyl-3'-yl)-amide | 395.1 | 1.95 |
| 450 | 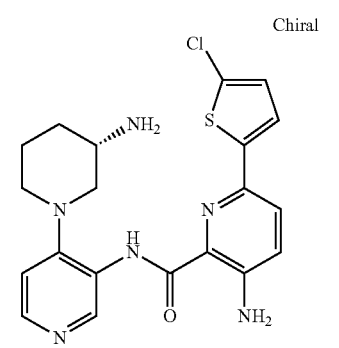 [SMILES: Nc1ccc(-c2ccc(Cl)s2)nc1C(=O)Nc1cnccc1N1CCC[C@H](N)C1] Chiral | 3-Amino-6-(5-chloro-thiophen-2-yl)-pyridine-2-carboxylic acid (3-amino-3,4,5,6-tetrahydro-2H-[1,4']bipyridinyl-3'-yl)-amide | 429.1 | 2.23 |

-continued

| Example | Structure | Name | MH+ | LC |
|---|---|---|---|---|
| 451 | 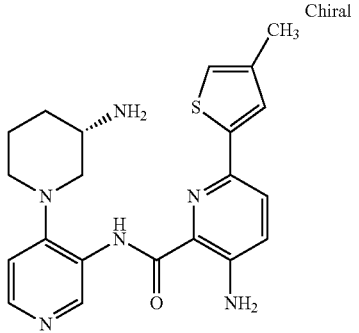 [SMILES: Cc1csc(-c2ccc(N)c(C(=O)Nc3cnccc3N3CCC[C@H](N)C3)n2)c1] Chiral | 3-Amino-6-(4-methyl-thiophen-2-yl)-pyridine-2-carboxylic acid (3-amino-3,4,5,6-tetrahydro-2H-[1,4']bipyridinyl-3'-yl)-amide | 409.2 | 2.14 |
| 452 | 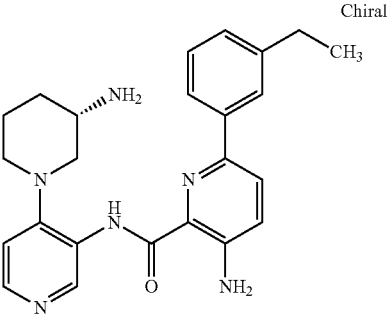 [SMILES: CCc1cccc(-c2ccc(N)c(C(=O)Nc3cnccc3N3CCC[C@H](N)C3)n2)c1] Chiral | 3-Amino-6-(3-ethyl-phenyl)-pyridine-2-carboxylic acid (3-amino-3,4,5,6-tetrahydro-2H-[1,4']bipyridinyl-3'-yl)-amide | 417.2 | 2.43 |
| 453 | 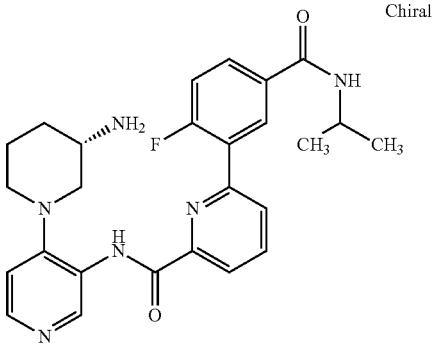 [SMILES: CC(C)NC(=O)c1ccc(F)c(-c2cccc(C(=O)Nc3cnccc3N3CCC[C@H](N)C3)n2)c1] Chiral | 6-(2-Fluoro-5-isopropylcarbamoyl-phenyl)-pyridine-2-carboxylic acid (3-amino-3,4,5,6-tetrahydro-2H-[1,4']bipyridinyl-3'-yl)-amide | 477.2 | 2.06 |
| 454 | 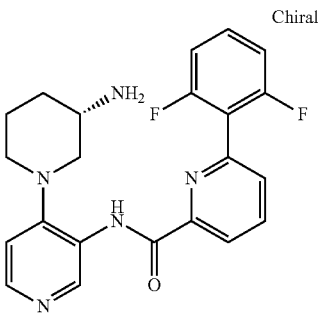 [SMILES: N[C@H]1CCCN(c2ccncc2NC(=O)c2cccc(-c3c(F)cccc3F)n2)C1] Chiral | 6-(2,6-Difluoro-phenyl)-pyridine-2-carboxylic acid (3-amino-3,4,5,6-tetrahydro-2H-[1,4']bipyridinyl-3'-yl)-amide | 410.1 | 2.02 |

| Example | Structure | Name | MH+ | LC |
|---|---|---|---|---|
| 455 | 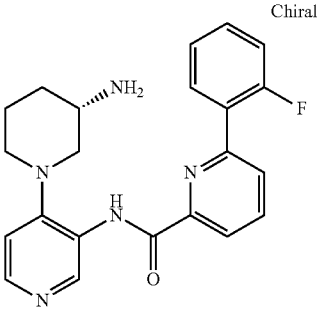 [SMILES: N[C@H]1CCCN(c2ccncc2NC(=O)c2cccc(-c3ccccc3F)n2)C1] Chiral | 6-(2-Fluoro-phenyl)-pyridine-2-carboxylic acid (3-amino-3,4,5,6-tetrahydro-2H-[1,4']bipyridinyl-3'-yl)-amide | 392.2 | 2.10 |
| 456 | 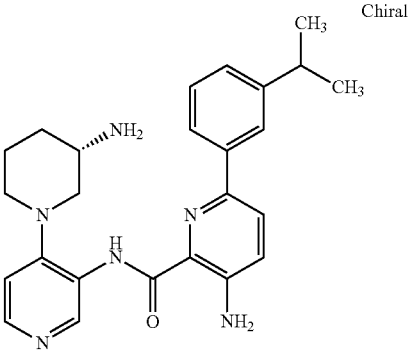 [SMILES: CC(C)c1cccc(-c2ccc(N)c(C(=O)Nc3cnccc3N3CCC[C@H](N)C3)n2)c1] Chiral | 3-Amino-6-(3-isopropyl-phenyl)-pyridine-2-carboxylic acid (3-amino-3,4,5,6-tetrahydro-2H-[1,4']bipyridinyl-3'-yl)-amide | 431.2 | 2.61 |
| 457 | 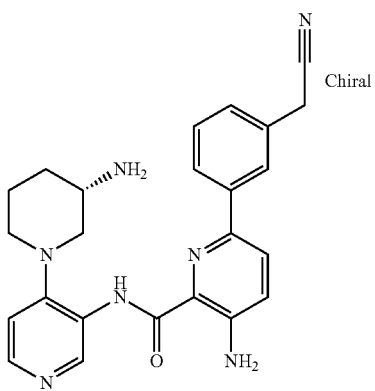 [SMILES: N#CCc1cccc(-c2ccc(N)c(C(=O)Nc3cnccc3N3CCC[C@H](N)C3)n2)c1] Chiral | 3-Amino-6-(3-cyanomethyl-phenyl)-pyridine-2-carboxylic acid (3-amino-3,4,5,6-tetrahydro-2H-[1,4']bipyridinyl-3'-yl)-amide | 428.2 | 2.06 |
| 458 | 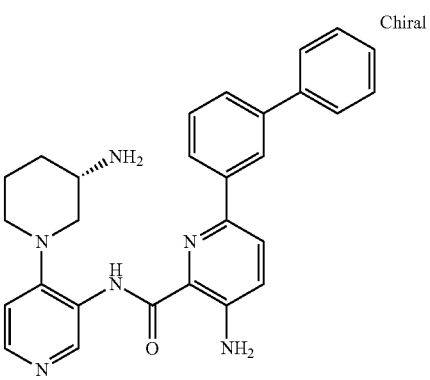 [SMILES: Nc1ccc(-c2cccc(-c3ccccc3)c2)nc1C(=O)Nc1cnccc1N1CCC[C@H](N)C1] Chiral | 3-Amino-6-biphenyl-3-yl-pyridine-2-carboxylic acid (3-amino-3,4,5,6-tetrahydro-2H-[1,4']bipyridinyl-3'-yl)-amide | 465.2 | 2.71 |

-continued

| Example | Structure | Name | MH+ | LC |
|---|---|---|---|---|
| 459 | Chiral | 3-Amino-6-(3-bromo-phenyl)-pyridine-2-carboxylic acid (3-amino-3,4,5,6-tetrahydro-2H-[1,4']bipyridinyl-3'-yl)-amide | 467.1 | 2.30 |
| 460 | Chiral | 3-Amino-6-(3-trifluoromethyl-phenyl)-pyridine-2-carboxylic acid (3-amino-3,4,5,6-tetrahydro-2H-[1,4']bipyridinyl-3'-yl)-amide | 457.2 | 2.41 |
| 461 | Chiral | 3-Amino-6-(3-cyano-phenyl)-pyridine-2-carboxylic acid (3-amino-3,4,5,6-tetrahydro-2H-[1,4']bipyridinyl-3'-yl)-amide | 414.2 | 2.02 |
| 462 | Chiral | 3-Amino-6-(2,6-difluoro-phenyl)-pyridine-2-carboxylic acid (3-amino-3,4,5,6-tetrahydro-2H-[1,4']bipyridinyl-3'-yl)-amide | 425.2 | 2.26 |

| Example | Structure | Name | MH+ | LC |
|---|---|---|---|---|
| 463 | Chiral | 3-Amino-6-(2-fluoro-phenyl)-pyridine-2-carboxylic acid (3-amino-3,4,5,6-tetrahydro-2H-[1,4']bipyridinyl-3'-yl)-amide | 407.2 | 2.29 |
| 464 | Chiral | 3-Amino-6-[3-(2-chloro-benzyloxy)-2,6-difluoro-phenyl]-pyridine-2-carboxylic acid (3-amino-3,4,5,6-tetrahydro-2H-[1,4']bipyridinyl-3'-yl)-amide | 565.2 | 2.98 |
| 465 | Chiral | 3-Amino-6-[2,6-difluoro-3-(2-fluoro-benzyloxy)-phenyl]-pyridine-2-carboxylic acid (3-amino-3,4,5,6-tetrahydro-2H-[1,4']bipyridinyl-3'-yl)-amide | 549.2 | 2.70 |
| 466 | Chiral | 3-Amino-6-(3-butoxy-2,6-difluoro-phenyl)-pyridine-2-carboxylic acid (3-amino-3,4,5,6-tetrahydro-2H-[1,4']bipyridinyl-3'-yl)-amide | 497.3 | 2.83 |

| Example | Structure | Name | MH+ | LC |
| --- | --- | --- | --- | --- |
| 467 | 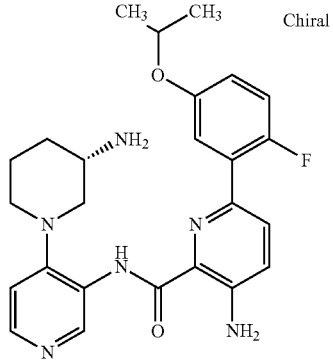 [SMILES: CC(C)Oc1ccc(F)c(-c2ccc(N)c(C(=O)Nc3cnccc3N3CCC[C@H](N)C3)n2)c1] Chiral | 3-Amino-6-(2-fluoro-5-isopropoxy-phenyl)-pyridine-2-carboxylic acid (3-amino-3,4,5,6-tetrahydro-2H-[1,4']bipyridinyl-3'-yl)-amide | 465.3 | 2.59 |
| 468 | 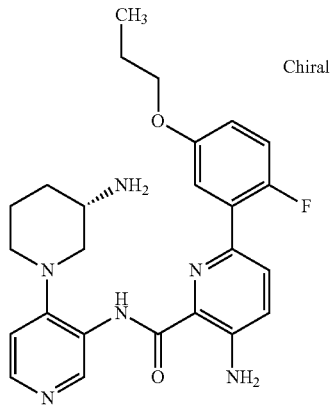 [SMILES: CCCOc1ccc(F)c(-c2ccc(N)c(C(=O)Nc3cnccc3N3CCC[C@H](N)C3)n2)c1] Chiral | 3-Amino-6-(2-fluoro-5-propoxy-phenyl)-pyridine-2-carboxylic acid (3-amino-3,4,5,6-tetrahydro-2H-[1,4']bipyridinyl-3'-yl)-amide | 465.2 | 2.68 |
| 469 | 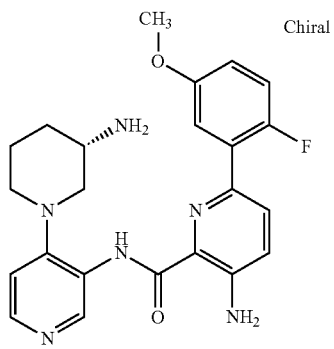 [SMILES: COc1ccc(F)c(-c2ccc(N)c(C(=O)Nc3cnccc3N3CCC[C@H](N)C3)n2)c1] Chiral | 3-Amino-6-(5-ethoxy-2-fluoro-phenyl)-pyridine-2-carboxylic acid (3-amino-3,4,5,6-tetrahydro-2H-[1,4']bipyridinyl-3'-yl)-amide | 451.2 | 2.47 |
| 470 | 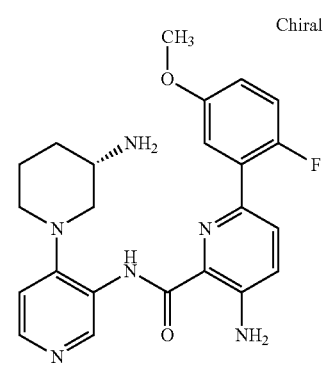 [SMILES: COc1ccc(F)c(-c2ccc(N)c(C(=O)Nc3cnccc3N3CCC[C@H](N)C3)n2)c1] Chiral | 3-Amino-6-(2-fluoro-5-methoxy-phenyl)-pyridine-2-carboxylic acid (3-amino-3,4,5,6-tetrahydro-2H-[1,4']bipyridinyl-3'-yl)-amide | 437.2 | 2.33 |

| Example | Structure | Name | MH+ | LC |
|---|---|---|---|---|
| 471 | 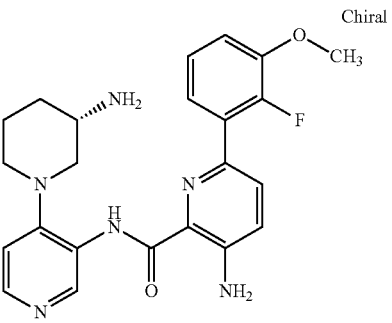 [SMILES: COc1cccc(-c2ccc(N)c(C(=O)Nc3cnccc3N3CCC[C@H](N)C3)n2)c1F] Chiral | 3-Amino-6-(2-fluoro-3-methoxy-phenyl)-pyridine-2-carboxylic acid (3-amino-3,4,5,6-tetrahydro-2H-[1,4']bipyridinyl-3'-yl)-amide | 437.2 | 2.26 |
| 472 | 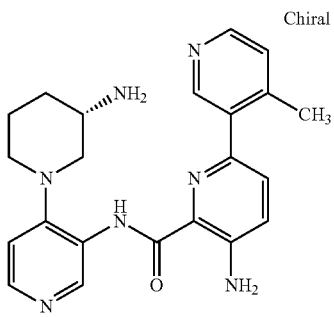 [SMILES: Cc1ccncc1-c1ccc(N)c(C(=O)Nc2cnccc2N2CCC[C@H](N)C2)n1] Chiral | 5-Amino-4'-methyl-[2,3']bi-pyridinyl-6-carboxylic acid (3-amino-3,4,5,6-tetrahydro-2H-[1,4']bipyridinyl-3'-yl)-amide | 404.2 | 1.18 |
| 473 | 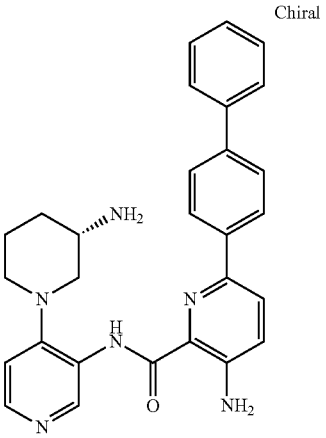 [SMILES: Nc1ccc(-c2ccc(-c3ccccc3)cc2)nc1C(=O)Nc1cnccc1N1CCC[C@H](N)C1] Chiral | 3-Amino-6-biphenyl-4-yl-pyridine-2-carboxylic acid (3-amino-3,4,5,6-tetrahydro-2H-[1,4']bipyridinyl-3'-yl)-amide | 465.2 | 2.71 |
| 474 | 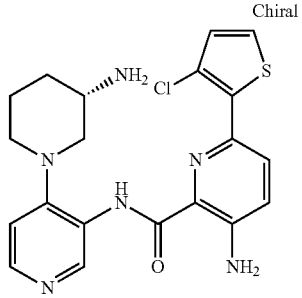 [SMILES: Nc1ccc(-c2sccc2Cl)nc1C(=O)Nc1cnccc1N1CCC[C@H](N)C1] Chiral | 3-Amino-6-(3-chloro-thiophen-2-yl)-pyridine-2-carboxylic acid (3-amino-3,4,5,6-tetrahydro-2H-[1,4']bipyridinyl-3'-yl)-amide | 429.1 | 2.21 |

-continued

| Example | Structure | Name | MH+ | LC |
|---|---|---|---|---|
| 475 | 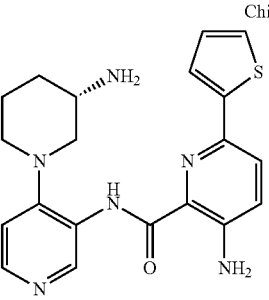 | 3-Amino-6-thiophen-2-yl-pyridine-2-carboxylic acid (3-amino-3,4,5,6-tetrahydro-2H-[1,4']bipyridinyl-3'-yl)-amide | 395.2 | 1.97 |
| 476 | 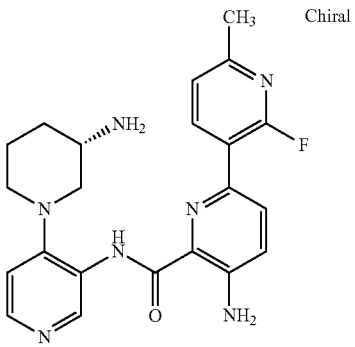 [SMILES: Cc1ccc(-c2ccc(N)c(C(=O)Nc3cnccc3N3CCC[C@H](N)C3)n2)c(F)n1] | 5-Amino-2'-fluoro-6'-methyl-[2,3']bipyridinyl-6-carboxylic acid (3-amino-3,4,5,6-tetrahydro-2H-[1,4']bipyridinyl-3'-yl)-amide | 422.2 | 1.93 |
| 477 | 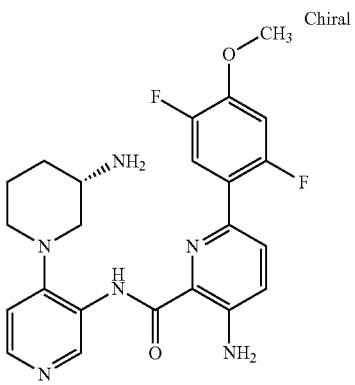 [SMILES: COc1cc(F)c(-c2ccc(N)c(C(=O)Nc3cnccc3N3CCC[C@H](N)C3)n2)cc1F] | 3-Amino-6-(2,5-difluoro-4-methoxy-phenyl)-pyridine-2-carboxylic acid (3-amino-3,4,5,6-tetrahydro-2H-[1,4']bipyridinyl-3'-yl)-amide | 455.2 | 2.29 |
| 478 | 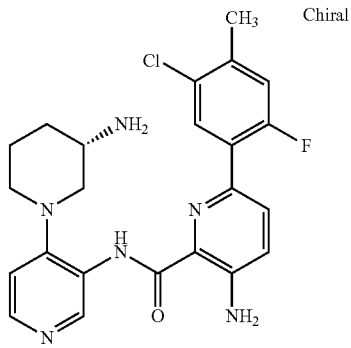 [SMILES: Cc1cc(F)c(-c2ccc(N)c(C(=O)Nc3cnccc3N3CCC[C@H](N)C3)n2)cc1Cl] | 3-Amino-6-(5-chloro-2-fluoro-4-methyl-phenyl)-pyridine-2-carboxylic acid (3-amino-3,4,5,6-tetrahydro-2H-[1,4']bipyridinyl-3'-yl)-amide | 455.2 | 2.48 |

-continued

| Example | Name | MH+ | LC |
|---|---|---|---|
| 479 | 3-Amino-6-(3-chloro-2-fluoro-phenyl)-pyridine-2-carboxylic acid (3-amino-3,4,5,6-tetrahydro-2H-[1,4']bipyridinyl-3'-yl)-amide | 441.2 | 2.36 |
| 480 | 3-Amino-6-(4-sulfamoyl-phenyl)-pyridine-2-carboxylic acid (3-amino-3,4,5,6-tetrahydro-2H-[1,4']bipyridinyl-3'-yl)-amide | 468.2 | 1.73 |
| 481 | 3-Amino-6-(3-sulfamoyl-phenyl)-pyridine-2-carboxylic acid (3-amino-3,4,5,6-tetrahydro-2H-[1,4']bipyridinyl-3'-yl)-amide | 468.2 | 1.74 |
| 482 | 5,6'-Diamino-5'-trifluoromethyl-[2,3']bipyridinyl-6-carboxylic acid (3-amino-3,4,5,6-tetrahydro-2H-[1,4']bipyridinyl-3'-yl)-amide | 473.1 | 1.688 (7.838) |

-continued

| Example | Structure | Name | MH+ | LC |
|---|---|---|---|---|
| 483 | 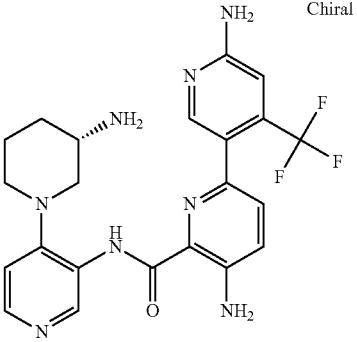 [SMILES: Nc1cc(C(F)(F)F)c(-c2ccc(N)c(C(=O)Nc3cnccc3N3CCC[C@H](N)C3)n2)cn1] Chiral | 5,6'-Diamino-4'-trifluoromethyl-[2,3']bipyridinyl-6-carboxylic acid (3-amino-3,4,5,6-tetrahydro-2H-[1,4']bipyridinyl-3'-yl)-amide | 473.2 | 1.56 |
| 484 | 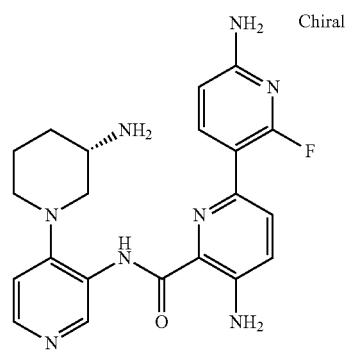 [SMILES: Nc1ccc(-c2ccc(N)c(C(=O)Nc3cnccc3N3CCC[C@H](N)C3)n2)c(F)n1] Chiral | 5,6'-Diamino-2'-fluoro-[2,3']bi-pyridinyl-6-carboxylic acid (3-amino-3,4,5,6-tetrahydro-2H-[1,4']bipyridinyl-3'-yl)-amide | 423.2 | 1.69 |
| 485 | 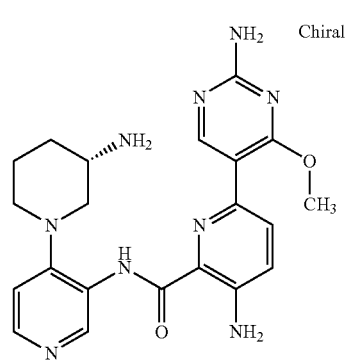 [SMILES: COc1nc(N)ncc1-c1ccc(N)c(C(=O)Nc2cnccc2N2CCC[C@H](N)C2)n1] Chiral | 3-Amino-6-(2-amino-4-methoxy-pyrimidin-5-yl)-pyridine-2-carboxylic acid (3-amino-3,4,5,6-tetrahydro-2H-[1,4']bipyridinyl-3'-yl)-amide | 436.2 | 1.26 |
| 486 | 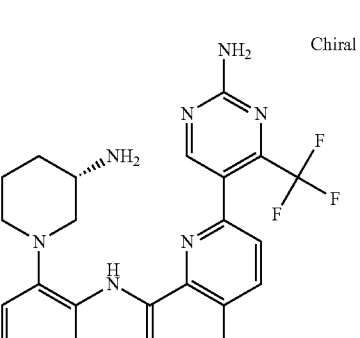 Chiral | 3-Amino-6-(2-amino-4-trifluoromethyl-pyrimidin-5-yl)-pyridine-2-carboxylic acid (3-amino-3,4,5,6-tetrahydro-2H-[1,4']bipyridinyl-3'-yl)-amide | 474.2 | 1.87 |

| Example | Structure | Name | MH+ | LC |
|---|---|---|---|---|
| 487 | 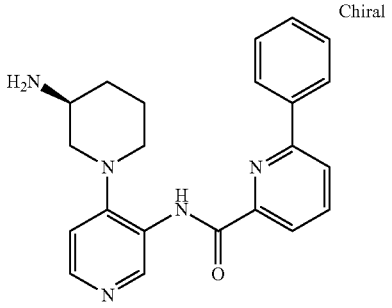 [SMILES: N[C@H]1CCCN(c2ccncc2NC(=O)c2cccc(-c3ccccc3)n2)C1] Chiral | 6-Phenyl-pyridine-2-carboxylic acid (3-amino-3,4,5,6-tetrahydro-2H-[1,4']bipyridinyl-3'-yl)-amide | 374.2 | 2.01 |
| 488 | 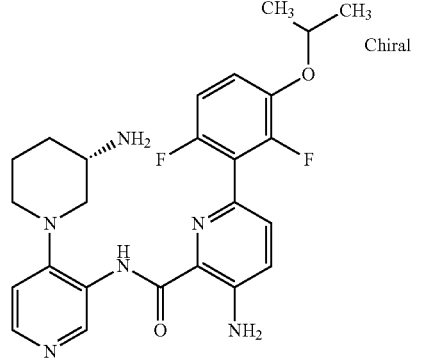 [SMILES: CC(C)Oc1ccc(F)c(-c2ccc(N)c(C(=O)Nc3cnccc3N3CCC[C@H](N)C3)n2)c1F] Chiral | 3-Amino-6-(2,6-difluoro-3-isopropoxy-phenyl)-pyridine-2-carboxylic acid (3-amino-3,4,5,6-tetrahydro-2H-[1,4']bipyridinyl-3'-yl)-amide | 483.2 | 2.51 |
| 489 | 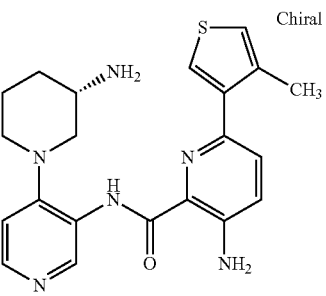 [SMILES: Cc1cscc1-c1ccc(N)c(C(=O)Nc2cnccc2N2CCC[C@H](N)C2)n1] Chiral | 3-Amino-6-(4-methyl-thiophen-3-yl)-pyridine-2-carboxylic acid (3-amino-3,4,5,6-tetrahydro-2H-[1,4']bipyridinyl-3'-yl)-amide | 409.2 | 2.11 |
| 490 | 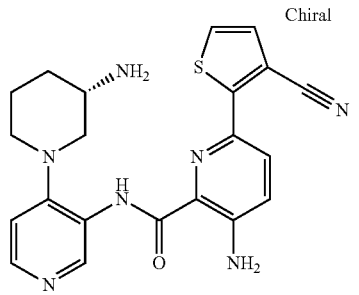 [SMILES: N#Cc1ccsc1-c1ccc(N)c(C(=O)Nc2cnccc2N2CCC[C@H](N)C2)n1] Chiral | 3-Amino-6-(3-cyano-thiophen-2-yl)-pyridine-2-carboxylic acid (3-amino-3,4,5,6-tetrahydro-2H-[1,4']bipyridinyl-3'-yl)-amide | 420.2 | 1.96 |

-continued

| Example | Structure | Name | MH+ | LC |
|---|---|---|---|---|
| 491 | 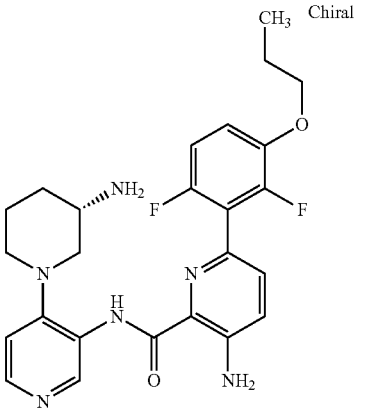 [SMILES: CCCOc1ccc(F)c(-c2ccc(N)c(C(=O)Nc3cnccc3N3CCC[C@H](N)C3)n2)c1F] | 3-Amino-6-(2,6-difluoro-3-propoxy-phenyl)-pyridine-2-carboxylic acid (3-amino-3,4,5,6-tetrahydro-2H-[1,4']bipyridinyl-3'-yl)-amide | 483.2 | 2.70 |
| 492 | 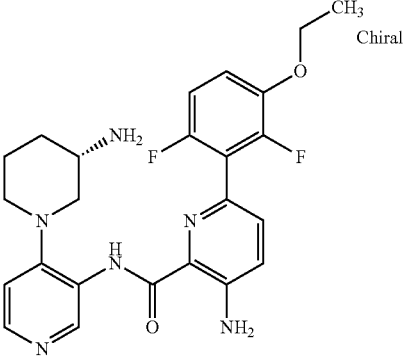 [SMILES: CCOc1ccc(F)c(-c2ccc(N)c(C(=O)Nc3cnccc3N3CCC[C@H](N)C3)n2)c1F] | 3-Amino-6-(3-ethoxy-2,6-difluoro-phenyl)-pyridine-2-carboxylic acid (3-amino-3,4,5,6-tetrahydro-2H-[1,4']bipyridinyl-3'-yl)-amide | 469.2 | 2.29 |
| 493 | 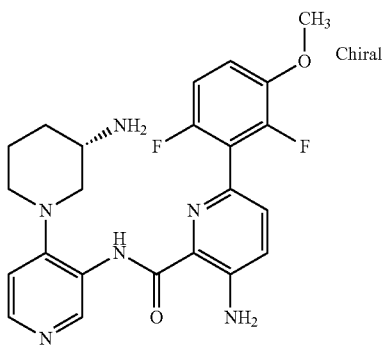 [SMILES: COc1ccc(F)c(-c2ccc(N)c(C(=O)Nc3cnccc3N3CCC[C@H](N)C3)n2)c1F] | 3-Amino-6-(2,6-difluoro-3-methoxy-phenyl)-pyridine-2-carboxylic acid (3-amino-3,4,5,6-tetrahydro-2H-[1,4']bipyridinyl-3'-yl)-amide | 455.2 | 2.17 |
| 494 | 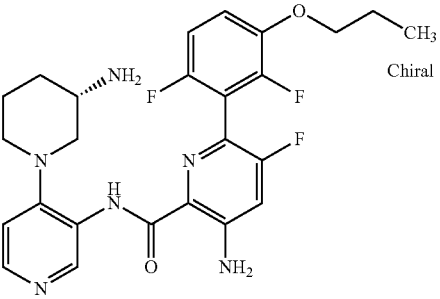 [SMILES: CCCOc1ccc(F)c(-c2nc(C(=O)Nc3cnccc3N3CCC[C@H](N)C3)c(N)cc2F)c1F] | 3-Amino-6-(2,6-difluoro-3-propoxy-phenyl)-5-fluoro-pyridine-2-carboxylic acid (3-amino-3,4,5,6-tetrahydro-2H-[1,4']bipyridinyl-3'-yl)-amide | 501.2 | 2.63 |

| Example | Structure | Name | MH+ | LC |
|---|---|---|---|---|
| 495 | 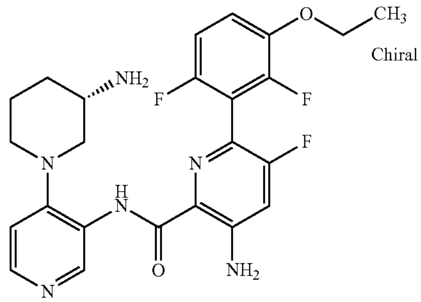 [SMILES: CCOc1ccc(F)c(-c2nc(C(=O)Nc3cnccc3N3CCC[C@H](N)C3)c(N)cc2F)c1F] | 3-Amino-6-(3-ethoxy-2,6-difluoro-phenyl)-5-fluoro-pyridine-2-carboxylic acid (3-amino-3,4,5,6-tetrahydro-2H-[1,4']bipyridinyl-3'-yl)-amide | 487.2 | 2.38 |
| 496 | 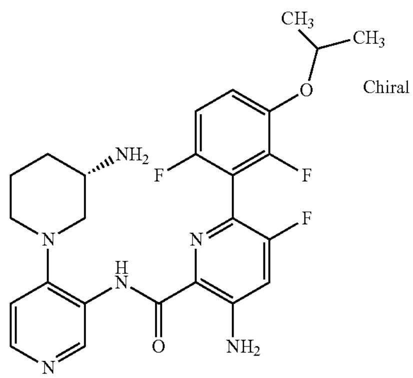 [SMILES: CC(C)Oc1ccc(F)c(-c2nc(C(=O)Nc3cnccc3N3CCC[C@H](N)C3)c(N)cc2F)c1F] | 3-Amino-6-(2,6-difluoro-3-isopropoxy-phenyl)-5-fluoro-pyridine-2-carboxylic acid (3-amino-3,4,5,6-tetrahydro-2H-[1,4']bipyridinyl-3'-yl)-amide | 501.2 | 2.48 |
| 497 | 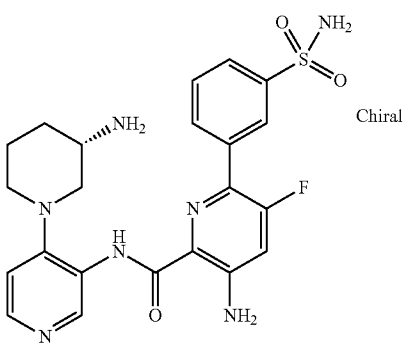 [SMILES: Nc1cc(F)c(-c2cccc(S(N)(=O)=O)c2)nc1C(=O)Nc1cnccc1N1CCC[C@H](N)C1] | 3-Amino-5-fluoro-6-(3-sulfamoyl-phenyl)-pyridine-2-carboxylic acid (3-amino-3,4,5,6-tetrahydro-2H-[1,4']bipyridinyl-3'-yl)-amide | 486.1 | 1.77 |
| 498 | 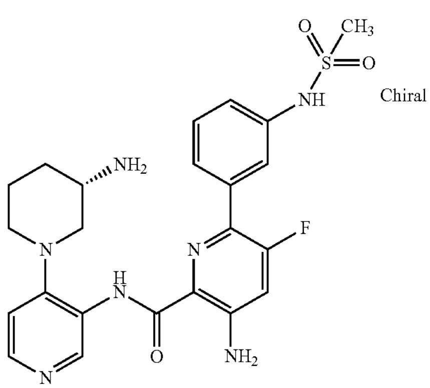 [SMILES: CS(=O)(=O)Nc1cccc(-c2nc(C(=O)Nc3cnccc3N3CCC[C@H](N)C3)c(N)cc2F)c1] | 3-Amino-5-fluoro-6-(3-methanesulfonylamino-phenyl)-pyridine-2-carboxylic acid (3-amino-3,4,5,6-tetrahydro-2H-[1,4']bipyridinyl-3'-yl)-amide | 500.2 | 1.96 |

| Example | Structure | Name | MH+ | LC |
|---|---|---|---|---|
| 499 | Chiral | 3-Amino-5-fluoro-6-phenyl-pyridine-2-carboxylic acid (3-amino-3,4,5,6-tetrahydro-2H-[1,4']bipyridinyl-3'-yl)-amide | 407.1 | 2.18 |
| 500 | Chiral | 6-(3-Acetylamino-phenyl)-3-amino-5-fluoro-pyridine-2-carboxylic acid (3-amino-3,4,5,6-tetrahydro-2H-[1,4']bipyridinyl-3'-yl)-amide | 464.2 | 1.90 |
| 501 | Chiral | 3-Amino-5-fluoro-6-(5-fluoro-2-methoxy-phenyl)-pyridine-2-carboxylic acid (3-amino-3,4,5,6-tetrahydro-2H-[1,4']bipyridinyl-3'-yl)-amide | 455.2 | 2.24 |
| 502 | Chiral | 3-Amino-5-fluoro-6-(2-fluoro-5-methoxy-phenyl)-pyridine-2-carboxylic acid (3-amino-3,4,5,6-tetrahydro-2H-[1,4']bipyridinyl-3'-yl)-amide | 455.2 | 2.26 |

-continued

| Example | Structure | Name | MH+ | LC |
|---|---|---|---|---|
| 503 | 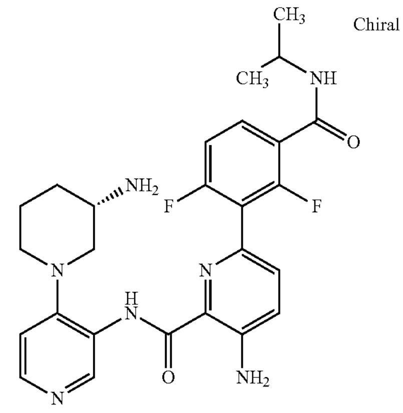 [SMILES: CC(C)NC(=O)c1ccc(F)c(-c2ccc(N)c(C(=O)Nc3cnccc3N3CCC[C@H](N)C3)n2)c1F] | 3-Amino-6-(2,6-difluoro-3-isopropylcarbamoyl-phenyl)-pyridine-2-carboxylic acid (3-amino-3,4,5,6-tetrahydro-2H-[1,4']bipyridinyl-3'-yl)-amide | 510.3 | 2.10 |
| 504 | 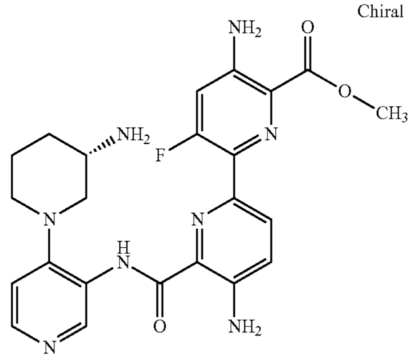 [SMILES: COC(=O)c1nc(-c2ccc(N)c(C(=O)Nc3cnccc3N3CCC[C@H](N)C3)n2)c(F)cc1N] | 5,5'-Diamino-6'-(3-amino-3,4,5,6-tetrahydro-2H-[1,4']bipyridinyl-3'-ylcarbamoyl)-3-fluoro-[2,2']bipyridinyl-6-carboxylic acid methyl ester | 481.2 | 1.90 |
| 505 | 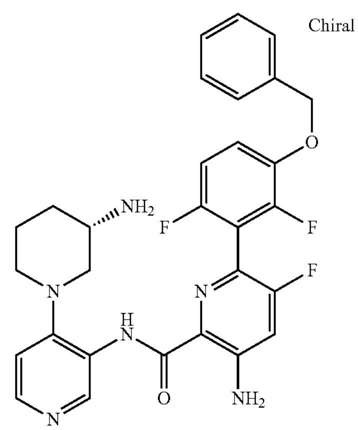 [SMILES: Nc1cc(F)c(-c2c(F)ccc(OCc3ccccc3)c2F)nc1C(=O)Nc1cnccc1N1CCC[C@H](N)C1] | 3-Amino-6-(3-benzyloxy-2,6-difluoro-phenyl)-5-fluoro-pyridine-2-carboxylic acid (3-amino-3,4,5,6-tetrahydro-2H-[1,4']bipyridinyl-3'-yl)-amide | 549.2 | 2.80 |
| 506 | 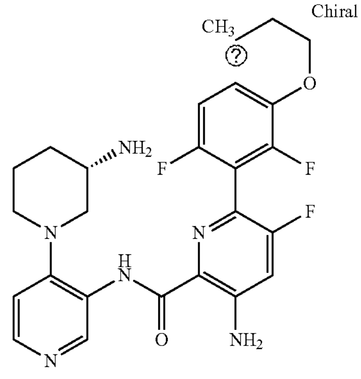 | 3-Amino-6-(3-butoxy-2,6-difluoro-phenyl)-5-fluoro-pyridine-2-carboxylic acid (3-amino-3,4,5,6-tetrahydro-2H-[1,4']bipyridinyl-3'-yl)-amide | 515.3 | 2.83 |

-continued

| Example | Structure | Name | MH+ | LC |
|---|---|---|---|---|
| 507 | 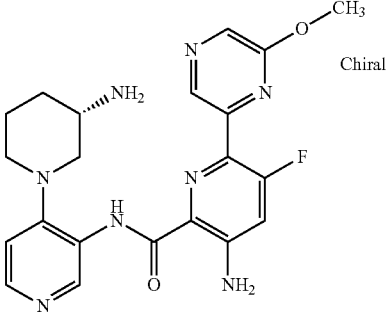 [SMILES: COc1cncc(-c2nc(C(=O)Nc3cnccc3N3CCC[C@H](N)C3)c(N)cc2F)n1] | 3-Amino-5-fluoro-6-(6-methoxy-pyrazin-2-yl)-pyridine-2-carboxylic acid (3-amino-3,4,5,6-tetrahydro-2H-[1,4']bipyridinyl-3'-yl)-amide | 439.2 | 1.95 |
| 508 | 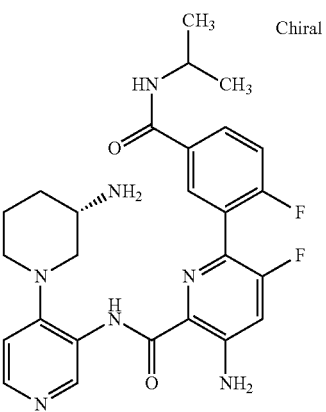 [SMILES: CC(C)NC(=O)c1ccc(F)c(-c2nc(C(=O)Nc3cnccc3N3CCC[C@H](N)C3)c(N)cc2F)c1] | 3-Amino-5-fluoro-6-(2-fluoro-5-isopropylcarbamoyl-phenyl)-pyridine-2-carboxylic acid (3-amino-3,4,5,6-tetrahydro-2H-[1,4']bipyridinyl-3'-yl)-amide | 510.3 | 2.14 |
| 509 | 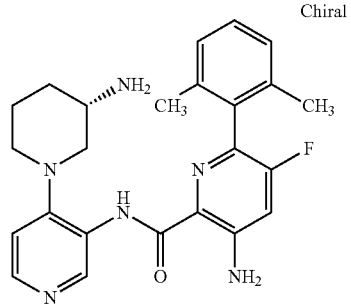 [SMILES: Cc1cccc(C)c1-c1nc(C(=O)Nc2cnccc2N2CCC[C@H](N)C2)c(N)cc1F] | 3-Amino-6-(2,6-dimethyl-phenyl)-5-fluoro-pyridine-2-carboxylic acid (3-amino-3,4,5,6-tetrahydro-2H-[1,4']bipyridinyl-3'-yl)-amide | 435.2 | 2.41 |
| 510 | 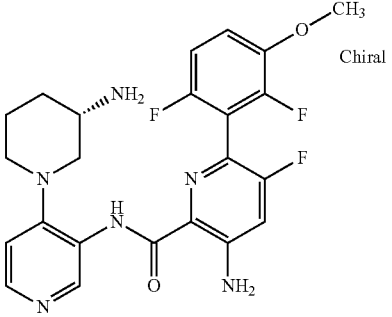 [SMILES: COc1ccc(F)c(-c2nc(C(=O)Nc3cnccc3N3CCC[C@H](N)C3)c(N)cc2F)c1F] | 3-Amino-6-(2,6-difluoro-3-methoxy-phenyl)-5-fluoro-pyridine-2-carboxylic acid (3-amino-3,4,5,6-tetrahydro-2H-[1,4']bipyridinyl-3'-yl)-amide | 473.2 | 2.32 |

-continued

| Example | Structure | Name | MH+ | LC |
|---|---|---|---|---|
| 511 | Chiral | 5-Amino-3-fluoro-2'-methoxy-[2,3']bipyridinyl-6-carboxylic acid (3-amino-3,4,5,6-tetrahydro-2H-[1,4']bipyridinyl-3'-yl)-amide | 438.2 | 1.93 |
| 512 | Chiral | 5-Amino-3-fluoro-6'-methoxy-[2,2']bipyridinyl-6-carboxylic acid (3-amino-3,4,5,6-tetrahydro-2H-[1,4']bipyridinyl-3'-yl)-amide | 438.2 | 1.89 |
| 513 | Chiral | 5-Amino-3-fluoro-[2,4']bipyridinyl-6-carboxylic acid (3-amino-3,4,5,6-tetrahydro-2H-[1,4']bipyridinyl-3'-yl)-amide | 408.2 | 1.24 |
| 514 | Chiral | 5,6'-Diamino-3-fluoro-[2,3']bipyridinyl-6-carboxylic acid (3-amino-3,4,5,6-tetrahydro-2H-[1,4']bipyridinyl-3'-yl)-amide | 423.2 | 1.34 |

| Example | Structure | Name | MH+ | LC |
|---|---|---|---|---|
| 515 | 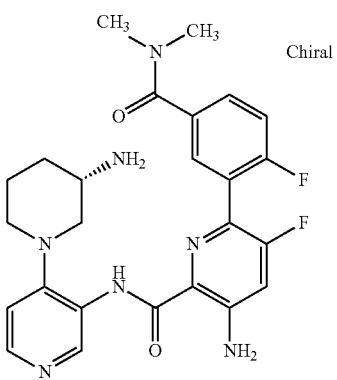 [SMILES: CN(C)C(=O)c1ccc(F)c(-c2nc(C(=O)Nc3cnccc3N3CCC[C@H](N)C3)c(N)cc2F)c1] Chiral | 3-Amino-6-(5-dimethylcarbamoyl-2-fluoro-phenyl)-5-fluoro-pyridine-2-carboxylic acid (3-amino-3,4,5,6-tetrahydro-2H-[1,4']bipyridinyl-3'-yl)-amide | 496.2 | 2.14 |
| 516 | 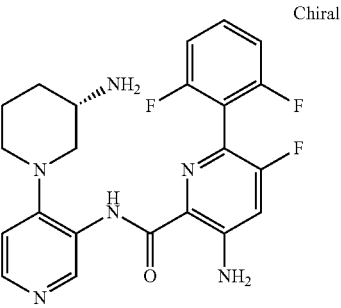 [SMILES: Nc1cc(F)c(-c2c(F)cccc2F)nc1C(=O)Nc1cnccc1N1CCC[C@H](N)C1] Chiral | 3-Amino-6-(2,6-difluoro-phenyl)-5-fluoro-pyridine-2-carboxylic acid (3-amino-3,4,5,6-tetrahydro-2H-[1,4']bipyridinyl-3'-yl)-amide | 443.2 | 2.25 |
| 517 | 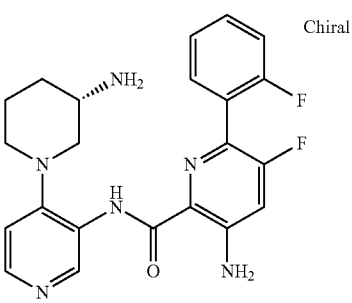 [SMILES: Nc1cc(F)c(-c2ccccc2F)nc1C(=O)Nc1cnccc1N1CCC[C@H](N)C1] Chiral | 3-Amino-5-fluoro-6-(2-fluoro-phenyl)-pyridine-2-carboxylic acid (3-amino-3,4,5,6-tetrahydro-2H-[1,4']bipyridinyl-3'-yl)-amide | 425.2 | 2.25 |
| 518 | 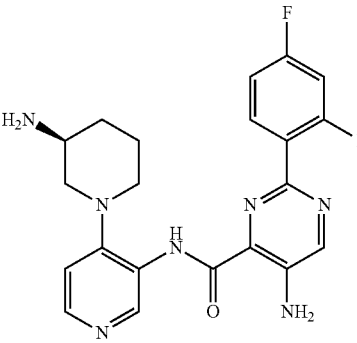 | 5-Amino-2-(2,4-difluoro-phenyl)-pyrimidine-4-carboxylic acid (3-amino-3,4,5,6-tetrahydro-2H-[1,4']bipyridinyl-3'-yl)-amide | 426.2 | 1.89 |

-continued

| Example | Structure | Name | MH+ | LC |
|---|---|---|---|---|
| 519 | 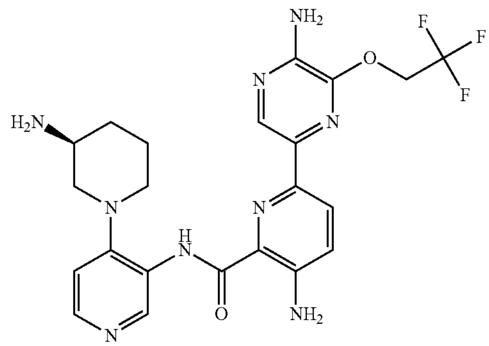 [SMILES: Nc1ccc(-c2cnc(N)c(OCC(F)(F)F)n2)nc1C(=O)Nc1cnccc1N1CCC[C@H](N)C1] | 3-Amino-6-[5-amino-6-(2,2,2-trifluoro-ethoxy)-pyrazin-2-yl]-pyridine-2-carboxylic acid (3-amino-3,4,5,6-tetrahydro-2H-[1,4']bipyridinyl-3'-yl)-amide | 504.2 | 2.10 |
| 520 | 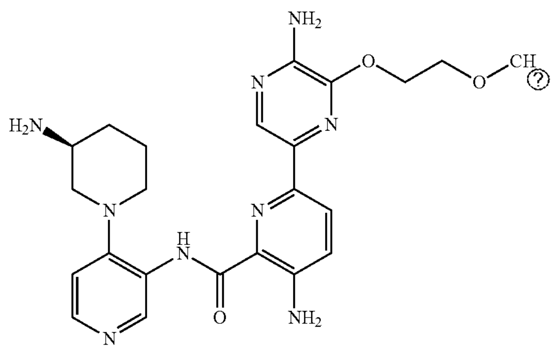 [SMILES: COCCOc1nc(-c2ccc(N)c(C(=O)Nc3cnccc3N3CCC[C@H](N)C3)n2)cnc1N] | 3-Amino-6-[5-amino-6-(2-methoxy-ethoxy)-pyrazin-2-yl]-pyridine-2-carboxylic acid (3-amino-3,4,5,6-tetrahydro-2H-[1,4']bipyridinyl-3'-yl)-amide | 480.2 | 1.64 |
| 521 | 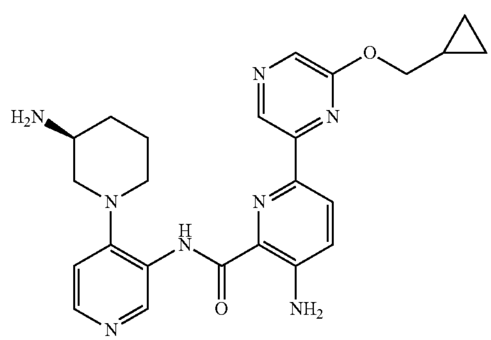 [SMILES: Nc1ccc(-c2cncc(OCC3CC3)n2)nc1C(=O)Nc1cnccc1N1CCC[C@H](N)C1] | 3-Amino-6-(6-cyclopropylmethoxy-pyrazin-2-yl)-pyridine-2-carboxylic acid (3-amino-3,4,5,6-tetrahydro-2H-[1,4']bipyridinyl-3'-yl)-amide | 461.1 | 2.38 |
| 522 | 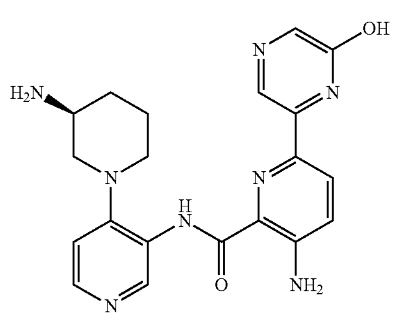 [SMILES: Nc1ccc(-c2cncc(O)n2)nc1C(=O)Nc1cnccc1N1CCC[C@H](N)C1] | 3-Amino-6-(6-hydroxy-pyrazin-2-yl)-pyridine-2-carboxylic acid (3-amino-3,4,5,6-tetrahydro-2H-[1,4']bipyridinyl-3'-yl)-amide | 407.1 | 1.35 |

-continued

| Example | Structure | Name | MH+ | LC |
|---|---|---|---|---|
| 523 | 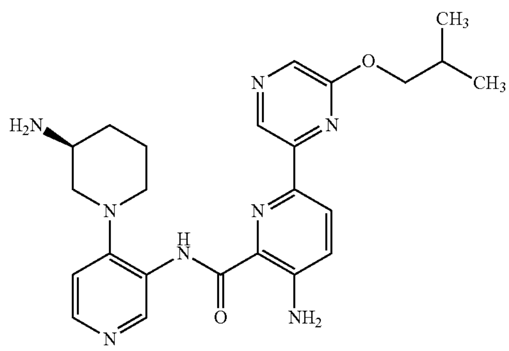 [SMILES: CC(C)COc1cncc(-c2ccc(N)c(C(=O)Nc3cnccc3N3CCC[C@H](N)C3)n2)n1] | 3-Amino-6-(6-isobutoxy-pyrazin-2-yl)-pyridine-2-carboxylic acid (3-amino-3,4,5,6-tetrahydro-2H-[1,4']bipyridinyl-3'-yl)-amide | 463.2 | 2.59 |
| 524 | 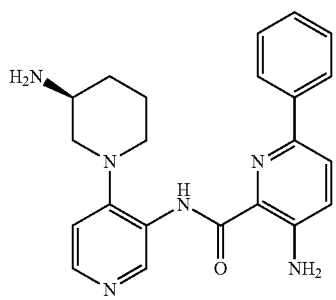 [SMILES: Nc1ccc(-c2ccccc2)nc1C(=O)Nc1cnccc1N1CCC[C@H](N)C1] | 3-Amino-6-phenyl-pyridine-2-carboxylic acid (3-amino-3,4,5,6-tetrahydro-2H-[1,4']bipyridinyl-3'-yl)-amide | 389.1 | 2.07 |
| 525 | 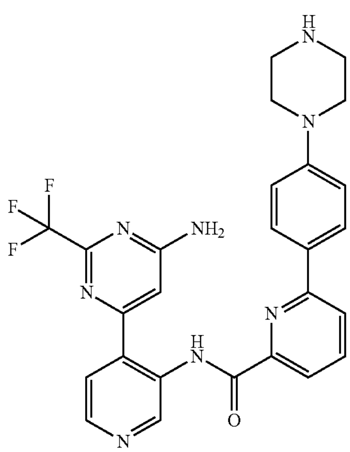 [SMILES: Nc1cc(-c2ccncc2NC(=O)c2cccc(-c3ccc(N4CCNCC4)cc3)n2)nc(C(F)(F)F)n1] | 6-(4-Piperazin-1-yl-phenyl)-pyridine-2-carboxylic acid [4-(6-amino-2-trifluoromethyl-pyrimidin-4-yl)-pyridin-3-yl]-amide | 521.1 | 2.20 |
| 526 | 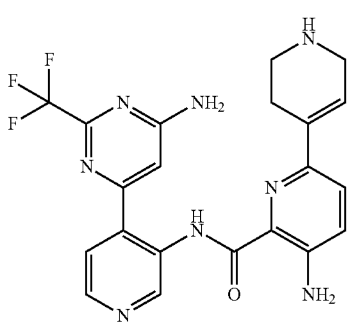 [SMILES: Nc1cc(-c2ccncc2NC(=O)c2nc(C3=CCNCC3)ccc2N)nc(C(F)(F)F)n1] | 5-Amino-1',2',3',6'-tetrahydro-[2,4']bipyridinyl-6-carboxylic acid [4-(6-amino-2-trifluoromethyl-pyrimidin-4-yl)-pyridin-3-yl]-amide | 457.2 | 1.83 |

-continued

| Example | Structure | Name | MH+ | LC |
|---|---|---|---|---|
| 527 | 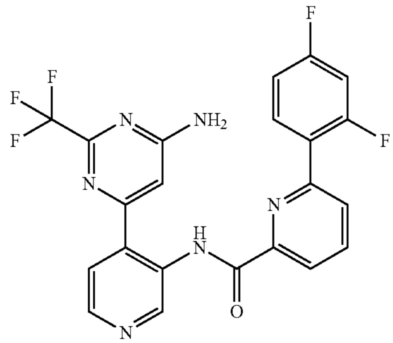 [SMILES: Nc1cc(-c2ccncc2NC(=O)c2cccc(-c3ccc(F)cc3F)n2)nc(C(F)(F)F)n1] | 6-(2,4-Difluoro-phenyl)-pyridine-2-carboxylic acid [4-(6-amino-2-trifluoromethyl-pyrimidin-4-yl)-pyridin-3-yl]-amide | 473.0 | 3.33 |
| 528 | 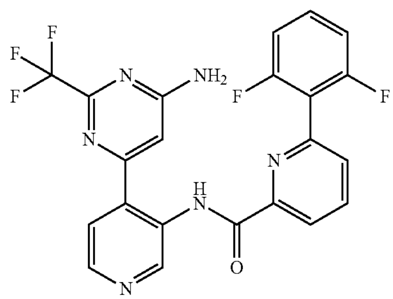 [SMILES: Nc1cc(-c2ccncc2NC(=O)c2cccc(-c3c(F)cccc3F)n2)nc(C(F)(F)F)n1] | 6-(2,6-Difluoro-phenyl)-pyridine-2-carboxylic acid [4-(6-amino-2-trifluoromethyl-pyrimidin-4-yl)-pyridin-3-yl]-amide | 473.0 | 3.16 |
| 529 | 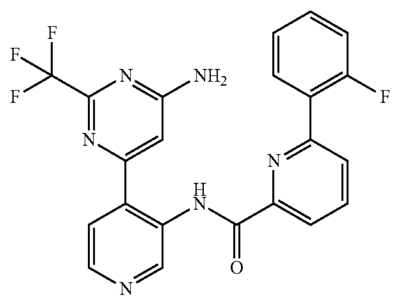 [SMILES: Nc1cc(-c2ccncc2NC(=O)c2cccc(-c3ccccc3F)n2)nc(C(F)(F)F)n1] | 6-(2-Fluoro-phenyl)-pyridine-2-carboxylic acid [4-(6-amino-2-trifluoromethyl-pyrimidin-4-yl)-pyridin-3-yl]-amide | 455.1 | 3.21 |
| 530 | 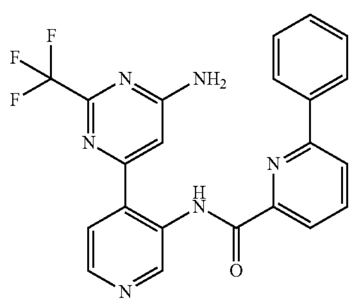 [SMILES: Nc1cc(-c2ccncc2NC(=O)c2cccc(-c3ccccc3)n2)nc(C(F)(F)F)n1] | 6-Phenyl-pyridine-2-carboxylic acid [4-(6-amino-2-trifluoromethyl-pyrimidin-4-yl)-pyridin-3-yl]-amide | 437.1 | 3.15 |
| 531 | 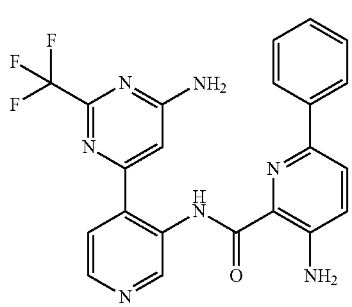 [SMILES: Nc1cc(-c2ccncc2NC(=O)c2nc(-c3ccccc3)ccc2N)nc(C(F)(F)F)n1] | 3-Amino-6-phenyl-pyridine-2-carboxylic acid [4-(6-amino-2-trifluoromethyl-pyrimidin-4-yl)-pyridin-3-yl]-amide | 452.1 | 3.03 |

| Example | Structure | Name | MH+ | LC |
|---|---|---|---|---|
| 532 | 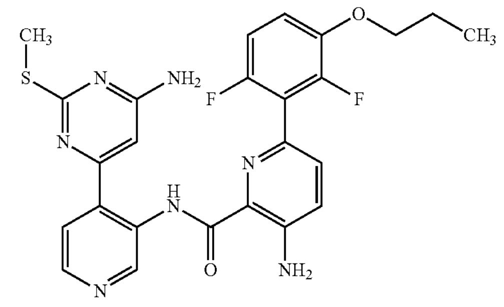 [SMILES: CCCOc1ccc(F)c(-c2ccc(N)c(C(=O)Nc3cnccc3-c3cc(N)nc(SC)n3)n2)c1F] | 3-Amino-6-(2,6-difluoro-3-propoxy-phenyl)-pyridine-2-carboxylic acid [4-(6-amino-2-methylsulfanyl-pyrimidin-4-yl)-pyridin-3-yl]-amide | 524.1 | 3.33 |
| 533 | 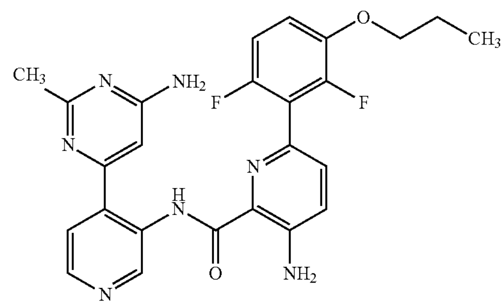 [SMILES: CCCOc1ccc(F)c(-c2ccc(N)c(C(=O)Nc3cnccc3-c3cc(N)nc(C)n3)n2)c1F] | 3-Amino-6-(2,6-difluoro-3-propoxy-phenyl)-pyridine-2-carboxylic acid [4-(6-amino-2-methyl-pyrimidin-4-yl)-pyridin-3-yl]-amide | 492.1 | 2.85 |
| 534 | 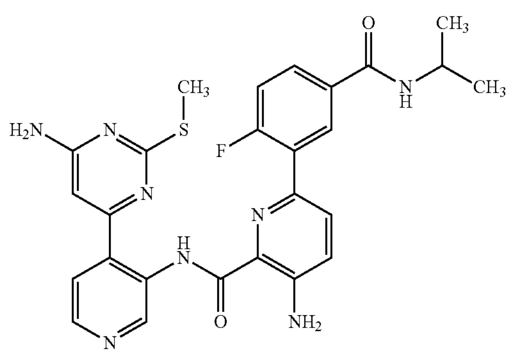 [SMILES: CSc1nc(N)cc(-c2ccncc2NC(=O)c2nc(-c3cc(C(=O)NC(C)C)ccc3F)ccc2N)n1] | 3-Amino-6-(2-fluoro-5-isopropylcarbamoyl-phenyl)-pyridine-2-carboxylic acid [4-(6-amino-2-methylsulfanyl-pyrimidin-4-yl)-pyridin-3-yl]-amide | 533.2 | 2.70) |
| 535 | 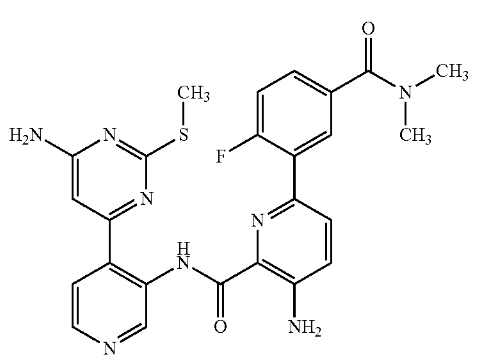 [SMILES: CSc1nc(N)cc(-c2ccncc2NC(=O)c2nc(-c3cc(C(=O)N(C)C)ccc3F)ccc2N)n1] | 3-Amino-6-(5-dimethylcarbamoyl-2-fluoro-phenyl)-pyridine-2-carboxylic acid [4-(6-amino-2-methylsulfanyl-pyrimidin-4-yl)-pyridin-3-yl]-amide | 519.2 | 2.51 |

| Example | Structure | Name | MH+ | LC |
|---|---|---|---|---|
| 536 | 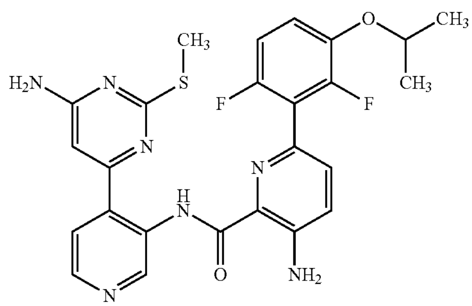 [SMILES: CSc1nc(N)cc(-c2ccncc2NC(=O)c2nc(-c3c(F)ccc(OC(C)C)c3F)ccc2N)n1] | 3-Amino-6-(2,6-difluoro-3-isopropoxy-phenyl)-pyridine-2-carboxylic acid [4-(6-amino-2-methylsulfanyl-pyrimidin-4-yl)-pyridin-3-yl]-amide | 524.0 | 3.26 |
| 537 | 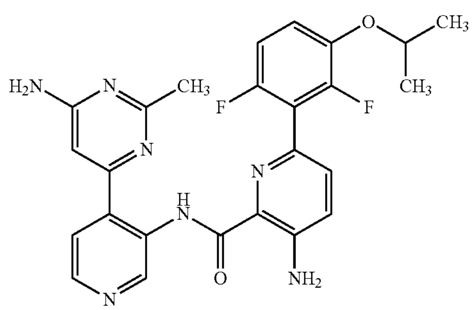 [SMILES: Cc1nc(N)cc(-c2ccncc2NC(=O)c2nc(-c3c(F)ccc(OC(C)C)c3F)ccc2N)n1] | 3-Amino-6-(2,6-difluoro-3-isopropoxy-phenyl)-pyridine-2-carboxylic acid [4-(6-amino-2-methyl-pyrimidin-4-yl)-pyridin-3-yl]-amide | 492.2 | 2.72 |
| 538 | 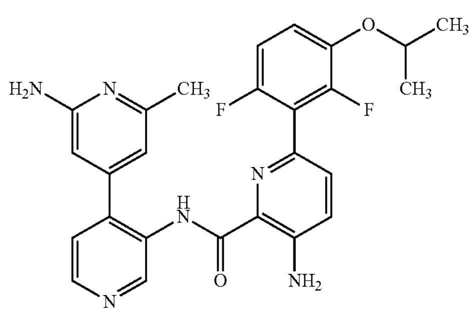 [SMILES: Cc1cc(-c2ccncc2NC(=O)c2nc(-c3c(F)ccc(OC(C)C)c3F)ccc2N)cc(N)n1] | 3-Amino-6-(2,6-difluoro-3-isopropoxy-phenyl)-pyridine-2-carboxylic acid (2'-amino-6'-methyl-[4,4']bipyridinyl-3-yl)-amide | 491.2 | 2.57 |
| 539 | 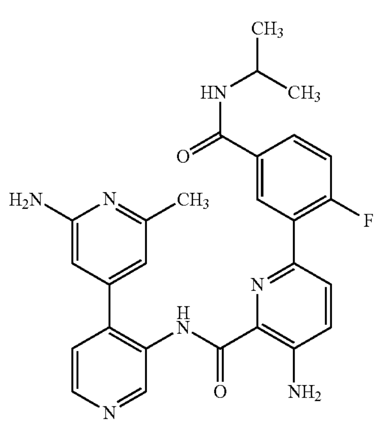 [SMILES: Cc1cc(-c2ccncc2NC(=O)c2nc(-c3cc(C(=O)NC(C)C)ccc3F)ccc2N)cc(N)n1] | 3-Amino-6-(2-fluoro-5-isopropylcarbamoyl-phenyl)-pyridine-2-carboxylic acid (2'-amino-6'-methyl-[4,4']bi-pyridinyl-3-yl)-amide | 500.2 | 2.15 |

-continued

| Example | Structure | Name | MH+ | LC |
|---|---|---|---|---|
| 540 | 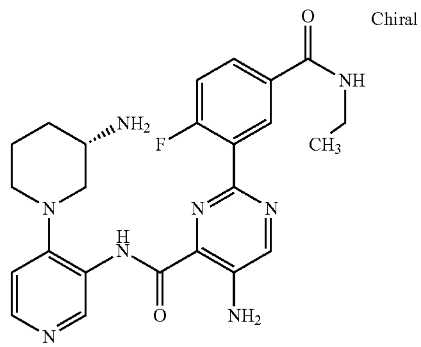 [SMILES: CCNC(=O)c1ccc(F)c(-c2ncc(N)c(C(=O)Nc3cnccc3N3CCC[C@H](N)C3)n2)c1] | 5-Amino-2-(5-ethylcarbamoyl-2-fluoro-phenyl)-pyrimidine-4-carboxylic acid (3-amino-3,4,5,6-tetrahydro-2H-[1,4']bipyridinyl-3'-yl)-amide | 479.2 | 1.64 |
| 541 | 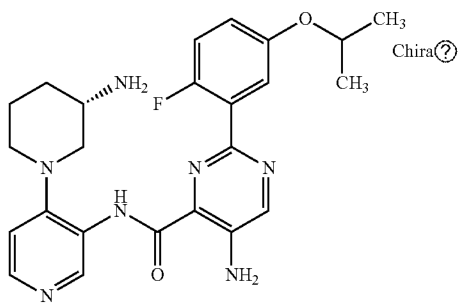 [SMILES: CC(C)Oc1ccc(F)c(-c2ncc(N)c(C(=O)Nc3cnccc3N3CCC[C@H](N)C3)n2)c1] | 5-Amino-2-(2-fluoro-5-isopropoxy-phenyl)-pyrimidine-4-carboxylic acid (3-amino-3,4,5,6-tetrahydro-2H-[1,4']bipyridinyl-3'-yl)-amide | 466.3 | 2.15 |
| 542 | 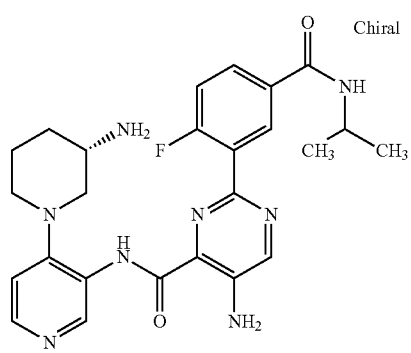 [SMILES: CC(C)NC(=O)c1ccc(F)c(-c2ncc(N)c(C(=O)Nc3cnccc3N3CCC[C@H](N)C3)n2)c1] | 5-Amino-2-(2-fluoro-5-isopropylcarbamoyl-phenyl)-pyrimidine-4-carboxylic acid (3-amino-3,4,5,6-tetrahydro-2H-[1,4']bipyridinyl-3'-yl)-amide | 493.2 | 1.84 |
| 543 | 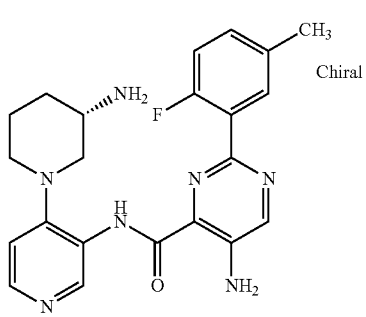 [SMILES: Cc1ccc(F)c(-c2ncc(N)c(C(=O)Nc3cnccc3N3CCC[C@H](N)C3)n2)c1] | 5-Amino-2-(2-fluoro-5-methyl-phenyl)-pyrimidine-4-carboxylic acid (3-amino-3,4,5,6-tetrahydro-2H-[1,4']bipyridinyl-3'-yl)-amide | 422.1 | 1.97 |

-continued

| Example | Structure | Name | MH+ | LC |
|---|---|---|---|---|
| 544 | 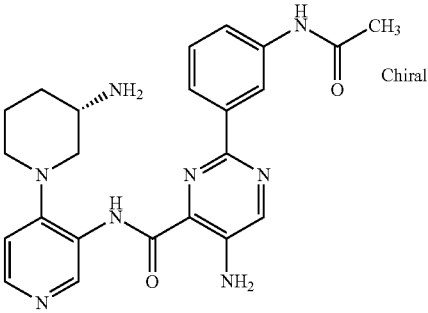 [SMILES: CC(=O)Nc1cccc(-c2ncc(N)c(C(=O)Nc3cnccc3N3CCC[C@H](N)C3)n2)c1] | 2-(3-Acetylamino-phenyl)-5-amino-pyrimidine-4-carboxylic acid (3-amino-3,4,5,6-tetrahydro-2H-[1,4']bipyridinyl-3'-yl)-amide | 447.2 | 1.63 |
| 545 | 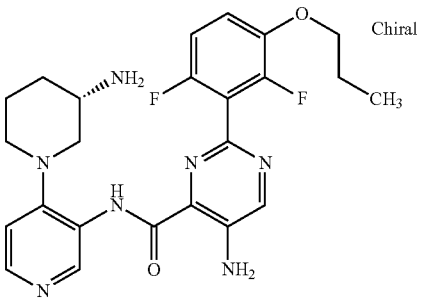 [SMILES: CCCOc1ccc(F)c(-c2ncc(N)c(C(=O)Nc3cnccc3N3CCC[C@H](N)C3)n2)c1F] | 5-Amino-2-(2,6-difluoro-3-propoxy-phenyl)-pyrimidine-4-carboxylic acid (3-amino-3,4,5,6-tetrahydro-2H-[1,4']bipyridinyl-3'-yl)-amide | 484.2 | 2.19 |
| 546 | 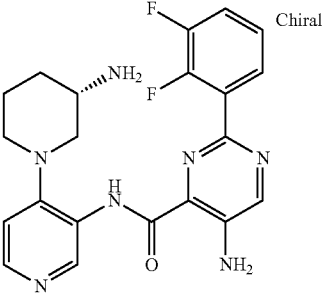 [SMILES: Nc1cnc(-c2cccc(F)c2F)nc1C(=O)Nc1cnccc1N1CCC[C@H](N)C1] | 5-Amino-2-(2,3-difluoro-phenyl)-pyrimidine-4-carboxylic acid (3-amino-3,4,5,6-tetrahydro-2H-[1,4']bipyridinyl-3'-yl)-amide | 426.2 | 1.85 |
| 547 | 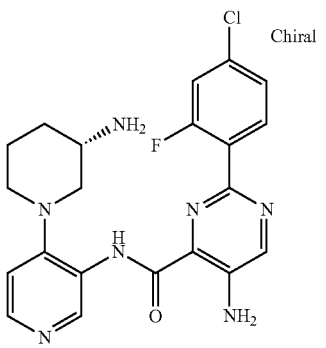 [SMILES: Nc1cnc(-c2ccc(Cl)cc2F)nc1C(=O)Nc1cnccc1N1CCC[C@H](N)C1] | 5-Amino-2-(4-chloro-2-fluoro-phenyl)-pyrimidine-4-carboxylic acid (3-amino-3,4,5,6-tetrahydro-2H-[1,4']bipyridinyl-3'-yl)-amide | 442.1 | 2.05 |
| 548 | 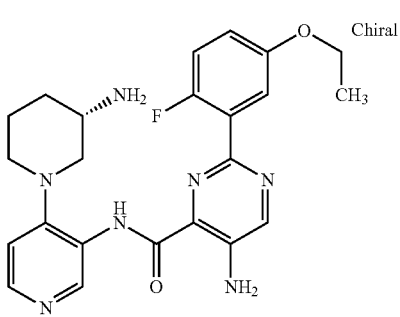 [SMILES: CCOc1ccc(F)c(-c2ncc(N)c(C(=O)Nc3cnccc3N3CCC[C@H](N)C3)n2)c1] | 5-Amino-2-(5-ethoxy-2-fluoro-phenyl)-pyrimidine-4-carboxylic acid (3-amino-3,4,5,6-tetrahydro-2H-[1,4']bipyridinyl-3'-yl)-amide | 452.2 | 2.02 |

-continued

| Example | Name | MH+ | LC |
|---|---|---|---|
| 549 | 5-Amino-2-(2-fluoro-5-methoxy-phenyl)-pyrimidine-4-carboxylic acid (3-amino-3,4,5,6-tetrahydro-2H-[1,4']bipyridinyl-3'-yl)-amide | 438.1 | 1.84 |
| 550 | 5-Amino-2-(2-fluoro-5-propoxy-phenyl)-pyrimidine-4-carboxylic acid (3-amino-3,4,5,6-tetrahydro-2H-[1,4']bipyridinyl-3'-yl)-amide | 466.2 | 2.25 |
| 551 | 5-Amino-2-(2-methoxy-phenyl)-pyrimidine-4-carboxylic acid (3-amino-3,4,5,6-tetrahydro-2H-[1,4']bipyridinyl-3'-yl)-amide | 420.1 | 1.64 |
| 552 | 5-Amino-2'-fluoro-[2,3']bi-pyridinyl-6-carboxylic acid (3-amino-3,4,5,6-tetrahydro-2H-[1,3']bipyridinyl-4'-yl)-amide | 408.1 | 1.88 |
| 553 | 6-(2-Fluoro-5-isopropylcarbamoyl-phenyl)-pyridine-2-carboxylic acid [4-(6-amino-2-trifluoromethyl-pyrimidin-4-yl)-pyridin-3-yl]-amide | 540.3 | 2.91 |

| Example | Structure | Name | MH+ | LC |
|---|---|---|---|---|
| 554 | 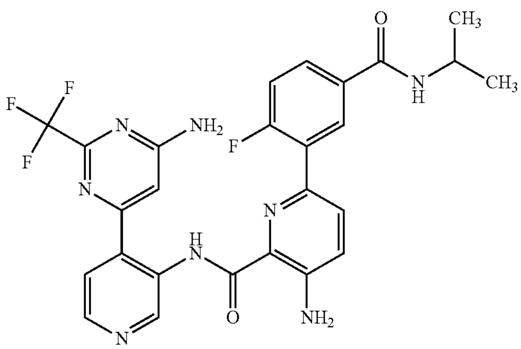 [SMILES: CC(C)NC(=O)c1ccc(F)c(-c2ccc(N)c(C(=O)Nc3cnccc3-c3cc(N)nc(C(F)(F)F)n3)n2)c1] | 3-Amino-6-(2-fluoro-5-isopropylcarbamoyl-phenyl)-pyridine-2-carboxylic acid [4-(6-amino-2-trifluoromethyl-pyrimidin-4-yl)-pyridin-3-yl]-amide | 555.2 | 2.83 |
| 555 | 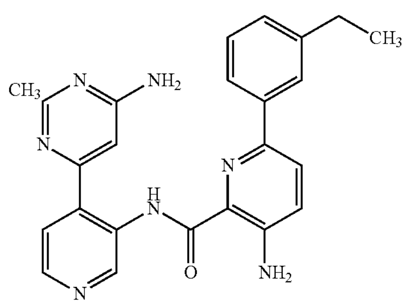 | 3-Amino-6-(3-ethyl-phenyl)-pyridine-2-carboxylic acid [4-(6-amino-2-methyl-pyrimidin-4-yl)-pyridin-3-yl]-amide | 426.1 | 2.72 |
| 556 | 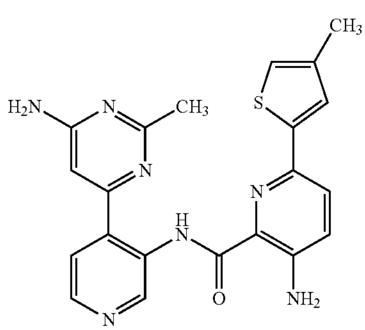 [SMILES: Cc1csc(-c2ccc(N)c(C(=O)Nc3cnccc3-c3cc(N)nc(C)n3)n2)c1] | 3-Amino-6-(4-methyl-thiophen-2-yl)-pyridine-3-carboxylic acid [4-(6-amino-2-methyl-pyrimidin-4-yl)-pyridin-3-yl]-amide | 418.1 | 2.33 |
| 557 | 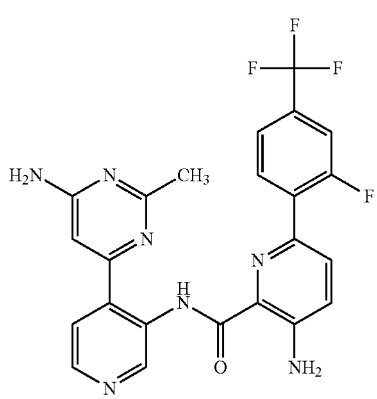 [SMILES: Cc1nc(N)cc(-c2ccncc2NC(=O)c2nc(-c3ccc(C(F)(F)F)cc3F)ccc2N)n1] | 3-Amino-6-(2-fluoro-4-trifluoromethyl-phenyl)-pyridine-2-carboxylic acid [4-(6-amino-2-methyl-pyrimidin-4-yl)-pyridin-3-yl]-amide | 484.2 | 2.86 |

-continued

| Example | Structure | Name | MH+ | LC |
|---|---|---|---|---|
| 558 | 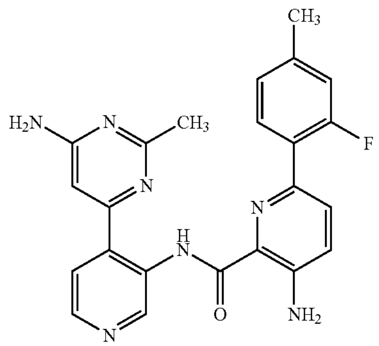 [SMILES: Cc1ccc(-c2ccc(N)c(C(=O)Nc3cnccc3-c3cc(N)nc(C)n3)n2)c(F)c1] | 3-Amino-6-(2-fluoro-4-methyl-phenyl)-pyridine-2-carboxylic acid [4-(6-amino-2-methyl-pyrimidin-4-yl)-pyridin-3-yl]-amide | 430.2 | 2.57 |
| 559 | 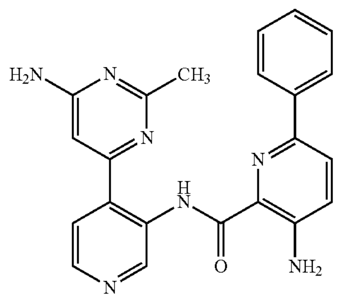 [SMILES: Cc1nc(N)cc(-c2ccncc2NC(=O)c2nc(-c3ccccc3)ccc2N)n1] | 3-Amino-6-phenyl-pyridine-2-carboxylic acid [4-(6-amino-2-methyl-pyrimidin-4-yl)-pyridin-3-yl]-amide | 398.2 | 2.26 |
| 560 | 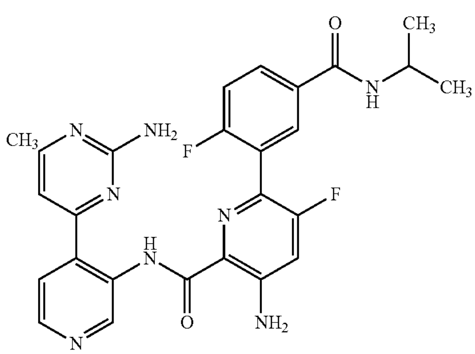 | 3-Amino-5-fluoro-6-(2-fluoro-5-isopropylcarbamoyl-phenyl)-pyridine-2-carboxylic acid [4-(2-amino-6-methyl-pyrimidin-4-yl)-pyridin-3-yl]-amide | 519.2 | 2.70 |
| 561 | 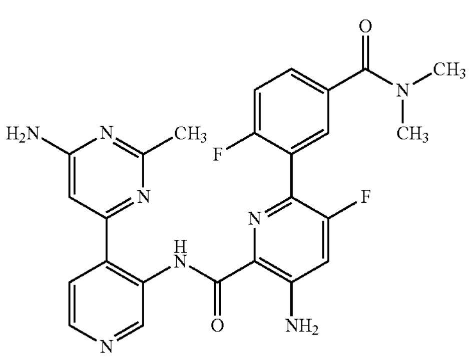 [SMILES: Cc1nc(N)cc(-c2ccncc2NC(=O)c2nc(-c3cc(C(=O)N(C)C)ccc3F)c(F)cc2N)n1] | 3-Amino-6-(5-dimethylcarbamoyl-2-fluoro-phenyl)-5-fluoro-pyridine-2-carboxylic acid [4-(6-amino-2-methyl-pyrimidin-4-yl)-pyridin-3-yl]-amide | 505.1 | 2.22 |

| Example | Structure | Name | MH+ | LC |
|---------|-----------|------|-----|-----|
| 562 | 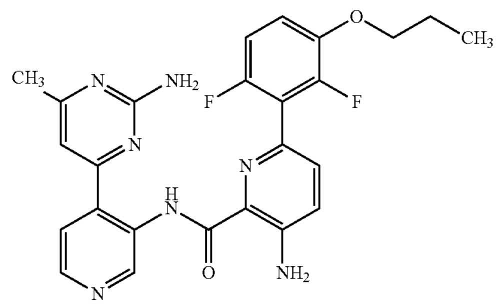 [SMILES: CCCOc1ccc(F)c(-c2ccc(N)c(C(=O)Nc3cnccc3-c3cc(C)nc(N)n3)n2)c1F] | 3-Amino-6-(2,6-difluoro-3-propoxy-phenyl)-pyridine-2-carboxylic acid [4-(2-amino-6-methyl-pyrimidin-4-yl)-pyridin-3-yl]-amide | 492.1 | 3.11 |
| 563 | 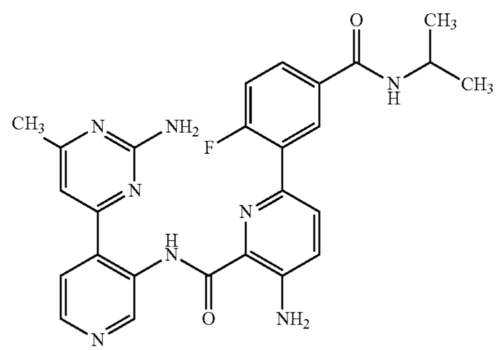 [SMILES: Cc1cc(-c2ccncc2NC(=O)c2nc(-c3cc(C(=O)NC(C)C)ccc3F)ccc2N)nc(N)n1] | 3-Amino-6-(2-fluoro-5-isopropylcarbamoyl-phenyl)-pyridine-2-carboxylic acid [4-(2-amino-6-methyl-pyrimidin-4-yl)-pyridin-3-yl]-amide | 501.2 | 2.38 |
| 564 | 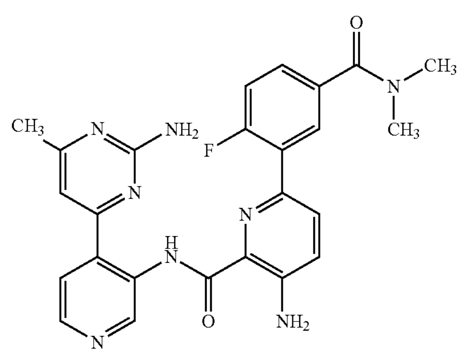 | 3-Amino-6-(5-dimethylcarbamoyl-2-fluoro-phenyl)-pyridine-2-carboxylic acid [4-(2-amino-6-methyl-pyrimidin-4-yl)-pyridin-3-yl]-amide | 487.2 | 2.24 |
| 565 | 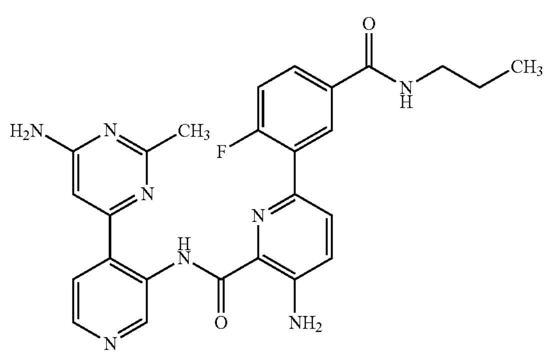 [SMILES: CCCNC(=O)c1ccc(F)c(-c2ccc(N)c(C(=O)Nc3cnccc3-c3cc(N)nc(C)n3)n2)c1] | 3-Amino-6-(2-fluoro-5-propylcarbamoyl-phenyl)-pyridine-2-carboxylic acid [4-(6-amino-2-methyl-pyrimidin-4-yl)-pyridin-3-yl]-amide | 501.2 | 2.29 |

-continued

| Example | Structure | Name | MH+ | LC |
|---|---|---|---|---|
| 566 | Chiral | 3-Amino-6-(3-morpholin-4-ylmethyl-phenyl)-pyridine-2-carboxylic acid (3-amino-3,4,5,6-tetrahydro-2H-[1,4']bipyridinyl-3'-yl)-amide | 488.0 | 1.43 |
| 567 | 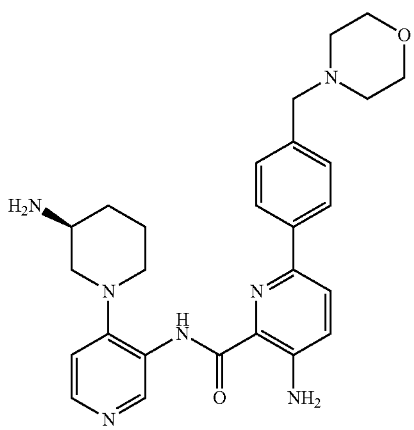 [SMILES: Nc1ccc(-c2ccc(CN3CCOCC3)cc2)nc1C(=O)Nc1cnccc1N1CCC[C@H](N)C1] | 3-Amino-6-(4-morpholin-4-ylmethyl-phenyl)-pyridine-2-carboxylic acid (3-amino-3,4,5,6-tetrahydro-2H-[1,4']bipyridinyl-3'-yl)-amide | 488.0 | 1.42 |
| 568 | Chiral | 3-Fluoro-6-phenyl-pyridine-2-carboxylic acid (3-amino-3,4,5,6-tetrahydro-2H-[1,4']bipyridinyl-3'-yl)-amide | 392.2 | 1.96 |
| 569 | Chiral | 3-Fluoro-6-(2-fluoro-5-isopropylcarbamoyl-phenyl)-pyridine-2-carboxylic acid (3-amino-3,4,5,6-tetrahydro-2H-[1,4']bipyridinyl-3'-yl)-amide | 495.2 | 2.02 |

| Example | Structure | Name | MH+ | LC |
|---|---|---|---|---|
| 570 | 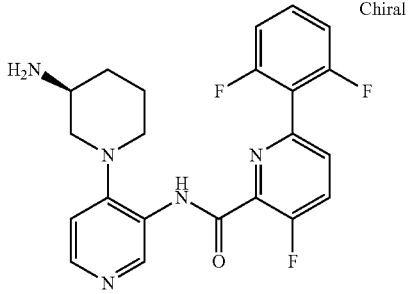 [SMILES: N[C@H]1CCCN(c2ccncc2NC(=O)c2nc(-c3c(F)cccc3F)ccc2F)C1] Chiral | 6-(2,6-Difluoro-phenyl)-3-fluoro-pyridine-2-carboxylic acid (3-amino-3,4,5,6-tetrahydro-2H-[1,4']bipyridinyl-3'-yl)-amide | 428.2 | 2.03 |
| 571 | 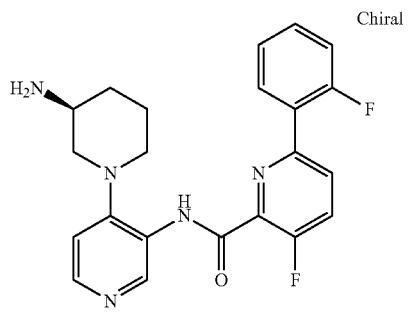 [SMILES: N[C@H]1CCCN(c2ccncc2NC(=O)c2nc(-c3ccccc3F)ccc2F)C1] Chiral | 3-Fluoro-6-(2-fluoro-phenyl)-pyridine-2-carboxylic acid (3-amino-3,4,5,6-tetrahydro-2H-[1,4']bipyridinyl-3'-yl)-amide | 410.2 | 2.08 |
| 572 | 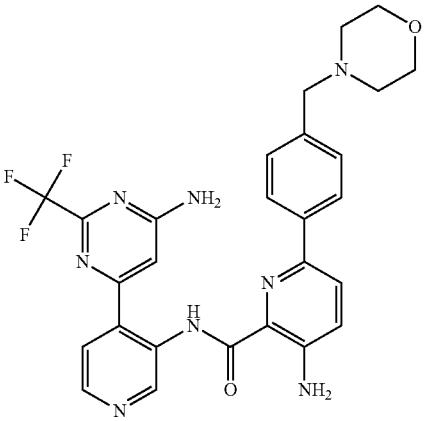 [SMILES: Nc1cc(-c2ccncc2NC(=O)c2nc(-c3ccc(CN4CCOCC4)cc3)ccc2N)nc(C(F)(F)F)n1] | 3-Amino-6-(4-morpholin-4-ylmethyl-phenyl)-pyridine-2-carboxylic acid [4-(6-amino-2-trifluoromethyl-pyrimidin-4-yl)-pyridin-3-yl]-amide | 551.1 | 2.10 |
| 573 | 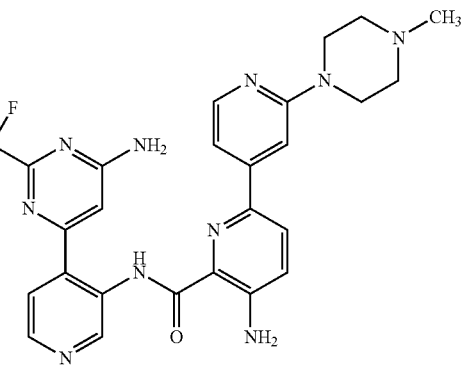 | 5-Amino-2'-(4-methyl-piperazin-1-yl)-[2,4']bipyridinyl-6-carboxylic acid [4-(6-amino-2-trifluoromethyl-pyrimidin-4-yl)-pyridin-3-yl]-amide | 551.1 | 1.73 |

-continued

| Example | Structure | Name | MH+ | LC |
| --- | --- | --- | --- | --- |
| 574 | 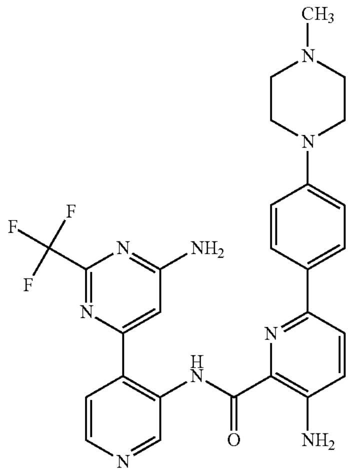 [SMILES: CN1CCN(c2ccc(-c3ccc(N)c(C(=O)Nc4cnccc4-c4cc(N)nc(C(F)(F)F)n4)n3)cc2)CC1] | 3-Amino-6-[4-(4-methyl-piperazin-1-yl)-phenyl]-pyridine-2-carboxylic acid [4-(6-amino-2-trifluoromethyl-pyrimidin-4-yl)-pyridin-3-yl]-amide | 550.1 | 2.14 |
| 575 | 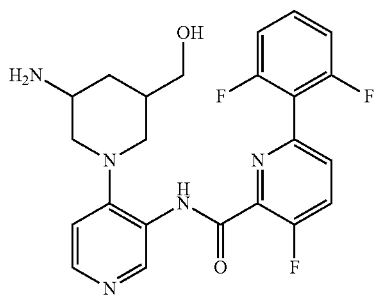 [SMILES: NC1CC(CO)CN(c2ccncc2NC(=O)c2nc(-c3c(F)cccc3F)ccc2F)C1] | 6-(2,6-Difluoro-phenyl)-3-fluoro-pyridine-2-carboxylic acid (5-amino-3-hydroxymethyl-3,4,5,6-tetrahydro-2H-[1,4']bipyridinyl-3'-yl)-amide | 458.1 | 2.10 |
| 576 | 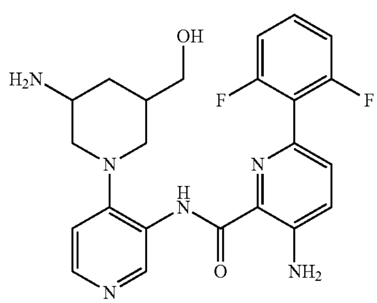 [SMILES: Nc1ccc(-c2c(F)cccc2F)nc1C(=O)Nc1cnccc1N1CC(N)CC(CO)C1] | 3-Amino-6-(2,6-difluoro-phenyl)-pyridine-2-carboxylic acid (5-amino-3-hydroxymethyl-3,4,5,6-tetrahydro-2H-[1,4']bipyridinyl-3'-yl)-amide | 455.1 | 1.89 |
| 577 | 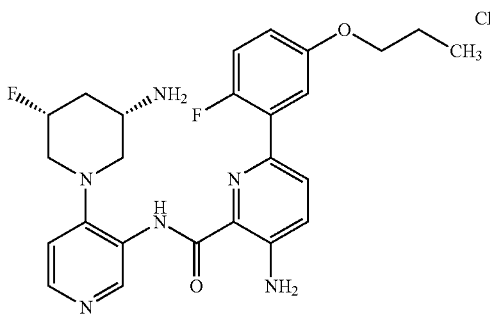 | 3-Amino-6-(2-fluoro-5-propoxy-phenyl)-pyridine-2-carboxylic acid (3-amino-5-fluoro-3,4,5,6-tetrahydro-2H-[1,4']bipyridinyl-3'-yl)-amide | 483.1 | 2.53 |

-continued

| Example | Structure | Name | MH+ | LC |
|---|---|---|---|---|
| 578 | Chiral | 3-Amino-6-phenyl-pyridine-2-carboxylic acid (3-amino-5-fluoro-3,4,5,6-tetrahydro-2H-[1,4']bipyridinyl-3'-yl)-amide | 407.1 | 1.94 |
| 579 | Chiral | 3-Amino-6-(2-fluoro-5-propoxy-phenyl)-pyridine-2-carboxylic acid (3-amino-5-methoxy-3,4,5,6-tetrahydro-2H-[1,4']bi-pyridinyl-3'-yl)-amide | 495.2 | 2.48 |
| 580 | Chiral | 3-Amino-6-phenyl-pyridine-2-carboxylic acid (3-amino-5-methoxy-3,4,5,6-tetrahydro-2H-[1,4']bipyridinyl-3'-yl)-amide | 419.1 | 1.97 |
| 581 | Chiral | 3-Amino-6-(2-fluoro-5-propoxy-phenyl)-pyridine-2-carboxylic acid (3-amino-5-hydroxy-3,4,5,6-tetrahydro-2H-[1,4']bipyridinyl-3'-yl)-amide | 481.2 | 2.45 |
| 582 | Chiral | 3-Amino-6-phenyl-pyridine-2-carboxylic acid (3-amino-5-hydroxy-3,4,5,6-tetrahydro-2H-[1,4']bipyridinyl-3'-yl)-amide | 405.1 | 1.86 |

Method 14

Example 583

Synthesis of 3-amino-6-(2-fluorophenyl)-N-(4-(piperidin-1-yl)pyridin-3-yl)picolinamide

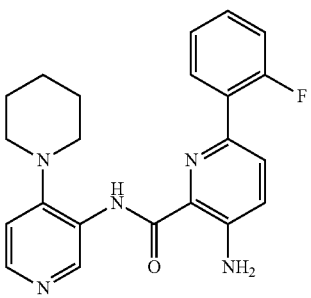

A solution of 3-amino-6-bromo-N-(4-(piperidin-1-yl)pyridin-3-yl)picolinamide (1.0 eq), 2-fluorophenyl boronic acid (3.0 eq.), Pd(dppf)Cl$_2$—CH$_2$Cl$_2$ (0.15 eq.) in 3:1 DME/2M Na$_2$CO$_3$ (concentration=0.1 M) was heated at 120° C. with microwave irradiation for 1200 seconds. The organic layer was separated, concentrated and directly purified by reverse phase HPLC. After lyophilization, (S)-3-amino-N-(4-(3-aminopiperidin-1-yl)pyridin-3-yl)-6-(2-fluoro-4-methylphenyl) picolinamide was obtained (44%) as the TFA salt. LCMS (m/z): 421.2 (MH$^+$); LC R$_t$=2.23 min.

Alternatively, the free base and HCl salt of 3-amino-6-(2-fluorophenyl)-N-(4-(piperidin-1-yl)pyridin-3-yl)picolinamide could be obtained as described in Method 8.

The following compounds were prepared using Method 14. In some cases the anhydrous Suzuki conditions of method 12 (DMF as solvent with 10 equivalents of triethylamine) were used.

| ID | Structure | Name | MH+ | LC |
|---|---|---|---|---|
| 584 | 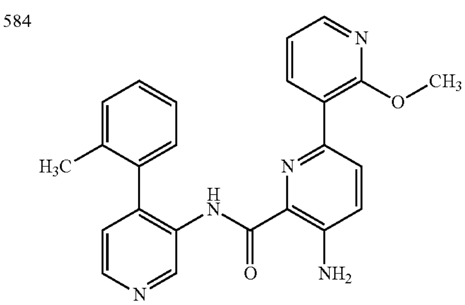 | 5-amino-2'-methoxy-[2,3']bipyridinyl-6-carboxylic acid (4-o-tolyl-pyridin-3-yl)-amide | 412.2 | 3.01 |
| 585 | 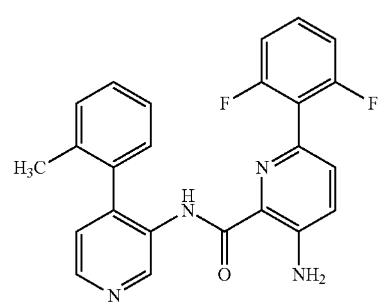 [SMILES: Cc1ccccc1-c1ccncc1NC(=O)c1nc(-c2c(F)cccc2F)ccc1N] | 3-amino-6-(2,6-difluoro-phenyl)-pyridine-2-carboxylic acid (4-o-tolyl-pyridin-3-yl)-amide | 417.1 | 3.24 |
| 586 | 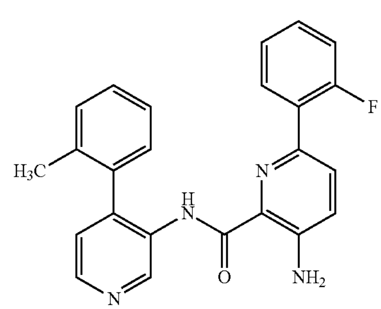 [SMILES: Cc1ccccc1-c1ccncc1NC(=O)c1nc(-c2ccccc2F)ccc1N] | 3-amino-6-(2-fluoro-phenyl)-pyridine-2-carboxylic acid (4-o-tolyl-pyridin-3-yl)-amide | 399.1 | 3.35 |

-continued

| ID | Structure | Name | MH+ | LC |
|---|---|---|---|---|
| 587 | 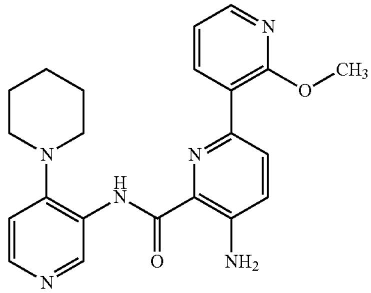 [SMILES: COc1ncccc1-c1ccc(N)c(C(=O)Nc2cnccc2N2CCCCC2)n1] | 5-amino-2'-methoxy-[2,3']bi-pyridinyl-6-carboxylic acid (3,4,5,6-tetrahydro-2H-[1,4']bipyridinyl-3'-yl)-amide | 405.2 | 2.83 |
| 588 | 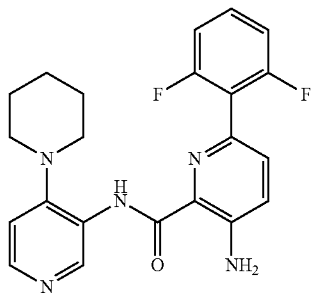 [SMILES: Nc1ccc(-c2c(F)cccc2F)nc1C(=O)Nc1cnccc1N1CCCCC1] | 3-amino-6-(2,6-difluoro-phenyl)-pyridine-2-carboxylic acid (3,4,5,6-tetrahydro-2H-[1,4']bipyridinyl-3,-yl)-amide | 410.2 | 3.14 |
| 589 | 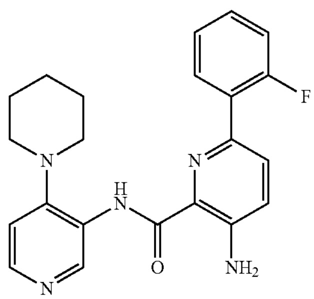 [SMILES: Nc1ccc(-c2ccccc2F)nc1C(=O)Nc1cnccc1N1CCCCC1] | 3-amino-6-(2-fluoro-phenyl)-pyridine-2-carboxylic acid (3,4,5,6-tetrahydro-2H-[1,4']bipyridinyl-3'-yl)-amide | 392.2 | 3.22 |
| 590 | 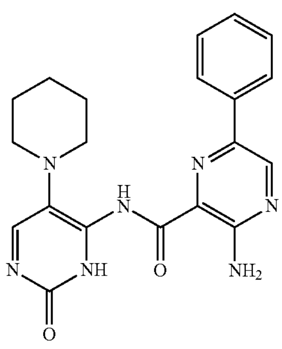 [SMILES: Nc1ncc(-c2ccccc2)nc1C(=O)Nc1[nH]c(=O)ncc1N1CCCCC1] | 3-amino-6-phenyl-pyrazine-2-carboxylic acid (2-oxo-5-piperidin-1-yl-2,3-dihydro-pyrimidin-4-yl)-amide | 392.1 | 2.95 |
| 591 | 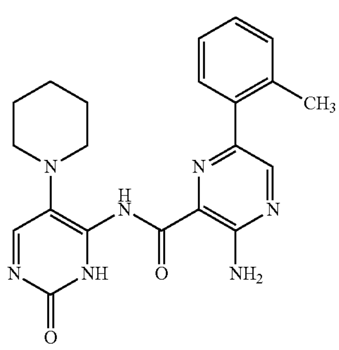 [SMILES: Cc1ccccc1-c1cnc(N)c(C(=O)Nc2[nH]c(=O)ncc2N2CCCCC2)n1] | 3-amino-6-o-tolyl-pyrazine-2-carboxylic acid (2-oxo-5-piperidin-1-yl-2,3-dihydro-pyrimidin-4-yl)-amide | 406.2 | 3.12 |

| ID | Structure | Name | MH+ | LC |
|---|---|---|---|---|
| 592 | 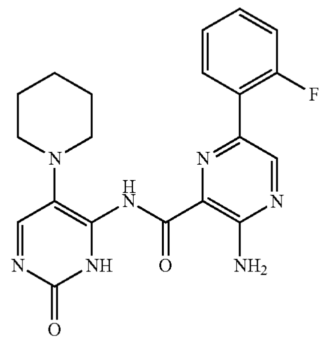 [SMILES: Nc1ncc(-c2ccccc2F)nc1C(=O)Nc1[nH]c(=O)ncc1N1CCCCC1] | 3-amino-6-(2-fluoro-phenyl)-pyrazine-2-carboxylic acid (2-oxo-5-piperidin-1-yl-2,3-dihydro-pyrimidin-4-yl)-amide | 410.1 | 3.01 |
| 593 | 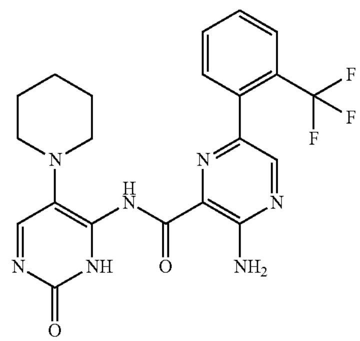 [SMILES: Nc1ncc(-c2ccccc2C(F)(F)F)nc1C(=O)Nc1[nH]c(=O)ncc1N1CCCCC1] | 3-amino-6-(2-trifluoromethyl-phenyl)-pyrazine-2-carboxylic acid (2-oxo-5-piperidin-1-yl-2,3-dihydro-pyrimidin-4-yl)-amide | 460.1 | 3.21 |
| 594 | 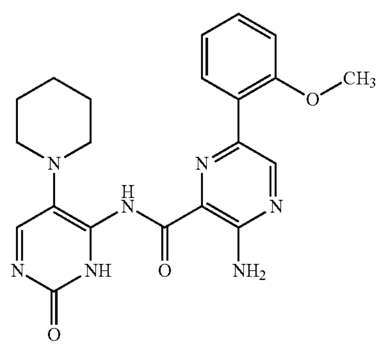 [SMILES: COc1ccccc1-c1cnc(N)c(C(=O)Nc2[nH]c(=O)ncc2N2CCCCC2)n1] | 3-amino-6-(2-methoxy-phenyl)-pyrazine-2-carboxylic acid (2-oxo-5-piperidin-1-yl-2,3-dihydro-pyrimidin-4-yl)-amide | 422.1 | 3 |
| 595 | 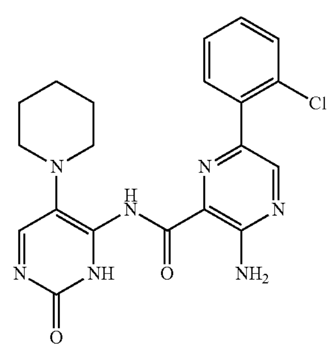 [SMILES: Nc1ncc(-c2ccccc2Cl)nc1C(=O)Nc1[nH]c(=O)ncc1N1CCCCC1] | 3-amino-6-(2-chloro-phenyl)-pyrazine-2-carboxylic acid (2-oxo-5-piperidin-1-yl-2,3-dihydro-pyrimidin-4-yl)-amide | 426.1 | 3.12 |

-continued

| ID | Structure | Name | MH+ | LC |
|---|---|---|---|---|
| 596 | 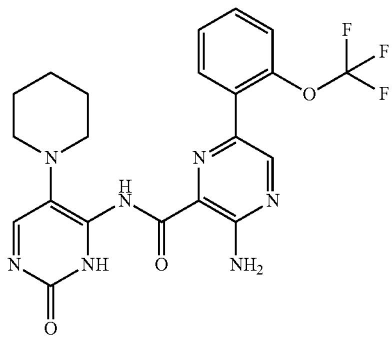 [SMILES: Nc1ncc(-c2ccccc2OC(F)(F)F)nc1C(=O)Nc1[nH]c(=O)ncc1N1CCCCC1] | 3-amino-6-(2-trifluoromethoxy-phenyl)-pyrazine-2-carboxylic acid (2-oxo-5-piperidin-1-yl-2,3-dihydro-pyrimidin-4-yl)-amide | 476.1 | 3.34 |

Method 15

Example 597

Synthesis of 3-amino-6-bromo-N-(4-(3-(1-methylpiperidin-4-ylamino) piperidin-1-yl)pyridin-3-yl)pyrazine-2-carboxamide

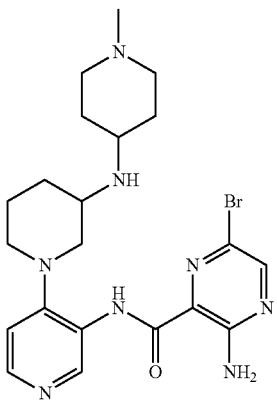 [SMILES: CN1CCC(NC2CCCN(c3ccncc3NC(=O)c3nc(Br)cnc3N)C2)CC1]

To a solution of 3-amino-N-(4-(3-aminopiperidin-1-yl)pyridin-3-yl)-6-bromopyrazine-2-carboxamide in $CH_2Cl_2$ at room temperature was added 1-methylpiperidin-4-one (1.5 eq) followed by sodium triacetoxyborohydride (5.0 eq). The reaction was stirred at room temperature for 12 hours, concentrated, purified by reverse phase HPLC and lyophilized to provide 3-amino-6-bromo-N-(4-(3-(1-methylpiperidin-4-ylamino)piperidin-1-yl)pyridin-3-yl)pyrazine-2-carboxamide, (66%). LCMS (m/z): 489.2 (MH$^+$).

Following Method 15, the following compounds were prepared.

| ID | Structure | Name | MH+ | LC |
|---|---|---|---|---|
| 598 | 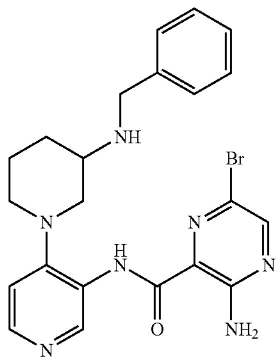 [SMILES: Nc1ncc(Br)nc1C(=O)Nc1cnccc1N1CCCC(NCc2ccccc2)C1] | 3-amino-6-bromo-pyrazine-2-carboxylic acid (3-benzylamino-3,4,5,6-tetrahydro-2H-[1,4']bipyridinyl-3'-yl)-amide | 482.1 | 2.31 |

-continued

| ID | Structure | Name | MH+ | LC |
|---|---|---|---|---|
| 599 | 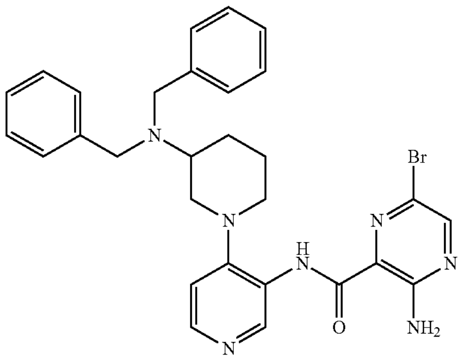 [SMILES: Nc1ncc(Br)nc1C(=O)Nc1cnccc1N1CCCC(N(Cc2ccccc2)Cc2ccccc2)C1] | 3-amino-6-bromo-pyrazine-2-carboxylic acid (3-dibenzylamino 3,4,5,6-tetrahydro-2H-[1,4']bi-pyridinyl-3'-yl)-amide | 572.2 | 2.42 |
| 600 | 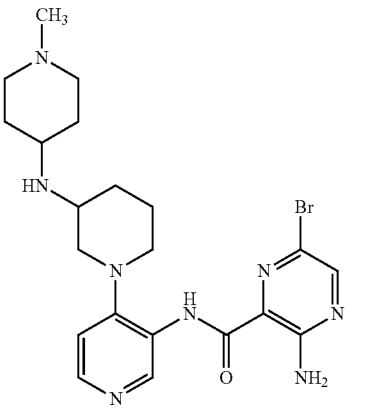 [SMILES: CN1CCC(NC2CCCN(c3ccncc3NC(=O)c3nc(Br)cnc3N)C2)CC1] | 3-amino-6-bromo-pyrazine-2-carboxylic acid [3-(1-methyl-piperidin-4-ylamino)-3,4,5,6-tetra-hydro-2H-[1,4']bipyridinyl-3'-yl]-amide | 489.2 | 1.29 |

Synthesis of trans (+/−)-Benzyl 3-(tert-butoxycarbonylamino)-4-hydroxypiperidine-1-carboxylate

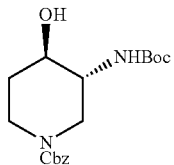 [SMILES: CC(C)(C)OC(=O)N[C@@H]1CN(C(=O)OCc2ccccc2)CC[C@H]1O]

Synthesis of trans (+/−)-Benzyl 4-(tert-butoxycarbonylamino)-3-hydroxypiperidine-1-carboxylate

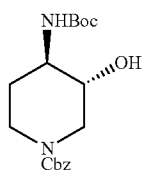 [SMILES: CC(C)(C)OC(=O)N[C@@H]1CCN(C(=O)OCc2ccccc2)C[C@H]1O]

A solution of (+/−) benzyl 7-oxa-3-azabicyclo[4.1.0]heptane-3-carboxylate (1.0 equiv.) in saturated ammonium hydroxide aqueous solution and ethanol (1:1, 0.05 M solution) in a sealed steel bomb was heated to 70° C. for 5 h. After all volatile materials were removed by $N_2$ gas stream, ethyl acetate and water were added for work-up. The crude regioisomeric mixture, (+/−) benzyl 3-amino-4-hydroxypiperidine-1-carboxylate and (+/−) benzyl 4-amino-3-hydroxypiperidine-1-carboxylate was reacted with $Boc_2O$ (1.0 equiv.) and triethylamine (1.0 equiv.) in dichloromethane (0.1 M solution). After stirred for 2 h at room temperature, the reaction mixture was extracted with dichloromethane. The polar (+/−)-benzyl 3-(tert-butoxycarbonylamino)-4-hydroxypiperidine-1-carboxylate and nonpolar (+/−)-benzyl 4-(tert-butoxycarbonylamino)-3-hydroxypiperidine-1-carboxylate were obtained by flash column chromatography (20% to 40% EtOAc in hexanes, 28% and 51% each). LCMS (m/z): 351.1 (MH+), $R_t$=0.81 min, LCMS (m/z): 351.1 (MH+), $R_t$=0.83 min.

The enantiomerically pure (3S,4S)-benzyl 3-(tert-butoxycarbonylamino)-4-hydroxypiperidine-1-carboxylate and (3R,4R)-benzyl 3-(tert-butoxycarbonylamino)-4-hydroxypiperidine-1-carboxylate were resolved by chiral HPLC (For analysis $R_t$=6.8 min and 9.1 min respectively; n-heptane:ethanol=70:30 (v:v), Chiralpak AD-H prep 250×4.6 mm at 1 mL/min. For preparative separation, n-heptane:ethanol=80:20 (v:v), Chiralpak AS 50×500 mm at 90 mL/min).

Method 16

Synthesis of (+/−)-Benzyl 3-(tert-butoxycarbonylamino)-4-(tert-butyldimethylsilyloxy)piperidine-1-carboxylate

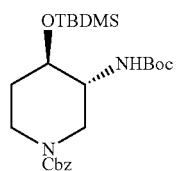 [SMILES: CC(C)(C)OC(=O)N[C@@H]1CN(C(=O)OCc2ccccc2)CC[C@H]1O[Si](C)(C)C(C)(C)C]

To a solution of (+/−)-benzyl 3-(tert-butoxycarbonylamino)-4-hydroxypiperidine-1-carboxylate (1.0 equiv.) in dichloromethane (0.1 M solution) was added imidazole (1.1 equiv.), DMAP (0.1 equiv.), and TBDMSCl (1.1 equiv.) sequentially The reaction mixture was stirred at room temperature for 20 h. After worked up with dichloromethane, the crude (+/−)-benzyl 3-(tert-butoxycarbonylamino)-4-(tert-butyldimethylsilyloxy)piperidine-1-carboxylate was purified by silica column chromatography (10% to 20% EtOAc in hexanes, 76%). LCMS (m/z): 365.2.

Synthesis of (3R,4R)-benzyl 3-(tert-butoxycarbonylamino)-4-(tert-butyldimethylsilyloxy)piperidine-1-carboxylate

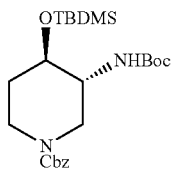 [SMILES: CC(C)(C)OC(=O)N[C@@H]1CN(C(=O)OCc2ccccc2)CC[C@H]1O[Si](C)(C)C(C)(C)C]

Following Method 16, (3R,4R)-benzyl 3-(tert-butoxycarbonylamino)-4-hydroxypiperidine-1-carboxylate was reacted with TBDMSCl, imidazole and DMAP yielding (3R,4R)-benzyl 3-(tert-butoxycarbonylamino)-4-(tert-butyldimethylsilyloxy)-piperidine-1-carboxylate. LCMS (m/z): 365.2 (MH$^+$); LC R$_t$=6.05 min.

Synthesis of (3S,4S)-benzyl 3-(tert-butoxycarbonylamino)-4-(tert-butyldimethylsilyloxy)piperidine-1-carboxylate

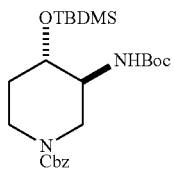 [SMILES: CC(C)(C)OC(=O)N[C@H]1CN(C(=O)OCc2ccccc2)CC[C@@H]1O[Si](C)(C)C(C)(C)C]

Following Method 16, (3S,4S)-benzyl 3-(tert-butoxycarbonylamino)-4-hydroxypiperidine-1-carboxylate was reacted with TBDMSCl, imidazole and DMAP yielding (3S,4S)-benzyl 3-(tert-butoxycarbonylamino)-4-(tert-butyldimethylsilyloxy)-piperidine-1-carboxylate. LCMS (m/z): 365.2 (MH$^+$); LC R$_t$=6.05 min.

Synthesis of (+/−)-Benzyl 4-(tert-butoxycarbonylamino)-3-(tert-butyldimethylsilyloxy)piperidine-1-carboxylate

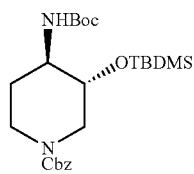 [SMILES: CC(C)(C)OC(=O)N[C@@H]1CCN(C(=O)OCc2ccccc2)C[C@H]1O[Si](C)(C)C(C)(C)C]

Following Method 16, (+/−)-benzyl 4-(tert-butoxycarbonylamino)-3-hydroxypiperidine-1-carboxylate was reacted with TBDMSCl, imidazole and DMAP yielding (+/−)-benzyl 4-(tert-butoxycarbonylamino)-3-(tert-butyldimethylsilyloxy)-piperidine-1-carboxylate, (81%). LCMS (m/z): 365.2 (MH$^+$); LC R$_t$=6.05 min.

Synthesis of (3R,4R)-Benzyl 3-(tert-butoxycarbonylamino)-4-fluoropiperidine-1-carboxylate and (3S,4S)-Benzyl 3-(tert-butoxycarbonylamino)-4-fluoropiperidine-1-carboxylate

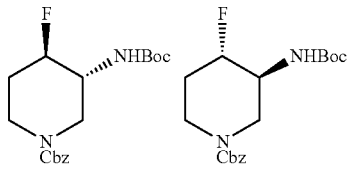 [SMILES: CC(C)(C)OC(=O)N[C@@H]1CN(C(=O)OCc2ccccc2)CC[C@H]1F ; CC(C)(C)OC(=O)N[C@H]1CN(C(=O)OCc2ccccc2)CC[C@@H]1F]

To a solution of (+/−)-benzyl 3-(tert-butoxycarbonylamino)-4-hydroxypiperidine-1-carboxylate (1.0 equiv.) in dichloromethane (0.3 M solution) was added DAST at −78° C. The reaction mixture was slowly warmed up to room temperature for 15 h. After quenched with saturated sodium bicarbonate aqueous solution, ethyl acetate and water were added for work-up. The (+/−)-benzyl 3-(tert-butoxycarbonylamino)-4-fluoropiperidine-1-carboxylate was obtained by silica column chromatography (30% EtOAc in hexanes, 40%). LCMS (m/z): 253.1; LC R$_t$=4.08 min. The enantiomerically pure (3R,4R)-benzyl 3-(tert-butoxycarbonylamino)-4-fluoropiperidine-1-carboxylate and (3S,4S)-benzyl 3-(tert-butoxycarbonylamino)-4-fluoropiperidine-1-carboxylate were resolved by chiral HPLC (for analysis: R$_t$=9.4 min and 12.6 min respectively; n-heptane:isopropanol=90:10 (v:v), Chiralpak AS 250×4.6 mm at 1 mL/min. For preparative separation, n-heptane:isopropanol=90:10 (v:v), Chiralpak AS 50×500 mm at 90 mL/min).

Synthesis of trans-(+/−)-Benzyl 4-fluoro-3-hydroxypiperidine-1-carboxylate

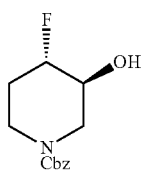 [SMILES: O=C(OCc1ccccc1)N1CC[C@H](F)[C@@H](O)C1]

A solution of (+/−)-benzyl 7-oxa-3-azabicyclo[4.1.0]heptane-3-carboxylate (1.0 equiv.) and Et$_3$N.3HF (1 equiv.) in a sealed glass flask were heated to 100° C. for 15 h. The reaction mixture was extracted with ethyl acetate, which was washed with water and brine. The organic phase was dried over anhydrous sodium sulfate and filtered. After volatile materials were removed, (+/−)-benzyl 4-fluoro-3-hydroxypiperidine-1-carboxylate was obtained by silica column chromatography (20% to 40% EtOAc in hexanes, 53%). LCMS (m/z): 254.1 (MH$^+$); LC R$_t$=2.86 min.

Synthesis of trans (+/−)-Benzyl 3-(1,3-dioxoisoindolin-2-yl)-4-fluoropiperidine-1-carboxylate

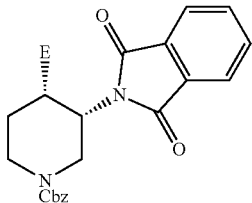

To a solution of triphenylphosphine (3.0 equiv.) in toluene (0.25 M solution) was added DEAD (3.0 equiv.) at room temperature, which was stirred for 15 min. Then, (+/−)-benzyl 4-fluoro-3-hydroxypiperidine-1-carboxylate (1.0 equiv.) was added to the reaction mixture. After being stirred for 10 min, phthalimide (3.0 equiv.) was added and the reaction mixture was stirred for 15 h. The reaction mixture was extracted with ethyl acetate, which was washed with water and brine. The organic phase was dried over anhydrous sodium sulfate and filtered. After volatile materials were removed, (+/−)-benzyl 3-(1,3-dioxoisoindolin-2-yl)-4-fluoropiperidine-1-carboxylate was obtained by silica column chromatography (10% to 20% EtOAc in hexanes, 20%). LCMS (m/z): 383.0 (MH$^+$), R$_f$=1.0 min.

Synthesis of (+/−)-Benzyl 3-(tert-butoxycarbonylamino)-4-oxopiperidine-1-carboxylate

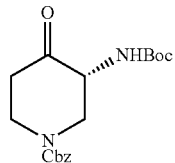 [SMILES: CC(C)(C)OC(=O)N[C@@H]1CN(C(=O)OCc2ccccc2)CCC1=O]

To a solution of (+/−)-benzyl 3-(tert-butoxycarbonylamino)-4-hydroxypiperidine-1-carboxylate in dichloromethane (0.1 M solution) was added Dess-Martin periodinane (1.5 equiv.). The reaction mixture was stirred at room temperature for 16 h. Then, the saturated NaHCO$_3$ and 0.1 N Na$_2$S$_2$O$_3$ aqueous solutions were added to the reaction mixture, which was stirred for 30 min and worked up with ethyl acetate. The crude benzyl 3-(tert-butoxycarbonylamino)-4-oxopiperidine-1-carboxylate was purified by flash chromatography (30% EtOAc in hexanes, 70%). LCMS (m/z): 249.2 (MH$^+$); LC R$_f$=3.98 min. $^1$H NMR (CDCl$_3$): 1.41 (1H, s), 2.1-2.59 (1H, m), 2.73 (1H, m), 3.09 (1H, m), 4.30 (1H, m), 4.52 (1H, m), 4.90 (1H, m), 5.19 (2H, m), 5.45 (1H, m), 7.39 (5H, m).

Synthesis of (+/−)-Benzyl 3-(tert-butoxycarbonylamino)-4,4-difluoropiperidine-1-carboxylate

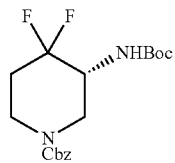 [SMILES: CC(C)(C)OC(=O)N[C@@H]1CN(C(=O)OCc2ccccc2)CCC1(F)F]

To a solution of (+/−)-benzyl 3-(tert-butoxycarbonylamino)-4-oxopiperidine-1-carboxylate in dichloromethane (0.3 M solution) was added DAST (3.0 equiv.). The reaction mixture was stirred at room temperature for 20 h. After quenched with saturated NaHCO$_3$ aqueous solution until no bubbling, the reaction mixture was extracted with CH$_2$Cl$_2$. The crude (+/−)-benzyl 3-(tert-butoxycarbonylamino)-4,4-difluoropiperidine-1-carboxylate was purified by flash chromatography (10% to 40% EtOAc in hexanes, 35%). LCMS (m/z): 271.0 (MH$^+$), LC R$_f$=4.2 min. $^1$H NMR (CDCl$_3$): 1.26 (9H, s), 1.90 (1H, m), 2.11 (1H, m), 2.98 (1H, t, J=11.2 Hz), 3.20 (1H, t, J=11.6), 4.00 (1H, m), 4.13 (1H, m), 4.76 (1H, m), 5.11 (1H, m), 7.36 (1H, m).

Method 17

Synthesis of cis-(+/−)-2-(4-fluoropiperidin-3-yl)isoindoline-1,3-dione

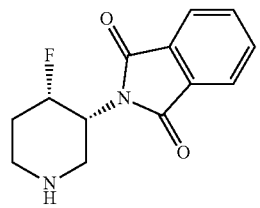 [SMILES: O=C1c2ccccc2C(=O)N1[C@@H]1CNCC[C@@H]1F]

To a solution of (+/−)-benzyl 3-(1,3-dioxoisoindolin-2-yl)-4-fluoropiperidine-1-carboxylate (1.0 equiv.) in ethanol and ethyl acetate (1:1, 0.2 M solution) was added Pd/C (20 wt %) under N$_2$ atmosphere. The reaction mixture was flushed with H$_2$ gas, equipped with H$_2$ gas balloon, and stirred for 16 h at room temperature. The reaction mixture was filtered through Celite® Pad and the filtrate was dried in vacuo. The crude (+/−)-2-(4-fluoropiperidin-3-yl)isoindoline-1,3-dione was used for the next step without further purification (>99%). LCMS (m/z): 249.1 (MH$^+$), R$_f$=0.49 min.

Synthesis of trans-(+/−)-tert-Butyl 4-fluoropiperidin-3-ylcarbamate

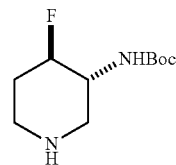 [SMILES: CC(C)(C)OC(=O)N[C@@H]1CNCC[C@H]1F]

Method 17 was followed using (+/−)trans-benzyl 3-(tert-butoxycarbonylamino)-4-fluoropiperidine-1-carboxylate (1.0 equiv.) yielding crude (+/−)-trans tert-butyl 4-fluoropiperidin-3-ylcarbamate (93%). LCMS (m/z): 219.2 (MH$^+$), LC R$_f$=0.45 min.

Synthesis of tert-butyl (3R,4R)-4-fluoropiperidin-3-ylcarbamate

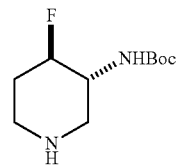 [SMILES: CC(C)(C)OC(=O)N[C@@H]1CNCC[C@H]1F]

Method 17 was followed using (3R,4R)-benzyl 3-(tert-butoxycarbonylamino)-4-fluoropiperidine-1-carboxylate (1.0 equiv.) yielding crude (+/−)-tert-butyl 4-fluoropiperidin-3-ylcarbamate (93%). LCMS (m/z): 219.2 (MH$^+$), LC R$_t$=0.45 min.

Synthesis of tert-butyl (3S,4S)-4-fluoropiperidin-3-ylcarbamate

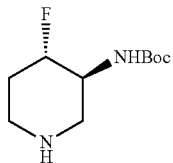 [SMILES: CC(C)(C)OC(=O)N[C@H]1CNCC[C@@H]1F]

Method 17 was followed using (3S,4S)-benzyl 3-(tert-butoxycarbonylamino)-4-fluoropiperidine-1-carboxylate (1.0 equiv.) yielding crude (+/−)-tert-butyl 4-fluoropiperidin-3-ylcarbamate (93%). LCMS (m/z): 219.2 (MH$^+$), LC R$_t$=0.45 min.

Synthesis of trans-(+/−)-Butyl 4-(tert-butyldimethylsilyloxy)piperidin-3-ylcarbamate

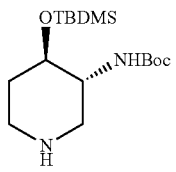 [SMILES: CC(C)(C)OC(=O)N[C@@H]1CNCC[C@H]1O[Si](C)(C)C(C)(C)C]

Method 17 was followed using (+/−)-benzyl 3-(tert-butoxycarbonylamino)-4-(tert-butyldimethylsilyloxy)piperidine-1-carboxylate (1.0 equiv.) yielding crude (+/−)-butyl 4-(tert-butyldimethylsilyloxy)piperidin-3-ylcarbamate (>99%). LCMS (m/z): 331.3 (MH$^+$).

Synthesis of tert-butyl (3R,4R)-4-(tert-butyldimethylsilyloxy)piperidin-3-ylcarbamate

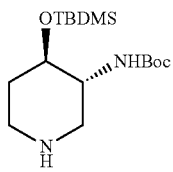 [SMILES: CC(C)(C)OC(=O)N[C@@H]1CNCC[C@H]1O[Si](C)(C)C(C)(C)C]

Method 17 was followed using (3R,4R)-benzyl 3-(tert-butoxycarbonylamino)-4-(tert-butyldimethylsilyloxy)piperidine-1-carboxylate (1.0 equiv.) yielding crude tert-butyl (3R,4R)-4-(tert-butyldimethylsilyloxy)piperidin-3-ylcarbamate (>99%). LCMS (m/z): 331.3 (MH$^+$).

Synthesis of tert-butyl (3R,4R)-4-(tert-butyldimethylsilyloxy)piperidin-3-ylcarbamate

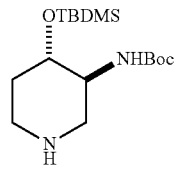 [SMILES: CC(C)(C)OC(=O)N[C@H]1CNCC[C@@H]1O[Si](C)(C)C(C)(C)C]

Method 17 was followed using (3S,4S)-benzyl 3-(tert-butoxycarbonylamino)-4-(tert-butyldimethylsilyloxy)piperidine-1-carboxylate (1.0 equiv.) yielding crude tert-butyl (3S,4S)-4-(tert-butyldimethylsilyloxy)piperidin-3-ylcarbamate (>99%). LCMS (m/z): 331.3 (MH$^+$).

Synthesis of trans-(+/−)-tert-Butyl 3-(tert-butyldimethylsilyloxy)piperidin-4-ylcarbamate

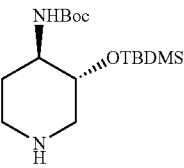 [SMILES: CC(C)(C)OC(=O)N[C@@H]1CCNC[C@H]1O[Si](C)(C)C(C)(C)C]

Method 17 was followed using (+/−)-benzyl 4-(tert-butoxycarbonylamino)-3-hydroxypiperidine-1-carboxylate (1.0 equiv.) yielding (+/−)-tert-butyl 3-(tert-butyldimethylsilyloxy)piperidin-4-ylcarbamate (>99%). LCMS (m/z): 331.2 (MH$^+$).

Synthesis of (+/−)-tert-Butyl 4,4-difluoropiperidin-3-ylcarbamate

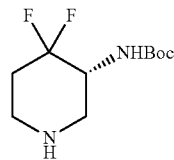 [SMILES: CC(C)(C)OC(=O)N[C@@H]1CNCCC1(F)F]

Method 17 was followed using (+/−)-benzyl 3-(tert-butoxycarbonylamino)-4,4-difluoropiperidine-1-carboxylate (1.0 equiv.) yielding crude (+/−)-tert-butyl 4,4-difluoropiperidin-3-ylcarbamate, (>99%). LCMS (m/z): 237.0 (MH$^+$).

Synthesis of trans-(+/−)-tert-Butyl 4-(tert-butyldimethylsilyloxy)-1-(3-nitropyridin-4-yl)piperidin-3-ylcarbamate

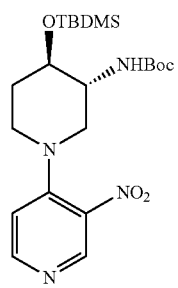 [SMILES: CC(C)(C)OC(=O)N[C@@H]1CN(c2ccncc2[N+](=O)[O-])CC[C@H]1O[Si](C)(C)C(C)(C)C]

Method 1 of Example 1 was followed using 1 eq each of 4-chloro-3-nitropyidine, trans-(+/−)-butyl 4-(tert-butyldimethylsilyloxy)piperidin-3-ylcarbamate and triethylamine in DMF yielding (+/−)-tert-butyl 4-(tert-butyldimethylsilyloxy)-1-(3-nitropyridin-4-yl)piperidin-3-ylcarbamate, (98%). LCMS (m/z): 453.3 (MH$^+$); LC R$_t$=4.01 min.

Synthesis of tert-butyl (3R,4R)-4-(tert-butyldimethylsilyloxy)-1-(3-nitropyridin-4-yl)piperidin-3-ylcarbamate

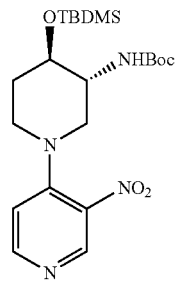 [SMILES: CC(C)(C)OC(=O)N[C@@H]1CN(c2ccncc2[N+](=O)[O-])CC[C@H]1O[Si](C)(C)C(C)(C)C]

Method 1 of Example 1 was followed using 1 eq each of 4-chloro-3-nitropyidine, tert-butyl (3R,4R)-4-(tert-butyldimethylsilyloxy)piperidin-3-ylcarbamate and triethylamine in DMF yielding tert-butyl (3R,4R)-4-(tert-butyldimethylsilyloxy)-1-(3-nitropyridin-4-yl)piperidin-3-ylcarbamate (98%). LCMS (m/z): 453.3 (MH$^+$); LC R$_t$=4.01 min.

Synthesis of tert-butyl (3S,4S)-4-(tert-butyldimethylsilyloxy)-1-(3-nitropyridin-4-yl)piperidin-3-ylcarbamate

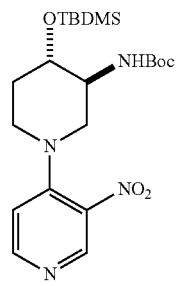 [SMILES: CC(C)(C)OC(=O)N[C@H]1CN(c2ccncc2[N+](=O)[O-])CC[C@@H]1O[Si](C)(C)C(C)(C)C]

Method 1 of Example 1 was followed using 1 eq each of 4-chloro-3-nitropyidine, tert-butyl (3S,4S)-4-(tert-butyldimethylsilyloxy)piperidin-3-ylcarbamate and triethylamine in DMF yielding tert-butyl (3S,4S)-4-(tert-butyldimethylsilyloxy)-1-(3-nitropyridin-4-yl)piperidin-3-ylcarbamate (98%). LCMS (m/z): 453.3 (MH$^+$); LC R$_t$=4.01 min.

Synthesis of trans-(+/−)-tert-butyl 3-(tert-butyldimethylsilyloxy)-1-(3-nitropyridin-4-yl)piperidin-4-ylcarbamate

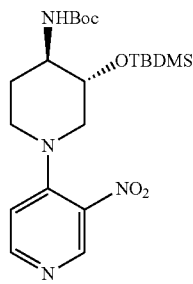 [SMILES: CC(C)(C)OC(=O)N[C@@H]1CCN(c2ccncc2[N+](=O)[O-])C[C@H]1O[Si](C)(C)C(C)(C)C]

Method 1 of Example 1 was followed using 1 eq each of 4-chloro-3-nitropyidine, (+/−)-tert-butyl 3-(tert-butyldimethylsilyloxy)piperidin-4-ylcarbamate and triethylamine in ethanol yielding (+/−)-tert-butyl 3-(tert-butyldimethylsilyloxy)-1-(3-nitropyridin-4-yl)piperidin-4-ylcarbamate, (75%). LCMS (m/z): 453.2 (MH$^+$); LC R$_t$=3.46 min.

Synthesis of trans-(+/−)-tert-Butyl 4-fluoro-1-(3-nitropyridin-4-yl)piperidin-3-ylcarbamate

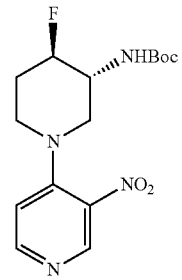 [SMILES: CC(C)(C)OC(=O)N[C@@H]1CN(c2ccncc2[N+](=O)[O-])CC[C@H]1F]

Method 1 of Example 1 was followed using 1 eq each of 4-chloro-3-nitropyidine, (+/−)-tert-butyl 4-fluoropiperidin-3-ylcarbamate and triethylamine in ethanol yielding (+/−)-tert-butyl 4-fluoro-1-(3-nitropyridin-4-yl)piperidin-3-ylcarbamate, (91%). LCMS (m/z): 341.0 (MH$^+$); LC R$_t$=2.37 min.

Synthesis of tert-butyl (3R,4R)-4-fluoro-1-(3-nitropyridin-4-yl)piperidin-3-ylcarbamate

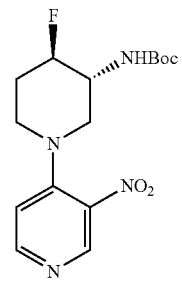 [SMILES: CC(C)(C)OC(=O)N[C@@H]1CN(c2ccncc2[N+](=O)[O-])CC[C@H]1F]

Method 1 of Example 1 was followed using 1 eq each of 4-chloro-3-nitropyidine, tert-butyl (3R,4R)-4-fluoropiperidin-3-ylcarbamate and triethylamine in ethanol yielding tert-butyl (3R,4R)-4-fluoro-1-(3-nitropyridin-4-yl)piperidin-3-ylcarbamate, (91%). LCMS (m/z): 341.0 (MH$^+$); LC R$_t$=2.37 min.

Synthesis of tert-butyl (3S,4S)-4-fluoro-1-(3-nitropyridin-4-yl)piperidin-3-ylcarbamate

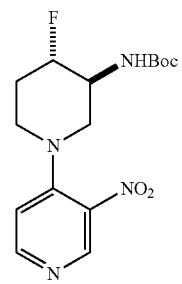

Method 1 of Example 1 was followed using 1 eq each of 4-chloro-3-nitropyidine, tert-butyl (3S,4S)-4-fluoropiperidin-3-ylcarbamate and triethylamine in ethanol yielding tert-butyl (3S,4S)-4-fluoro-1-(3-nitropyridin-4-yl)piperidin-3-ylcarbamate, (91%). LCMS (m/z): 341.0 (MH⁺); LC R$_t$=2.37 min.

Synthesis of (+/−)-tert-Butyl 4,4-difluoro-1-(3-nitropyridin-4-yl)piperidin-3-ylcarbamate

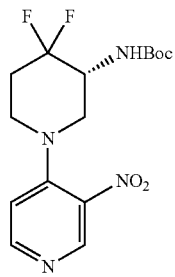 [SMILES: CC(C)(C)OC(=O)N[C@@H]1CN(c2ccncc2[N+](=O)[O-])CCC1(F)F]

Method 1 of Example 1 was followed using 1 eq each of 4-chloro-3-nitropyidine, (+/−)-tert-butyl 4,4-difluoropiperidin-3-ylcarbamate and triethylamine in ethanol yielding (+/−)-tert-butyl 4,4-difluoro-1-(3-nitropyridin-4-yl)piperidin-3-ylcarbamate, (91%). LCMS (m/z): 359.1 (MH⁺).

Synthesis of cis-(+/−)-2-(4-fluoro-1-(3-nitropyridin-4-yl)piperidin-3-yl)isoindoline-1,3-dione

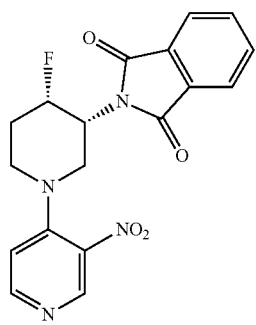 [SMILES: O=C1c2ccccc2C(=O)N1[C@@H]1CN(c2ccncc2[N+](=O)[O-])CC[C@@H]1F]

Method 1 of Example 1 was followed using 1 eq each of 4-chloro-3-nitropyidine, (+/−)-2-(4-fluoropiperidin-3-yl)isoindoline-1,3-dione and triethylamine in DMF yielding (+/−)-2-(4-fluoro-1-(3-nitropyridin-4-yl)piperidin-3-yl)isoindoline-1,3-dione, (45%). LCMS (m/z): 371.1 (MH⁺); LC R$_t$=2.23 min.

Synthesis of trans-(+/−)-tert-Butyl 1-(3-aminopyridin-4-yl)-4-(tert-butyldimethylsilyloxy)piperidin-3-ylcarbamate

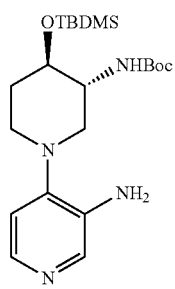 [SMILES: CC(C)(C)OC(=O)N[C@@H]1CN(c2ccncc2N)CC[C@H]1O[Si](C)(C)C(C)(C)C]

Following Method 2 of Example 49, (+/−)-tert-butyl 4-(tert-butyldimethylsilyloxy)-1-(3-nitropyridin-4-yl)piperidin-3-ylcarbamate in ethanol and ethyl acetate (1:1, 0.1 M solution) was reduced yielding (+/−)-tert-butyl 1-(3-aminopyridin-4-yl)-4-(tert-butyldimethylsilyloxy)piperidin-3-ylcarbamate, (>99%). LCMS (m/z): 423.2 (MH⁺); LC R$_t$=3.78 min.

Synthesis of tert-butyl (3R,4R)-1-(3-aminopyridin-4-yl)-4-(tert-butyldimethylsilyloxy)piperidin-3-ylcarbamate

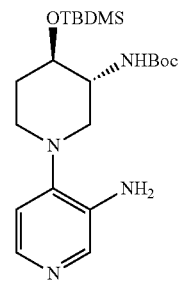 [SMILES: CC(C)(C)OC(=O)N[C@@H]1CN(c2ccncc2N)CC[C@H]1O[Si](C)(C)C(C)(C)C]

Following Method 2 of Example 49, tert-butyl (3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-(tert-butyldimethylsilyloxy)piperidin-3-ylcarbamate, (>99%). LCMS (m/z): 423.2 (MH⁺); LC R$_t$=3.78 min.

Synthesis of tert-butyl (3S,4S)-1-(3-aminopyridin-4-yl)-4-(tert-butyldimethylsilyloxy)piperidin-3-ylcarbamate

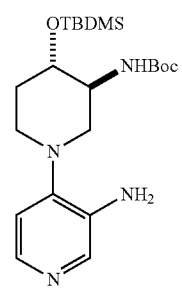

Following Method 2 of Example 49, tert-butyl (3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-(tert-butyldimethylsilyloxy)piperidin-3-ylcarbamate, (>99%). LCMS (m/z): 423.2 (MH⁺); LC R$_t$=3.78 min.

Synthesis of trans-(+/−)-tert-Butyl 1-(3-aminopyridin-4-yl)-3-(tert-butyldimethylsilyloxy)piperidin-4-ylcarbamate

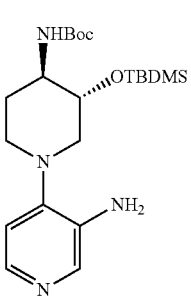 [SMILES: CC(C)(C)OC(=O)N[C@@H]1CCN(c2ccncc2N)C[C@H]1O[Si](C)(C)C(C)(C)C]

Following Method 2 of Example 49, (+/−)-tert-butyl 3-(tert-butyldimethylsilyloxy)-1-(3-nitropyridin-4-yl)piperidin-4-ylcarbamate in ethanol and ethyl acetate (1:1, 0.1 M solution) was reduced yielding (+/−)-tert-butyl 1-(3-aminopyridin-4-yl)-3-(tert-butyldimethylsilyloxy)piperidin-4-ylcarbamate, (>99%). LCMS (m/z): 423.3 (MH+); LC R$_t$=3.62 min.

Synthesis of trans-(+/−)-tert-butyl 1-(3-aminopyridin-4-yl)-4-fluoropiperidin-3-ylcarbamate

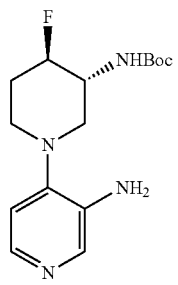 [SMILES: CC(C)(C)OC(=O)N[C@@H]1CN(c2ccncc2N)CC[C@H]1F]

Following Method 2 of Example 49, (+/−)-tert-butyl 4-fluoro-1-(3-nitropyridin-4-yl)piperidin-3-ylcarbamate in ethanol and ethyl acetate (1:1, 0.1 M solution) was reduced yielding (+/−)-tert-butyl 1-(3-aminopyridin-4-yl)-4-fluoropiperidin-3-ylcarbamate, (>99%). LCMS (m/z): 311.2 (MH+); LC R$_t$=2.14 min.

Synthesis of tert-butyl (3R,4R)-1-(3-aminopyridin-4-yl)-4-fluoropiperidin-3-ylcarbamate

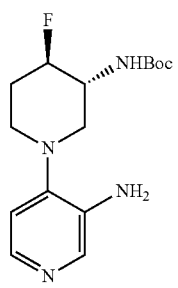 [SMILES: CC(C)(C)OC(=O)N[C@@H]1CN(c2ccncc2N)CC[C@H]1F]

Following Method 2 of Example 49, tert-butyl (3R,4R)-4-fluoro-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-fluoropiperidin-3-ylcarbamate, (>99%). LCMS (m/z): 311.2 (MH+); LC R$_t$=2.14 min.

Synthesis of tert-butyl (3S,4S)-1-(3-aminopyridin-4-yl)-4-fluoropiperidin-3-ylcarbamate

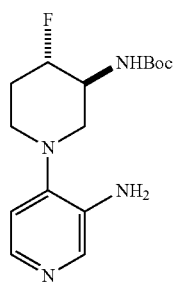 [SMILES: CC(C)(C)OC(=O)N[C@H]1CN(c2ccncc2N)CC[C@@H]1F]

Following Method 2 of Example 49, tert-butyl (3S,4S)-4-fluoro-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-fluoropiperidin-3-ylcarbamate, (>99%). LCMS (m/z): 311.2 (MH+); LC R$_t$=2.14 min.

Synthesis of (+/−)-tert-Butyl 1-(3-aminopyridin-4-yl)-4,4-difluoropiperidin-3-ylcarbamate

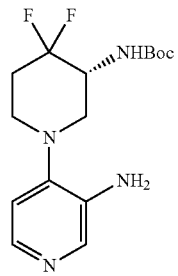 [SMILES: CC(C)(C)OC(=O)N[C@@H]1CN(c2ccncc2N)CCC1(F)F]

Following Method 2 of Example 49, (+/−)-tert-butyl 4,4-difluoro-1-(3-nitropyridin-4-yl)piperidin-3-ylcarbamate and triethylamine in ethanol and ethyl acetate (1:1, 0.1 M solution) was reduced yielding (+/−)-tert-butyl 1-(3-aminopyridin-4-yl)-4,4-difluoropiperidin-3-ylcarbamate, (>99%). LCMS (m/z): 329.1 (MH+).

Synthesis of cis-(+/−)-2-(1-(3-aminopyridin-4-yl)-4-fluoropiperidin-3-yl)isoindoline-1,3-dione

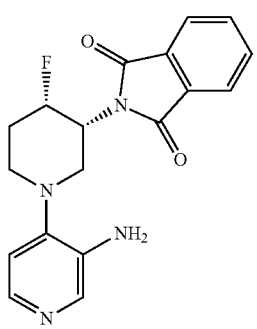 [SMILES: Nc1cnccc1N1CC[C@H](F)[C@H](N2C(=O)c3ccccc3C2=O)C1]

Following Method 2 of Example 49, (+/−)-2-(4-fluoro-1-(3-nitropyridin-4-yl)piperidin-3-yl)isoindoline-1,3-dione in ethanol and ethyl acetate (1:1, 0.1 M solution) was reduced yielding (+/−)-2-(1-(3-aminopyridin-4-yl)-4-fluoropiperidin-3-yl)isoindoline-1,3-dione, (87%). LCMS (m/z): 341.1 (MH+); LC R$_t$=2.23 min.

Method 18

Synthesis of 3-methylpiperidine-3-carboxylic acid

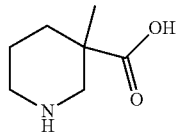

TFA was added to a solution of 1-(tert-butoxycarbonyl)-3-methylpiperidine-3-carboxylic acid (1 eq) in CH$_2$Cl$_2$ (0.5 M). After stirring for 3 h at rt the reaction mixture was concentrated in vacuo and azeotroped once with toluene to give 3-methylpiperidine-3-carboxylic acid (TFA salt). The crude product was used for the next step without further purification.

Method 19

Synthesis of 3-methyl-1-(3-nitropyridin-4-yl)piperidine-3-carboxylic acid

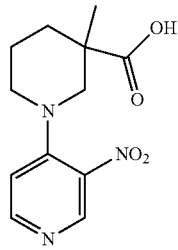 [SMILES: CC1(C(=O)O)CCCN(c2ccncc2[N+](=O)[O-])C1]

4-chloro-3-nitropyridine (1.1 eq) was added to a solution of 3-methylpiperidine-3-carboxylic acid (1 eq) and DIEA (3 eq) in iPrOH (0.1 M). The reaction mixture was heated in a 60° C. oil bath for 3 h then concentrated in vacuo. The crude residue was diluted with EtOAc and washed with 1.0 N NaOH. The combined aqueous washes were acidified to pH=4 with 1.0 N HCl and extracted with $CH_2Cl_2$. The combined organic phases were dried over anhydrous $MgSO_4$, filtered, and concentrated in vacuo to give 3-methyl-(3-nitropyridin-4-yl)piperidine-3-carboxylic acid. LC/MS (m/z): 266.2 ($MH^+$).

Synthesis of tert-butyl 3-methyl-1-(3-nitropyridin-4-yl)piperidin-3-ylcarbamate

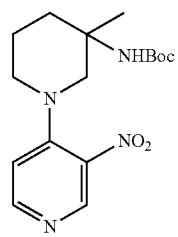 [SMILES: CC1(NC(=O)OC(C)(C)C)CCCN(c2ccncc2[N+](=O)[O-])C1]

Diphenylphosphoryl azide (1.2 eq) was added to a mixture of 3-methyl 1-(3-nitropyridin-4-yl)piperidine-3-carboxylic acid (1 eq) and anhydrous tBuOH (0.3 M), followed shortly by $Et_3N$ (2 eq). The reaction flask was fitted with an air-cooled reflux condenser and bubble vent, then heated in an 85° C. oil bath for 3 days. The crude mixture was diluted with EtOAc, washed with brine, then dried over anhydrous $MgSO_4$, filtered, and concentrated in vacuo. The crude residue was dissolved in $CH_2Cl_2$, loaded onto a $SiO_2$ column, and purified by flash chromatography (10-20-40% EtOAc in hexanes) to give tert-butyl 3-methyl-1-(3-nitropyridin-4-yl)piperidin-3-ylcarbamate. LC/MS (m/z): 337.2 ($MH^+$).

Synthesis of tert-butyl 1-(3-aminopyridin-4-yl)-3-methylpiperidin-3-ylcarbamate

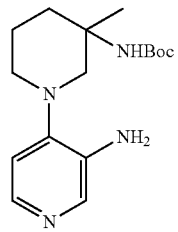

10% Palladium on carbon (0.1 eq) was added to a $N_2$-flushed solution of tert-butyl 3-methyl-1-(3-nitropyridin-4-yl)piperidin-3-ylcarbamate (1 eq) in MeOH (0.2 M). The reaction was purged with $H_2$ under atmospheric pressure for 16 h at it. The crude solids were filtered through a pad of Celite on a paper lined Buchner funnel, washed with EtOAc and MeOH, then concentrated in vacuo. The crude residue was dissolved in $CH_2Cl_2$, loaded onto a $SiO_2$ column, and purified by flash chromatography (1:2 EtOAc in hexanes+5% MeOH) to give tert-butyl 1-(3-aminopyridin-4-yl)-3-methylpiperidin-3-ylcarbamate. LC/MS (m/z): 307.2 ($MH^+$).

Synthesis of tert-butyl 3-(trifluoromethyl)-3-(trimethylsilyloxy)piperidine-1-carboxylate

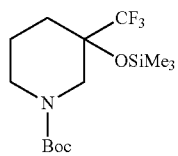

To an ice-bath cooled solution of tert-butyl 3-oxopiperidine-1-carboxylate (1 eq) in THF (0.4 M) was added trimethyl(trifluoromethyl)silane (1.2 eq) followed shortly by a 1.0M solution of TBAF in THF (0.05 eq). The reaction was warmed to it and stirred for 4 h, then concentrated in vacuo. The resulting residue was dissolved in EtOAc, washed with brine, then dried over anhydrous $MgSO_4$, filtered, and concentrated in vacuo to give tert-butyl 3-(trifluoromethyl)-3-(trimethylsilyloxy)piperidine-1-carboxylate, which was carried on crude and used without further purification.

Synthesis of tert-butyl 3-hydroxy-3-(trifluoromethyl)piperidine-1-carboxylate

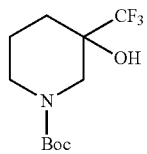 [SMILES: CC(C)(C)OC(=O)N1CCCC(O)(C(F)(F)F)C1]

A 1.0 M solution of TBAF in THF (1 eq) was added to a solution of tert-butyl 3-(trifluoromethyl)-3-(trimethylsilyloxy)piperidine-1-carboxylate (1 eq) in THF (0.2 M). After stirring for 16 h at rt the reaction mixture was concentrated in vacuo. The resulting residue was dissolved in EtOAc, washed with brine, then dried over anhydrous $MgSO_4$, filtered, and concentrated in vacuo. The crude residue was dissolved in $CH_2Cl_2$, loaded onto a $SiO_2$ column, and purified by flash chromatography to give tert-butyl 3-hydroxy-3-(trifluoromethyl)piperidine-1-carboxylate. $^{19}$F NMR (282 MHz, CDCl$_3$): δ −83.74 ppm; $^1$H NMR (300 MHz, CDCl$_3$): δ 4.04-4.16 (m, 2H), 2.72-3.01 (m, 2H), 1.50-2.04 (m, 4H), 1.47 (s, 9H).

Synthesis of 3-(trifluoromethyl)piperidin-3-ol

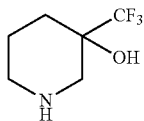

Method 18 was followed using tert-butyl 3-hydroxy-3-(trifluoromethyl)piperidine-1-carboxylate, yielding 3-(trifluoromethyl)piperidin-3-ol (TFA salt). The crude product was used for the next step without further purification.

Synthesis of 1-(3-nitropyridin-4-yl)-3-(trifluoromethyl)piperidin-3-ol

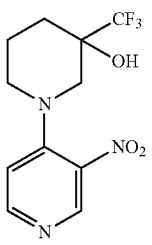 [SMILES: O=[N+]([O-])c1cnccc1N1CCCC(O)(C(F)(F)F)C1]

Method 19 was followed using 3-(trifluoromethyl)piperidin-3-ol, yielding 1-(3-nitropyridin-4-yl)-3-(trifluoromethyl)piperidin-3-ol. LC/MS (m/z): 292.0 (MH$^+$).

Synthesis of 1-(3-aminopyridin-4-yl)-3-(trifluoromethyl)piperidin-3-ol

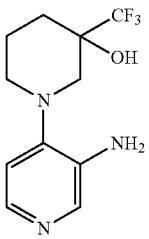

Method 2 of example 49 was followed using 1-(3-nitropyridin-4-yl)-3-(trifluoromethyl)piperidin-3-ol, yielding 1-(3-aminopyridin-4-yl)-3-(trifluoromethyl)piperidin-3-ol. LC/MS (m/z): 262.0 (MH$^+$).

Synthesis of tert-butyl (3S,5R)-5-(tert-butyldimethylsilyloxy)piperidin-3-ylcarbamate

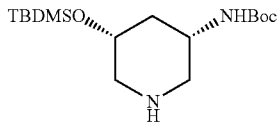 [SMILES: CC(C)(C)OC(=O)N[C@@H]1CNC[C@H](O[Si](C)(C)C(C)(C)C)C1]

tert-Butyl (3S,5R)-5-(tert-butyldimethylsilyloxy)piperidin-3-ylcarbamate was prepared according to the patent procedure as described by Y, Zhou; WO2005028467.

Synthesis of tert-butyl (3S,5R)-5-(tert-butyldimethylsilyloxy)-1-(3-nitropyridin-4-yl)piperidin-3-ylcarbamate

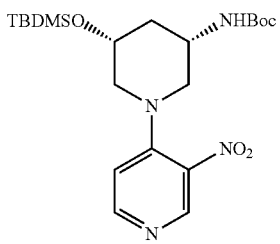

Method 19 was followed was followed using tert-Butyl (3S,5R)-5-(tert-butyldimethylsilyloxy)piperidin-3-ylcarbamate, yielding tert-butyl (3S,5R)-5-(tert-butyldimethylsilyloxy)-1-(3-nitropyridin-4-yl)piperidin-3-ylcarbamate. LC/MS (m/z): 453.2 (MH$^+$).

Synthesis of tert-butyl (3S,5R)-1-(3-aminopyridin-4-yl)-5-(tert-butyldimethylsilyloxy)piperidin-3-ylcarbamate

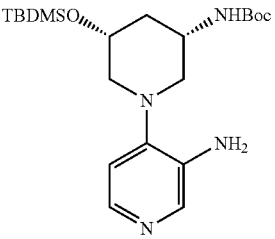 [SMILES: CC(C)(C)OC(=O)N[C@H]1C[C@@H](O[Si](C)(C)C(C)(C)C)CN(c2ccncc2[N+](=O)[O-])C1]

Method 2 was followed using tert-butyl (3S,5R)-5-(tert-butyldimethylsilyloxy)-1-(3-nitropyridin-4-yl)piperidin-3-ylcarbamate, yielding tert-butyl (3S,5R)-1-(3-aminopyridin-4-yl)-5-(tert-butyldimethylsilyloxy)piperidin-3-ylcarbamate. LC/MS (m/z): 423.2 (MH$^+$).

Synthesis of cis-(+/−)-1-(benzyloxycarbonyl)-5-(tert-butoxycarbonylamino)piperidine-3-carboxylic acid

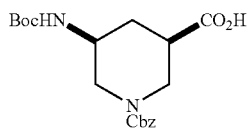 [SMILES: CC(C)(C)OC(=O)N[C@H]1C[C@@H](C(=O)O)CN(C(=O)OCc2ccccc2)C1]

To a solution of cis-(+/−)-5-(tert-butoxycarbonylamino)piperidine-3-carboxylic acid (1.0 eq.) in dichloromethane (0.2 M) was added DIEA (1.1 eq.), followed by N-(benzyloxycarbonyloxy)succinimide (1.0 eq.); the reaction was stirred at r.t. overnight. The solvent was removed under reduced pressure. To the crude was added EtOAc and 1N HCl. After extraction, the organic layer was washed with brine, dried and filtered, and concentrated to yield cis-(+/−)-1-(benzyloxycarbonyl)-5-(tert-butoxycarbonylamino)piperidine-3-carboxylic acid (99% yield) LCMS (m/z): 379.2 (MH+); LC R$_t$=3.55 min.

Synthesis of cis-(+/−)-benzyl 3,5-bis(tert-butoxycarbonylamino)piperidine-1-carboxylate

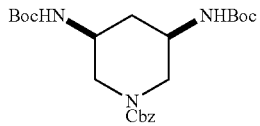 [SMILES: CC(C)(C)OC(=O)N[C@@H]1C[C@H](NC(=O)OC(C)(C)C)CN(C(=O)OCc2ccccc2)C1]

To a solution of cis-(+/−)-1-(benzyloxycarbonyl)-5-(tert-butoxycarbonylamino) piperidine-3-carboxylic acid (1.2 g, 3.17 mmol), DPPA (Diphenylphosphoryl azide, 1.04 g, 3.81 mmol) and DIEA (1.1 mL, 6.35 mmol) in t-BuOH (10 mL) was heated to 90° C. over night. The solvent was removed under reduced pressure. To the crude was added EtOAc (300 mL), the organic layer was washed with saturated NaHCO$_3$ (150 mL) and brine, dried and filtered, and concentrated to give the crude. The crude material was further purified by silica gel chromatography to yielding cis-(+/−)-benzyl 3,5-bis(tert-butoxycarbonylamino)piperidine-1-carboxylate, (23%). LCMS (m/z): 350(minus one Boc(MH+); LC R$_t$=4.40 min.

Synthesis of tert-butyl cis-(+/−)-piperidine-3,5-diyldicarbamate

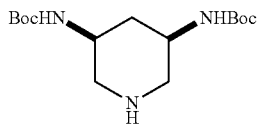 [SMILES: CC(C)(C)OC(=O)N[C@@H]1CNC[C@H](NC(=O)OC(C)(C)C)C1]

Method 17 was followed using cis-(+/−)-benzyl 3,5-bis(tert-butoxycarbonylamino)piperidine-1-carboxylate yielding tert-butyl cis-(+/−)-piperidine-3,5-diyldicarbamate, (% yield 99%). LCMS (m/z): 316.2 (MH+).

Synthesis of tert-butyl cis-(+/−)-1-(3-nitropyridin-4-yl)piperidine-3,5-diyldicarbamate

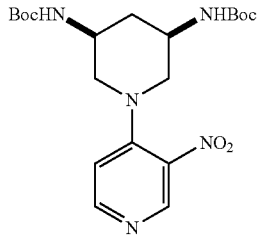 [SMILES: CC(C)(C)OC(=O)N[C@@H]1C[C@H](NC(=O)OC(C)(C)C)CN(c2ccncc2[N+](=O)[O-])C1]

Method 1 of Example 1 was followed using 1 equivalent each of 4-chloro-3-nitropyridine, tert-butyl cis-(+/−)-piperidine-3,5-diyldicarbamate and triethylamine in DMF yielding tert-butyl cis-(+/−)-1-(3-nitropyridin-4-yl)piperidine-3,5-diyldicarbamate, LCMS (m/z): 438.2 (MH+); LC R$_t$=2.95 min.

Synthesis of cis-tert-butyl (+/−)-1-(3-aminopyridin-4-yl)piperidine-3,5-diyldicarbamate

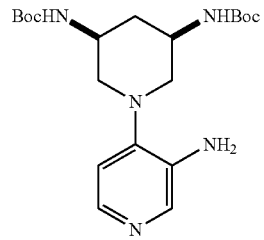

Following Method 2 of Example 49, cis-(+/−)-1-(3-nitropyridin-4-yl)piperidine-3,5-diyldicarbamate in ethanol was reduced yielding cis-tert-butyl (+/−)-1-(3-aminopyridin-4-yl)piperidine-3,5-diyldicarbamate, (78%). LCMS (m/z): 408.2 (MH+); LC R$_t$=2.63 min.

Synthesis of (S)-1-(3-nitropyridin-4-yl)piperidin-3-ol

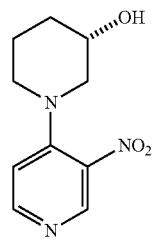 [SMILES: O=[N+]([O-])c1cnccc1N1CCC[C@H](O)C1]

Method 1 of Example 1 was followed using 1 equivalent each of 4-chloro-3-nitropyridine, (S)-3-hydroxypiperidine and triethylamine in DMF yielding (S)-1-(3-nitropyridin-4-yl)piperidin-3-ol, LCMS (m/z): 224.1 (MH+); LC R$_t$=1.06 min.

Synthesis of (R)-1-(3-nitropyridin-4-yl)piperidin-3-ol

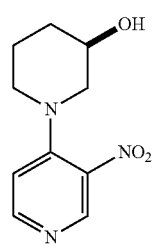 [SMILES: O=[N+]([O-])c1cnccc1N1CCC[C@@H](O)C1]

Method 1 of Example 1 was followed using 1 equivalent each of 4-chloro-3-nitropyridine, (R)-3-hydroxypiperidine and triethylamine in DMF yielding (R)-1-(3-nitropyridin-4-yl)piperidin-3-ol, LCMS (m/z): 224.1 (MH+); LC R$_t$=1.06 min.

Synthesis of (+/−)-1-(3-nitropyridin-4-yl)piperidin-3-ol

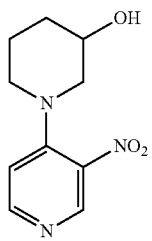

Method 1 of Example 1 was followed using 1 equivalent each of 4-chloro-3-nitropyridine, (+/−)-3-hydroxypiperidine and triethylamine in DMF yielding (+/−)-1-(3-nitropyridin-4-yl)piperidin-3-ol, LCMS (m/z): 224.1 (MH+); LC R$_t$=1.06 min.

Synthesis of (S)-4-(3-(tert-butyldimethylsilyloxy)piperidin-1-yl)-3-nitropyridine

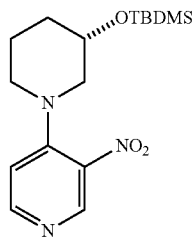 [SMILES: CC(C)(C)[Si](C)(C)O[C@H]1CCCN(c2ccncc2[N+](=O)[O-])C1]

To a solution of (S)-1-(3-nitropyridin-4-yl)piperidin-3-ol and TBDMSCl (2.1 equiv.) in DMF was added imidazole (4 equiv.). The reaction was heated to 50° C. overnight. The reaction was dissolved in EtOAC and washed with water followed by saturate brine, dried and filtered, and concentrated to give the crude. The crude material was further purified by silica gel chromatography to yield desired product (S)-4-(3-(tert-butyl dimethylsilyloxy)piperidin-1-yl)-3-nitropyridine. LCMS (m/z): 338.2 (MH+); LC R$_t$=3.43 min.

Synthesis of (R)-4-(3-(tert-butyldimethylsilyloxy)piperidin-1-yl)-3-nitropyridine

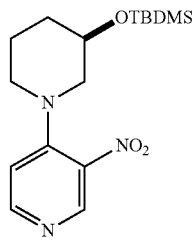 [SMILES: CC(C)(C)[Si](C)(C)O[C@@H]1CCCN(c2ccncc2[N+](=O)[O-])C1]

To a solution of (R)-1-(3-nitropyridin-4-yl) piperidin-3-ol and TBDMSCl (2.1 equiv.) in DMF was added imidazole (4 equiv.). The reaction was heated to 50° C. over night. The reaction was dissolved in EtOAc and washed with water followed by saturate brine, dried and filtered, and concentrated to give the crude. The crude material was further purified by silica gel chromatography to yield desired product (R)-4-(3-(tert-butyl dimethylsilyloxy)piperidin-1-yl)-3-nitropyridine. LCMS (m/z): 338.2 (MH+); LC R$_t$=3.43 min.

Synthesis of (+/−)-4-(3-(tert-butyldimethylsilyloxy)piperidin-1-yl)-3-nitropyridine

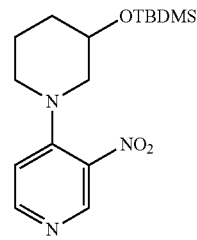

To a solution of (+/−)-1-(3-nitropyridin-4-yl)piperidin-3-ol and TBDMSCl (2.1 equiv.) in DMF was added imidazole (4 equiv.). The reaction was heated to 50° C. over night. The reaction was dissolved in EtOAc and washed with water followed by brine, dried and filtered, and concentrated to give the crude. The crude material was further purified by silica gel chromatography to yield desired product (+/−)-4-(3-(tert-butyl dimethylsilyloxy)piperidin-1-yl)-3-nitropyridine. LCMS (m/z): 338.2 (MH+); LC R$_t$=3.43 min.

Synthesis of (+/−)-4-(3-(tert-butyldimethylsilyloxy)piperidin-1-yl)pyridin-3-amine

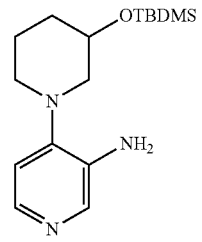

Following Method 2 of Example 49, (+/−)-4-(3-(tert-butyl dimethylsilyloxy)piperidin-1-yl)-3-nitropyridine in ethanol was reduced yielding tert-butyl (+/−)-4-(3-(tert-butyldimethylsilyloxy)piperidin-1-yl)pyridin-3-amine. LCMS (m/z): 308.2 (MH+); LC R$_t$=3.47 min.

Synthesis of (S)-4-(3-(tert-butyldimethylsilyloxy)piperidin-1-yl)pyridin-3-amine

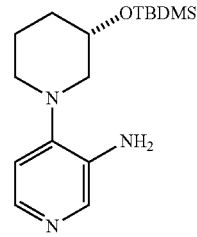 [SMILES: CC(C)(C)[Si](C)(C)OC1CCCN(c2ccncc2[N+](=O)[O-])C1]

Following Method 2 of Example 49, (S)-4-(3-(tert-butyl dimethylsilyloxy)piperidin-1-yl)-3-nitropyridine in ethanol was reduced yielding tert-butyl (S)-4-(3-(tert-butyldimethylsilyloxy)piperidin-1-yl)pyridin-3-amine (67% yield 3 steps). LCMS (m/z): 308.2 (MH+); LC $R_t$=3.47 min.

Synthesis of (R)-4-(3-(tert-butyldimethylsilyloxy) piperidin-1-yl)pyridin-3-amine

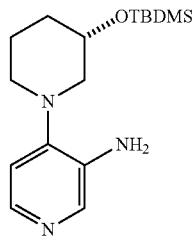 [SMILES: CC(C)(C)[Si](C)(C)O[C@H]1CCCN(c2ccncc2N)C1]

Following Method 2 of Example 49, (R)-4-(3-(tert-butyl dimethylsilyloxy)piperidin-1-yl)-3-nitropyridine in ethanol was reduced yielding tert-butyl (S)-4-(3-(tert-butyldimethyl-silyloxy)piperidin-1-yl)pyridin-3-amine. LCMS (m/z): 308.2 (MH+); LC $R_t$=3.47 min.

Synthesis of 3-amino-6-bromo-N-(4-(3-(tert-butyldimethylsilyloxy)piperidin-1-yl)pyridin-3-yl) picolinamide

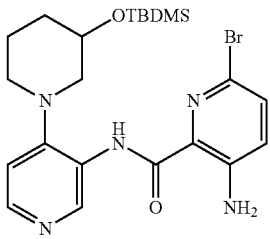

Following Method 11 of Example 305, tert-butyl (+/−)-4-(3-(tert-butyldimethylsilyloxy)piperidin-1-yl)pyridin-3-amine was coupled to 3-amino-6-bromopicolinic acid yielding 3-amino-6-bromo-N-(4-(3-(tert-butyldimethylsilyloxy) piperidin-1-yl)pyridin-3-yl)picolinamide. LCMS (m/z): 506.2 (MH+); LC $R_t$=4.03 min.

Synthesis of 3-amino-6-bromo-N-(4-(3-(tert-butyldimethylsilyloxy)piperidin-1-yl)pyridin-3-yl)picolinamide

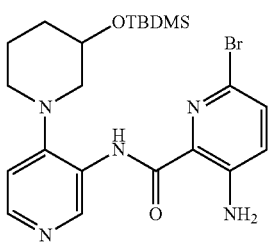 [SMILES: CC(C)(C)[Si](C)(C)OC1CCCN(c2ccncc2NC(=O)c2nc(Br)ccc2N)C1]

Following Method 11 of Example 305, tert-butyl (+/−)-4-(3-(tert-butyldimethylsilyloxy)piperidin-1-yl)pyridin-3-amine was coupled to 3-amino-6-bromopicolinic acid yielding 3-amino-6-bromo-N-(4-(3-(tert-butyldimethylsilyloxy)-piperidin-1-yl)pyridin-3-yl)picolinamide. LCMS (m/z): 506.2 (MH+); LC $R_t$=4.03 min.

Synthesis of (S)-3-amino-6-bromo-N-(4-(3-(tert-butyldimethylsilyloxy)piperidin-1-yl)pyridin-3-yl) picolinamide

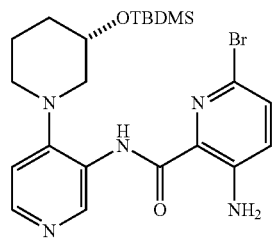 [SMILES: CC(C)(C)[Si](C)(C)OC1CCCN(c2ccncc2NC(=O)c2nc(Br)ccc2N)C1]

Following Method 11 of Example 305, tert-butyl (S)-4-(3-(tert-butyldimethylsilyloxy)piperidin-1-yl)pyridin-3-amine was coupled to 3-amino-6-bromopicolinic acid yielding (S)-3-amino-6-bromo-N-(4-(3-(tert-butyldimethyl-silyloxy)piperidin-1-yl)pyridin-3-yl)picolinamide. LCMS (m/z): 506.2 (MH+); LC $R_t$=4.03 min.

Synthesis of (R)-3-amino-6-bromo-N-(4-(3-(tert-butyldimethylsilyloxy)piperidin-1-yl)pyridin-3-yl) picolinamide

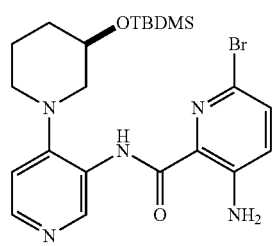 [SMILES: CC(C)(C)[Si](C)(C)O[C@@H]1CCCN(c2ccncc2NC(=O)c2nc(Br)ccc2N)C1]

Following Method 11 of Example 305, tert-butyl (R)-4-(3-(tert-butyldimethylsilyloxy)piperidin-1-yl)pyridin-3-amine was coupled to 3-amino-6-bromopicolinic acid yielding (R)-3-amino-6-bromo-N-(4-(3-(tert-butyldimethyl-silyloxy)piperidin-1-yl)pyridin-3-yl)picolinamide. LCMS (m/z): 506.2 (MH+); LC $R_t$=4.03 min.

Synthesis of benzyl 3-hydroxy-3-methylpiperidine-1-carboxylate

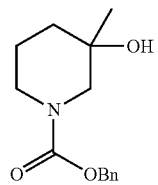

To a solution of benzyl 3-oxopiperidine-1-carboxylate (2.33 g, 10 mmol) in dry THF (50 mL) at −78° C. was added MeMgBr (3.6 mL, 3M solution in THF, 11 mmol) slowly. The reaction was allowed to stir at −78° C. for 10 min then slowly warmed to r.t. The reaction was quenched with NH$_4$Cl and dissolved in EtOAc (300 mL) and washed with saturated NH$_4$Cl and brine, dried and filtered, and concentrated to give the crude. The crude material was further purified by silica gel chromatography to yield benzyl 3-hydroxy-3-methylpiperidine-1-carboxylate. (53% yield). LCMS (m/z): 250.1 (MH$^+$); LC R$_t$=2.98 min.

Synthesis of 3-methylpiperidin-3-ol

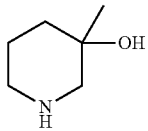

Method 17 was followed using benzyl 3-hydroxy-3-methylpiperidine-1-carboxylate yielding 3-methylpiperidin-3-ol (70%). LCMS (m/z): 116.1 (MH$^+$).

Synthesis of 3-methyl-1-(3-nitropyridin-4-yl)piperidin-3-ol

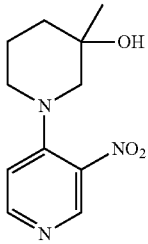 [SMILES: CC1(O)CCCN(c2ccncc2[N+](=O)[O-])C1]

Method 1 of Example 1 was followed using 1 equivalent each of 4-chloro-3-nitropyridine, 3-methylpiperidin-3-ol and triethyl amine in DMF yielding 3-methyl-1-(3-nitropyridin-4-yl)piperidin-3-ol. LCMS (m/z): 238.1 (MH$^+$); LC R$_t$=1.39 min.

Synthesis of 1-(3-aminopyridin-4-yl)-3-methylpiperidin-3-ol

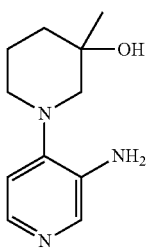

Following method 2 of Example 49, 3-methyl-1-(3-nitropyridin-4-yl)piperidin-3-olin ethanol was reduced yielding 1-(3-aminopyridin-4-yl)-3-methylpiperidin-3-ol, (80%). LCMS (m/z): 208.1 (MH$^+$); LC R$_t$=1.32 min.

Synthesis of Methyl 3-amino-5-fluoropicolinate

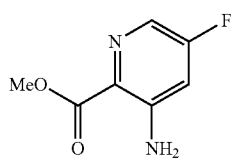

A solution of 2-bromo-5-fluoropyridin-3-amine (1.0 equiv.), triethylamine (1.6 equiv.), and Pd(BINAP)Cl$_2$ (0.0015 equiv.) in anhydrous methanol (0.4 M solution) in a sealed steel bomb was heated to 100° C. After 3 h, more Pd catalyst (0.0015 equiv.) was added, the reaction mixture was re-heated to the same temperature for 3 h. After cooled down to room temperature, a brown precipitate was filtered off and the filtrate was extracted with EtOAc, which was washed with water and brine, dried over anhydrous sodium sulfate, and filtered. After removing volatile materials, the crude yellow product was obtained and used for the next step without further purification (40%). LCMS (m/z): 271.2 (MH$^+$); LC R$_t$=3.56 min.

Synthesis of Methyl 3-amino-6-bromo-5-fluoropicolinate

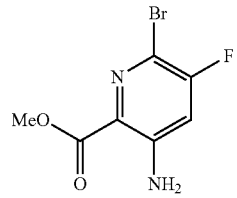

To a solution of methyl 3-amino-5-fluoropicolinate (1.0 equiv.) in acetonitrile (0.3 M solution) was added NBS (1.1 equiv.) for 2 minutes at room temperature. After quenched with water, the reaction mixture was extracted with EtOAc. The crude product was purified by silica column chromatography (20% to 50% EtOAc in hexanes) to give methyl 3-amino-6-bromo-5-fluoropicolinate, (41%). LCMS (m/z): 249.1 (MH$^+$); LC R$_t$=2.80 min.

Synthesis of 3-Amino-6-bromo-5-fluoropicolinic acid

To a solution of methyl 3-amino-5-fluoropicolinate (1.0 equiv.) in tetra-hydrofuran and methanol (2:1, 0.2 M solution) was added LiOH (1.8 equiv., 1 M aqueous solution) at room temperature. The reaction mixture was stirred for 3 h and neutralized with 1.0 N aqueous HCl solution. Then, the reaction mixture was extracted with EtOAc, which was washed with water and brine, dried over anhydrous sodium sulfate, and filtered. After removing volatile materials, the crude 3-amino-6-bromo-5-fluoropicolinic acid was obtained and used for the next step without further purification (92%). LCMS (m/z): 234.2 (MH$^+$); LC R$_t$=2.25 min.

Synthesis of 3-amino-6-(2,6-difluorophenyl)-5-fluoropicolinic acid

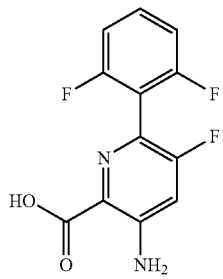

To a solution of methyl 3-amino-5-fluoropicolinate (1.0 equiv.) in DME/2M Na$_2$CO$_3$ (3:1, 0.05 M) equipped with microwave vial was added 2,6-difluorophenylboronic acid (3.0 equiv.) and Pd(dppf)Cl$_2$-DCM (0.1 equiv.). The reaction mixture was heated to 140° C. for 10 min in microwave reactor. After 2,6-difluorophenylboronic acid (3.0 equiv.) was added more, the reaction mixture was heated once more to 140° C. for 10 min in microwave reactor. After the reaction mixture was cooled to room temperature, H$_2$O and EtOAc were added and the organic phase was washed with brine, then dried with Na$_2$SO$_4$, and concentrated. The crude material was purified via preparative HPLC. The pure methyl 3-amino-6-(2,6-difluorophenyl)-5-fluoropicolinate was obtained after the pure fractions were neutralized with NaHCO$_3$, extracted with EtOAc, and concentrated (34%). The methyl 3-amino-6-(2,6-difluorophenyl)-5-fluoropicolinate (1.0 equiv.) was dissolved in THF and MeOH (2:1, 0.2 M) followed by addition of LiOH (1.8 equiv., 1 M aqueous solution). After the reaction mixture was stirred for 1.5 h at room temperature, the reaction mixture was quenched with 1 N HCl solution (1.8 equiv.) and extracted with EtOAc. The organic phase was washed with brine, then dried with Na$_2$SO$_4$, and concentrated. The crude 3-amino-6-(2,6-difluorophenyl)-5-fluoropicolinic acid was used for the next step without further purification (88%). LCMS (m/z): 269.0 (MH$^+$); LC R$_t$=3.26 min.

Synthesis of 3-amino-N-(4-chloropyridin-3-yl)-6-(2,6-difluorophenyl)-5-fluoropicolinamide

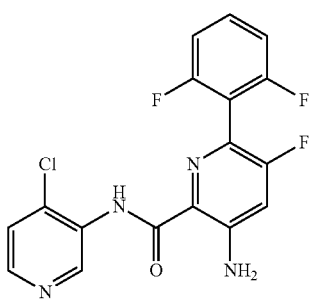 [SMILES: Nc1cc(F)c(-c2c(F)cccc2F)nc1C(=O)Nc1cnccc1Cl]

To a solution of 4-chloropyridin-3-amine (1.0 equiv.) and 3-amino-6-(2,6-difluorophenyl)-5-fluoropicolinic acid (1.0 equiv.) in NMP (1 M) was added HOAt and EDCI sequentially. The reaction mixture was stirred at room temperature for 2 days. The crude reaction was purified by prep HPLC to give 3-amino-N-(4-chloropyridin-3-yl)-6-(2,6-difluorophenyl)-5-fluoropicolinamide (14%). LCMS (m/z): 379.0 (MH$^+$); LC R$_t$=3.49 min

Synthesis of trans-(+/−)-tert-butyl 1-(3-(3-amino-6-bromopicolinamido)pyridin-4-yl)-4-fluoropiperidin-3-ylcarbamate

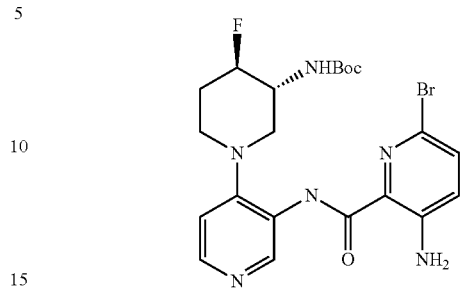

Following Method 11 of Example 305, trans-(+/−)-tert-butyl 1-(3-aminopyridin-4-yl)-4-fluoropiperidin-3-ylcarbamate and 3-amino-6-bromopicolinic acid were reacted yielding after purification (+/−)-tert-butyl 1-(3-(3-amino-6-bromopicolinamido)pyridin-4-yl)-4-fluoropiperidin-3-ylcarbamate, (20%). LCMS (m/z): 510.9 (MH$^+$).

Synthesis of trans-(+/−)-tert-butyl 1-(3-(3-amino-6-bromopicolinamido)pyridin-4-yl)-4-(tert-butyldimethylsilyloxy)piperidin-3-ylcarbamate

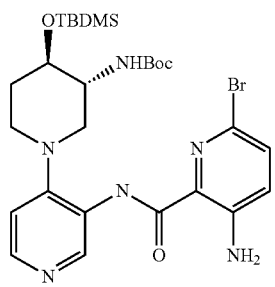 [SMILES: CC(C)(C)OC(=O)N[C@@H]1CN(c2ccncc2NC(=O)c2nc(Br)ccc2N)CC[C@H]1O[Si](C)(C)C(C)(C)C]

Following Method 11 of Example 305, trans-(+/−)-tert-butyl 1-(3-aminopyridin-4-yl)-4-(tert-butyldimethylsilyloxy)piperidin-3-ylcarbamate and 3-amino-6-bromo-picolinic acid was reacted yielding trans-(+/−)-tert-butyl 1-(3-(3-amino-6-bromo-picolinamido)pyridin-4-yl)-4-(tert-butyldimethylsilyloxy)piperidin-3-ylcarbamate, (27%). LCMS (m/z): 621.2 (MH$^+$); LC R$_t$=4.41 min.

Synthesis of (+/−)-tert-Butyl 143-(3-amino-6-bromopicolinamido)pyridin-4-yl)-3-(tert-butyldimethylsilyloxy)piperidin-4-ylcarbamate

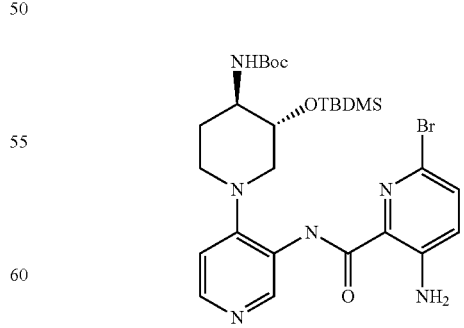

Following Method 11 of Example 305, trans-(+/−)-tert-butyl 1-(3-aminopyridin-4-yl)-3-(tert-butyldimethylsilyloxy)piperidin-4-ylcarbamate and 3-amino-6-bromo-picolinic acid was reacted yielding trans-(+/−)-tert-butyl 1-(3-(3-amino-6-bromopicolinamido)pyridin-4-yl)-3-(tert-butyldimethylsilyloxy)piperidin-4-yl-carbamate, (20%). LCMS (m/z): 623.2 (MH⁺); LC R$_t$=4.12 min.

Synthesis of trans-tert-Butyl 1-(3-(3-amino-6-bromo-5-fluoropicolinamido)pyridin-4-yl)-4-(tert-butyldimethylsilyloxy)piperidin-3-ylcarbamate

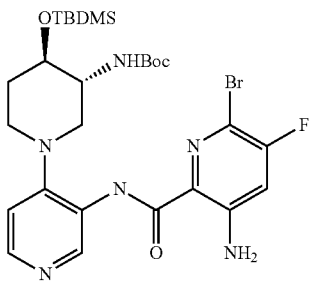 [SMILES: CC(C)(C)OC(=O)N[C@@H]1CN(c2ccncc2NC(=O)c2nc(Br)c(F)cc2N)CC[C@H]1O[Si](C)(C)C(C)(C)C]

Following Method 11 of Example 305, trans-(+/−)-tert-butyl 1-(3-aminopyridin-4-yl)-4-(tert-butyldimethylsilyloxy)piperidin-3-ylcarbamate and 3-amino-6-bromo-5-fluoropicolinic acid was reacted yielding trans-(+/−)-tert-butyl 1-(3-(3-amino-6-bromo-5-fluoropicolinamido)pyridin-4-yl)-4-(tert-butyldimethylsilyloxy)piperidin-3-yl-carbamate. LCMS (m/z): 641.2 (MH⁺); LC R$_t$=4.47 min.

Synthesis of trans-(+/−)-tert-Butyl 1-(3-(3-amino-6-bromo-5-fluoropicolinamido)pyridin-4-yl)-3-(tert-butyldimethylsilyloxy)piperidin-4-ylcarbamate

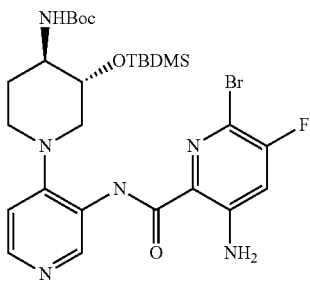 [SMILES: CC(C)(C)OC(=O)N[C@@H]1CCN(c2ccncc2NC(=O)c2nc(Br)c(F)cc2N)C[C@H]1O[Si](C)(C)C(C)(C)C]

Following Method 11 of Example 305, trans-(+/−)-tert-butyl 1-(3-aminopyridin-4-yl)-3-(tert-butyldimethylsilyloxy)piperidin-4-ylcarbamate and 3-amino-6-bromo-5-fluoropicolinic acid was reacted yielding trans-(+/−)-tert-butyl 1-(3-(3-amino-6-bromo-5-fluoropicolinamido)pyridin-4-yl)-3-(tert-butyldimethylsilyloxy)piperidin-4-yl-carbamate. LCMS (m/z): 641.2 (MH⁺); LC R$_t$=4.73 min.

Method 20

Synthesis of 5-amino-2-(2,6-difluorophenyl)pyrimidine-4-carboxylic acid

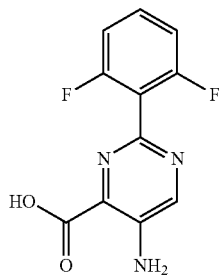

A 2.68 M NaOEt in EtOH solution (3 eq) was added to an ice-bath cooled mixture of 2,6-difluorobenzimidamide hydrochloride (2 eq) in EtOH (0.1 M). The resulting mixture was allowed to warm to rt and stirred under N$_2$ for 30 min. To the reaction mixture was added drop wise a solution of mucobromic acid (1 eq) in EtOH and the reaction was heated in a 50° C. oil bath for 2.5 hr. After cooling to rt the reaction mixture was concentrated in vacuo. H$_2$O and 1.0 N NaOH were added and the aqueous mixture was washed with EtOAc. The aqueous phase was acidified to pH=4 with 1.0 N HCl then extracted with EtOAc. Combined organic extracts were washed once with brine, then dried over anhydrous Na$_2$SO$_4$, filtered, and concentrated in vacuo to give 5-bromo-2-(2,6-difluorophenyl)pyrimidine-4-carboxylic acid. The crude product was used for the next step without further purification. LC/MS (m/z): 316.9 (MH⁺). LC: R$_t$: 2.426 min.

CuSO$_4$ (0.1 eq) was added to a mixture of 5-bromo-2-(2, 6-difluorophenyl)pyrimidine-4-carboxylic acid (1 eq) and 28% aqueous ammonium hydroxide solution in a microwave reaction vessel. The reaction mixture was heated in a microwave reactor at 110° C. for 25 min. The reaction vessel was cooled in dry ice for 30 min then unsealed and concentrated in vacuo. To the resulting solids was added 1.0 N HCl and the mixture was extracted with EtOAc. Combined organic extracts were washed once with brine, then dried over anhydrous Na$_2$SO$_4$, filtered, and concentrated in vacuo to give 5-amino-2-(2,6-difluorophenyl)pyrimidine-4-carboxylic acid. The crude product was used for the next step without further purification. LC/MS (m/z): 252.0 (MH⁺). LC: R$_t$: 2.043 min.

Synthesis of 5-amino-2-(2-fluorophenyl)pyrimidine-4-carboxylic acid

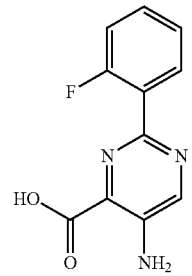

Following method 20, 5-amino-2-(2-fluorophenyl)pyrimidine-4-carboxylic acid was prepared starting from 2-fluorobenzimidamide hydrochloride. LC/MS (m/z): 234.0 (MH⁺), R$_t$: 0.70 min.

Synthesis of 5-amino-2-phenylpyrimidine-4-carboxylic acid

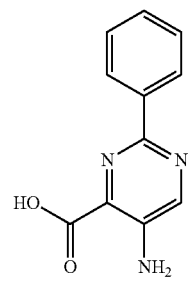

Following method 20, 5-amino-2-phenylpyrimidine-4-carboxylic acid was prepared starting from benzimidamide hydrochloride. LC/MS (m/z): 216.1 (MH+).

Synthesis of ethyl 5-amino-2-chloropyrimidine-4-carboxylate

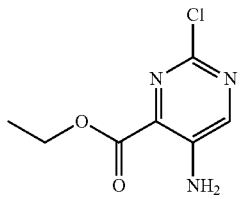

10% Palladium on carbon (0.2 eq) was added to a N₂-flushed mixture of ethyl 2,6-dichloro-5-nitropyrimidine-4-carboxylate (1 eq) and magnesium oxide (2 eq) in 1,4-dioxane (0.15 M). The reaction was purged with H₂ under atmospheric pressure at rt. After 16 h additional portions of 10% Pd/C (0.3 eq) and MgO (5 eq) were added and the reaction continued to purge with H₂ under atmospheric pressure for 6 h at rt. The crude solids were filtered through a pad of Celite on a paper lined Buchner funnel and washed with CH₂Cl₂. The filtrate was transferred to a separatory funnel, washed twice with H₂O and once with brine, then dried over anhydrous Na₂SO₄, filtered, and concentrated in vacuo. The crude product was dissolved in CH₂Cl₂, loaded onto a SiO₂ column, and purified by flash chromatography (10-20-30% EtOAc in hexanes) to give ethyl 5-amino-2-chloropyrimidine-4-carboxylate. LC/MS (m/z): 202.0 (MH+).

Synthesis of 5-amino-2-chloropyrimidine-4-carboxylic acid

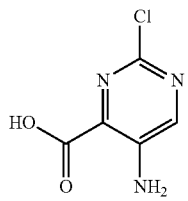 [SMILES: Nc1cnc(Cl)nc1C(=O)O]

A 0.5 M aqueous solution of LiOH (1.5 eq) was added to a stirring mixture of ethyl 5-amino-2-chloropyrimidine-4-carboxylate (1 eq) in H₂O (0.1 M) and THF (0.1M). The reaction was maintained for 2 h at rt. 1.0 N HCl was added and the crude residue was concentrated in vacuo to remove residual THF. The resulting solids were collected on a paper lined Buchner funnel and dried for 16 h under vacuum to give 5-amino-2-chloropyrimidine-4-carboxylic acid. LC/MS (m/z): 174.0 (MH+). HPLC: $R_t$: 1.148 min.

Synthesis of 3-nitro-5-phenylpicolinonitrile

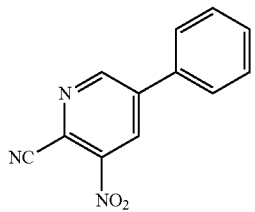 [SMILES: N#Cc1ncc(-c2ccccc2)cc1[N+](=O)[O-]]

5-bromo-3-nitropicolinonitrile (1 eq) and phenylboronic acid (1.5 eq) was mixed with 15 mL of 1,4-dioxane and 5 mL of 2 M Na₂CO₃ aqueous solution in a glass pressure tube. The reaction mixture was degassed by anhydrous N₂ stream for 5 min followed by the addition of Pd(dppf)Cl₂-DCM (0.1 eq). The reaction mixture was stirred at 100° C. for 3 hours. Then the mixture was diluted with 100 mL of ethyl acetate and washed with water, brine, then dried over MgSO₄, filtered, and evaporated under reduced pressure to give crude product, which was triturated by DCM, ether, hexanes to give the pure titled compound. LC/MS (m/z): 226.1 (MH+).

Synthesis of 3-amino-5-phenylpicolinic acid

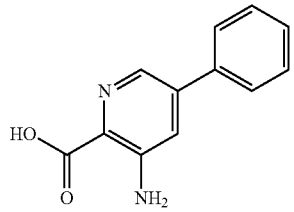 [SMILES: Nc1cc(-c2ccccc2)cnc1C(=O)O]

To a solution of 3-nitro-5-phenylpicolinonitrile (1 eq) in 10 mL of DMF was added tin (II) chloride dehydrate (7.0 eq) at room temperature. The reaction mixture was stirred at that temperature overnight. The mixture was diluted with 150 mL of ethyl acetate and 30 mL of triethyl amine. After filtration, the filtrate was concentrated under reduced pressure to give a solid, which was added 2 mL of concentrated HCl. The mixture was stirred in microwave at 90° C. for 10 minutes. After standing over night, the solid was collected by filtration, which was dissolved in 10 mL of 1N NaOH. The resulting mixture was extracted with 50 mL of ethyl acetate. The aqueous layer was acidified by 1 N HCl to pH 7.0 to yield 3-amino-5-phenylpicolinic acid, which was collected by filtration. LC/MS (m/z): 215.1 (MH+).

Synthesis of 6-bromo-5-fluoropicolinic acid

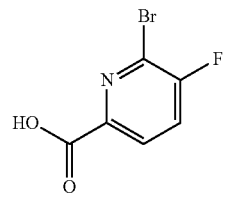 [SMILES: O=C(O)c1ccc(F)c(Br)n1]

To 2-bromo-3-fluoro-6-methylpyridine (2.0 g, 10.58 mmoles) in H₂O (30 mL) was added potassium permanganate (1.67 g, 10.58 mmoles). The solution was heated at 100° C. for 5 hours at which time more potassium permanganate (1.67 g, 10.58 mmoles) was added. After heating for an additional 48 hours the material was filtered through celite (4 cm×2 inches) and rinsed with H₂O (150 mL). The combined aqueous was acidified with 1N HCl to pH4, extracted with ethyl acetate (200 mL), washed with NaCl(sat.), dried over MgSO₄, filtered and concentrated to yield 6-bromo-5-fluoropicolinic acid (17%) as a white solid. LCMS (m/z): 221.9 (MH+); LC $R_t$=2.05 min.

325

Synthesis of (S)-tert-butyl 1-(3-(6-bromo-5-fluoropicolinamido)pyridin-4-yl)piperidin-3-ylcarbamate

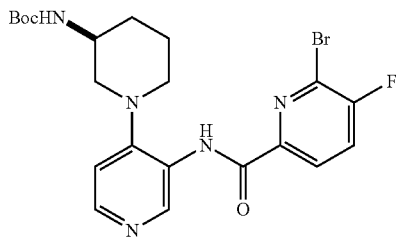 [SMILES: CC(C)(C)OC(=O)N[C@H]1CCCN(c2ccncc2NC(=O)c2ccc(F)c(Br)n2)C1]

Following Method 11 (Example 305), (S)-tert-butyl 1-(3-aminopyridin-4-yl)piperidin-3-ylcarbamate was coupled to 6-bromo-5-fluoropicolinic acid yielding crude (S)-tert-butyl 1-(3-(6-bromo-5-fluoropicolinamido)pyridin-4-yl)piperidin-3-ylcarbamate (92%) which was used as is. LCMS (m/z): 496.2 (MH+); LC $R_t$=2.90 min.

Synthesis of 6-bromo-3-fluoropicolinic acid

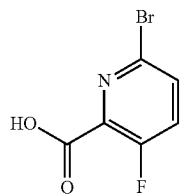 [SMILES: O=C(O)c1nc(Br)ccc1F]

To 6-bromo-3-fluoro-2-methylpyridine (2.0 g, 10.58 mmoles) in $H_2O$ (200 mL) was added potassium permanganate (1.67 g, 10.58 mmoles). The solution was heated at 100° C. for 16 hours at which time upon cooling the material was filtered through celite (4 cm×2 inches) and rinsed with $H_2O$ (150 mL). The combined aqueous was acidified with 1N HCl to pH4, extracted with ethyl acetate (2×200 mL), washed with NaCl(sat.), dried over $MgSO_4$, filtered and concentrated to yield 6-bromo-3-fluoropicolinic acid (18%) as a white solid. LCMS (m/z): 221.9 (MH+); LC $R_t$=1.71 min.

Synthesis of (S)-tert-butyl 1-(3-(6-bromo-3-fluoropicolinamido)pyridin-4-yl) piperidin-3-yl)carbamate

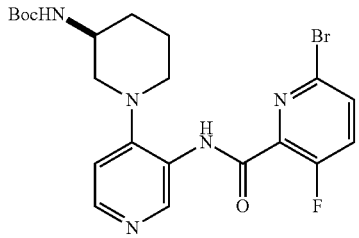 [SMILES: CC(C)(C)OC(=O)N[C@H]1CCCN(c2ccncc2NC(=O)c2nc(Br)ccc2F)C1]

Following Method 11 (Example 305), (S)-tert-butyl 1-(3-aminopyridin-4-yl)piperidin-3-ylcarbamate was coupled to 6-bromo-3-fluoropicolinic acid yielding (S)-tert-butyl 1-(3-(6-bromo-3-fluoropicolinamido)pyridin-4-yl)piperidin-3-ylcarbamate which was used directly as is. LCMS (m/z): 496.2 (MH+); LC $R_t$=2.71 min.

326

Synthesis of (S)-tert-butyl 1-(3-(6-bromopicolinamido)pyridin-4-yl)piperidin-3-ylcarbamate

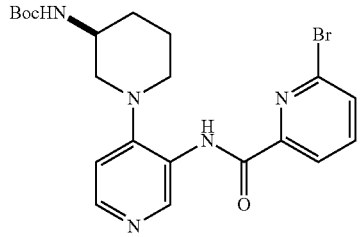 [SMILES: CC(C)(C)OC(=O)N[C@H]1CCCN(c2ccncc2NC(=O)c2cccc(Br)n2)C1]

Following Method 11 (Example 305), (S)-tert-butyl 1-(3-aminopyridin-4-yl)piperidin-3-ylcarbamate was coupled to 6-bromopicolinic acid yielding, after column chromatography (EtOAc as eluant), (S)-tert-butyl 1-(3-(6-bromopicolinamido)pyridin-4-yl)piperidin-3-ylcarbamate (82%). LCMS (m/z): 478.1 (MH+); LC $R_t$=2.84 min.

Synthesis of (S)-tert-butyl 1-(3-(5-amino-2-chloropyrimidine-4-carboxamido)pyridin-4-yl)piperidin-3-ylcarbamate

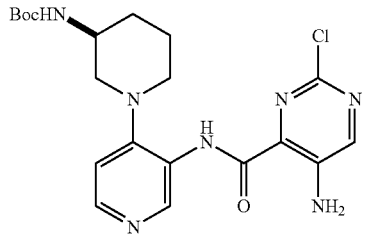 [SMILES: CC(C)(C)OC(=O)N[C@H]1CCCN(c2ccncc2NC(=O)c2nc(Cl)ncc2N)C1]

Following Method 11 (Example 305), (S)-tert-butyl 1-(3-aminopyridin-4-yl)piperidin-3-ylcarbamate was coupled to 5-amino-2-chloropyrimidine-4-carboxylic acid yielding, after column chromatography (EtOAc as eluant), (S)-tert-butyl 1-(3-(5-amino-2-chloropyrimidine-4-carboxamido)pyridin-4-yl)piperidin-3-yl-carbamate (10%). LCMS (m/z): 433.1 (MH+); LC $R_t$=2.46 min.

Method 21

Synthesis of 2-chloro-6-isobutoxypyrazine

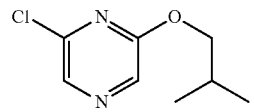

A flame-dried round bottom flask was charged with a suspension of 95% NaH (1.1 eq) in anhydrous THF (0.3 M). The stirring mixture was cooled to 0° C. in an ice-water bath and 2-methyl-1-propanol (1 eq) was added drop wise via syringe. After 30 min 2,6-dichloropyrazine (1 eq) was added, the reaction was warmed to rt and stirred for 3 h. The crude mixture was quenched with saturated aqueous $NH_4Cl$ and extracted with EtOAc. The combined organic phases were washed once each with $H_2O$ and brine, then dried over anhydrous $Na_2SO_4$, filtered, and concentrated in vacuo. The crude residue was dissolved in $CH_2Cl_2$, loaded onto a $SiO_2$ column, and purified by flash chromatography (9:1 hexanes/EtOAc eluent) to give 2-chloro-6-isobutoxypyrazine. LC/MS (m/z): 187.1 (MH+).

Synthesis of 2-chloro-6-(cyclopropylmethoxy)pyrazine

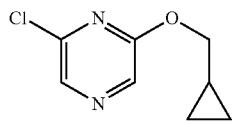 [SMILES: Clc1cncc(OCC2CC2)n1]

Following Method 21, 2-chloro-6-(cyclopropylmethoxy) pyrazine was prepared. LC/MS (m/z): 185.0 (MH+).

Synthesis of 2-chloro-6-ethoxypyrazine

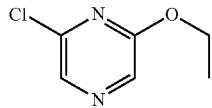

Following Method 21, 2-chloro-6-ethoxypyrazine was prepared. LC/MS (m/z): 159.0 (MH+).

Synthesis of 2-chloro-6-isopropoxypyrazine

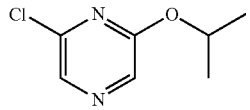

Following Method 21, 2-chloro-6-isopropoxypyrazine was prepared. LC/MS (m/z): 173.1 (MH+).

Synthesis of 2-chloro-6-propoxypyrazine

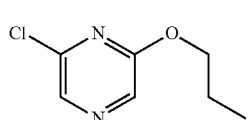

Following Method 21, 2-chloro-6-propoxypyrazine was prepared. LC/MS (m/z): 173.1 (MH+).

Synthesis of 2-(benzyloxy)-6-chloropyrazine

Following Method 21, 2-(benzyloxy)-6-chloropyrazine was prepared. LC/MS (m/z): 221.0 (MH+).

Method 22

Synthesis of 5-bromo-3-(2-methoxyethoxy)pyrazin-2-amine

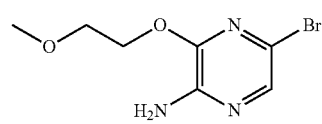

A flame-dried round bottom flask was charged with a suspension of 95% NaH (1.3 eq) in anhydrous THF (0.2 M). The stirring mixture was cooled to 0° C. in an ice-water bath and 2-methoxyethanol (1.2 eq) was added drop wise via syringe. After 30 min 3,5-dibromopyrazin-2-amine (1 eq) was added, the reaction was warmed to rt and stirred for 3 h. The crude mixture was quenched with saturated aqueous NH4Cl and extracted with EtOAc. The combined organic phases were washed once each with H2O and brine, then dried over anhydrous Na2SO4, filtered, and concentrated in vacuo to give 5-bromo-3-(2-methoxyethoxy)pyrazin-2-amine. LC/MS (m/z): 250.0 (MH+).

Synthesis of 5-bromo-3-(2,2,2-trifluoroethoxy)pyrazin-2-amine

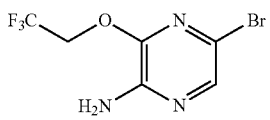

Following Method 22, 5-bromo-3-(2,2,2-trifluoroethoxy) pyrazin-2-amine was prepared. LC/MS (m/z): 274.0 (MH+).

Method 23

Synthesis of 3-(2-methoxyethoxy)-5-(4,4,5,5-tetramethyl-1,3,2-dioxaborolan-2-yl)pyrazin-2-amine

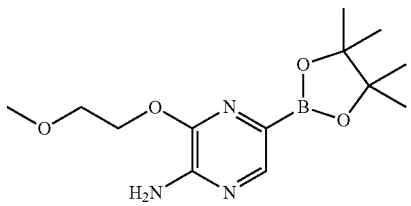

To a solution of 5-bromo-3-(2-methoxyethoxy)pyrazin-2-amine (1 eq) in dioxane (0.25 M) in a microwave reaction vessel was added bispinacolatodiboron (2 eq), Pd(dba)2 (0.05 eq), PCy3 (0.075 eq) and KOAc (3 eq). The reaction mixture was then heated twice in a microwave reactor at 110° C. for 600 sec. The crude product was used for the next step without workup or further purification. LC/MS (m/z): 214.1/296.1 (MH+).

Synthesis of 5-(4,4,5,5-tetramethyl-1,3,2-dioxaborolan-2-yl)-3-(2,2,2-trifluoroethoxy)pyrazin-2-amine

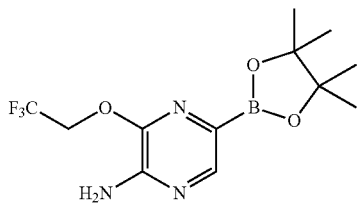

Following Method 23, 5-(4,4,5,5-tetramethyl-1,3,2-dioxaborolan-2-yl)-3-(2,2,2-trifluoroethoxy)pyrazin-2-amine was prepared from 5-bromo-3-(2,2,2-trifluoroethoxy)pyrazin-2-amine. LC/MS (m/z): 238.1 (MH$^+$).

Method 24

Synthesis of tert-butyl 6-chloro-2-methylpyrimidin-4-ylcarbamate

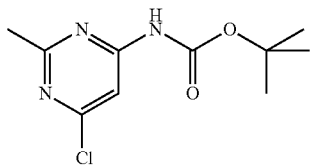 [SMILES: Cc1nc(Cl)cc(NC(=O)OC(C)(C)C)n1]

To a solution of 6-chloro-2-methylpyrimidin-4-amine (1.0 equiv.) in THF (0.17M) was added BOC$_2$O (1.1 equiv.) and DMAP (cat.). The reaction was allowed to stir overnight, then concentrated to a yellow crude, and filtered through a pad of SiO$_2$ eluting with EtOAc and hexanes (1:1) to afford an off-white solid (78%). LCMS (m/z): 244.1 (MH$^+$); LC R$_t$=3.69 min.

Synthesis of 4-chloro-N,N-di-BOC-6-methylpyrimidin-2-amine

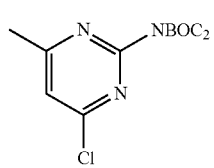

Method 24 was followed using 4-chloro-6-methylpyrimidin-2-amine (1.0 equiv.), BOC$_2$O (2.0 equiv.), and DMAP (cat.) to afford 4-chloro-N,N-di-BOC-6-methylpyrimidin-2-amine in 71%. LCMS (m/z): 344.2 (MH$^+$); LC R$_t$=4.3 min.

Synthesis of 4-chloro-N,N-di-BOC-6-methoxypyrimidin-2-amine

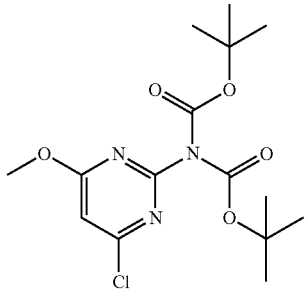 [SMILES: COc1cc(Cl)nc(N(C(=O)OC(C)(C)C)C(=O)OC(C)(C)C)n1]

Method 24 was followed using 4-chloro-6-methoxypyrimidin-2-amine (1.0 equiv.), Boc$_2$O (2.0 equiv.), and DMAP (cat.) to afford 4-chloro-N,N-di-BOC-6-methoxypyrimidin-2-amine in >95%. LCMS (m/z): 360.2 (MH$^+$); LC R$_t$=5.70 min.

Synthesis of 6-chloro-N,N-di-BOC-2-(methylthio)pyrimidin-4-amine

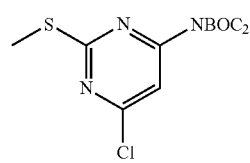

Method 24 was followed using 6-chloro-2-(methylthio)pyrimidin-4-amine (1.0 equiv.), BOC$_2$O (2.0 equiv.), and DMAP (cat.) to afford 6-chloro-N,N-di-BOC-2-(methylthio)pyrimidin-4-amine in >95%. LCMS (m/z): 376.1 (MH$^+$); LC R$_t$=4.9 min.

Synthesis of tert-butyl 6-chloro-2-(trifluoromethyl)pyrimidin-4-ylcarbamate

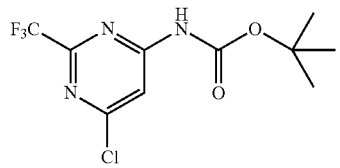 [SMILES: CC(C)(C)OC(=O)Nc1cc(Cl)nc(C(F)(F)F)n1]

Method 24 was followed using 6-chloro-2-(trifluoromethyl)pyrimidin-4-amine (1.0 equiv.), BOC$_2$O (1.0 equiv.), and DMAP (cat.) to afford tert-butyl 6-chloro-2-(trifluoromethyl)pyrimidin-4-ylcarbamate in 64%. LCMS (m/z): 298.1 (MH$^+$); LC R$_t$=4.73 min.

Synthesis of benzyl 4-chloropyridin-3-ylcarbamate

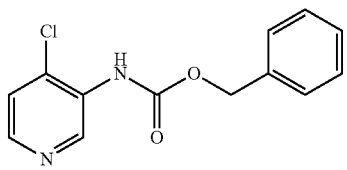 [SMILES: O=C(Nc1cnccc1Cl)OCc1ccccc1]

A solution of benzyl chloroformate (1.1 equiv.) in THF (1.85 M) was slowly added to a solution of 3-amino-4-chloropyridine (1.0 equiv.) and pyridine (1.5 equiv.) in THF (1.0 M) and stirred at rt for 3.5 hours (formation of a precipitate over time). The reaction was quenched with H$_2$O (100 mL), extracted with EtOAc (200 mL), washed with NaCl$_{(sat.)}$ (75 mL), dried over MgSO$_4$, filtered and the volatiles were removed in vacuo. The product precipitated from a mixture of hexane/EtOAc yielding benzyl 4-chloropyridin-3-ylcarbamate (34%). LCMS (m/z): 263.1 (MH$^+$); LC R$_t$=2.33 min.

331

Synthesis of benzyl 4-(4,4,5,5-tetramethyl-1,3,2-dioxaboronlan.2-yl)pyridine-3-ylcarbamate

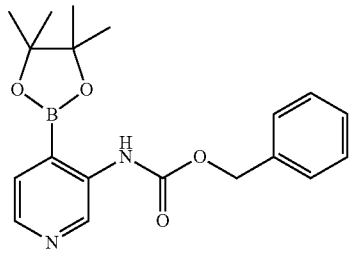 [SMILES: CC1(C)OB(c2ccncc2NC(=O)OCc2ccccc2)OC1(C)C]

A solution of benzyl 4-chloropyridin-3-ylcarbamate (1.0 equiv.), bis(pinacolato)diboron (2.0 equiv.), Pd$_2$(dba)$_3$ (0.05 equiv.), PCy$_3$ (0.075 equiv.), KOAc (2.0 equiv.) in dioxane (0.19 M) was degassed by bubbling nitrogen through for 10 min in a round-bottomed flask. The flask was heated to 90° C. for 3 hours, cooled to room temperature, filtered through activated charcoal and Celite and washed with EtOAc. Upon concentration of the filtrate, a thick dark brown product was obtained. LCMS (m/z): 273 (MH$^+$ for the corresponding boronic acid); LC R$_t$=1.93 min.

Method 25

Synthesis of tert-butyl 6-(3-(benzylcarbamate-amino)-pyridin-4-yl)-2-(trifluoromethyl)pyrimidin-4-ylcarbamate

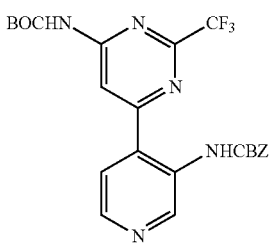

To the crude solution of benzyl 4-(4,4,5,5-tetramethyl-1,3,2-dioxaboronlan.2-yl)pyridine-3-ylcarbamate (3.0 equiv.) was added Pd(dppf)Cl$_2$-DCM (0.10 equiv.), tert-butyl 6-chloro-2-(trifluoromethyl)pyrimidin-4-ylcarbamate (1.0 equiv.), and DME/2M Na$_2$CO$_3$ (3:1, 0.08 M). The reaction was heated to 90° C. for one hour, then cooled to room temperature, H$_2$O and EtOAc were added, the organic layer was extracted, washed with brine and dried with Na$_2$SO$_4$. Upon concentration, the crude was passed through a pad of SiO$_2$, washing with EtOAc. The reaction was concentrated to almost dryness, and hexane was added. The precipitate was filtered to give the product as a light yellow powder. The filtrate was concentrated to almost dryness, added more hexane and filtered the precipitate. Total yield=50%. LCMS (m/z): 490.1 (MH$^+$); LC R$_t$=4.11 min.

332

Synthesis of benzyl 4-(2-(di-BOC-amino)-6-methylpyrimidin-4-yl)pyridin-3-ylcarbamate

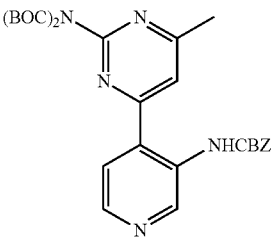

Method 25 was followed using 4-chloro-N,N-di-BOC-6-methylpyrimidin-2-amine (1.0 equiv.), benzyl 4-(4,4,5,5-tetramethyl-1,3,2-dioxaboronlan.2-yl)pyridine-3-ylcarbamate (3 equiv.), Pd(dppf)Cl$_2$-DCM (0.10 equiv.) in DME/2M Na$_2$CO$_3$ (3:1, 0.07M) at 70° C. for 30 min. Purification via SiO$_2$ column chromatography eluting with EtOAc and hexanes (2.5:1) afforded benzyl 4-(2-(di-BOC-amino)-6-methylpyrimidin-4-yl)pyridin-3-ylcarbamate in 69% yield. LCMS (m/z): 536.2 (MH$^+$); LC R$_t$=4.2 min.

Method 26

Synthesis of tert-butyl 6-(3-aminopyridin-4-yl)-2-(trifluoromethyl)pyrimidin-4-ylcarbamate

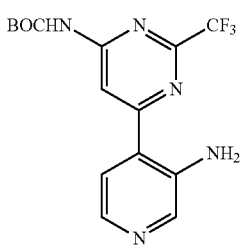

A solution of tert-butyl 6-(3-(benzylcarbamate-amino)pyridin-4-yl)-2-(trifluoromethyl)pyrimidin-4-ylcarbamate was stirred in EtOAc and EtOH (3:1, M) (heterogeneous solution). Pd/C (10% by weight) was added and the reaction was stirred under a hydrogen balloon for 2 days. Upon completion, the solution was filtered through Celite and washed with EtOAc. The filtrate was concentrated to give a brown solid (>95%). LCMS (m/z): 356.1 (MH$^+$); LC R$_t$=2.80 min.

Synthesis of 4-(3-aminopyridin-4-yl)-N,N-di-BOC-6-methylpyrimidin-2-amine

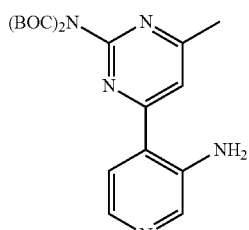

Method 26 was followed using benzyl 4-(2-(di-BOC-amino)-6-methylpyrimidin-4-yl)pyridin-3-ylcarbamate (1.0 equiv.), Pd/C (20% by weight) in EtOAc yielding 4-(3-aminopyridin-4-yl)-N,N-di-BOC-6-methylpyrimidin-2-amine in 90% yield. LCMS (m/z): 402.3 (MH$^+$); LC R$_t$=3.0 min.

Synthesis of 4-(4,4,5,5-tetramethyl-1,3,2-dioxaborolan-2-yl)pyridin-3-amine

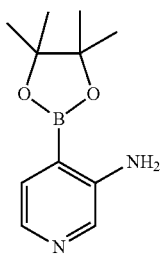 [SMILES: CC1(C)OB(c2ccncc2N)OC1(C)C]

A solution of benzyl 4-chloropyridin-3-ylcarbamate (1.0 equiv.), bis(pinacolato)diboron (2.0 equiv.), Pd$_2$(dba)$_3$ (0.05 equiv.), PCy$_3$ (0.075 equiv.), KOAc (2 equiv.) in dioxane (0.19 M) was degassed by bubbling nitrogen through for 10 min in a round-bottomed flask. The flask was heated to 90° C. for 16 hours, cooled to room temperature, filtered through activated charcoal and Celite, washed with EtOAc and concentrated to give a thick dark brown product. LCMS (m/z): 139.0 (MH$^+$ for the corresponding boronic acid).

Synthesis of 6-(3-aminopyridin-4-yl)-N,N-di-BOC-2-(methylthio)pyrimidin-4-amine

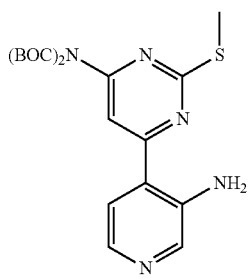

Method 26 was followed using 6-chloro-N,N-di-BOC-2-(methyl-thio)pyrimidin-4-amine (1.0 equiv.), 4-(4,4,5,5-tetramethyl-1,3,2-dioxaborolan-2-yl)pyridin-3-amine (3.0 equiv.), Pd(dppf)Cl2-DCM (0.10 equiv.) in DME/2M Na$_2$CO$_3$ (0.07M) at 90° C. for 30 min. Purification via SiO$_2$ column chromatography eluting with EtOAc and hexanes (1:1) afforded 6-(3-aminopyridin-4-yl)-N,N-di-BOC-2-(methyl-thio)pyrimidin-4-amine in 32% yield. LCMS (m/z): 434.2 (MH$^+$); LC R$_t$=3.56 min.

Synthesis of tert-butyl 6-(3-aminopyridin-4-yl)-2-methylpyrimidin-4-ylcarbamate

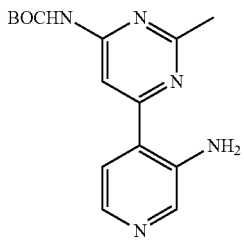

Method 26 was followed using tert-butyl 6-chloro-2-methylpyrimidin-4-ylcarbamate (1.0 equiv.), 4-(4,4,5,5-tetramethyl-1,3,2-dioxaborolan-2-yl)pyridin-3-amine (3.0 equiv.), Pd(dppf)Cl$_2$-DCM (0.10 equiv.) in DME/2M Na$_2$CO$_3$ (3:1, 0.07M) at 80° C. for 30 min. Purification via SiO$_2$ column chromatography eluting with EtOAc afforded tert-butyl 6-(3-aminopyridin-4-yl)-2-methylpyrimidin-4-ylcarbamate in 26% yield. LCMS (m/z): 302.1 (MH$^+$); LC R$_t$=2.23 min.

Synthesis of 4-(3-aminopyridin-4-yl)-6-methoxy-N,N-di-BOC-pyrimidin-2-amine

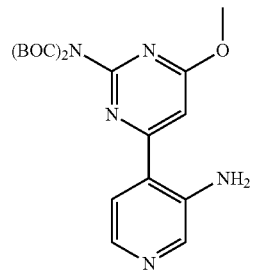

Method 26 was followed using 4-chloro-N,N-di-BOC-6-methoxypyrimidin-2-amine (1.0 equiv.), 4-(4,4,5,5-tetramethyl-1,3,2-dioxaborolan-2-yl)-pyridin-3-amine (3.0 equiv.), Pd(dppf)Cl$_2$-DCM (0.10 equiv.) in DME/2M Na$_2$CO$_3$ (0.07M) at 90° C. for 30 min. Purification via SiO$_2$ column chromatography eluting with EtOAc and hexanes (1:1) afforded 4-(3-aminopyridin-4-yl)-6-methoxy-N,N-di-BOC-pyrimidin-2-amine in 13% yield). LCMS (m/z): 418.1 (MH$^+$).

Synthesis of N2-(3,4-dimethoxybenzyl)-6-(trifluoromethyl)-4,4'-bipyridine-2,3'-diamine

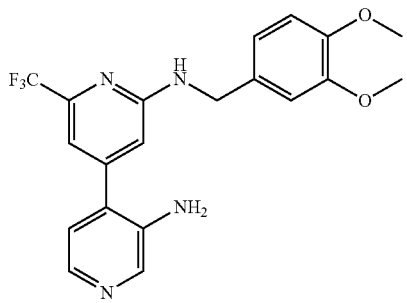 [SMILES: COc1ccc(CNc2cc(-c3ccncc3N)cc(C(F)(F)F)n2)cc1OC]

Method 26 was followed using N-(3,4-dimethoxybenzyl)-4-iodo-6-(tri-fluoromethyl)pyridin-2-amine (1.0 equiv.), 4-(4,4,5,5-tetramethyl-1,3,2-dioxaborolan-2-yl)pyridin-3-amine (3 equiv.), Pd(dppf)Cl$_2$ DCM (0.10 equiv.) in DME/2M Na$_2$CO$_3$ (3:1, 0.07 M) at 50° C. for 45 min. Purification via reverse phase HPLC afforded N$^2$-(3,4-dimethoxybenzyl)-6-(trifluoromethyl)-4,4'-bipyridine-2,3'-diamine in 38% yield. LCMS (m/z): 402.1 (MH$^+$); LC R$_t$=3.0 min.

Method 27

Synthesis of tert-butyl 6-(3-(3-amino-6-bromopicolinamido)pyridine-4-yl)-2-(trifluoromethyl)pyrimidin-4-ylcarbamate

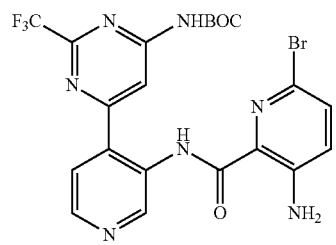

A solution of tert-butyl 6-(3-aminopyridin-4-yl)-2-(trifluoro-methyl)pyrimidin-4-ylcarbamate (1.0 equiv.), 3-amino-6-bromopicolinic acid (1.0 equiv.), HOAt (1.0 equiv.), and EDC (1.0 equiv.) in DMF at a concentration of (0.2 M) was stirred for 3 hrs then heated to 50° C. overnight (homogeneous solution). Water was added to the reaction and the precipitate was filtered. The solid was further purified via SiO$_2$ column chromatography eluting with DCM/MeOH (10%) to yield a brown solid as the desired product (81%). LCMS (m/z): 554.1/556.1 (MH$^+$); LC R$_t$=3.77 min.

Synthesis of 3-amino-6-bromo-N-(4-(6-(di-BOC-amino)-2-(methylthio)pyrimidin-4-yl)pyridin-3-yl)picolinamide

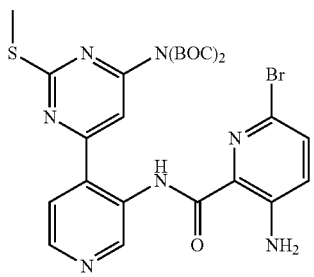

Method 27 was followed using 6-(3-aminopyridin-4-yl)-N,N-di-BOC-2-(methylthio)pyrimidin-4-amine (1.0 equiv.), 3-amino-6-bromopicolinic acid (1.0 equiv), EDC (1.0 equiv.), and HOAt (1.0 equiv.) in DMF yielding 3-amino-6-bromo-N-(4-(6-(di-BOC-amino)-2-(methylthio)pyrimidin-4-yl)pyridin-3-yl)picolinamide in 30% yield. LCMS (m/z): 632.1/634.0 (MH$^+$); LC R$_t$=4.55 min.

Synthesis of tert-butyl 6-(3-(3-amino-6-bromopicolinamido)pyridine-4-yl)-2-methylpyrimidin-4-ylcarbamate

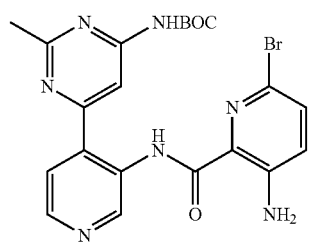

Method 27 was followed using tert-butyl 6-(3-aminopyridin-4-yl)-2-methylpyrimidin-4-ylcarbamate (1.0 equiv.), 3-amino-6-bromopicolinic acid (1.0 equiv), EDC (1.0 equiv.), and HOAt (1.0 equiv.) in DMF yielding tert-butyl 64343-amino-6-bromopicolinamido)pyridine-4-yl)-2-methylpyrimidin-4-ylcarbamate in 74% yield. LCMS (m/z): 499.9/501.9 (MH$^+$); LC R$_t$=3.36 min.

Synthesis of 3-amino-6-bromo-N-(4-(2-(di-BOC-amino)-6-methylpyrimidin-4-yl)pyridin-3-yl)picolinamide

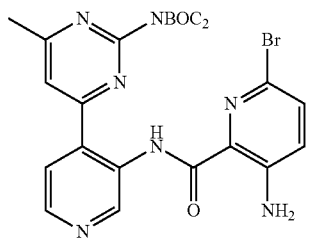

Method 27 was followed using 4-(3-aminopyridin-4-yl)-N,N-di-BOC-6-methylpyrimidin-2-amine (1.0 equiv.), 3-amino-6-bromopicolinic acid (1.0 equiv), EDC (1.0 equiv.), and HOAt (1.0 equiv.) in DMF yielding 3-amino-6-bromo-N-(4-(2-(di-BOC-amino)-6-methylpyrimidin-4-yl)pyridin-3-yl)picolinamide in 12% yield. LCMS (m/z): 602.2 (MH$^+$); LC R$_t$=3.60 min.

Synthesis of tert-butyl 6-(3-(3-amino-6-bromo-5-fluoropicolinamido)pyridin-4-yl)-2-methylpyrimidin-4-ylcarbamate

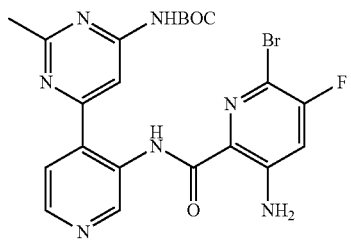

Method 27 was followed using tert-butyl 6-(3-aminopyridin-4-yl)-2-methylpyrimidin-4-ylcarbamate (1.0 equiv.), 3-amino-6-bromo-5-fluoropicolinic acid (1.0 equiv.), EDC (1.0 equiv.), and HOAt (1.0 equiv.) in DMF yielding tert-butyl 6-(3-(3-amino-6-bromo-5-fluoropicolinamido)pyridin-4-yl)-2-methylpyrimidin-4-ylcarbamate in 15% yield. LCMS (m/z): 520.1 (MH$^+$); LC R$_t$=3.4 min.

Synthesis of tert-butyl 443-(3-amino-6-bromo-5-fluoropicolinamido)pyridin-4-yl)-6-methylpyrimidin-2-ylcarbamate

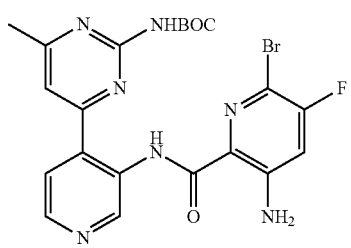

Method 27 was followed using tert-butyl 4-(3-aminopyridin-4-yl)-2-methylpyrimidin-4-ylcarbamate (1.0 equiv.), 3-amino-6-bromo-5-fluoropicolinic acid (1.0 equiv.), EDC (1.0 equiv.), and HOAt (1.0 equiv.) in DMF yielding tert-butyl 4-(3-(3-amino-6-bromo-5-fluoropicolinamido)pyridin-4- yl)-6-methylpyrimidin-2-ylcarbamate 20% yield. LCMS (m/z): 618.1 (MH¹); LC R$_t$=3.5 min.

Synthesis of tert-butyl 6-(3-(6-bromopicolinamido)pyridin-4-yl)-2-(trifluoromethyl)pyrimidin-4-ylcarbamate

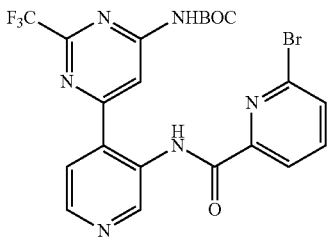

Method 27 was followed using tert-butyl 6-(3-aminopyridin-4-yl)-2-(trifluoromethyl)pyrimidin-4-ylcarbamate (1.0 equiv.), 6-bromopicolinic acid (1.0 equiv.), EDC (1.0 equiv.), and HOAt (1.0 equiv.) in NMP yielding tert-butyl 6-(3-(6-bromopicolinamido)pyridin-4-yl)-2-(trifluoromethyl)pyrimidin-4-ylcarbamate>95% yield. LCMS (m/z): 539/541 (MH⁺); LC R$_t$=3.97 min.

Synthesis of 2-chloro-3-iodo-6-(trifluoromethyl)pyridine

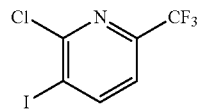

To a cooled solution (−78° C.) of n-BuLi (1.0 equiv.) in THF (0.8M) was added diisopropylamine (1.0 equiv.) dropwise, maintaining the internal temperature under −70° C. The solution was stirred for 30 min, then 2-chloro-6-(trifluoromethyl)pyridine (1.0 equiv.) in THF was added dropwise. The solution was stirred for another 30 min, then I2 was added as a solid. Stirred for 1 hr at −78° C., then allowed the reaction to warm to room temperature overnight. The solution was quenched by addition of H$_2$O, extracted with EtOAc, then washed with brine, and concentrated. The crude material was purified via SiO$_2$ column chromatography eluting with EtOAc and hexanes (1:10) to yield 2-chloro-3-iodo-6-(trifluoromethyl)pyridine in 35% yield. LCMS (m/z): 307.8 (MH⁺); LC R$_t$=4.18 min.

Synthesis of 2-chloro-4-iodo-6-(trifluoromethyl)pyridine

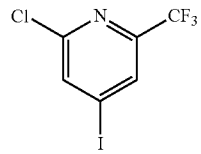

To a cooled (−75° C.) solution of THF was added n-BuLi (1.1 equiv.), followed by diisopropylamine (1.1 equiv.), dropwise. The reaction was stirred for 10 min, then 2-chloro-3-iodo-6-(trifluoromethyl)pyridine (1.0 equiv.) was added dropwise in THF. The solution was stirred at −75° C. for 1 hr, then quenched with the addition of 1N HCl, extracted with EtOAc, washed with brine, dried with MgSO$_4$, and concentrated to give a tan solid in 85% yield. LCMS (m/z): 307.8 (MH⁺); LC R$_t$=4.28 min.

Synthesis of N-(3,4-dimethoxybenzyl)-4-iodo-6-(trifluoromethyl)pyridin-2-amine

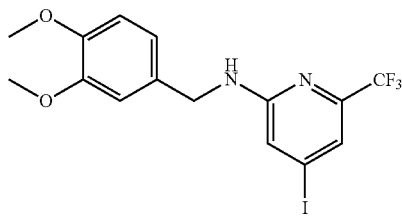 [SMILES: COc1ccc(CNc2cc(I)cc(C(F)(F)F)n2)cc1OC]

A solution of 2-chloro-4-iodo-6-(trifluoromethyl)pyridine (1.0 equiv.), (3,4-dimethoxyphenyl)methanamide (5.0 equiv.), and Et$_3$N (5.0 equiv.) in NMP (0.7M) was microwaved to 100° C. for 10 min. The solution was directly purified via reverse phase HPLC, the pure fractions were neutralized with solid NaHCO$_3$, extracted with EtOAc, dried with MgSO$_4$, and concentrated to give N-(3,4-dimethoxybenzyl)-4-iodo-6-(trifluoromethyl)pyridin-2-amine in 36% yield. LCMS (m/z): 347.1 (MH⁺); LC R$_t$=3.96 min.

Synthesis of methyl 3-amino-6-(2,6-difluorophenyl)picolinate

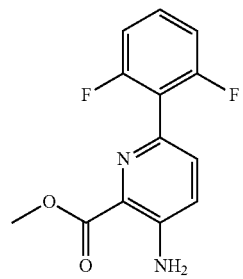 [SMILES: COC(=O)c1nc(-c2c(F)cccc2F)ccc1N]

A solution of methyl 3-amino-6-bromopicolinate (1.0 equiv.), 2,6-difluorophenyl-boronic acid (3.0 equiv), and Pd(dppf)Cl$_2$-DCM (0.1 equiv.) in 3:1 DME/2M Na$_2$CO$_3$ (0.5M) was subjected to microwave irradiation at 120° C. for 15 min intervals. The reaction was filtered and washed with EtOAc. The organic was partitioned with H$_2$O (25 mL), was further washed with NaCl$_{(sat.)}$ (25 mL), was dried over MgSO$_4$, and the volatiles were removed in vacuo. The residue was diluted in EtOAc and passed through a silica gel plug and the volatiles were removed in vacuo yielding methyl 3-amino-6-(2,6-difluorophenyl)picolinate (47%). LCMS (m/z): 265.1 (MH⁺); LC R$_t$=2.70 min.

Synthesis of 3-amino-6-(2,6-difluorophenyl)picolinic acid

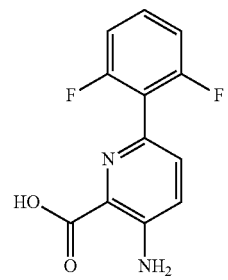 [SMILES: Nc1ccc(-c2c(F)cccc2F)nc1C(=O)O]

To a solution of methyl 3-amino-6-(2,6-difluorophenyl)picolinate (1.0 equiv) in THF (0.5M), was added 1M LiOH (4.0 equiv). After stirring for 4 hours at 60° C., 1 N HCl (4.0 equiv.) was added and the THF was removed in vacuo. The resulting solid was filtered and rinsed with cold H₂O (3×20 mL) to yield 3-amino-6-(2,6-difluorophenyl)picolinic acid (90%). LCMS (m/z): 251.1 (MH⁺); LC R$_t$=2.1 min.

Synthesis of methyl 3-amino-6-(thiazol-2-yl)picolinate

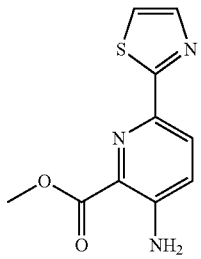 [SMILES: COC(=O)c1nc(-c2nccs2)ccc1N]

A solution of methyl 3-amino-6-bromopicolinate (1.0 equiv.), 2-thiazolylzinc bromide 0.5 M solution in THF (3.0 equiv.), and Pd(dppf)Cl₂-DCM (0.05 equiv.) was stirred at 80° C. for 1.5 hours. The reaction was filtered and washed with EtOAc. The organic was washed with H₂O (100 mL), and further washed with NaCl$_{(sat.)}$ (50 mL), dried over MgSO₄, and the volatiles were removed in vacuo. The product was crystallized with hexane/EtOAc (1:1) to yield methyl 3-amino-6-(thiazol-2-yl)picolinate (51%). LCMS (m/z): 236.1 (MH⁺); LC R$_t$=2.3 min.

Synthesis of 3-amino-6-(thiazol-2-yl)picolinic acid

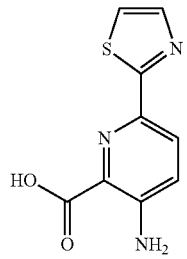

To a solution of methyl 3-amino-6-(thiazol-2-yl)picolinate (1.0 equiv) in THF (0.5M), was added 1M LiOH (4.0 equiv). After stirring for 4 hours at 60° C., 1 N HCl (4.0 equiv.) was added and the THF was removed in vacuo. The resulting solid was filtered and rinsed with cold H2O (3×20 mL) to yield 3-amino-6-(thiazol-2-yl)picolinic acid (61%). LCMS (m/z): 222.1 (MH⁺); LC R$_t$=1.9 min.

Synthesis of methyl 3-amino-6-(2-fluoro-5-isopropylcabamoyl)phenyl)picolinate

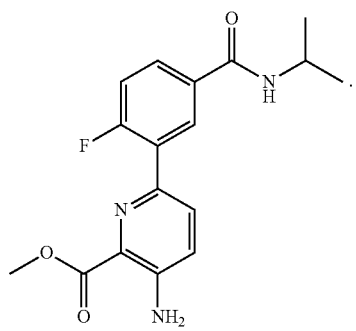 [SMILES: COC(=O)c1nc(-c2cc(C(=O)NC(C)C)ccc2F)ccc1N]

A solution of methyl 3-amino-6-bromopicolinate (1.0 equiv.), N-iso-propyl 3-borono-4-fluorobenzamide (1.1 equiv.), and Pd(dppf)Cl₂-DCM (0.15 equiv.) in DME/2M Na₂CO₃ (3:1), at a concentration of 0.5 M, was stirred at 120° C. for 1.5 hours. The reaction was filtered and washed with EtOAc. The organic was partitioned with H₂O (25 mL), washed with NaCl$_{(sat.)}$ (25 mL), dried over MgSO₄, and the volatiles were removed in vacuo. The residue was diluted in EtOAc and passed through a silica gel plug and the volatiles were removed in vacuo yielding methyl 3-amino-6-(2-fluoro-5-iso-propylcabamoyl)phenyl)picolinate (60%). LCMS (m/z): 332.2 (MH⁺); LC R$_t$=2.9 min.

Synthesis of 3-amino-6-(2-fluoro-5-isopropylcabamoyl)phenyl)picolinic acid

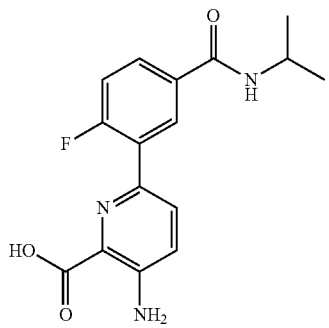 [SMILES: CC(C)NC(=O)c1ccc(F)c(-c2ccc(N)c(C(=O)O)n2)c1]

To a solution of methyl 3-amino-6-(2-fluoro-5-isopropyl-cabamoyl)phenyl)picolinate (1.0 equiv) in THF (0.5M), was added 1M LiOH (4.0 equiv). After stirring for 4 hours at 60° C., 1 N HCl (4.0 equiv.) was added and the THF was removed in vacuo. The resulting solid was filtered and rinsed with cold H₂O (3×20 mL) to yield 3-amino-6-(2-fluoro-5-isopropyl-cabamoyl)phenyl)picolinic acid (98%). LCMS (m/z): 318.1 (MH⁺); LC R$_t$=2.4 min

Synthesis of 3-amino-N-(4-chloropyridin-3-yl)-6-(2,6-difluorophenyl)picolinamide

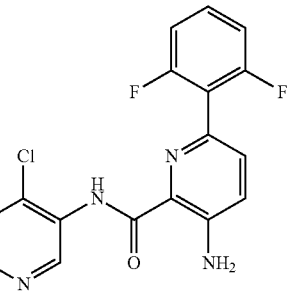

A solution of 3-amino-6-(2,6-difluorophenyl)picolinic acid (1.0 equiv.), 4-chloropyridin-3-amine (2.0 equiv.), HOAt (1.0 equiv.), and EDC (1.0 equiv.) in DCM at a concentration of (0.2M) was stirred for 24 hr. Water was added to the reaction, followed by EtOAc. The organic layer was separated, dried with brine, MgSO₄, and concentrated. The crude material was purified via SiO₂ column chromatography eluting with EtOAc and hexanes (1:1) to give the product as a light yellow solid (21% yield). LCMS (m/z): 361.1 (MH⁺); LC R$_t$=3.28 min.

Method 28

Synthesis of 3-amino-6-(2,6-difluorophenyl)-N-(3'-fluoro-4,4'-bipyridin-3-yl)picolinamide

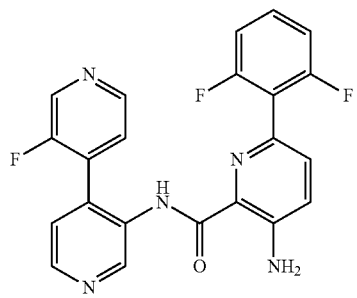 [SMILES: Nc1ccc(-c2c(F)cccc2F)nc1C(=O)Nc1cnccc1-c1ccncc1F]

A solution of 3-amino-N-(4-chloropyridin-3-yl)-6-(2,6-difluoro-phenyl)picolinamide (1.0 equiv.), 3-fluoropyridin-4-yl boronic acid (3.0 equiv.), and Pd(dppf)Cl$_2$-DCM (0.10 equiv.) in DME/2M Na$_2$CO$_3$ (3:1) was heated to 120° C. with microwave irradiation for 10 min. Upon cooling, the reaction was extracted with EtOAc, the organic layer was dried with Na$_2$SO$_4$ and concentrated. The crude material was purified via reverse phase HPLC. The product fraction was lyophilized to give 3-amino-6-(2,6-difluorophenyl)-N-(3'-fluoro-4,4'-bipyridin-3-yl)picolinamide as the TFA salt in 12% yield. LCMS (m/z): 404.1 (MH$^+$); LC R$_t$=2.92 min.

The following compounds were prepared using Method 28:

| Example | Structure | Name | MH+ | LC |
|---|---|---|---|---|
| 601 | 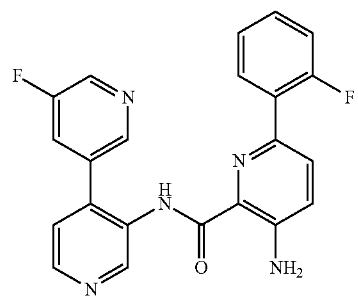 [SMILES: Nc1ccc(-c2ccccc2F)nc1C(=O)Nc1cnccc1-c1cncc(F)c1] | 3-amino-N-(5-fluoro-3,4'-bipyridin-3-yl)-6-(2-fluorophenyl)pyridine-2-carboxamide | 404.1 | 2.96 |
| 602 | 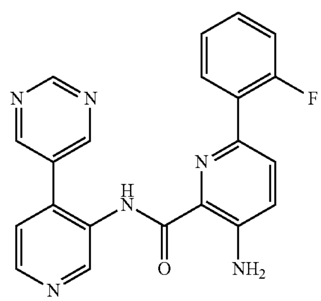 [SMILES: Nc1ccc(-c2ccccc2F)nc1C(=O)Nc1cnccc1-c1cncnc1] | 3-amino-6-(2-fluorophenyl)-N-(4-pyrimidin-5-ylpyridin-3-yl)pyridine-2-carboxamide | 387.1 | 2.62 |
| 603 | 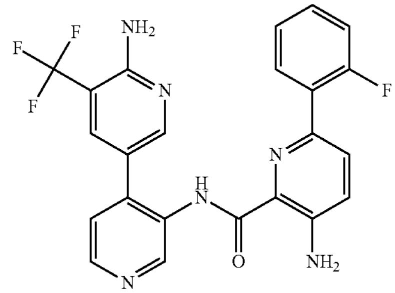 [SMILES: Nc1ccc(-c2ccccc2F)nc1C(=O)Nc1cnccc1-c1cnc(N)c(C(F)(F)F)c1] | 3-amino-N-[6-amino-5-(trifluoromethyl)-3,4'-bipyridin-3'-yl]-6-(2-fluorophenyl)pyridine-2-carboxamide | 469.1 | 2.90 |
| 604 | 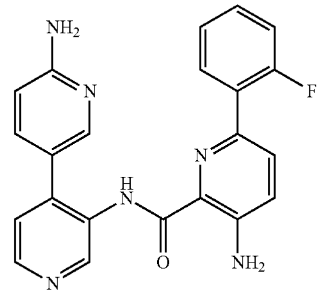 [SMILES: Nc1ccc(-c2ccncc2NC(=O)c2nc(-c3ccccc3F)ccc2N)cn1] | 3-amino-N-(6-amino-3,4'-bipyridin-3'-yl)-6-(2-fluoro-phenyl)pyridine-2-carboxamide | 401.1 | 2.04 |

-continued

| Example | Structure | Name | MH+ | LC |
|---|---|---|---|---|
| 605 | 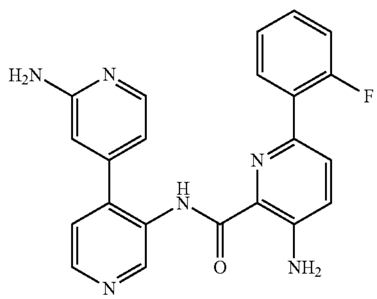 [SMILES: Nc1cc(-c2ccncc2NC(=O)c2nc(-c3ccccc3F)ccc2N)ccn1] | 3-amino-N-(2'-amino-4,4'-bipyridin-3-yl)-6-(2-fluorophenyl)pyridine-2-carboxamide | 401.1 | 2.13 |
| 606 | 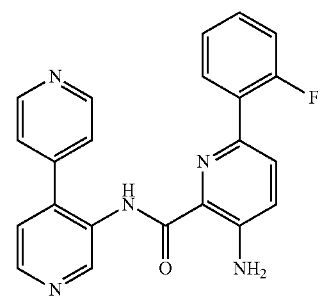 [SMILES: Nc1ccc(-c2ccccc2F)nc1C(=O)Nc1cnccc1-c1ccncc1] | 3-amino-N-4,4'-bipyridin-3-yl-6-(2-fluorophenyl)-pyridine-2-carboxamide | 386.1 | 2.36 |
| 607 | 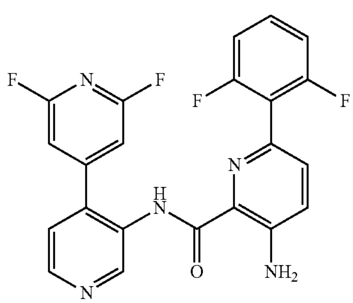 [SMILES: Nc1ccc(-c2c(F)cccc2F)nc1C(=O)Nc1cnccc1-c1cc(F)nc(F)c1] | 3-amino-N-(2',6'-difluoro-4,4'-bipyridin-3-yl)-6-(2,6-difluorophenyl)pyridine-2-carboxamide | 440.1 | 3.34 |
| 608 | 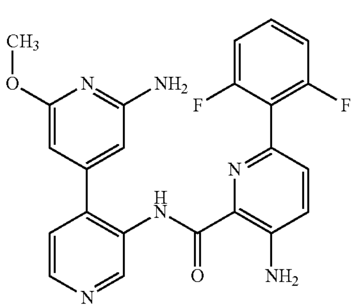 | 3-Amino-6-(2,6-difluoro-phenyl)-pyridine-2-carboxylic acid (6'-amino-2'-methoxy-[4,4']bi-pyridinyl-3-yl)-amide | 449.1 | 2.44 |
| 609 | 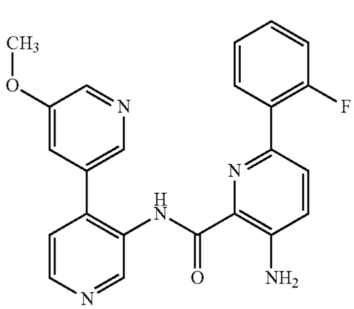 [SMILES: COc1cncc(-c2ccncc2NC(=O)c2nc(-c3ccccc3F)ccc2N)c1] | 3-amino-6-(2-fluorophenyl)-N-(5-methoxy-3,4'-bipyfidin-3'-yl)pyridine-2-carboxamide | 416.2 | 2.65 |

-continued

| Example | Name | MH+ | LC |
|---|---|---|---|
| 610 | 3-amino-6-(2-fluorophenyl)-N-(3'-methoxy-4,4'-bipyridin-3-yl)pyridine-2-carboxamide | 416.1 | 2.47 |
| 611 | 3-amino-6-(2-fluorophenyl)-N-(2-methoxy-3,4'-bipyridin-3'-yl)pyridine-2-carboxamide | 416.1 | 3.07 |
| 612 | 3-amino-6-(2,6-difluorophenyl)-N-(2-hydroxy-5'-methyl-4,4'-bipyridin-3-yl)pyridine-2-carboxamide | 434.0 | 2.22 |
| 613 | 3-amino-6-(2-fluorophenyl)-N-(3'-methyl-4,4'-bipyridin-3-yl)pyridine-2-carboxamide | 400.1 | 2.31 |
| 614 | 3-amino-6-(2-fluorophenyl)-N-(2'-hydroxy-4,4'-bipyridin-3-yl)pyridine-2-carboxamide | 402.0 | 2.22 |

-continued

| Example | Structure | Name | MH+ | LC |
|---|---|---|---|---|
| 615 | 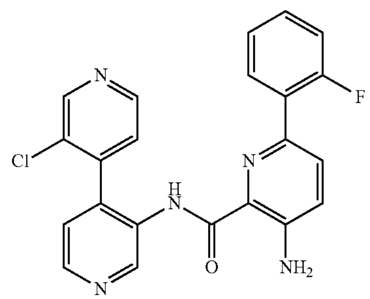 [SMILES: Nc1ccc(-c2ccccc2F)nc1C(=O)Nc1cnccc1-c1ccncc1Cl] | 3-amino-N-(3'-chloro-4,4'-bipyridin-3-yl)-6-(2-fluorophenyl)pyridine-2-carboxamide | 420.1 | 3.02 |
| 616 | 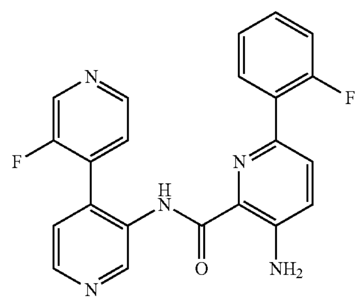 [SMILES: Nc1ccc(-c2ccccc2F)nc1C(=O)Nc1cnccc1-c1ccncc1F] | 3-amino-N-(3'-fluoro-4,4'-bipyridin-3-yl)-6-(2-fluorophenyl)pyridine-2-carboxamide | 404.1 | 2.92 |
| 617 | 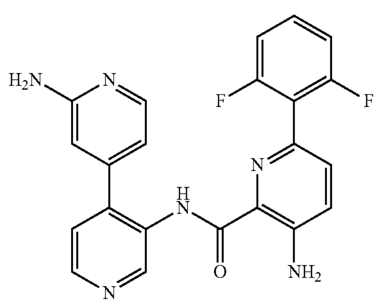 [SMILES: Nc1cc(-c2ccncc2NC(=O)c2nc(-c3c(F)cccc3F)ccc2N)ccn1] | 3-amino-N-(2'-amino-4,4'-bipyridin-3-yl)-6-(2,6-difluorophenyl)pyridine-2-carboxamide | 419.1 | 2.09 |
| 618 | 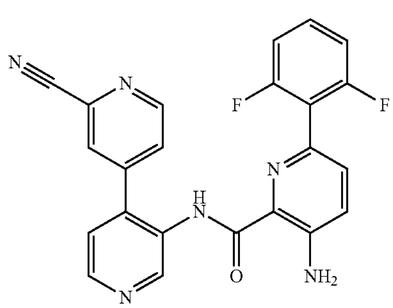 [SMILES: N#Cc1cc(-c2ccncc2NC(=O)c2nc(-c3c(F)cccc3F)ccc2N)ccn1] | 3-amino-N-(2'-cyano-4,4'-bipyridin-3-yl)-6-(2,6-difluorophenyl)pyridine-2-carboxamide | 429.1 | 2.93 |

Method 29

Synthesis of 3-amino-N-(4-(6-aminopyrazin-2-yl)pyridine-3-yl)-6-(2-fluorophenyl)picolinamide

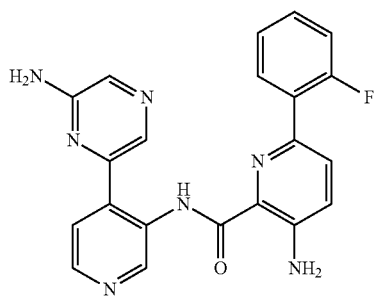

A solution of 3-amino-N-(4-chloropyridin-3-yl)-6-(2,6-difluoro-phenyl)picolinamide (1.0 equiv.), bis(pinacolato)diboron (2.0 equiv.), Pd(dppf)Cl$_2$-DCM (0.10 equiv.), KOAc (2.0 equiv.) in dioxane (0.19 M) was stirred in the microwave for 5 min at 120° C. then 10 min at 120° C. The reaction was filtered and concentrated. To the crude was added 6-chloro-pyrazin-2-amine (2.0 equiv.) and more Pd(dppf)Cl$_2$-DCM (0.10 equiv.) in DME/2M Na$_2$CO$_3$ (3:1, 0.1M). The reaction was heated to 100° C. in the oil bath for 2 hrs. Cooled to room temperature, added H$_2$O and EtOAc, the organic layer was extracted, dried with brine and Na$_2$SO$_4$, and concentrated. The crude mixture was purified via reverse-phase HPLC and the pure fractions were lyophilized to give 3-amino-N-(4-(6-aminopyrazin-2-yl)pyridine-3-yl)-6-(2-fluorophenyl)picolinamide as the TFA salt in 19% yield. LCMS (m/z): 402.1 (MH$^+$); LC R$_t$=2.58 min.

The following compounds were prepared using Method 29:

| Example | Structure | Name | MH+ | LC |
|---|---|---|---|---|
| 619 | 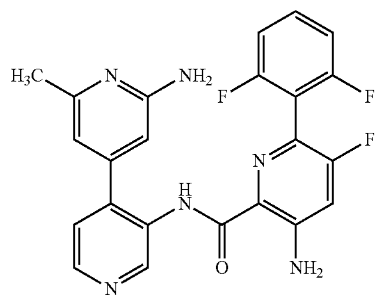 [SMILES: Cc1cc(-c2ccncc2NC(=O)c2nc(-c3c(F)cccc3F)c(F)cc2N)cc(N)n1] | 3-amino-N-(2'-amino-6'-methyl-4,4'-bipyridin-3-yl)-6-(2,6-difluorophenyl)-5-fluoropyridine-2-carboxamide | 451.2 | 2.29 |
| 620 | 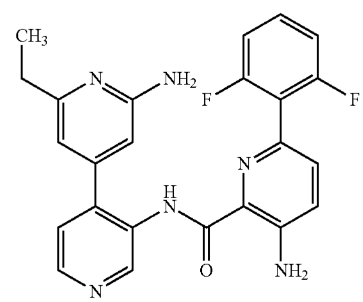 [SMILES: CCc1cc(-c2ccncc2NC(=O)c2nc(-c3c(F)cccc3F)ccc2N)cc(N)n1] | 3-Amino-6-(2,6-difluoro-phenyl)-pyridine-2-carboxylic acid (6'-amino-2'-ethyl-[4,4']bipyridinyl-3-yl)-amide | 447.1 | 2.34 |
| 621 | 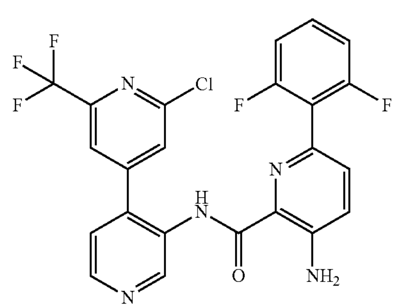 | 3-amino-N-[2'-chloro-6'-(trifluoromethyl)-4,4'-bipyridin-3-yl]-6-(2,6-difluorophenyl)pyridine-2-carboxamide | 506.1 | 3.75 |

-continued

| Example | Structure | Name | MH+ | LC |
|---------|-----------|------|-----|-----|
| 622 | 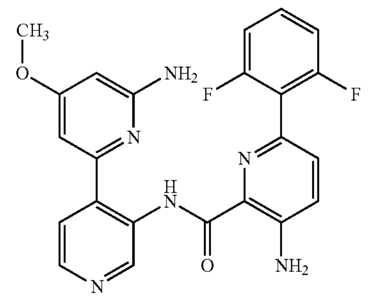 [SMILES: COc1cc(N)nc(-c2ccncc2NC(=O)c2nc(-c3c(F)cccc3F)ccc2N)c1] | 3-Amino-6-(2,6-difluoro-phenyl)-pyridine-2-carboxylic acid (6-amino-4-methoxy-[2,4']bipyridinyl-3'-yl)-amide | 449.1 | 2.46 |
| 623 | 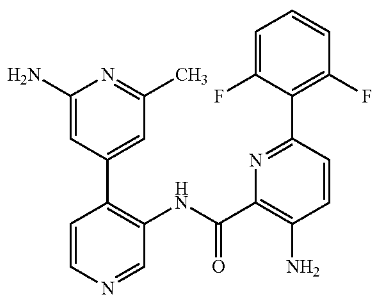 | 3-amino-N-(2'-amino-6'-methyl-4,4'-bipyridin-3-yl)-6-(2,6-difluorophenyl)pyridine-2-carboxamide | 433.1 | 2.28 |
| 624 | 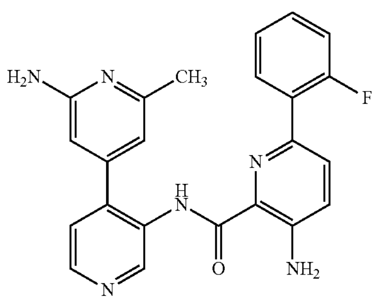 [SMILES: Cc1cc(-c2ccncc2NC(=O)c2nc(-c3ccccc3F)ccc2N)cc(N)n1] | 3-amino-N-(2'-amino-6'-methyl-4,4'-bipyridin-3-yl)-6-(2-fluorophenyl)pyridine-2-carboxamide | 2.0 | 2.22 |
| 625 | 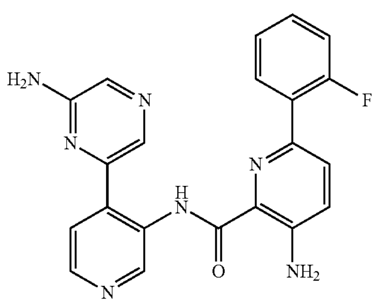 [SMILES: Nc1cncc(-c2ccncc2NC(=O)c2nc(-c3ccccc3F)ccc2N)n1] | 3-amino-N-[4-(6-amino-pyrazin-2-yl)pyridin-3-yl]-6-(2-fluorophenyl)pyridine-2-carboxamide | 402.1 | 2.58 |
| 626 | 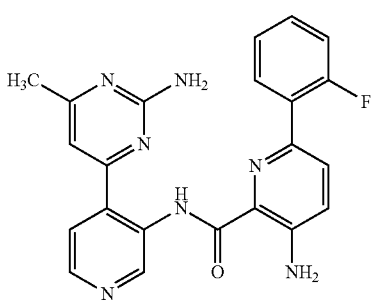 | 3-amino-N-[4-(2-amino-6-methylpyrimidin-4-yl)-pyridine-3-yl]-6-(2-fluoro-phenyl)pyridine-2-carboxamide | 416.1 | 2.62 |

| Example | Structure | Name | MH+ | LC |
|---|---|---|---|---|
| 627 | 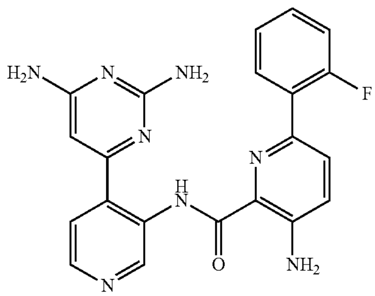 [SMILES: Cc1cc(-c2ccncc2NC(=O)c2nc(-c3ccccc3F)ccc2N)nc(N)n1] | 3-amino-N-[4-(2,6-diaminopyrimidin-4-yl)pyridin-3-yl]-6-(2-fluorophenyl)pyridine-2-carboxamide | 417.0 | 2.13 |
| 628 | 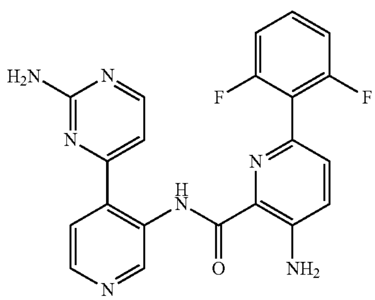 | 3-amino-N-[4-(2-aminopyrimidin-4-yl)pyridin-3-yl]-6-(2,6-difluorophenyl)pyridine-2-carboxamide | 420.1 | 2.51 |
| 629 | 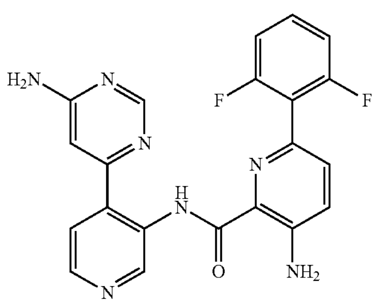 [SMILES: Nc1cc(-c2ccncc2NC(=O)c2nc(-c3c(F)cccc3F)ccc2N)ncn1] | 3-amino-N-[4-(6-aminopyrimidin-4-yl)pyridin-3-yl]-6-(2,6-difluorophenyl)pyridine-2-carboxamide | 420.1 | 2.56 |
| 630 | 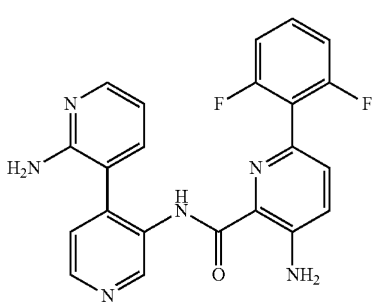 | 3-amino-N-(2-amino-3,4'-bipyridin-3'-yl)-6-(2,6-difluorophenyl)pyridine-2-carboxamide | 419.1 | 2.12 |

Method 30

Synthesis of (s)-3-amino-N-(4-(3-aminopiperidin-1-yl)pyridine-3-yl)-6-cyclohexylpicolinamide

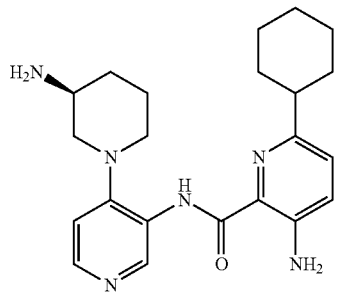 [SMILES: Nc1ccc(C2CCCCC2)nc1C(=O)Nc1cnccc1N1CCC[C@H](N)C1]

A solution of (S)-tert-butyl 1-(3-(3-amino-6-bromo-picolinamido)pyridin-4-yl)piperidin-3-ylcarbamate (1.0 equiv.), cyclohexylzinc bromide (0.5 M solution in THF, 3.0 equiv), Pd$_2$(dba)$_3$ (0.1 equiv.), and P(2-furyl)$_3$ (0.2 equiv.) were heated to 65° C. for 18 hrs. Two more equivalents of zinc bromide reagent were added if the reaction was not complete after 18 hrs. The mixture was cooled to rt and concentrated to give the crude material. The crude mixture was then stirred in DCM/TFA (25%) until completion. Concentrated the reaction to dryness and purified via reverse phase HPLC. The pure fractions were lyophilized to give the TFA salt product (40%). LCMS (m/z): 395.3 (MH$^+$); LC R$_t$=2.34 min.

Synthesis of 3-amino-N-(4-(6-amino-2-(trifluoromethyl)pyrimidin-4-yl)pyridin-3-yl)-6-(thiazol-2-yl)picolinamide

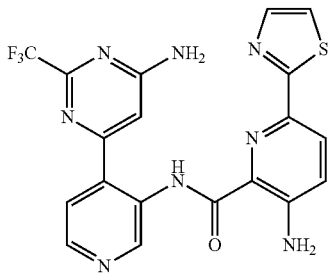 [SMILES: Nc1cc(-c2ccncc2NC(=O)c2nc(-c3nccs3)ccc2N)nc(C(F)(F)F)n1]

Following method 30, a solution of tert-butyl 6-(3-(3-amino-6-bromopicolinamido)pyridine-4-yl)-2-(trifluoromethyl)pyrimidin-4-ylcarbamate (1.0 equiv.), 2-thiazolylzincbromide (3.5 equiv.), and Pd(dppf)Cl$_2$-DCM (0.10 equiv.) in THF was microwaved at 100° C. for 15 min. The reaction was concentrated to dryness under vacuo, then stirred in DCM/TFA (25%) for two hours. Upon concentration and purification via reverse phase HPLC, 3-amino-N-(4-(6-amino-2-(trifluoro-methyl)pyrimidin-4-yl)pyridin-3-yl)-6-(thiazol-2-yl)picolinamide was obtained as the TFA salt in 48% yield. LCMS (m/z): 459.1 (MH$^+$); LC R$_t$=2.46 min.

The following compounds were also prepared using Method 30:

| Example | Structure | Name | MH+ | LC |
|---|---|---|---|---|
| 631 | Chiral | N-{4-[(3S)-3-amino-piperidin-1-yl]pyridin-3-yl}-6-(1,3-thiazol-2-yl)pyridine-2-carboxamide | 381.1 | 1.54 |
| 632 | Chiral | 3-amino-N-{4-[(3S)-3-aminopiperidin-1-yl]pyridin-3-yl}-6-(1,3-thiazol-2-yl)-pyridine-2-carboxamide | 396.1 | 1.56 |

-continued

| Example | Structure | Name | MH+ | LC |
|---|---|---|---|---|
| 633 | 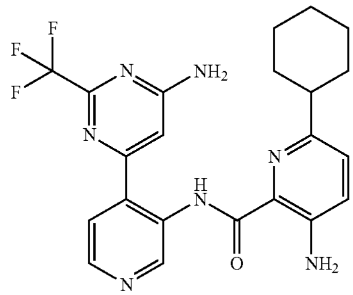 [SMILES: Nc1cc(-c2ccncc2NC(=O)c2nc(C3CCCCC3)ccc2N)nc(C(F)(F)F)n1] | 3-Amino-6-cyclohexyl-pyridine-2-carboxylic acid [4-(6-amino-2-trifluoro-methyl-pyrimidin-4-yl)-pyridin-3-yl]-amide | 457.9 | 3.44 |
| 634 | 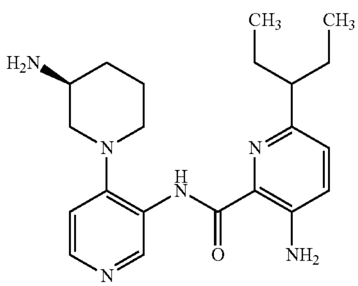 [SMILES: CCC(CC)c1ccc(N)c(C(=O)Nc2cnccc2N2CCC[C@H](N)C2)n1] | 3-Amino-6-(1-ethyl-propyl)-pyridine-2-carboxylic acid (3-amino-3,4,5,6-tetrahydro-2H-[1,4']bipyridinyl-3'-yl)-amide | 383.2 | 2.44 |
| 635 | 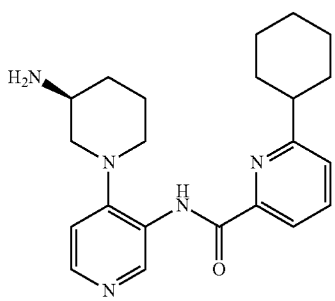 [SMILES: N[C@H]1CCCN(c2ccncc2NC(=O)c2cccc(C3CCCCC3)n2)C1] | 6-Cyclohexyl-pyridine-2-carboxylic acid (3-amino-3,4,5,6-tetrahydro-2H-[1,4']bipyridinyl-3'-yl)-amide | 380.2 | 2.24 |
| 636 | 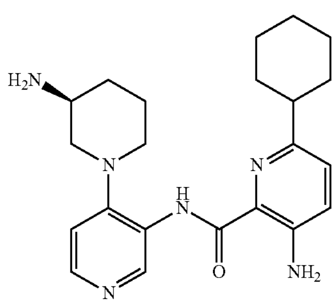 [SMILES: Nc1ccc(C2CCCCC2)nc1C(=O)Nc1cnccc1N1CCC[C@H](N)C1] | 3-Amino-6-cyclohexyl-pyridine-2-carboxylic acid (3-amino-3,4,5,6-tetrahydro-2H-[1,4']bipyridinyl-3'-yl)-amide | 395.3 | 2.34 |
| 637 | 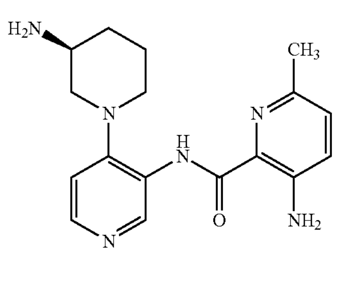 [SMILES: Cc1ccc(N)c(C(=O)Nc2cnccc2N2CCC[C@H](N)C2)n1] | 3-amino-N-{4-[(3S)-3-aminopiperidin-1-yl]pyridin-3-yl}-6-methylpyridine-2-carboxamide | 327.1 | 1.38 |

-continued

| Example | Name | MH+ | LC |
|---|---|---|---|
| 638 | 3-amino-N-{4-[(3S)-3-aminopiperidin-1-yl]pyridin-3-yl}-6-cyclopropyl-pyridine-2-carboxamide | 353.1 | 1.70 |
| 639 | 3-amino-N-{4-[(3S)-3-aminopiperidin-1-yl]pyridin-3-yl}-6-ethylpyridine-2-carboxamide | 341.1 | 1.59 |
| 640 | 3-amino-N-[2'-amino-6'-(trifluoromethyl)-4,4'-bipyridin-3-yl]-6-(1,3-thiazol-2-yl)pyridine-2-carboxamide | 458.1 | 2.59 |
| 641 | 3-amino-N-(2'-amino-6'-methyl-4,4'-bipyridin-3-yl)-6-(1,3-thiazol-2-yl)pyridine-2-carboxamide | 404.1 | 1.79 |
| 642 | 3-amino-N-{4-[6-amino-2-(trifluoromethyl)pyrimidin-4-yl]pyridin-3-yl}-6-(1,3-thiazol-2-yl)pyridine-2-carboxamide | 459.1 | 2.46 |

-continued

| Example | Structure | Name | MH+ | LC |
|---|---|---|---|---|
| 643 | 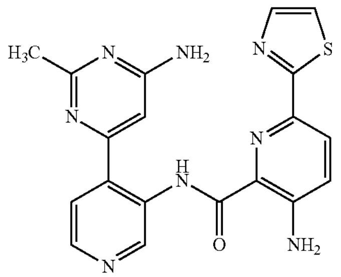 [SMILES: Cc1nc(N)cc(-c2ccncc2NC(=O)c2nc(-c3nccs3)ccc2N)n1] | 3-amino-N-[4-(6-amino-2-methylpyrimidin-4-yl)pyridin-3-yl]-6-(1,3-thiazol-2-yl)pyridine-2-carboxamide | 405.0 | 1.74 |
| 644 | 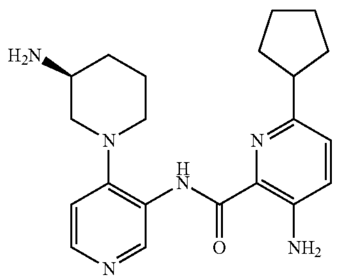 [SMILES: Nc1ccc(C2CCCC2)nc1C(=O)Nc1cnccc1N1CCC[C@H](N)C1] | 3-Amino-6-cyclopentyl-pyridine-2-carboxylic acid (3-amino-3,4,5,6-tetrahydro-2H-[1,4']bipyridinyl-3'-yl)-amide | 381.3 | 2.13 |
| 645 | 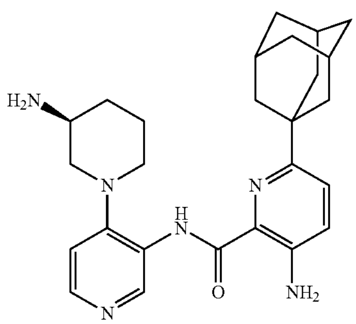 [SMILES: Nc1ccc(C23CC4CC(CC(C4)C2)C3)nc1C(=O)Nc1cnccc1N1CCC[C@H](N)C1] | 6-Adamantan-1-yl-3-amino-pyridine-2-carboxylic acid (3-amino-3,4,5,6-tetrahydro-2H-[1,4']bipyridinyl-3'-yl)-amide | 447.2 | 2.70 |
| 646 | 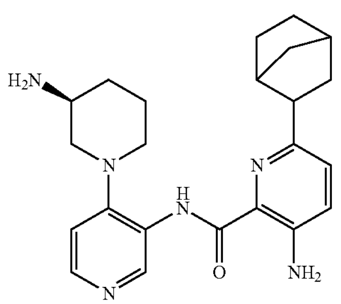 [SMILES: Nc1ccc(C2CC3CCC2C3)nc1C(=O)Nc1cnccc1N1CCC[C@H](N)C1] | 3-Amino-6-bicyclo[2.2.1]hept-2-yl-pyridine-2-carboxylic acid (3-amino-3,4,5,6-tetrahydro-2H-[1,4']bipyridinyl-3'-yl)-amide | 407.2 | 2.37 |
| 647 | 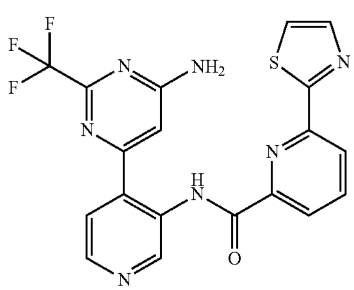 [SMILES: Nc1cc(-c2ccncc2NC(=O)c2cccc(-c3nccs3)n2)nc(C(F)(F)F)n1] | N-{4-[6-amino-2-(trifluoromethyl)pyrimidin-4-yl]-pyridin-3-yl}-6-(1,3-thiazol-2-yl)pyridine-2-carboxamide | 444.1 | 2.67 |

Synthesis of 4-chloro-6-methylpyridin-2-amine

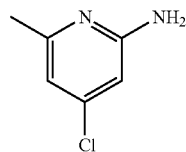

To a 10% aqueous solution of dioxane (0.1 M) was added 4,6-dichloropyridin-2-amine (1.0 equiv.), trimethylboroxine (1.5 equiv.), Pd(PPh$_3$)$_4$ (0.10 equiv.) and K$_2$CO$_3$ (3.0 equiv.). The solution was heated in an oil bath to 120° C. for 18 hrs, cooled to room temperature (not all of starting material was consumed), extracted with EtOAc, dried with Na$_2$SO$_4$, and concentrated. The crude material was purified via SiO$_2$ column chromatography eluting with 5% MeOH/DCM to yield an off-white solid in 23% yield. LCMS (m/z): 143 (MH$^+$); LC R$_t$=1.11 min.

Synthesis of 6-methyl-3'-nitro-4,4'-bipyridin-2-amine

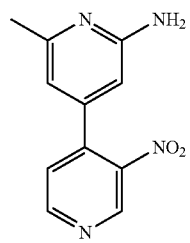 [SMILES: Cc1cc(-c2ccncc2[N+](=O)[O-])cc(N)n1]

To a solution of 4-chloro-6-methylpyridin-2-amine (1.0 equiv.) in dioxane was added bis(pinacolato)diboron (2.0 equiv.), Pd$_2$(dba)$_3$ (0.05 equiv.), PCy$_3$ (0.075 equiv.), and KOAc (3.0 equiv.). The reaction was heated for 3 hrs at 110° C., then filtered, and concentrated. The crude material was dried under vacuo, then dissolved in DME/2M Na$_2$CO$_3$ (3:1), 4-chloro-3-nitropyridine (2.0 equiv.) was added, followed by Pd(dppf)Cl$_2$-DCM (0.1 equiv.). The mixture was heated to 120° C. for 1 hr, then EtOAc and H$_2$O were added, the organic phase was removed, dried with Na$_2$SO$_4$, and concentrated. Purification via SiO$_2$ column chromatography eluting with EtOAc yielded 6-methyl-3'-nitro-4,4'-bipyridin-2-amine in 35% yield. LCMS (m/z): 231.1 (MH$^+$) LC R$_t$=1.47 min.

Synthesis of 6-ethyl-N,N-di-BOC-3'-nitro-4,4'-bipyridin-2-amine

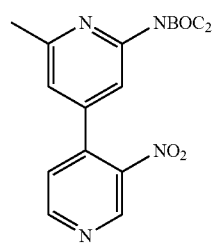

To a solution of 6-methyl-3'-nitro-4,4'-bipyridin-2-amine in THF (0.09M) was added BOC$_2$O (2.2 equiv.), Et$_3$N (2.5 equiv.), and DMAP (cat.). After 5 hrs, the solution was concentrated and filtered through a plug of SiO$_2$ eluting with EtOAc to yield 6-ethyl-N,N-di-BOC-3'-nitro-4,4'-bipyridin-2-amine in >95% yield. LCMS (m/z): 431.1 (MH$^+$); LC R$_t$=4.29 min.

Synthesis of 6-ethyl-N2,N2-di-BOC-4,4'-bipyridine-2,3'-diamine

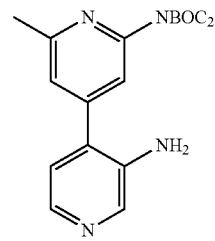

To a solution of 6-methyl-N,N-di-BOC-3'-nitro-4,4'-bipyridin-2-amine in EtOH/EtOAc (1:1, 0.2M) was added Pd/C (10% by weight) and the reaction was stirred under a H$_2$ balloon for 18 hrs. Filtered through Celite, washed with EtOAc and concentrated the filtrate to afford 6-ethyl-N$^2$,N$^2$-di-BOC-4,4'-bipyridine-2,3'-diamine in >95% yield. LCMS (m/z): 401.0 (MH$^+$); LC R$_t$=2.81 min.

Synthesis of 3-amino-6-bromo-N-(2'-(di-BOC-amino)-6'-methyl-4,4'-bipyridin-3-yl)picolinamide

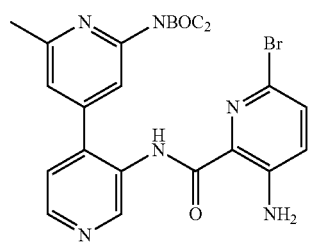

Method 27 was followed using 6-methyl-N$^2$,N$^2$-di-BOC-4,4'-bipyridine-2,3'-diamine (1.0 equiv.), 3-amino-6-bromopicolinic acid (1.0 equiv.), EDC (1.0 equiv.), HOAt (1.0 equiv.) in NMP (0.48M) to yield 3-amino-6-bromo-N-(2'-(di-BOC-amino)-6'-methyl-4,4'-bipyridin-3-yl)picolinamide (35%). LCMS (m/z): 599.1/601.1 (MH$^+$); LC R$_t$=3.69 min.

Synthesis of 4-chloro-6-ethylpyridin-2-amine

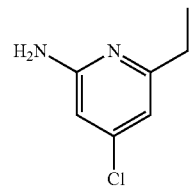

To a solution of 4,6-dichloropyridin-2-amine (1.0 equiv.) in THF (0.1M) was added Pd(dppf)Cl$_2$-DCM (0.1M), K$_2$CO$_3$ (3.0 equiv.), and Et$_2$Zn (1.2 equiv.). The reaction was heated to 70° C. for 18 hrs. Upon cooling to room temperature, NH$_4$Cl(sat.) was added, the mixture was extracted with EtOAc, dried with Na$_2$SO$_4$, and concentrated. The crude material was purified via SiO$_2$ column chromatography eluting with DCM/MeOH (2%) to yield 4-chloro-6-ethylpyridin-2-amine in 33% yield. LCMS (m/z): 157.1 (MH$^+$).

Synthesis of
4-chloro-6-ethyl-N,N-di-BOC-pyridin-2-amine

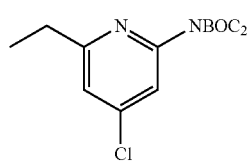

Method 24 was followed using 4-chloro-6-ethylpyridin-2-amine (1.0 equiv.), BOC$_2$O (2.0 equiv.), and DMAP (cat.) in DCM to yield 4-chloro-6-ethyl-N,N-di-BOC-pyridin-2-amine (27% yield). LCMS (m/z): 357.1 (MH$^+$); LC R$_t$=4.11 min.

Synthesis of 6-ethyl-N,N-di-BOC-4-(4,4,5,5-tetramethyl-1,3,2-dioxaborolan-2-yl)pyridin-2-amine

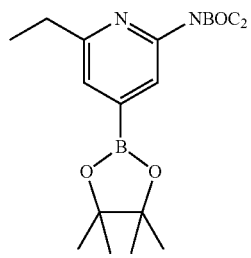

A solution of 4-chloro-6-ethyl-N,N-di-BOC-pyridin-2-amine (1.0 equiv.), bis(pinacolato)diboron (2.0 equiv.), Pd$_2$(dba)$_3$ (0.05 equiv.), PCy$_3$ (0.075 equiv.), KOAc (2.0 equiv.) in dioxane (0.19 M) was degassed by bubbling nitrogen through for 10 min in a round-bottomed flask. The flask was heated to 90° C. for 3 hours, cooled to room temperature, filtered through activated charcoal and Celite and washed with EtOAc. Upon concentration of the filtrate, a thick dark brown crude 6-ethyl-N,N-di-BOC-4-(4,4,5,5-tetramethyl-1,3,2-dioxaborolan-2-yl)pyridin-2-amine. LCMS (m/z): 367.1 (MH$^+$ for the corresponding boronic acid).

Synthesis of 3-amino-N-(2'-amino-6'-fluoro-4,4'-bipyridin-3-yl)-6-(2,6-difluorophenyl)picolinamide

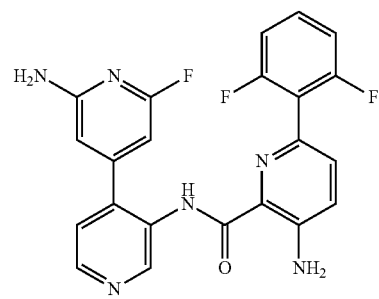 [SMILES: Nc1cc(-c2ccncc2NC(=O)c2nc(-c3c(F)cccc3F)ccc2N)cc(F)n1]

A solution of 3-amino-N-(2',6'-difluoro-4,4'-bipyridin-3-yl)-6-(2,6-difluorophenyl)picolinamide (1.0 equiv.) in NMP and NH$_4$OH (2:3, 0.05M) was heated in the microwave at 120° C. for 8 min. The mixture was directly purified via reverse phase HPLC to afford 3-amino-N-(2'-amino-6'-fluoro-4,4'-bipyridin-3-yl)-6-(2,6-difluorophenyl)picolinamide as the TFA salt. LCMS (m/z): 437.1 (MH$^+$); LC R$_t$=2.79 min.

Synthesis of 5-amino-N-(2'-amino-6'-methyl-4,4'-bipyridin-3-yl)-3'-fluoro-2,2'-bipyridine-6-carboxamide

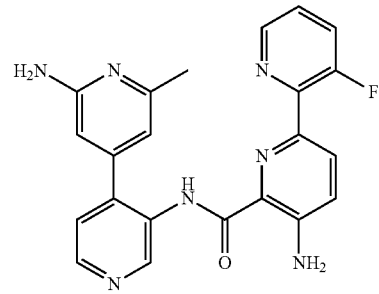 [SMILES: Cc1cc(-c2ccncc2NC(=O)c2nc(-c3ncccc3F)ccc2N)cc(N)n1]

To a solution of degassed dioxane (0.03M) was added 3-amino-6-bromo-N-(2'-(di-BOC-amino)-6'-methyl-4,4'-bipyridin-3-yl)picolinamide (1.0 equiv.), bis(pinacolato)diboron (2.0 equiv.), Pd$_2$(dba)$_3$ (0.05 equiv.), PCy$_3$ (0.075 equiv.), and KOAc (3.0 equiv.). The solution was heated to 90° C. for 16 hrs until all starting material was consumed. Filtered the reaction and concentrated the filtrate. The crude was dried under vacuo, then dissolved in DME/2M Na$_2$CO$_3$ (3:1, 0.05M), followed by addition of 2-bromo-3-fluoropyridine (2.0 equiv.) and Pd(dppf)Cl$_2$-DCM (0.10 equiv.). The reaction was heated to 100° C. in an oil bath until consumption of the boronic ester. Cooled to room temperature, added H$_2$O and EtOAc, the organic phase was washed with brine, then dried with Na$_2$SO$_4$, and concentrated. The crude material was purified via SiO$_2$ column chromatography eluting with EtOAc and hexanes (1:1) and the pure product was concentrated and stirred in DCM/TFA (25%) until completion of the deprotection. The reaction was concentrated to dryness and purified via reverse phase HPLC to afford 5-amino-N-(2'- amino-6'-methyl-4,4'-bipyridin-3-yl)-3'-fluoro-2,2'-bipyridine-6-carboxamide. LCMS (m/z): 416.2 (MH⁺); LC R$_t$=1.77 min.

Method 31

Synthesis of 3-amino-N-(4-(6-amino-2-(trifluoromethyl)-pyrimidin-4-yl)pyridin-3-yl)-6-(thiazol-4-yl)picolinamide

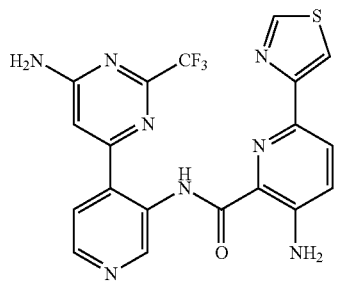 [SMILES: Nc1cc(-c2ccncc2NC(=O)c2nc(-c3cscn3)ccc2N)nc(C(F)(F)F)n1]

A solution of tert-butyl 6-(3-(3-amino-6-bromopicolinamido)pyridine-4-yl)-2-(trifluoromethyl)pyrimidin-4-ylcarbamate (1.0 equiv.), 4-(tributylstannyl)thiazole (3.0 equiv.), and Pd(PPh₃)₄ (0.10 equiv.) in dioxane (0.10M) was microwaved at a 120° C. for 10 min. The reaction was then purified directly via reverse phase HPLC and lyophilized. The product was then stirred in DCM/TFA (25%) until completion of the deprotection, concentrated and purified via reverse phase HPLC and lyophilized to give 3-amino-N-(4-(6-amino-2-(trifluoromethyl)pyrimidin-4-yl)pyridin-3-yl)-6-(thiazol-4-yl)-picolinamide in 14% yield as the TFA salt. LCMS (m/z): 459.1 (MH⁺); LC R$_t$=2.49 min.

Synthesis of (S)-3-amino-N-(4-(3-aminopiperidin-1-yl)pyridin-3-yl)-6-(oxazol-2-yl)picolinamide

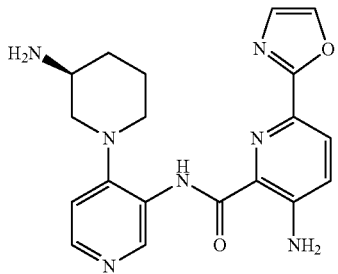 [SMILES: Nc1ccc(-c2ncco2)nc1C(=O)Nc1cnccc1N1CCC[C@H](N)C1]

Method 31 was followed using (S)-tert-butyl 1-(3-(3-amino-6-bromopicolinamido)pyridin-4-yl)piperidin-3-ylcarbamate (1.0 equiv.), 2-(tributyl-stannyl)oxazole (3.0 equiv.), and Pd(PPh3)4 (0.10 equiv.) in dioxane yielding (S)-3-amino-N-(4-(3-aminopiperidin-1-yl)pyridin-3-yl)-6-(oxazol-2-yl)picolinamide in 55% yield as the TFA salt. LCMS (m/z): 380.1 (MH⁺); LC R$_t$=1.55 min.

Synthesis of (S)-3-amino-N-(4-(3-aminopiperidin-1-yl)pyridin-3-yl)-6-cyclopropylpicolinamide

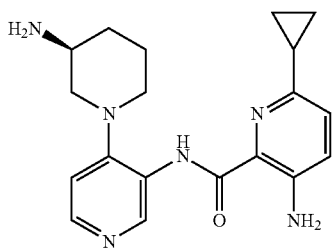 [SMILES: Nc1ccc(C2CC2)nc1C(=O)Nc1cnccc1N1CCC[C@H](N)C1]

Method 31 was followed using (S)-tert-butyl 1-(3-(3-amino-6-bromopicolinamido)pyridin-4-yl)piperidin-3-ylcarbamate (1.0 equiv.), 2-cyclopropyl-4,4,5,5-tetramethyl-1,3,2-dioxaborolante (3.0 equiv.), and Pd(dppf)Cl₂-DCM (0.10 equiv.) at 140° C. for 10 min yielding (S)-3-amino-N-(4-(3-aminopiperidin-1-yl)pyridin-3-yl)-6-cyclopropylpicolinamide in 8% yield. LCMS (m/z): 353.1 (MH⁺); LC R$_t$=1.59 min.

Method 32

Synthesis of 3-amino-N-(4-((3R,4R)-3-amino-4-hydroxypiperidin-1-yl)pyridin-3-yl)-6-(2,6-difluorophenyl)picolinamide

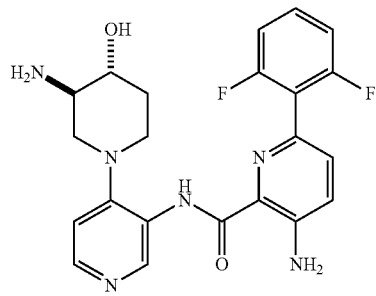 [SMILES: Nc1ccc(-c2c(F)cccc2F)nc1C(=O)Nc1cnccc1N1CC[C@@H](O)[C@H](N)C1]

3-amino-6-(2,6-difluorophenyl)picolinic acid and tert-butyl (3R,4R)-1-(3-aminopyridin-4-yl)-4-(tert-butyldimethylsilyloxy)piperidin-3-ylcarbamate were coupled following method 11 (example 249), to yield tert-butyl (3R,4R)-1-(3-(3-amino-6-(2,6-difluorophenyl)picolinamido)pyridin-4-yl)-4-(tert-butyldimethylsilyloxy)piperidin-3-ylcarbamate after HPLC purification. Alternatively, tert-butyl (3R,4R)-1-(3-(3-amino-6-(2,6-difluorophenyl)picolinamido)pyridin-4-yl)-4-(tert-butyldimethylsilyloxy)-piperidin-3-ylcarbamate could be obtained starting with tert-butyl (3R,4R)-1-(3-(3-amino-6-bromo-picolinamido)pyridin-4-yl)-4-(tert-butyldimethylsilyloxy)piperidin-3-yl-carbamate and 2,6 difluorophenylboronic acid following the Suzuki procedure outlined in method 14. The TBDMS deprotection of tert-butyl (3R,4R)-1-(3-(3-amino-6-(2,6-difluorophenyl)picolinamido)pyridin-4-yl)-4-(tert-butyldimethylsilyloxy)piperidin-3-yl-carbamate was performed with 6N HCl, THF, methanol (1:2:1) at room temperature for 2 h. After volatile materials were removed, the crude material was stirred in 30% TFA in dichloromethane for 2 hours. After volatile materials were removed in vacuo, purification and lyophilization yielded 3-amino-N-(4-((3R,4R)-3-amino-4-hydroxy-piperidin-1-yl)pyridin-3-yl)-6-(2,6-difluorophenyl)picolinamide. HPLC. LCMS (m/z): 441.2 (MH⁺); LC R$_t$=2.03 min.

The following compounds were made using method 32:

| Example | Structure | Name | MH+ | LC |
|---|---|---|---|---|
| 648 | Chiral | 5-Amino-2-(2,6-difluoro-phenyl)-pyrimidine-4-carboxylic acid (3-hydroxy-3,4,5,6-tetrahydro-2H-[1,4']bipyridinyl-3'-yl)-amide | 427.2 | 2.18 |
| 649 | Chiral | 5-Amino-2-(2-fluoro-phenyl)-pyrimidine-4-carboxylic acid (3-hydroxy-3,4,5,6-tetrahydro-2H-[1,4']bipyridinyl-3'-yl)-amide | 409.2 | 2.26 |
| 650 | Chiral | 5-Amino-2-phenyl-pyrimidine-4-carboxylic acid (3-hydroxy-3,4,5,6-tetrahydro-2H-[1,4']bipyridinyl-3'-yl)-amide | 391.2 | 2.37 |
| 651 | Chiral | 3-Amino-6-(2-fluoro-5-isopropylcarbamoyl-phenyl)-pyridine-2-carboxylic acid (3-hydroxy-3,4,5,6-tetrahydro-2H-[1,4']bipyridinyl-3'-yl)-amide | 493.2 | 2.46 |

-continued

| Example | Structure | Name | MH+ | LC |
|---|---|---|---|---|
| 652 | Chiral | 3-Amino-6-(2,6-difluoro-3-isopropoxy-phenyl)-pyridine-2-carboxylic acid (3-hydroxy-3,4,5,6-tetrahydro-2H-[1,4']bipyridinyl-3'-yl)-amide | 484.3 | 2.94 |
| 653 | Chiral | 3-Amino-6-(2,6-difluoro-phenyl)-pyridine-2-carboxylic acid (3-hydroxy-3,4,5,6-tetrahydro-2H-[1,4']bipyridinyl-3'-yl)-amide | 426.2 | 2.66 |
| 654 | 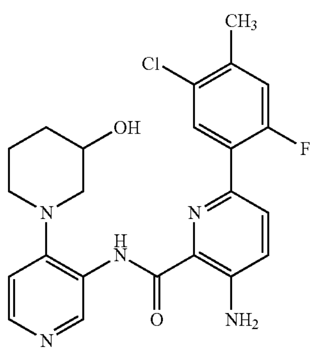 [SMILES: Cc1cc(F)c(-c2ccc(N)c(C(=O)Nc3cnccc3N3CCCC(O)C3)n2)cc1Cl] | 3-Amino-6-(5-chloro-2-fluoro-4-methyl-phenyl)-pyridine-2-carboxylic acid (3-hydroxy-3,4,5,6-tetrahydro-2H-[1,4']bipyridinyl-3'-yl)-amide | 456.1 | 3.15 |
| 655 | 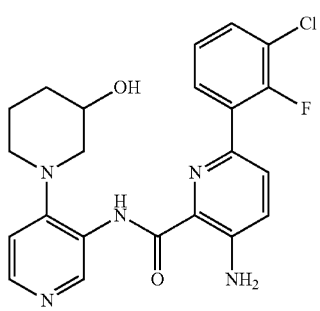 [SMILES: Nc1ccc(-c2cccc(Cl)c2F)nc1C(=O)Nc1cnccc1N1CCCC(O)C1] | 3-Amino-6-(3-chloro-2-fluoro-phenyl)-pyridine-2-carboxylic acid (3-hydroxy-3,4,5,6-tetrahydro-2H-[1,4']bipyridinyl-3'-yl)-amide | 442.1 | 2.96 |

-continued

| Example | Structure | Name | MH+ | LC |
|---|---|---|---|---|
| 656 | 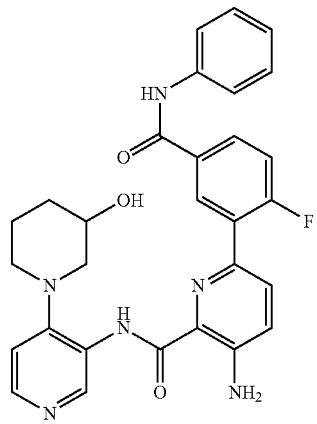 [SMILES: Nc1ccc(-c2cc(C(=O)Nc3ccccc3)ccc2F)nc1C(=O)Nc1cnccc1N1CCCC(O)C1] | 3-Amino-6-(2-fluoro-5-phenyl-carbamoyl-phenyl)-pyridine-2-carboxylic acid (3-hydroxy-3,4,5,6-tetrahydro-2H-[1,4']bi-pyridinyl-3'-yl)-amide | 527.2 | 2.88 |
| 657 | 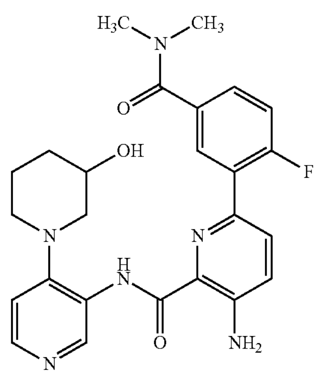 [SMILES: CN(C)C(=O)c1ccc(F)c(-c2ccc(N)c(C(=O)Nc3cnccc3N3CCCC(O)C3)n2)c1] | 3-Amino-6-(5-dimethyl-carbamoyl-2-fluoro-phenyl)-pyridine-2-carboxylic acid (3-hydroxy-3,4,5,6-tetrahydro-2H-[1,4']bipyridinyl-3'-yl)-amide | 479.2 | 2.27 |
| 658 | 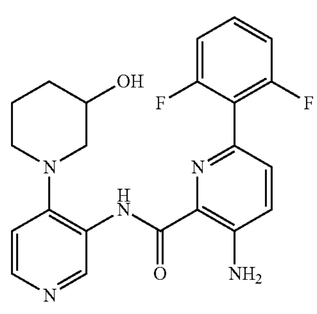 [SMILES: Nc1ccc(-c2c(F)cccc2F)nc1C(=O)Nc1cnccc1N1CCCC(O)C1] | 3-Amino-6-(2,6-difluoro-phenyl)-pyridine-2-carboxylic acid (3-hydroxy-3,4,5,6-tetra-hydro-2H-[1,4']bipyridinyl-3'-yl)-amide | 426.2 | 2.63 |
| 659 | Chiral | 3-Amino-6-(2-fluoro-phenyl)-pyridine-2-carboxylic acid (3-hydroxy-3,4,5,6-tetrahydro-2H-[1,4']bipyridinyl-3'-yl)-amide | 408.2 | 2.66 |

-continued

| Example | Structure | Name | MH+ | LC |
|---|---|---|---|---|
| 660 | Chiral | 3-Amino-6-(2-fluoro-phenyl)-pyridine-2-carboxylic acid (3-hydroxy-3,4,5,6-tetrahydro-2H-[1,4']bipyridinyl-3'-yl)-amide | 408.2 | 2.65 |
| 661 | 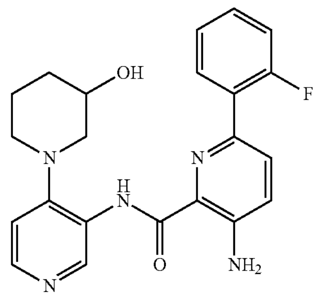 | 3-Amino-6-(2-fluoro-phenyl)-pyridine-2-carboxylic acid (3-hydroxy-3,4,5,6-tetrahydro-2H-[1,4']bipyridinyl-3'-yl)-amide | 408.2 | 2.64 |
| 662 | 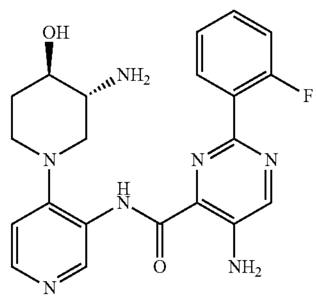 [SMILES: Nc1cnc(-c2ccccc2F)nc1C(=O)Nc1cnccc1N1CC[C@@H](O)[C@H](N)C1] | 5-Amino-2-(2-fluoro-phenyl)-pyrimidine-4-carboxylic acid (3-amino-4-hydroxy-3,4,5,6-tetrahydro-2H-[1,4']bipyridinyl-3'-yl)-amide | 424.2 | 1.67 |
| 663 | 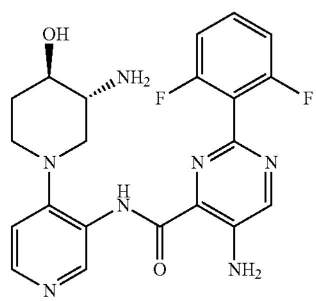 [SMILES: Nc1cnc(-c2c(F)cccc2F)nc1C(=O)Nc1cnccc1N1CC[C@@H](O)[C@H](N)C1] | 5-Amino-2-(2,6-difluoro-phenyl)-pyrimidine-4-carboxylic acid (3-amino-4-hydroxy-3,4,5,6-tetrahydro-2H-[1,4']bipyridinyl-3'-yl)-amide | 442.2 | 1.57 |
| 664 | 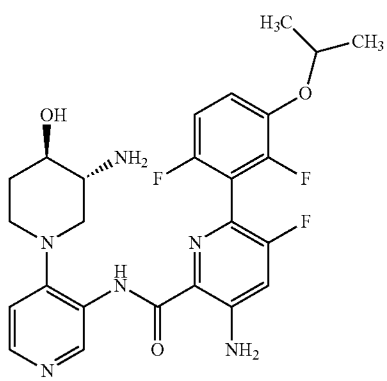 [SMILES: CC(C)Oc1ccc(F)c(-c2nc(C(=O)Nc3cnccc3N3CC[C@@H](O)[C@H](N)C3)c(N)cc2F)c1F] | 3-Amino-6-(2,6-difluoro-3-isopropoxy-phenyl)-5-fluoro-pyridine-2-carboxylic acid (3-amino-4-hydroxy-3,4,5,6-tetrahydro-2H-[1,4']bipyridinyl-3'-yl)-amide | 517.2 | 2.48 |

-continued

| Example | Structure | Name | MH+ | LC |
|---|---|---|---|---|
| 665 | 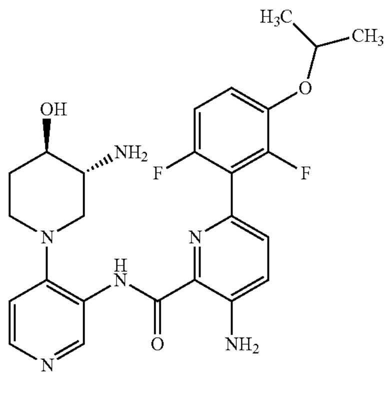 [SMILES: CC(C)Oc1ccc(F)c(-c2ccc(N)c(C(=O)Nc3cnccc3N3CC[C@@H](O)[C@H](N)C3)n2)c1F] | 3-Amino-6-(2,6-difluoro-3-isopropoxy-phenyl)-pyridine-2-carboxylic acid (3-amino-4-hydroxy-3,4,5,6-tetrahydro-2H-[1,4']bipyridinyl-3'-yl)-amide | 499.2 | 2.38 |
| 666 | 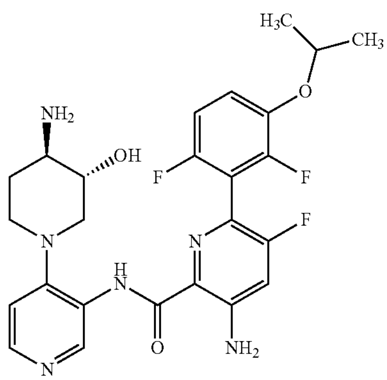 [SMILES: CC(C)Oc1ccc(F)c(-c2nc(C(=O)Nc3cnccc3N3CC[C@@H](N)[C@H](O)C3)c(N)cc2F)c1F] | 3-Amino-6-(2,6-difluoro-3-isopropoxy-phenyl)-5-fluoro-pyridine-2-carboxylic acid (4-amino-3-hydroxy-3,4,5,6-tetrahydro-2H-[1,4']bipyridinyl-3'-yl)-amide | 517.2 | 2.47 |
| 667 | 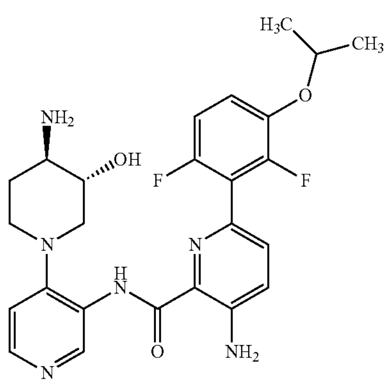 [SMILES: CC(C)Oc1ccc(F)c(-c2ccc(N)c(C(=O)Nc3cnccc3N3CC[C@@H](N)[C@H](O)C3)n2)c1F] | 3-Amino-6-(2,6-difluoro-3-isopropoxy-phenyl)-pyridine-2-carboxylic acid (4-amino-3-hydroxy-3,4,5,6-tetrahydro-2H-[1,4']bipyridinyl-3'-yl)-amide | 499.2 | 2.36 |
| 668 | 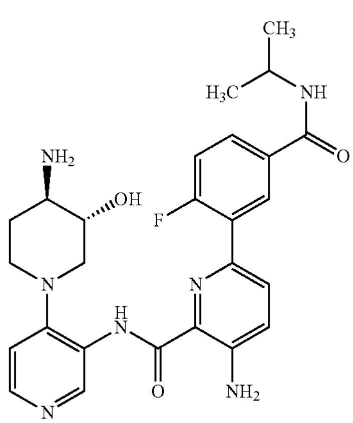 [SMILES: CC(C)NC(=O)c1ccc(F)c(-c2ccc(N)c(C(=O)Nc3cnccc3N3CC[C@@H](N)[C@H](O)C3)n2)c1] | 3-Amino-6-(2-fluoro-5-isopropylcarbamoyl-phenyl)-pyridine-2-carboxylic acid (4-amino-3-hydroxy-3,4,5,6-tetrahydro-2H-[1,4']bipyridinyl-3'-yl)-amide | 508.3 | 1.96 |

| Example | Structure | Name | MH+ | LC |
|---|---|---|---|---|
| 669 | 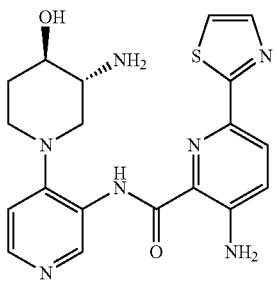 | 3-Amino-6-thiazol-2-yl-pyridine-2-carboxylic acid (3-amino-4-hydroxy-3,4,5,6-tetrahydro-2H-[1,4']bipyridinyl-3'-yl)-amide | 412.1 | 1.48 |
| 670 | 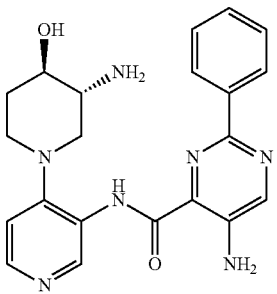 [SMILES: Nc1cnc(-c2ccccc2)nc1C(=O)Nc1cnccc1N1CC[C@@H](O)[C@H](N)C1] | 5-Amino-2-phenyl-pyrimidine-4-carboxylic acid (3-amino-4-hydroxy-3,4,5,6-tetrahydro-2H-[1,4']bipyridinyl-3'-yl)-amide | 406.2 | 1.72 |
| 671 | 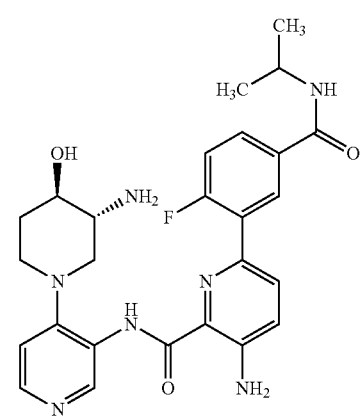 [SMILES: CC(C)NC(=O)c1ccc(F)c(-c2ccc(N)c(C(=O)Nc3cnccc3N3CC[C@@H](O)[C@H](N)C3)n2)c1] | 3-Amino-6-(2-fluoro-5-isopropylcarbamoyl-phenyl)-pyridine-2-carboxylic acid (3-amino-4-hydroxy-3,4,5,6-tetrahydro-2H-[1,4']bipyridinyl-3'-yl)-amide | 508.3 | 2.00 |
| 672 | 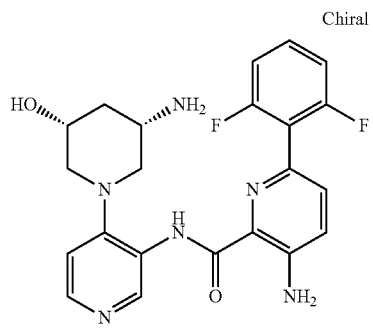 [SMILES: Nc1ccc(-c2c(F)cccc2F)nc1C(=O)Nc1cnccc1N1C[C@@H](N)C[C@@H](O)C1] | 3-Amino-6-(2,6-difluoro-phenyl)-pyridine-2-carboxylic acid (3-amino-5-hydroxy-3,4,5,6-tetrahydro-2H-[1,4']bipyridinyl-3'-yl)-amide | 441.2 | 1.89 |

| Example | Structure | Name | MH+ | LC |
|---|---|---|---|---|
| 673 | 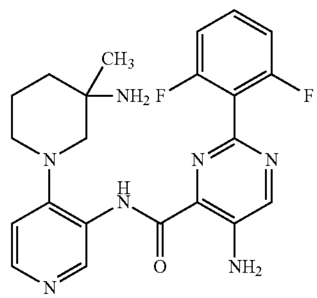 [SMILES: CC1(N)CCCN(c2ccncc2NC(=O)c2nc(-c3c(F)cccc3F)ncc2N)C1] | 5-Amino-2-(2,6-difluoro-phenyl)-pyrimidine-4-carboxylic acid (3-amino-3-methyl-3,4,5,6-tetrahydro-2H-[1,4']bipyridinyl-3'-yl)-amide | 440.1 | 1.76 |
| 674 | 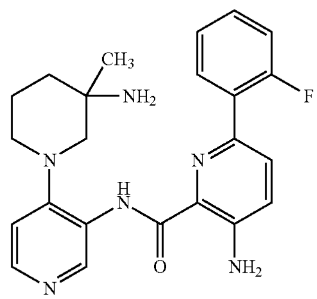 [SMILES: CC1(N)CCCN(c2ccncc2NC(=O)c2nc(-c3ccccc3F)ccc2N)C1] | 3-Amino-6-(2-fluoro-phenyl)-pyridine-2-carboxylic acid (3-amino-3-methyl-3,4,5,6-tetrahydro-2H-[1,4']bipyridinyl-3'-yl)-amide | 421.2 | 2.13 |
| 675 | 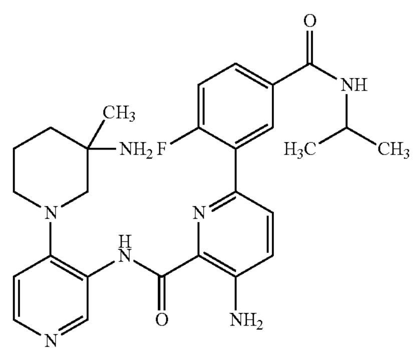 [SMILES: CC(C)NC(=O)c1ccc(F)c(-c2ccc(N)c(C(=O)Nc3cnccc3N3CCCC(C)(N)C3)n2)c1] | 3-Amino-6-(2-fluoro-5-isopropylcarbamoyl-phenyl)-pyridine-2-carboxylic acid (3-amino-3-methyl-3,4,5,6-tetrahydro-2H-[1,4']bipyridinyl-3'-yl)-amide | 506.2 | 2.08 |
| 676 | 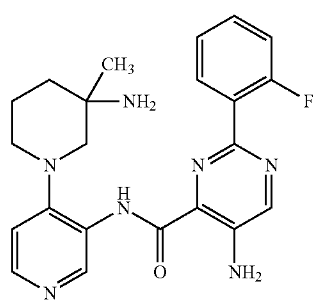 [SMILES: CC1(N)CCCN(c2ccncc2NC(=O)c2nc(-c3ccccc3F)ncc2N)C1] | 5-Amino-2-(2-fluoro-phenyl)-pyrimidine-4-carboxylic acid (3-amino-3-methyl-3,4,5,6-tetrahydro-2H-[1,4']bipyridinyl-3'-yl)-amide | 422.1 | 1.73 |
| 677 | 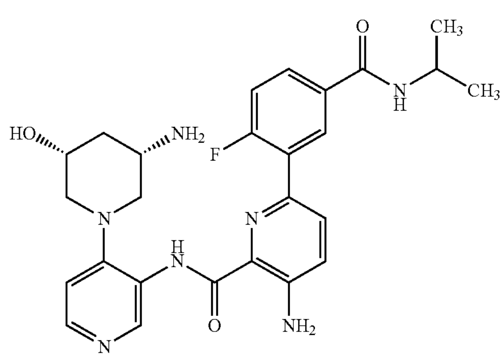 [SMILES: CC(C)NC(=O)c1ccc(F)c(-c2ccc(N)c(C(=O)Nc3cnccc3N3C[C@@H](N)C[C@@H](O)C3)n2)c1] | 3-Amino-6-(2-fluoro-5-isopropylcarbamoyl-phenyl)-pyridine-2-carboxylic acid (3-amino-5-hydroxy-3,4,5,6-tetrahydro-2H-[1,4']bipyridinyl-3'-yl)-amide | 508.1 | 1.89 |

| Example | Structure | Name | MH+ | LC |
|---|---|---|---|---|
| 678 | Chiral | 3-Amino-6-(2-fluoro-phenyl)-pyridine-2-carboxylic acid (5-amino-3-hydroxy-3,4,5,6-tetrahydro-2H-[1,4']bipyridinyl-3'-yl)-amide | 423.2 | 1.87 |
| 679 | Chiral | 3-Amino-6-(2,6-difluoro-phenyl)-pyridine-2-carboxylic acid (3-amino-4-hydroxy-3,4,5,6-tetrahydro-2H-[1,4']bipyridinyl-3'-yl)-amide | 441.2 | 2.04 |
| 680 | Chiral | 3-Amino-6-(2,6-difluoro-phenyl)-pyridine-2-carboxylic acid (3-amino-4-hydroxy-3,4,5,6-tetrahydro-2H-[1,4']bipyridinyl-3'-yl)-amide | 441.2 | 2.04 |
| 681 | Chiral | 5-Fluoro-6-phenyl-pyridine-2-carboxylic acid (3-amino-4-hydroxy-3,4,5,6-tetrahydro-2H-[1,4']bipyridinyl-3'-yl)-amide | 408.1 | 1.99 |

| Example | Structure | Name | MH+ | LC |
|---|---|---|---|---|
| 682 | Chiral | 5-Fluoro-6-(2-fluoro-phenyl)-pyridine-2-carboxylic acid (3-amino-4-hydroxy-3,4,5,6-tetrahydro-2H-[1,4']bipyridinyl-3'-yl)-amide | 426.1 | 2.01 |
| 683 | Chiral | 6-(2,6-Difluoro-phenyl)-5-fluoro-pyridine-2-carboxylic acid (3-amino-4-hydroxy-3,4,5,6-tetrahydro-2H-[1,4']bipyridinyl-3'-yl)-amide | 444.1 | 1.99 |
| 684 | Chiral | 5-Fluoro-6-(2-fluoro-phenyl)-pyridine-2-carboxylic acid (5-amino-3-hydroxy-3,4,5,6-tetrahydro-2H-[1,4']bipyridinyl-3'-yl)-amide | 426.1 | 1.89 |
| 685 | Chiral | 3-Amino-6-(2-fluoro-5-propoxy-phenyl)-pyridine-2-carboxylic acid (5-amino-3-hydroxy-3,4,5,6-tetrahydro-2H-[1,4']bipyridinyl-3'-yl)-amide | 481.1 | 2.39 |

Method 33

Synthesis of (S)-tert-butyl 1-(3-(3-amino-6-(4,4,5,5-tetramethyl-1,3,2-dioxaborolan-2-yl)picolinamido)pyridin-4-yl)piperidin-3-ylcarbamate

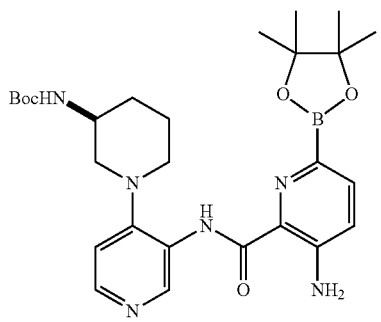 [SMILES: CC(C)(C)OC(=O)N[C@H]1CCCN(c2ccncc2NC(=O)c2nc(B3OC(C)(C)C(C)(C)O3)ccc2N)C1]

A solution of (S)-tert-butyl 1-(3-(3-amino-6-bromo-picolinamido)pyridin-4-yl)piperidin-3-ylcarbamate (1.0 eq), bis(pinacolato)diboron (2.0 equiv.), KOAc (3 equiv.), triscyclohexylphosphine (0.075 eq.) in dioxane (0.16 M) was degassed by bubbling argon through for 10 min at which time Pd$_2$(dba)$_3$ (0.05 eq.) was added. The glass vessel was sealed and heated at 90° C. for 3 hours, cooled to room temperature, filtered, washed with EtOAc and concentrated to give a thick dark brown crude product which was used as is. LCMS (m/z): 457.2 (MH$^+$ for the corresponding boronic acid).

Synthesis of (S)-tert-butyl 1-(3-(3-amino-6-bromo-5-fluoropicolinamido)pyridin-4-yl)piperidin-3-ylcarbamate

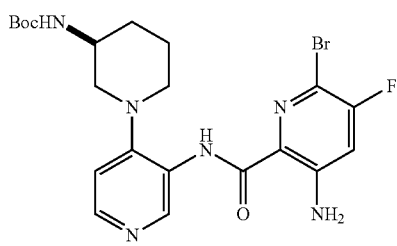 [SMILES: CC(C)(C)OC(=O)N[C@H]1CCCN(c2ccncc2NC(=O)c2nc(Br)c(F)cc2N)C1]

Following Method 11 of Example 305, (+/−)-tert-butyl 1-(3-aminopyridin-4-yl)-4-fluoropiperidin-3-ylcarbamate and 3-amino-6-bromo-5-fluoro-picolinic acid were reacted yielding (S)-tert-butyl 1-(3-(3-amino-6-bromo-5-fluoro-picolinamido)pyridin-4-yl)piperidin-3-ylcarbamate (40%). LCMS (m/z): 509.0 (MH$^+$), LC R$_t$=3.04 min.

Synthesis of (S)-tert-butyl 1-(3-(3-amino-5-fluoro-6-(4,4,5,5-tetramethyl-1,3,2-dioxaborolan-2-yl)picolinamido)pyridin-4-yl)piperidin-3-ylcarbamate

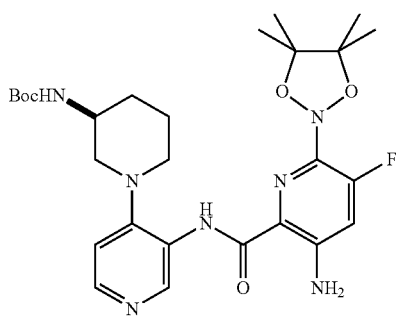 [SMILES: CC(C)(C)OC(=O)N[C@H]1CCCN(c2ccncc2NC(=O)c2nc(N3OC(C)(C)C(C)(C)O3)c(F)cc2N)C1]

Starting with (S)-tert-butyl 1-(3-(3-amino-6-bromo-5-fluoro-picolinamido)pyridin-4-yl)piperidin-3-ylcarbamate, method 33 was followed yielding (S)-tert-butyl 1-(3-(3-amino-5-fluoro-6-(4,4,5,5-tetramethyl-1,3,2-dioxaborolan-2-yl)-picolinamido)pyridin-4-yl)piperidin-3-ylcarbamate. LCMS (m/z): 475.2 (MH$^+$ for the corresponding boronic acid); LC R$_t$=2.16 min.

Synthesis of tert-butyl (3R,4R)-1-(3-(3-amino-6-(4,4,5,5-tetramethyl-1,3,2-dioxaborolan-2-yl)picolinamido)pyridin-4-yl)-4-(tert-butyldimethylsilyloxy)piperidin-3-ylcarbamate

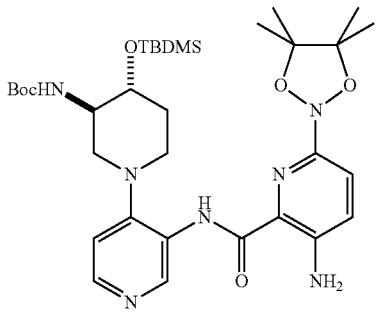 [SMILES: CC(C)(C)OC(=O)N[C@@H]1CN(c2ccncc2NC(=O)c2nc(N3OC(C)(C)C(C)(C)O3)ccc2N)CC[C@H]1O[Si](C)(C)C(C)(C)C]

Starting with tert-butyl (3R,4R)-1-(3-(3-amino-6-bromo-picolinamido)-pyridin-4-yl)-4-(tert-butyldimethylsilyloxy)piperidin-3-ylcarbamate, method 33 was followed yielding tert-butyl (3R,4R)-1-(3-(3-amino-6-(4,4,5,5-tetramethyl-1,3,2-dioxaborolan-2-yl)picolinamido)pyridin-4-yl)-4-(tert-butyldimethylsilyloxy)piperidin-3-ylcarbamate. LCMS (m/z): 587.3 (MH$^+$ for the corresponding boronic acid).

Method 34

Synthesis of (S)-5-amino-N-(4-(3-aminopiperidin-1-yl)-pyridin-3-yl)-2,2'-bipyridine-6-carboxamide

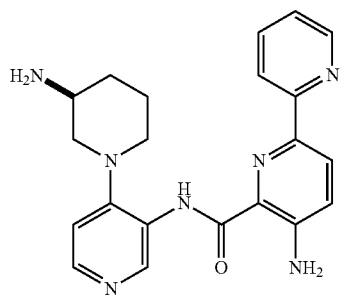 [SMILES: Nc1ccc(-c2ccccn2)nc1C(=O)Nc1cnccc1N1CCC[C@H](N)C1]

A solution of (S)-tert-butyl 1-(3-(3-amino-6-(4,4,5,5-tetramethyl-1,3,2-dioxaborolan-2-yl)picolinamido)pyridin-4-yl)piperidin-3-ylcarbamate (1.0 eq), 2-bromo-pyridine (1.0 eq) and Pd(dppf)Cl$_2$-DCM (0.10 equiv.) in 3:1 dimethoxyethane/2M Na$_2$CO$_3$ was heated in the microwave at 110° C. for 15 minutes. The organic layer was separated, the volatiles were removed in vacuo and the crude material was purified by RP HPLC to yield the N-Boc product after lyophilization. The Boc group was removed by treating with 25% TFA/CH$_2$Cl$_2$ for 2 hours. After removal of volatiles in vacuo, purification by RP HPLC and lyophilization (S)-5-amino-N-(4-(3-aminopiperidin-1-yl)-pyridin-3-yl)-2,2'-bipyridine-6-carboxamide was obtained (12%). The free base and HCl salt can be obtained as described in Method 9 (Example 115). HPLC. LCMS 390.2 (MH$^+$); LC R$_t$=1.11 min. HCl salt, $^1$H NMR (DMSO$_{d6}$): δ 10.46 (s, 1H), 9.15 (s, 1H), 8.61-8.65 (m, 1H), 8.44-8.47 (m, 1H), 8.34 (d, J=9.0 Hz, 2H), 7.90-8.05 (m, 3H), 7.41 (d, J=8.7 Hz, 2H), 7.22-7.33 (m, 3H), 2.75-3.60 (m, 5H), 1.20-1.95 (m, 4H).

For compounds prepared using method 34 that contained hydroxyl functionalities, the silyl protecting groups were removed prior to Boc removal as described in Method 32.

The following compounds were prepared using method 34:

| Example | Structure | Name | MH+ | LC |
|---|---|---|---|---|
| 686 | 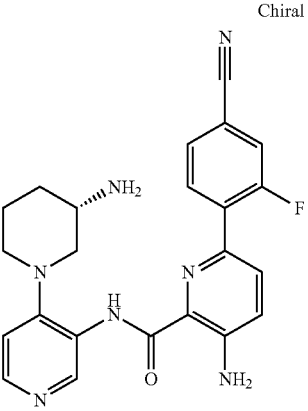 [SMILES: N#Cc1ccc(-c2ccc(N)c(C(=O)Nc3cnccc3N3CCC[C@H](N)C3)n2)c(F)c1] Chiral | 3-Amino-6-(4-cyano-2-fluoro-phenyl)-pyridine-2-carboxylic acid (3-amino-3,4,5,6-tetra-hydro-2H-[1,4']bipyridinyl-3'-yl)-amide | 432.2 | 2.15 |
| 687 | 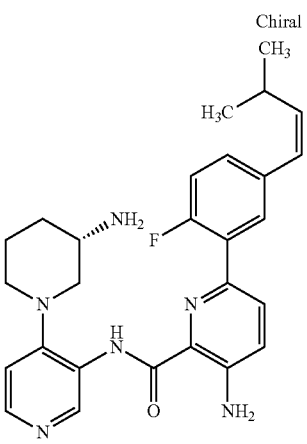 [SMILES: CC(C)/C=C\c1ccc(F)c(-c2ccc(N)c(C(=O)Nc3cnccc3N3CCC[C@H](N)C3)n2)c1] Chiral | 3-Amino-6-[2-fluoro-5-(3-methyl-but-1-enyl)-phenyl]-pyridine-2-carboxylic acid (3-amino-3,4,5,6-tetrahydro-2H-[1,4']bipyridinyl-3'-yl)-amide | 475.2 | 2.83 |
| 688 | 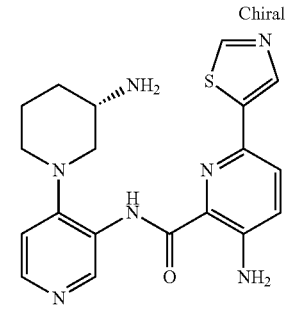 [SMILES: Nc1ccc(-c2cncs2)nc1C(=O)Nc1cnccc1N1CCC[C@H](N)C1] Chiral | 3-Amino-6-thiazol-5-yl-pyridine-2-carboxylic acid (3-amino-3,4,5,6-tetrahydro-2H-[1,4']bipyridinyl-3'-yl)-amide | 396.1 | 1.52 |
| 689 | 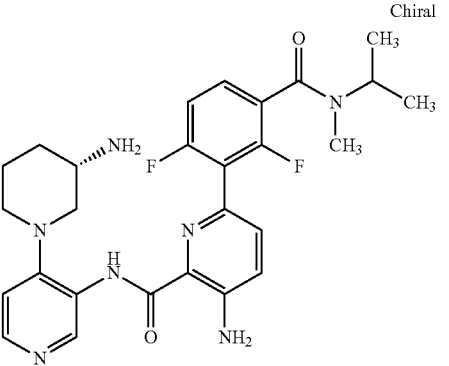 [SMILES: CC(C)N(C)C(=O)c1ccc(F)c(-c2ccc(N)c(C(=O)Nc3cnccc3N3CCC[C@H](N)C3)n2)c1F] Chiral | 3-Amino-6-[2,6-difluoro-3-(isopropyl-methyl-carbamoyl)-phenyl]-pyridine-2-carboxylic acid (3-amino-3,4,5,6-tetra-hydro-2H-[1,4']bipyridinyl-3'-yl)-amide | 524.3 | 2.28 |

-continued

| Example | Name | MH+ | LC |
|---------|------|-----|-----|
| 690 | 5-Amino-3'-fluoro-[2,2']bipyridinyl-6-carboxylic acid (3-hydroxy-3,4,5,6-tetrahydro-2H-[1,4']bipyridinyl-3'-yl)-amide | 409.2 | 1.72 |
| 691 | 5'-Amino-[2,2']bipyridinyl-5,6'-dicarboxylic acid 5-amide 6'-[(3-amino-3,4,5,6-tetrahydro-2H-[1,4']bipyridinyl-3-yl)-amide] | 433.2 | 1.30 |
| 692 | 3-Amino-6-isoquinolin-4-yl-pyridine-2-carboxylic acid (3-amino-3,4,5,6-tetrahydro-2H-[1,4']bipyridinyl-3'-yl)-amide | 440.2 | 1.53 |
| 693 | 5-Amino-1'-oxy-[2,2']bipyridinyl-6-carboxylic acid (3-amino-3,4,5,6-tetrahydro-2H-[1,4']bipyridinyl-3'-yl)-amide | 406.2 | 1.37 |

-continued

| Example | Structure | Name | MH+ | LC |
|---|---|---|---|---|
| 694 | Chiral | 3-Amino-6-(3-methoxy-pyrazin-2-yl)-pyridine-2-carboxylic acid (3-amino-3,4,5,6-tetrahydro-2H-[1,4']bipyridinyl-3'-yl)-amide | 421.2 | 1.77 |
| 695 | Chiral | 5-Amino-6'-benzyloxy-[2,2']bi-pyridinyl-6-carboxylic acid (3-amino-3,4,5,6-tetrahydro-2H-[1,4']bipyridinyl-3'-yl)-amide | 496.3 | 2.77 |
| 696 | Chiral | 5-Amino-5'-methoxy-[2,2']bi-pyridinyl-6-carboxylic acid (3-amino-3,4,5,6-tetrahydro-2H-[1,4']bipyridinyl-3'-yl)-amide | 420.2 | 1.38 |
| 697 | Chiral | 5-Amino-3'-methoxy-[2,2']bi-pyridinyl-6-carboxylic acid (3-amino-3,4,5,6-tetrahydro-2H-[1,4']bipyridinyl-3'-yl)-amide | 420.2 | 1.29 |

-continued

| Example | Structure | Name | MH+ | LC |
|---|---|---|---|---|
| 698 | 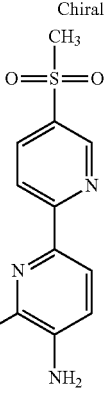 | 5-Amino-5'-methanesulfonyl-[2,2']bipyridinyl-6-carboxylic acid (3-amino-3,4,5,6-tetrahydro-2H-[1,4']bipyridinyl-3'-yl)-amide | 468.2 | 1.70 |
| 699 | 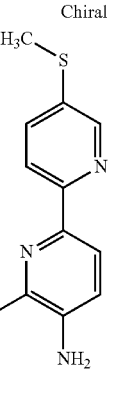 | 5-Amino-5'-methylsulfanyl-[2,2']bipyridinyl-6-carboxylic acid (3-amino-3,4,5,6-tetrahydro-2H-[1,4']bipyridinyl-3'-yl)-amide | 436.2 | 1.54 |
| 700 | 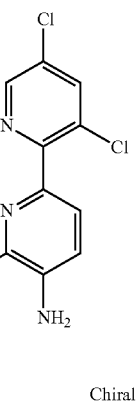 | 5-Amino-3',5'-dichloro-[2,2']bipyridinyl-6-carboxylic acid (3-amino-3,4,5,6-tetrahydro-2H-[1,4']bipyridinyl-3'-yl)-amide | 458.1 | 2.17 |
| 701 | 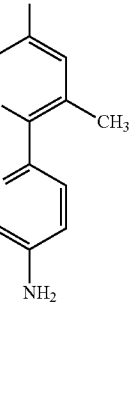 | 5-Amino-5'-chloro-3'-methyl-[2,2']bipyridinyl-6-carboxylic acid (3-amino-3,4,5,6-tetrahydro-2H-[1,4']bipyridinyl-3'-yl)-amide | 438.2 | 1.92 |

-continued

| Example | Structure | Name | MH+ | LC |
|---|---|---|---|---|
| 702 | Chiral | 5-Amino-3'-fluoro-[2,2']bipyridinyl-6-carboxylic acid (3-amino-3,4,5,6-tetrahydro-2H-[1,4']bipyridinyl-3'-yl)-amide | 408.2 | 1.65 |
| 703 | Chiral | 5-Amino-6'-pyrazol-1-yl-[2,2']bipyridinyl-6-carboxylic acid (3-amino-3,4,5,6-tetrahydro-2H-[1,4']bipyridinyl-3'-yl)-amide | 456.2 | 2.21 |
| 704 | Chiral | 5'-Amino-[2,2']bipyridinyl-4,6'-dicarboxylic acid 4-amide 6'-[(3-amino-3,4,5,6-tetrahydro-2H-[1,4']bipyridinyl-3'-yl)-amide] | 433.2 | 1.28 |
| 705 | Chiral | 5,5'-Diamino-6'-methoxy-[2,2']bipyridinyl-6-carboxylic acid (3-amino-3,4,5,6-tetrahydro-2H-[1,4']bipyridinyl-3'-yl)-amide | 435.2 | 1.70 |

| Example | Structure | Name | MH+ | LC |
|---|---|---|---|---|
| 706 | 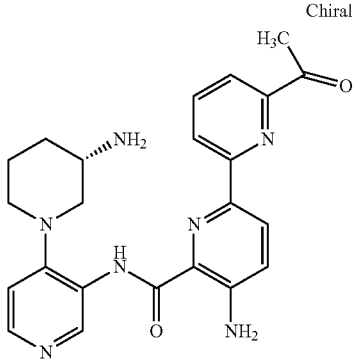 [SMILES: CC(=O)c1cccc(-c2ccc(N)c(C(=O)Nc3cnccc3N3CCC[C@H](N)C3)n2)n1] Chiral | 6'-Acetyl-5-amino-[2,2']bi-pyridinyl-6-carboxylic acid (3-amino-3,4,5,6-tetrahydro-2H-[1,4']bipyridinyl-3'-yl)-amide | 432.2 | 2.06 |
| 707 | 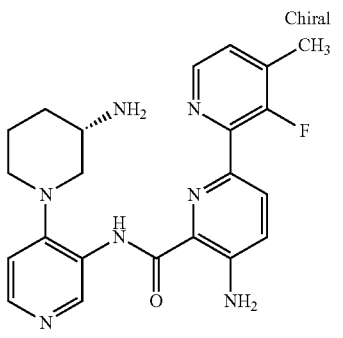 [SMILES: Cc1ccnc(-c2ccc(N)c(C(=O)Nc3cnccc3N3CCC[C@H](N)C3)n2)c1F] Chiral | 5-Amino-3'-fluoro-4'-methyl-[2,2']bipyridinyl-6-carboxylic acid (3-amino-3,4,5,6-tetra-hydro-2H-[1,4']bipyridinyl-3'-yl)-amide | 422.2 | 1.48 |
| 708 | 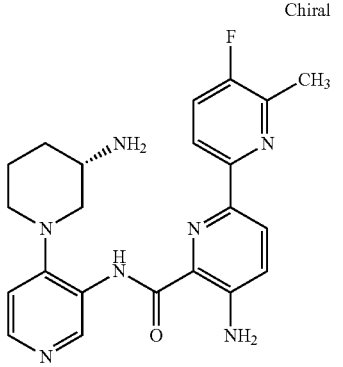 [SMILES: Cc1nc(-c2ccc(N)c(C(=O)Nc3cnccc3N3CCC[C@H](N)C3)n2)ccc1F] Chiral | 5-Amino-5'-fluoro-6'-methyl-[2,2']bipyridinyl-6-carboxylic acid (3-amino-3,4,5,6-tetra-hydro-2H-[1,4']bipyridinyl-3'-yl)-amide | 422.2 | 1.75 |
| 709 | 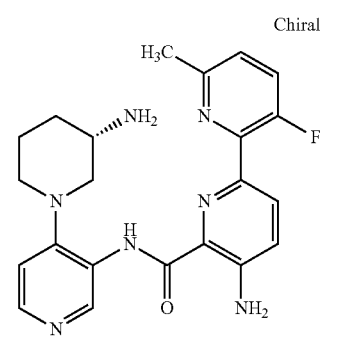 [SMILES: Cc1ccc(F)c(-c2ccc(N)c(C(=O)Nc3cnccc3N3CCC[C@H](N)C3)n2)n1] Chiral | 5-Amino-3'-fluoro-6'-methyl-[2,2']bipyridinyl-6-carboxylic acid (3-amino-3,4,5,6-tetra-hydro-2H-[1,4']bipyridinyl-3'-yl)-amide | 422.2 | 1.49 |

-continued

| Example | Structure | Name | MH+ | LC |
|---|---|---|---|---|
| 710 | 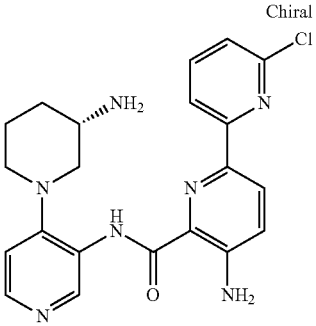 [SMILES: Nc1ccc(-c2cccc(Cl)n2)nc1C(=O)Nc1cnccc1N1CCC[C@H](N)C1] Chiral | 5-Amino-6'-chloro-[2,2']bi-pyridinyl-6-carboxylic acid (3-amino-3,4,5,6-tetrahydro-2H-[1,4']bipyridinyl-3'-yl)-amide | 424.2 | 2.06 |
| 711 | 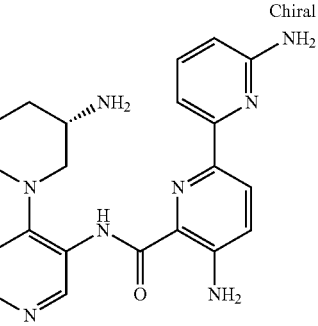 Chiral | 5,6'-Diamino-[2,2']bipyridinyl-6-carboxylic acid (3-amino-3,4,5,6-tetrahydro-2H-[1,4']bi-pyridinyl-3'-yl)-amide | 405.2 | 1.29 |
| 712 | 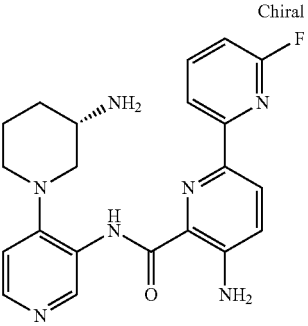 [SMILES: Nc1ccc(-c2cccc(F)n2)nc1C(=O)Nc1cnccc1N1CCC[C@H](N)C1] Chiral | 5-Amino-6'-fluoro-[2,2']bi-pyridinyl-6-carboxylic acid (3-amino-3,4,5,6-tetrahydro-2H-[1,4']bipyridinyl-3'-yl)-amide | 408.2 | 1.89 |
| 713 | 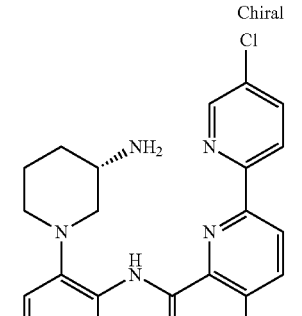 Chiral | 5-Amino-5'-chloro-[2,2']bi-pyridinyl-6-carboxylic acid (3-amino-3,4,5,6-tetrahydro-2H-[1,4']bipyridinyl-3'-yl)-amide | 424.2 | 1.85 |

-continued

| Example | Structure | Name | MH+ | LC |
|---|---|---|---|---|
| 714 | 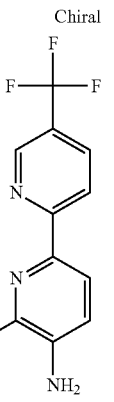 Chiral | 5-Amino-5'-trifluoromethyl-[2,2']bipyridinyl-6-carboxylic acid (3-amino-3,4,5,6-tetrahydro-2H-[1,4']bipyridinyl-3'-yl)-amide | 458.2 | 2.15 |
| 715 | 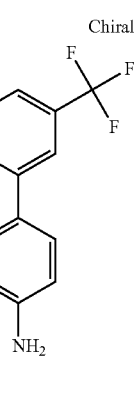 Chiral | 5-Amino-4'-trifluoromethyl-[2,2']bipyridinyl-6-carboxylic acid (3-amino-3,4,5,6-tetrahydro-2H-[1,4']bipyridinyl-3'-yl)-amide | 458.2 | 2.08 |
| 716 | 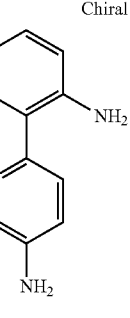 Chiral | 5,3'-Diamino-[2,2']bipyridinyl-6-carboxylic acid (3-amino-3,4,5,6-tetrahydro-2H-[1,4']bipyridinyl-3'-yl)-amide | 405.2 | 1.07 |
| 717 | 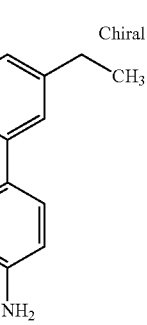 Chiral | 5-Amino-4'-ethyl-[2,2']bipyridinyl-6-carboxylic acid (3-amino-3,4,5,6-tetrahydro-2H-[1,4']bipyridinyl-3'-yl)-amide | 418.2 | 1.44 |

-continued

| Example | Structure | Name | MH+ | LC |
|---|---|---|---|---|
| 718 | 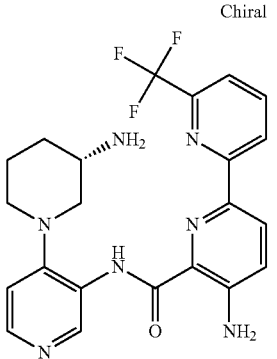 [SMILES: Nc1ccc(-c2cccc(C(F)(F)F)n2)nc1C(=O)Nc1cnccc1N1CCC[C@H](N)C1] Chiral | 5-Amino-6'-trifluoromethyl-[2,2']bipyridinyl-6-carboxylic acid (3-amino-3,4,5,6-tetrahydro-2H-[1,4']bipyridinyl-3'-yl)-amide | 458.2 | 2.40 |
| 719 | 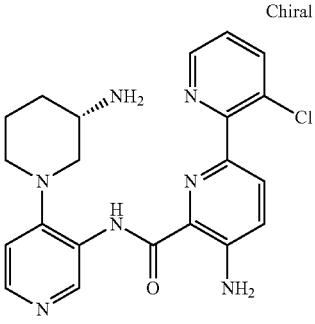 [SMILES: Nc1ccc(-c2ncccc2Cl)nc1C(=O)Nc1cnccc1N1CCC[C@H](N)C1] Chiral | 5-Amino-3'-chloro-[2,2']bipyridinyl-6-carboxylic acid (3-amino-3,4,5,6-tetrahydro-2H-[1,4']bipyridinyl-3'-yl)-amide | 424.1 | 1.81 |
| 720 | 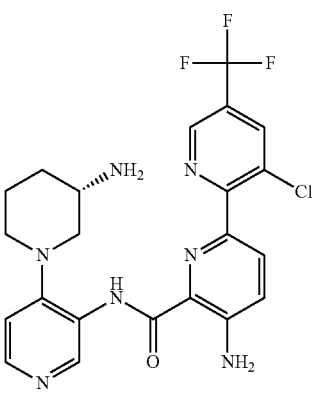 Chiral | 5-Amino-3-chloro-5'-trifluoromethyl-[2,2']bipyridinyl-6-carboxylic acid (3-amino-3,4,5,6-tetrahydro-2H-[1,4']bipyridinyl-3'-yl)-amide | 492.2 | 2.29 |
| 721 | 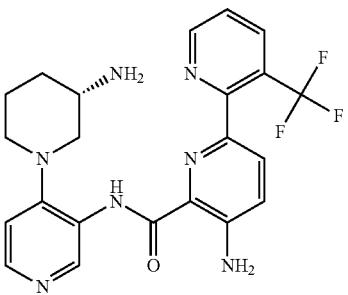 Chiral | 5-Amino-3'-trifluoromethyl-[2,2']bipyridinyl-6-carboxylic acid (3-amino-3,4,5,6-tetrahydro-2H-[1,4']bipyridinyl-3'-yl)-amide | 458.2 | 1.94 |

-continued

| Example | Structure | Name | MH+ | LC |
|---|---|---|---|---|
| 722 | 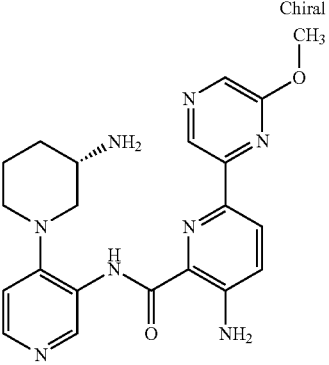 [SMILES: COc1cncc(-c2ccc(N)c(C(=O)Nc3cnccc3N3CCC[C@H](N)C3)n2)n1] Chiral | 3-Amino-6-(6-methoxy-pyrazin-2-yl)-pyridin-2-carboxylic acid (3-amino-3,4,5,6-tetrahydro-2H-[1,4']bipyridinyl-3'-yl)-amide | 421.2 | 1.93 |
| 723 | 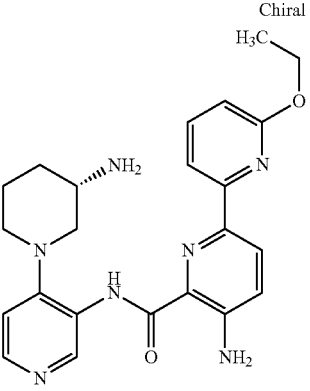 [SMILES: CCOc1cccc(-c2ccc(N)c(C(=O)Nc3cnccc3N3CCC[C@H](N)C3)n2)n1] Chiral | 5-Amino-6'-ethoxy-[2,2']bi-pyridinyl-6-carboxylic acid (3-amino-3,4,5,6-tetrahydro-2H-[1,4']bipyridinyl-3'-yl)-amide | 434.2 | 2.05 |
| 724 | 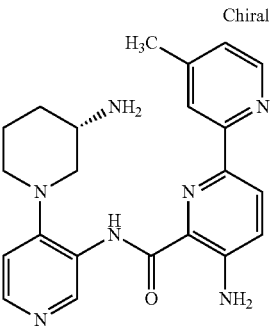 [SMILES: Cc1ccnc(-c2ccc(N)c(C(=O)Nc3cnccc3N3CCC[C@H](N)C3)n2)c1] Chiral | 5-Amino-4'-methyl-[2,2']bi-pyridinyl-6-carboxylic acid (3-amino-3,4,5,6-tetrahydro-2H-[1,4']bipyridinyl-3'-yl)-amide | 404.2 | 1.26 |
| 725 | 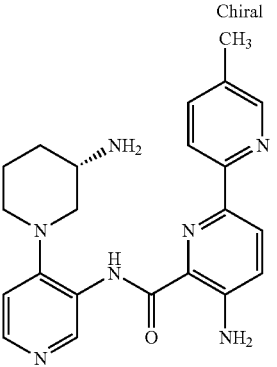 [SMILES: Cc1ccc(-c2ccc(N)c(C(=O)Nc3cnccc3N3CCC[C@H](N)C3)n2)nc1] Chiral | 5-Amino-5'-methyl-[2,2']bi-pyridinyl-6-carboxylic acid (3-amino-3,4,5,6-tetrahydro-2H-[1,4']bipyridinyl-3'-yl)-amide | 404.2 | 1.25 |

| Example | Structure | Name | MH+ | LC |
|---|---|---|---|---|
| 726 | Chiral | 5-Amino-6'-methyl-[2,2']bi-pyridinyl-6-carboxylic acid (3-amino-3,4,5,6-tetrahydro-2H-[1,4']bipyridinyl-3'-yl)-amide | 404.2 | 1.14 |
| 727 | Chiral | 5-Amino-5'-fluoro-[2,2']bi-pyridinyl-6-carboxylic acid (3-amino-3,4,5,6-tetrahydro-2H-[1,4']bipyridinyl-3'-yl)-amide | 408.2 | 1.64 |
| 728 | Chiral | 3-Amino-6-(2-amino-pyrimidin-4-yl)-pyridine-2-carboxylic acid (3-amino-3,4,5,6-tetrahydro-2H-[1,4']bipyridinyl-3'-yl)-amide | 406.1 | 1.17 |
| 729 | Chiral | 3-Amino-6-(5-amino-pyrazin-2-yl)-pyridine-2-carboxylic acid (3-amino-3,4,5,6-tetrahydro-2H-[1,4']bipyridinyl-3'-yl)-amide | 406.1 | 1.37 |

| Example | Structure | Name | MH+ | LC |
|---|---|---|---|---|
| 730 | Chiral | 5-Amino-[2,2']bipyridinyl-6-carboxylic acid (3-amino-3,4,5,6-tetrahydro-2H-[1,4']bipyridinyl-3'-yl)-amide | 390.2 | 1.11 |
| 731 | Chiral | 3-Amino-6-(5-amino-6-methoxy-pyrazin-2-yl)-pyridine-2-carboxylic acid (3-amino-3,4,5,6-tetrahydro-2H-[1,4']bipyridinyl-3'-yl)-amide | 436.2 | 1.50 |
| 732 | 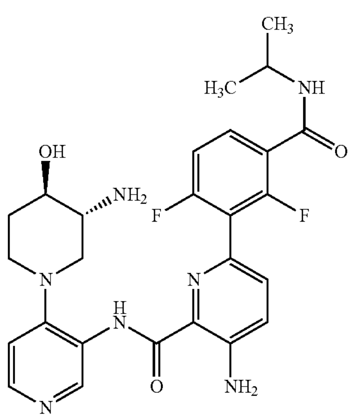 [SMILES: CC(C)NC(=O)c1ccc(F)c(-c2ccc(N)c(C(=O)Nc3cnccc3N3CC[C@@H](O)[C@H](N)C3)n2)c1F] | 3-Amino-6-(2,6-difluoro-3-isopropylcarbamoyl-phenyl)-pyridine-2-carboxylic acid (3-amino-4-hydroxy-3,4,5,6-tetrahydro-2H-[1,4']bipyridinyl-3'-yl)-amide | 526.3 | 1.91 |
| 733 | 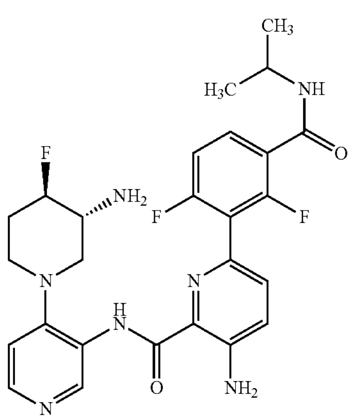 [SMILES: CC(C)NC(=O)c1ccc(F)c(-c2ccc(N)c(C(=O)Nc3cnccc3N3CC[C@@H](F)[C@H](N)C3)n2)c1F] | 3-Amino-6-(2,6-difluoro-3-isopropylcarbamoyl-phenyl)-pyridine-2-carboxylic acid (3-amino-4-fluoro-3,4,5,6-tetrahydro-2H-[1,4']bipyridinyl-3'-yl)-amide | 528.3 | 2.02 |

-continued

| Example | Structure | Name | MH+ | LC |
|---|---|---|---|---|
| 734 | 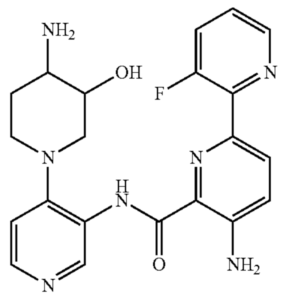 [SMILES: Nc1ccc(-c2ncccc2F)nc1C(=O)Nc1cnccc1N1CCC(N)C(O)C1] | 5-Amino-3'-fluoro-[2,2']bi-pyridinyl-6-carboxylic acid (4-amino-3-hydroxy-3,4,5,6-tetra-hydro-2H-[1,4']bipyridinyl-3'-yl)-amide | 424.2 | 1.25 |
| 735 | 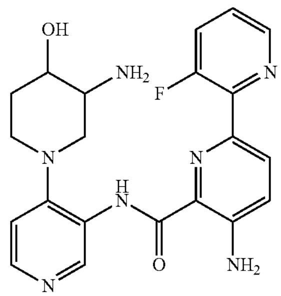 [SMILES: Nc1ccc(-c2ncccc2F)nc1C(=O)Nc1cnccc1N1CCC(O)C(N)C1] | 5-Amino-3'-fluoro-[2,2']bi-pyridinyl-6-carboxylic acid (3-amino-4-hydroxy-3,4,5,6-tetra-hydro-2H-[1,4']bipyridinyl-3'-yl)-amide | 424.2 | 1.37 |
| 736 | Chiral | 3-Amino-6-(2,6-difluoro-3-isopropylcarbamoyl-phenyl)-5-fluoro-pyridine-2-carboxylic acid (3-amino-3,4,5,6-tetra-hydro-2H-[1,4']bipyridinyl-3'-yl)-amide | 528.2 | 2.13 |
| 737 | Chiral | 5-Amino-3,3'-difluoro-4'-methyl-[2,2']bipyridinyl-6-carboxylic acid (3-amino-3,4,5,6-tetrahydro-2H-[1,4']bi-pyridinyl-3'-yl)-amide | 440.2 | 1.88 |

| Example | Structure | Name | MH+ | LC |
|---|---|---|---|---|
| 738 | 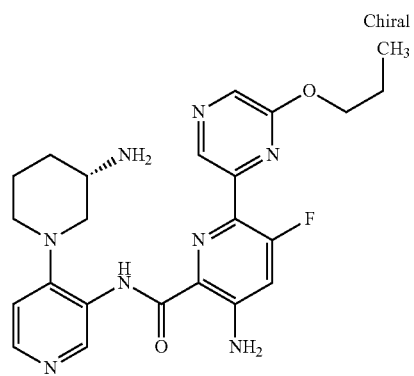 [SMILES: CCCOc1cncc(-c2nc(C(=O)Nc3cnccc3N3CCC[C@H](N)C3)c(N)cc2F)n1] Chiral | 3-Amino-5-fluoro-6-(6-propoxy-pyrazin-2-yl)-pyridine-2-carboxylic acid (3-amino-3,4,5,6-tetrahydro-2H-[1,4']bipyridinyl-3'-yl)-amide | 467.2 | 2.34 |
| 739 | 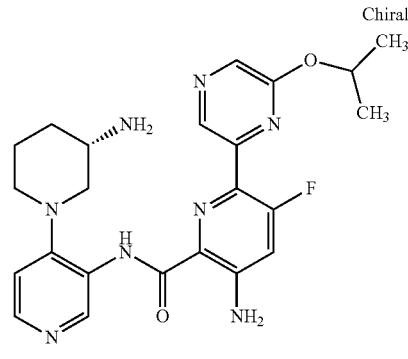 [SMILES: CC(C)Oc1cncc(-c2nc(C(=O)Nc3cnccc3N3CCC[C@H](N)C3)c(N)cc2F)n1] Chiral | 3-Amino-5-fluoro-6-(6-isopropoxy-pyrazin-2-yl)-pyridine-2-carboxylic acid (3-amino-3,4,5,6-tetrahydro-2H-[1,4']bipyridinyl-3'-yl)-amide | 467.2 | 2.31 |
| 740 | 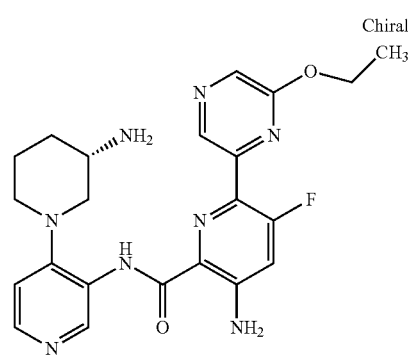 [SMILES: CCOc1cncc(-c2nc(C(=O)Nc3cnccc3N3CCC[C@H](N)C3)c(N)cc2F)n1] Chiral | 3-Amino-6-(6-ethoxy-pyrazin-2-yl)-5-fluoro-pyridine-2-carboxylic acid (3-amino-3,4,5,6-tetrahydro-2H-[1,4']bipyridinyl-3'-yl)-amide | 453.2 | 2.11 |
| 741 | 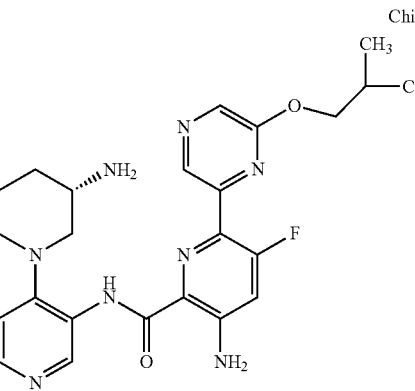 Chiral | 3-Amino-5-fluoro-6-(6-isobutoxy-pyrazin-2-yl)-pyridine-2-carboxylic acid (3-amino-3,4,5,6-tetrahydro-2H-[1,4']bipyridinyl-3'-yl)-amide | 481.2 | 2.53 |

| Example | Structure | Name | MH+ | LC |
|---|---|---|---|---|
| 742 | Chiral | 5,5'-Diamino-6'-(3-amino-3,4,5,6-tetrahydro-2H-[1,4']bipyridinyl-3'-ylcarbamoyl)-3,3'-difluoro-[2,2']bipyridinyl-6-carboxylic acid methyl ester | 499.2 | 1.86 |
| 743 | Chiral | 5-Amino-3'-chloro-3-fluoro-[2,2']bipyridinyl-6-carboxylic acid (3-amino-3,4,5,6-tetrahydro-2H-[1,4']bipyridinyl-3'-yl)-amide | 442.2 | 1.96 |
| 744 | Chiral | 5-Amino-3,3'-difluoro-[2,2']bipyridinyl-6-carboxylic acid (3-amino-3,4,5,6-tetrahydro-2H-[1,4']bipyridinyl-3'-yl)-amide | 426.2 | 1.75 |
| 745 | Chiral | 5-Amino-3,3'-difluoro-6'-methyl-[2,2']bipyridinyl-6-carboxylic acid (3-amino-3,4,5,6-tetrahydro-2H-[1,4']bipyridinyl-3'-yl)-amide | 440.2 | 1.82 |

| Example | Structure | Name | MH+ | LC |
|---------|-----------|------|-----|-----|
| 746 | 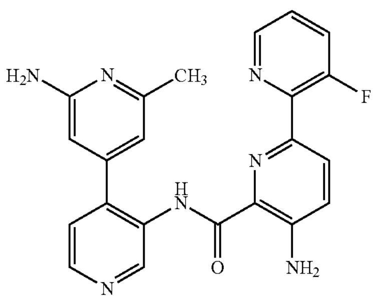 | 5-Amino-3'-fluoro-[2,2']bi-pyridinyl-6-carboxylic acid (2'-amino-6'-methyl-[4,4']bi-pyridinyl-3-yl)-amide | 416.2 | 1.77 |
| 747 | Chiral | 3-Amino-6-(6-propoxy-pyrazin-2-yl)-pyridine-2-carboxylic acid (3-amino-3,4,5,6-tetrahydro-2H-[1,4']bipyridinyl-3'-yl)-amide | 449.2 | 2.34 |
| 748 | Chiral | 3-Amino-6-(6-isopropoxy-pyrazin-2-yl)-pyridine-2-carboxylic acid (3-amino-3,4,5,6-tetrahydro-2H-[1,4']bipyridinyl-3'-yl)-amide | 449.2 | 2.29 |
| 749 | Chiral | 3-Amino-6-(6-ethoxy-pyrazin-2-yl)-pyridine-2-carboxylic acid (3-amino-3,4,5,6-tetrahydro-2H-[1,4']bipyridinyl-3'-yl)-amide | 435.2 | 2.12 |

| Example | Structure | Name | MH+ | LC |
|---|---|---|---|---|
| 750 | 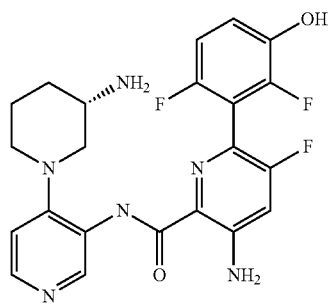 [SMILES: Nc1cc(F)c(-c2c(F)ccc(O)c2F)nc1C(=O)Nc1cnccc1N1CCC[C@H](N)C1] Chiral | 3-Amino-6-(6-benzyloxy-pyrazin-2-yl)-pyridine-2-carboxylic acid (3-amino-3,4,5,6-tetrahydro-2H-[1,4']bi-pyridinyl-3'-yl)-amide | 497.1 | 2.62 |

Example 751

3-Amino-N-(4-((S)-3-aminopiperidin-1-ylpyridin-3-yl)-6-(2,6-difluoro-3-hydroxyphenyl)-5-fluoropicolinamide

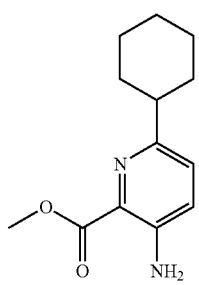 [SMILES: COC(=O)c1nc(C2CCCCC2)ccc1N]

Method 2 of Example 49 was followed using 3-amino-N-(4-((S)-3-aminopiperidin-1-yl)pyridin-3-yl)-6-(3-(benzyloxy)-2,6-difluorophenyl)-5-fluoropicolinamide with 20 wt % Pd/C in methanol (0.1 M solution). The Boc protected product was purified by preparative HPLC. After volatile materials were removed, the crude material was stirred in 30% TFA in dichloromethane. After volatile materials were removed in vacuo, 3-amino-N-(4-((S)-3-aminopiperidin-1-yl)pyridin-3-yl)-6-(2,6-difluoro-3-hydroxyphenyl)-5-fluoropicolinamide was obtained by preparative HPLC. LCMS (m/z): 459.2 (MH+); LC R$_t$=2.10 min.

Synthesis of methyl 3-amino-6-cyclohexylpicolinate

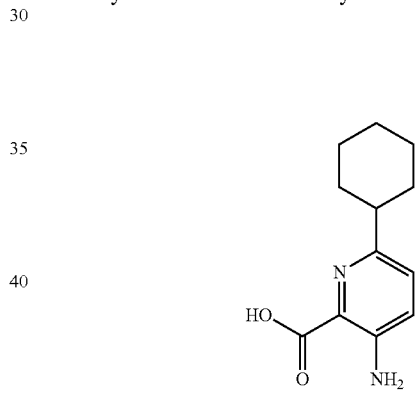

A solution of methyl 3-amino-6-bromopicolinate (1.0 equiv.), cyclohexyl zincbromide 0.5 M solution in THF (1.5 equiv.), and tetrakis(triphenylphosphine)-palladium(0) (0.05 equiv.) was stirred at 50° C. for 15 minutes. The reaction was filtered and washed with EtOAc. The organic was washed with H$_2$O (100 mL), NaCl$_{(sat.)}$ (50 mL), dried over MgSO$_4$, and the volatiles were removed in vacuo. The product was purified on silica utilizing the Isco 0-65% gradient of hexane/EtOAc to yield methyl 3-amino-6-cyclohexylpicolinate (98%). LCMS (m/z): 235.2 (MH+); LC R$_t$=1.89 min.

Synthesis of 3-amino-6-cyclohexylpicolinic acid

To a solution of methyl 3-amino-6-cyclohexylpicolinate (1.0 equiv) in THF, at a concentration of 0.5 M, was added 1M LiOH (4.0 equiv). After stirring for 4 hours at room temperature, 1 N HCl (4.0 equiv.) was added and the THF was removed in vacuo. The resulting solid was filtered, rinsed with cold H$_2$O (3×20 mL) yielding 3-amino-6-cyclohexylpicolinic acid (18%). LCMS (m/z): 221.0 (MH+); LC R$_t$=4.1 min To a solution of (3R,5R)-3-(tert-butyldimethylsilyloxy)-5-fluoropiperidine (1 eq) in 30 mL of methanol was added 3.8M HCl in isopropanol (4 eq). The reaction mixture was allowed to stand at room temperature for 3 hours at which point it was concentrated under reduced pressure. The resulting residue was diluted with 120 mL of EtOAc, washed with sat. aq. sodium bicarbonate, brine, then dried over anhydrous MgSO$_4$, filtered, and concentrated in vacuo. The crude residue was purified by flash chromatography (EtOAc:hexanes=2:1) to give (3R,5R)-benzyl 3-fluoro-5-hydroxypiperidine-1-carboxylate, (94%). LC/MS (m/z): 254.2 (MH+).

Synthesis of (3S,5R)-benzyl 3-azido-5-fluoropiperidine-1-carboxylate

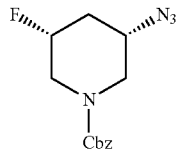 [SMILES: [N-]=[N+]=N[C@H]1C[C@@H](F)CN(C(=O)OCc2ccccc2)C1]

To a solution of (3R,5R)-benzyl 3-fluoro-5-hydroxypiperidine-1-carboxylate (1 eq) in 14 mL of dichloromethane was added triethyl amine (3 eq) and methanesulfonyl chloride (1.5 eq) at 0° C. The reaction mixture was allowed to stir at room temperature for 1.5 hours. The crude mixture was diluted with 120 mL of diethyl ether, washed with sat. aq. sodium bicarbonate, brine, then dried over anhydrous MgSO$_4$, filtered, and concentrated in vacuo. The crude residue was dissolved in 16 mL of NMP. Sodium azide (3.0 eq) was added and the resulting suspension was stirred at 80° C. overnight. The reaction mixture was diluted with 200 mL of EtOAc and 100 mL of hexanes, washed with water, brine, then dried over anhydrous MgSO$_4$, filtered, and concentrated in vacuo. The crude residue was purified by flash chromatography (EtOAc: hexanes=1:3) to give the titled compound (90%). LC/MS (m/z): 251.1 (MH$^+$-28).

Synthesis of (3S,5R)-benzyl 3-(tert-butoxycarbonylamino)-5-fluoropiperidine-1-carboxylate

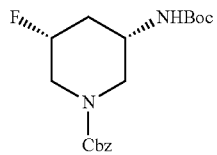 [SMILES: CC(C)(C)OC(=O)N[C@H]1C[C@@H](F)CN(C(=O)OCc2ccccc2)C1]

To a solution of (3S,5R)-benzyl 3-azido-5-fluoropiperidine-1-carboxylate (1 eq) in a mixture of 11 mL of pyridine and 1.5 mL of ammonium hydroxide was added 1M trimethylphosphine (3 eq) at room temperature. The reaction mixture was stirred at room temperature for 3 hours at which point the solvents were removed under reduced pressure to give a yellow oil. The oil was again dissolved in 100 mL of ethanol and concentrated to remove ammonium hydroxide completely. The residue was dissolved in 12 ml of 1,4-dioxane and 12 mL of sat. aq. NaHCO$_3$ was added. Di-tert-butyl dicarbonate (4 eq) in 6 mL of THF was added dropwise at 0° C. The mixture was allowed to stir at room temperature for 1 hour. The crude mixture was diluted with 150 mL of EtOAc, washed with brine, then dried over anhydrous MgSO$_4$, filtered, and concentrated in vacuo. The crude residue was purified by flash chromatography (EtOAc:hexanes=1:1) to give the titled compound (95%). LC/MS (m/z): 253.1 (MH$^+$-100).

Synthesis of tert-butyl (3S,5R)-5-fluoro-1-(3-nitropyridin-4-yl)piperidin-3-ylcarbamate

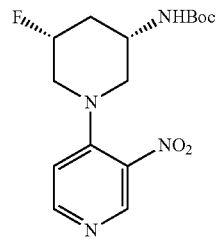 [SMILES: CC(C)(C)OC(=O)N[C@H]1C[C@@H](F)CN(c2ccncc2[N+](=O)[O-])C1]

To a solution of (3S,5R)-benzyl 3-(tert-butoxycarbonylamino)-5-fluoropiperidine-1-carboxylate (1 eq) in 28 methanol was added 10% Pd/C (0.1 eq). The resulting suspension was stirred at H$_2$ atmosphere for 1 hours. The crude solids were filtered through a pad of Celite on a paper lined Buchner funnel, washed with MeOH, then concentrated in vacuo. The residue was dissolved in 33 mL of isopropanol and DIPEA (2.5 eq) and 4-chloro-3-nitropyridine (1.5 eq) were added. The reaction mixture was stirred at 80° C. for 2 hours, at which point the reaction mixture was allowed to cool to room temperature and concentrated under reduced pressure. The residue was diluted with 150 mL of EtOAc, washed with brine, then dried over anhydrous MgSO$_4$; filtered, and concentrated in vacuo. The crude residue was purified by flash chromatography (5% methanol in EtOAc:hexanes=1:1) to give the titled compound (90%). LC/MS (m/z): 341.1 (MH$^+$). HPLC: R$_t$: 2.115 min.

Synthesis of tert-Butyl (3S,5R)-1-(3-aminopyridin-4-yl)-5-fluoropiperidin-3-ylcarbamate

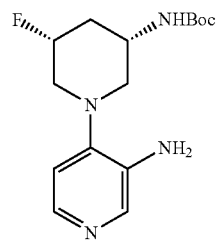

Following Method 2 of Example 49, tert-butyl (3S,5R)-5-fluoro-1-(3-nitropyridin-4-yl)piperidin-3-ylcarbamate was reduced yielding tert-Butyl (3S,5R)-1-(3-aminopyridin-4-yl)-5-fluoropiperidin-3-ylcarbamate. LC/MS (m/z): 311.1 (MH$^+$).

Synthesis of tert-butyl (3S,5R)-1-(3-(3-amino-6-bromopicolinamido)pyridin-4-yl)-5-fluoropiperidin-3-ylcarbamate

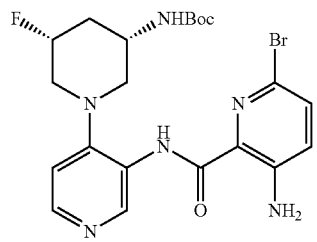 [SMILES: CC(C)(C)OC(=O)N[C@H]1C[C@@H](F)CN(c2ccncc2NC(=O)c2nc(Br)ccc2N)C1]

Following Method 11 of Example 305, tert-Butyl (3S,5R)-1-(3-aminopyridin-4-yl)-5-fluoropiperidin-3-ylcarbamate and 3-amino-6-bromopicolinic acid were coupled yielding after column chromatography tert-butyl (3S,5R)-1-(3-(3-amino-6-bromopicolinamido)pyridin-4-yl)-5-fluoropiperidin-3-ylcarbamate. LC/MS (m/z): 509.1/511.1 (MH+).

Synthesis of cis (+/−)-1-benzyl 3-methyl 5-(tert-butoxycarbonylamino)piperidine-1,3-dicarboxylate

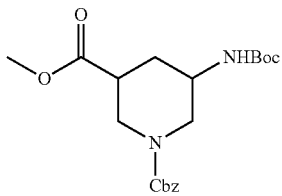 [SMILES: COC(=O)C1CC(NC(=O)OC(C)(C)C)CN(C(=O)OCc2ccccc2)C1]

To a solution of cis (+/−)-1-(benzyloxycarbonyl)-5-(tert-butoxycarbonylamino)piperidine-3-carboxylic acid (1.0 eq), methanol (20 eq.) and EDC (1.3 eq) in dichloromethane at a concentration of 0.25 M at 0*C was added dimethylaminopyridine (0.1 eq). After stirring for 48 hours as the reaction was allowed to warm to rt the volatiles were removed in vacuo. Upon addition of ethyl actetate and washing with H$_2$O (3×), 1N HCl, NaHCO$_{3(sat.)}$ and brine, the solution was dried over MgSO$_4$, filtered, concentrated and purified by column chromatography (25% ethyl acetate/hexanes) to yield cis (+/−)-1-benzyl 3-methyl 5-(tert-butoxycarbonylamino)piperidine-1,3-dicarboxylate. LCMS (m/z): 293.1 (MH-Boc+); LC R$_t$=4.09 min Synthesis of cis (+/−)-benzyl 3-(tert-butoxycarbonylamino)-5-(hydroxymethyl)piperidine-1-carboxylate

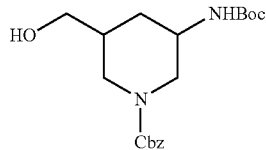

A solution of cis (+/−)-1-benzyl 3-methyl 5-(tert-butoxycarbonylamino)piperidine-1,3-dicarboxylate (1.0 eq.) in THF at a concentration of 0.08 M was cooled at 0*C and then LiCl (2.3 eq.) and sodium borohydride (2.3 eq.) were added. After stirring for 20 hours as the reaction warmed to rt, the pH was adjusted with 1M citric acid to pH 4-5. After removal of the volatiles in vacuo, the product was extracted in dichloromethane, washed with H$_2$O and brine, dried over MgSO$_4$. Upon filtering and removal of the volatiles in vacuo, cis (+/−)-benzyl 3-(tert-butoxycarbonylamino)-5-(hydroxymethyl)piperidine-1-carboxylate was obtained as a white foamy solid. LCMS (m/z): 265.0 (MH-Boc+); LC R$_t$=3.37 min.

Synthesis of cis (+/−)-benzyl 3-(tert-butoxycarbonylamino)-5-((tert-butyldimethylsilyloxy)methyl)piperidine-1-carboxylate

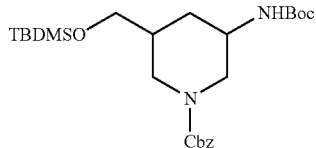 [SMILES: CC(C)(C)OC(=O)NC1CC(CO[Si](C)(C)C(C)(C)C)CN(C(=O)OCc2ccccc2)C1]

A solution of cis (+/−)-benzyl 3-(tert-butoxycarbonylamino)-5-(hydroxymethyl)piperidine-1-carboxylate (1.0 eq.), imidazole (1.1 eq.), tert-butyl-dimethylsilylchloride (1.1 eq.) and dimethylaminopyridine (0.1 eq.) in dichloromethane at a concentration of 0.1 M was sired for 18 hours at which time the volatiles were removed in vacuo. Direct purification of the crude material by column chromatography (20% ethyl acetate/hexanes) yielded cis (+/−)-benzyl 3-(tert-butoxycarbonylamino)-5-((tert-butyldimethylsilyloxy)methyl)piperidine-1-carboxylate. LCMS (m/z): 379.0 (MH-Boc+); LC R$_t$=5.95 min.

Synthesis of cis (+/−)-tert-butyl 5-((tert-butyldimethylsilyloxy)-methyl)piperidin-3-ylcarbamate

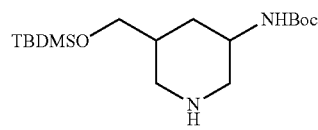 [SMILES: CC(C)(C)OC(=O)NC1CNCC(CO[Si](C)(C)C(C)(C)C)C1]

Method 17 was followed to deprotect cis (+/−)-benzyl 3-(tert-butoxycarbonylamino)-5-((tert-butyldimethylsilyloxy)methyl)piperidine-1-carboxylate yielding cis (+/−)-tert-butyl 5-((tert-butyldimethylsilyloxy)methyl)piperidin-3-ylcarbamate. LCMS (m/z): 344.1 (MH+).

Synthesis of cis (+/−)-tert-butyl 5-((tert-butyldimethylsilyloxy)methyl)-1-(3-nitropyridin-4-yl) piperidin-3-ylcarbamate

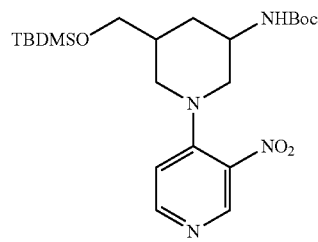 [SMILES: CC(C)(C)OC(=O)NC1CC(CO[Si](C)(C)C(C)(C)C)CN(c2ccncc2[N+](=O)[O-])C1]

Method 1 of Example 1 was followed using cis (+/−)-tert-butyl 5-((tert-butyldimethylsilyloxy)methyl)piperidin-3-ylcarbamate and 4-chloro-3-nitropydidine yielding cis (+/−)-tert-butyl 5-((tert-butyldimethylsilyloxy)methyl)-1-(3-nitropyridin-4-yl)piperidin-3-ylcarbamate. LCMS (m/z): 467.0 (MH+); LC R$_t$=4.02 min.

Synthesis of cis (+/−)-tert-butyl 1-(3-aminopyridin-4-yl)-5-((tert-butyldimethylsilyloxy)methyl)piperidin-3-ylcarbamate

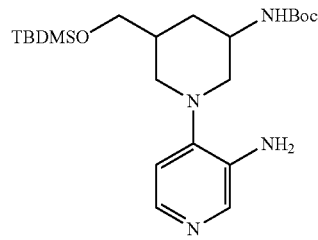 [SMILES: CC(C)(C)OC(=O)NC1CC(CO[Si](C)(C)C(C)(C)C)CN(c2ccncc2N)C1]

Following Method 2 of Example 49, cis (+/−)-tert-butyl 5-((tert-butyldimethylsilyloxy)methyl)-1-(3-nitropyridin-4-yl)piperidin-3-ylcarbamate was reduced yielding cis (+/−)- tert-butyl 1-(3-aminopyridin-4-yl)-5-((tert-butyldimethylsilyloxy)methyl)piperidin-3-ylcarbamate. LCMS (m/z): 437.2 (MH⁺); LC R$_t$=3.86 min.

Synthesis of cis (+/−)-tert-butyl 1-(3-(3-amino-6-bromopicolinamido)pyridin-4-yl)-5-(hydroxymethyl)piperidin-3-ylcarbamate

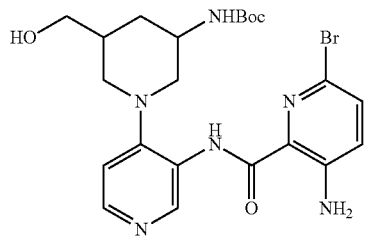 [SMILES: CC(C)(C)OC(=O)NC1CC(CO)CN(c2ccncc2NC(=O)c2nc(Br)ccc2N)C1]

Following Method 11 of Example 305, cis (+/−)-tert-butyl 1-(3-aminopyridin-4-yl)-5-((tert-butyldimethylsilyloxy)methyl)piperidin-3-ylcarbamate and 6-bromo-3-aminopicolinic acid were coupled. Following purification by RP HPLC the product fractions were allowed to stand at it overnight in the 0.1% TFA acetonitrile/water solution which removed the silyl group. Upon subsequent lyophilization, cis (+/−)-tert-butyl 1-(3-(3-amino-6-bromopicolinamido)pyridin-4-yl)-5-(hydroxymethyl)piperidin-3-ylcarbamate was obtained and used in Suzuki reactions directly. LCMS (m/z): 521.0/523.1 (MH⁺); LC R$_t$=2.58 min.

Synthesis of cis (+/−)-tert-butyl 1-(3-(6-bromo-3-fluoropicolinamido)pyridin-4-yl)-5-(hydroxymethyl)piperidin-3-ylcarbamate

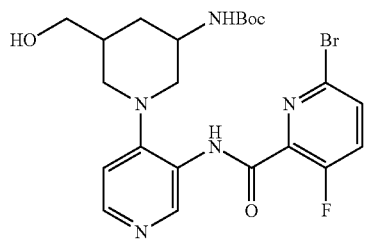 [SMILES: CC(C)(C)OC(=O)NC1CC(CO)CN(c2ccncc2NC(=O)c2nc(Br)ccc2F)C1]

Following Method 11 of Example 305, cis (+/−)-tert-butyl 1-(3-aminopyridin-4-yl)-5-((tert-butyldimethylsilyloxy)methyl)piperidin-3-ylcarbamate and 6-bromo-3-fluoropicolinic acid were coupled. Following purification by RP HPLC the product fractions were allowed to stand at it overnight in the 0.1% TFA acetonitile/water solution which removed the silyl group. Upon subsequent lyophilization, cis (+/−)-tert-butyl 1-(3-(6-bromo-3-fluoropicolinamido)pyridin-4-yl)-5-(hydroxymethyl)piperidin-3-ylcarbamate was obtained and used in Suzuki reactions directly. LCMS (m/z): 524.0/526.0 (MH⁺); LC R$_t$=2.90 min.

Synthesis of cis (+/−)-benzyl 3-(tert-butoxycarbonylamino)-5-(fluoromethyl)piperidine-1-carboxylate

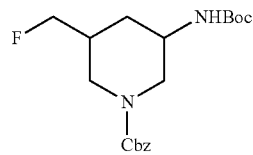

A solution of cis (+/−)-benzyl 3-(tert-butoxycarbonylamino)-5-(hydroxymethyl)piperidine-1-carboxylate (1 eq.), perfluorobutanesulfonylfluoride (2 eq.), triethylamine-HF (4 eq.) and triethylamine (6 eq.) in tetrahydrofuran at a concentration of 0.16 M was stirred for 36 hours. Upon dilution with ethyl acetate (50×) the solution was washed with 1N HCl, NaHCO₃$_{(sat.)}$ and brine, was dried over MgSO₄, filtered, concentrated and purified by column chromatography (25-40% ethyl acetate/hexanes) to yield cis (+/−)-benzyl 3-(tert-butoxycarbonylamino)-5-(fluoromethyl)piperidine-1-carboxylate (45% yield). LCMS (m/z): 267.1 (MH⁺); LC R$_t$=4.23 min.

Synthesis of cis (+/−)-tert-butyl 5-(fluoromethyl)piperidin-3-ylcarbamate

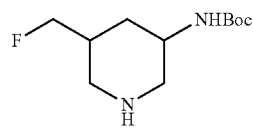

Method 17 was followed to deprotect cis (+/−)-benzyl 3-(tert-butoxycarbonylamino)-5-(fluoromethyl)piperidine-1-carboxylate yielding cis (+/−)-tert-butyl 5-(fluoromethyl)piperidin-3-ylcarbamate. LCMS (m/z): 233.1 (MH⁺).

Synthesis of cis (+/−)-tert-butyl 5-(fluoromethyl)-1-(3-nitropyridin-4-yl)piperidin-3-ylcarbamate

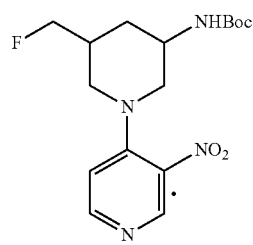

Method 1 of Example 1 was followed using cis (+/−)-tert-butyl 5-(fluoromethyl)piperidin-3-ylcarbamate and 4-chloro-3-nitropyridine yielding cis (+/−)-tert-butyl 5-(fluoromethyl)-1-(3-nitropyridin-4-yl)piperidin-3-ylcarbamate. LCMS (m/z): 355.1 (MH⁺); LC R$_t$=2.41 min.

Synthesis of cis (+/−)-tert-butyl 1-(3-aminopyridin-4-yl)-5-(fluoromethyl)piperidin-3-ylcarbamate

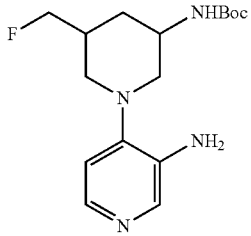 [SMILES: CC(C)(C)OC(=O)NC1CC(CF)CN(c2ccncc2N)C1]

Following Method 2 of Example 49, cis (+/−)-tert-butyl 5-(fluoromethyl)-1-(3-nitropyridin-4-yl)piperidin-3-ylcarbamate was reduced yielding cis (+/−)-tert-butyl 1-(3-aminopyridin-4-yl)-5-(fluoromethyl)piperidin-3-ylcarbamate. LCMS (m/z): 325.1 (MH$^+$); LC R$_t$=2.27 min.

Synthesis of tert-butyl (3R,4R)-1-(3-(6-bromo-5-fluoropicolinamido)pyridin-4-yl)-4-(tert-butyldimethylsilyloxy)piperidin-3-ylcarbamate

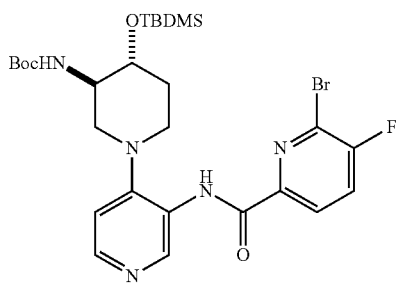 [SMILES: CC(C)(C)OC(=O)N[C@@H]1CN(c2ccncc2NC(=O)c2ccc(F)c(Br)n2)CC[C@H]1O[Si](C)(C)C(C)(C)C]

Following Method 11 of Example 305, tert-butyl (3R,4R)-1-(3-aminopyridin-4-yl)-4-(tert-butyldimethylsilyloxy)piperidin-3-ylcarbamate and 6-bromo-5-fluoropicolinic acid were coupled to yield tert-butyl (3R,4R)-1-(3-(6-bromo-5-fluoropicolinamido)pyridin-4-yl)-4-(tert-butyldimethylsilyloxy)piperidin-3-ylcarbamate. LCMS (m/z): 510.0/512.0 (MH$^+$); LC R$_t$=4.51 min.

Synthesis of tert-butyl (3S,5R)-1-(3-(6-bromo-5-fluoropicolinamido)pyridin-4-yl)-5-(tert-butyldimethylsilyloxy)piperidin-3-ylcarbamate

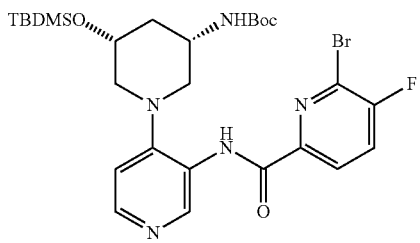 [SMILES: CC(C)(C)OC(=O)N[C@H]1C[C@@H](O[Si](C)(C)C(C)(C)C)CN(c2ccncc2NC(=O)c2ccc(F)c(Br)n2)C1]

Following Method 11 of Example 305, tert-butyl (3S,5R)-1-(3-aminopyridin-4-yl)-5-(tert-butyldimethylsilyloxy)piperidin-3-ylcarbamate and 6-bromo-5-fluoropicolinic acid were coupled to yield tert-butyl (3S,5R)-1-(3-(6-bromo-5-fluoropicolinamido)pyridin-4-yl)-5-(tert-butyldimethylsilyloxy)piperidin-3-ylcarbamate. LCMS (m/z): 624.1/626.1 (MH$^+$).

Synthesis of tert-butyl (3S,5R)-1-(3-(3-amino-6-bromopicolinamido)pyridin-4-yl)-5-(tert-butyldimethylsilyloxy)piperidin-3-ylcarbamate

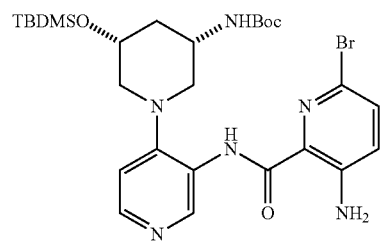 [SMILES: CC(C)(C)OC(=O)N[C@H]1C[C@@H](O[Si](C)(C)C(C)(C)C)CN(c2ccncc2NC(=O)c2nc(Br)ccc2N)C1]

Following Method 11 of Example 305, tert-butyl (3S,5R)-1-(3-aminopyridin-4-yl)-5-(tert-butyldimethylsilyloxy)piperidin-3-ylcarbamate and 6-bromo-3-aminopicolinic acid were coupled to yield tert-butyl (3S,5R)-1-(3-(3-amino-6-bromopicolinamido)pyridin-4-yl)-5-(tert-butyldimethylsilyloxy)piperidin-3-ylcarbamate. LCMS (m/z): 621.1/623.2 (MH$^+$).

Synthesis of (3R,4R)-benzyl 3-(tert-butoxycarbonylamino)-4-(methylsulfonyloxy)piperidine-1-carboxylate

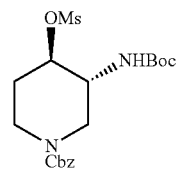 [SMILES: CC(C)(C)OC(=O)N[C@@H]1CN(C(=O)OCc2ccccc2)CC[C@H]1OS(C)(=O)=O]

To a solution of (3R,4R)-benzyl 3-(tert-butoxycarbonylamino)-4-hydroxypiperidine-1-carboxylate in dichloromethane (0.13 M) was added triethylamine (1.5 equiv.) followed by methanesulfonyl chloride (1.3 equiv.). The reaction was allowed to stir at room temperature for 15 h. The solution was then quenched with saturated NaHCO$_3$, extracted with dichloromethane, dried with sodium sulfate, and concentrated to give the crude product in >95% yield. LCMS (m/z): 428.9/328.9 (MH$^+$), LC R$_t$=3.81 min.

Synthesis of (3aR,7aS)-benzyl 2-oxohexahydrooxazolo[4,5-c]pyridine-5(6H)-carboxylate

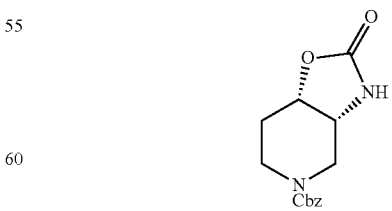

A solution of (3R,4R)-benzyl 3-(tert-butoxycarbonylamino)-4-(methylsulfonyloxy)piperidine-1-carboxylate in pyridine (0.16 M) was heated to 120° C. in the microwave for 10 minutes. The solution was then concentrated to almost dryness and the forming solid was filtered to give the desired product. The filtrate was further purified via silica gel column chromatography eluting with ethyl acetate (100%) to give the product in 75% combined yield. LCMS (m/z): 277.1 (MH+), LC $R_t$=2.33 min.

Synthesis of (3S,4S)-benzyl 3-(tert-butoxycarbonylamino)-4-(methylsulfonyloxy)piperidine-1-carboxylate

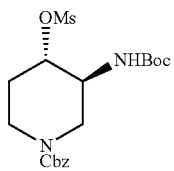

To a solution of (3S,4S)-benzyl 3-(tert-butoxycarbonylamino)-4-hydroxypiperidine-1-carboxylate in dichloromethane (0.13 M) was added triethylamine (1.5 equiv.) followed by methanesulfonyl chloride (1.3 equiv.). The reaction was allowed to stir at room temperature for 15 h. The solution was then quenched with saturated NaHCO$_3$, extracted with dichloromethane, dried with sodium sulfate, and concentrated to give the crude product in >95% yield. LCMS (m/z): 428.9/328.9 (MH+), LC $R_t$=3.81 min.

Synthesis of (3aS,7aR)-benzyl 2-oxohexahydrooxazolo[4,5-c]pyridine-5(6H)-carboxylate

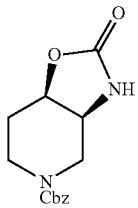 [SMILES: O=C1N[C@H]2CN(C(=O)OCc3ccccc3)CC[C@H]2O1]

The previously described method for the enantiomeric compound was followed using (3S,4S)-benzyl 3-(tert-butoxycarbonylamino)-4-(methylsulfonyloxy)-piperidine-1-carboxylate (1.0 equiv.) to yield (3aS,7aR)-benzyl 2-oxohexahydro-oxazolo[4,5-c]pyridine-5(6H)-carboxylate in 62% yield. LCMS (m/z): 277.1 (MH+), LC $R_t$=2.33 min.

Synthesis of (3aR,7aS)-5-benzyl 3-tert-butyl 2-oxotetrahydrooxazolo[4,5-c]pyridine-3,5(2H,6H)-dicarboxylate

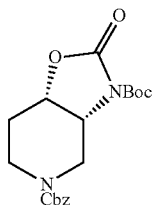

To a solution of (3aR,7aS)-benzyl 2-oxohexahydrooxazolo[4,5-c]pyridine-5(6H)-carboxylate (1.0 equiv.) in dichloromethane (0.09 M) was added BOC$_2$O (1.1 equiv.), triethylamine (1.1 equiv.), and a catalytic amount of DMAP. The reaction was stirred at room temperature for one hour at which point it was concentrated under vacuo and filtered through a plug of silica gel eluting with ethylacetate. The product was dried under vacuo to give a white solid in 75% yield. LCMS (m/z): 277.2 (MH+), LC $R_t$=3.43 min.

Synthesis of (3aS,7aR)-5-benzyl 3-tert-butyl 2-oxotetrahydrooxazolo[4,5-c]pyridine-3,5(2H,6H)-dicarboxylate

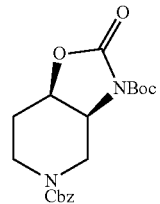 [SMILES: CC(C)(C)OC(=O)N1C(=O)O[C@@H]2CCN(C(=O)OCc3ccccc3)C[C@@H]21]

The previously described method for the enantiomeric compound was followed using (3aS,7aR)-benzyl 2-oxohexahydrooxazolo[4,5-c]pyridine-5(6H)-carboxylate (1.0 equiv.) to yield (3aS,7aR)-5-benzyl 3-tert-butyl 2-oxotetrahydrooxazolo[4,5-c]pyridine-3,5(2H,6H)-dicarboxylate in 90% yield. LCMS (m/z): 277.2 (MH+), LC $R_t$=3.43 min.

Synthesis of (3aR,7aS)-tert-butyl 5-(3-nitropyridin-4-yl)-2-oxohexahydrooxazolo[4,5-c]pyridine-3(2H)-carboxylate

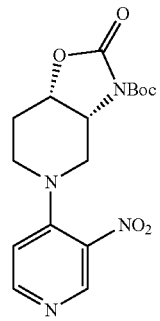 [SMILES: CC(C)(C)OC(=O)N1C(=O)O[C@H]2CCN(c3ccncc3[N+](=O)[O-])C[C@H]21]

Following Method 17, the Cbz group of (3aR,7aS)-5-benzyl 3-tert-butyl 2-oxotetrahydrooxazolo[4,5-c]pyridine-3,5 (2H,6H)-dicarboxylate was removed and the resulting amine was reacted with 4-chloro-3-nitropyridine following Method 1 to yield (3aR,7aS)-tert-butyl 5-(3-nitropyridin-4-yl)-2-oxohexahydrooxazolo[4,5-c]pyridine-3(2H)-carboxylate as a yellow foam in 89% yield. LCMS (m/z): 365.1 (MH+), LC $R_t$=1.79 min.

Synthesis of (3aS,7aR)-tert-butyl 5-(3-nitropyridin-4-yl)-2-oxohexahydrooxazolo[4,5-c]pyridine-3(2H)-carboxylate

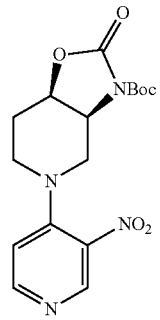 [SMILES: CC(C)(C)OC(=O)N1C(=O)O[C@@H]2CCN(c3ccncc3[N+](=O)[O-])C[C@@H]21]

The previously described method for the enantiomeric compound was followed using (3aS,7aR)-5-benzyl 3-tertbutyl 2-oxotetrahydrooxazolo[4,5-c]pyridine-3,5(2H,6H)-dicarboxylate (1.0 equiv.) to yield (3aS,7aR)-tert-butyl 5-(3-nitropyridin-4-yl)-2-oxohexahydrooxazolo[4,5-c]pyridine-3(2H)-carboxylate in 88% yield. LCMS (m/z): 365.1 (MH+), LC R$_t$=1.79 min.

Synthesis of (3aR,7aS)-tert-butyl 5-(3-aminopyridin-4-yl)-2-oxohexahydro-oxazolo[4,5-c]pyridine-3(2H)-carboxylate

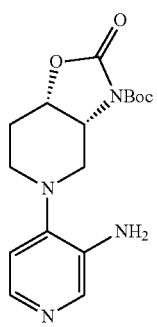

Following Method 2 of Example 49, (3aR,7aS)-tert-butyl 5-(3-nitropyridin-4-yl)-2-oxohexahydrooxazolo[4,5-c]pyridine-3(2H)-carboxylate in EtOH and EtOAc (1:1, 0.15 M) was reduced yielding (3aR,7aS)-tert-butyl 5-(3-aminopyridin-4-yl)-2-oxohexahydrooxazolo[4,5-c]pyridine-3(2H)-carboxylate in >95% yield. LCMS (m/z): 335.0 (MH+), LC R$_t$=1.68 min.

Synthesis of (3aS,7aR)-tert-butyl 5-(3-aminopyridin-4-yl)-2-oxohexahydrooxazolo[4,5-c]pyridine-3(2H)-carboxylate

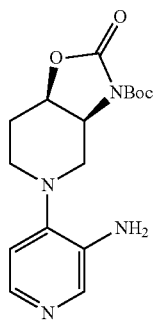

The previously described method for the enantiomeric compound was followed yielding (3aS,7aR)-tert-butyl 5-(3-aminopyridin-4-yl)-2-oxohexahydro-oxazolo[4,5-c]pyridine-3(2H)-carboxylate in 97% yield. LCMS (m/z): 335.0 (MH+), LC R$_t$=1.68 min.

Synthesis of (3aR,7aS)-tert-butyl 5-(3-(3-amino-6-(2,6-difluorophenyl)picolinamido)-pyridin-4-yl)-2-oxohexahydrooxazolo[4,5-c]pyridine-3(2H)-carboxylate

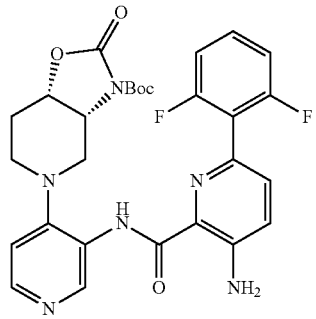 [SMILES: CC(C)(C)OC(=O)N1C(=O)O[C@H]2CCN(c3ccncc3NC(=O)c3nc(-c4c(F)cccc4F)ccc3N)C[C@H]21]

To a solution of (3aR,7aS)-tert-butyl 5-(3-aminopyridin-4-yl)-2-oxohexahydrooxazolo[4,5-c]pyridine-3(2H)-carboxylate (1.0 equiv.) in DMF (0.3 M) was added 3-amino-6-(2,6-difluorophenyl)picolinic acid (1.2 equiv.), EDC (1.2 equiv.) and HOAt (1.2 equiv.). The solution was stirred for 15 h. To the mixture was added water and the precipitate was filtered. To the filtrate was added EtOAc, and the organic solution was extracted (3 times), dried with Na$_2$SO$_4$, and concentrated to give an orange syrup. The crude was triturated with EtOAc and hexanes mixture and the precipitate was filtered off to give pure product in 46% yield. LCMS (m/z): 567.0 (MH+), LC R$_t$=3.03 min.

Synthesis of (3aS,7aR)-tert-butyl 5-(3-(3-amino-6-(2,6-difluorophenyl)picolinamido)pyridin-4-yl)-2-oxohexahydrooxazolo[4,5-c]pyridine-3(2H)-carboxylate

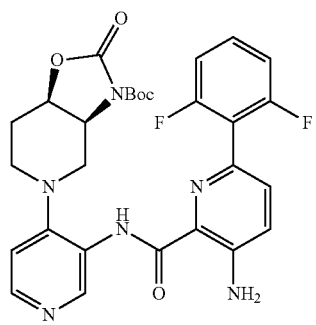 [SMILES: CC(C)(C)OC(=O)N1C(=O)O[C@@H]2CCN(c3ccncc3NC(=O)c3nc(-c4c(F)cccc4F)ccc3N)C[C@@H]21]

The previously described method for the enantiomeric compound was followed using (3aS,7aR)-tert-butyl 5-(3-aminopyridin-4-yl)-2-oxohexahydro-oxazolo[4,5-c]pyridine-3(2H)-carboxylate to give (3aS,7aR)-tert-butyl 5-(3-(3-amino-6-(2,6-difluorophenyl)picolinamido)pyridin-4-yl)-2-oxohexahythooxazolo[4,5-c]pyridine-3(2H)-carboxylate. LCMS (m/z): 567.0 (MH+), R$_t$=2.86 min.

Synthesis of (3aR,7aS)-tert-butyl 5-(3-(3-amino-6-(2-fluoro-5-(isopropylcarbamoyl)phenyl)picolinamido)pyridin-4-yl)-2-oxohexahydrooxazolo[4,5-c]pyridine-3(2H)-carboxylate

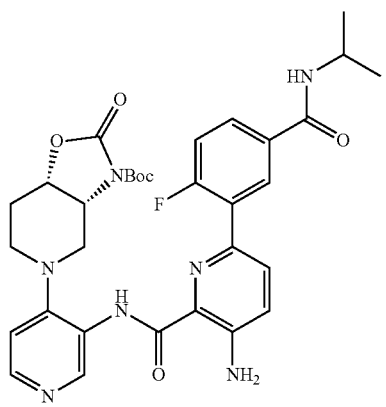 [SMILES: CC(C)NC(=O)c1ccc(F)c(-c2ccc(N)c(C(=O)Nc3cnccc3N3CC[C@@H]4OC(=O)N(C(=O)OC(C)(C)C)[C@@H]4C3)n2)c1]

To a solution of (3aR,7aS)-tert-butyl 5-(3-aminopyridin-4-yl)-2-oxohexahydrooxazolo[4,5-c]pyridine-3(2H)-carboxylate (1.0 equiv.) in DMF (0.3 M) was added 3-amino-6-(2-fluoro-5-(isopropylcarbamoyl)phenyl)picolinic acid (1.2 equiv.), EDC (1.2 equiv.) and HOAt (1.2 equiv.). The solution was stirred for 15 h. To the mixture was added water and the precipitate was filtered. To the filtrate was added EtOAc, and the organic solution was extracted (3 times), dried with Na₂SO₄, and concentrated to give an orange syrup. The crude was triturated with EtOAc and hexanes mixture and the precipitate was filtered off to give (3aR,7aS)-tert-butyl 5-(3-(3-amino-6-(2-fluoro-5-(isopropylcarbamoyl)phenyl)picolinamido)pyridin-4-yl)-2-oxohexahydro-oxazolo[4,5-c]pyridine-3(2H)-carboxylate. LCMS (m/z): 634.3.

Method 35

Synthesis of 3-amino-N-(4-((3R,4S)-3-amino-4-hydroxypiperidin-1-yl)-pyridin-3-yl)-6-(2,6-difluorophenyl)picolinamide

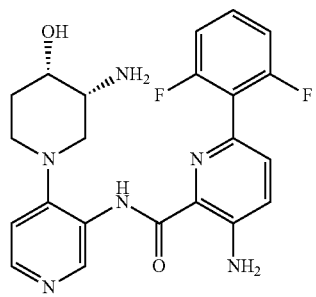 [SMILES: Nc1ccc(-c2c(F)cccc2F)nc1C(=O)Nc1cnccc1N1CC[C@H](O)[C@H](N)C1]

To a solution of (3aR,7aS)-tert-butyl 5-(3-(3-amino-6-(2,6-difluoro-phenyl)picolinamido)pyridin-4-yl)-2-oxohexahydrooxazolo[4,5-c]pyridine-3(2H)-carboxylate in MeOH (0.06M) was added Cs₂CO₃ (0.5 equiv.) and the reaction was stirred for 3 h. The mixture was then concentrated to dryness under vacuo and the crude was stirred in TFA and DCM (25% TFA) until completion. The reaction was concentrated and purified via reverse phase HPLC. Upon lyophilization, a white powder was obtained as the TFA salt. LCMS (m/z): 441.1 (MH⁺), LC R$_t$=1.95 min.

The following compounds were prepared using Method 35:

| Example | Structure | Name | MH+ | LC |
|---|---|---|---|---|
| 752 | Chiral | 3-Amino-6-(2,6-difluoro-phenyl)-pyridine-2-carboxylic acid (3-amino-4-hydroxy-3,4,5,6-tetrahydro-2H-[1,4']bipyridinyl-3'-yl)-amide | 441.0 | 1.98 |
| 753 | Chiral | 3-Amino-6-(2-fluoro-5-isopropylcarbamoyl-phenyl)-pyridine-2-carboxylic acid (3-amino-4-hydroxy-3,4,5,6-tetrahydro-2H-[1,4']bipyridinyl-3'-yl)-amide | 508.0 | 1.98 |

| Example | Structure | Name | MH+ | LC |
|---|---|---|---|---|
| 754 | Chiral | 3-Amino-6-(2,6-difluoro-phenyl)-pyridine-2-carboxylic acid (3-amino-4-hydroxy-3,4,5,6-tetra-hydro-2H-[1,4']bipyridinyl-3'-yl)-amide | 441.1 | 1.95 |

Example 755

Synthesis of (S)-3-amino-N-(4-(3-aminopiperidin-1-yl)pyridin-3-yl)-6-(2-fluoro-5-isopentylphenyl)picolinamide

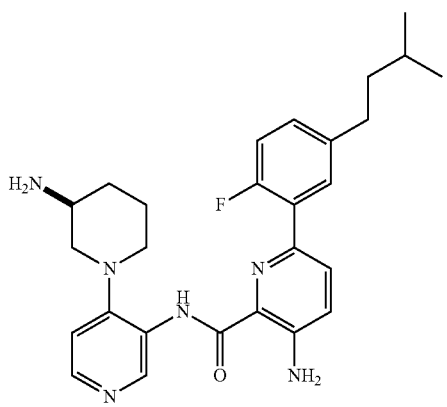 [SMILES: CC(C)CCc1ccc(F)c(-c2ccc(N)c(C(=O)Nc3cnccc3N3CCC[C@H](N)C3)n2)c1]

Method 2 of Example 49 was followed using (S,Z)-tert-butyl 1-(3-(3-amino-6-(2-fluoro-5-(3-methylbut-1-enyl)phenyl)picolinamido)pyridin-4-yl)piperidin-3-ylcarbamate which after Boc deprotection with 25% TFA/CH$_2$Cl$_2$ yielded (S)-3-amino-N-(4-(3-aminopiperidin-1-yl)pyridin-3-yl)-6-(2-fluoro-5-isopentylphenyl)picolinamide (35%). LCMS (m/z): 477.3 (MH$^+$); LC R$_t$=2.91 min.

Example 756

Pim1 ATP Depletion Assay

The activity of PIM1 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 5 nM Pim1 kinase and 80 µM BAD peptide, SEQ ID No. 1, (RSRHSSYPAGT-OH) in assay buffer (50 mM HEPES pH 7.5, 5 mM MgCl$_2$, 1 mM DTT, 0.05% BSA) is added into each well. After 15 minutes, 10 µl of 40 µM ATP in assay buffer is added. Final assay concentrations are 2.5 nM PIM1, 20 M ATP, 40 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining. ATP detected via luminescence on the Victor2 (Perkin. Either). Compounds of the foregoing examples were tested by the Pim1 ATP depletion assay and found to exhibit an IC$_{50}$ values as shown in Example 763, below. IC$_{50}$, the half maximal inhibitory concentration, represents the concentration of a test compound that is required for 50% inhibition of its target in vitro.

Example 757

Pim2 ATP Depletion Assay

The activity of PIM2 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-Well plates at 0.5 µl per well. To start the reaction, 10 µl of 10 nM Pim2 kinase and 20 µM BAD peptide, SEQ ID No. 1, (RSRHSSYPAGT-OH) in assay buffer (50 mM HEPES pH 7.5, 5 mM MgCl$_2$, 1 mM DTT, 0.05% BSA) is added into each well. After 15 minutes, 10 µl of 8 µM ATP in assay buffer is added. Final assay concentrations are 5 nM PIM2, 4 µM ATP, 10 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via, luminescence on the Victor2 (Perkin Elmer). Compounds of the foregoing examples were tested by the Pim2 ATP depletion assay and found to exhibit an IC$_{50}$ values as shown in Example 763, below.

Example 758

Pim3 ATP Depletion Assay

The activity of PIM3 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim3 kinase and 200 µM BAD peptide, SEQ ID No. 1, (RSRHSSYPAGT-OH) in assay buffer (50 mM HEPES pH 7.5, 5 mM MgCl$_2$, 1 mM DTT, 0.05% BSA) is added into each well. After 15 minutes, 10 µl of 80 µM ATP in assay buffer is added. Final assay concentrations are 5 nM PIM1, 40 µM ATP, 100 µM BAD peptide and 2.5% DMSO. The reaction is performed until approximately 50% of the ATP is depleted, then stopped by the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim3 ATP depletion assay and found to exhibit an $IC_{50}$ values as shown, in Example 763, below.

Example 759

Flt3 AlphaScreen Assay

The activity of Flt3 is measured using a homogeneous bead based system quantifying the amount of phosphorylated peptide substrate resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 300 pM Flt3 kinase and 700 µM ATP in assay buffer (50 mM Hepes, pH=7.5, 5 mM $MgCl_2$, 0.05% BSA, 1 mM DTT) is added into each well followed by 10 µl of 500 nM SHC peptide, SEQ ID No. 2, (Biotin-GGLFDDPSYVNVQNL-NH2) in assay buffer. Final assay concentrations are 150 pM Flt3, 350 µM ATP, 250 nM SHC peptide and 2.5% DMSO. The reaction is performed for 2.5 hours, then stopped by the addition of 10 µl 60 mM EDTA. 25 µl of 1.2 µg/ml PY20 antibody, 48.4 µg/ml Protein A Alpha Screen beads, and 48.4 µg/ml streptavidin coated Alpha Screen beads in detection buffer (50 mM Tris pH 7.5, 0.01% Tween-20) is added to the stopped reactions. The stopped reactions are incubated overnight in the dark. The phosphorylated peptide is detected via an oxygen anion initiated chemiluminescence/fluorescence cascade using the Envision plate reader (Perkin Elmer). Compounds of the foregoing examples were tested by the Flt3 Alpha assay and found to exhibit an $IC_{50}$ values as shown in Example 762, below.

Example 760

KDR AlphaScreen Assay

The activity of KDR is measured using a homogeneous bead based system quantifying the amount of phosphorylated peptide substrate resulting from kinase-catalyzed phosphoryl transfer to a peptide substrate. Compounds to be tested are dissolved in 100% DMSO and directly distributed to a white 384-well plate at 0.5 µl per well. To start the reaction, 10 µl of 2 µM VEGF5 peptide, SEQ ID No. 3, (Biotin-GGGGQDGKDYIVLPI-NH2) in assay buffer (50 mM Hepes, pH=7.5, 5 mM MnCl2, 0.1% BSA, 0.01% Tween-20, 1 mM DTT) is added to each well followed by the addition of 10 µl of 250 pM KDR kinase and 2 µM ATP in assay buffer. Final assay concentrations are 125 pM KDR, 1 µM ATP, 1 µM VEGF5 peptide and 2.5% DMSO. The reaction is performed for 2 hours, then stopped by the addition of 25 µl of 0.24 µg/ml PY20 antibody, 96.8 µg/ml Protein A Alpha Screen beads, and 96.8 µg/ml streptavidin coated Alpha Screen beads in stop/detection buffer (50 mM Hepes, pH=7.5, 10 mM EDTA, 0.1% BSA, 0.01% Tween-20). The stopped reactions are incubated overnight in the dark. The phosphorylated peptide is detected via an oxygen anion initiated chemiluminescence/fluorescence cascade using the Envision plate reader (Perkin Elmer). Compounds of the foregoing examples were tested by the KDR Alpha Screen assay and found to exhibit an $IC_{50}$ values as shown in Example 762, below.

Example 761

Cell Proliferation Assay

HEL 92.1.7 cells (ATTC No. TIB-180, an erythroleukemia line derived from malignant peripheral blood), MV4-11 cells (ATCC No. CRL-9591, a human acute monocytic leukemia line) and PC3 cells (ATCC No. CRL-1435, a human prostatic adenocarcinoma line) were cultured in RPMI1640 supplemented with 10% FBS, sodium pyruvate and antibiotics. Cells were plated in the same medium at a density of 1000 cells per well into 96 well tissue culture plates, with outside wells vacant, on the day of assay.

KMS11 (human myeloma cell line), were cultured in IMDM supplemented with 10% FBS, sodium pyruvate and antibiotics. Cells were plated in the same medium at a density of 2000 cells per well into 96 well tissue culture plates, with outside wells vacant, on the day of assay. MM1.s (human myeloma cell line), were cultured in RPMI1640 supplemented with 10% FBS, sodium pyruvate and antibiotics. Cells were plated in the same medium at a density of 5000 cells per well into 96 well tissue culture plates, with outside wells vacant, on the day of assay.

Test compounds supplied in DMSO were diluted into DMSO at 500 times the desired final concentrations before dilution into culture media to 2 times final concentrations. Equal volumes of 2× compounds were added to the cells in 96 well plates and incubated at 37° C. for 3 days.

After 3 days plates were equilibrated to room temperature and equal volume of CellTiter-G low Reagent (Promega) was added to the culture wells. The plates were agitated briefly and luminescent signal was measured with luminometer. The percent inhibition of the signal seen in cells treated with DMSO alone vs. cells treated with control compound was calculated and used to determine $EC_{50}$ values (i.e., the concentration of a test compound that is required to obtain 50% of the maximum effect in the cells) for tested compounds, as shown in Example 763.

Example 762

In vitro PKCε Assay

An in vitro PKCε assay was run using 10 nM final concentration of human full length PKCε enzyme purchased from InVitrogen. Peptide substrate with the sequence, SEQ ID No. 4, ERMRPRKRQGSVRRRV-OH was used at final concentration of 40 uM, and ATP at 20 uM. Lipid activator, 0.05 mg/ml of phosphatidylserine and 0.005 mg/ml diacylglycerol, was purchased from Millipore. Reaction buffer was consisted of 20 mM, Hepes pH7.4, 5 mM $MgCl_2$, and 0.03% Triton X-100. After 2-3 hours reaction time, the assay readout was developed with KinaseGlo Plus reagent from Promega. Representative compounds of the foregoing examples were tested by the PKCε assay and, found to exhibit an $IC_{50}$ as shown below, where (+) represents an $IC_{50}$ greater than or equal to 25 µM, (++) represents an $IC_{50}$ greater than or equal to 10 µM but less than 25 µM, (+++) represents an $IC_{50}$ greater than or equal to 1 µM but less than 10 µM, and (++++) represents an $IC_{50}$ less than 1 µM.

| Example | PKCε IC50 (µM) | Flt3 IC50 (µM) | KDR IC50 (µM) |
| --- | --- | --- | --- |
| 118 | ++++ |  | ++++ |
| 119 | ++++ |  | +++ |
| 120 | +++ |  |  |
| 121 | + |  | ++++ |
| 122 | ++++ |  |  |
| 123 | ++++ |  | +++ |
| 124 | ++ | ++ |  |
| 125 | ++ |  | +++ |
| 126 | ++++ |  | +++ |
| 127 | +++ |  | + |
| 128 | + |  |  |
| 129 | +++ |  |  |
| 130 | ++++ |  | +++ |
| 131 | + |  | ++++ |
| 132 | ++++ |  | ++++ |
| 133 | + |  | +++ |

-continued

| Example | PKCε IC50 (μM) | Flt3 IC50 (μM) | KDR IC50 (μM) |
|---|---|---|---|
| 134 | +++ | | +++ |
| 135 | ++++ | | +++ |
| 136 | +++ | | |
| 137 | ++++ | | |
| 138 | + | | |
| 139 | ++++ | | |
| 140 | +++ | | |
| 141 | +++ | | |
| 142 | +++ | | |
| 143 | + | | |
| 144 | +++ | | |
| 145 | + | | |
| 146 | ++++ | | |
| 147 | ++++ | | |
| 148 | ++ | | |
| 149 | +++ | | |
| 150 | +++ | | |
| 151 | + | | |
| 152 | ++++ | | |
| 153 | + | | |
| 154 | ++++ | | |
| 155 | +++ | | |
| 156 | +++ | | |
| 157 | + | | |
| 158 | + | | |
| 159 | + | | ++++ |
| 160 | + | | |
| 161 | + | | ++++ |
| 163 | | | ++ |
| 164 | | | ++ |
| 165 | | | ++ |
| 166 | | | ++ |
| 171 | ++ | | |
| 173 | ++++ | | ++ |
| 174 | +++ | | + |
| 175 | +++ | | + |
| 175 | +++ | | + |
| 176 | ++++ | | +++ |
| 177 | ++++ | | |
| 178 | ++++ | | |
| 179 | ++++ | | |
| 180 | ++++ | | |
| 182 | +++ | | +++ |
| 183 | ++ | | +++ |
| 184 | ++++ | | ++ |
| 185 | +++ | | +++ |
| 186 | +++ | | +++ |
| 187 | ++++ | | + |
| 188 | ++++ | | +++ |
| 189 | ++++ | | |
| 190 | + | | |
| 191 | ++++ | | |
| 192 | + | | |
| 193 | ++++ | | |
| 194 | + | | |
| 195 | ++++ | | + |
| 196 | +++ | | + |
| 199 | +++ | | +++ |
| 201 | ++++ | | ++ |
| 202 | ++++ | | + |
| 203 | ++++ | | + |
| 204 | ++++ | | |
| 204 | ++++ | | +++ |
| 205 | ++++ | | +++ |
| 206 | ++++ | | +++ |
| 211 | ++++ | | +++ |
| 212 | ++++ | | ++ |
| 213 | +++ | | + |
| 214 | ++++ | | ++ |
| 215 | +++ | | + |
| 216 | +++ | | + |
| 217 | ++ | | + |
| 217 | ++++ | | ++ |
| 218 | +++ | | + |
| 219 | +++ | | + |
| 222 | +++ | | + |
| 223 | ++++ | | + |
| 223 | ++++ | | + |
| 224 | +++ | | + |
| 225 | +++ | | + |
| 226 | +++ | | + |
| 227 | +++ | | + |
| 228 | ++++ | | ++ |
| 229 | +++ | | + |
| 230 | ++++ | | + |
| 231 | ++ | | ++ |
| 232 | ++ | | ++ |
| 233 | +++ | | +++ |
| 235 | ++++ | | ++ |
| 236 | + | | ++ |
| 237 | +++ | | ++++ |
| 238 | + | | ++++ |
| 239 | ++++ | | |
| 240 | ++++ | | |
| 241 | +++ | | |
| 242 | + | | |
| 243 | +++ | | + |
| 244 | +++ | | ++ |
| 249 | | | ++ |
| 261 | | | +++ |
| 264 | | | ++++ |
| 265 | | | ++ |
| 268 | | | +++ |
| 275 | | | ++ |
| 304 | +++ | | ++++ |
| 312 | ++ | | |
| 320 | ++ | | + |
| 322 | +++ | | + |
| 332 | +++ | | + |
| 333 | ++ | | + |
| 336 | ++ | | + |
| 340 | +++ | | ++ |
| 341 | ++++ | | +++ |
| 342 | +++ | | +++ |
| 343 | +++ | | +++ |
| 344 | ++ | | + |
| 345 | ++++ | | ++++ |
| 346 | ++++ | | |
| 347 | ++++ | | |
| 348 | ++++ | | |
| 349 | +++ | | |
| 350 | ++++ | | |
| 351 | ++++ | | |
| 352 | ++++ | | |
| 353 | ++++ | | |
| 354 | +++ | | |
| 355 | +++ | | |
| 356 | +++ | | |
| 357 | +++ | | |
| 359 | ++++ | | ++++ |
| 360 | +++ | | ++++ |
| 361 | ++++ | | ++++ |
| 362 | ++++ | | ++++ |
| 363 | ++++ | | ++++ |
| 364 | ++++ | | ++++ |
| 364 | ++++ | | +++ |
| 365 | ++++ | | ++++ |
| 366 | ++++ | | ++++ |
| 367 | ++++ | | ++++ |
| 368 | ++++ | | ++++ |
| 369 | ++++ | | ++++ |
| 370 | ++++ | | ++++ |
| 371 | +++ | | |
| 372 | ++++ | | ++++ |
| 373 | ++++ | | ++++ |
| 374 | ++++ | | +++ |
| 375 | ++++ | | +++ |
| 376 | ++++ | | + |
| 377 | ++++ | | +++ |
| 378 | ++++ | | + |
| 379 | ++++ | | +++ |
| 380 | ++++ | | ++++ |
| 381 | ++++ | | +++ |
| 382 | ++++ | | +++ |

| Example | PKCε IC50 (μM) | Flt3 IC50 (μM) | KDR IC50 (μM) |
|---|---|---|---|
| 383 | ++++ | | +++ |
| 384 | ++++ | | +++ |
| 385 | ++++ | | +++ |
| 386 | ++++ | | +++ |
| 387 | +++ | | ++ |
| 388 | ++++ | | ++++ |
| 389 | ++++ | | +++ |
| 390 | ++++ | | +++ |
| 391 | +++ | | + |
| 400 | +++ | | ++++ |
| 400 | +++ | | |
| 401 | ++++ | | |
| 402 | +++ | | |
| 403 | ++++ | | |
| 404 | +++ | | |
| 405 | ++ | | |
| 406 | +++ | | + |
| 410 | +++ | | + |
| 411 | ++ | | + |
| 418 | ++ | | + |
| 422 | ++ | | + |
| 424 | +++ | | + |
| 425 | +++ | | ++ |
| 427 | ++ | | |
| 431 | +++ | | + |
| 433 | +++ | | ++ |
| 434 | ++ | | + |
| 435 | ++ | | ++++ |
| 436 | +++ | | +++ |
| 437 | ++++ | | +++ |
| 438 | + | | +++ |
| 439 | +++ | | +++ |
| 440 | + | | +++ |
| 441 | ++ | | ++++ |
| 447 | | | ++ |
| 454 | | | ++ |
| 455 | | | ++ |
| 482 | + | | ++ |
| 483 | ++ | | + |
| 484 | ++ | | + |
| 485 | + | | ++ |
| 487 | | | ++ |
| 505 | | | ++ |
| 519 | | | ++ |
| 520 | | | +++ |
| 521 | | | +++ |
| 522 | | | +++ |
| 523 | | | ++ |
| 524 | | | +++ |
| 534 | | | +++ |
| 535 | | | ++ |
| 538 | | | ++ |
| 542 | | | ++ |
| 543 | | | ++ |
| 544 | | | ++ |
| 545 | | | ++ |
| 547 | | | ++ |
| 549 | | | ++ |
| 550 | | | ++ |
| 552 | +++ | | +++ |
| 590 | +++ | | ++++ |
| 592 | +++ | | |
| 593 | + | | |
| 594 | + | | |
| 595 | + | | |
| 596 | + | | |
| 597 | +++ | | + |
| 598 | +++ | | +++ |
| 612 | | | +++ |
| 614 | | | +++ |
| 629 | | | ++ |
| 644 | | | ++ |
| 648 | | | ++ |
| 649 | | | ++ |
| 650 | | | ++ |

Example 763

$IC_{50}$ and $EC_{50}$ Activity of Compounds of the Invention

Using the procedures of Examples 756 (Pim1 ATP depletion assay), 757 (Pim2 ATP depletion assay), and 758 (Pim3 ATP depletion assay), the $IC_{50}$ concentration of compounds of the previous examples were determined as shown in the following table, where (+) represents an $IC_{50}$ greater than or equal to 25 μM, (++) represents an $IC_{50}$ greater than or equal to 10 μM but less than 25 μM, (+++) represents an $IC_{50}$ greater than or equal to 1 μM but less than 10 μM, and (++++) represents an $IC_{50}$ less than 1 μM.

Using the procedures of Example 761 (cell proliferation assay), the $EC_{50}$ concentration of compounds of the previous examples in were determined in HEL 92.1.7, MV4-11 cells and PC3 cells as shown in the following table, where (+) represents an $EC_{50}$ greater than 10 μM, (++) represents an $EC_{50}$ greater than 5 μM but less than or equal to 10 μM, (+++) represents an $EC_{50}$ greater than 1 μM but less than or equal to 5 μM, and (++++) represents an $EC_{50}$ less than or equal to 1 μM.

| Ex. No | IC50 (μM) | | | EC50 (μM) | | | | |
|---|---|---|---|---|---|---|---|---|
| | PIM1 | PIM2 | PIM3 | HEL 92.1.7 | MV-4-11 | PC3 | KMS11 | MM1.s |
| 118 | ++++ | +++ | ++++ | | | | | |
| 119 | ++++ | ++++ | ++++ | | | | | |
| 120 | ++++ | +++ | ++++ | | | +++ | | |
| 121 | ++++ | ++++ | ++++ | | | | | |
| 122 | ++++ | +++ | +++ | | | ++++ | | |
| 123 | ++++ | +++ | ++++ | ++++ | | | | |
| 124 | +++ | + | +++ | | | | | |
| 125 | +++ | + | ++ | | | | | |
| 126 | ++++ | +++ | ++++ | | | ++ | | |
| 127 | +++ | + | + | | | | | |
| 128 | +++ | + | ++ | | | | | |
| 130 | ++++ | ++++ | ++++ | ++ | | | | |
| 131 | ++++ | ++++ | ++++ | ++++ | | | | |
| 132 | ++++ | ++++ | ++++ | | | | | |
| 133 | ++++ | ++++ | ++++ | | | | | |
| 134 | ++++ | ++++ | ++++ | | | | | |
| 135 | ++++ | ++++ | ++++ | | | | | |
| 136 | ++++ | ++++ | ++++ | | | | | |
| 137 | ++++ | ++++ | ++++ | | | | | |
| 138 | ++++ | ++++ | ++++ | | | | | |
| 139 | ++++ | ++++ | ++++ | | | | | |
| 140 | ++++ | ++++ | ++++ | | | | | |
| 141 | ++++ | ++++ | ++++ | | | | | |
| 142 | ++++ | ++++ | ++++ | +++ | | | | |
| 143 | ++++ | ++++ | ++++ | +++ | | | | |
| 145 | ++++ | ++++ | ++++ | +++ | | | | |
| 146 | ++++ | ++++ | ++++ | + | | | | |
| 147 | ++++ | ++++ | ++++ | ++ | | | | |
| 148 | ++++ | ++++ | ++++ | + | | | | |
| 150 | ++++ | ++++ | ++++ | +++ | | | | |
| 151 | ++++ | ++++ | ++++ | + | | | | |
| 152 | ++++ | ++++ | ++++ | | | | | |
| 153 | ++++ | ++++ | ++++ | | | | | |
| 154 | ++++ | ++++ | ++++ | | | | | |
| 155 | ++++ | ++++ | ++++ | ++ | | | | |
| 156 | ++++ | ++++ | ++++ | | | | | |
| 157 | ++++ | ++++ | ++++ | + | | | | |
| 158 | ++++ | ++++ | ++++ | | | | | |
| 159 | ++++ | ++++ | ++++ | ++ | | | | |
| 160 | ++++ | ++++ | ++++ | + | | | | |
| 161 | ++++ | ++++ | ++++ | + | | | | |
| 162 | ++++ | ++++ | ++++ | | | | | |
| 163 | ++++ | ++++ | ++++ | | | | | |
| 164 | ++++ | ++++ | ++++ | | | | | |
| 165 | ++++ | ++++ | ++++ | | | | | |
| 166 | ++++ | ++++ | ++++ | | | | | |

| Ex. No | IC50 (μM) PIM1 | PIM2 | PIM3 | EC50 (μM) HEL 92.1.7 | MV-4-11 | PC3 | KMS11 | MM1.s |
|---|---|---|---|---|---|---|---|---|
| 167 | ++++ | +++ | ++++ | | | | | |
| 168 | ++++ | ++++ | ++++ | | | | | |
| 169 | ++++ | ++++ | ++++ | | | | | |
| 170 | ++++ | +++ | ++++ | | | | | |
| 171 | ++++ | +++ | ++++ | | | | | |
| 173 | ++++ | ++++ | ++++ | +++ | | ++ | | |
| 174 | ++++ | ++++ | ++++ | + | | | | |
| 177 | ++++ | ++++ | ++++ | + | | | | |
| 175 | ++++ | ++++ | ++++ | + | | | | |
| 176 | ++++ | ++++ | ++++ | +++ | | +++ | | |
| 177 | ++++ | ++++ | ++++ | | | | | |
| 178 | ++++ | ++++ | ++++ | | | | | |
| 179 | ++++ | ++++ | ++++ | +++ | | | | |
| 180 | ++++ | ++++ | ++++ | ++++ | | | | |
| 181 | ++++ | ++++ | ++++ | ++++ | | | | |
| 182 | ++++ | ++++ | ++++ | ++++ | | | | |
| 183 | ++++ | ++++ | ++++ | ++++ | | | | |
| 184 | ++++ | +++ | ++++ | ++++ | | | | |
| 185 | ++++ | ++++ | ++++ | ++++ | | | | |
| 186 | ++++ | ++++ | ++++ | | | | | |
| 187 | ++++ | ++++ | ++++ | +++ | ++++ | +++ | | |
| 188 | ++++ | +++ | ++++ | | | | | |
| 189 | ++++ | +++ | ++++ | | | | | |
| 191 | ++++ | + | +++ | | | | | |
| 192 | + | + | + | | | | | |
| 193 | ++++ | +++ | ++++ | | | ++++ | | |
| 194 | + | + | + | | | | | |
| 195 | ++++ | ++++ | ++++ | | | + | | |
| 196 | +++ | ++ | +++ | | | | | |
| 197 | + | + | + | | | | | |
| 198 | + | + | + | | | | | |
| 199 | +++ | + | + | | | | | |
| 199 | +++ | + | ++ | | | | | |
| 199 | +++ | + | ++ | | | | | |
| 200 | ++ | + | + | | | | | |
| 201 | ++++ | ++++ | ++++ | | | ++ | | |
| 202 | +++ | + | +++ | | | +++ | | |
| 203 | ++++ | +++ | ++++ | | | ++++ | | |
| 204 | ++++ | ++++ | ++++ | | | | | |
| 205 | ++++ | ++++ | ++++ | | | ++++ | | |
| 206 | ++++ | +++ | ++++ | | | | | |
| 207 | ++++ | ++ | ++++ | | | ++ | | |
| 208 | ++++ | +++ | ++++ | | | ++++ | | |
| 209 | ++ | + | + | | | +++ | | |
| 210 | ++++ | +++ | ++++ | | | ++++ | | |
| 211 | ++++ | ++++ | ++++ | | | | | |
| 212 | ++++ | ++++ | ++++ | | | | | |
| 213 | +++ | + | +++ | | | | | |
| 214 | ++++ | +++ | ++++ | | | +++ | | |
| 215 | ++++ | +++ | ++++ | | | | | |
| 216 | +++ | + | +++ | | | | | |
| 217 | ++++ | + | +++ | | | ++ | | |
| 218 | ++++ | ++ | ++++ | | | | | |
| 219 | ++++ | ++ | ++++ | | | | | |
| 220 | ++++ | ++ | ++++ | | | | | |
| 221 | ++++ | +++ | ++++ | | | | | |
| 222 | ++++ | ++ | ++++ | | | + | | |
| 223 | ++++ | +++ | ++++ | | | | | |
| 224 | ++++ | + | +++ | | | | | |
| 225 | ++++ | ++ | ++++ | | | | | |
| 226 | ++++ | +++ | ++++ | | | | | |
| 227 | +++ | + | +++ | | | | | |
| 228 | ++++ | ++ | ++++ | | | ++ | | |
| 229 | ++++ | +++ | ++++ | | | | | |
| 230 | ++++ | ++++ | ++++ | | | | | |
| 231 | +++ | + | +++ | | | | | |
| 232 | ++ | + | ++ | | | | | |
| 233 | +++ | + | +++ | | | | | |
| 234 | +++ | + | ++ | | | | | |
| 235 | ++++ | ++++ | ++++ | + | | | | |
| 236 | ++++ | ++++ | ++++ | | | | | |
| 237 | ++++ | ++++ | ++++ | | | | | |
| 238 | ++++ | ++++ | ++++ | | | | | |
| 239 | ++++ | ++++ | ++++ | + | | | | |
| 240 | ++++ | ++++ | ++++ | | | | | |
| 241 | ++++ | ++++ | ++++ | | | | | |
| 242 | ++++ | ++++ | ++++ | | | | | |
| 243 | +++ | ++ | +++ | | | | | |
| 244 | +++ | ++ | +++ | | | | | |
| 245 | + | + | ++ | | | | | |
| 246 | ++++ | ++++ | ++++ | | | | | |
| 247 | ++++ | ++++ | ++++ | | | | | |
| 248 | ++++ | ++++ | ++++ | | | | | |
| 249 | ++++ | ++++ | ++++ | | | | | |
| 250 | ++++ | ++++ | ++++ | | | | | |
| 251 | ++++ | ++++ | ++++ | | | | | |
| 252 | ++++ | ++++ | ++++ | | | | | |
| 253 | ++++ | ++++ | ++++ | | | | | |
| 254 | ++++ | ++++ | ++++ | | | | | |
| 255 | ++++ | ++++ | ++++ | | | | | |
| 256 | ++++ | ++++ | ++++ | | | | | |
| 257 | ++++ | ++++ | ++++ | | | | | |
| 258 | ++++ | ++++ | ++++ | | | | | |
| 259 | ++++ | ++++ | ++++ | | | | | |
| 260 | ++++ | ++++ | ++++ | | | | | |
| 261 | ++++ | ++++ | ++++ | | | | | |
| 262 | ++++ | +++ | ++++ | | | | | |
| 263 | ++++ | ++++ | ++++ | | | | | |
| 264 | ++++ | ++++ | ++++ | | | | | |
| 265 | ++++ | ++++ | ++++ | | | | | |
| 266 | ++++ | ++++ | ++++ | | | | | |
| 267 | ++++ | ++++ | ++++ | | | | | |
| 268 | ++++ | ++++ | ++++ | | | | | |
| 269 | ++++ | ++++ | ++++ | | | | | |
| 270 | ++++ | ++++ | ++++ | | | | | |
| 271 | ++++ | ++++ | ++++ | | | | | |
| 272 | ++++ | ++++ | ++++ | | | | | |
| 273 | ++++ | ++++ | ++++ | | | | | |
| 274 | ++++ | ++++ | ++++ | | | | | |
| 275 | ++++ | ++++ | ++++ | | | | | |
| 276 | ++++ | ++++ | ++++ | | | | +++ | ++ |
| 277 | ++++ | ++++ | ++++ | | | | | |
| 278 | ++++ | ++++ | ++++ | | | | | |
| 279 | ++++ | ++++ | ++++ | | | | | |
| 280 | ++++ | ++++ | ++++ | | | | | |
| 281 | ++++ | ++++ | ++++ | | | | | |
| 282 | ++++ | ++++ | ++++ | | | | | |
| 283 | ++++ | ++++ | ++++ | | | | | |
| 284 | ++++ | ++++ | ++++ | | | | | |
| 285 | ++++ | ++++ | ++++ | | | | | |
| 286 | ++++ | ++++ | ++++ | | | | | |
| 287 | ++++ | ++++ | ++++ | | | | | |
| 288 | ++++ | ++++ | ++++ | | | | | |
| 289 | ++++ | ++++ | ++++ | | | | | |
| 290 | ++++ | ++++ | ++++ | | | | +++ | +++ |
| 291 | ++++ | ++++ | ++++ | | | | | |
| 292 | ++++ | ++++ | ++++ | | | | ++++ | ++++ |
| 293 | ++++ | ++++ | ++++ | | | | | |
| 294 | ++++ | ++++ | ++++ | | | | | |
| 295 | ++++ | +++ | ++++ | | | | | |
| 296 | ++++ | ++++ | ++++ | | | | | |
| 297 | ++++ | ++++ | ++++ | | | | | |
| 298 | ++++ | ++++ | ++++ | | | | ++++ | ++++ |
| 299 | ++++ | ++++ | ++++ | | | | | |
| 300 | ++++ | ++++ | ++++ | | | | ++++ | ++++ |
| 301 | ++++ | ++++ | ++++ | | | | | |
| 302 | ++++ | ++++ | ++++ | | | | | |
| 303 | ++++ | ++++ | ++++ | | | | | |
| 304 | ++++ | + | +++ | | | | | |
| 312 | ++++ | +++ | ++++ | | | | | |
| 317 | ++++ | ++++ | ++++ | +++ | | + | +++ | ++++ |
| 318 | ++++ | ++++ | ++++ | | | | | |
| 319 | ++++ | ++++ | ++++ | +++ | | | | |
| 320 | ++++ | ++++ | ++++ | + | | | | |
| 321 | ++++ | ++++ | ++++ | +++ | | | | |
| 322 | ++++ | ++++ | ++++ | ++++ | | ++ | | |

| Ex. No | IC50 (μM) PIM1 | PIM2 | PIM3 | EC50 (μM) HEL 92.1.7 | MV-4-11 | PC3 | KMS11 | MM1.s |
|---|---|---|---|---|---|---|---|---|
| 323 | ++++ | ++++ | ++++ | ++++ | | +++ | | |
| 324 | ++++ | ++++ | ++++ | ++++ | | | | |
| 325 | ++++ | ++++ | ++++ | | | | | |
| 326 | ++++ | ++++ | ++++ | +++ | | | | |
| 327 | ++++ | ++++ | ++++ | +++ | | | | |
| 328 | ++++ | ++++ | ++++ | +++ | | | ++++ | ++++ |
| 329 | ++++ | ++++ | ++++ | ++ | | | | |
| 330 | ++++ | ++++ | ++++ | + | | | | |
| 331 | ++++ | ++++ | ++++ | +++ | | | | |
| 332 | ++++ | ++++ | ++++ | +++ | | | | |
| 333 | ++++ | ++++ | ++++ | +++ | | | | |
| 334 | ++++ | ++++ | ++++ | ++ | | | | |
| 335 | ++++ | ++++ | ++++ | ++ | | | | |
| 336 | ++++ | ++++ | ++++ | | | | | |
| 337 | ++++ | ++++ | ++++ | ++ | | | | |
| 338 | ++++ | ++++ | ++++ | | | | | |
| 339 | ++++ | ++++ | ++++ | +++ | | | | |
| 340 | ++++ | ++++ | ++++ | +++ | | | | |
| 341 | ++++ | ++++ | ++++ | +++ | | | | |
| 342 | ++++ | ++++ | ++++ | ++++ | | | | |
| 343 | ++++ | ++++ | ++++ | ++++ | | | | |
| 344 | ++++ | ++++ | ++++ | + | | | | |
| 345 | ++++ | ++++ | ++++ | ++++ | | ++++ | | |
| 346 | ++++ | ++++ | ++++ | ++++ | | | | |
| 347 | ++++ | ++++ | ++++ | ++++ | | | | |
| 348 | ++++ | ++++ | ++++ | ++++ | | +++ | | |
| 349 | ++++ | ++++ | ++++ | ++++ | | | | |
| 350 | ++++ | ++++ | ++++ | ++++ | | | | |
| 351 | ++++ | ++++ | ++++ | | | | | |
| 352 | ++++ | ++++ | ++++ | ++++ | | | | |
| 353 | ++++ | ++++ | ++++ | ++++ | | | | |
| 355 | ++++ | ++++ | ++++ | + | | | | |
| 356 | ++++ | ++++ | ++++ | + | | | | |
| 357 | ++++ | ++++ | ++++ | +++ | | | | |
| 358 | ++++ | ++++ | ++++ | ++++ | | | | |
| 359 | ++++ | ++++ | ++++ | | | ++++ | | |
| 360 | +++ | + | +++ | | | | | |
| 361 | ++++ | ++++ | ++++ | | | | | |
| 362 | ++++ | ++++ | ++++ | | | ++++ | | |
| 363 | ++++ | ++++ | ++++ | | | ++++ | | |
| 364 | ++++ | ++++ | ++++ | | | ++++ | | |
| 365 | ++++ | +++ | ++++ | | | + | | |
| 366 | ++++ | +++ | ++++ | | | | | |
| 367 | ++++ | ++++ | ++++ | | | ++++ | | |
| 368 | ++++ | ++++ | ++++ | | | ++++ | | |
| 369 | ++++ | ++++ | ++++ | | | | | |
| 370 | ++++ | ++++ | ++++ | | | ++ | | |
| 371 | ++++ | ++++ | ++++ | | | | | |
| 372 | ++++ | ++++ | ++++ | | | +++ | | |
| 376 | ++++ | ++++ | ++++ | | | + | | |
| 377 | ++++ | ++++ | ++++ | | | | | |
| 378 | ++++ | ++ | +++ | | | +++ | | |
| 379 | ++++ | +++ | ++++ | | | | | |
| 380 | ++++ | +++ | ++++ | | | | | |
| 381 | ++++ | ++++ | ++++ | | | | | |
| 382 | ++++ | +++ | ++++ | | | +++ | | |
| 383 | ++++ | +++ | ++++ | | | | | |
| 384 | ++++ | +++ | +++ | | | | | |
| 385 | ++++ | +++ | ++++ | | | | | |
| 386 | ++++ | +++ | ++++ | | | | | |
| 387 | +++ | + | +++ | | | | | |
| 388 | ++++ | +++ | ++++ | | | | | |
| 389 | ++++ | +++ | +++ | | | +++ | | |
| 390 | ++++ | + | +++ | | | | | |
| 391 | +++ | + | +++ | | | | | |
| 393 | ++++ | ++++ | ++++ | | | +++ | | |
| 395 | ++++ | + | +++ | | | +++ | | |
| 396 | ++++ | +++ | ++++ | | | +++ | | |
| 397 | ++++ | ++++ | ++++ | | | ++++ | | |
| 398 | +++ | ++ | +++ | | | | | |
| 399 | ++++ | ++++ | ++++ | | | ++++ | | |
| 401 | ++++ | ++++ | ++++ | ++ | | | | |
| 402 | ++++ | ++++ | ++++ | ++ | | | | |
| 403 | ++++ | ++++ | ++++ | | | | | |
| 404 | ++++ | ++++ | ++++ | | | | | |
| 405 | ++++ | ++++ | ++++ | | | | | |
| 406 | ++++ | ++++ | ++++ | | | | | |
| 407 | ++++ | ++++ | ++++ | | | | | |
| 408 | ++++ | ++++ | ++++ | | | | | |
| 409 | ++++ | ++++ | ++++ | | | | | |
| 410 | ++++ | ++++ | ++++ | +++ | | | | |
| 411 | ++++ | ++++ | ++++ | | | | | |
| 412 | ++++ | ++++ | ++++ | ++ | | | | |
| 413 | ++++ | ++++ | ++++ | ++++ | | | | |
| 414 | ++++ | ++++ | ++++ | +++ | | | | |
| 415 | ++++ | ++++ | ++++ | ++++ | | | | |
| 416 | ++++ | ++++ | ++++ | | | | | |
| 417 | ++++ | ++++ | ++++ | | | | | |
| 418 | ++++ | ++++ | ++++ | +++ | | | | |
| 419 | ++++ | ++++ | ++++ | +++ | | | | |
| 420 | ++++ | ++++ | ++++ | | | | | |
| 421 | ++++ | ++++ | ++++ | +++ | | + | | |
| 422 | ++++ | ++++ | ++++ | +++ | | + | | |
| 423 | ++++ | ++++ | ++++ | +++ | | | | |
| 424 | ++++ | ++++ | ++++ | +++ | | ++ | | |
| 425 | ++++ | ++++ | ++++ | ++++ | | ++ | ++++ | ++++ |
| 426 | ++++ | ++++ | ++++ | ++ | | | | |
| 427 | ++++ | ++++ | ++++ | +++ | | | | |
| 428 | ++++ | ++++ | ++++ | ++ | | | | |
| 429 | ++++ | ++++ | ++++ | ++ | | | | |
| 430 | ++++ | ++++ | ++++ | +++ | | | | |
| 431 | ++++ | ++++ | ++++ | +++ | | | | |
| 432 | ++++ | ++++ | ++++ | +++ | | | | |
| 433 | ++++ | ++++ | ++++ | +++ | ++++ | | | |
| 434 | ++++ | ++++ | ++++ | +++ | ++++ | | | |
| 435 | +++ | +++ | +++ | | | | | |
| 436 | +++ | + | +++ | | | | | |
| 437 | ++++ | ++++ | ++++ | | | | | |
| 438 | +++ | + | +++ | | | | | |
| 439 | +++ | + | +++ | | | | | |
| 440 | + | + | ++ | | | | | |
| 441 | +++ | + | +++ | | | | | |
| 442 | ++++ | ++++ | ++++ | | | | +++ | ++ |
| 443 | ++++ | ++++ | ++++ | | | | +++ | ++ |
| 444 | ++++ | ++++ | ++++ | | | | | |
| 445 | ++++ | ++++ | ++++ | | | | +++ | +++ |
| 446 | ++++ | ++++ | ++++ | | | | | |
| 447 | ++++ | ++++ | ++++ | | | | | |
| 448 | ++++ | ++++ | ++++ | | | | | |
| 449 | ++++ | ++++ | ++++ | | | | | |
| 450 | ++++ | ++++ | ++++ | | | | | |
| 451 | ++++ | ++++ | ++++ | | | | | |
| 452 | ++++ | ++++ | ++++ | | | | | |
| 453 | ++++ | ++++ | ++++ | | | | | |
| 454 | ++++ | ++++ | ++++ | | | | +++ | ++ |
| 455 | ++++ | ++++ | ++++ | | | | | |
| 456 | ++++ | ++++ | ++++ | | | | | |
| 457 | ++++ | ++++ | ++++ | | | | | |
| 458 | ++++ | ++++ | ++++ | | | | | |
| 459 | ++++ | ++++ | ++++ | | | | | |
| 460 | ++++ | ++++ | ++++ | | | | | |
| 461 | ++++ | ++++ | ++++ | | | | | |
| 462 | ++++ | ++++ | ++++ | | | | +++ | +++ |
| 463 | ++++ | ++++ | ++++ | | | | | |
| 464 | ++++ | ++++ | ++++ | | | | | |
| 465 | ++++ | ++++ | ++++ | | | | | |
| 466 | ++++ | ++++ | ++++ | | | | | |
| 467 | ++++ | ++++ | ++++ | | | | | |
| 468 | ++++ | ++++ | ++++ | | | | | |
| 469 | ++++ | ++++ | ++++ | | | | | |
| 470 | ++++ | ++++ | ++++ | | | | | |
| 471 | ++++ | ++++ | ++++ | | | | | |
| 472 | ++++ | ++++ | ++++ | | | | | |
| 473 | ++++ | ++++ | ++++ | | | | | |
| 474 | ++++ | ++++ | ++++ | | | | | |
| 475 | ++++ | ++++ | ++++ | | | | | |

| Ex. No | IC50 (μM) PIM1 | PIM2 | PIM3 | EC50 (μM) HEL 92.1.7 | MV-4-11 | PC3 | KMS11 | MM1.s |
|---|---|---|---|---|---|---|---|---|
| 476 | ++++ | ++++ | ++++ | | | | | |
| 477 | ++++ | ++++ | ++++ | | | | | |
| 478 | ++++ | ++++ | ++++ | | | | | |
| 479 | ++++ | ++++ | ++++ | | | | | |
| 480 | ++++ | ++++ | ++++ | | | | | |
| 481 | ++++ | ++++ | ++++ | | | | | |
| 482 | ++++ | ++++ | ++++ | | | | | |
| 483 | ++++ | ++++ | ++++ | | | | | |
| 484 | ++++ | ++++ | ++++ | | | | | |
| 485 | ++++ | ++++ | ++++ | | | | | |
| 486 | ++++ | ++++ | ++++ | | | | | |
| 487 | ++++ | ++++ | ++++ | | | | | |
| 488 | ++++ | ++++ | ++++ | | | | | |
| 489 | ++++ | ++++ | ++++ | | | | | |
| 490 | ++++ | ++++ | ++++ | | | | | |
| 491 | ++++ | ++++ | ++++ | | | | +++ | +++ |
| 492 | ++++ | ++++ | ++++ | | | | | |
| 493 | ++++ | ++++ | ++++ | | | | | |
| 494 | ++++ | ++++ | ++++ | | | | ++++ | +++ |
| 495 | ++++ | ++++ | ++++ | | | | | |
| 496 | ++++ | ++++ | ++++ | | | | ++++ | ++++ |
| 497 | ++++ | ++++ | ++++ | | | | | |
| 498 | ++++ | ++++ | ++++ | | | | | |
| 499 | ++++ | ++++ | ++++ | | | | | |
| 500 | ++++ | ++++ | ++++ | | | | | |
| 501 | ++++ | ++++ | ++++ | | | | | |
| 502 | ++++ | ++++ | ++++ | | | | | |
| 503 | ++++ | ++++ | ++++ | | | | | |
| 504 | ++++ | ++++ | ++++ | | | | | |
| 505 | ++++ | ++++ | ++++ | | | | | |
| 506 | ++++ | ++++ | ++++ | | | | | |
| 507 | ++++ | ++++ | ++++ | | | | | |
| 508 | ++++ | ++++ | ++++ | | | | | |
| 509 | ++++ | ++++ | ++++ | | | | | |
| 510 | ++++ | ++++ | ++++ | | | | | |
| 511 | ++++ | ++++ | ++++ | | | | | |
| 512 | ++++ | ++++ | ++++ | | | | | |
| 513 | ++++ | ++++ | ++++ | | | | | |
| 514 | ++++ | ++++ | ++++ | | | | | |
| 515 | ++++ | ++++ | ++++ | | | | | |
| 516 | ++++ | ++++ | ++++ | | | | ++++ | ++++ |
| 517 | ++++ | ++++ | ++++ | | | | +++ | +++ |
| 519 | ++++ | ++++ | ++++ | | | | | |
| 520 | ++++ | ++++ | ++++ | | | | ++ | ++ |
| 521 | ++++ | ++++ | ++++ | | | | | |
| 522 | ++++ | ++++ | ++++ | | | | | |
| 523 | ++++ | ++++ | ++++ | | | | | |
| 524 | ++++ | ++++ | ++++ | | | | | |
| 525 | ++++ | ++++ | ++++ | | | | | |
| 526 | ++++ | ++++ | ++++ | | | | | |
| 527 | ++++ | ++++ | ++++ | | | | | |
| 528 | ++++ | ++++ | ++++ | | | | | |
| 529 | ++++ | ++++ | ++++ | | | | | |
| 530 | ++++ | ++++ | ++++ | | | | | |
| 531 | ++++ | ++++ | ++++ | | | | | |
| 532 | ++++ | ++++ | ++++ | | | | | |
| 533 | ++++ | ++++ | ++++ | | | | | |
| 534 | ++++ | ++++ | ++++ | | | | | |
| 535 | ++++ | ++++ | ++++ | | | | | |
| 536 | ++++ | ++++ | ++++ | | | | | |
| 537 | ++++ | ++++ | ++++ | | | | | |
| 538 | ++++ | ++++ | ++++ | | | | | |
| 539 | ++++ | ++++ | ++++ | | | | | |
| 540 | ++++ | ++++ | ++++ | | | | | |
| 541 | ++++ | ++++ | ++++ | | | | | |
| 542 | ++++ | ++++ | ++++ | | | | | |
| 543 | ++++ | ++++ | ++++ | | | | | |
| 544 | ++++ | ++++ | ++++ | | | | | |
| 545 | ++++ | ++++ | ++++ | | | | | |
| 546 | ++++ | ++++ | ++++ | | | | | |
| 547 | ++++ | ++++ | ++++ | | | | | |
| 548 | ++++ | ++++ | ++++ | | | | | |
| 549 | ++++ | ++++ | ++++ | | | | | |
| 550 | ++++ | ++++ | ++++ | | | | | |
| 551 | ++++ | ++++ | ++++ | | | | | |
| 552 | ++++ | ++++ | ++++ | | | | | |
| 553 | ++++ | ++++ | ++++ | | | | | |
| 554 | ++++ | ++++ | ++++ | | | | | |
| 555 | ++++ | ++++ | ++++ | | | | | |
| 556 | ++++ | ++++ | ++++ | | | | | |
| 557 | ++++ | ++++ | ++++ | | | | | |
| 558 | ++++ | ++++ | ++++ | | | | | |
| 559 | ++++ | ++++ | ++++ | | | | | |
| 560 | ++++ | ++++ | ++++ | | | | | |
| 561 | ++++ | ++++ | ++++ | | | | | |
| 562 | ++++ | ++++ | ++++ | | | | | |
| 563 | ++++ | ++++ | ++++ | | | | | |
| 564 | ++++ | ++++ | ++++ | | | | | |
| 565 | ++++ | ++++ | ++++ | | | | | |
| 566 | ++++ | ++++ | ++++ | | | | | |
| 567 | ++++ | ++++ | ++++ | | | | | |
| 568 | ++++ | ++++ | ++++ | | | | | |
| 569 | ++++ | ++++ | ++++ | | | | | |
| 570 | ++++ | ++++ | ++++ | | | | +++ | +++ |
| 571 | ++++ | ++++ | ++++ | | | | | |
| 572 | ++++ | ++++ | ++++ | | | | | |
| 573 | ++++ | ++++ | ++++ | | | | | |
| 574 | ++++ | ++++ | ++++ | | | | | |
| 575 | ++++ | ++++ | +++ | | | | | |
| 576 | ++++ | ++++ | ++++ | | | | | |
| 577 | ++++ | ++++ | ++++ | | | | +++ | +++ |
| 578 | ++++ | ++++ | ++++ | | | | | |
| 579 | ++++ | ++++ | ++++ | | | | ++++ | +++ |
| 580 | ++++ | ++++ | ++++ | | | | +++ | +++ |
| 581 | ++++ | ++++ | ++++ | | | | | |
| 582 | ++++ | +++ | ++++ | | | | | |
| 584 | ++++ | +++ | ++++ | | | | | |
| 585 | ++++ | ++++ | ++++ | | | | | |
| 586 | ++++ | +++ | ++++ | | | | | |
| 587 | ++++ | ++++ | ++++ | ++++ | | | | |
| 588 | ++++ | ++++ | ++++ | | | | | |
| 589 | ++++ | ++++ | ++++ | | | | | |
| 590 | ++++ | ++++ | ++++ | +++ | | | | |
| 591 | ++++ | ++++ | ++++ | ++ | | | | |
| 592 | ++++ | ++++ | ++++ | ++++ | | | | |
| 593 | ++++ | ++++ | ++++ | | | | | |
| 594 | ++++ | ++++ | ++++ | | | | | |
| 595 | ++++ | ++++ | ++++ | | | | | |
| 596 | ++++ | ++++ | ++++ | | | | | |
| 597 | ++++ | +++ | ++++ | | | | | |
| 598 | ++++ | +++ | ++++ | | | | | |
| 599 | ++++ | +++ | +++ | | | | | |
| 600 | ++++ | +++ | ++++ | | | | | |
| 601 | ++++ | ++++ | ++++ | | | | | |
| 602 | ++++ | +++ | ++++ | | | | | |
| 603 | ++++ | ++++ | ++++ | | | | | |
| 604 | ++++ | ++++ | ++++ | | | | | |
| 605 | ++++ | ++++ | ++++ | | | | | |
| 606 | ++++ | ++++ | ++++ | | | | | |
| 607 | ++++ | ++++ | ++++ | | | | | |
| 608 | ++++ | ++++ | ++++ | | | | | |
| 609 | ++++ | ++++ | ++++ | | | | | |
| 610 | ++++ | ++++ | ++++ | | | | | |
| 611 | ++++ | ++++ | ++++ | | | | | |
| 612 | ++++ | +++ | ++++ | | | | | |
| 613 | ++++ | ++++ | ++++ | | | | | |
| 614 | ++++ | ++++ | ++++ | | | | | |
| 615 | ++++ | ++++ | ++++ | | | | | |
| 616 | ++++ | ++++ | ++++ | | | | | |
| 617 | ++++ | ++++ | ++++ | | | | | |
| 618 | ++++ | ++++ | ++++ | | | | | |
| 619 | ++++ | ++++ | ++++ | | | | | |
| 620 | ++++ | ++++ | ++++ | | | | | |
| 621 | ++++ | ++++ | ++++ | | | | | |
| 622 | ++++ | ++++ | ++++ | | | | | |
| 623 | ++++ | ++++ | ++++ | | | | | |

|  | IC50 (μM) | | | EC50 (μM) | | | | |
|---|---|---|---|---|---|---|---|---|
| Ex. No | PIM1 | PIM2 | PIM3 | HEL 92.1.7 | MV-4-11 | PC3 | KMS11 | MM1.s |
| 624 | ++++ | ++++ | ++++ | | | | | |
| 625 | ++++ | ++++ | ++++ | | | | | |
| 626 | ++++ | ++++ | ++++ | | | | | |
| 627 | ++++ | ++++ | ++++ | | | | | |
| 628 | ++++ | ++++ | ++++ | | | | | |
| 629 | ++++ | ++++ | ++++ | | | | | |
| 630 | ++++ | ++++ | ++++ | | | | | |
| 631 | ++++ | ++++ | ++++ | | | | | |
| 632 | ++++ | ++++ | ++++ | | | | | |
| 633 | ++++ | ++++ | ++++ | | | | | |
| 634 | ++++ | ++++ | ++++ | | | | | |
| 635 | ++++ | ++++ | ++++ | | | | | |
| 636 | ++++ | ++++ | ++++ | | | | | |
| 637 | ++++ | ++++ | ++++ | | | | | |
| 638 | ++++ | ++++ | ++++ | | | | | |
| 639 | ++++ | ++++ | ++++ | | | | | |
| 640 | ++++ | ++++ | ++++ | | | | | |
| 641 | ++++ | ++++ | ++++ | | | | | |
| 642 | ++++ | ++++ | ++++ | | | | | |
| 643 | ++++ | ++++ | ++++ | | | | | |
| 644 | ++++ | ++++ | ++++ | | | | | |
| 645 | ++++ | ++++ | ++++ | | | | | |
| 646 | ++++ | ++++ | ++++ | | | | | |
| 647 | ++++ | ++++ | ++++ | | | | | |
| 648 | ++++ | ++++ | ++++ | | | | | |
| 649 | ++++ | ++++ | ++++ | | | | | |
| 650 | ++++ | ++++ | ++++ | | | | | |
| 651 | ++++ | ++++ | ++++ | | | | | |
| 652 | ++++ | ++++ | ++++ | | | | | |
| 653 | ++++ | ++++ | ++++ | | | | | |
| 654 | ++++ | ++++ | ++++ | | | | | |
| 655 | ++++ | ++++ | ++++ | | | | | |
| 656 | ++++ | ++++ | ++++ | | | | | |
| 657 | ++++ | ++++ | ++++ | | | | | |
| 658 | ++++ | ++++ | ++++ | | | | | |
| 659 | ++++ | ++++ | ++++ | | | | | |
| 660 | ++++ | ++++ | ++++ | | | | | |
| 661 | ++++ | ++++ | ++++ | | | | | |
| 662 | ++++ | ++++ | ++++ | | | | | |
| 663 | ++++ | ++++ | ++++ | | | | | |
| 664 | ++++ | ++++ | ++++ | | | | | |
| 665 | ++++ | ++++ | ++++ | | | | | |
| 666 | ++++ | ++++ | ++++ | | | | | |
| 667 | ++++ | ++++ | ++++ | | | | | |
| 668 | ++++ | ++++ | ++++ | | | | | |
| 669 | ++++ | ++++ | ++++ | | | | | |
| 670 | ++++ | ++++ | ++++ | | | | | |
| 671 | ++++ | ++++ | ++++ | | | | | |
| 672 | ++++ | ++++ | ++++ | | | | | |
| 673 | ++++ | ++++ | ++++ | | | | | |
| 674 | ++++ | ++++ | ++++ | | | | | |
| 675 | ++++ | ++++ | ++++ | | | | | |
| 676 | ++++ | ++++ | ++++ | | | | | |
| 677 | ++++ | ++++ | ++++ | | | | | |
| 678 | ++++ | ++++ | ++++ | | | | | |
| 679 | ++++ | ++++ | ++++ | | | | +++ | ++++ |
| 680 | ++++ | ++++ | ++++ | | | | | |
| 681 | ++++ | ++++ | ++++ | | | | | |
| 682 | ++++ | ++++ | ++++ | | | | | |
| 683 | ++++ | ++++ | ++++ | | | | ++++ | +++ |
| 684 | ++++ | ++++ | ++++ | | | | | |
| 685 | ++++ | ++++ | ++++ | | | | | |
| 686 | ++++ | ++++ | ++++ | | | | | |
| 687 | ++++ | ++++ | ++++ | | | | | |
| 688 | ++++ | ++++ | ++++ | | | | | |
| 689 | ++++ | ++++ | ++++ | | | | | |
| 690 | ++++ | ++++ | ++++ | | | | | |
| 691 | ++++ | ++++ | ++++ | | | | | |
| 692 | ++++ | ++++ | ++++ | | | | | |
| 693 | ++++ | ++++ | ++++ | | | | | |
| 694 | ++++ | ++++ | ++++ | | | | | |
| 695 | ++++ | ++++ | ++++ | | | | | |
| 696 | ++++ | ++++ | ++++ | | | | | |
| 697 | ++++ | +++ | ++++ | | | | | |
| 698 | ++++ | ++++ | ++++ | | | | | |
| 699 | ++++ | ++++ | ++++ | | | | | |
| 700 | ++++ | ++++ | ++++ | | | | | |
| 701 | ++++ | ++++ | ++++ | | | | | |
| 702 | ++++ | ++++ | ++++ | | | | +++ | +++ |
| 703 | ++++ | ++++ | ++++ | | | | | |
| 704 | ++++ | ++++ | ++++ | | | | | |
| 705 | ++++ | ++++ | ++++ | | | | | |
| 706 | ++++ | ++++ | ++++ | | | | | |
| 707 | ++++ | ++++ | ++++ | | | | | |
| 708 | ++++ | ++++ | ++++ | | | | | |
| 709 | ++++ | ++++ | ++++ | | | | | |
| 710 | ++++ | ++++ | ++++ | | | | | |
| 711 | ++++ | ++++ | ++++ | | | | | |
| 712 | ++++ | ++++ | ++++ | | | | | |
| 713 | ++++ | ++++ | ++++ | | | | | |
| 714 | ++++ | ++++ | ++++ | | | | | |
| 715 | ++++ | ++++ | ++++ | | | | | |
| 716 | ++++ | ++++ | ++++ | | | | | |
| 717 | ++++ | ++++ | ++++ | | | | | |
| 718 | ++++ | ++++ | ++++ | | | | | |
| 719 | ++++ | ++++ | ++++ | | | | | |
| 720 | ++++ | ++++ | ++++ | | | | | |
| 721 | ++++ | ++++ | ++++ | | | | | |
| 722 | ++++ | ++++ | ++++ | | | | | |
| 723 | ++++ | ++++ | ++++ | | | | | |
| 724 | ++++ | ++++ | ++++ | | | | | |
| 725 | ++++ | ++++ | ++++ | | | | | |
| 726 | ++++ | ++++ | ++++ | | | | | |
| 727 | ++++ | ++++ | ++++ | | | | | |
| 728 | ++++ | ++++ | ++++ | | | | | |
| 729 | ++++ | ++++ | ++++ | | | | | |
| 730 | ++++ | ++++ | ++++ | | | | | |
| 731 | ++++ | ++++ | ++++ | | | | | |
| 732 | ++++ | ++++ | ++++ | | | | | |
| 733 | ++++ | ++++ | ++++ | | | | | |
| 734 | ++++ | ++++ | ++++ | | | | | |
| 735 | ++++ | ++++ | ++++ | | | | | |
| 736 | ++++ | ++++ | ++++ | | | | ++++ | +++ |
| 737 | ++++ | ++++ | ++++ | | | | | |
| 738 | ++++ | ++++ | ++++ | | | | | |
| 739 | ++++ | ++++ | ++++ | | | | | |
| 740 | ++++ | ++++ | ++++ | | | | | |
| 741 | ++++ | ++++ | ++++ | | | | | |
| 742 | ++++ | ++++ | ++++ | | | | | |
| 743 | ++++ | ++++ | ++++ | | | | | |
| 744 | ++++ | ++++ | ++++ | | | | +++ | +++ |
| 745 | ++++ | ++++ | ++++ | | | | | |
| 746 | ++++ | ++++ | ++++ | | | | | |
| 747 | ++++ | ++++ | ++++ | | | | | |
| 748 | ++++ | ++++ | ++++ | | | | | |
| 749 | ++++ | ++++ | ++++ | | | | | |
| 750 | ++++ | ++++ | ++++ | | | | | |
| 751 | ++++ | ++++ | ++++ | | | | | |
| 752 | ++++ | ++++ | ++++ | | | | | |
| 753 | ++++ | ++++ | ++++ | | | | +++ | ++++ |
| 754 | ++++ | ++++ | ++++ | | | | ++++ | +++ |
| 755 | ++++ | ++++ | ++++ | | | | | |

While illustrative embodiments have been illustrated and described, it will be appreciated that various changes can be made therein without departing from the spirit and scope of the invention.

The embodiments of the invention in which an exclusive property or privilege is claimed are defined as follows:

1. A compound of Formula III, or a stereoisomer, tautomer, or pharmaceutically acceptable salt thereof,

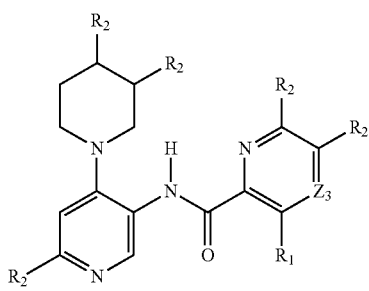
(III)

wherein,
$Z_3$ is $CR_2$;
$R_1$ is selected from the group consisting of hydrogen, halo, alkyl, and —$NHR_3$;
each $R_2$ is independently selected from the group consisting of hydrogen, halo, hydroxyl, and substituted or unsubstituted alkyl, alkoxy, amino, aryl, heteroaryl, cycloalkyl, and hetero cycloalkyl; and
$R_3$ is hydrogen.

2. A compound of claim 1 wherein $R_1$ is hydrogen.

3. A compound of claim 1 wherein each $R_2$ is independently selected from the group consisting of hydrogen, halo, hydroxyl, amino, and substituted or unsubstituted alkyl and phenyl.

4. A compound of claim 1 having the following Formula IV, or a stereoisomer, tautomer, or pharmaceutically acceptable salt thereof,

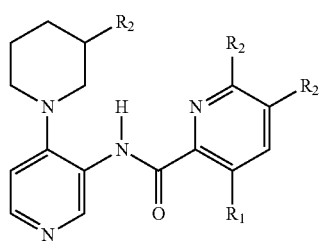
(IV)

wherein,
$R_1$ is selected from the group consisting of hydrogen, halo, and —$NHR_3$;
each $R_2$ is independently selected from the group consisting of hydrogen, halo, hydroxyl, and substituted or unsubstituted alkyl, alkoxy, amino, aryl, heteroaryl, cycloalkyl, hetero cycloalkyl; and
$R_3$ is hydrogen.

5. A composition comprising a therapeutically effective amount of compound of claim 1, or a stereoisomer, tautomer, or pharmaceutically acceptable salt thereof, together with a pharmaceutically acceptable carrier.

6. The compound of claim 2, where $Z_1$ is $CR_2$ wherein $R_2$ is substituted or unsubstituted phenyl.

7. The compound of claim 1, wherein $R_1$ is amino.

8. A compound selected from the group consisting of:

162
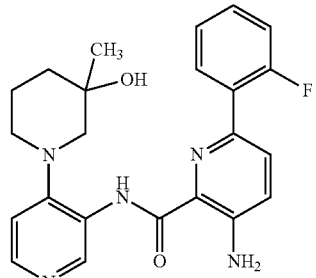

163
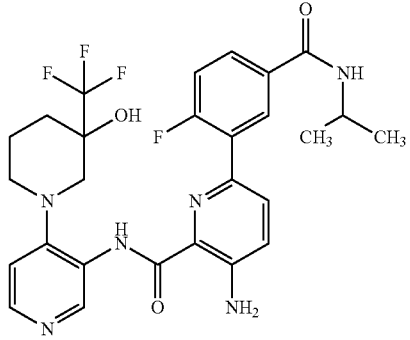

164
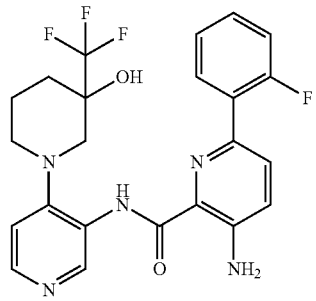

175
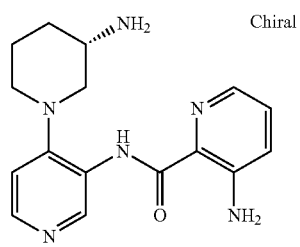
Chiral

248
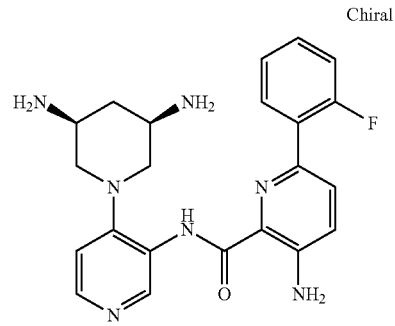
Chiral

251 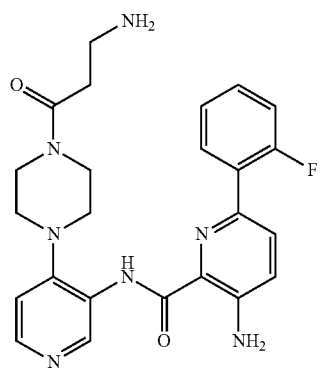
252 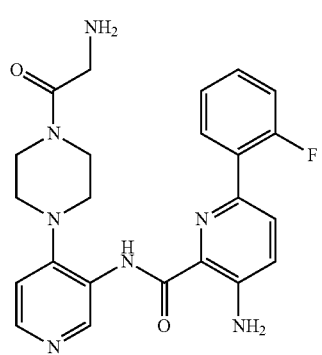
253 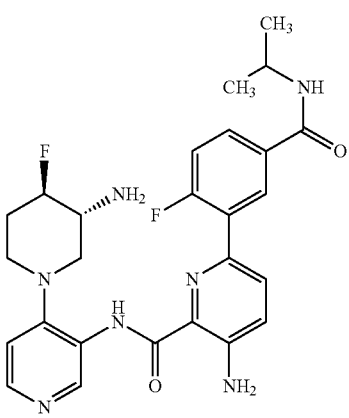
254 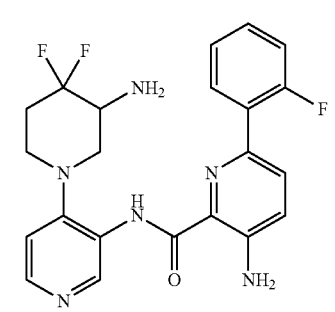
255 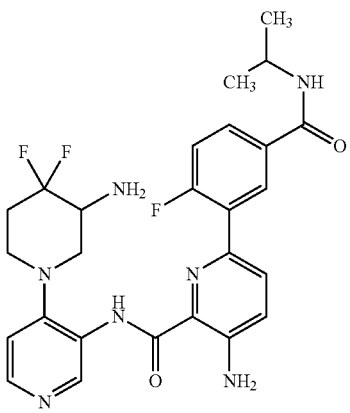
257 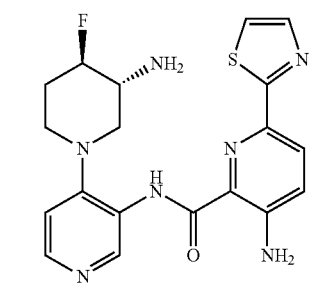
258 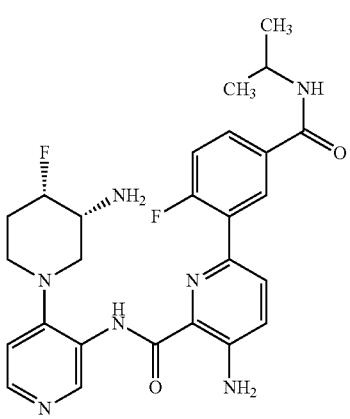
259 Chiral 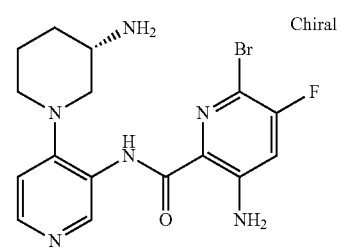
260 Chiral 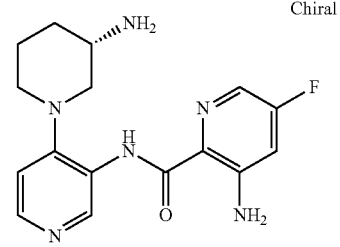

264
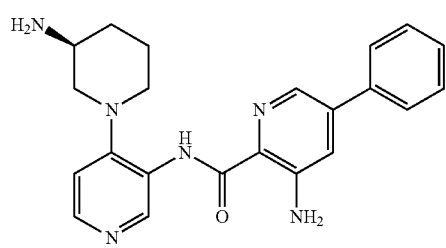
276
Chiral
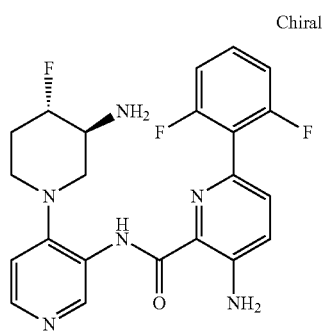
277
Chiral
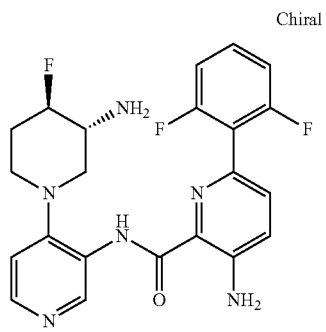
278
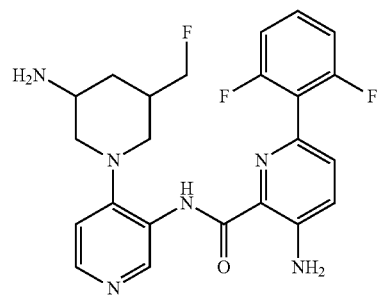
279
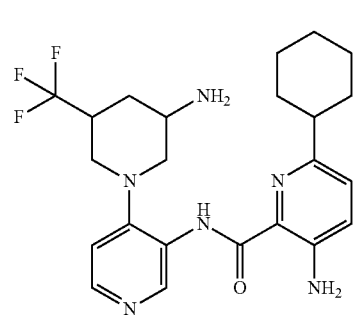
280
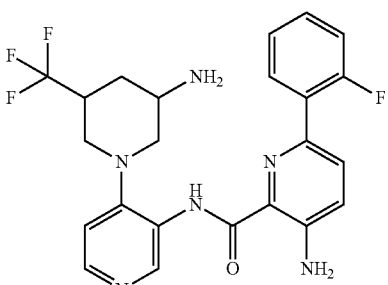
281
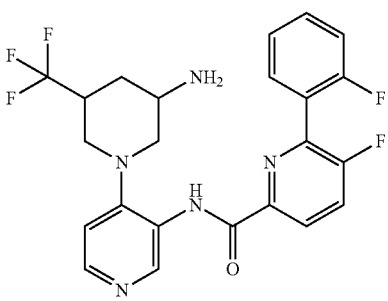
282
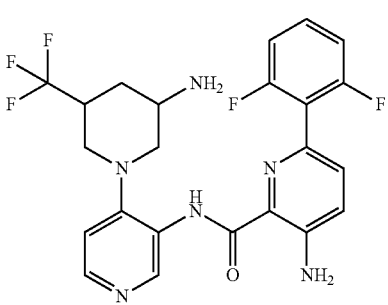
283
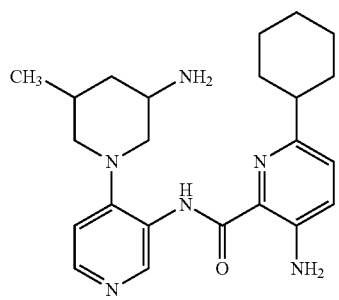
284
Chiral
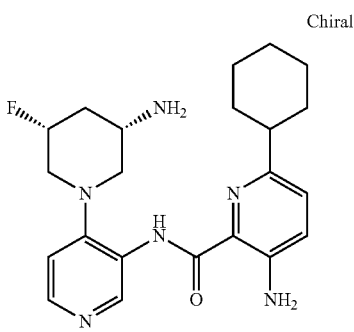

285 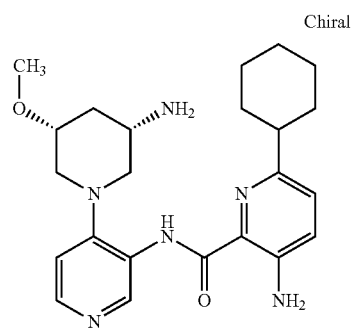
286 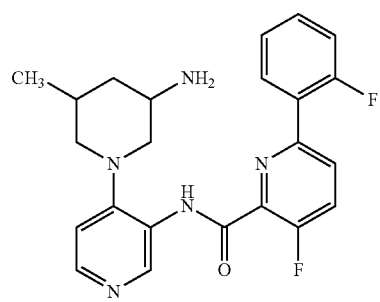
287 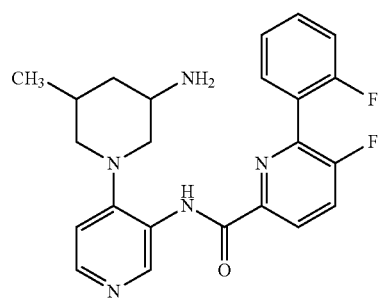
288 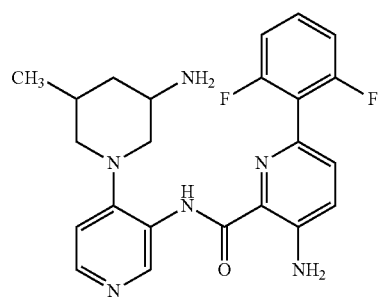
289 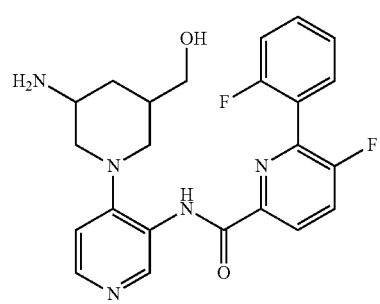
292 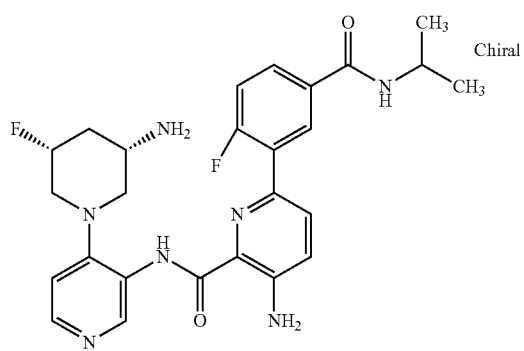
293 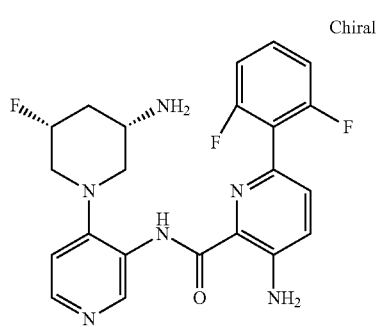
294 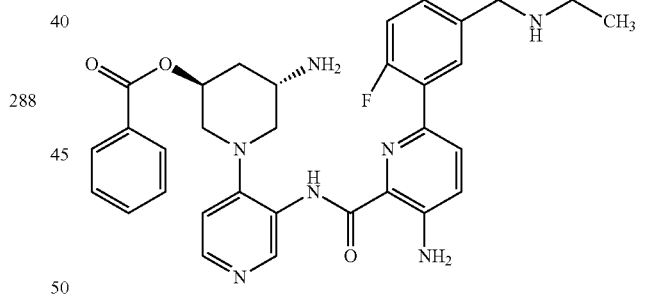
295 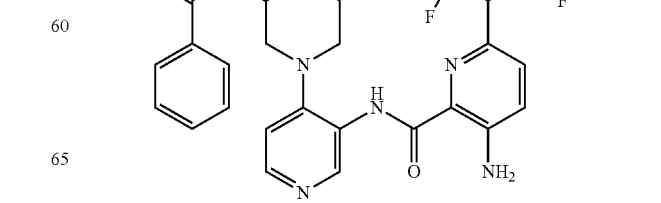

296
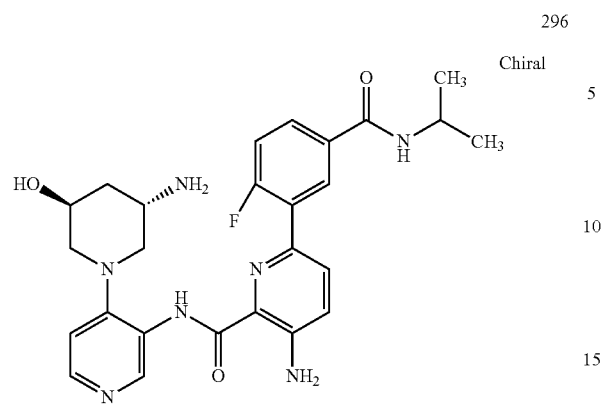
297
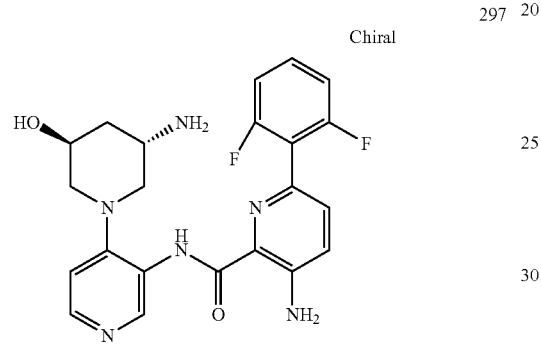
298
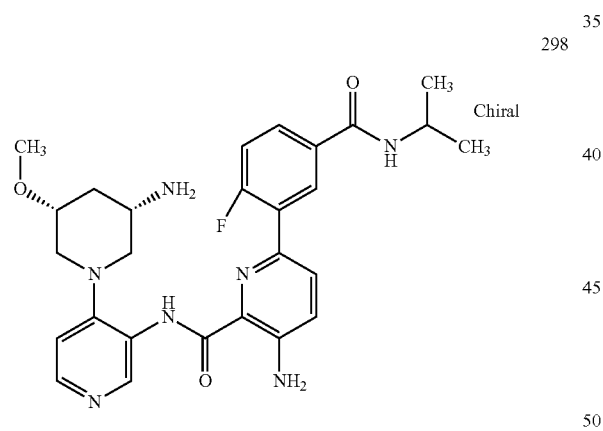
299
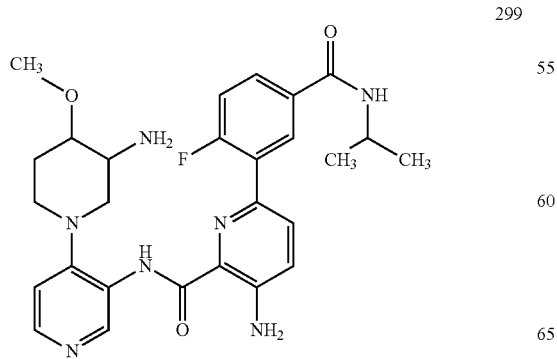
300
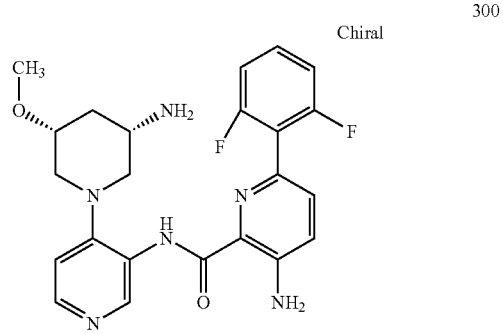
301
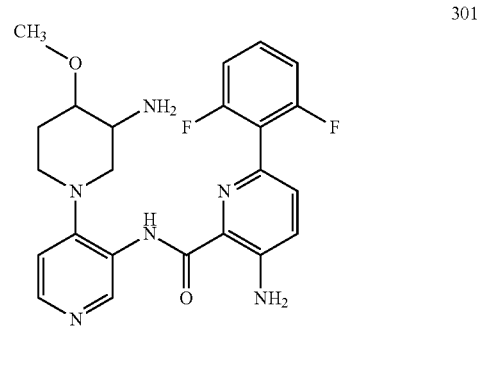
302
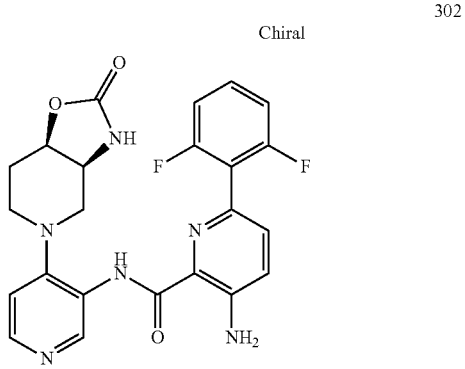
303
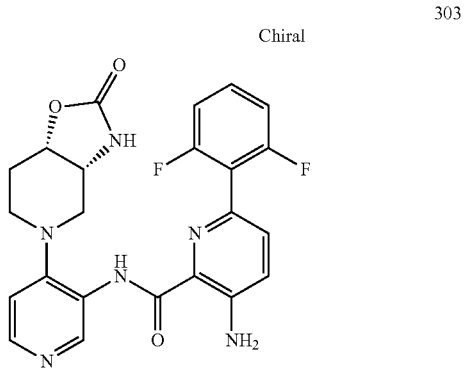

| 317 | 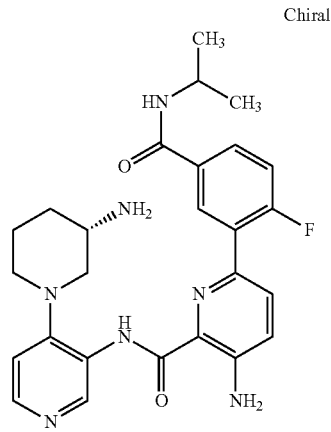 | 320 | 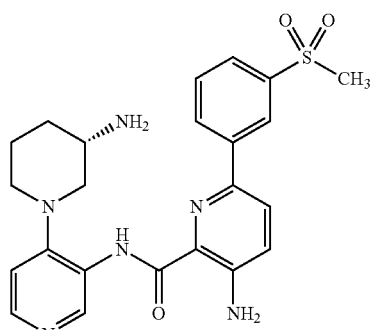 |
| 318 | 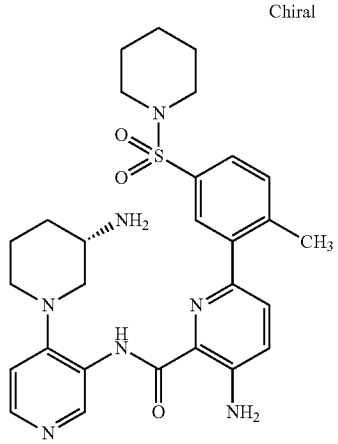 | 321 | 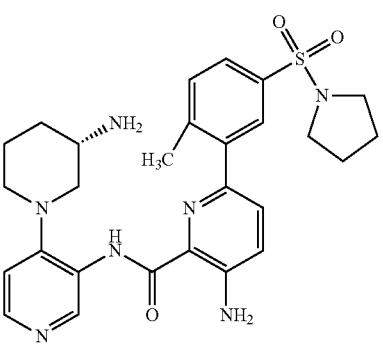 |
| | | 322 | 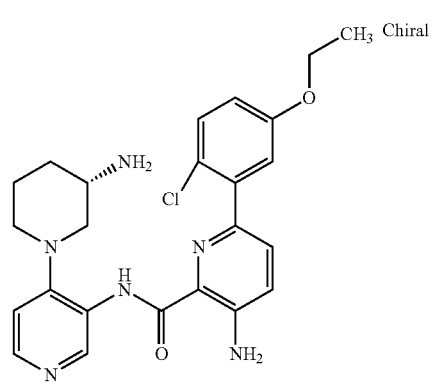 |
| 319 | 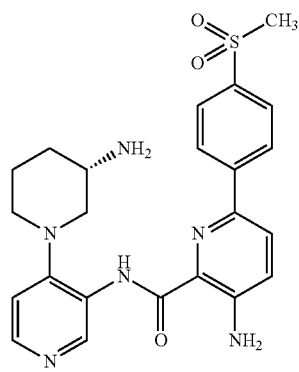 | 323 | 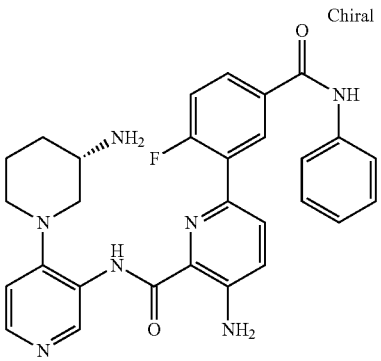 |

324 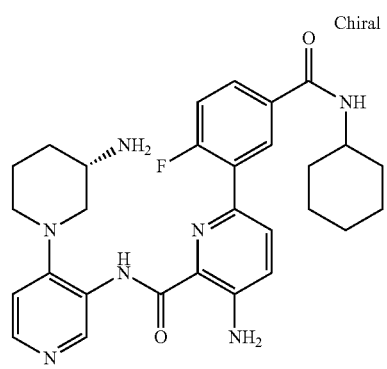
325 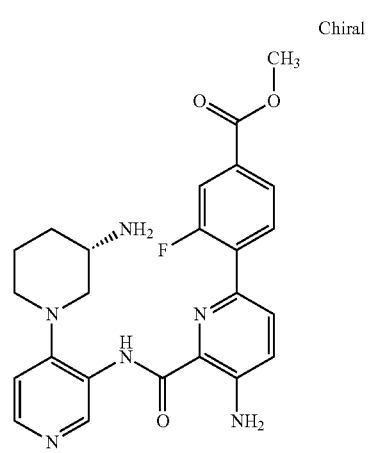
326 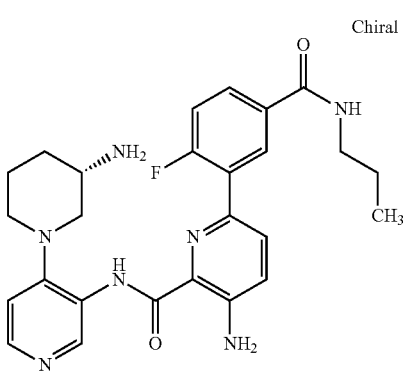
327 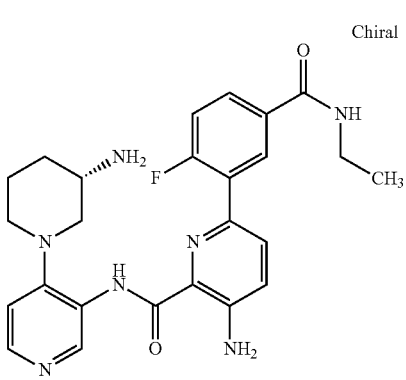
328 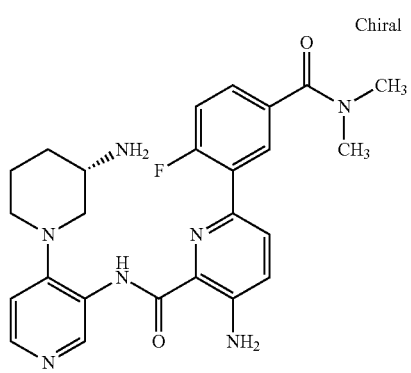
329 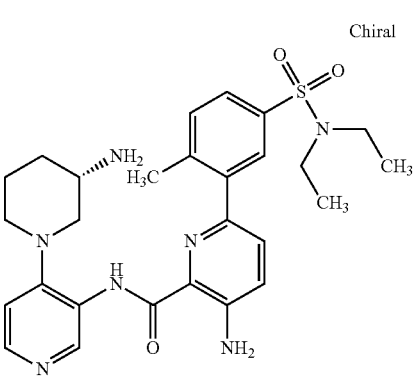
330 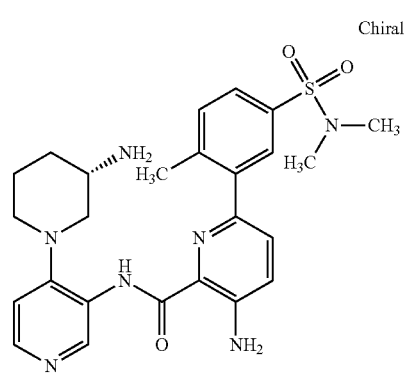
331 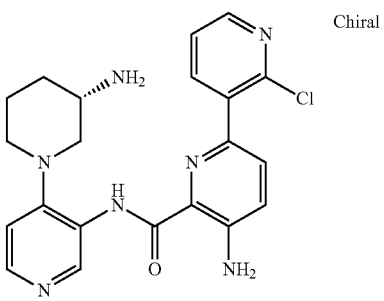

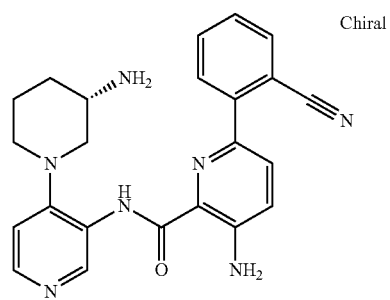
332
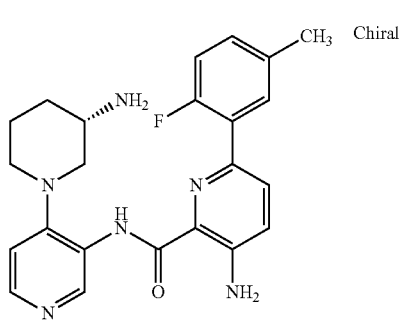
333
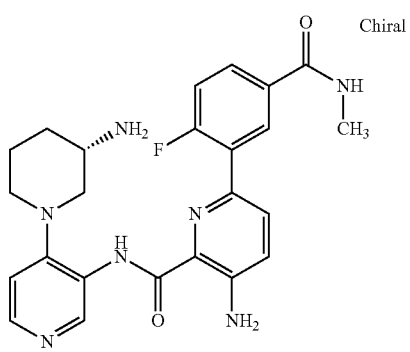
334
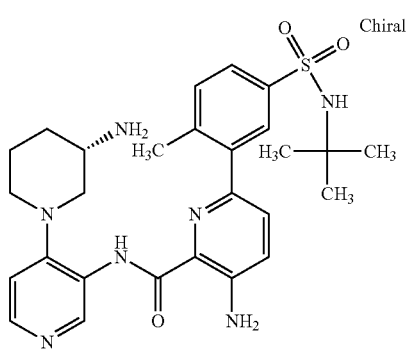
335
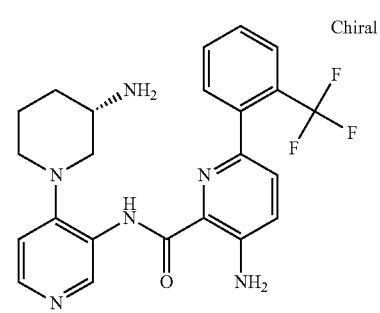
336
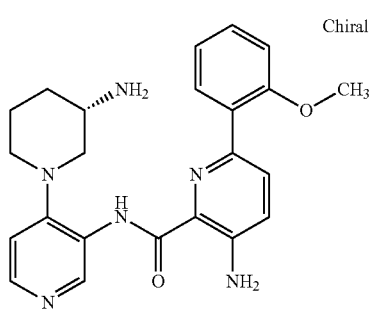
337
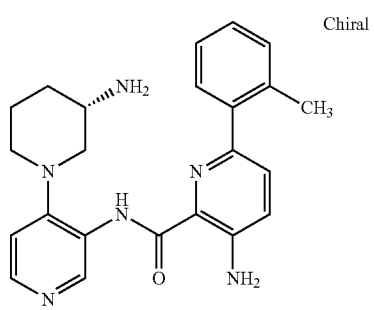
338
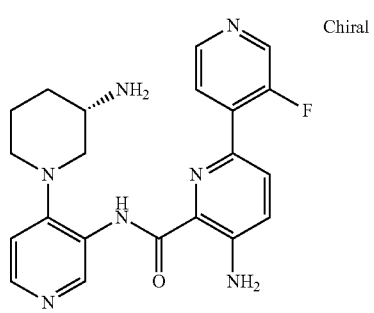
339
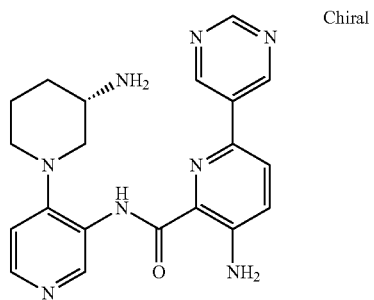
407
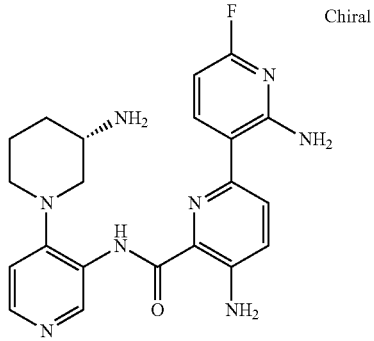
408

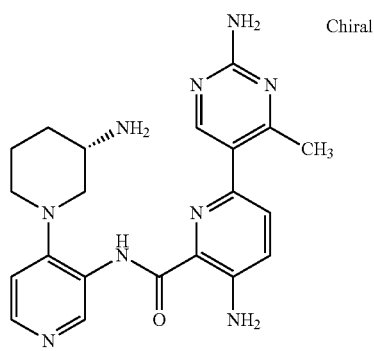 409
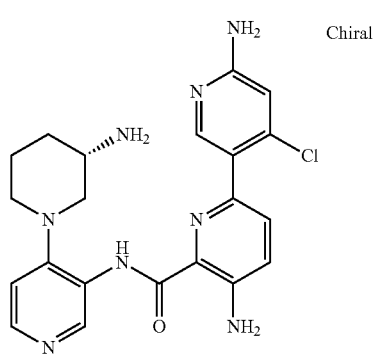 410
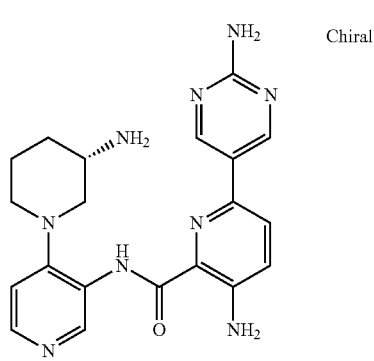 411
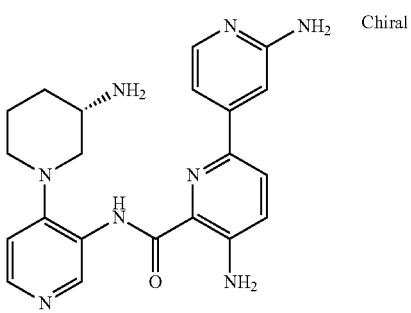 412
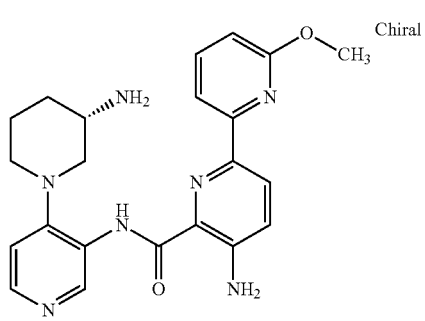 413
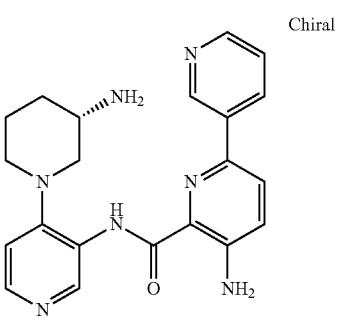 414
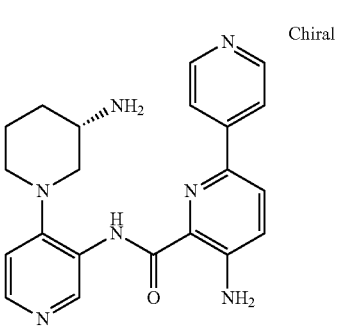 415
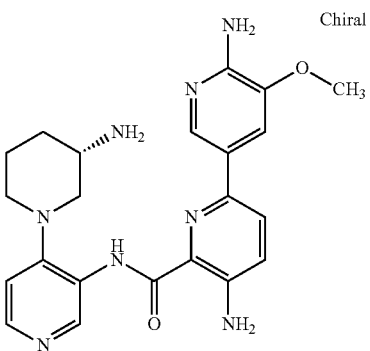 416

417 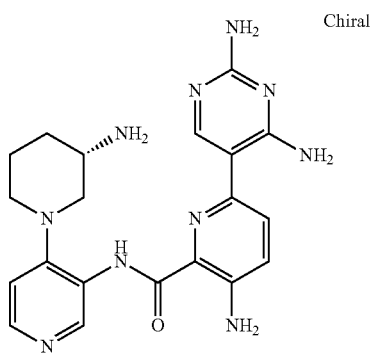
418 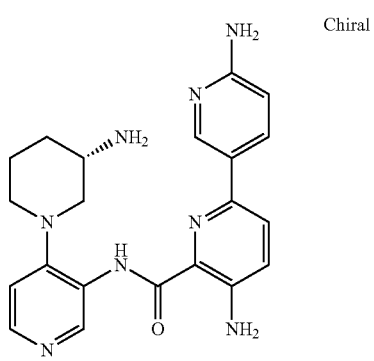
419 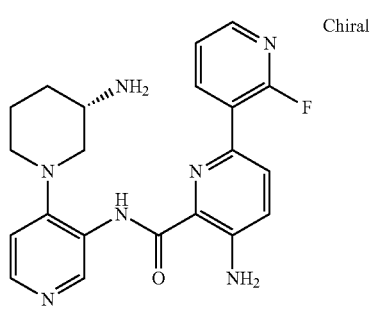
420 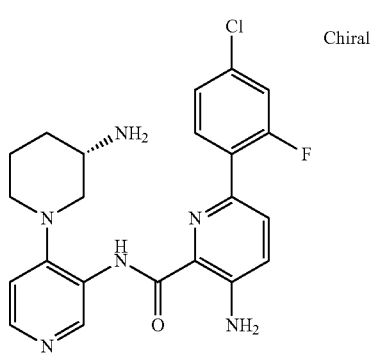
421 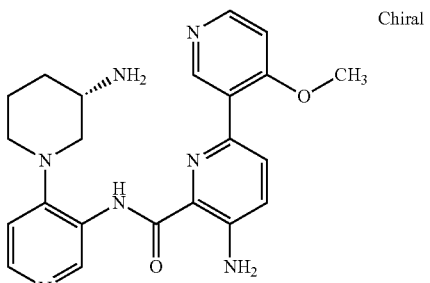
422 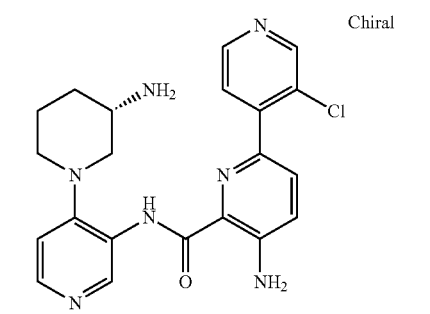
423 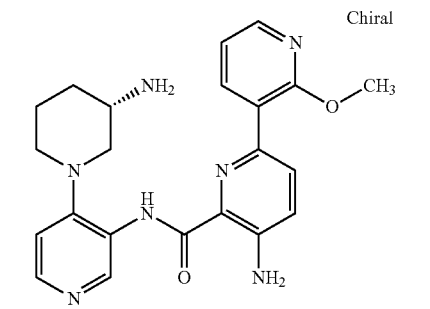
424 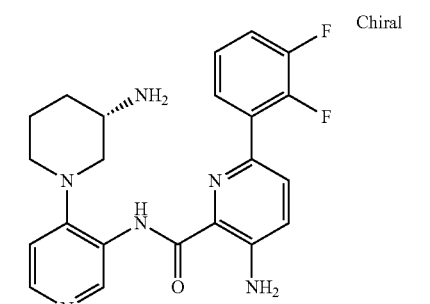
425 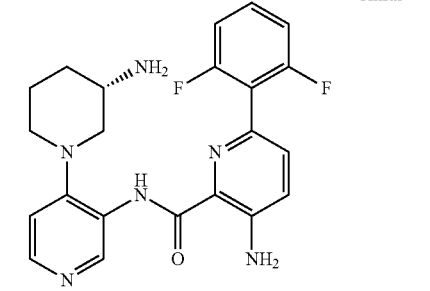

426 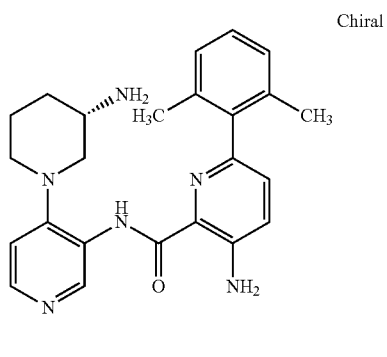
427 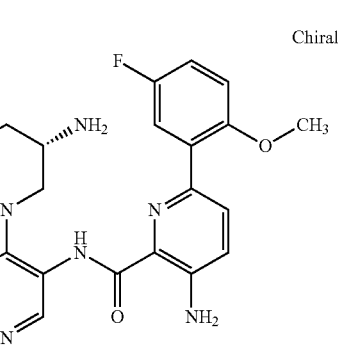
428 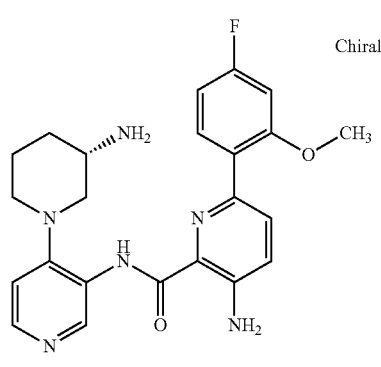
429 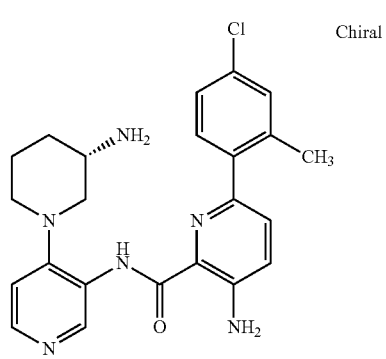
430 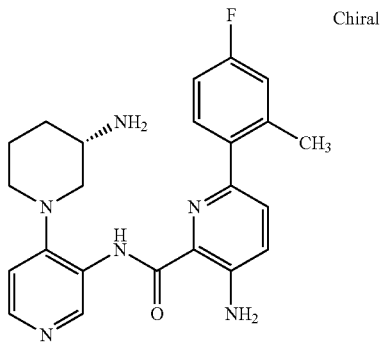
431 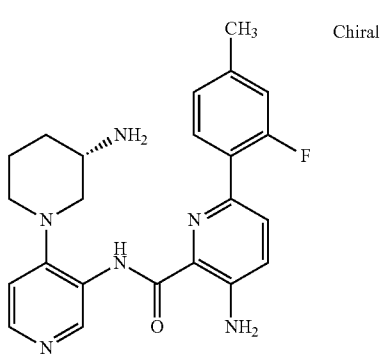
432 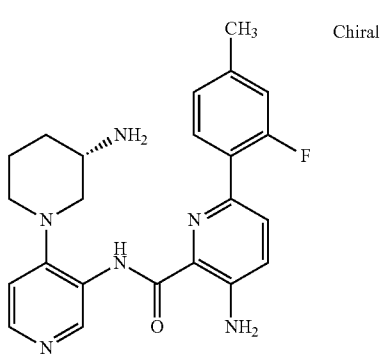
433 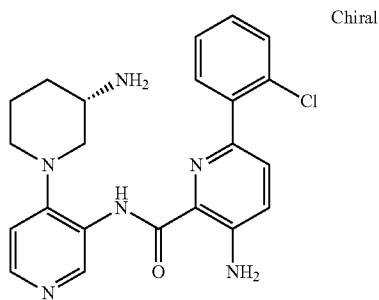

434 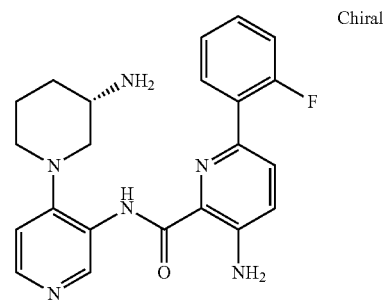
442 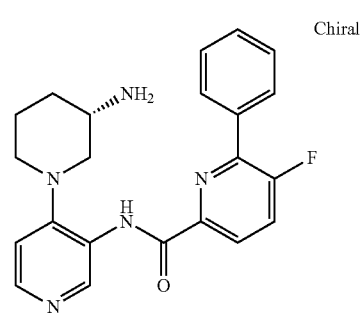
443 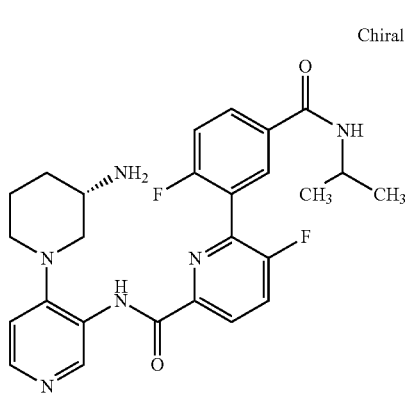
444 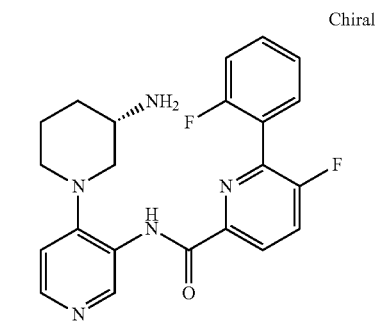
445 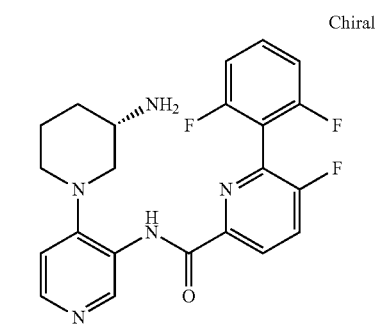
446 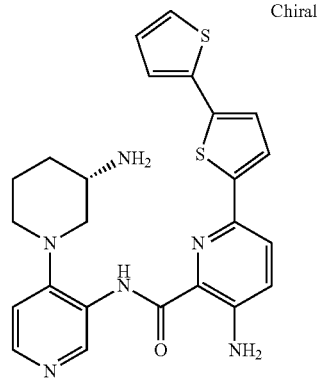
447 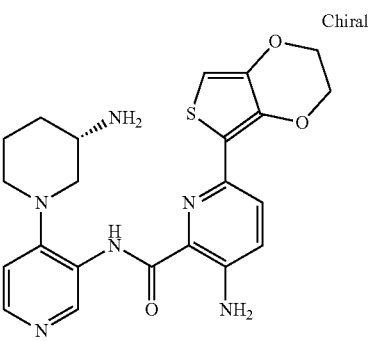
448 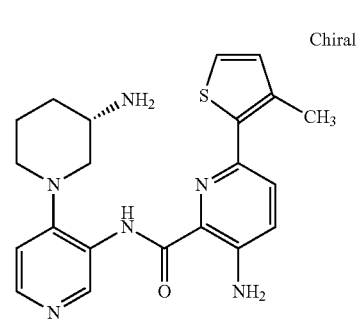
449 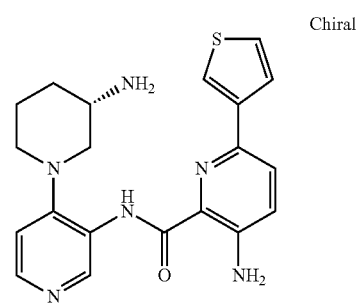

450 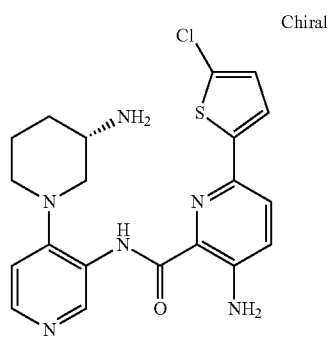
451 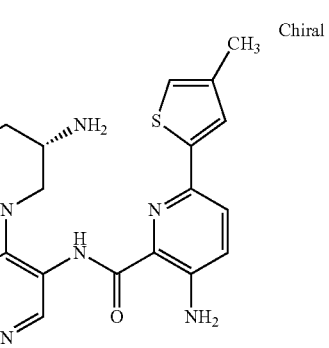
452 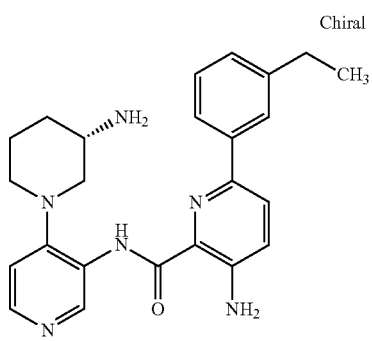
453 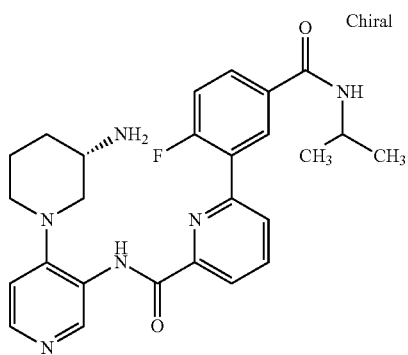
454 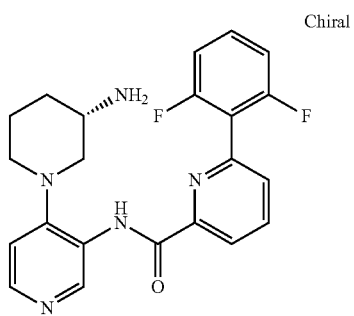
455 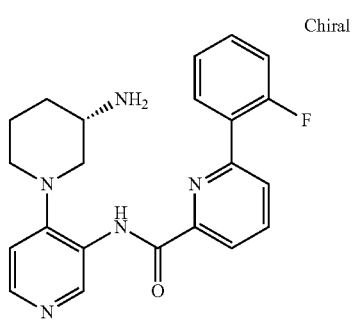
456 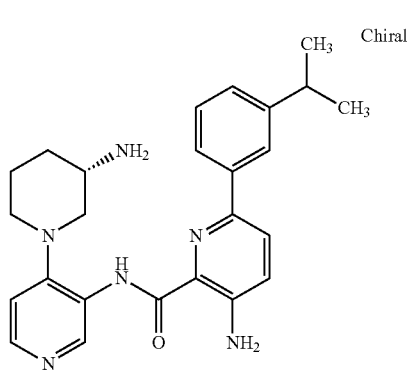
457 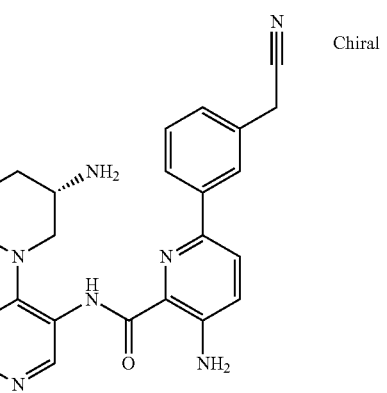

| | |
|---|---|
| 458 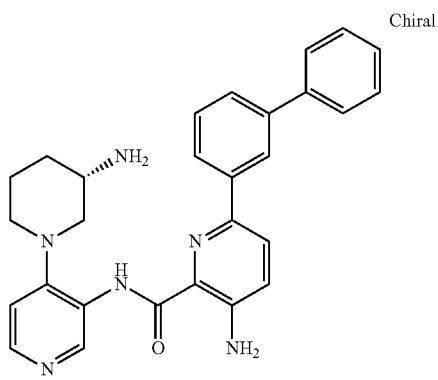 | 462 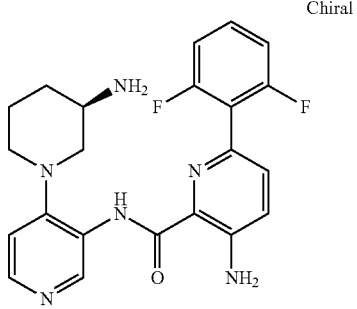 |
| 459 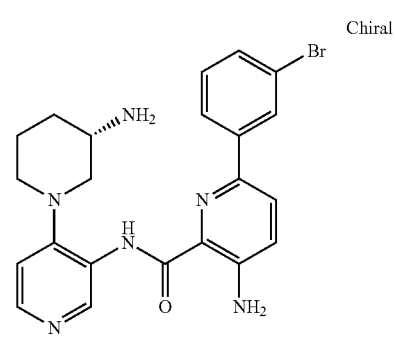 | 463 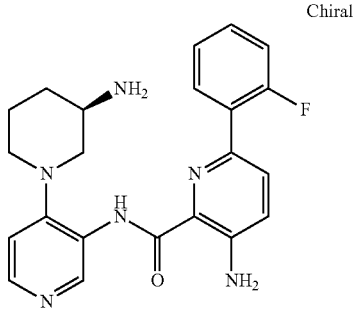 |
| 460 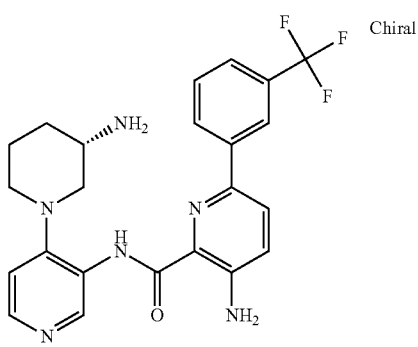 | 464 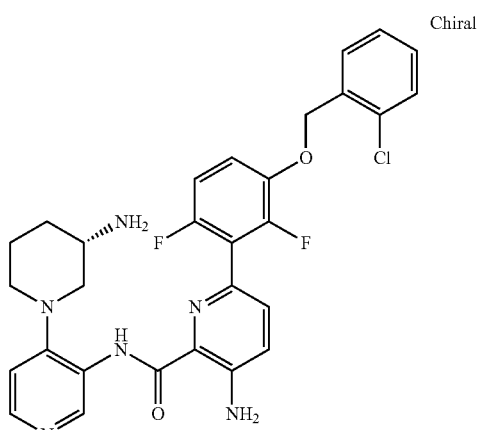 |
| 461 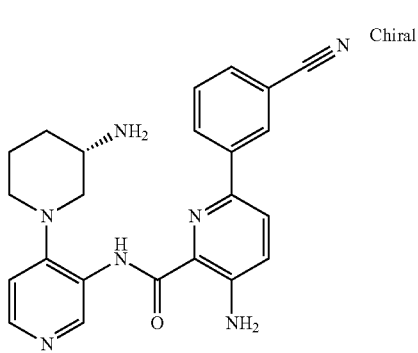 | 465 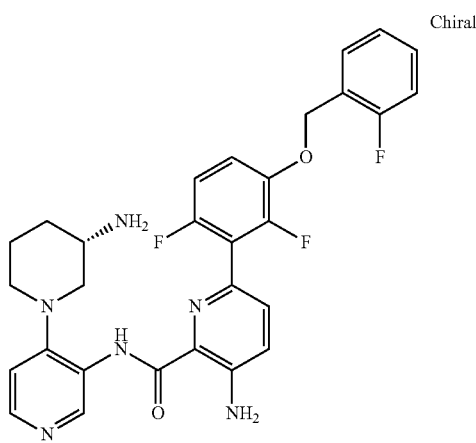 |

466 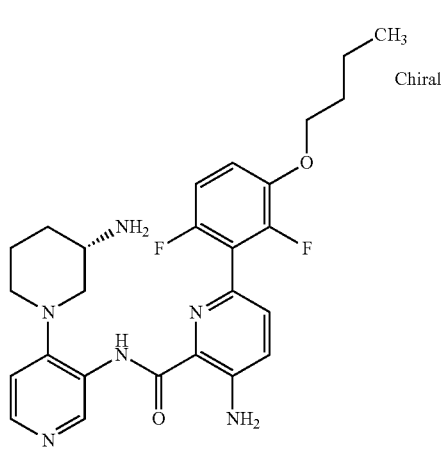
467 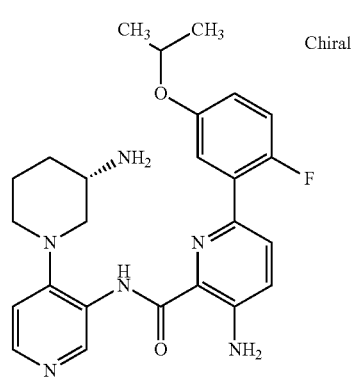
468 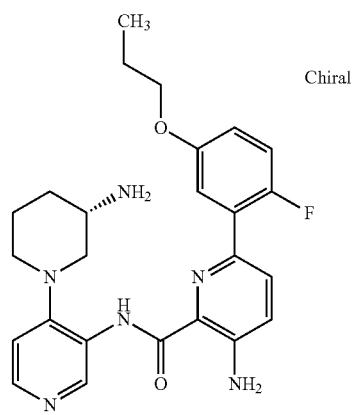
469 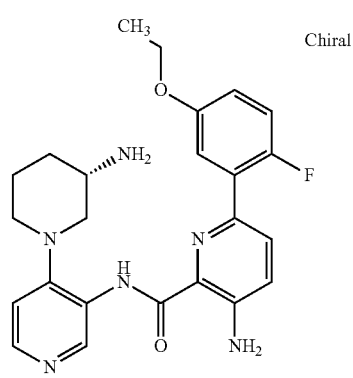
470 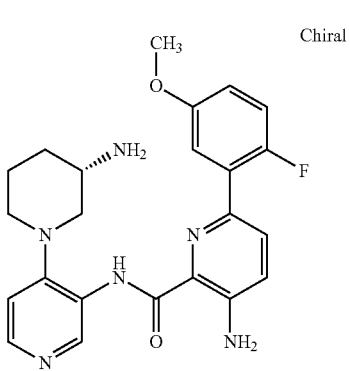
471 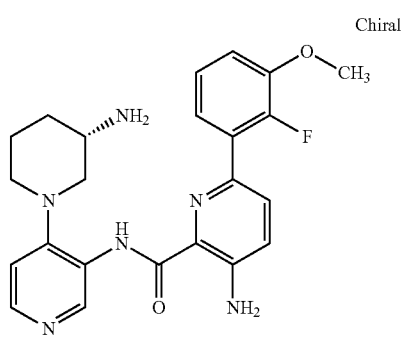
472 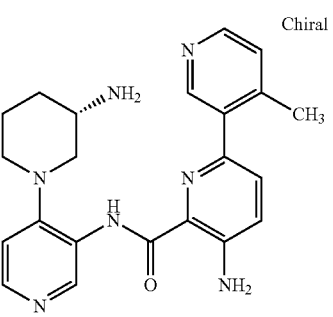
473 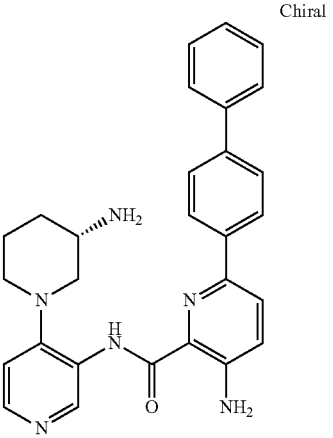

| 474 | 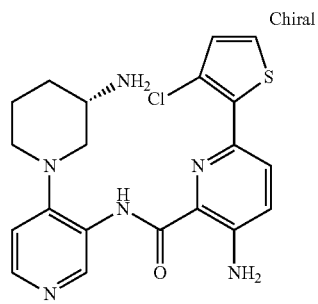 | 478 | 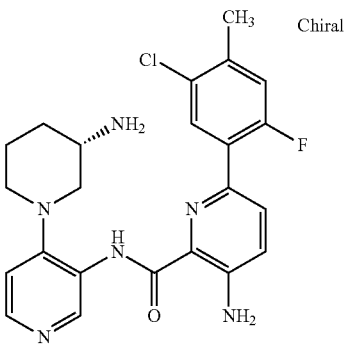 |
| 475 | 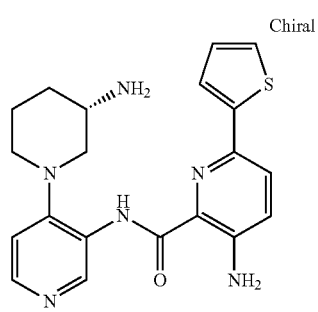 | 479 | 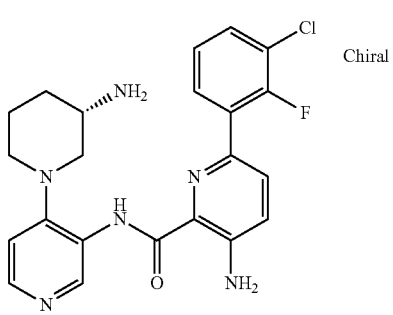 |
| 476 | 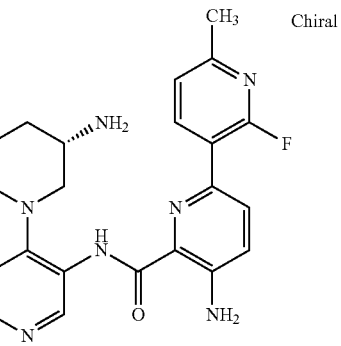 | 480 | 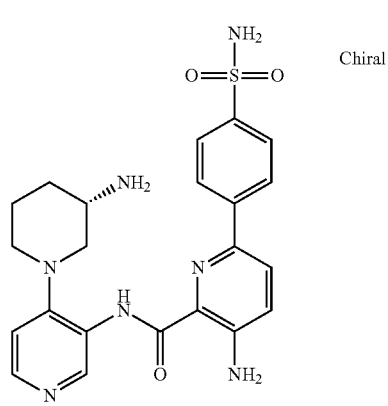 |
| 477 | 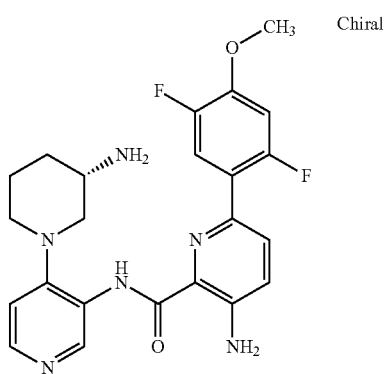 | 481 | 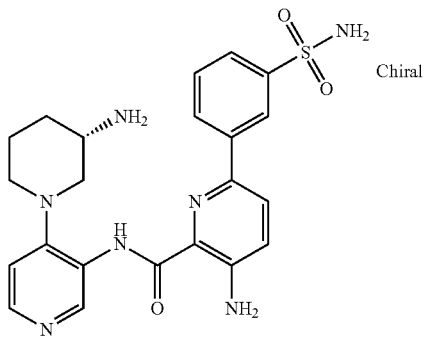 |

| | |
|---|---|
| 482 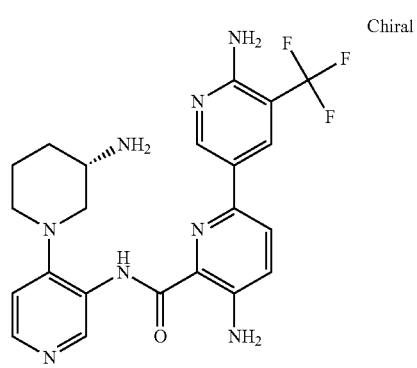 Chiral | 486 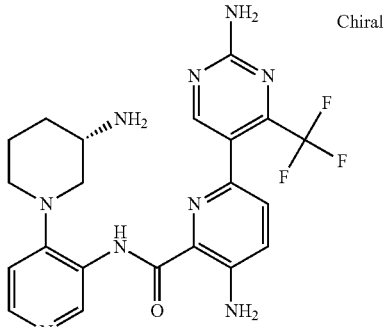 Chiral |
| 483 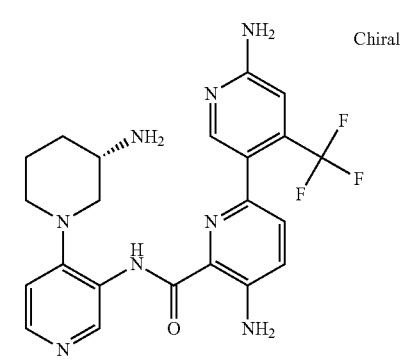 Chiral | 487 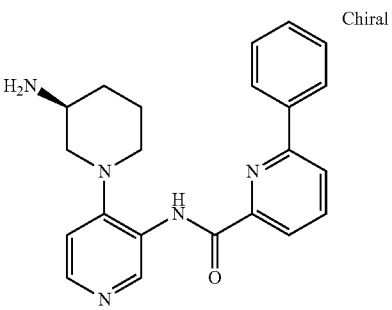 Chiral |
| 484 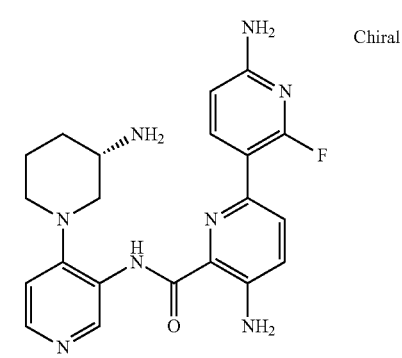 Chiral | 488 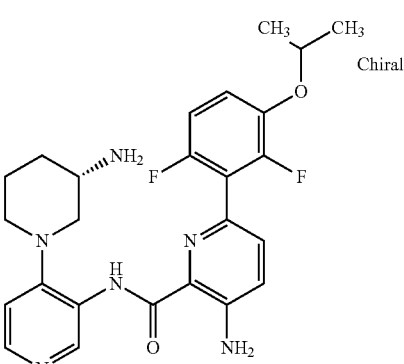 Chiral |
| 485 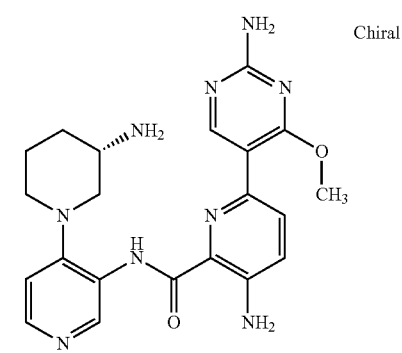 Chiral | 489 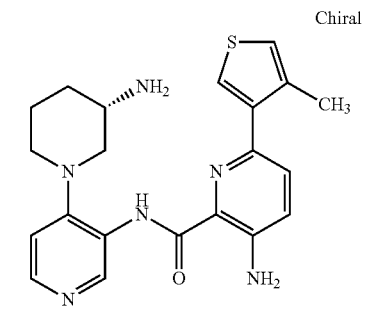 Chiral |
| | 490 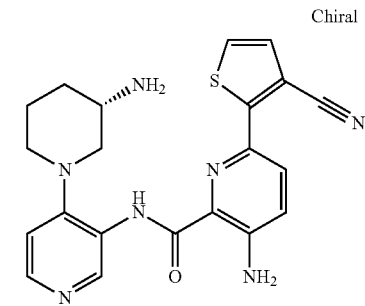 Chiral |

489
-continued
491
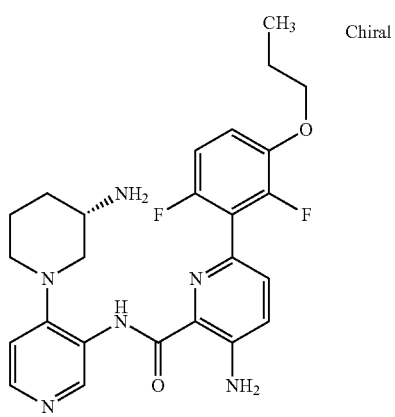
492
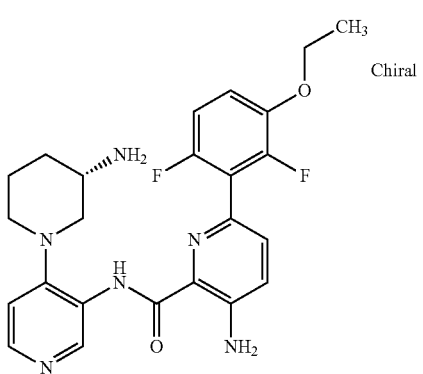
493
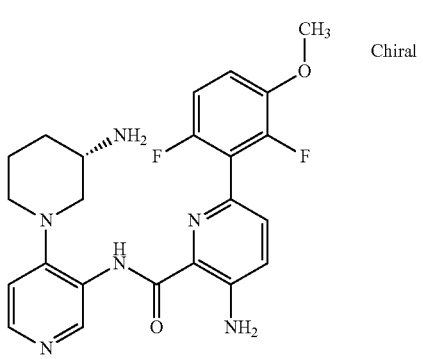
494
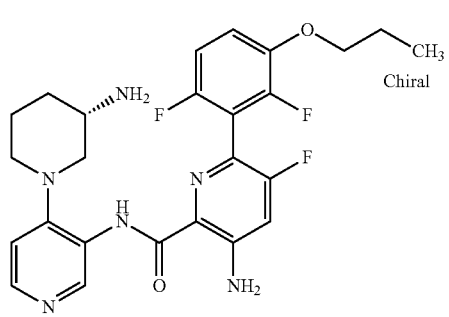
490
-continued
495
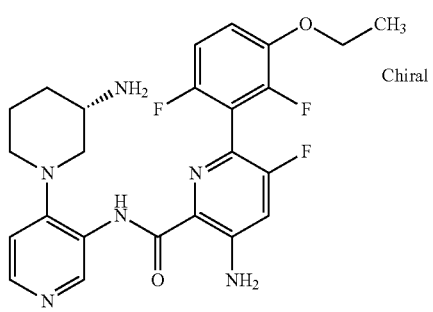
496
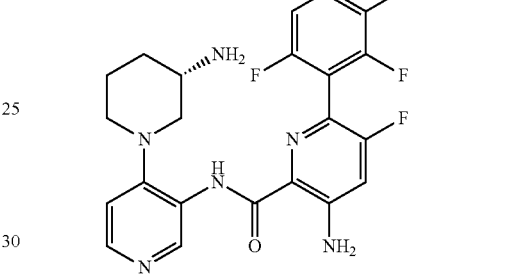
497
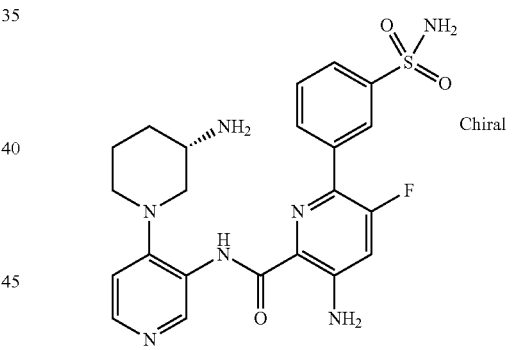
498
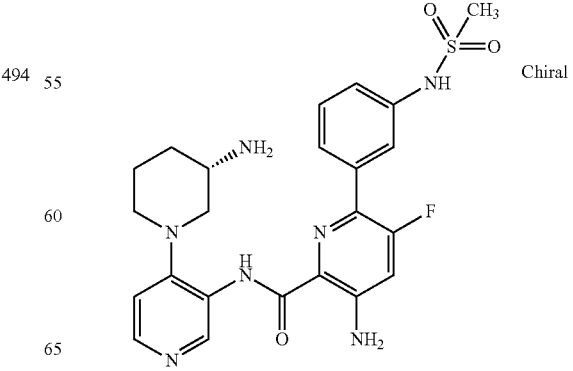

499
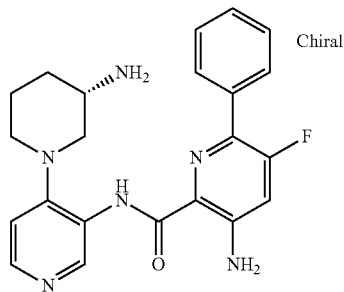
500
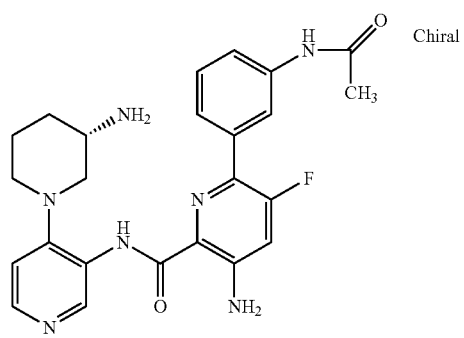
501
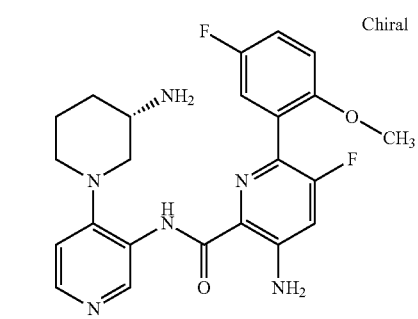
502
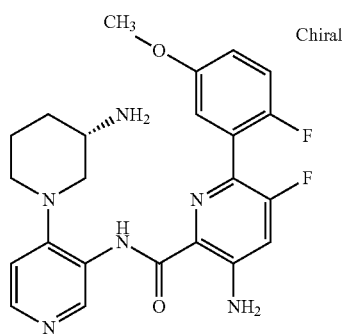
503
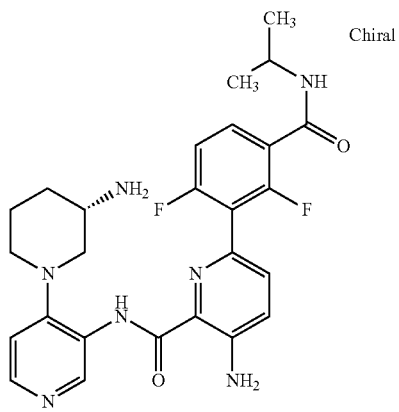
504
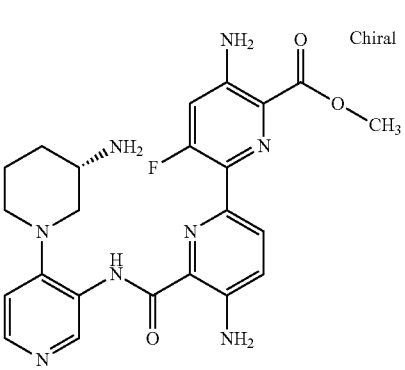
505
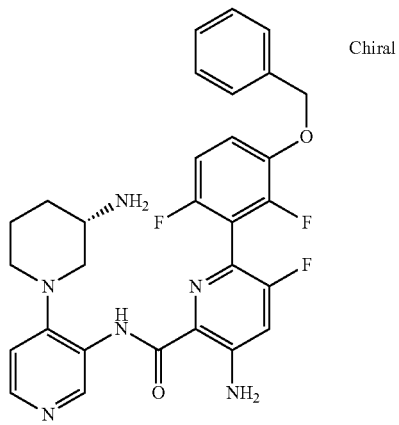
506
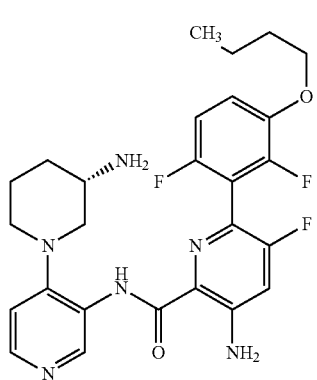

507 Chiral
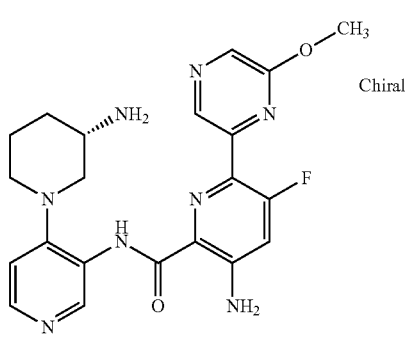
508 Chiral
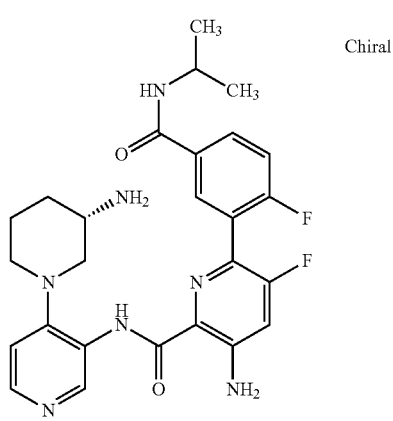
509 Chiral
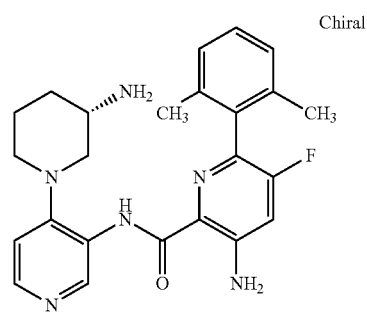
510 Chiral
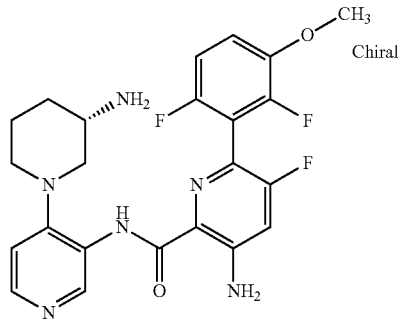
511 Chiral
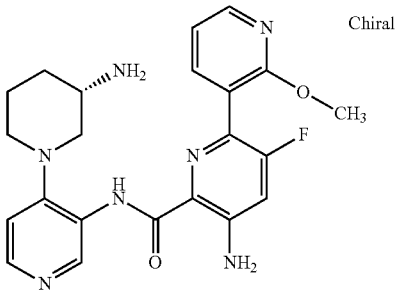
512 Chiral
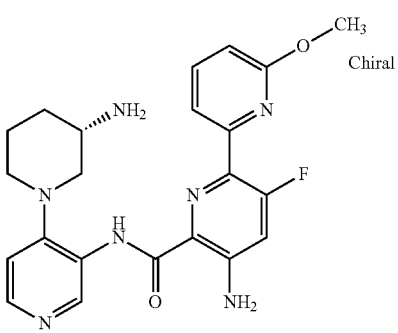
513 Chiral
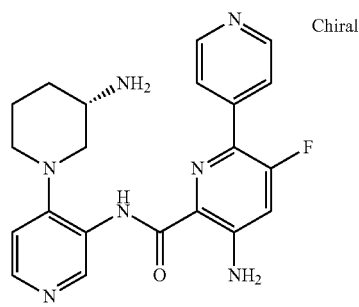
514 Chiral
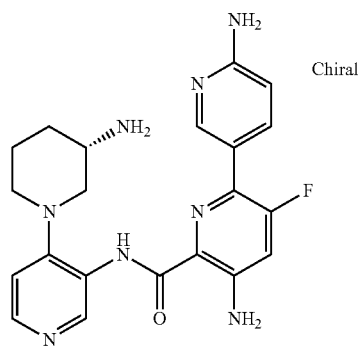

495
515 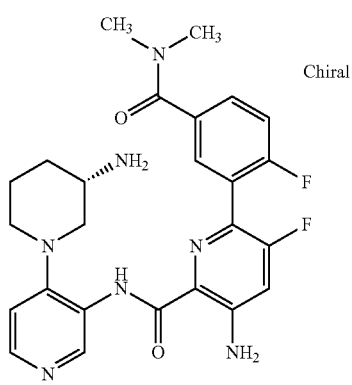
516 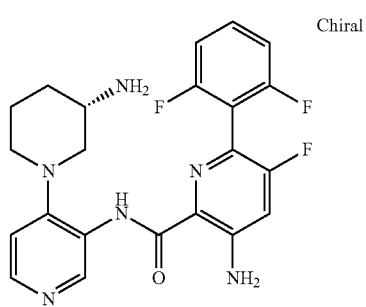
517 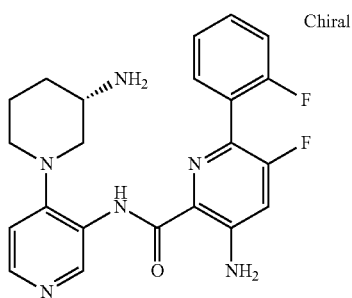
519 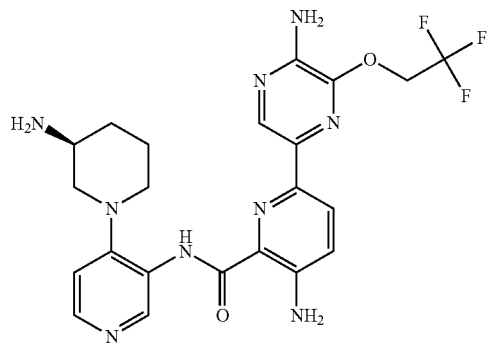
496
520 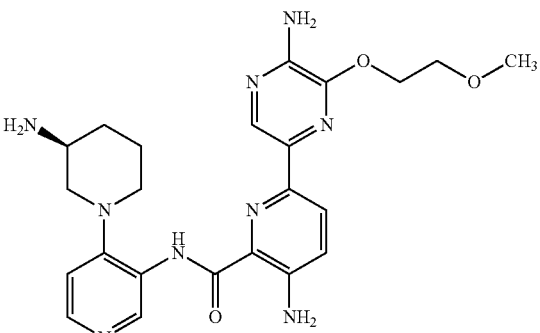
521 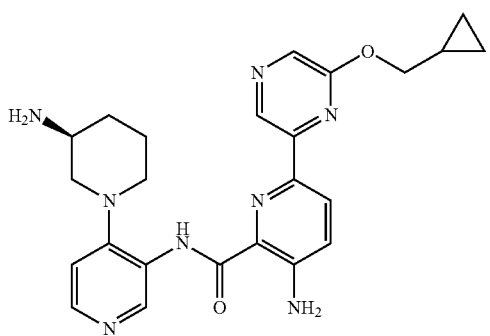
522 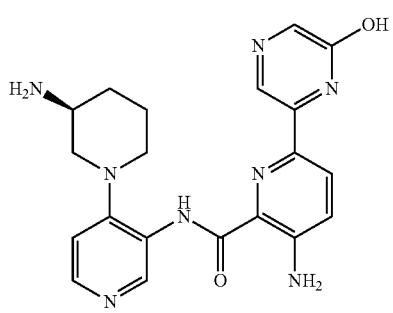
523 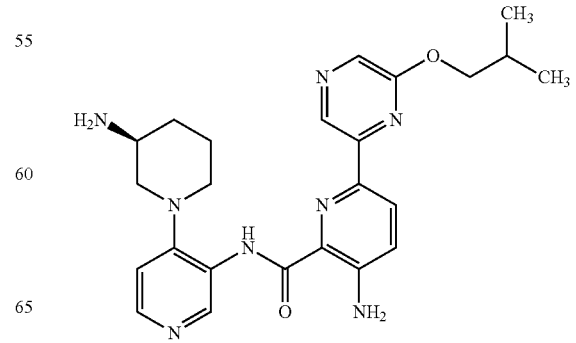

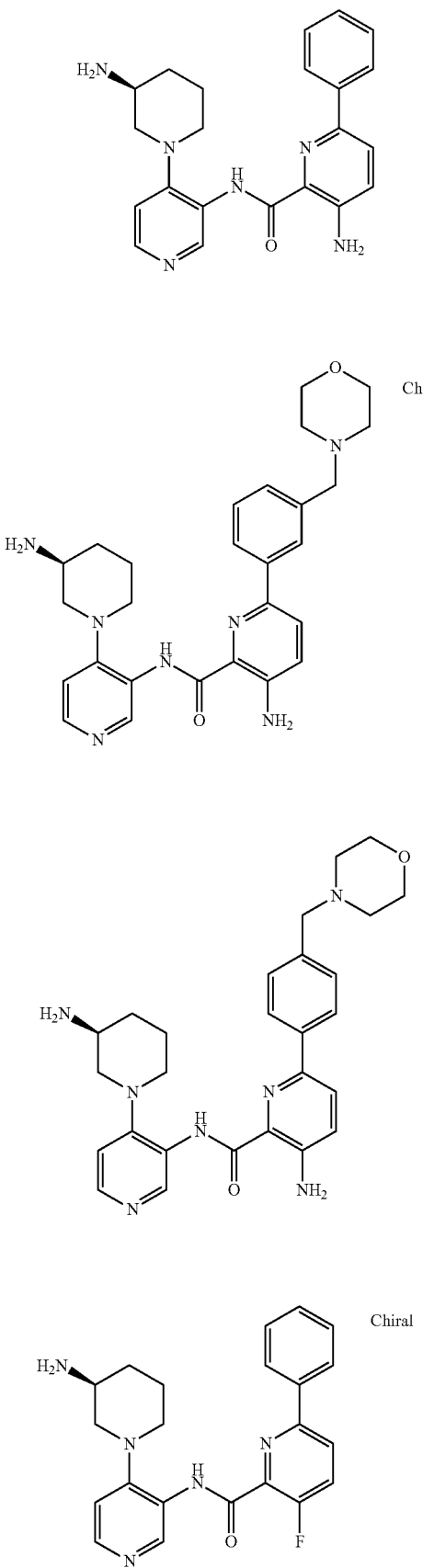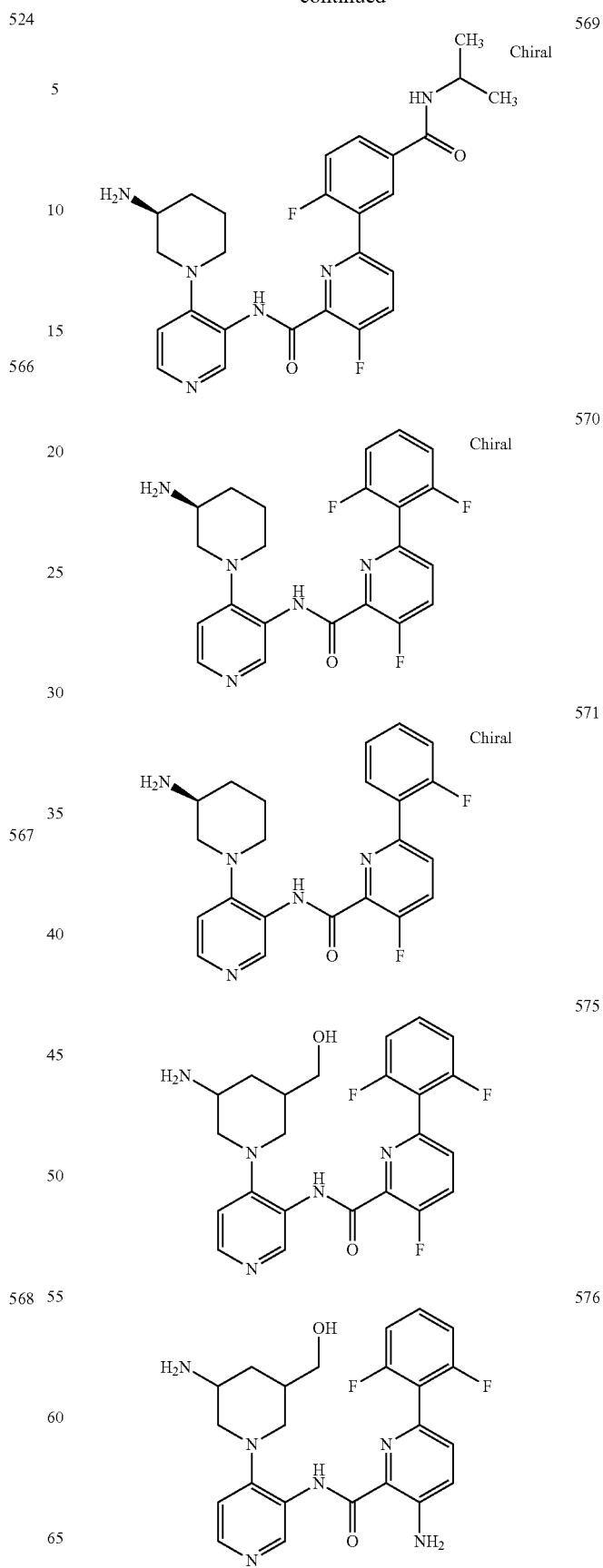

-continued
577
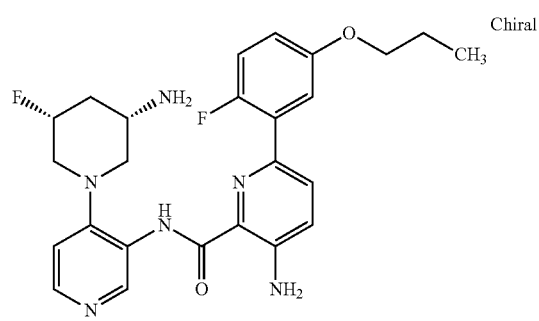
578
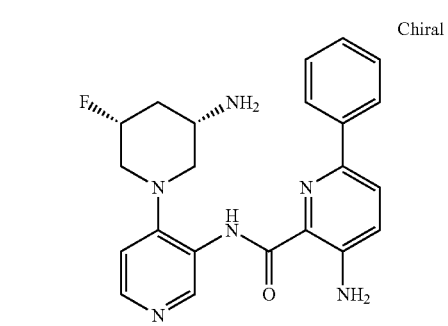
579
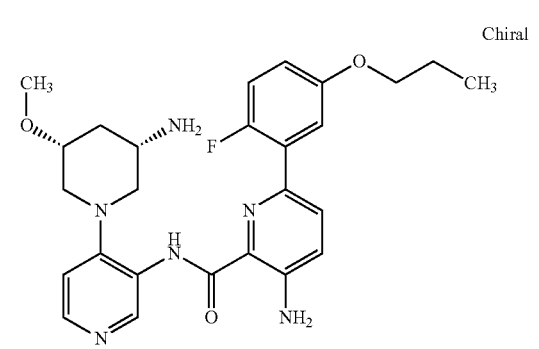
580
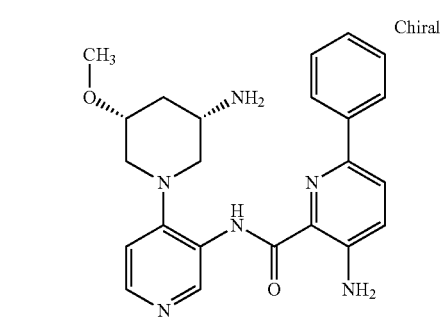
-continued
581
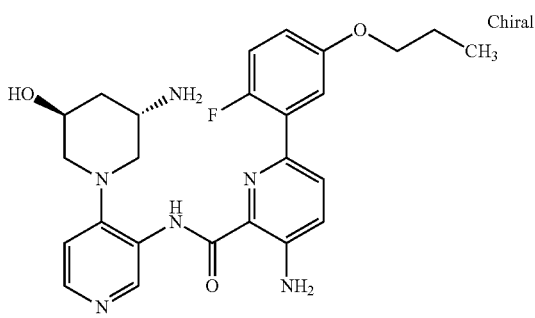
582
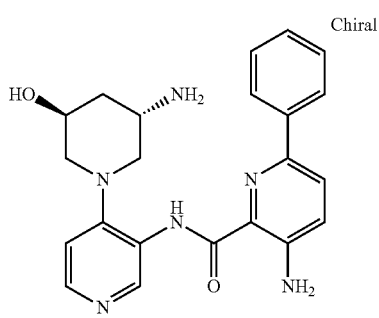
587
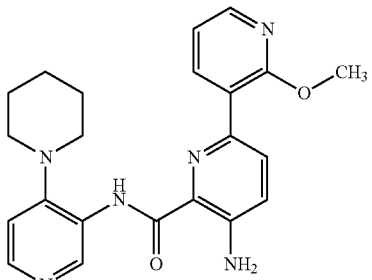
588
589
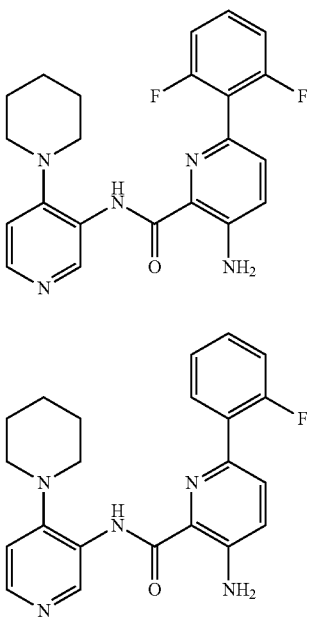

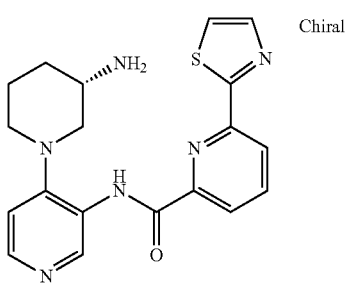 631
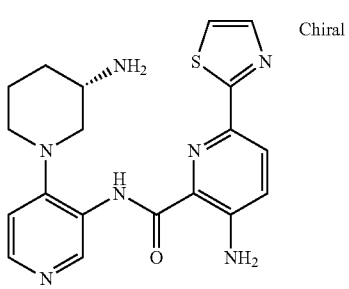 632
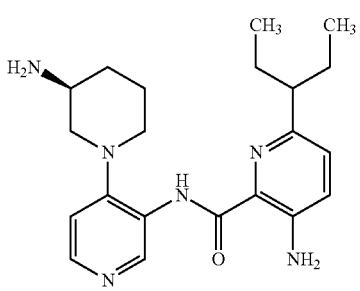 634
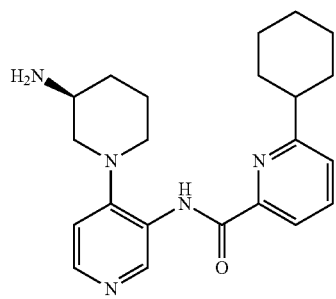 635
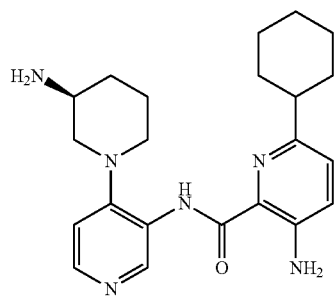 636
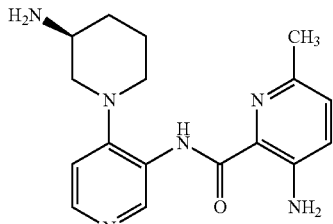 637
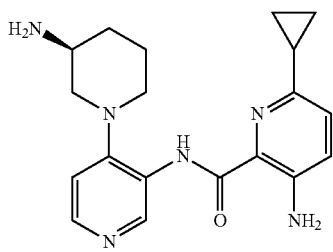 638
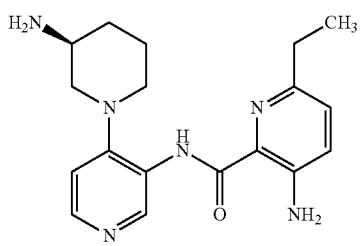 639
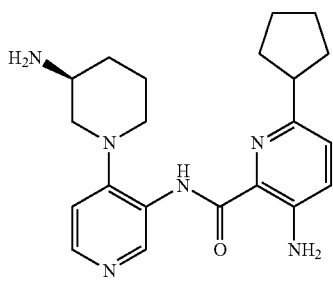 644
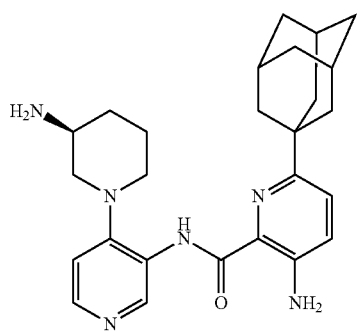 645

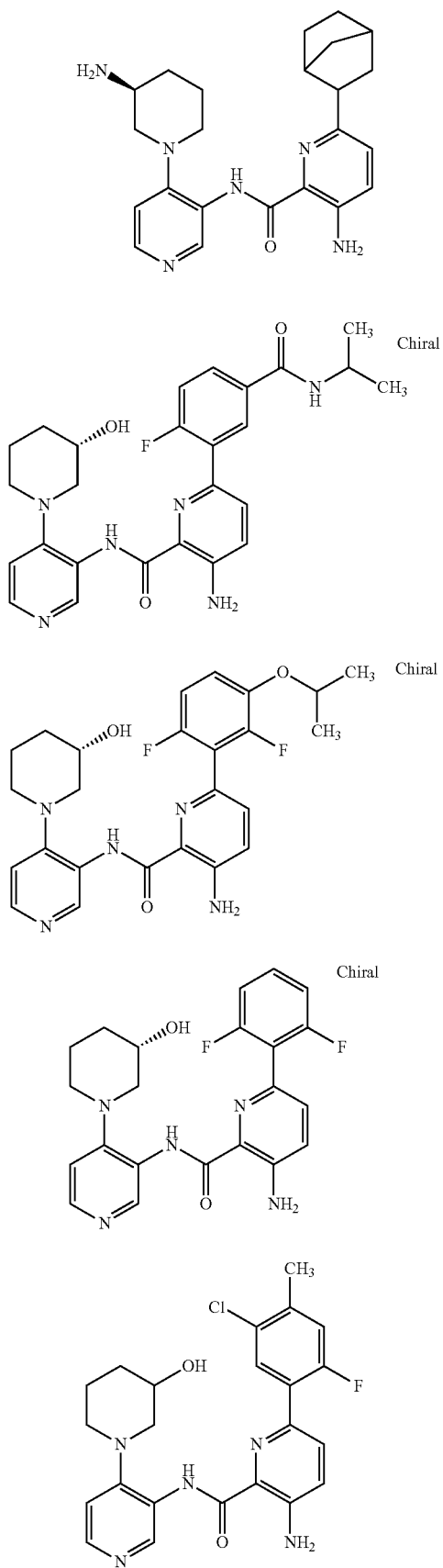
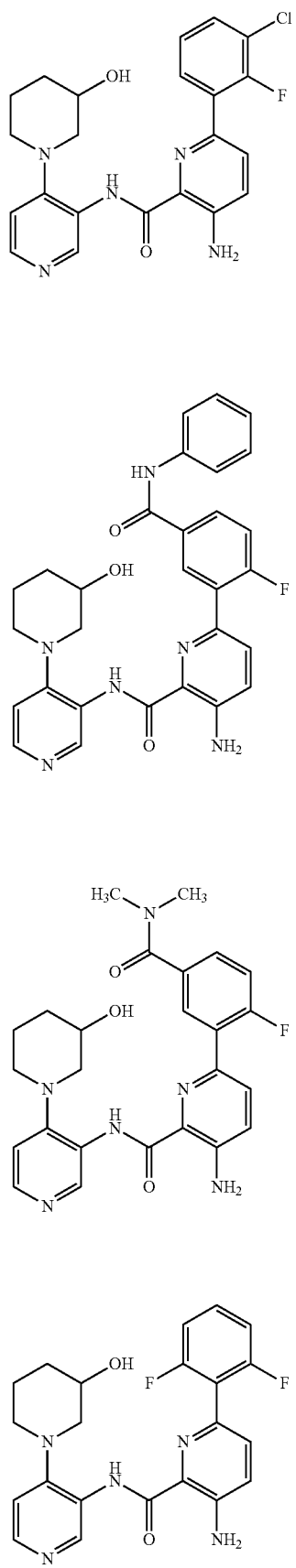

659
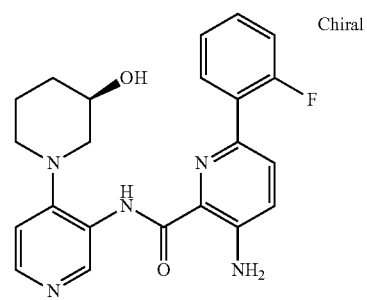
660
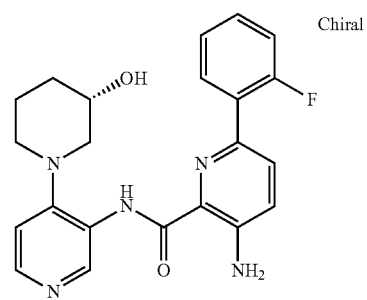
661
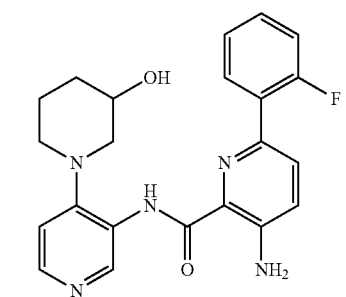
664
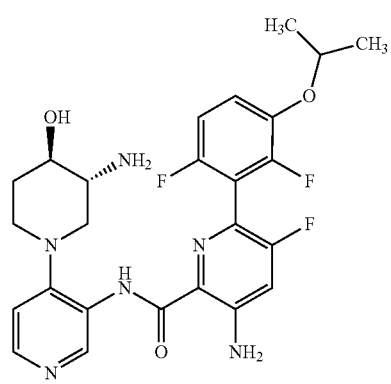
665
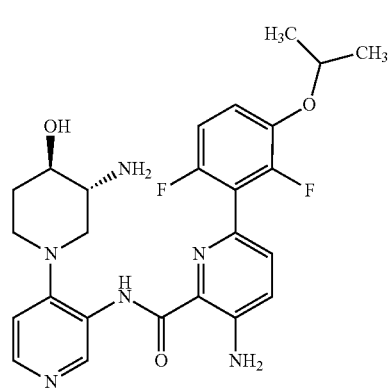
666
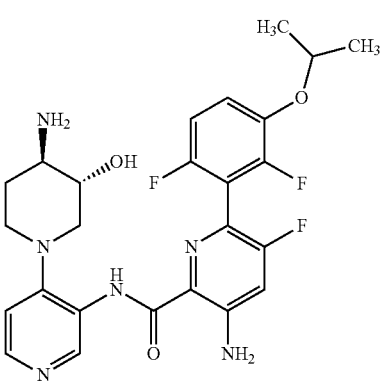
667
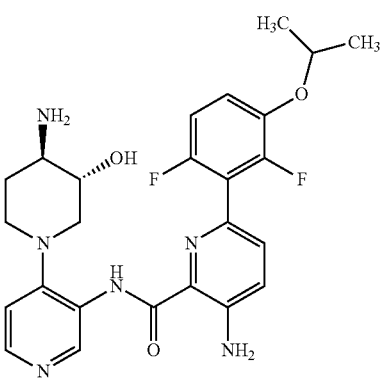
668
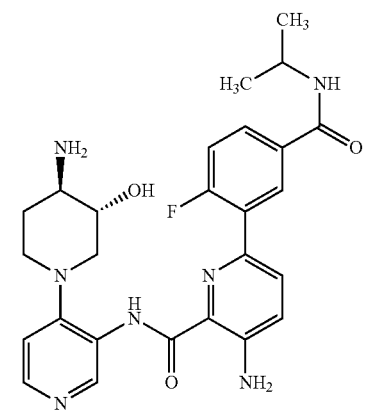
669
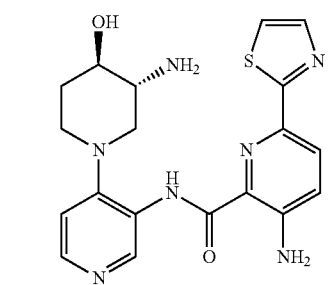

671 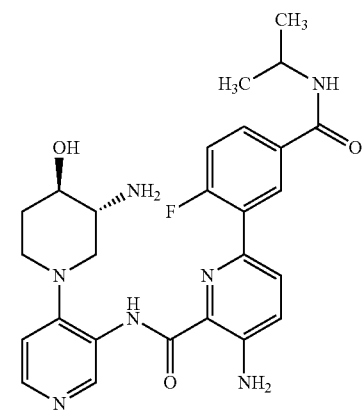
672 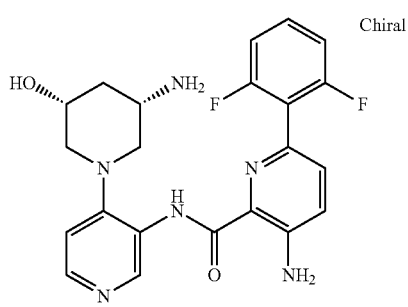
Chiral
674 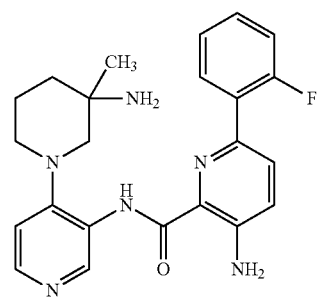
675 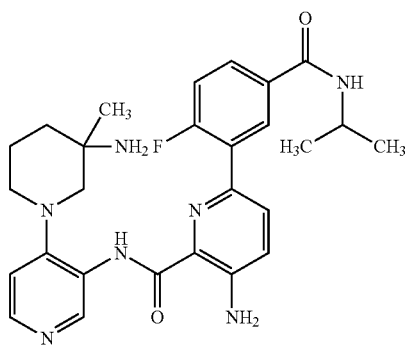
677 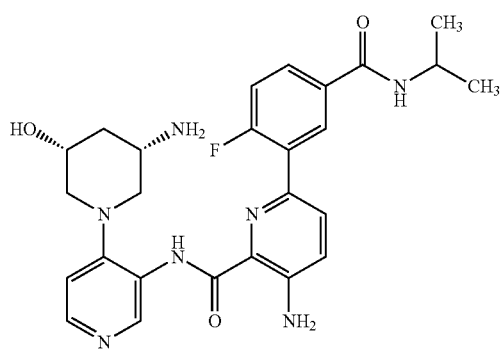
678 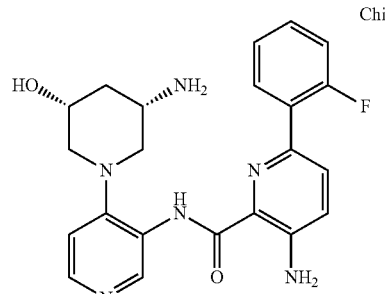
Chiral
679 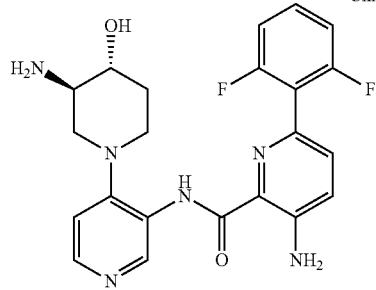
Chiral
680 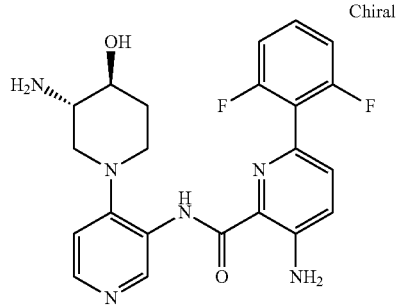
Chiral
681 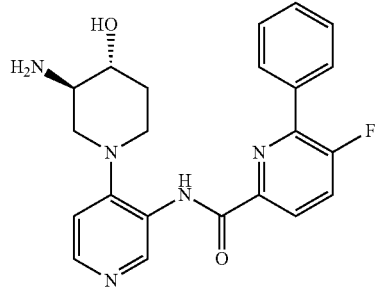
Chiral

| 682 | 686 |
| --- | --- |
| 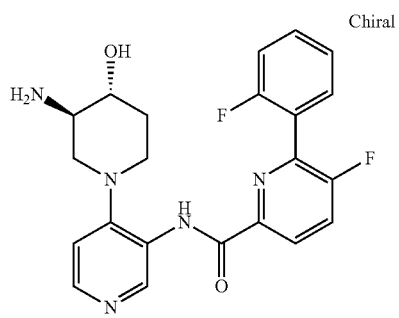 | 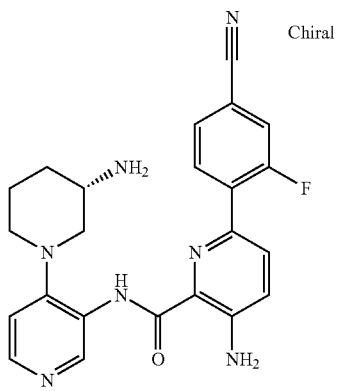 |
| 683 | 687 |
| 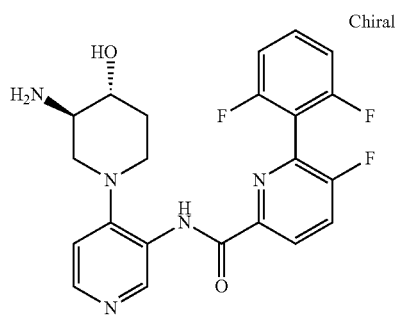 | 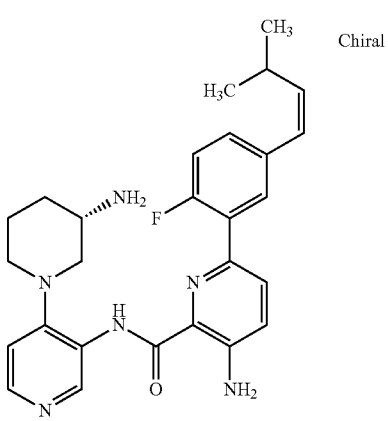 |
| 684 | 688 |
| 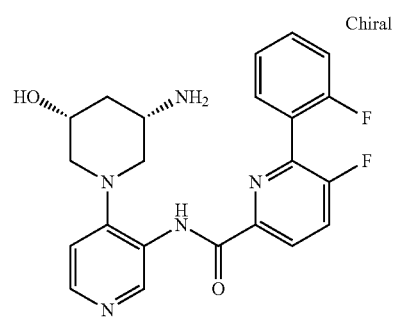 | 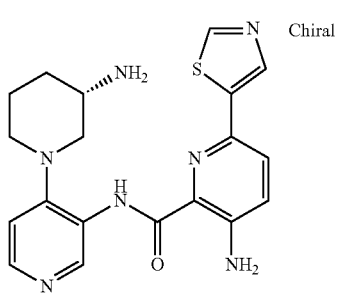 |
| 685 | 689 |
| 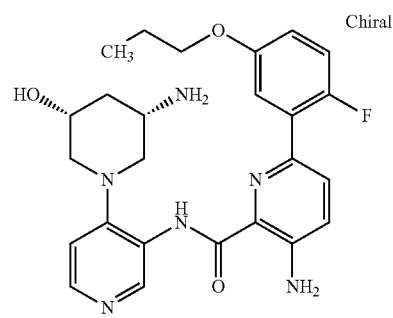 | 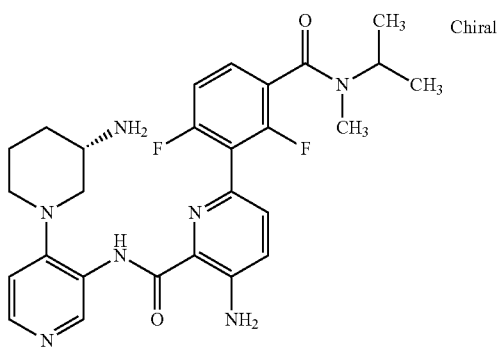 |

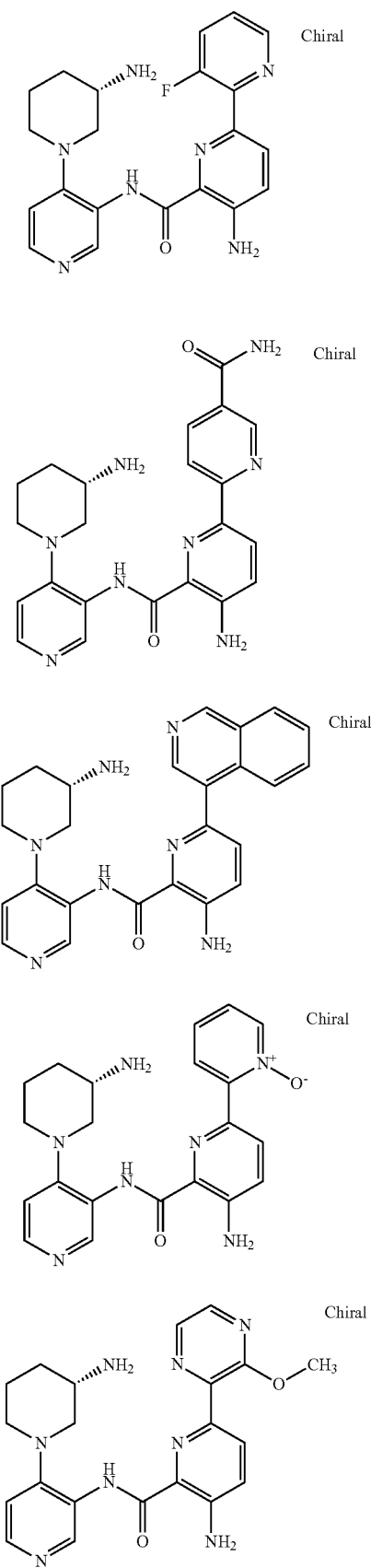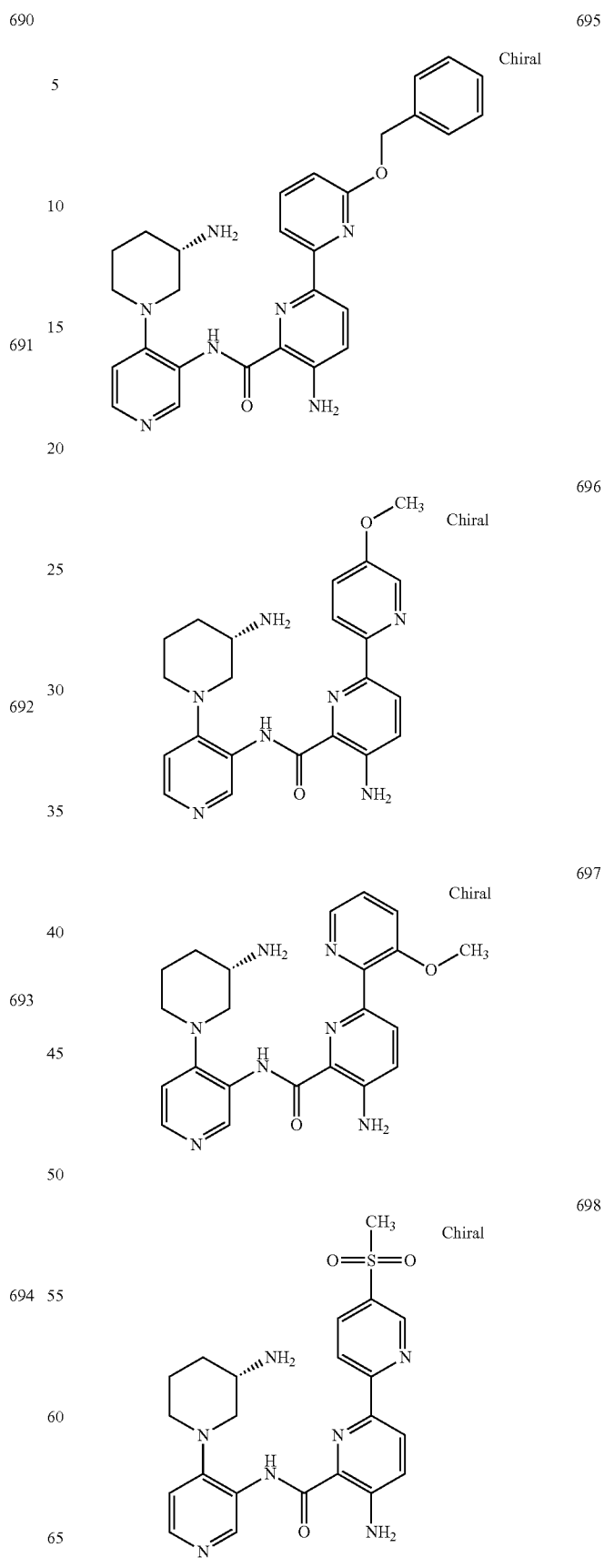

| 699 | 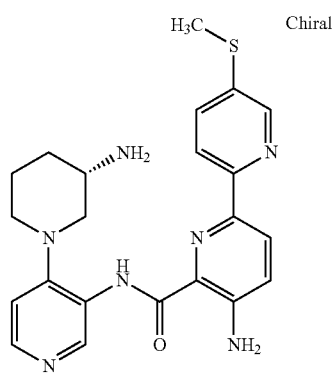 | 703 | 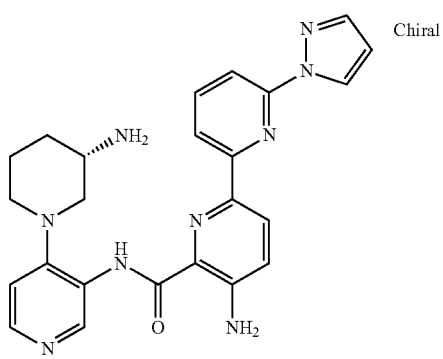 |
| 700 | 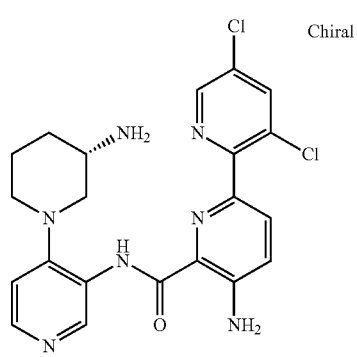 | 704 | 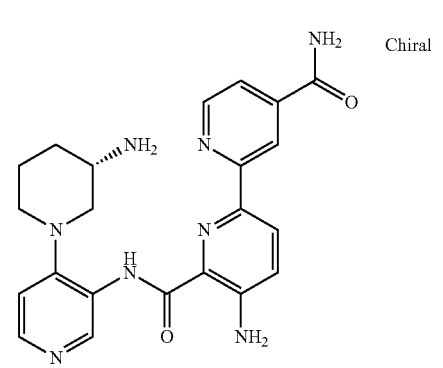 |
| 701 | 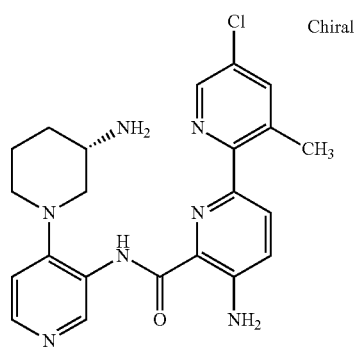 | 705 | 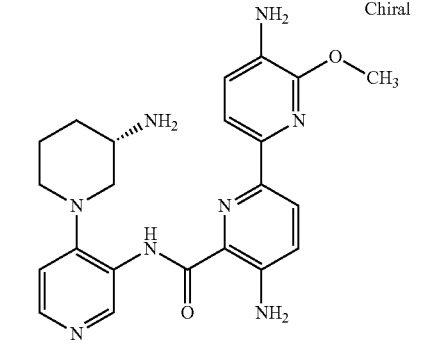 |
| 702 | 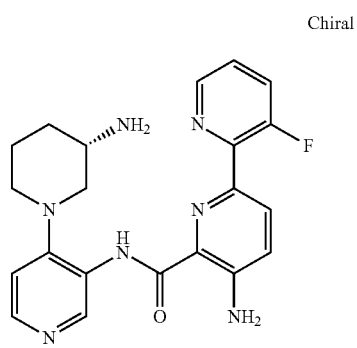 | 706 | 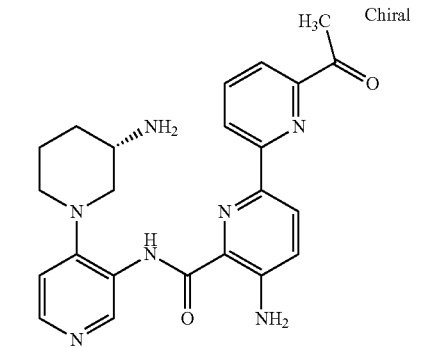 |

707 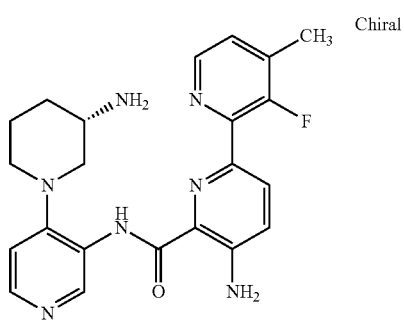
708 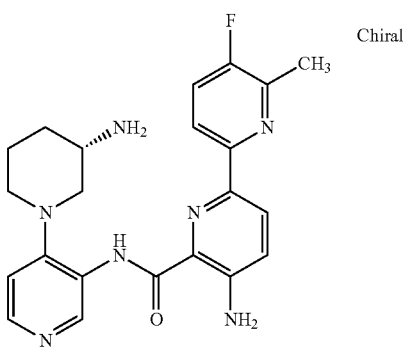
709 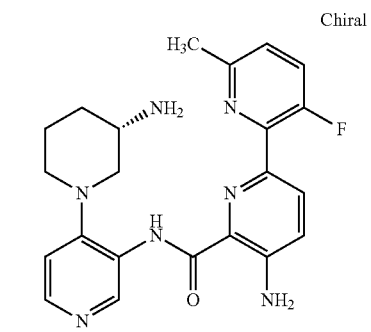
710 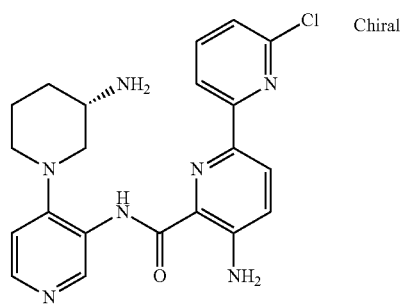
711 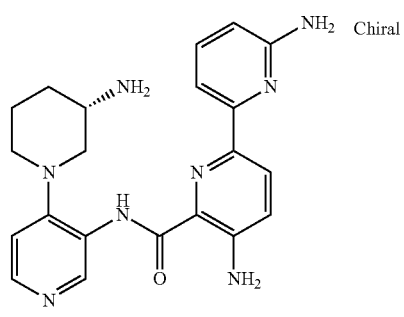
712 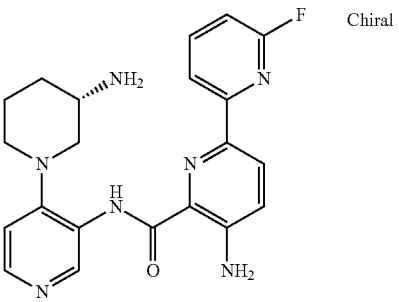
713 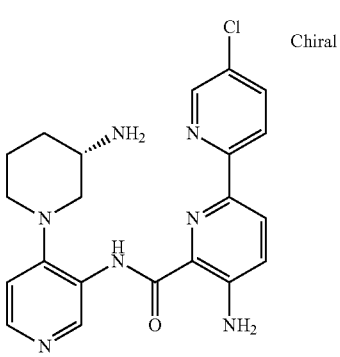
714 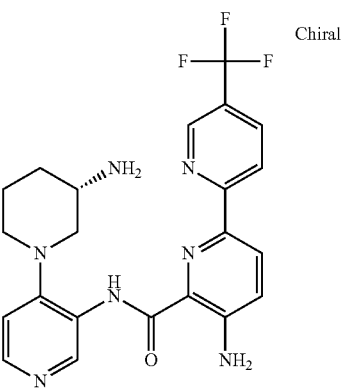
715 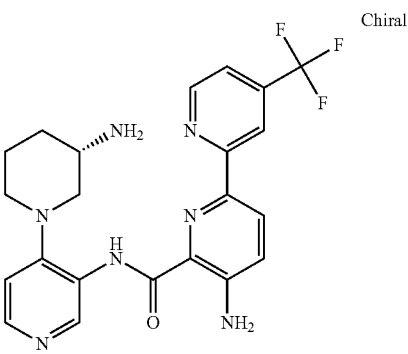

716 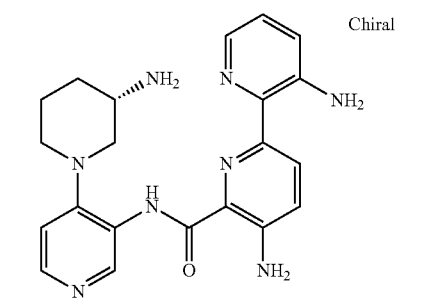
717 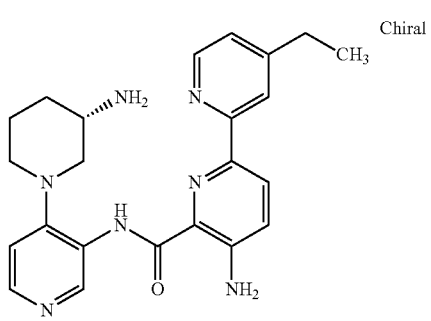
718 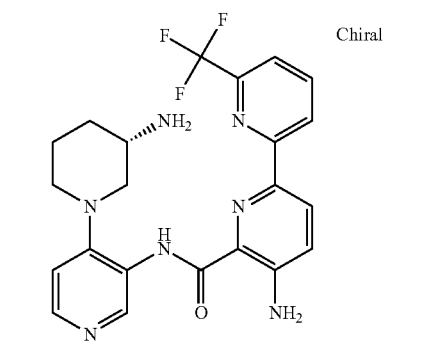
719 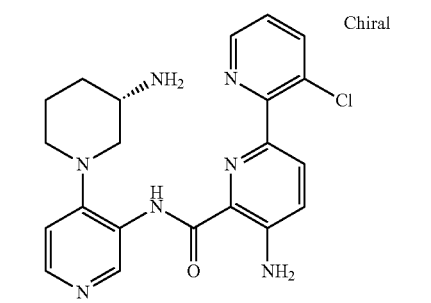
720 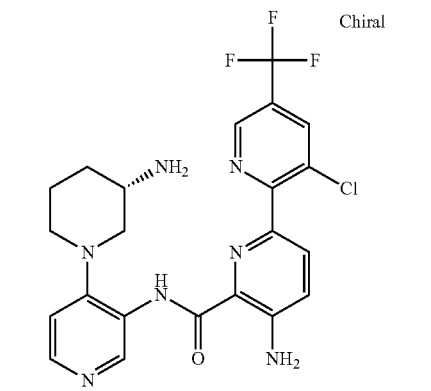
721 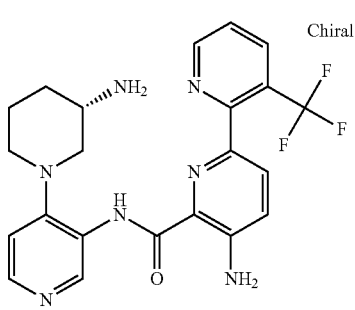
722 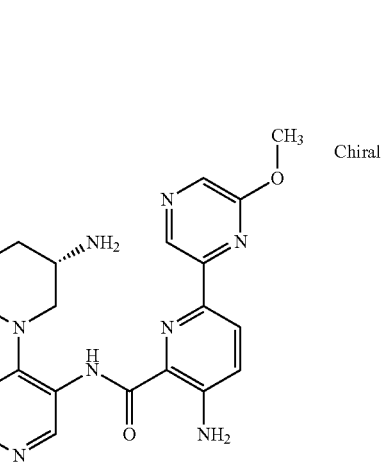
723 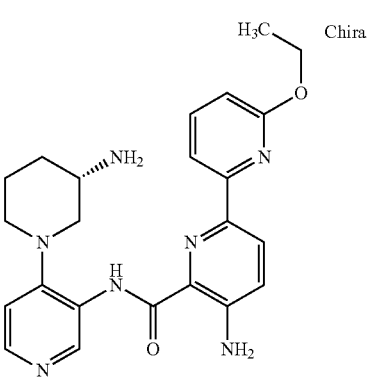
724 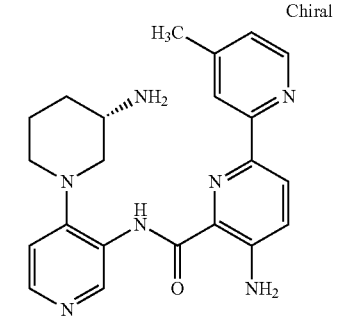

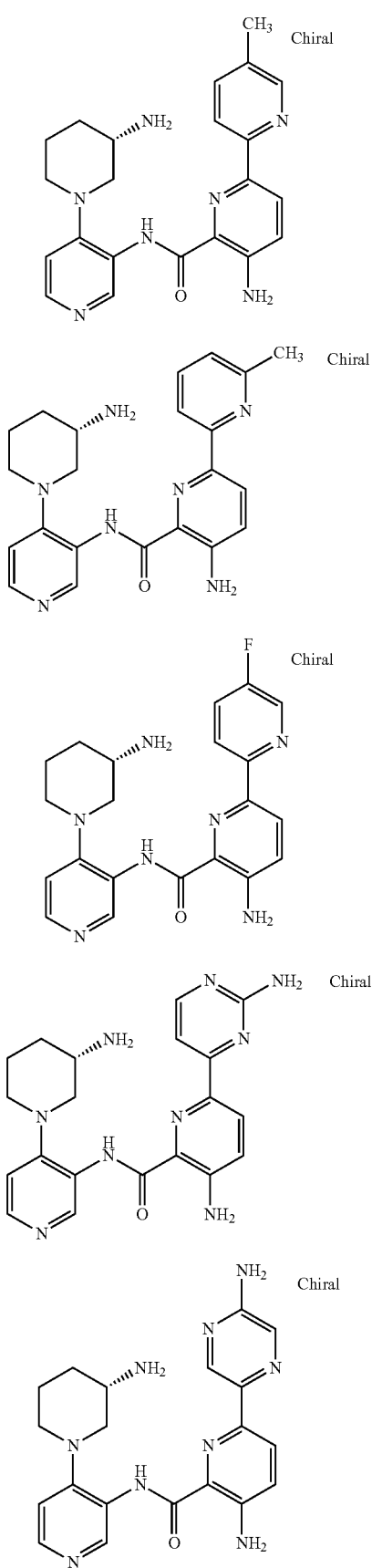
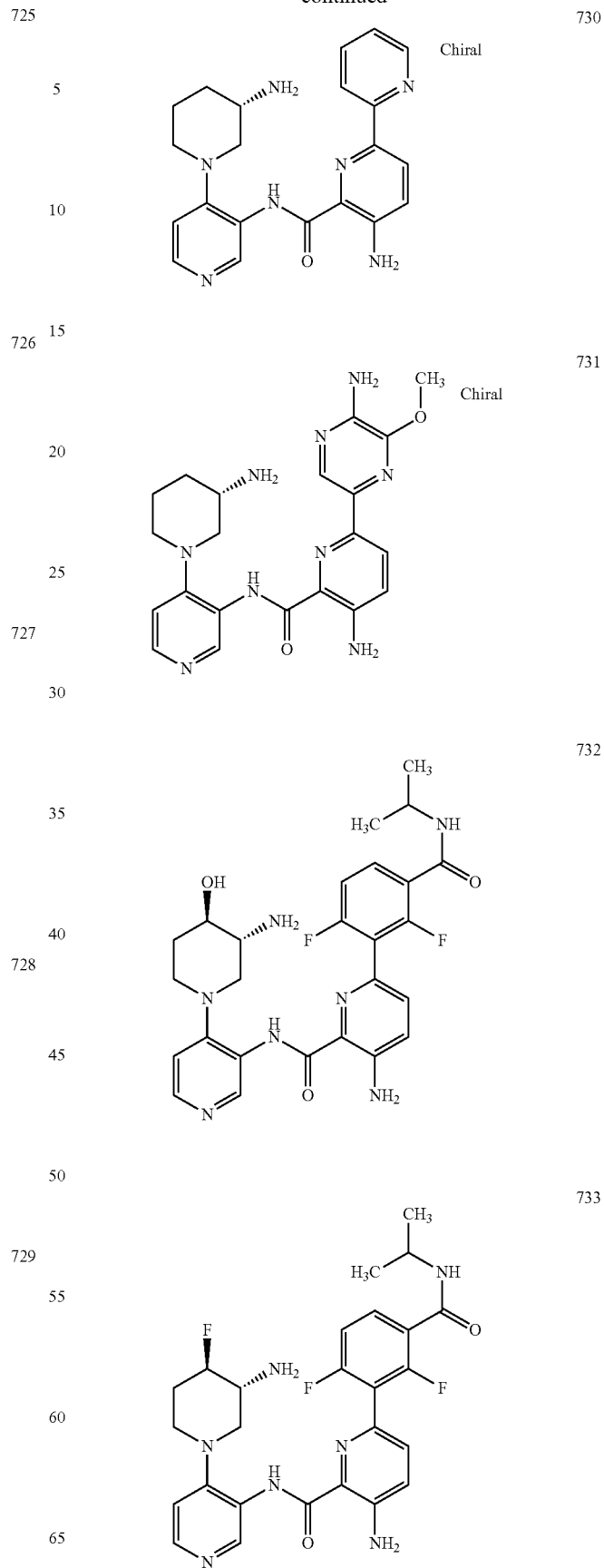

| 521 | 522 |
|---|---|
| -continued | -continued |
734
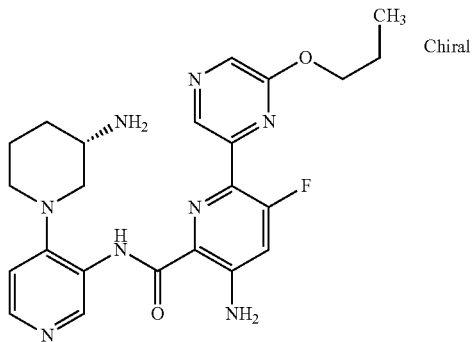
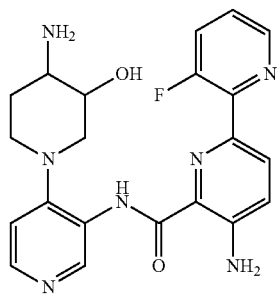
735
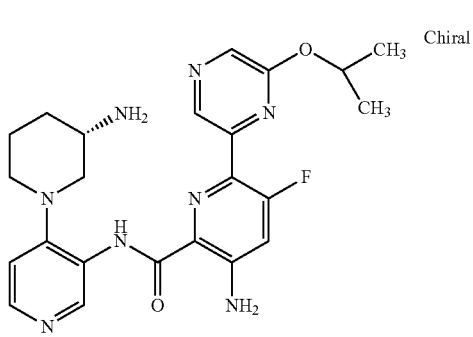
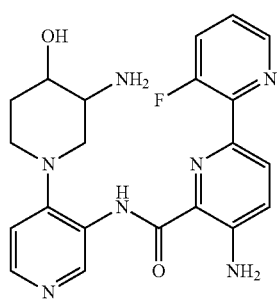
736
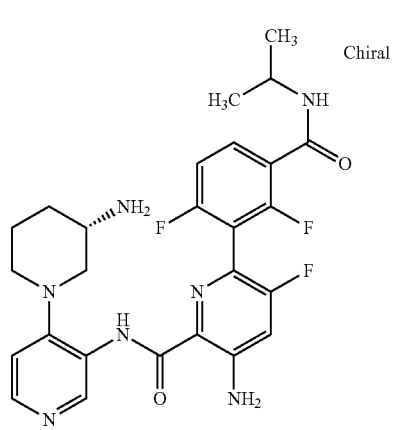
740
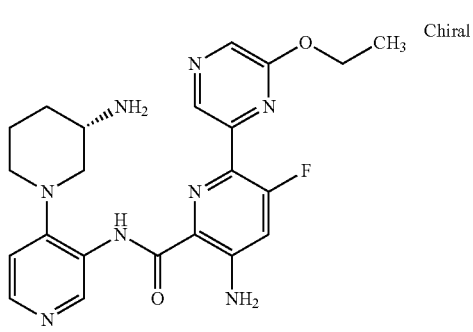
737
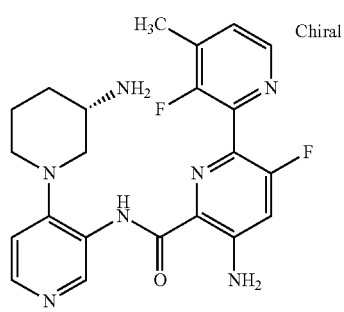
741
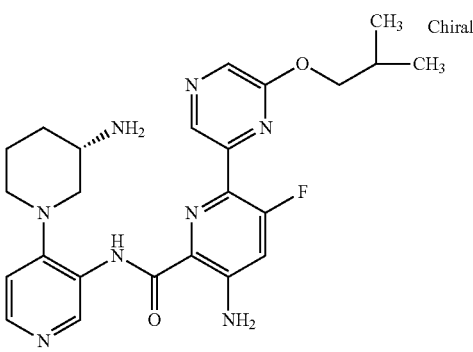

742 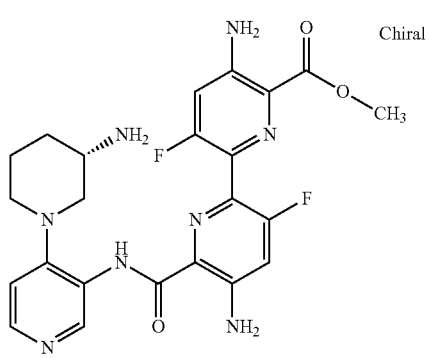
743 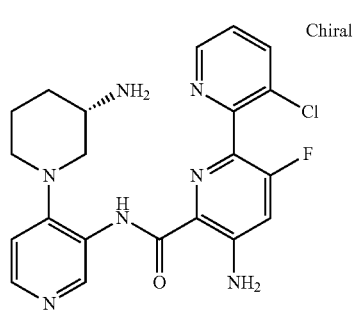
744 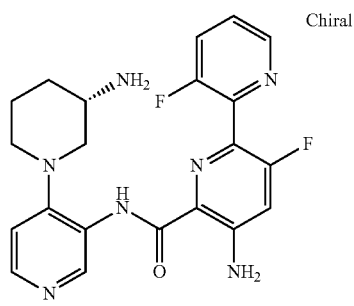
745 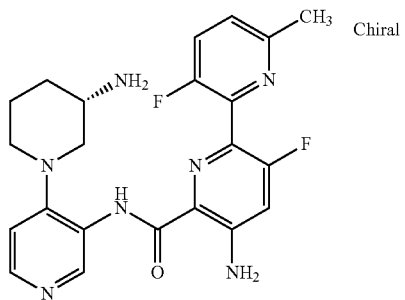
747 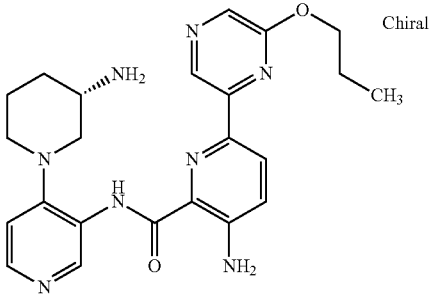
748 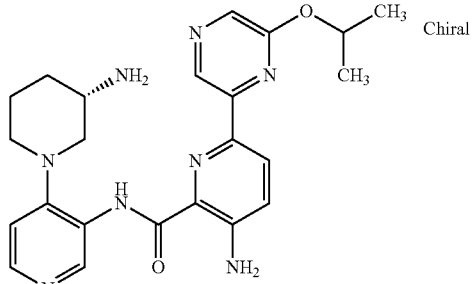
749 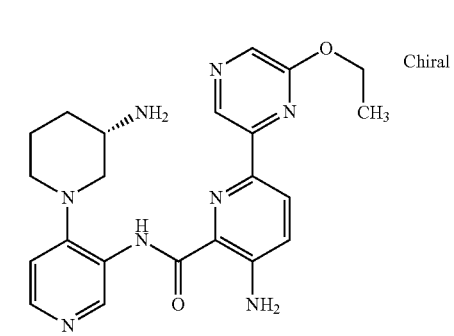
750 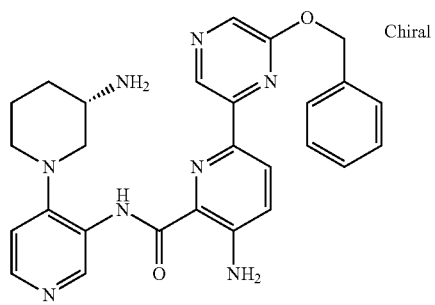
752 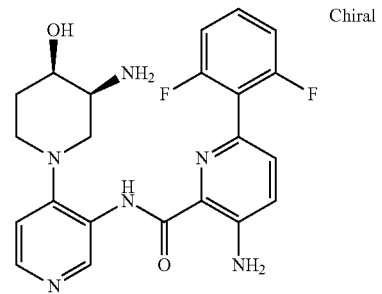
753 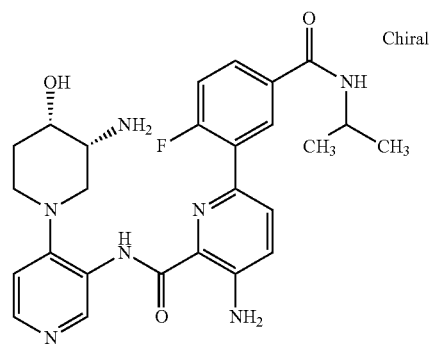

754
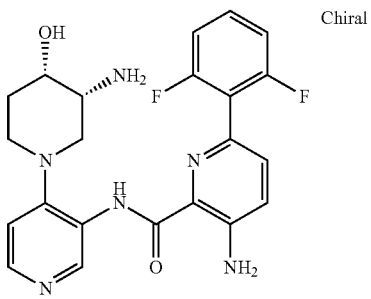
and the pharmaceutically acceptable salts thereof.
9. A composition comprising a therapeutically effective amount of compound of claim 8, or a pharmaceutically acceptable salt thereof, together with a pharmaceutically acceptable carrier.
* * * * *